United States Patent
Degnan et al.

(10) Patent No.: US 8,026,257 B2
(45) Date of Patent: Sep. 27, 2011

(54) SUBSTITUTED HETEROCYCLIC ETHERS AND THEIR USE IN CNS DISORDERS

(75) Inventors: Andrew P. Degnan, Rocky Hill, CT (US); George O. Tora, Langhorne, PA (US); Derek J. Denhart, Durham, CT (US); Vivekananda M. Vrudhula, Killingworth, CT (US); John E. Macor, Guilford, CT (US); Joanne J. Bronson, Durham, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 717 days.

(21) Appl. No.: 12/165,967

(22) Filed: Jul. 1, 2008

(65) Prior Publication Data
US 2009/0018132 A1    Jan. 15, 2009

Related U.S. Application Data

(60) Provisional application No. 60/949,013, filed on Jul. 11, 2007.

(51) Int. Cl.
C07D 413/14 (2006.01)
C07D 401/12 (2006.01)
A61K 31/5377 (2006.01)
A61K 31/4439 (2006.01)

(52) U.S. Cl. ............ 514/322; 514/323; 514/234.5; 544/129; 546/199; 546/201

(58) Field of Classification Search .............. 514/322, 514/323, 234.5; 546/199, 201; 544/129
See application file for complete search history.

(56) References Cited

U.S. PATENT DOCUMENTS

| | | | |
|---|---|---|---|
| 5,620,989 A | 4/1997 | Harrison et al. | |
| 5,760,018 A | 6/1998 | Baker et al. | |
| 2004/0072867 A1 | 4/2004 | Shih et al. | |
| 2006/0019992 A1 | 1/2006 | Wu et al. | |
| 2006/0223830 A1 | 10/2006 | De Nanteuil et al. | |
| 2007/0249607 A1 | 10/2007 | Degnan et al. | |
| 2008/0027056 A1 | 1/2008 | Parker et al. | |

FOREIGN PATENT DOCUMENTS

| | | |
|---|---|---|
| EP | 0 337 167 | 10/1989 |
| WO | WO 03/078376 | 9/2003 |
| WO | WO 2004/022539 | 3/2004 |

OTHER PUBLICATIONS

U.S. Appl. No. 60/987,478, filed Nov. 13, 2007, Bronson et al.
U.S. Appl. No. 12/169,874, filed Jul. 9, 2008, Schmitz et al.
Stevenson, G.I. et al., "4,4-Disubstituted Piperidine High-Affinity $NK_1$ Antagonists: Structure-Activity Relationships and in Vivo Activity", J. Med. Chem., vol. 41, No. 23, pp. 4623-4635 (1998).
Stevenson, G.I. et al., "4,4-Disubstituted Piperidines: A New Class of $NK_1$ Antagonist", J. Med. Chem., vol. 38, No. 8, pp. 1264-1266 (1995).

*Primary Examiner* — Joseph Kosack
*Assistant Examiner* — Matthew Coughlin
(74) *Attorney, Agent, or Firm* — James Epperson

(57) ABSTRACT

The invention encompasses compounds of Formula I, including pharmaceutically acceptable salts, their pharmaceutical compositions, and their use in treating CNS disorders.

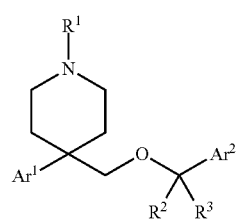

17 Claims, No Drawings

SUBSTITUTED HETEROCYCLIC ETHERS AND THEIR USE IN CNS DISORDERS

CROSS REFERENCE TO RELATED APPLICATIONS

This application claims the benefit of U.S. provisional application No. 60/949,013, filed Jul. 11, 2007.

BACKGROUND OF THE INVENTION

Tachykinins are a group of naturally occurring peptides found widely distributed throughout mammals, both within the central nervous system and in the peripheral nervous and circulatory systems. The three known mammalian tachykinins are Neurokinin-1 (NK-1, substance P), Neurokinin A, and Neurokinin B. These compounds act as neurotransmitters and immunomodulators and may contribute to the pathophysiology of a wide variety of human diseases.

Receptors for tachykinins have been identified and include neurokinin-1 (NK-1 or Substance P-preferring), NK-2 (Neurokinin A-preferring) and NK-3 (Neurokinin B-preferring). NK-1 receptor antagonists are being developed for the treatment of physiological conditions associated with an excess or imbalance of tachykinins, particularly substance P. Such conditions include affective disorders such as anxiety, depression, obsessive compulsive disorder, bulimia, and panic disorder. See Gentsch et al. *Behav. Brain Res.* 2002, 133, 363; Varty et al. *Neuropsychopharmacology* 2002, 27, 371; Papp et al. *Behav. Brain Res.* 2000, 115, 19; Kramer et al. *Science* 1998, 281, 1640; and Rosen et al. *Bioorg. Med. Chem. Lett.* 1998, 8, 281. Robust antidepressant activity has been reported for two NK-1 antagonists, MK-869 (M. S. Kramer, et al., Science 1998, 281 1640) and CP-122,721 (T. J. Rosen, et al., Bioorganic and Medicinal Chemistry Letters 1998, 8, 28 and CNS Drug News, Dec. 24, 2000).

Selective serotonin reuptake inhibitors (SSRI's) have proven to be effective in treating depression, but have the disadvantages of delayed onset of antidepressant activity, limited efficacy, and significant side effects. See Novel strategies for pharmacotherapy of depression, K. A. Maubach, N. M. J. Rupniak, M. S. Kramer, and R. G. Hill, Current Opinion in Chemical Biology 1999, 3, 491-499. Selective serotonin reuptake inhibitors (SSRIs) in combination with other agents can be useful for the treatment of depression and other disorders and combination SERT/NK1 compounds should also be useful for these conditions. For example, the combination of SSRIs with dopamine reuptake inhibitors such bupropion and modafanil have shown clinical benefit relative to SSRIs alone, primarily due to superior side effect profiles (Bodkin et al, 1997, J Clin Psychiatry, 58: 137-145; Kennedy et al, 2002, J Clin Psychiatry, 63:181-186). Additionally, the combination of SSRIs with 5-HT1A antagonists such as pindolol have shown improved clinical response relative to SSRIs alone (Artigas F et al, 1994, Arch Gen Psychiatry 51:248-251; Blier P and Bergeron R, 1995, J Clin Psychopharmacol 15:217-222). Finally, combining SSRIs with antipsychotics, such as fluoxetine plus olanzapine, has provided superior profiles in certain depressed populations including psychotic depression and bipolar depression (Corya et al, 2003, J Clin Psychiatry, 64:1349-1356; Rothschild et al, 2004, J Clin Psychopharmacol, 24:365-373).

NK-1 antagonists are believed to modulate 5-HT function via noradrenergic pathways and have been shown to attenuate presynaptic $5\text{-}HT_{1A}$ receptor function. NK-1 antagonists offer an alternative approach for treating depression in patients that respond poorly to the SSRI's and other available drugs and the combination of serotonin reuptake inhibition with NK-1 antagonism may lead to new classes of drugs with improved characteristics.

DESCRIPTION OF THE INVENTION

The invention encompasses compounds of Formula I and related compound and compositions including pharmaceutically acceptable salts and their use in treating CNS disorders related to levels of tachykinins or serotonin or both.

One aspect of the invention are compounds of Formula I

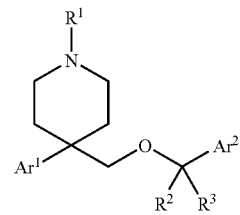

where:
$R^1$ is hydrogen or alkyl;
$R^2$ is hydrogen, alkyl, cyanoalkyl, haloalkyl, hydroxylalkyl, alkoxyalkyl, aminoalkyl, alkylaminoalkyl, dialkylaminoalkyl, cyano, carboxy, alkoxycarbonyl, aminocarbonyl, N-alkylaminocarbonyl, or N,N-dialkylaminocarbonyl;
$R^3$ is hydrogen or alkyl;
$Ar^1$ is phenyl or pyridinyl and is substituted with 0-3 substituents selected from the group consisting of halo, alkyl, haloalkyl, and cyano;
$Ar^2$ is indolyl, indazolyl, benzimidazolyl, or benzotriazolyl and is substituted with 0-3 substituents selected from the group consisting of halo, alkyl, cycloalkyl, (cycloalkyl)alkyl, haloalkyl, cyanoalkyl, hydroxy, alkoxy, haloalkoxy, cyano, amino, alkylamino, dialkylamino, pyrrolidinyl, piperidinyl, piperazinyl, (alkyl)piperazinyl, morpholinyl, thiomorpholinyl, and $Ar^3$; and
$Ar^3$ is phenyl substituted with 0-3 substituents selected from the group consisting of halo, alkyl, haloalkyl, alkoxy, haloalkoxy, and cyano;
or a pharmaceutically acceptable salt thereof.

Another aspect of the invention is a compound of formula I where
$R^1$ is hydrogen or alkyl;
$R^2$ is hydrogen or alkyl
$R^3$ is hydrogen or alkyl;
$Ar^1$ is phenyl or pyridinyl and is substituted with 0-3 substituents selected from the group consisting of halo, alkyl, haloalkyl, and cyano;
$Ar^2$ is indolyl, indazolyl, benzimidazolyl, or benzotriazolyl and is substituted with 0-3 substituents selected from the group consisting of halo, alkyl, cycloalkyl, (cycloalkyl)alkyl, haloalkyl, hydroxy, alkoxy, haloalkoxy, cyano, amino, alkylamino, dialkylamino, pyrrolidinyl, piperidinyl, piperazinyl, (alkyl)piperazinyl, morpholinyl, thiomorpholinyl, and $Ar^3$; and
$Ar^3$ is phenyl substituted with 0-3 substituents selected from the group consisting of halo, alkyl, haloalkyl, alkoxy, haloalkoxy, and cyano;
or a pharmaceutically acceptable salt thereof.

Another aspect of the invention are compounds of Formula I where $R^1$ is hydrogen.

Another aspect of the invention are compounds of Formula I where $R^1$ is methyl.

Another aspect of the invention are compounds of Formula I where $R^2$ and $R^3$ are hydrogen.

Another aspect of the invention are compounds of Formula I where $R^2$ is methyl and $R^3$ is hydrogen.

Another aspect of the invention are compounds of Formula I where $Ar^1$ is phenyl.

Another aspect of the invention are compounds of Formula I where $Ar^1$ is monohalophenyl.

Another aspect of the invention are compounds of Formula I where $Ar^1$ is p-fluorophenyl.

Another aspect of the invention is a compound of formula I where $Ar^2$ is indazolyl, benzimidazolyl, or benzotriazolyl and is substituted with 0-3 substituents selected from the group consisting of halo, alkyl, cycloalkyl, (cycloalkyl)alkyl, haloalkyl, hydroxy, alkoxy, haloalkoxy, cyano, amino, alkylamino, dialkylamino, pyrrolidinyl, piperidinyl, piperazinyl, (alkyl)piperazinyl, morpholinyl, thiomorpholinyl, and $Ar^3$.

Another aspect of the invention is a compound of formula I where $Ar^2$ is indazolyl and is substituted with 0-3 substituents selected from the group consisting of halo, alkyl, cycloalkyl, (cycloalkyl)alkyl, haloalkyl, cyanoalkyl, hydroxy, alkoxy, haloalkoxy, cyano, amino, alkylamino, dialkylamino, pyrrolidinyl, piperidinyl, piperazinyl, (alkyl)piperazinyl, morpholinyl, thiomorpholinyl, and $Ar^3$.

Another aspect of the invention is a compound of formula I where $Ar^2$ is indazolyl substituted with 0-3 substituents selected from the group consisting of halo, alkyl, cycloalkyl, (cycloalkyl)alkyl, haloalkyl, hydroxy, alkoxy, haloalkoxy, cyano, amino, alkylamino, dialkylamino, pyrrolidinyl, piperidinyl, piperazinyl, (alkyl)piperazinyl, morpholinyl, thiomorpholinyl, and $Ar^3$.

Another aspect of the invention is a compound of formula I where $Ar^2$ is indolyl substituted with 0-3 substituents selected from the group consisting of halo, alkyl, cycloalkyl, (cycloalkyl)alkyl, haloalkyl, hydroxy, alkoxy, haloalkoxy, cyano, amino, alkylamino, dialkylamino, pyrrolidinyl, piperidinyl, piperazinyl, (alkyl)piperazinyl, morpholinyl, thiomorpholinyl, and $Ar^3$.

Another aspect of the invention is a compound of formula I where $Ar^2$ is benzimidazolyl substituted with 0-3 substituents selected from the group consisting of halo, alkyl, cycloalkyl, (cycloalkyl)alkyl, haloalkyl, hydroxy, alkoxy, haloalkoxy, cyano, amino, alkylamino, dialkylamino, pyrrolidinyl, piperidinyl, piperazinyl, (alkyl)piperazinyl, morpholinyl, thiomorpholinyl, and $Ar^3$. Another aspect of the invention is a compound of formula I where $Ar^2$ is benzotriazolyl substituted with 0-3 substituents selected from the group consisting of halo, alkyl, cycloalkyl, (cycloalkyl)alkyl, haloalkyl, hydroxy, alkoxy, haloalkoxy, cyano, amino, alkylamino, dialkylamino, pyrrolidinyl, piperidinyl, piperazinyl, (alkyl)piperazinyl, morpholinyl, thiomorpholinyl, and $Ar^3$.

Any scope of a substituent, including $R^1$, $R^2$, $R^3$, $Ar^1$, $Ar^2$, and $Ar^3$, can be used independently with the scope of any other instance of a substituent.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some Formula I compounds have tautomeric forms, for example, the tautomeric moieties shown below. The invention includes all tautomeric forms of the compounds.

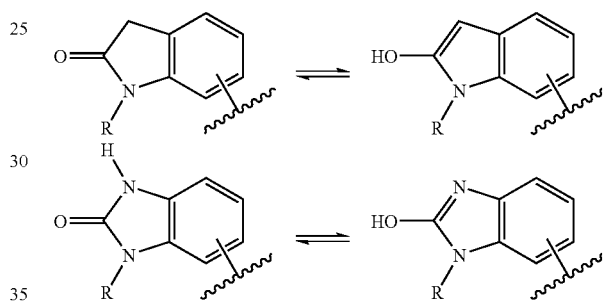

Some Formula I compounds contain at least one asymmetric carbon atom, an example of which is shown below. The invention includes all stereoisomeric forms of the compounds, both mixtures and separated isomers. Mixtures of stereoisomers can be separated into individual isomers by methods known in the art.

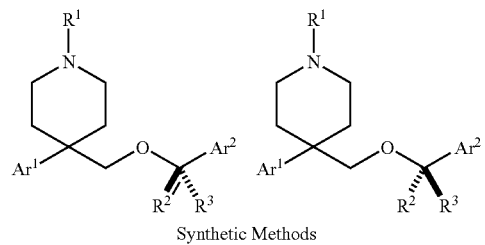

Synthetic Methods

Compounds of Formula I can be made according to methods known in the art and those illustrated in the schemes below and in the specific embodiments section. The compounds can be made by reasonable variations known in the art. The variables describing general structural formulas and features in the synthetic schemes are distinct from and should not be confused with the variables in the claims or the rest of the specification. These variables are meant only to illustrate how to make some of the compounds of this invention. For this section, a benzene ring with an H in the middle can represent a phenyl or heteroaryl moiety, for example pyridinyl or pyrimidinyl.

Scheme 1.
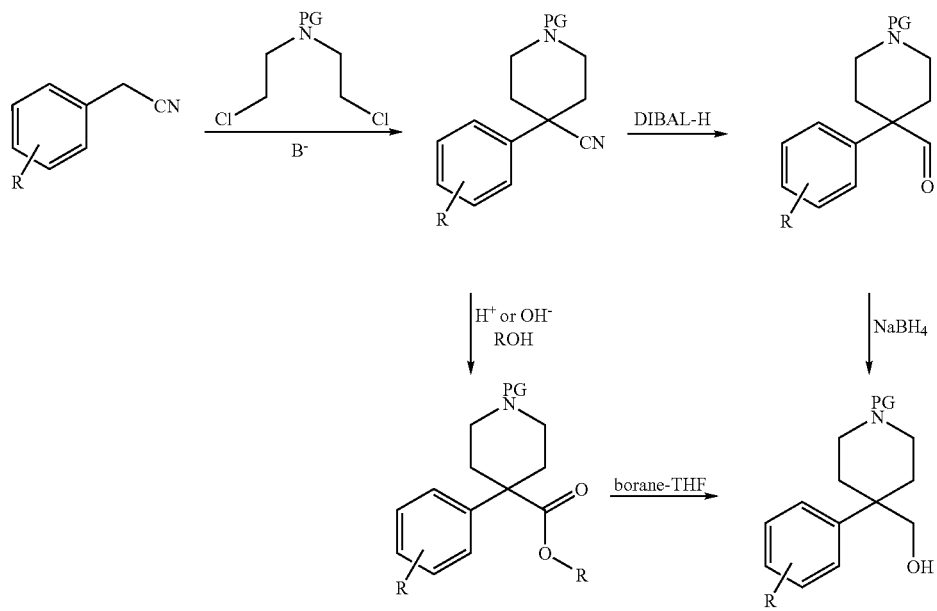
Scheme 2.
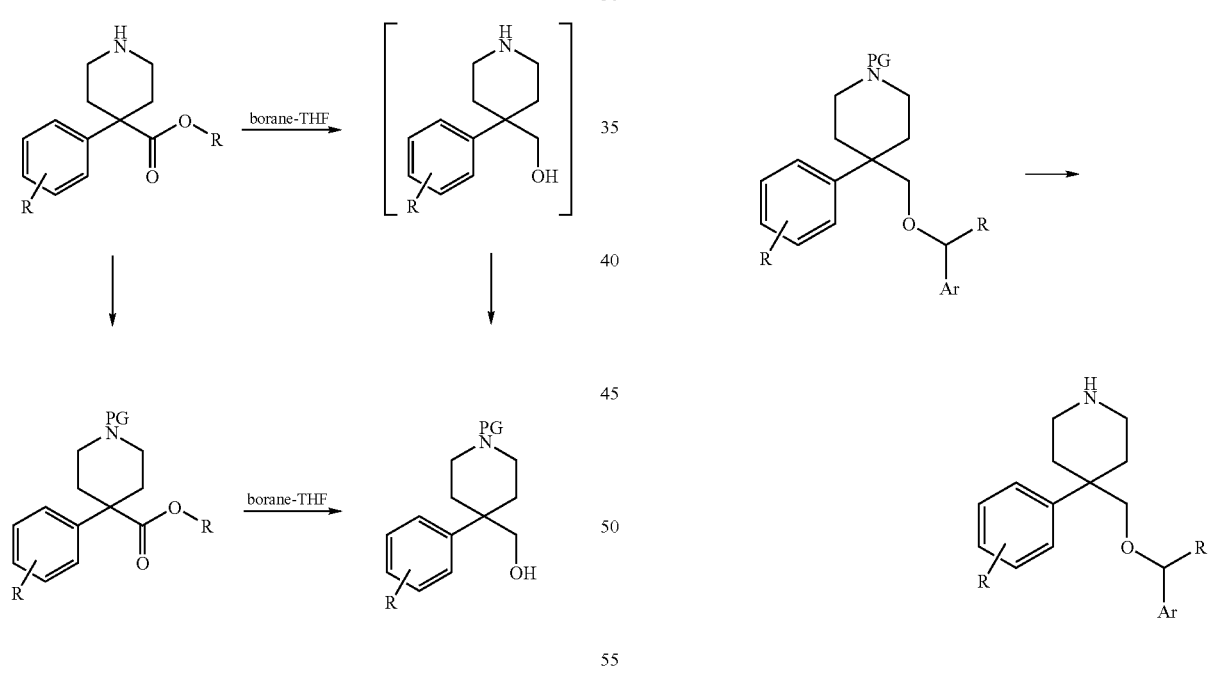
-continued
Scheme 3.
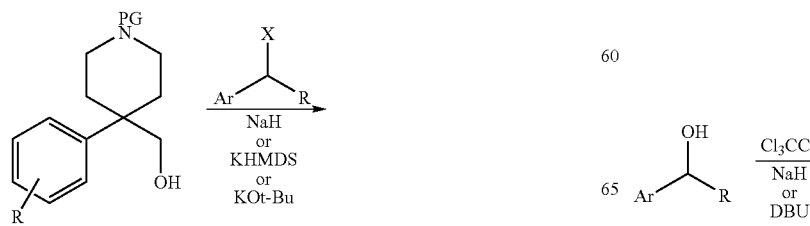
Scheme 4.
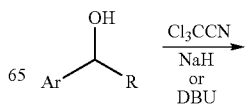

7
-continued
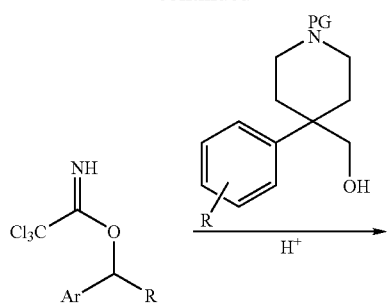
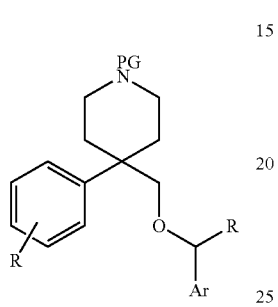
Scheme 5.
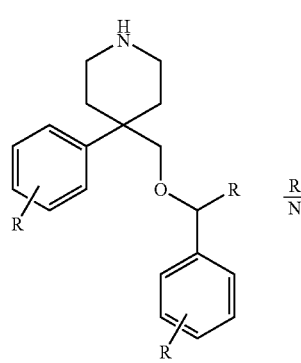
8
Scheme 6.
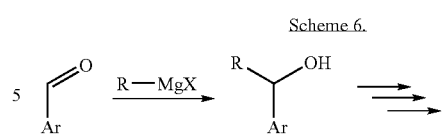
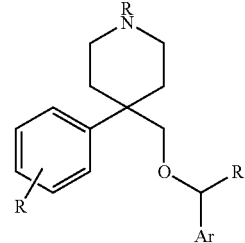
Scheme 7.
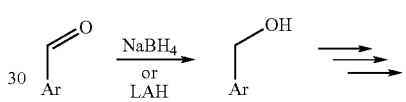
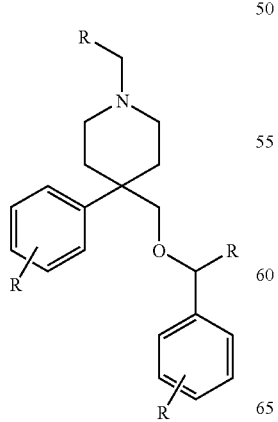
Scheme 8.
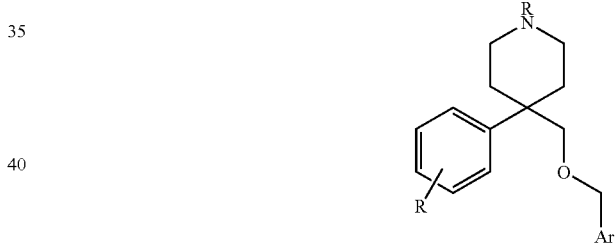
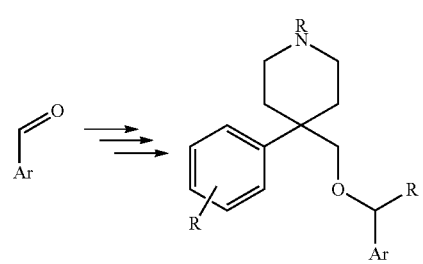

Scheme 9.
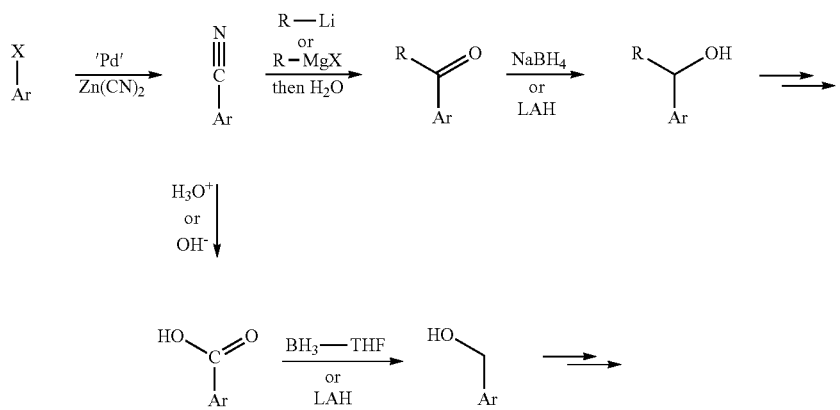
Scheme 10.
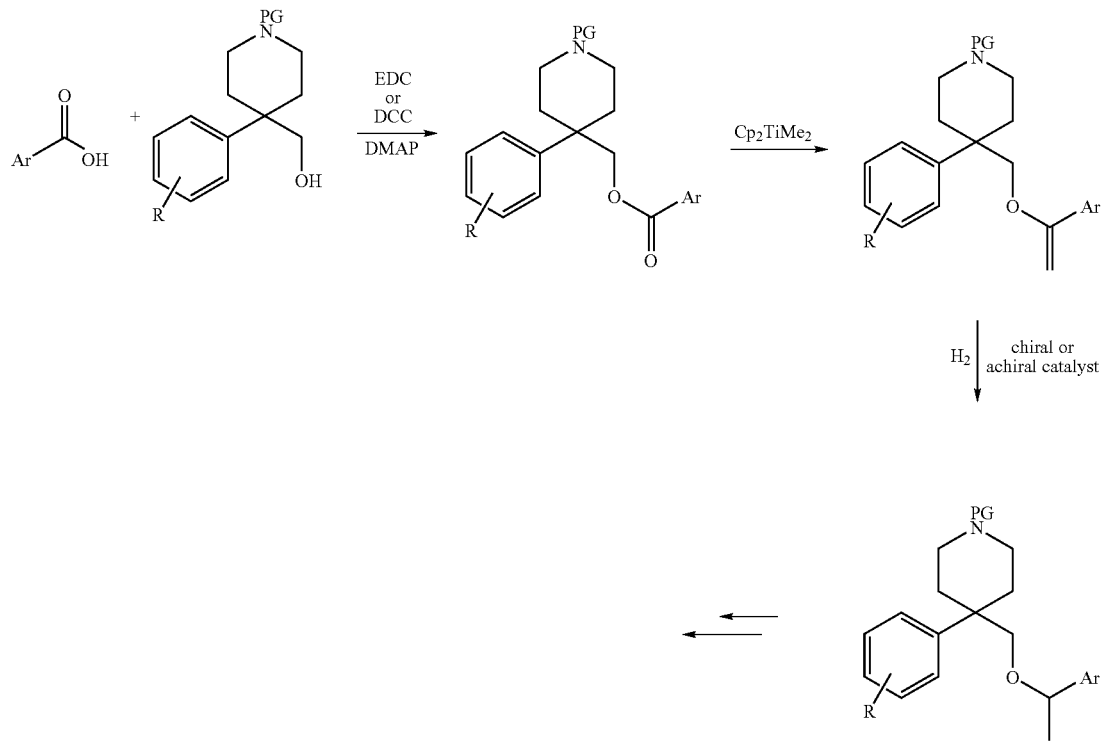
Scheme 11.
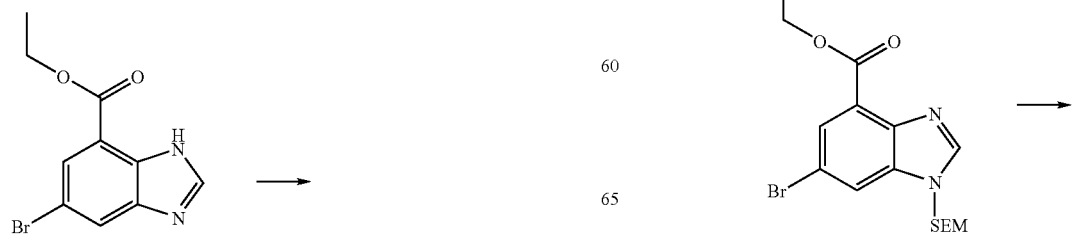

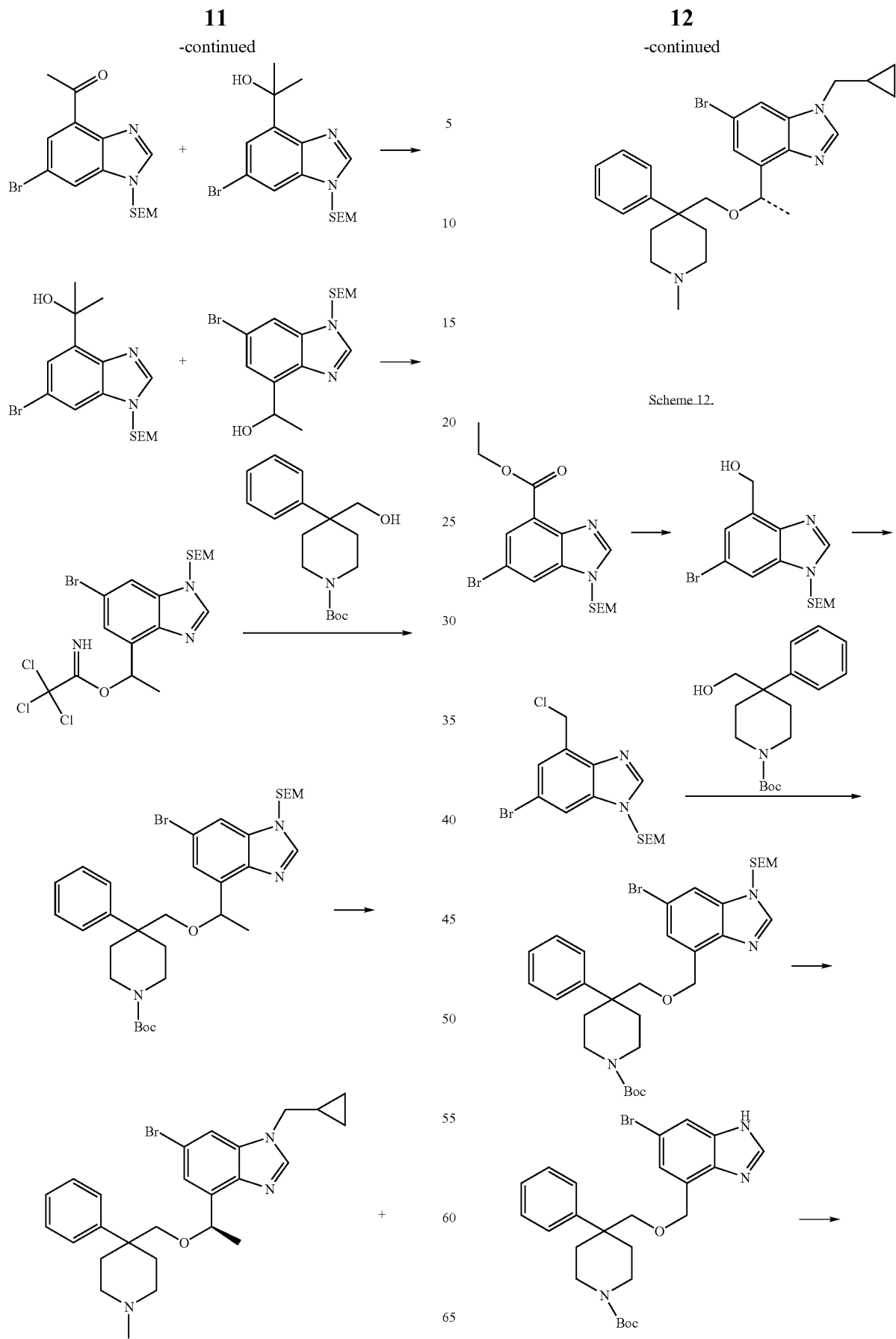

-continued

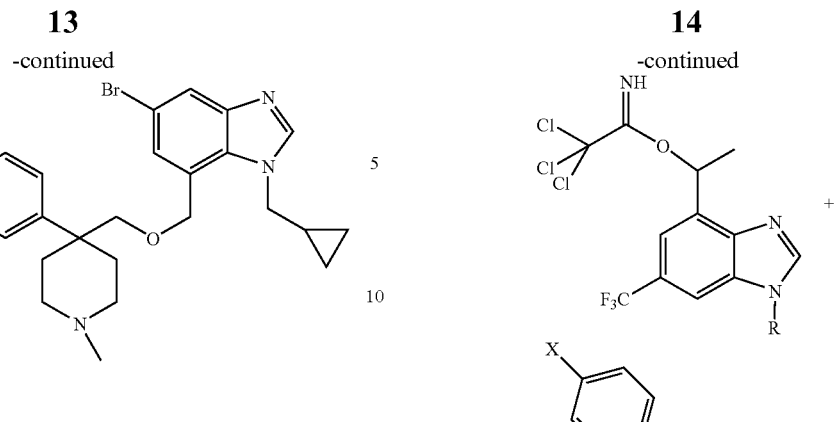

Scheme 13.

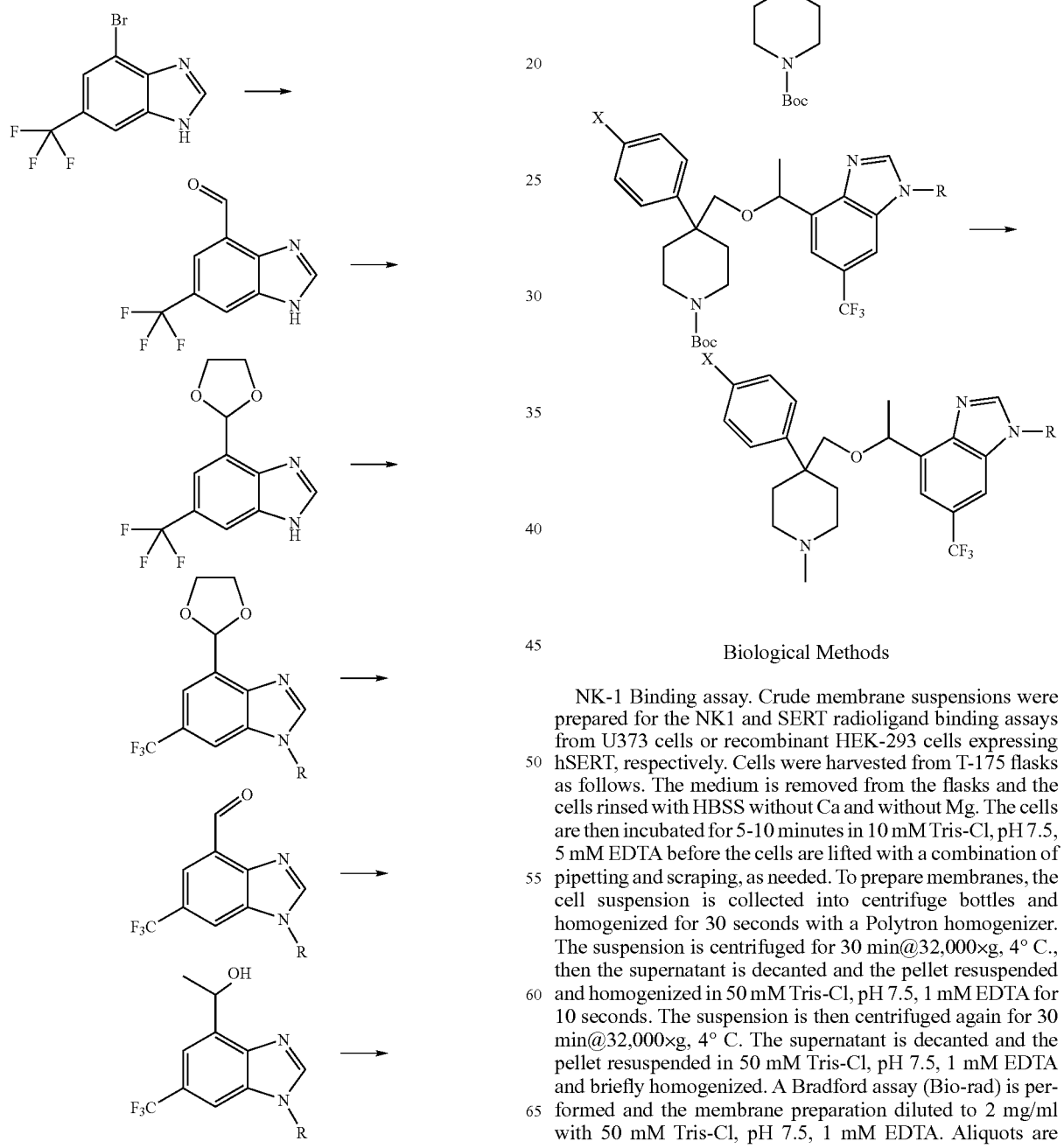

Biological Methods

NK-1 Binding assay. Crude membrane suspensions were prepared for the NK1 and SERT radioligand binding assays from U373 cells or recombinant HEK-293 cells expressing hSERT, respectively. Cells were harvested from T-175 flasks as follows. The medium is removed from the flasks and the cells rinsed with HBSS without Ca and without Mg. The cells are then incubated for 5-10 minutes in 10 mM Tris-Cl, pH 7.5, 5 mM EDTA before the cells are lifted with a combination of pipetting and scraping, as needed. To prepare membranes, the cell suspension is collected into centrifuge bottles and homogenized for 30 seconds with a Polytron homogenizer. The suspension is centrifuged for 30 min@32,000×g, 4° C., then the supernatant is decanted and the pellet resuspended and homogenized in 50 mM Tris-Cl, pH 7.5, 1 mM EDTA for 10 seconds. The suspension is then centrifuged again for 30 min@32,000×g, 4° C. The supernatant is decanted and the pellet resuspended in 50 mM Tris-Cl, pH 7.5, 1 mM EDTA and briefly homogenized. A Bradford assay (Bio-rad) is performed and the membrane preparation diluted to 2 mg/ml with 50 mM Tris-Cl, pH 7.5, 1 mM EDTA. Aliquots are prepared, and then frozen and stored at −80° C.

NK1 radioligand binding assay. Compounds are dissolved in 100% DMSO at a concentration 100× the desired highest assay concentration, serially diluted 1:3 in 100% DMSO, and 0.6 ul/well of each solution is dispensed to a Nunc polypropylene, round bottom, 384 well plate. 100% inhibition is defined with 0.6 ul/well of 1 mM L-733,060 (Sigma L-137) dissolved in DMSO. 30 ul/well of a 2×U373 membrane preparation (267 ug/ml in 100 mM Tris-Cl, pH 7.5, 6 mM $MgCl_2$, 0.2% (v/v) Sigma mammalian protease inhibitor cocktail (Sigma P-8340), and 4 ug/ml chymostatin, Sigma C-7268) and 30 ul/well of a 2× radioligand solution (400 pM [$^{125}$I]Substance P (Perkin ElmerNEX-190) in 1% (w/v) BSA (Sigma A-2153), 0.1 mg/ml bacitracin, Sigma B-0125) are added to the well and the reaction incubated for 1 hour at room temperature. The contents of the assay plate are then transferred to a Millipore Multiscreen$_{HTS}$ GF/B filter plate which has been pretreated with 0.5% PEI for at least one hour. The plate is vacuum filtered and washed with 7 washes of 100 ul/well of 20 mM Tris-Cl, pH 7.5, 0.5% (w/v) BSA chilled to 4° C. The filtration and washing is completed in less than 90 s. The plates are air-dried overnight, 12 ul/well of MicroScint scintillation fluid added, and the plates counted in a Trilux.

SERT radioligand binding assay. Compounds are dissolved in 100% DMSO at a concentration 100× the desired highest assay concentration, serially diluted 1:3 in 100% DMSO, and 0.4 ul/well of each solution is dispensed to a Nunc polypropylene, round bottom, 384 well plate. 100% inhibition is defined with 0.4 ul/well of 1 mM fluoxetine (Sigma F-132) dissolved in DMSO. 20 ul/well of a 2× HEK-hSERT membrane preparation (15 ug/ml in 50 mM Tris-Cl, pH 7.5, 120 mM NaCl, 5mM KCl) and 20 ul/well of a 2× radioligand solution (520 pM [$^{125}$I]RTI-55 (Perkin-Elmer NEX-272) in 50 mM Tris-Cl, pH 7.5, 120 mM NaCl, 5mM KCl) are added to each well and the reaction incubated for 1 hour at room temperature. The contents of the assay plate are then transferred to a Millipore MultiscreenHTs GF/B filter plate which has been pretreated with 0.5% PEI for at least one hour. The plate is vacuum filtered and washed with 7 washes of 100 ul/well of 50 mM Tris-Cl, pH 7.5, 120 mM NaCl, 5 mM KCl chilled to 4° C. The filtration and washing is completed in less than 90 s. The plates are air-dried overnight, 12 ul/well of MicroScint scintillation fluid added, and the plates counted in a Trilux.

Data analysis. The raw data are normalized to percent inhibition using control wells defining 0% (DMSO only) and 100% (selective inhibitor) inhibition which are run on each plate. Each plate is run in triplicate, and the concentration response curve thus generated is fit using the four-parameter dose response equation, Y=Bottom+(Top-Bottom)/(1+10^((LogIC$_{50}$−X)*HillSlope)) in order to determine the IC$_{50}$ value for each compound. The radioligand concentration chosen for each assay corresponds to the $K_d$ concentration determined through saturation binding analysis for each assay. NK-1 and serotonin transporter binding results are shown in Table 1.

TABLE 1

| Example | Structure | NK-1 IC$_{50}$ (nM) | SERT IC$_{50}$ (nM) |
|---|---|---|---|
| 1 | 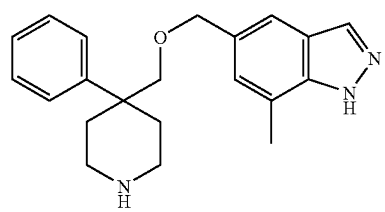 | C | A |
| 2 | 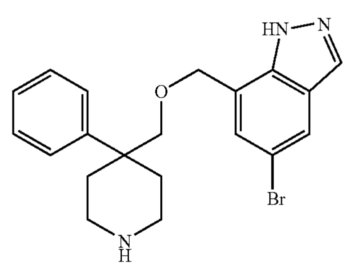 | A | A |
| 3 | 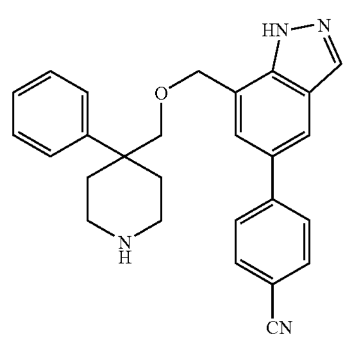 | A | A |

TABLE 1-continued

| Example | Structure | NK-1 IC$_{50}$ (nM) | SERT IC$_{50}$ (nM) |
|---------|-----------|---------------------|---------------------|
| 4 | 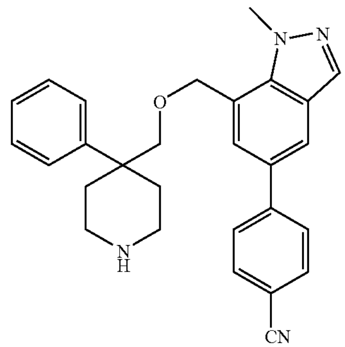 | B | A |
| 5 | 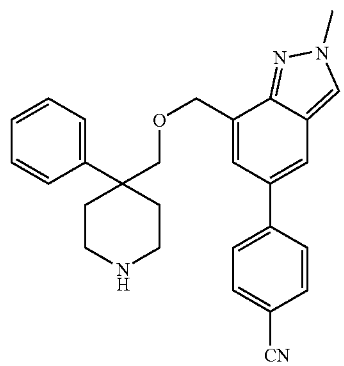 | C | A |
| 6 | 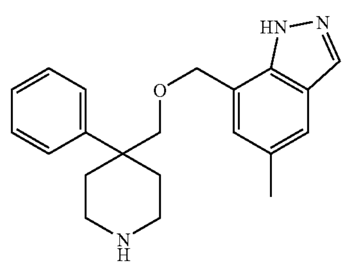 | A | A |
| 7 | 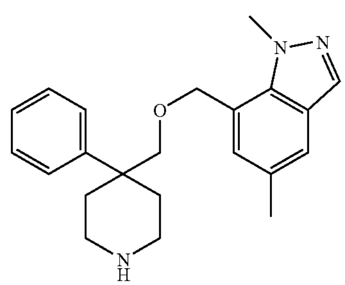 | A | A |
| 8 | 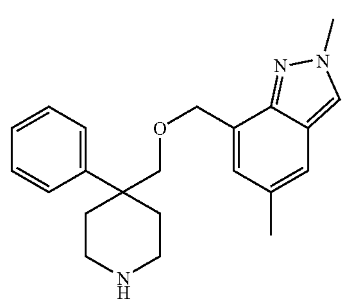 | A | A |

TABLE 1-continued
| Example | Structure | NK-1 IC$_{50}$ (nM) | SERT IC$_{50}$ (nM) |
|---|---|---|---|
| 9 | 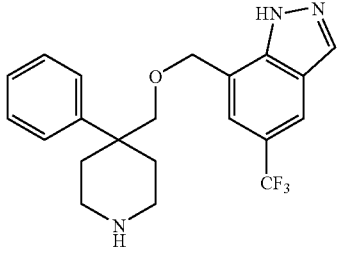 | A | A |
| 10 | 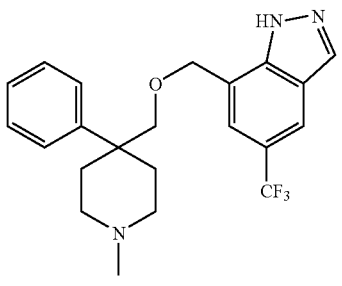 | A | A |
| 11 | 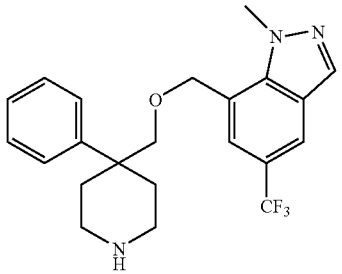 | A | A |
| 12 | 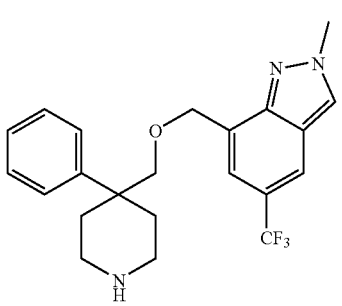 | A | A |
| 13 | 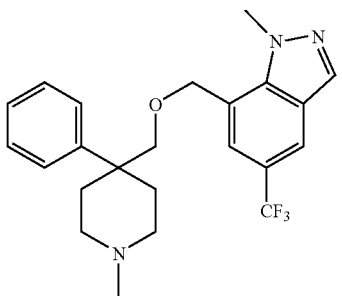 | A | A |

TABLE 1-continued

| Example | Structure | NK-1 IC$_{50}$ (nM) | SERT IC$_{50}$ (nM) |
|---|---|---|---|
| 14 | 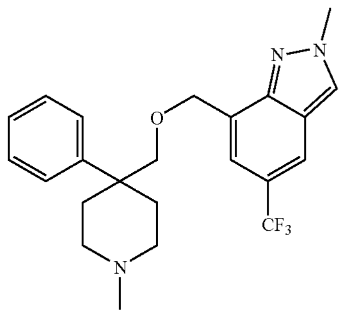 | A | A |
| 15 | 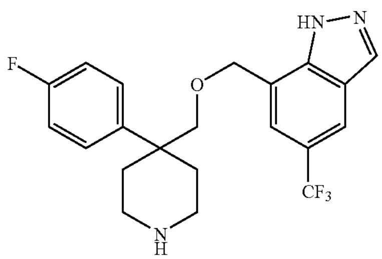 | A | A |
| 16 | 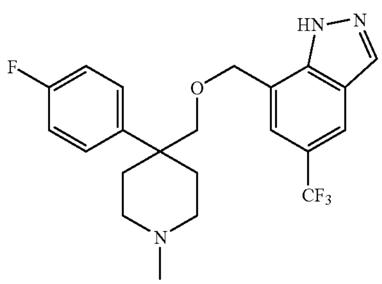 | A | A |
| 17 | 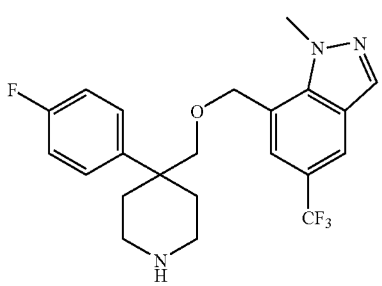 | A | A |
| 18 | 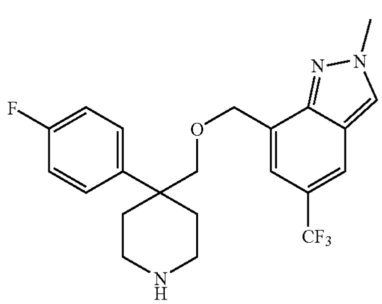 | A | A |

TABLE 1-continued

| Example | Structure | NK-1 IC$_{50}$ (nM) | SERT IC$_{50}$ (nM) |
|---|---|---|---|
| 19 | 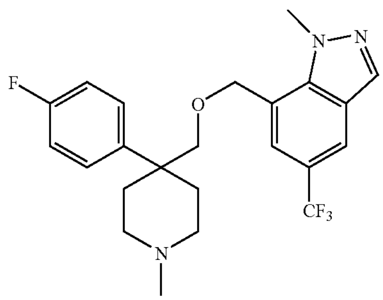 | A | A |
| 20 | 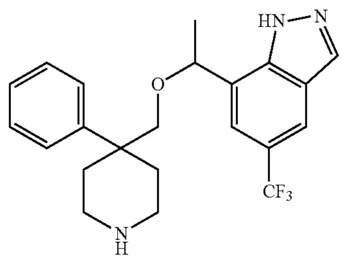 | A | A |
| 21 | 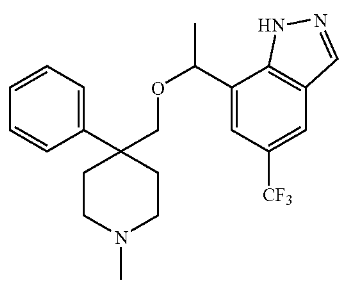 | A | A |
| 22 | 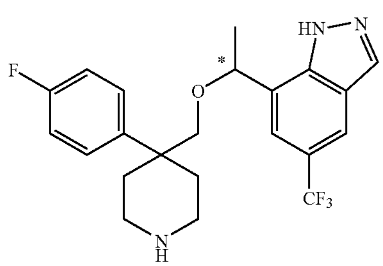 | B | A |
| 23 | 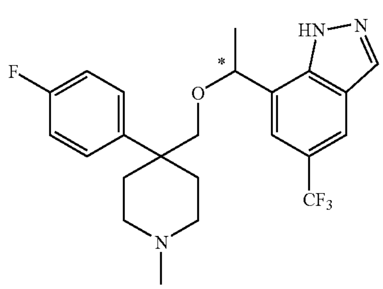 | B | A |

TABLE 1-continued

| Example | Structure | NK-1 IC$_{50}$ (nM) | SERT IC$_{50}$ (nM) |
|---|---|---|---|
| 24 | 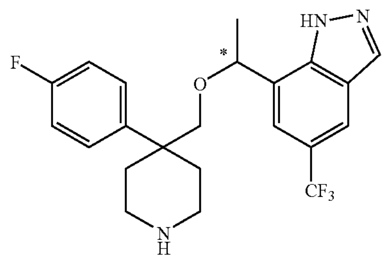 | A | A |
| 25 | 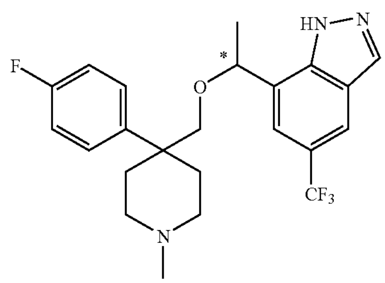 | A | A |
| 26 | 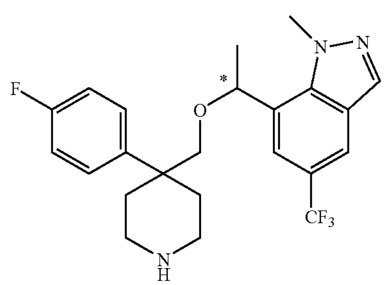 | B | A |
| 27 | 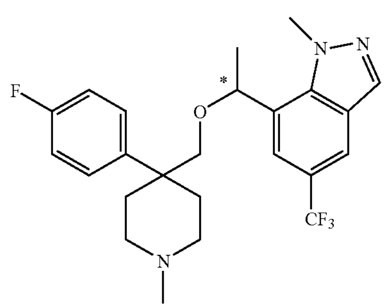 | B | A |
| 28 | 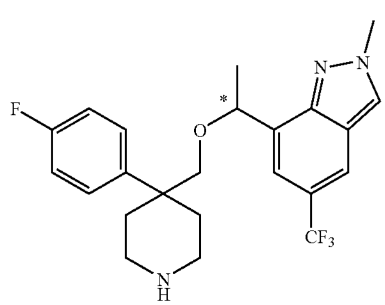 | C | B |

TABLE 1-continued

| Example | Structure | NK-1 IC$_{50}$ (nM) | SERT IC$_{50}$ (nM) |
|---|---|---|---|
| 29 | 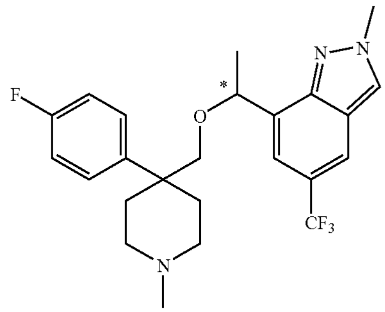 | C | A |
| 30 | 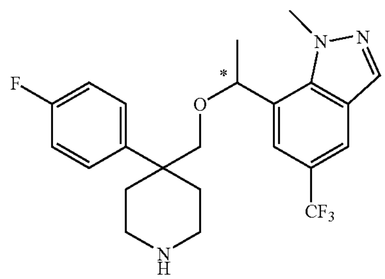 | A | A |
| 31 | 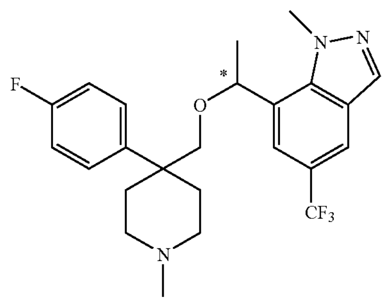 | A | A |
| 32 | 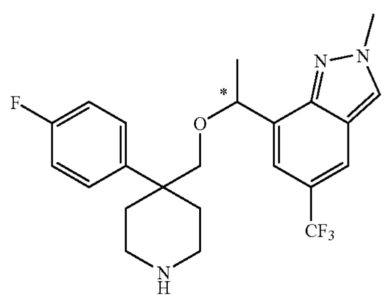 | A | A |
| 33 | 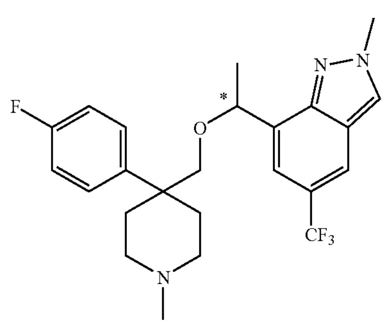 | A | A |

TABLE 1-continued

| Example | Structure | NK-1 IC$_{50}$ (nM) | SERT IC$_{50}$ (nM) |
|---|---|---|---|
| 34 | 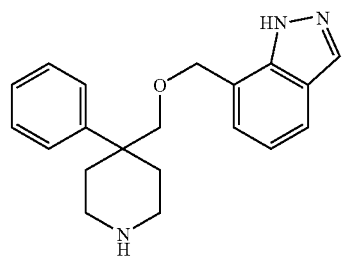 | B | A |
| 35 | 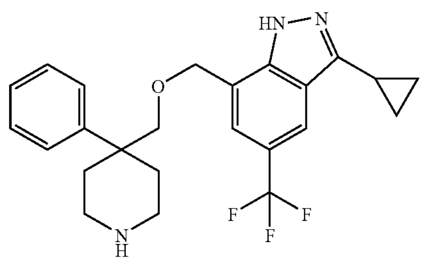 | A | A |
| 36 | 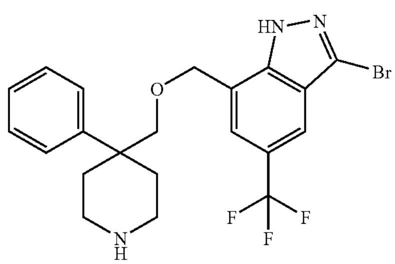 | A | A |
| 37 | 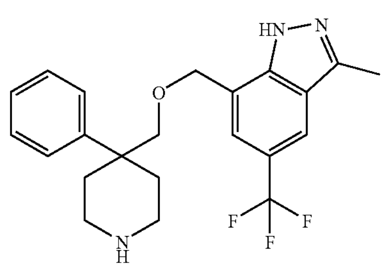 | A | A |
| 38 | 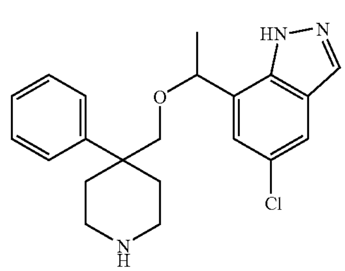 | A | A |

TABLE 1-continued
| Example | Structure | NK-1 IC$_{50}$ (nM) | SERT IC$_{50}$ (nM) |
|---|---|---|---|
| 39 | 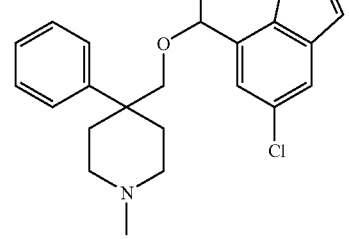 | A | A |
| 40 | 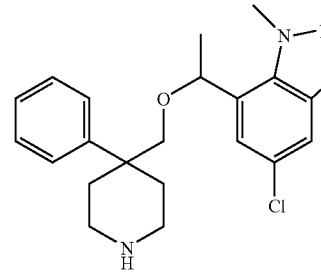 | A | A |
| 41 | 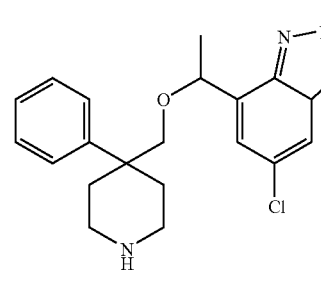 | A | A |
| 42 | 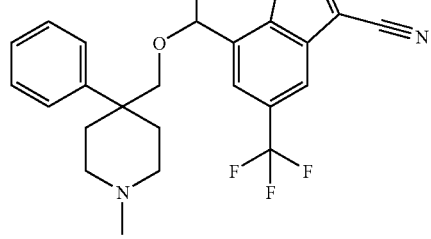 | A | B |
| 43 | 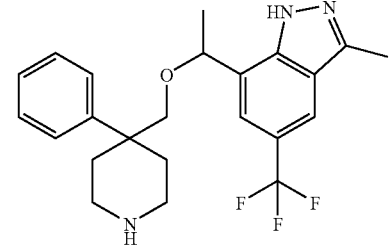 | A | A |

TABLE 1-continued

| Example | Structure | NK-1 IC$_{50}$ (nM) | SERT IC$_{50}$ (nM) |
|---|---|---|---|
| 44 | 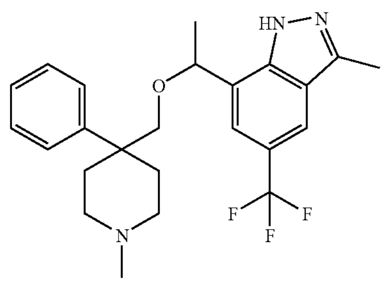 | A | A |
| 45 | 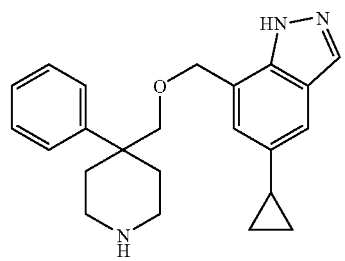 | A | A |
| 46 | 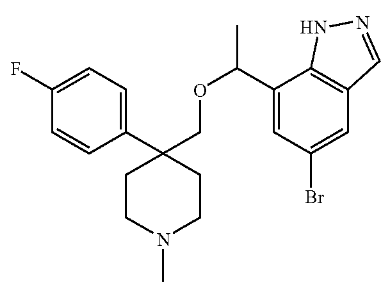 | A | A |
| 47 | 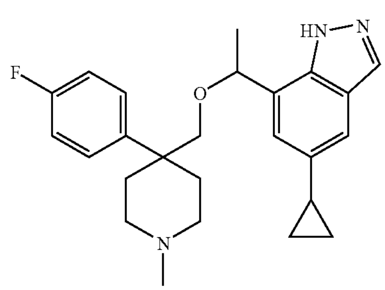 | A | A |
| 48 | 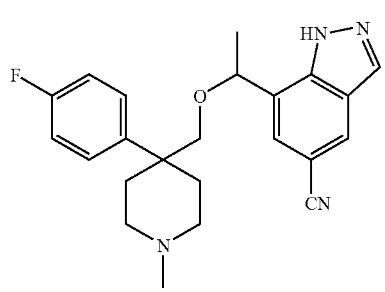 | A | A |

TABLE 1-continued

| Example | Structure | NK-1 IC$_{50}$ (nM) | SERT IC$_{50}$ (nM) |
|---|---|---|---|
| 49 | 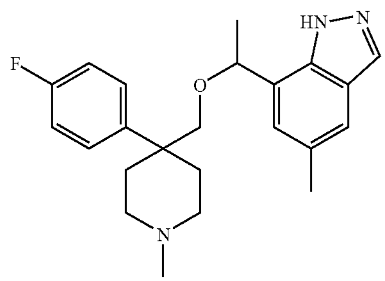 | A | A |
| 50 | 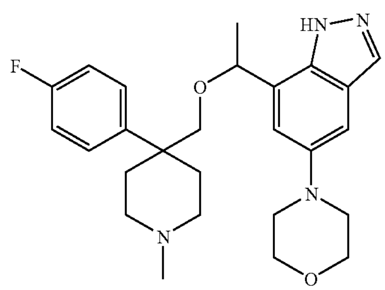 | B | A |
| 51 | 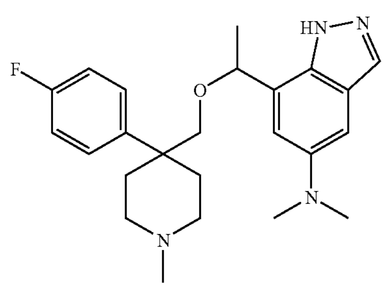 | A | A |
| 52 | 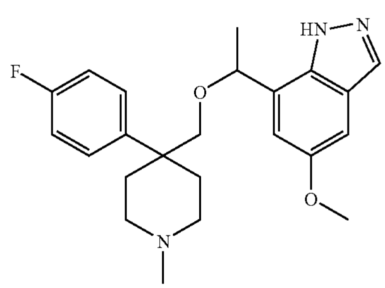 | A | A |
| 53 | 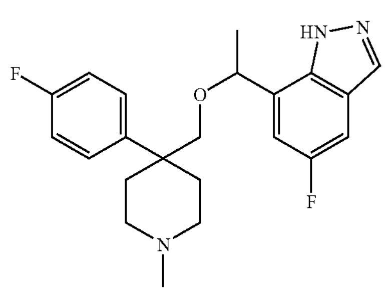 | A | A |

TABLE 1-continued
| Example | Structure | NK-1 IC$_{50}$ (nM) | SERT IC$_{50}$ (nM) |
|---|---|---|---|
| 54 | 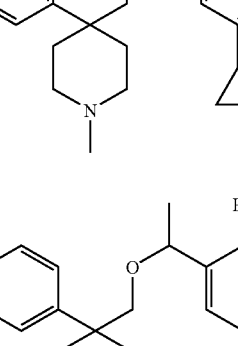 | A | A |
| 55 | 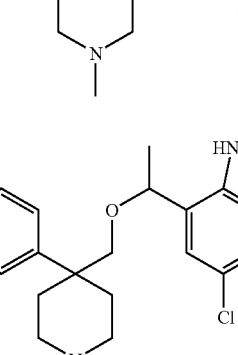 | A | A |
| 56 | 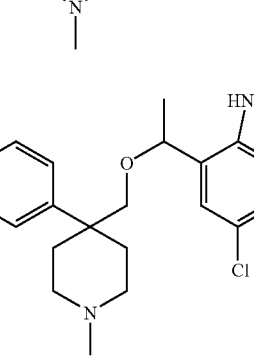 | A | A |
| 57 | 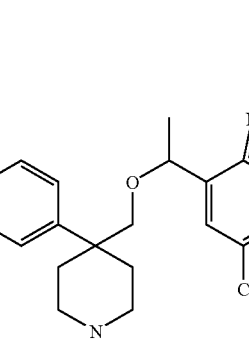 | A | A |
| 58 | 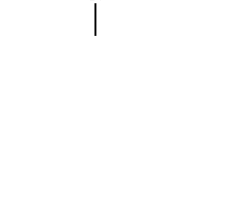 | A | A |

TABLE 1-continued
| Example | Structure | NK-1 IC$_{50}$ (nM) | SERT IC$_{50}$ (nM) |
|---|---|---|---|
| 59 | 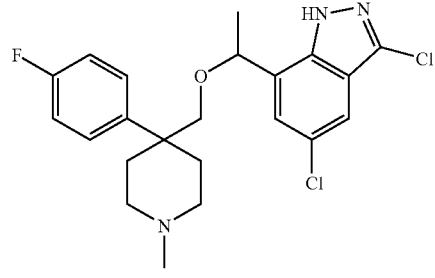 | A | A |
| 60 | 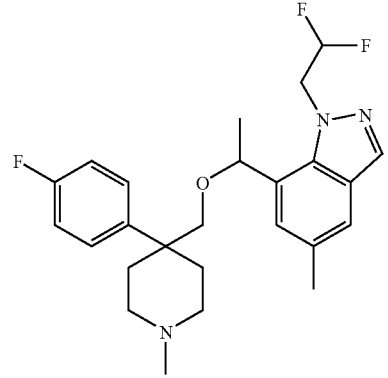 | A | A |
| 61 | 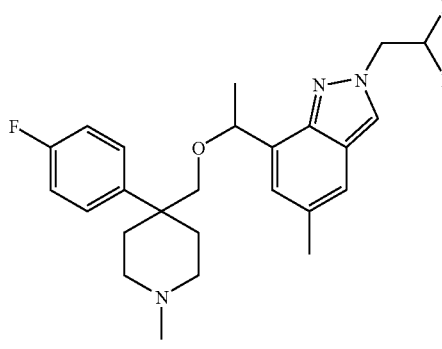 | A | A |
| 62 | 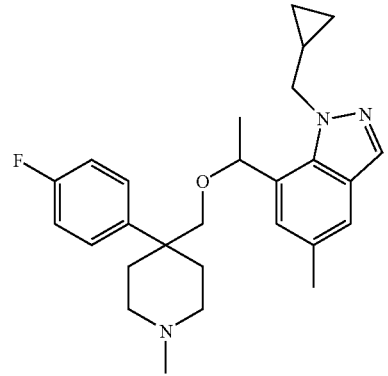 | A | A |

TABLE 1-continued
| Example | Structure | NK-1 IC$_{50}$ (nM) | SERT IC$_{50}$ (nM) |
|---|---|---|---|
| 63 | 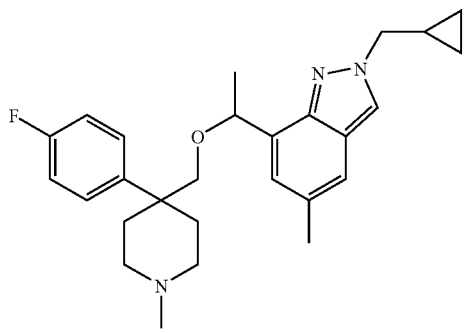 | A | A |
| 64 | 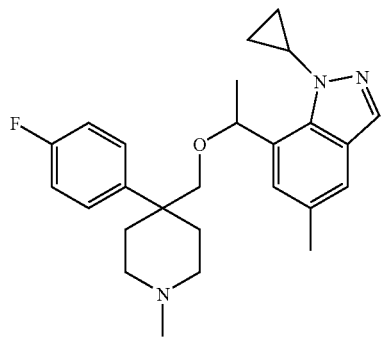 | A | A |
| 65 | 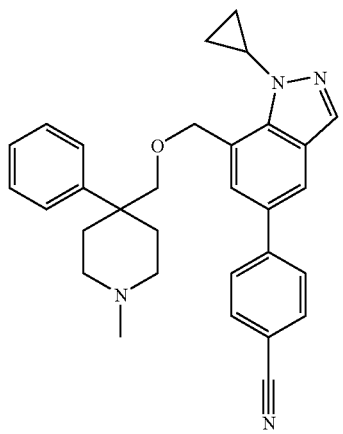 | B | A |
| 66 | 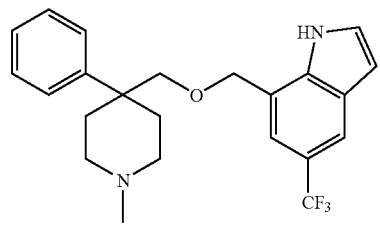 | A | A |

TABLE 1-continued

| Example | Structure | NK-1 IC$_{50}$ (nM) | SERT IC$_{50}$ (nM) |
|---------|-----------|---------------------|----------------------|
| 67 | 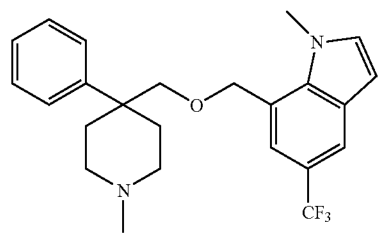 | A | A |
| 68 | 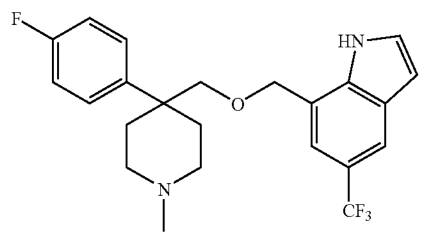 | A | A |
| 69 | 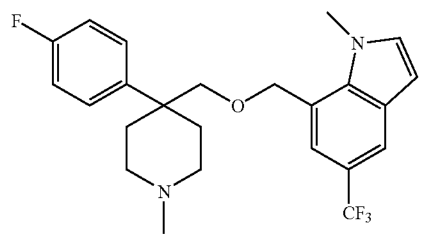 | A | A |
| 70 | 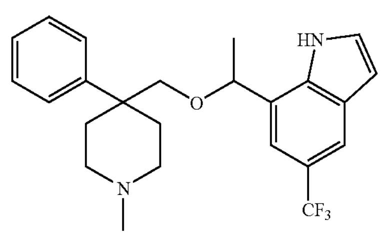 | A | B |
| 71 | 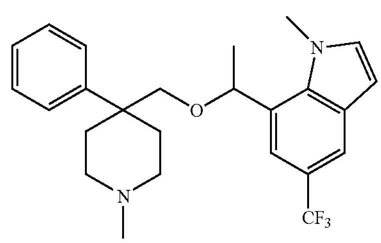 | A | A |
| 72 | 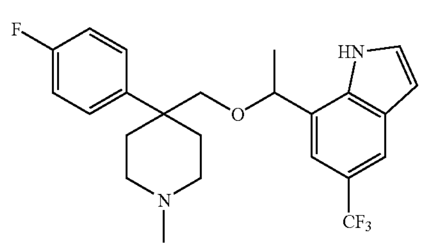 | A | A |

TABLE 1-continued

| Example | Structure | NK-1 IC$_{50}$ (nM) | SERT IC$_{50}$ (nM) |
|---|---|---|---|
| 73 | 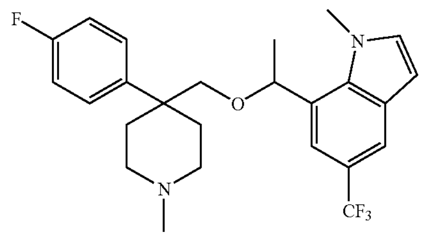 | A | A |
| 74 | 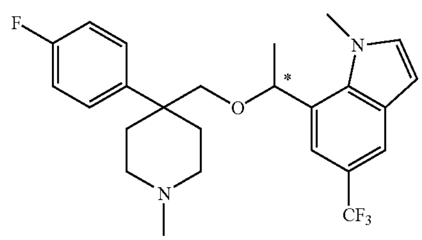 | C | B |
| 75 | 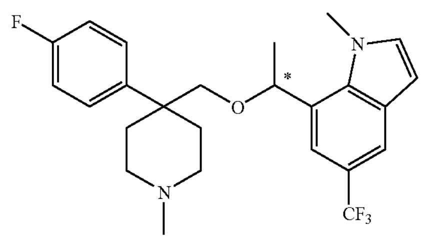 | A | A |
| 76 | 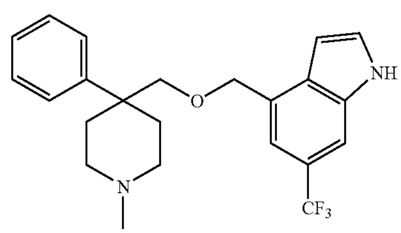 | A | A |
| 77 | 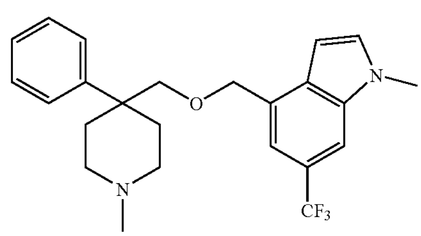 | A | A |
| 78 | 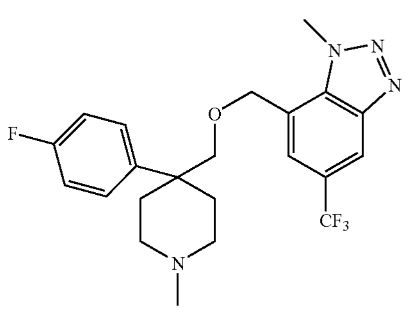 | B | A |

TABLE 1-continued

| Example | Structure | NK-1 IC$_{50}$ (nM) | SERT IC$_{50}$ (nM) |
|---------|-----------|---------------------|---------------------|
| 79 | 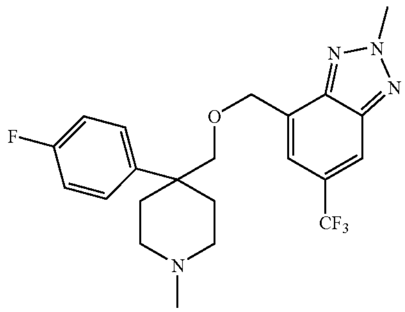 | A | A |
| 80 | 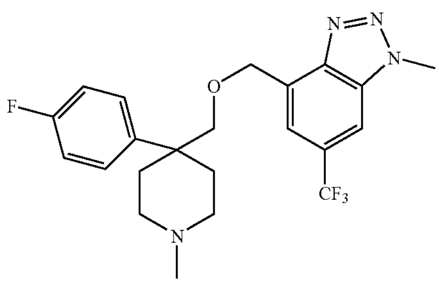 | B | A |
| 81 | 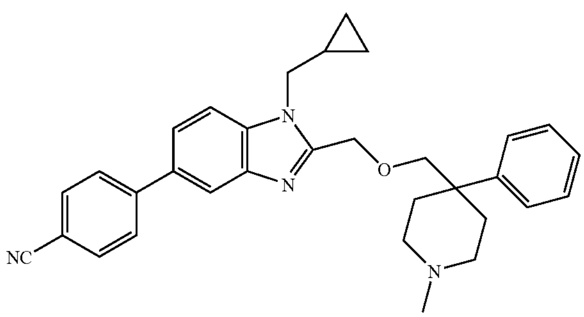 | C | A |
| 82 | 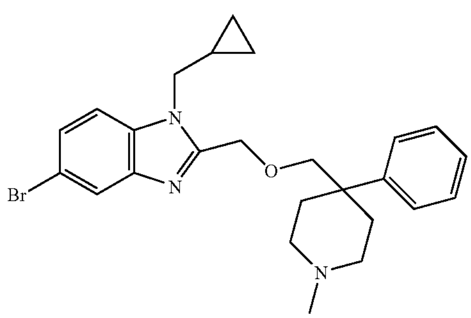 | C | A |
| 83 | 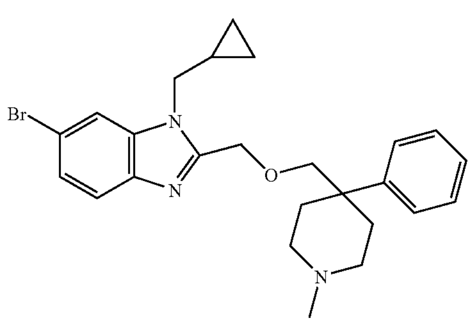 | C | A |

TABLE 1-continued

| Example | Structure | NK-1 IC$_{50}$ (nM) | SERT IC$_{50}$ (nM) |
|---|---|---|---|
| 84 | 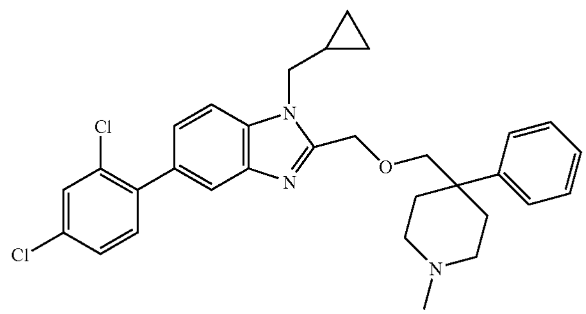 | C | A |
| 85 | 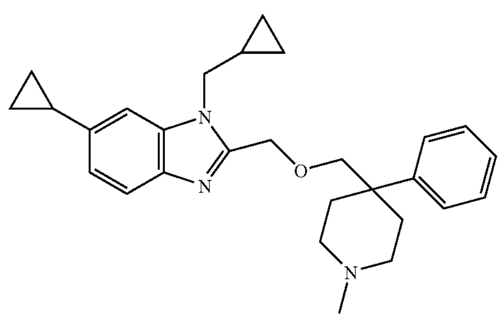 | C | A |
| 86 | 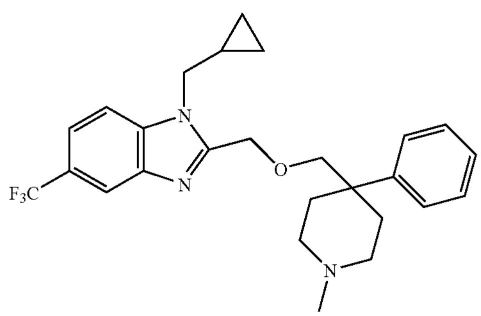 | C | A |
| 87 | 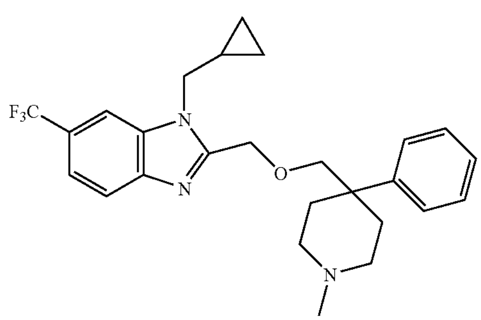 | C | A |
| 88 | 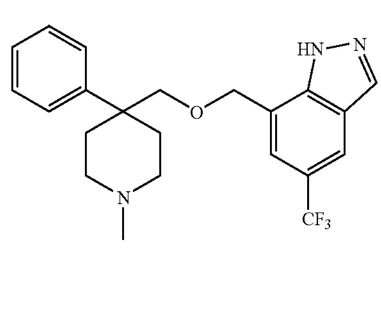 | B | A |

TABLE 1-continued

| Example | Structure | NK-1 IC$_{50}$ (nM) | SERT IC$_{50}$ (nM) |
|---|---|---|---|
| 89 | 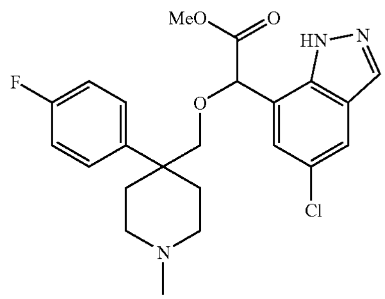 | C | A |
| 90 | 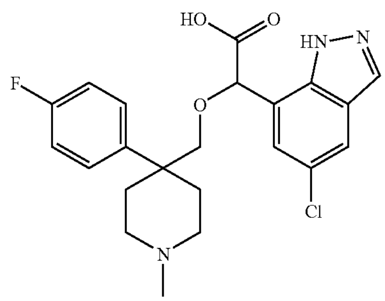 | C | A |
| 91 | 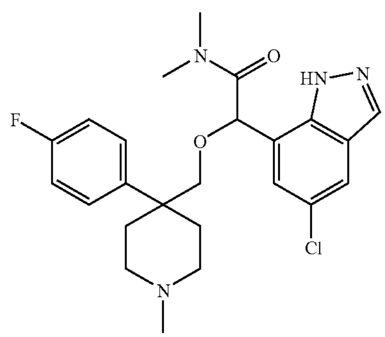 | C | A |
| 92 | 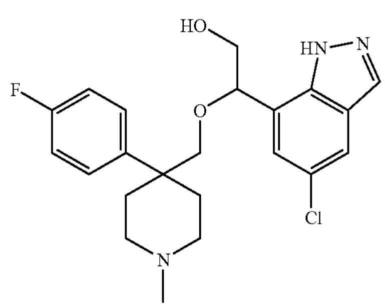 | A | A |
| 93 | 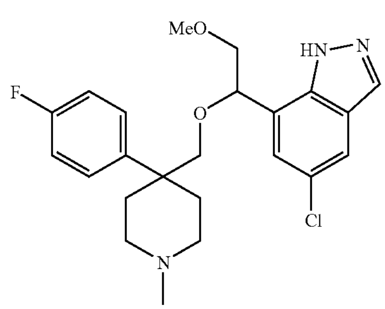 | A | A |

TABLE 1-continued

| Example | Structure | NK-1 IC$_{50}$ (nM) | SERT IC$_{50}$ (nM) |
|---|---|---|---|
| 94 | 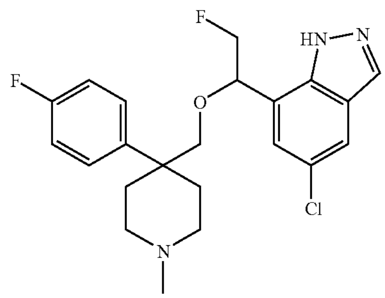 | A | A |
| 95 | 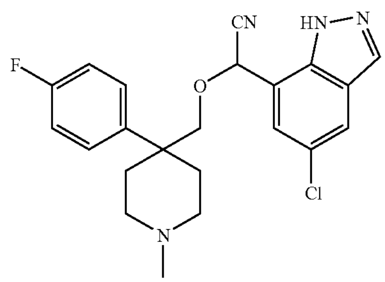 | A | A |
| 96 | 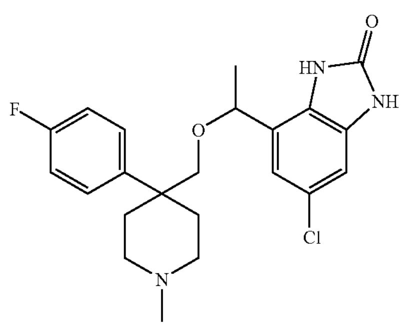 | B | A |
| 97 | 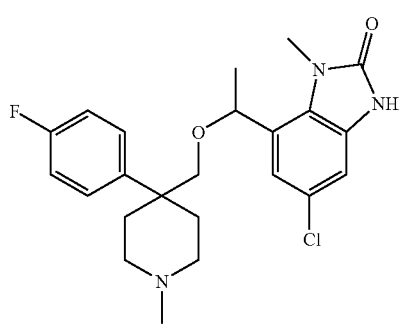 | B | A |
| 98 | 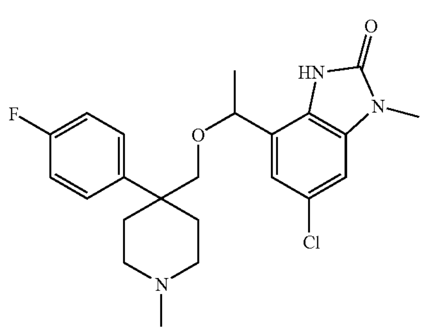 | A | A |

TABLE 1-continued

| Example | Structure | NK-1 IC$_{50}$ (nM) | SERT IC$_{50}$ (nM) |
|---|---|---|---|
| 99 | 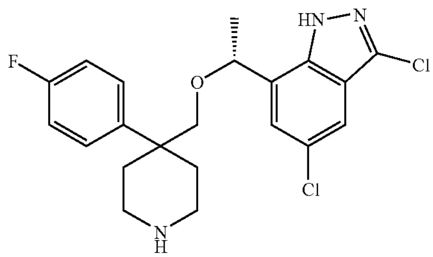 | A | A |
| 100 | 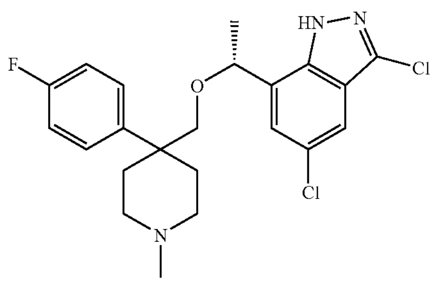 | A | A |
| 101 | 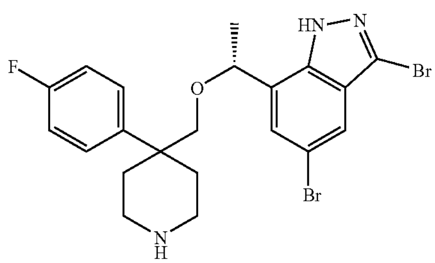 | A | A |
| 102 | 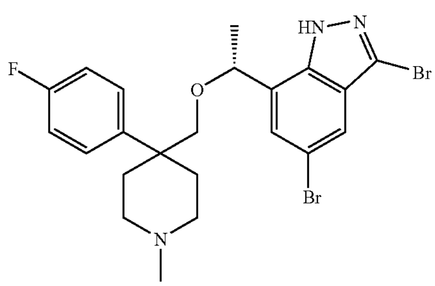 | A | A |
| 103 | 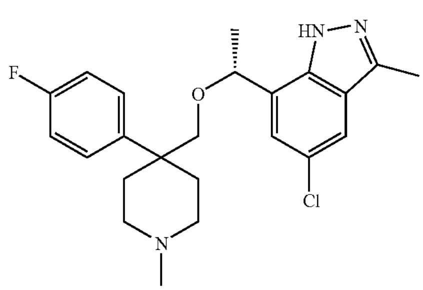 | A | A |

TABLE 1-continued
| Example | Structure | NK-1 IC$_{50}$ (nM) | SERT IC$_{50}$ (nM) |
|---|---|---|---|
| 104 | 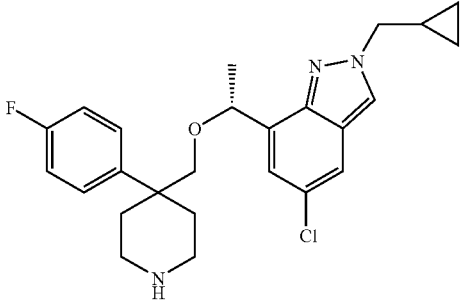 | A | A |
| 105 | 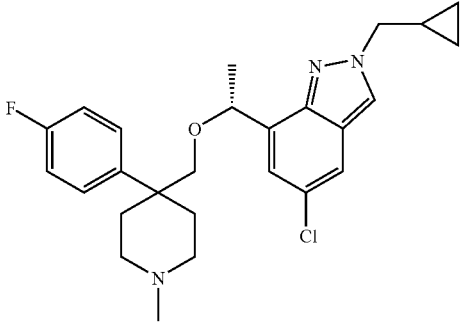 | A | A |
| 106 | 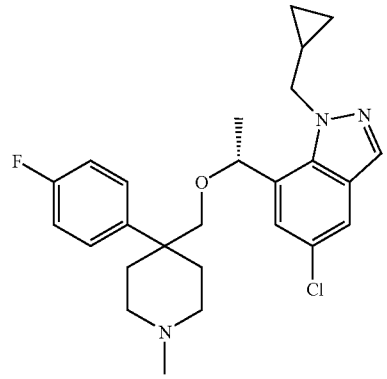 | A | A |
| 107 | 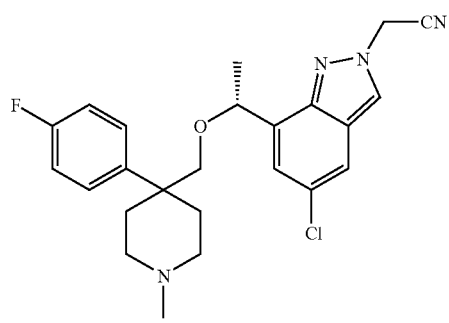 | A | A |

TABLE 1-continued
| Example | Structure | NK-1 IC$_{50}$ (nM) | SERT IC$_{50}$ (nM) |
|---|---|---|---|
| 108 | 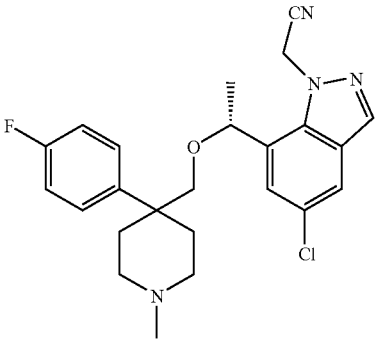 | A | A |
| 109 | 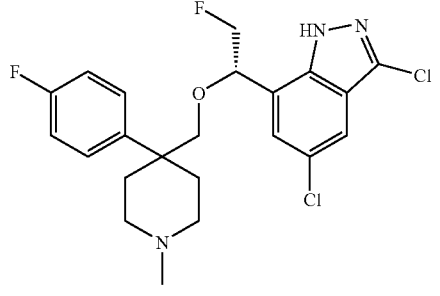 | A | A |
| 110 | 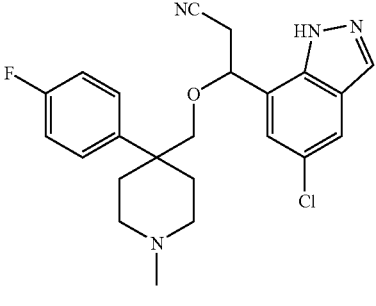 | A | A |
| 111 | 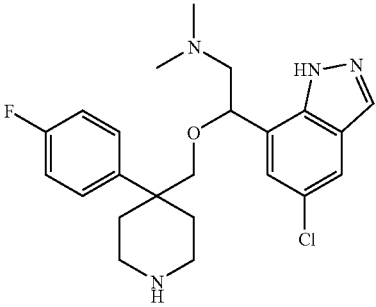 | C | A |

TABLE 1-continued

| Example | Structure | NK-1 IC$_{50}$ (nM) | SERT IC$_{50}$ (nM) |
|---|---|---|---|
| 112 | 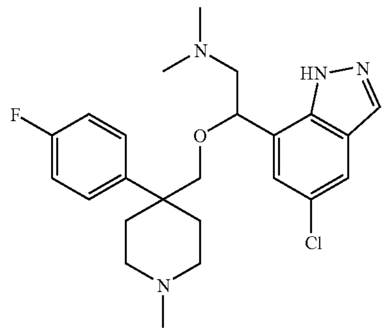 | C | B |
| 113 | 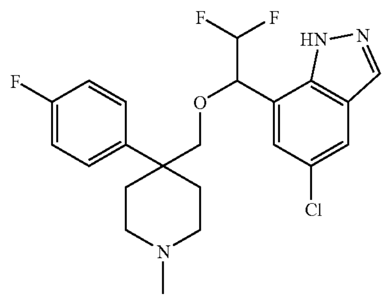 | A | A |
| 114 | 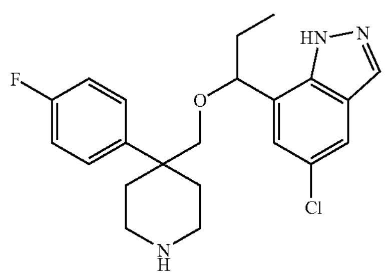 | A | A |
| 115 | 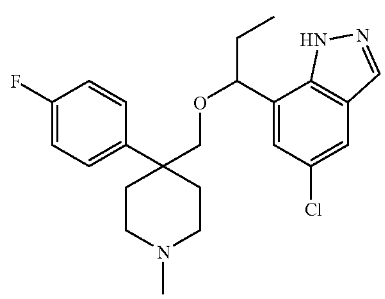 | A | A |
| 116 | 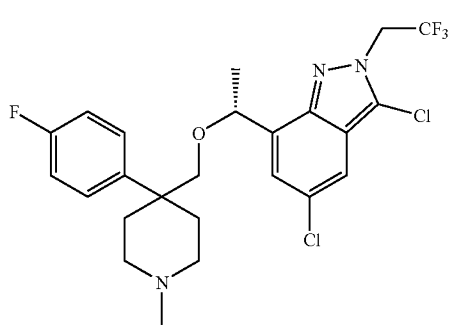 | A | A |

TABLE 1-continued
| Example | Structure | NK-1 IC$_{50}$ (nM) | SERT IC$_{50}$ (nM) |
|---|---|---|---|
| 117 | 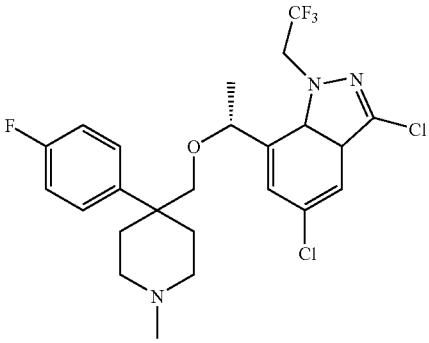 | A | A |
| 118 | 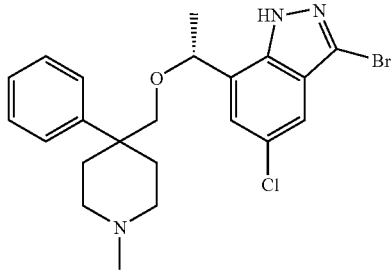 | A | A |
| 119 | 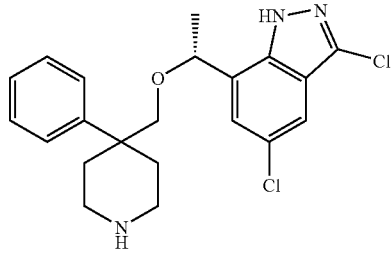 | A | A |
| 120 | 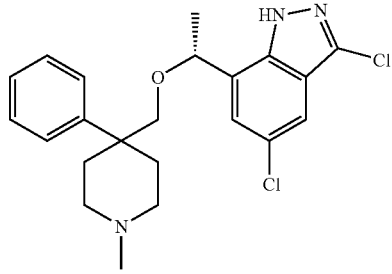 | A | A |
| 121 | 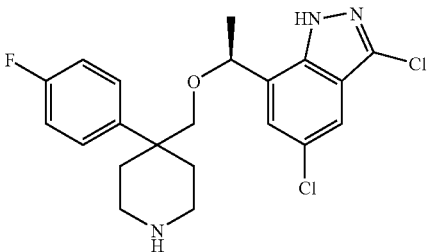 | C | A |

TABLE 1-continued

| Example | Structure | NK-1 IC$_{50}$ (nM) | SERT IC$_{50}$ (nM) |
|---|---|---|---|
| 122 | 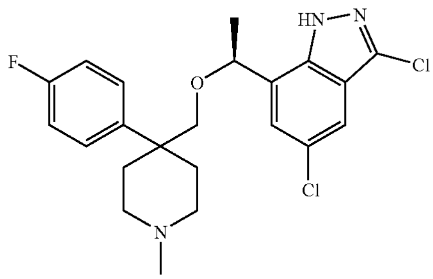 | C | A |
| 123 | 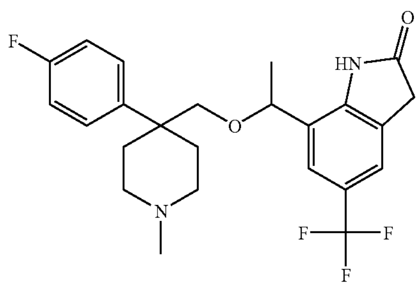 | A | A |
| 124 | 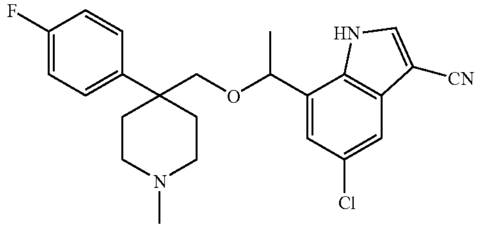 | A | A |
| 125 | 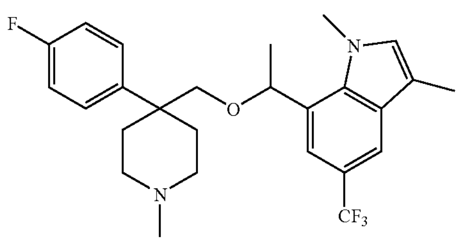 | A | A |
| 126 | 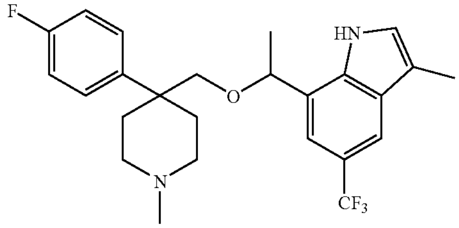 | A | A |
| 127 | 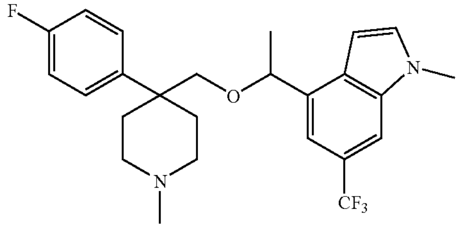 | A | A |

TABLE 1-continued
| Example | Structure | NK-1 IC$_{50}$ (nM) | SERT IC$_{50}$ (nM) |
|---|---|---|---|
| 128 | 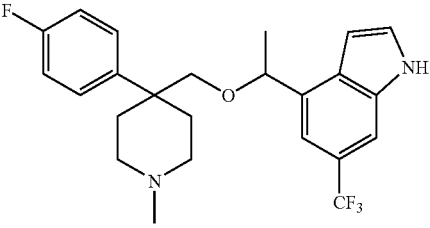 | A | A |
| 129 | 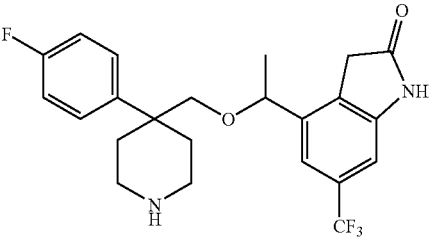 | B | A |
| 130 | 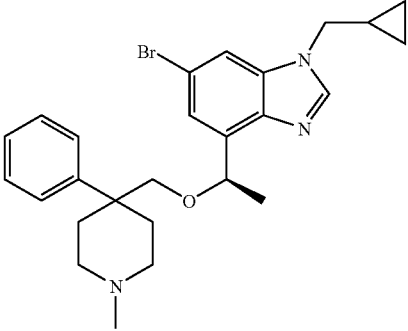 | C | A |
| 131 | 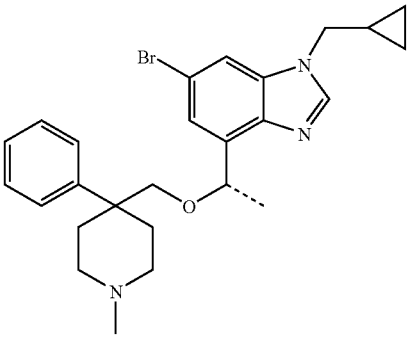 | A | A |
| 132 | 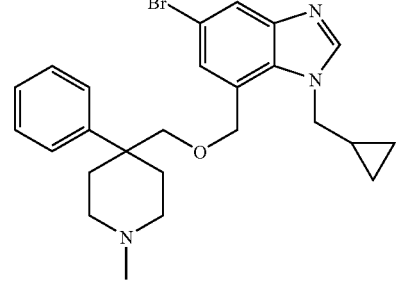 | A | A |

TABLE 1-continued
| Example | Structure | NK-1 IC$_{50}$ (nM) | SERT IC$_{50}$ (nM) |
|---|---|---|---|
| 133 | 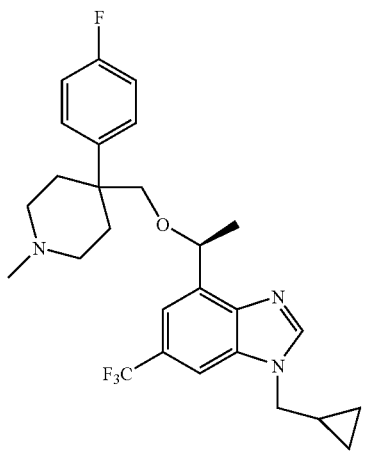 | C | A |
| 134 | 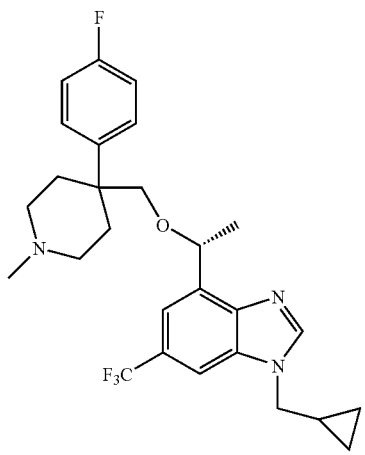 | A | A |
| 135 | 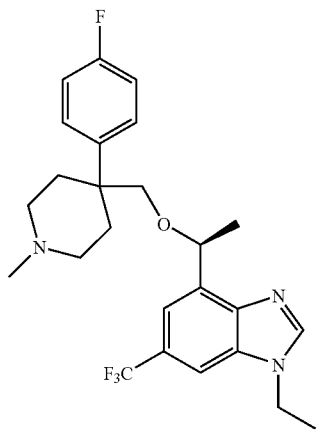 | C | A |

TABLE 1-continued

| Example | Structure | NK-1 IC$_{50}$ (nM) | SERT IC$_{50}$ (nM) |
|---|---|---|---|
| 136 | 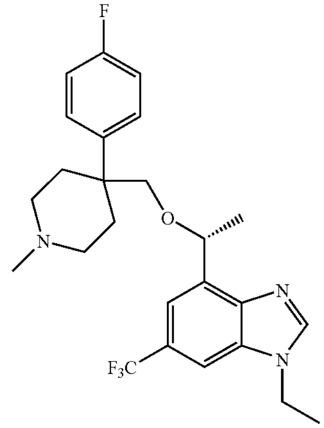 | A | A |
| 137 | 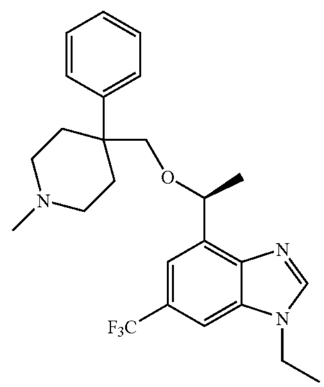 | B | A |
| 138 | 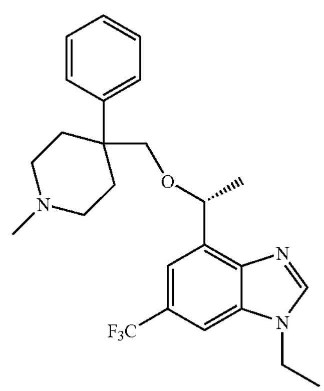 | A | A |

Values:
A = 0.01-100 nM;
B = 100-300 nM;
C >300 nM.

Pharmaceutical Composition and Methods of Use

The compounds of Formula I demonstrate inhibition of neurokinin-1 or serotonin reuptake or both. Inhibition of these receptors correlates with efficacy for affective disorders such as anxiety, depression, obsessive compulsive disorder, bulimia, and panic disorder. As such, the compounds of Formula I can be useful for the treatment of these disorders and other aspects of the invention are compositions and methods of using the compounds to treat these conditions and other conditions associated with aberrant levels of tachykinins or serotonin or both.

The compounds of this invention are generally given as pharmaceutical compositions comprised of a therapeutically effective amount of a compound of Formula I, or a pharmaceutically acceptable salt, and a pharmaceutically acceptable carrier and may contain conventional expients. A therapeutically effective amount is the amount needed to provide a meaningful patient benefit as determined by practitioners in that art. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques and conventional excipients (such as binding and wetting agents) and vehicles (such as water and alcohols).

Solid compositions are normally formulated in dosage units providing from about 1 to about 1000 mg of the active ingredient per dose. Some examples of solid dosage units are 1 mg, 10 mg, 100 mg, 250 mg, 500 mg, and 1000 mg. Liquid compositions are generally in a unit dosage range of 1-100 mg/mL. Some examples of liquid dosage units are 1 mg/mL, 10 mg/mL, 25 mg/mL, 50 mg/mL, and 100 mg/mL. Generally, the dosage unit will be in a unit range similar to agents of that class used clinically, for example fluoxetine.

The invention encompasses all conventional modes of administration; oral and parenteral methods are preferred. Generally, the dosing regimen will be similar to agents of that class used clinically, for example fluoxetine. Typically, the daily dose will be 0.01-100 mg/kg body weight daily. Generally, more compound is required orally and less parenterally. The specific dosing regime, however, should be determined by a physician using sound medical judgement.

Tachykinin and serotonin modulators are associated with depression. Accordingly, another aspect of the invention are methods for treating depressive disorders including Major Depressive Disorders (MDD), bipolar depression, unipolar depression, single or recurrent major depressive episodes, recurrent brief depression, catatonic features, melancholic features including feeding disorders, such as anorexia, weight loss, atypical features, anxious depression, or postpartum onset. Other central nervous system disorders encompassed within the term MDD include neurotic depression, post-traumatic stress disorders (PTSD) and social phobia, with early or late onset dementia of the Alzheimer's type, with depressed mood, vascular dementia with depressed mood, mood disorders and tolerance induced by drugs such as alcohol, amphetamines, cocaine, inhalants, opioids, sedatives, anxiolytics and other substances, schizoaffective disorder of the depressed type, and adjustment disorder with depressed mood.

Tachykinin and serotonin modulators are also associated with the treatment or prevention of schizophrenic disorders. Accordingly, another aspect of the invention are methods for treating schizophrenic disorders including paranoid schizophrenia, disorganized schizophrenia, catatonic schizophrenia, undifferentiated schizophrenia, residual schizophrenia.

Tachykinin and serotonin modulators are also associated with the treatment or prevention of anxiety. Accordingly, another aspect of the invention are methods for treating anxiety disorders including panic disorders, agoraphobia, phobias, obsessive-compulsive disorder, stress disorders including post-traumatic stress disorders, generalized anxiety disorders, acute stress disorders and mixed anxiety-depression disorders.

Tachykinin and serotonin modulators are also associated with the treatment or prevention of cognitive disorders. Accordingly, another aspect of the invention are methods for treating cognitive disorders including dementia, and amnesia disorders. Tachykinin and serotonin modulators are also associated with the treatment or prevention of memory and cognition in healthy humans.

Tachykinin and serotonin modulators are also associated with use as analgesics. Accordingly, another aspect of the invention are methods for treating pain, including the treatment of traumatic pain such as postoperative pain, chronic pain such as arthritic pain such as occurring in osteo-, rheumatoid or psoriatic arthritis, neuropathic pain such as postherpetic neuralgia, trigeminal neuralgia, segmental or intercostal neuralgia, fibromyalgia, peripheral neuropathy, diabetic neuropathy, chemotherapy-induced neuropathy, AIDS-related neuropathy, various forms of headache such as migraine, acute or chronic tension headache, cluster headaches, maxillary sinus pain, cancer pain, pain of bodily origin, gastrointestinal pain, sport's injury pain, dysmennorrhoea, menstrual pain, meningitis, musculoskeletal pain, low back pain e.g. spinal stenosis, prolapsed disc, sciatica, angina, ankylosing spondyolitis, gout, burns, scar pain, itch and thalamic pain such as post stroke thalamic pain.

Tachykinin and serotonin modulators are also associated with the treatment or prevention of sleep disorders. Accordingly, another aspect of the invention are methods for treating sleep disorders including insomnia, sleep apnea, narcolepsy, and circadian rhymic disorders.

Tachykinin and serotonin modulators are also associated with the treatment or prevention of inflammation. Accordingly, another aspect of the invention are methods for treating inflammation, including the treatment of inflammation in asthma, influenza and chronic bronchitis, in the treatment of inflammatory diseases of the gastrointestinal tract such as Crohn's disease, ulcerative colitis, inflammatory bowel disease and non-steroidal anti-inflammatory drug induced damage, inflammatory diseases of the skin such as herpes and eczema, inflammatory diseases of the bladder such as cystitis and urge incontinence, and eye and dental inflammation.

Tachykinin and serotonin modulators are also associated with the treatment or prevention of allergic disorders. Accordingly, another aspect of the invention are methods for treating allergic disorders, in particular allergic disorders of the skin such as urticaria, and allergic disorders of the airways such as rhinitis.

Tachykinin and serotonin modulators are also associated with the treatment or prevention of emesis, nausea, retching and vomiting. Accordingly, another aspect of the invention are methods for treating these disorders.

Tachykinin and serotonin modulators are also associated with the treatment or prevention of premenstrual dysphoric disorder (PMDD), in chronic fatigue syndrome and multiple sclerosis. Accordingly, another aspect of the invention are methods for treating these disorders.

DESCRIPTION OF SPECIFIC EMBODIMENTS

The following experimental procedures describe the synthesis of some Formula I compounds. Standard chemistry conventions are used in the text unless otherwise noted. The experimental encompass reasonable variations known in the art. The following HPLC conditions may be used where indicated.

HPLC Method 1: Phenomenex C18 4.6×50 mm, A=90% $H_2O$/10% MeOH, B=90% MeOH/10% $H_2O$, Modifier 0.1% TFA, 0.00 min=0% B, 4.0 min=100% B, 5.0 min=100% B, Flow rate=4 mL/min.

HPLC Method 2: Phenomenex C18 4.6×50 mm, A=90% $H_2O$/10% MeOH, B=90% MeOH/10% $H_2O$, Modifier 0.1% TFA, 0.00 min=0% B, 3.0 min=100% B, 4.0 min=100% B, Flow rate=4 mL/min.

HPLC Method 3: Phenomenex C18 4.6×30 mm, A=90% H₂O/10% MeOH, B=90% MeOH/10% H₂O, Modifier 0.1% TFA, 0.00 min=0% B, 4.0 min=100% B, 5.0 min=100% B, Flow rate=4 mL/min.

HPLC method 4: Phenomenex Luna 3.0×50 mm, A=90% H₂O/10% MeOH, B=90% MeOH/10% H₂O, Modifier 0.1% TFA, 0.00 min=0% B, 4.0 min=100% B, Flow rate=4 mL/min.

HPLC Method 5: Phenomenex C18 4.6×50 mm, A=90% H₂O/10% MeOH, B=90% MeOH/10% H₂O, Modifier 0.1% TFA, 0.00 min=60% B, 4.0 min=100% B, 5.0 min=100% B, Flow rate=4 mL/min.

HPLC Method 6: Phenomenex C18 4.6×50 mm, A=90% H₂O/10% MeOH, B=90% MeOH/10% H₂O, Modifier 0.1% TFA, 0.00 min=50% B, 4.0 min=100% B, 5.0 min=100% B, Flow rate=4 mL/min.

HPLC Method 7: Phenomenex C18 4.6×50 mm, A=90% H₂O/10% MeOH, B=90% MeOH/10% H₂O, Modifier 0.1% TFA, 0.00 min=40% B, 4.0 min=100% B, 5.0 min=100% B, Flow rate=4 mL/min HPLC Method 8: Phenomenex C18 4.6×50 mm, A=90% H₂O/10% MeOH, B=90% MeOH/10% H₂O, Modifier 0.1% TFA, 0.00 min=70% B, 4.0 min=100% B, 5.0 min=100% B, Flow rate=4 mL/min HPLC method 9: Phenomenex C18 4.6×50 mm, A=95% H₂O/5% ACN, B=95% ACN/5% H₂O, Modifier 10 mM NH₄OAc, 0.00 min=0% B, 4 min=100% B 5min=100% B, Flow rate=4 mL/min HPLC method 10: Phenomenex C18 4.6×50 mm, A=95% H₂O/5% ACN, B=95% ACN/5% H₂O, Modifier 10 mM NH₄OAc, 0.00 min=40% B, 4 min=100% B 5 min=100% B, Flow rate=4 mL/min HPLC Method 11: Waters Atlantis 30×100 mm, A=90% H₂O/10% MeOH, B=90% MeOH/10% H₂O, Modifier 0.1% TFA, 0.00 min=40% B, 12 min=100% B, 15.0 min=100% B, Flow rate=40 mL/min.

HPLC Method 12: Waters Atlantis 30×100 mm, A=90% H₂O/10% MeOH, B=90% MeOH/10% H₂O, Modifier 0.1% TFA, 0.00 min=20% B, 12 min=100% B, 15.0 min=100% B, Flow rate=40 mL/min.

HPLC Method 13: Waters Atlantis 30×100 mm, A=90% H₂O/10% MeOH, B=90% MeOH/10% H₂O, Modifier 0.1% TFA, 0.00 min=50% B, 12 min=100% B, 15.0 min=100% B, Flow rate=40 mL/min.

HPLC Method 14: Waters Atlantis 30×100 mm, A=90% H₂O/10% MeOH, B=90% MeOH/10% H₂O, Modifier 0.1% TFA, 0.00 min=0% B, 20 min=100% B, 22.0 min=100% B, Flow rate=40 mL/min.

HPLC Method 15: Waters Atlantis 30×100 mm, A=90% H₂O/10% MeOH, B=90% MeOH/10% H₂O, Modifier 0.1% TFA, 0.00 min=10% B, 15 min=100% B, 18.0 min=100% B, Flow rate=40 mL/min.

HPLC Method 16: Waters Atlantis 30×100 mm, A=90% H₂O/10% MeOH, B=90% MeOH/10% H₂O, Modifier 0.1% TFA, 0.00 min=40% B, 15 min=100% B, 18.0 min=100% B, Flow rate=40 mL/min.

HPLC Method 17: Waters Atlantis 30×100 mm, A=90% H₂O/10% MeOH, B=90% MeOH/10% H₂O, Modifier 0.1% TFA, 0.00 min=60% B, 12 min=100% B, 18.0 min=100% B, Flow rate=40 mL/min.

HPLC Method 18: Waters Atlantis 30×100 mm, A=90% H₂O/10% MeOH, B=90% MeOH/10% H₂O, Modifier 0.1% TFA, 0.00 min=10% B, 12 min=100% B, 17.0 min=100% B, Flow rate=40 mL/min.

HPLC method 19: Phenomenex C18 4.6×50 mm, A=95% H₂O/5% ACN, B=95% ACN/5% H₂O, Modifier 10 mM NH₄OAc, 0.00 min=60% B, 4 min=100% B 5 min=100% B, Flow rate=4 mL/min.

SFC Method 1: Chiralcel OD-H analytical column, 4.6×250 mm, 5 μm, Mobile Phase: 15% MeOH (0.1% DEA) in CO2 for 18 min., 5 min. flush@40%, 5 min. equilibration@15%. Temp: 35° C., Flow rate: 2.0 mL/min. for 20 min, UV monitored@220 nm.

SFC Method 2: Chiralcel OD-H analytical column, 4.6×250 mm, 5 μm, Mobile Phase: 10% MeOH (0.1% DEA) in CO2; Temp: 35° C.; Flow rate: 2.0 mL/min. for 16 min; UV monitored@220 nm.

SFC Method 3: Chiralcel OD-H analytical column, 4.6×250 mm, 5 μm, Mobile Phase: 7% MeOH (0.1% DEA) in CO2; Temp: 35° C.; Flow rate: 2.0 mL/min. for 22 min; UV monitored@220 nm.

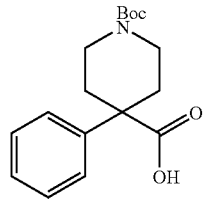

Intermediate 1

1-(tert-Butoxycarbonyl)-4-phenylpiperidine-4-carboxylic acid. To a suspension of 4-phenyl-4-piperidinecarboxylic acid p-methylbenzenesulfonate (100 g, 265 mmol) and triethylamine (111 mL, 795 mmol) in tetrahydrofuran (1200 mL) was added di-tert-butyl dicarbonate (63.6 g, 291 mmol). The reaction was slowly heated to a gentle reflux and held there for 1 h. After one hour, gas evolution had ended and the reaction had become a clear solution. The reaction was cooled to room temperature and concentrated to remove most of the tetrahydrofuran. The residue was dissolved in water/diethyl ether and the aqueous made very basic by the addition of 10 M sodium hydroxide (50 mL). The aqueous was washed with diethyl ether (2×) which was discarded. The aqueous was transferred to an erlenmeyer flask and made acidic (ca. pH 5) by addition of acetic acid to give a white precipitate. The precipitate was collected by filtration and air dried overnight to give a white powder. The last traces of water were removed under high vacuum to give 78.9 g (98%). ¹H-NMR (CD₃OD, 500 MHz) δ 10.5 (bs, 1H), 7.39 (m, 2H), 7.33 (m, 2H), 7.26 (m, 1H), 3.90 (bs, 2H), 3.08, (bs, 2H), 2.48 (d, J=13.4 Hz, 2H), 1.85 (m, 2H), 1.44 (s, 9H); ¹³C NMR (126 MHz, CDCl₃) δ ppm 179.6, 155.0, 141.6, 128.8, 127.6, 126.1, 79.9, 49.3, 41.7, 33.4, 28.5. Mass spec.: 328.12 (MNa)⁺.

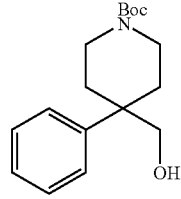

Intermediate 2 tert-Butyl 4-(hydroxymethyl)-4-phenylpiperidine-1-carboxylate. To a suspension of 1-(tert-butoxycarbonyl)-4-phenylpiperidine-4-carboxylic acid (40 g, 131 mmol) in tetrahydrofuran (131 mL) at room temperature was added borane tetrahydrofuran complex (1 M in tetrahydrofuran, 131 mL, 131 mmol). There was effervescence and the substrate quickly went into solution. The reaction was stirred at room temperature for 3 days. The reaction was cooled to 0° C. and quenched by the cautious addition of 1 M sodium hydroxide. The reaction was diluted with diethyl ether, washed with water (2×), then brine, dried over magnesium sulfate, and concentrated. Trituration with 10% EtOAc/Hex (300 mL) gave a white powder which was collected by filtration to give 36.9 g (97%). $^1$H-NMR (CD$_3$OD, 500 MHz) δ 7.35-7.43 (m, 4H), 7.24-7.26 (m, 1H), 3.78-3.85 (m, 2H), 3.49 (s, 2H), 2.97 (m, 2H), 2.17-2.21 (m, 2H), 1.77-1.87 (m, 2H), 1.46 (s, 9H). Mass spec.: 292.17 (MH)$^+$.

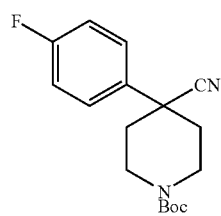

Intermediate 3 tert-Butyl 4-cyano-4-(4-fluorophenyl)piperidine-1-carboxylate. 2-(4-Fluorophenyl)acetonitrile (1.35 g, 10.0 mmol) and tert-butyl bis(2-chloroethyl)carbamate (2.42 g, 10.0 mmol) were combined in dimethylformamide (30 mL) and cooled to 0° C. The reaction was treated with sodium hydride (760 mg, 30.0 mmol) in several portions. The ice bath was removed and the reaction heated at 60° C. for 24 h. After cooling to room temperature, the mixture was poured into ice water and extracted with ethyl acetate (2×). The organic layers were pooled together, washed with brine (2×), dried over sodium sulfate, and concentrated. Column chromatography on silica gel (15% ethyl acetate/hexanes) gave 1.65 g (54%). $^1$H-NMR (CDCl$_3$, 500 MHz) δ 7.39-7.44 (m, 2H), 7.04-7.10 (m, 2H), 4.23-4.27 (m, 2H), 3.12-3.21 (m, 2H), 2.03-2.07 (m, 2H), 1.82-1.92 (m, 2H), 1.45 (s, 9H). Mass spec.: 327.11 (MNa)$^+$.

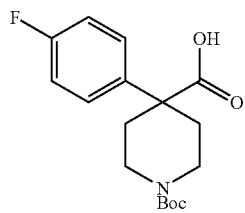

Intermediate 4

1-(tert-Butoxycarbonyl)-4-(4-fluorophenyl)piperidine-4-carboxylic acid. tert-Butyl 4-cyano-4-(4-fluorophenyl)piperidine-1-carboxylate (0.35 g, 1.15 mmol) was dissolved in ethanol (3.0 mL) and sodium hydroxide (50% in water, 3.0 mL). The reaction mixture was then heated at reflux for 6 h. After cooling to room temperature, the mixture was concentrated in vacuo to remove most of the ethanol. The residue was poured into water/ethyl acetate. The product was extracted with water (2×) and the organics discarded. The aqueous layers were pooled together and acidified to pH 2.0 with 1 N hydrochloric acid. The resulting precipitate was filtered and dried in vacuo for several hours to afford 0.24 g (64%) as a white powder. $^1$H-NMR (CD$_3$OD, 500 MHz) δ 7.46-7.48 (m, 2H), 7.07-7.11 (m, 2H), 3.94-3.98 (m, 2H), 3.10 (m, 2H), 2.50-2.53 (m, 2H), 1.78-1.83 (m, 2H), 1.48 (s, 9H). Mass spec.: 346.20 (MNa)$^+$.

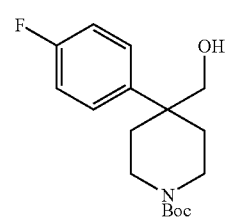

Intermediate 5 tert-Butyl 4-(4-fluorophenyl)-4-(hydroxymethyl)piperidine-1-carboxylate. 1-(tert-Butoxycarbonyl)-4-(4-fluorophenyl)piperidine-4-carboxylic acid (9.5 g, 29.3 mmol) was suspended in tetrahydrofuran (60 mL) and cooled to 0° C. To this solution was added borane tetrahydrofuran complex (1 M in tetrahydrofuran, 59 mL, 59 mmol) cautiously over 15 min. The reaction mixture was allowed to warm to room temperature overnight and then heated at reflux for 24 h. The mixture was cooled to 0° C., treated with excess methanol, diluted with ethyl acetate, washed with 1 N sodium hydroxide (2×), then brine (2×), dried over sodium sulfate, and concentrated. Column chromatography on silica gel (40% ethyl acetate/hexanes) gave 6.6 g (72%) as a white powder. $^1$H-NMR (CDCl$_3$, 500 MHz) 7.24-7.29 (m, 2H), 7.00-7.05 (m, 2H), 3.66-3.71 (m, 2H), 3.49 (s, 2H), 2.96-3.05 (m, 2H), 2.06-2.10 (m, 2H), 1.69-1.77 (m, 2H), 1.40 (s, 9H). Mass spec.: 310.21 (MH)$^+$.

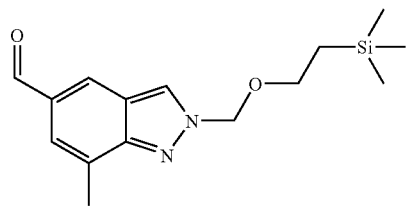

Intermediate 6

7-Methyl-2-((2-(trimethylsilyl)ethoxy)methyl)-2H-indazole-5-carbaldehyde. The title compound was prepared according to the literature procedure (Luo, J. Org. Chem. 2006, 5392).

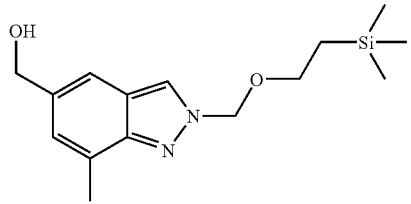

Intermediate 7

(7-Methyl-2-((2-(trimethylsilyl)ethoxy)methyl)-2H-indazol-5-yl)methanol. To a solution of 7-methyl-2-((2-(trimethylsilyl)ethoxy)methyl)-2H-indazole-5-carbaldehyde (150 mg, 0.516 mmol) in ethanol (4 mL) at room temperature was added sodium borohydride (19.5 mg, 0.516 mmol). The reaction was stirred at room temperature for 20 min, cooled to 0°

C., and quenched by the cautious addition of saturated ammonium chloride. The reaction was poured into diethyl ether and washed with water (2×), then brine, dried over magnesium sulfate, and concentrated to give 139 mg (92%) as an oil. $^1$H-NMR (CDCl$_3$, 500 MHz) δ 7.97 (s, 1H), 7.38 (s, 1H), 7.01 (s, 1H), 5.65 (s, 2H), 4.64 (s, 2H), 3.58 (m, 2H), 2.57 (s, 3H), 2.51 (bs, 1H), 0.89 (m, 2H), −0.07 (s, 9H); $^{13}$C NMR (126 MHz, CDCl$_3$) δ ppm 148.9, 135.1, 128.2, 125.5, 122.9, 121.7, 115.4, 81.5, 67.2, 65.6, 17.7, 17.1, −1.5.

Intermediate 8

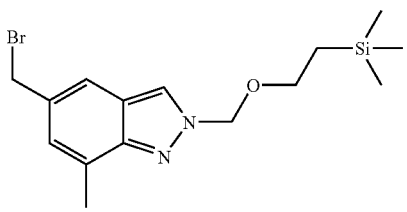

5-(Bromomethyl)-7-methyl-2-((2-(trimethylsilyl)ethoxy)methyl)-2H-indazole. To a solution of (7-methyl-2-((2-(trimethylsilyl)ethoxy)methyl)-2H-indazol-5-yl)methanol (138 mg, 0.472 mmol) and carbon tetrabromide (235 mg, 0.708 mmol) in tetrahydrofuran (1 mL) at 0° C. was added triphenylphosphine (186 mg, 0.708 mmol). The resulting solution was stirred at room temperature for 30 min. The reaction was diluted with several volumes of pentane and filtered to remove undissolved solids. The organics were concentrated and purified by column chromatography (5→12% EtOAc/Hex) to give 114 mg (68%) as a colorless oil. $^1$H-NMR (CDCl$_3$, 500 MHz) δ 8.03 (s, 1H), 7.48 (s, 1H), 7.06 (s, 1H), 5.68 (s, 2H), 4.55 (s, 2H), 3.61 (m, 2H), 2.59 (s, 3H), 0.91 (m, 2H), −0.05 (s, 9H); $^{13}$C NMR (126 MHz, CDCl$_3$) δ ppm 148.8, 131.6, 129.0, 126.6, 123.3, 121.6, 118.1, 81.7, 67.3, 35.4, 17.7, 17.1, −1.5.

Intermediate 9

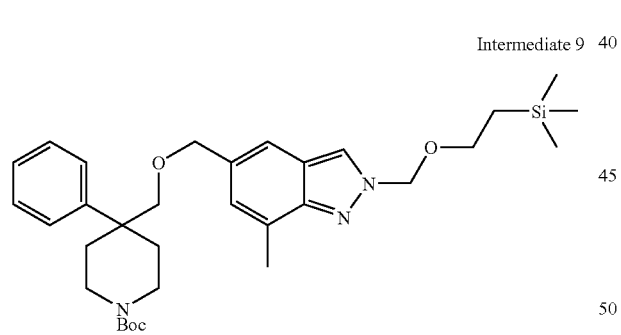

tert-Butyl 4-(((7-methyl-2-((2-(trimethylsilyl)ethoxy)methyl)-2H-indazol-5-yl)methoxy)methyl)-4-phenylpiperidine-1-carboxylate. To a solution of tert-butyl 4-(hydroxymethyl)-4-phenylpiperidine-1-carboxylate (102 mg, 0.350 mmol) and 5-(bromomethyl)-7-methyl-2-((2-(trimethylsilyl)ethoxy)methyl)-2H-indazole (113 mg, 0.318 mmol) in dimethylformamide (0.75 mL) at 0° C. was added sodium hydride (16.8 mg, 0.70 mmol). The resulting solution was stirred at at 0° C. for 30 min. The reaction was quenched by the cautious addition of saturated ammonium chloride and diluted with diethyl ether. The ethereal was washed with water (2×), then brine, dried over magnesium sulfate, and concentrated. Column chromatography (12%→25% EtOAc/Hex) gave 170 mg (94%) as a colorless oil. $^1$H-NMR (CDCl$_3$, 500 MHz) δ 7.99 (s, 1H), 7.31-7.40 (m, 4H), 7.25 (m, 1H), 7.21 (s, 1H), 6.79 (s, 1H), 5.70 (s, 2H), 4.37 (s, 2H), 3.73 (bs, 2H), 3.63 (m, 2H), 3.40 (s, 2H), 3.04 (m, 2H), 2.57 (s, 3H), 2.16 (m, 2H), 1.91 (m, 2H), 1.43 (s, 9H), 0.94 (m, 2H), −0.03 (s, 9H); $^{13}$C NMR (126 MHz, CDCl$_3$) δ ppm 155.1, 149.2, 143.3, 132.5, 128.5, 128.1, 127.4, 126.3, 125.7, 122.9, 121.9, 116.1, 81.8, 79.3, 78.9, 73.8, 67.4, 41.8, 40.1 (br), 32.0, 28.6, 18.0, 17.2, −1.3.

Intermediate 10

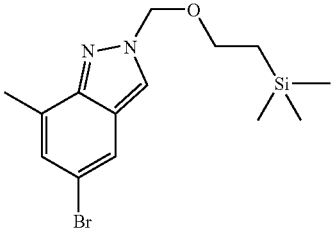

5-Bromo-7-methyl-2-((2-(trimethylsilyl)ethoxy)methyl)-2H-indazole. To a solution of 5-bromo-7-methyl-1H-indazole (2.0 g, 9.48 mmol) and N-methyldicyclohexylamine (2.74 mL, 12.8 mmol) in tetrahydrofuran (25 mL) at 0° C. was added (2-(chloromethoxy)ethyl)trimethylsilane (2.10 mL, 11.9 mmol). The ice bath was removed and stirring continued for 4 h. The reaction was poured into diethyl ether, washed with water (3×), then 1 M potassium bisulfate, then water, then brine, dried over magnesium sulfate, and concentrated. Column chromatography (8%→12% EtOAc/Hex) gave 3.03 g (94%) as a faint yellow oil. $^1$H-NMR (CDCl$_3$, 500 MHz) δ 8.02 (s, 1H), 7.66 (s, 1H), 7.13 (s, 1H), 5.70 (s, 2H), 3.62 (t, J=8.2 Hz, 2H), 2.60 (s, 3H), 0.93 (t, J=8.2 Hz, 2H), 0.04 (s, 9H); $^{13}$C-NMR (CDCl$_3$, 126 MHz), δ 147.8, 130.4, 128.9, 123.1, 122.3, 120.1, 115.8, 81.9, 67.6, 17.9, 17.0, −1.3.

Intermediates 11 and 12

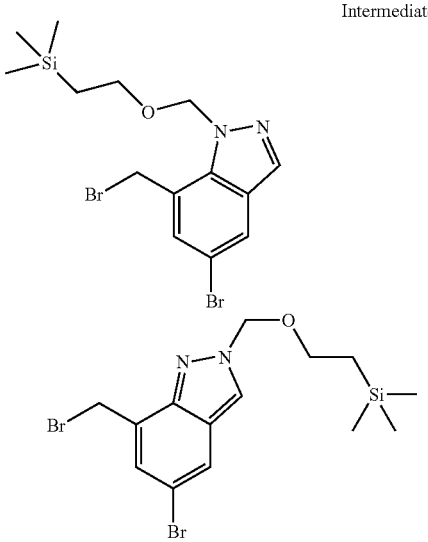

5-Bromo-7-(bromomethyl)-1-((2-(trimethylsilyl)ethoxy)methyl)-1H-indazole and 5-Bromo-7-(bromomethyl)-2-((2-(trimethylsilyl)ethoxy)methyl)-2H-indazole. A flask was charged with 5-bromo-7-methyl-2-((2-(trimethylsilyl)ethoxy)methyl)-2H-indazole (2.0 g, 5.86 mmol), N-bromosuccinimide (1.04 g, 5.86 mmol), benzoic peroxyanhydride (0.043 g, 0.18 mmol), and carbon tetrachloride (12 mL). The reaction was heated at reflux overnight. The reaction was concentrated. The resulting residue was suspended in diethyl ether (10 mL). To this was added pentane (20 mL). After stirring for 5 min, the solid was removed by filtration and the mother liquor concentrated. The residue was purified by column chromatography (3%→8% EtOAc/Hex) to give 3 fractions. The fastest eluting fraction was concentrated to give 5-bromo-7-(bromomethyl)-1-((2-(trimethylsilyl)ethoxy)methyl)-1H-indazole (0.95 g, 39%). The slowest eluting fraction was concentrated to give 5-bromo-7-(bromomethyl)-2-((2-(trimethylsilyl)ethoxy)methyl)-2H-indazole (420 mg, 17%). 5-Bromo-7-(bromomethyl)-1-((2-(trimethylsilyl)ethoxy)methyl)-1H-indazole: $^1$H-NMR (CDCl$_3$, 500 MHz) δ 7.95 (s, 1H), 7.84 (d, J=1.5 Hz, 1H), 7.49 (d, J=1.5 Hz, 1H), 5.98 (s, 2H), 4.93 (s, 2H), 3.50 (t, J=8.2 Hz, 2H), 0.85 (t, J=8.2 Hz, 2H), <0.10 (s, 9H); $^{13}$C-NMR (CDCl$_3$, 126 MHz) δ 136.2, 133.5, 132.0, 128.4, 124.6, 123.1, 114.1, 80.4, 66.4, 29.8, 17.9, −1.4. 5-Bromo-7-(bromomethyl)-2-((2-(trimethylsilyl)ethoxy)methyl)-2H-indazole: $^1$H-NMR (CDCl$_3$, 500 MHz) δ 8.07 (s, 1H), 7.79 (d, J=1.5 Hz, 1H), 7.41 (d, J=1.5 Hz, 1H), 5.72 (s, 2H), 4.84 (s, 2H), 3.64 (t, J=8.2 Hz, 2H), 0.93 (t, J=8.2 Hz, 2H), 0.00 (s, 9H); $^{13}$C-NMR (CDCl$_3$, 126 MHz) δ 145.6, 130.2, 129.3, 123.8, 123.4, 122.8, 115.2, 82.1, 67.9, 28.2, 18.0, −1.3.

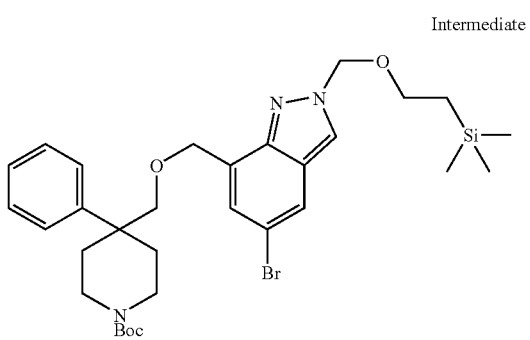

Intermediate 13 tert-Butyl 4-(((5-bromo-2-((2-(trimethylsilyl)ethoxy)methyl)-2H-indazol-7-yl)methoxy)methyl)-4-phenylpiperidine-1-carboxylate. A flask was charged with 5-bromo-7-(bromomethyl)-2-((2-(trimethylsilyl)ethoxy)methyl)-2H-indazole (0.61 g, 1.45 mmol), tert-butyl 4-(hydroxymethyl)-4-phenylpiperidine-1-carboxylate (0.444 g, 1.52 mmol), and dimethylformamide (5 mL). The reaction was cooled to 0° C. and treated with sodium hydride (0.073 g, 3.05 mmol) in several portions. After stirring for 15 min, the ice bath was removed and stirring continued for 15 min. The reaction was cooled to 0° C. and quenched by the cautious addition of saturated ammonium chloride. The reaction was poured into diethyl ether, washed with water (3×), then brine, dried over magnesium sulfate, and concentrated. Column chromatography (12%→25% EtOAc/Hex) gave 720 mg (79%) as a gum. $^1$H-NMR (CDCl$_3$, 500 MHz) δ 8.00 (s, 1H), 7.70 (d, J=1.5 Hz, 1H), 7.38 (m, 4H), 7.24 (m, 1H), 7.13 (d, J=1.5 Hz, 1H), 5.65 (s, 2H), 4.81 (s, 2H), 3.76 (bs, 2H), 3.58 (t, J=8.2 Hz, 2H), 3.53 (s, 2H), 3.06 (m, 2H), 2.22 (m, 2H), 1.95 (m, 2H), 1.44 (s, 9H), 0.91 (t, J=8.2 Hz, 2H), 0.00 (s, 9H); $^{13}$C-NMR (CDCl$_3$, 126 MHz) δ 155.1, 145.5, 142.9, 130.5, 128.6, 127.4, 126.6, 126.5, 123.3, 122.2, 121.3, 116.0, 81.9, 80.0, 79.4, 68.5, 67.6, 41.9, 40.3 (br), 32.0, 28.6, 17.9, −1.3. Mass spec.: 630.14 (MH)$^+$.

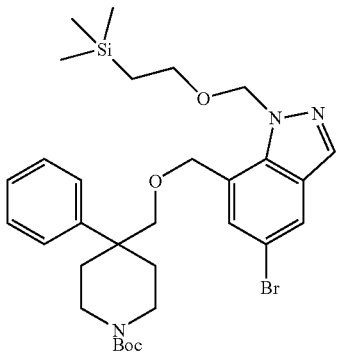

Intermediate 14 tert-Butyl 4-(((5-bromo-1-((2-(trimethylsilyl)ethoxy)methyl)-1H-indazol-7-yl)methoxy)methyl)-4-phenylpiperidine-1-carboxylate. A flask was charged with 5-bromo-7-(bromomethyl)-1-((2-(trimethylsilyl)ethoxy)methyl)-1H-indazole (220 mg, 0.52 mmol), tert-butyl 4-(hydroxymethyl)-4-phenylpiperidine-1-carboxylate (160 mg, 0.55 mmol), and dimethylformamide (2.5 mL). The reaction was cooled to 0° C. and treated with sodium hydride (26.4 mg, 1.1 mmol) in several portions. After stirring for 15 min, the ice bath was removed and stirring continued for 15 min. The reaction was cooled to 0° C. and quenched by the cautious addition of saturated ammonium chloride. The reaction was poured into diethyl ether, washed with water (3×), then brine, dried over magnesium sulfate, and concentrated. Column chromatography (12%→25% EtOAc/Hex) gave 233 mg (71%) as a gum. $^1$H-NMR (CDCl$_3$, 500 MHz) δ 7.87 (s, 1H), 7.78 (d, J=1.5 Hz, 1H), 7.27 (d, J=1.8 Hz, 1H), 7.19 (m, 5H), 5.32 (s, 2H), 4.65 (s, 2H), 3.67 (bs, 2H), 3.41 (s, 2H), 3.36 (t, J=8.2 Hz, 2H), 3.00 (m, 2H), 2.11 (m, 2H), 1.76 (m, 2H), 1.41 (s, 9H), 0.75 (t, J=8.2 Hz, 2H), −0.10 (s, 9H); $^{13}$C-NMR (CDCl$_3$, 126 MHz) δ 155.0, 142.7, 137.1, 133.1, 131.4, 128.4, 127.8, 127.1, 126.4, 123.5, 122.8, 113.7, 79.4, 79.1, 78.8, 70.4, 66.0, 41.5, 40.2 (br), 32.1, 28.6, 17.8, −1.40.

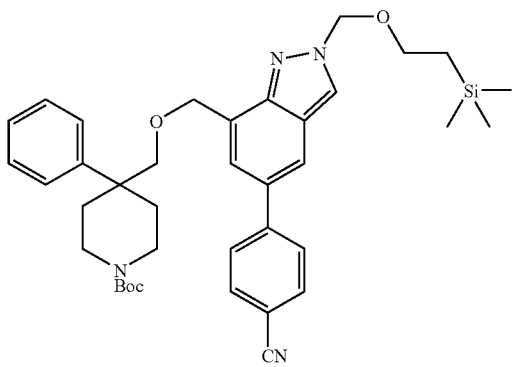

Intermediate 15 tert-Butyl 4-(((5-(4-cyanophenyl)-2-((2-(trimethylsilyl)ethoxy)methyl)-2H-indazol-7-yl)methoxy)methyl)-4-phenylpiperidine-1-carboxylate. A microwave tube was charged with tert-butyl 4-(((5-bromo-2-((2-(trimethylsilyl)ethoxy)methyl)-2H-indazol-7-yl)methoxy)methyl)-4-phenylpiperidine-1-carboxylate (400 mg, 0.63 mmol), 4-cyanophenylboronic acid (280 mg, 1.90 mmol), and tetrakis(triphenylphosphine)-palladium(0) (36.6 mg, 0.032 mmol). The tube was flushed with nitrogen and treated with tetrahydrofuran (12 mL) and potassium hydroxide (1 M in water) (1.90 mL, 1.90 mmol). The tube was sealed and heated at 110° C. for 1 h via microwave. The reaction was cooled, poured into diethyl ether, washed with water (2×), then brine, dried over magnesium sulfate, and concentrated. Column chromatography (25%→32% EtOAc/Hex) gave 391 mg (94%) as an oil. $^1$H-NMR (CDCl$_3$, 500 MHz) δ 8.16 (s, 1H), 7.76 (d, J=1.2 Hz, 1H), 7.71 (d, J=8.2 Hz, 2H), 7.61 (d, J=8.6 Hz, 2H), 7.40 (m, 2H), 7.31 (m, 3H), 7.19 (m, 1H), 5.70 (s, 2H), 4.92 (s, 2H), 3.73 (br, 2H), 3.63 (t, J=8.2 Hz, 2H), 3.59 (s, 2H), 3.06 (m, 2H), 2.22 (m, 2H), 1.94 (m, 2H), 1.40 (s, 9H), 0.94 (t, J=8.2 Hz, 2H), −0.03 (s, 9H); $^{13}$C-NMR (CDCl$_3$, 126 MHz) δ 155.1, 146.8, 146.3, 143.2, 133.4, 132.6, 129.5, 128.5, 127.8, 127.4, 126.3, 123.8, 122.7, 122.6, 119.1, 118.1, 110.5, 82.0, 79.9, 79.4, 68.9, 67.7, 41.8, 40.3 (br), 32.2, 28.6, 17.9, −1.3.

Intermediate 16

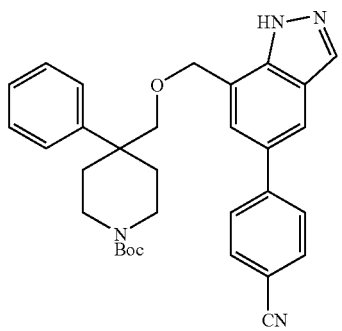

tert-Butyl 4-(((5-(4-cyanophenyl)-1H-indazol-7-yl)methoxy)methyl)-4-phenylpiperidine-1-carboxylate. To a solution of 4-(7-(((4-phenylpiperidin-4-yl)methoxy)methyl)-1H-indazol-5-yl)benzonitrile (280 mg, 0.66 mmol) in dichloromethane (3 mL) at 0° C. was added di-tert-butyl dicarbonate (152 mg, 0.70 mmol). The ice bath was removed and the reaction was stirred for 1 h. The reaction was quenched by addition of 2 M ammonia in methanol. After stirring 5 min, the reaction was concentrated and purified by column chromatography (EtOAc/Hex) to give 241 mg (70%) as an amorphous foam solid. $^1$H-NMR (CDCl$_3$, 500 MHz) δ 9.70 (s, 1H), 8.02 (s, 1H), 7.80 (s, 1H), 7.66 (m, 4H), 7.47 (m, 2H), 7.39 (m, 3H), 7.28 (s, 1H), 4.75 (s, 2H), 3.72 (br, 2H), 3.58 (s, 2H), 3.09 (m, 2H), 2.24 (m, 2H), 1.82 (m, 2H), 1.43 (s, 9H); $^{13}$C-NMR (CDCl$_3$, 126 MHz) δ 155.0, 145.9, 142.8, 128.5, 135.0, 132.7, 132.2, 129.1, 127.9, 127.13, 127.06, 124.4, 123.5, 121.7, 119.0, 110.6, 80.5, 79.6, 72.2, 41.6, 40.3 (br), 32.5, 28.6.

Intermediates 17 and 18

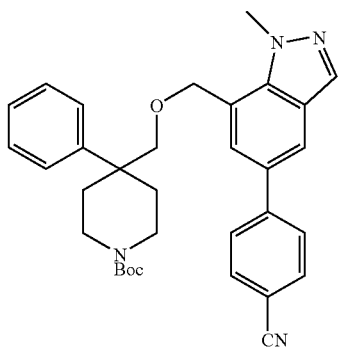

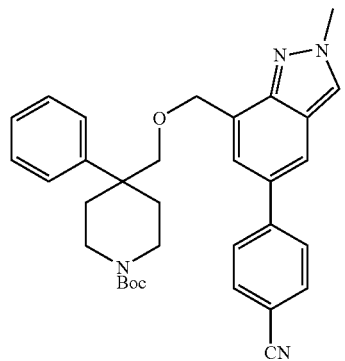

tert-Butyl 4-(((5-(4-cyanophenyl)-1-methyl-1H-indazol-7-yl)methoxy)methyl)-4-phenylpiperidine-1-carboxylate and tert-Butyl 4-(((5-(4-cyanophenyl)-2-methyl-2H-indazol-7-yl)methoxy)methyl)-4-phenylpiperidine-1-carboxylate.

To a solution of tert-butyl 4-(((5-(4-cyanophenyl)-1H-indazol-7-yl)methoxy)methyl)-4-phenylpiperidine-1-carboxylate (100 mg, 0.191 mmol) in dimethylformamide (1 mL) at 0° C. was added sodium hydride (60% in mineral oil, 9.6 mg, 0.24 mmol). After 5 min, the reaction was treated with iodomethane (0.015 mL, 0.24 mmol). After 30 min, the reaction was quenched by addition of saturated ammonium chloride and poured into diethyl ether. The organics were washed with water (3×), then brine, dried over magnesium sulfate, and concentrated. Column chromatography (25%→100% EtOAc/Hex) gave two fractions. The faster eluting fraction was concentrated to give tert-butyl 4-(((5-(4-cyanophenyl)-1-methyl-1H-indazol-7-yl)methoxy)methyl)-4-phenylpiperidine-1-carboxylate (63 mg, 61%). The second fraction was concentrated to give tert-butyl 4-(((5-(4-cyanophenyl)-2-methyl-2H-indazol-7-yl)methoxy)methyl)-4-phenylpiperidine-1-carboxylate (29 mg, 28%). tert-Butyl 4-(((5-(4-cyanophenyl)-1-methyl-1H-indazol-7-yl)methoxy)methyl)-4-phenylpiperidine-1-carboxylate: $^1$H-NMR (CDCl$_3$, 500 MHz) δ 7.98 (s, 1H), 7.85 (d, J=1.5 Hz, 1H), 7.69 (m, 4H), 7.34 (d, J=1.5 Hz, 1H), 7.24 (m, 4H), 7.18 (m, 1H), 4.72 (s, 2H), 3.93 (s, 3H), 3.68 (bs, 2H), 3.47 (s, 2H), 2.99 (m, 2H), 2.13 (m, 2H), 1.78 (m, 2H), 1.40 (s, 9H); $^{13}$C-NMR (CDCl$_3$, 126 MHz) δ 155.0, 145.6, 142.7, 138.5, 133.5, 132.7, 131.4, 128.5, 127.9, 127.8, 127.2, 126.5, 126.3, 121.1, 120.3, 119.1, 110.5, 79.5, 79.2, 71.1, 41.5, 40.2 (br), 38.1, 32.2, 28.5. Mass spec.: 559.18 (MNa)$^+$. tert-Butyl 4-(((5-(4-cyanophenyl)-2-methyl-2H-indazol-7-yl)methoxy)methyl)-4-phenylpiperidine-1-carboxylate: $^1$H-NMR (CDCl$_3$, 500 MHz) δ 7.94 (s, 1H), 7.72 (m, 3H), 7.61 (m, 2H), 7.39 (m, 2H), 7.23-7.35 (m, 3H), 7.19 (m, 1H), 4.89 (s, 2H), 4.21 (s, 3H), 3.72 (bs, 2H), 3.58 (s, 2H), 3.06 (m, 2H), 2.21 (m, 2H), 1.93 (m, 2H), 1.42 (s, 9H); $^{13}$C-NMR (CDCl$_3$, 126 MHz) δ 155.1, 147.0, 146.4, 143.2, 132.9, 132.6, 128.7, 128.5, 127.8, 127.4, 126.3, 124.9, 122.5, 122.4, 119.2, 117.7, 110.3, 79.8, 79.4, 69.0, 41.8, 40.7, 40.2 (br), 32.1, 28.6. Mass spec.: 559.23 (MNa)$^+$.

Intermediate 19

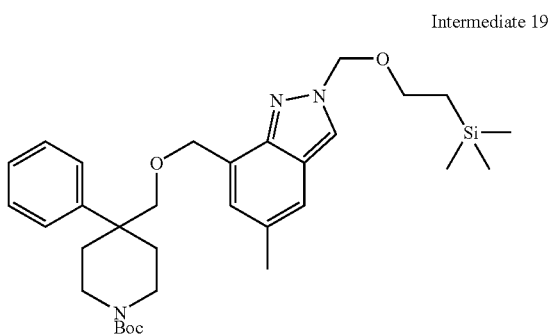

tert-Butyl 4-(((5-methyl-2-((2-(trimethylsilyl)ethoxy)methyl)-2H-indazol-7-yl)methoxy)methyl)-4-phenylpiperidine-1-carboxylate. A microwave tube was charged with tert-butyl 4-(((5-bromo-2-((2-(trimethylsilyl)ethoxy)methyl)-2H-indazol-7-yl)methoxy)methyl)-4-phenylpiperidine-1-carboxylate (200 mg, 0.3 17 mmol), trimethylboroxine (0.089 mL, 0.634 mmol), tetrahydrofuran (1.5 mL), sodium carbonate (4 M in water, 0.24 mL, 0.95 mmol), and tetrakis(triphenylphosphine)-palladium(0) (18.3 mg, 0.016 mmol). The tube was flushed with nitrogen, sealed, and heated at 110° C. for 2 h via microwave. The reaction was cooled, poured into diethyl ether, washed with water (2×), then brine, dried over magnesium sulfate, and concentrated. Column chromatography (25% EtOAc/Hex) gave 86 mg (50%) as a colorless oil. $^1$H-NMR (CDCl$_3$, 500 MHz) δ 7.94 (s, 1H), 7.20-7.45 (m, 6H), 6.86 (s, 1H), 5.65 (s, 2H), 4.84 (s, 2H), 3.74 (bs, 2H), 3.58 (t, J=7.9 Hz, 2H), 3.54 (s, 2H), 3.07 (m, 2H), 2.33 (s, 3H), 2.20 (m, 2H), 1.97 (m, 2H), 1.44 (s, 9H), 0.91 (t, J=7.6 Hz, 2H), −0.04 (s, 9H); $^{13}$C-NMR (CDCl$_3$, 126 MHz) δ 155.1, 146.1, 143.2, 131.6, 128.5, 127.9, 127.4, 126.4, 126.0, 122.6, 121.9, 117.3, 81.7, 79.6, 79.3, 69.0, 67.3, 41.9, 40.3 (br), 32.0, 28.6, 22.0, 17.9, −1.3. Mass spec.: 566.35 (MH)$^+$.

Intermediate 20

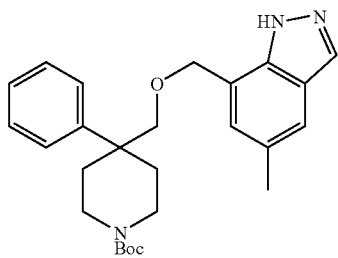

tert-Butyl 4-(((5-methyl-1H-indazol-7-yl)methoxy)methyl)-4-phenylpiperidine-1-carboxylate. tert-Butyl 4-(((5-methyl-2-((2-(trimethylsilyl)ethoxy)methyl)-2H-indazol-7-yl)methoxy)methyl)-4-phenylpiperidine-1-carboxylate (85 mg, 0.15 mmol) was dissolved in trifluoroacetic acid (50% in dichloromethane, 3 mL) and stirred at room temperature for 2 h. The reaction was concentrated and loaded onto a strong cation exchange cartridge in methanol. The column was flushed with several volumes of methanol which were discarded. The product was eluted with 2 M ammonia in methanol and concentrated to give 50 mg (99%). The crude amine was dissolved in dichloromethane (3 mL), cooled to 0° C., and treated with di-tert-butyl dicarbonate (41 mg, 0.186 mmol). The reaction was stirred at 0° C. for 1 h. The reaction was quenched by addition of 2 M ammonia in methanol and the ice bath removed. After stirring 5 min, the reaction was concentrated and purified by column chromatography (25%→50% EtOAc/Hex) to give 52.5 mg (81%) as a colorless film. $^1$H-NMR (CDCl$_3$, 500 MHz) δ 9.41 (bs, 1H), 7.86 (s, 1H), 7.47 (m, 2H), 7.38 (m, 4H), 6.89 (s, 1H), 4.65 (s, 2H), 3.71 (bs, 2H), 3.52 (s, 2H), 3.09 (m, 2H), 2.38 (s, 3H), 2.22 (m, 2H), 1.80 (m, 2H), 1.43 (s, 9H); $^{13}$C-NMR (CDCl$_3$, 126 MHz) δ 155.1, 142.8, 137.3, 133.8, 129.9, 129.1, 127.1, 126.1, 124.1, 120.3, 119.2, 80.2, 79.5, 72.4, 41.6, 40.1 (br), 32.4, 28.6, 21.3.

Intermediates 21 and 22

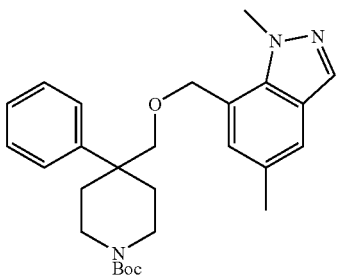

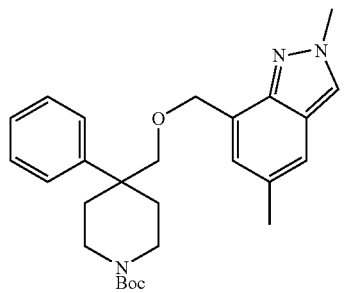

tert-Butyl 4-(((1,5-dimethyl-1H-indazol-7-yl)methoxy)methyl)-4-phenylpiperidine-1-carboxylate and tert-Butyl 4-(((2,5-dimethyl-2H-indazol-7-yl)methoxy)methyl)-4-phenylpiperidine-1-carboxylate. To a solution of tert-butyl 4-(((5-methyl-1H-indazol-7-yl)methoxy)methyl)-4-phenylpiperidine-1-carboxylate (38 mg, 0.087 mmol) in dimethylformamide (1 mL) at 0° C. was added sodium hydride (60% in mineral oil, 7.0 mg, 0.174 mmol). After 5 min, the reaction was treated with iodomethane (11 μL, 0.174 mmol). After 30 min, the reaction was quenched by addition of saturated ammonium chloride and poured into diethyl ether. The organics were washed with water (2×), then brine, dried over magnesium sulfate, and concentrated. Column chromatography (25%→75% EtOAc/Hex) gave two fractions. The faster eluting fraction was concentrated to give tert-butyl 4-(((1,5-dimethyl-1H-indazol-7-yl)methoxy)methyl)-4-phenylpiperidine-1-carboxylate (24 mg, 61%). Concentration of the second fraction gave tert-butyl 4-(((2,5-dimethyl-2H-indazol-7-yl)methoxy)methyl)-4-phenylpiperidine-1-carboxylate (8 mg, 20%). tert-Butyl 4-(((1,5-dimethyl-1H-indazol-7-yl)methoxy)methyl)-4-phenylpiperidine-1-carboxylate: $^1$H-NMR (CDCl$_3$, 500 MHz) δ 7.81 (s, 1H), 7.39 (s, 1H), 7.15-7.30 (m, 5H), 6.92 (s, 1H), 4.63 (s, 2H), 3.90 (s, 3H), 3.65 (bs, 2H), 3.41 (s, 2H), 3.00 (m, 2H), 2.39 (s, 3H), 2.10 (m, 2H), 1.79 (m, 2H), 1.41 (s, 9H); $^{13}$C-NMR (CDCl$_3$, 126 MHz) δ 155.1, 142.9, 137.3, 132.1, 130.8, 129.3, 128.5, 127.2, 126.4, 126.0, 120.6, 119.8, 79.4, 78.7, 71.3, 41.5, 40.1 (br), 38.0, 32.1, 28.6, 21.0. tert-Butyl 4-(((2,5-dimethyl-2H-indazol-7-yl)methoxy)methyl)-4-phenylpiperidine-1-carboxylate: $^1$H-NMR (CDCl$_3$, 500 MHz) δ 7.72 (s, 1H), 7.30-7.43 (m, 4H), 7.22 (m, 2H), 6.84 (s, 1H), 4.81 (s, 2H), 4.15 (s, 3H), 3.71 (bs, 2H), 3.53 (s, 2H), 3.06 (m, 2H), 2.32 (s, 3H), 2.17 (m, 2H), 1.97 (m, 2H), 1.43 (s, 9H); $^{13}$C-NMR (CDCl$_3$, 126 MHz) δ 155.1, 146.3, 143.3, 131.0, 128.5, 127.4, 127.1, 126.3, 125.7, 122.9, 122.5, 117.0, 79.4, 79.3, 69.1, 41.9, 40.3, 40.2 (br), 32.0, 28.6, 21.9.

Intermediate 23

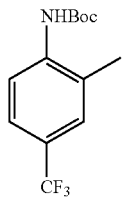

tert-Butyl 2-methyl-4-(trifluoromethyl)phenylcarbamate. To a solution of tert-butyl 4-(trifluoromethyl)phenylcarbamate (13.2 g, 50.5 mmol) at −78° C. was added tert-butyllithium (1.7 in pentane, 62.4 mL, 106 mmol). The reaction was allowed to gradually warm to −20° C. in the ice bath (ca. 1 h). The reaction was recooled to −78° C. and treated with iodomethane (3.79 mL, 61 mmol). The reaction was allowed to gradually warm to 0° C. and held there for 15 min. The reaction was quenched by addition of saturated ammonium chloride. The mixture was poured onto diethyl ether, washed with water (3×), then brine, dried over magnesium sulfate, and concentrated. The solid was triturated with pentane and filtered to collect a first crop (10.4 g, 75%). The mother liquor gave a second crop of solid (2.15 g, 15%) which was again collected by filtration. $^1$H-NMR (CDCl$_3$, 500 MHz) δ 8.06 (d, J=8.2 Hz, 1H), 7.44 (d, J=8.9 Hz, 1H), 7.38 (s, 1H), 6.40 (bs, 1H), 2.28 (s, 3H), 1.53 (s, 9H); $^{13}$C-NMR (CDCl$_3$, 126 MHz) δ 152.5, 139.8, 127.2 (q, J=3.8 Hz), 126.2, 125.0 (q, J=33 Hz), 124.4 (q, J=272 Hz), 124.2 (q, J=3.8 Hz), 119.5, 81.3, 28.4, 17.7. Mass spec.: 298.00 (MNa)$^+$.

Intermediate 24

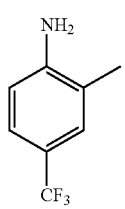

2-Methyl-4-(trifluoromethyl)aniline. tert-Butyl 2-methyl-4-(trifluoromethyl)phenylcarbamate (1 1.6 g, 42 mmol) was dissolved in trifluoroacetic acid (17% in dichloromethane, 90 mL) and stirred at room temperature for 30 min. The reaction was concentrated and taken up in water/pentane. The aqueous was neutralized with saturated sodium bicarbonate, and the layers separated. The organics were dried over magnesium sulfate and concentrated to give 7.8 g (quant.). $^1$H-NMR (CDCl$_3$, 500 MHz) δ 7.25-7.40 (m, 2H), 6.67 (d, J=7.9 Hz, 1H), 3.87 (bs, 2H), 2.18 (s, 3H); $^{13}$C-NMR (CDCl$_3$, 126 MHz) δ 147.7, 127.5 (q, J=3.8 Hz), 125.0 (q, J=271 Hz), 124.4 (q, J=3.8 Hz), 120.3 (q, J=33 Hz), 114.1, 17.2. Mass spec.: 176.03 (MH)$^+$.

Intermediate 25

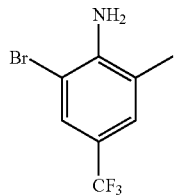

2-Bromo-6-methyl-4-(trifluoromethyl)aniline. To a suspension of 2-methyl-4-(trifluoromethyl)aniline (7.78 g, 44.4 mmol), potassium bromide (1.59 g, 13.3 mmol), and ammonium heptamolybdate tetrahydrate (140 mg, 0.111 mmol) in acetic acid (40 mL) at room temperature (in a room temperature waterbath) was added sodium perborate tetrahydrate (1.88 g, 12.2 mmol). After 10 min, the reaction was treated with an additional portion of potassium bromide (1.59 g, 13.3 mmol), ammonium heptamolybdate tetrahydrate (140 mg, 0.111 mmol), and sodium perborate tetrahydrate (1.88 g, 12.2 mmol). After 10 min, the reaction was treated with an additional portion of potassium bromide (1.59 g, 13.3 mmol), ammonium heptamolybdate tetrahydrate (140 mg, 0.111 mmol), and sodium perborate tetrahydrate (1.88 g, 12.2 mmol). After 10 min, the reaction was treated with an additional portion of potassium bromide (1.59 g, 13.33 mmol), ammonium heptamolybdate tetrahydrate (140 mg, 0.111 mmol), and sodium perborate tetrahydrate (1.88 g, 12.2 mmol). After 1 h, the reaction was treated with a final portion of everything in half the amounts of the previous additions. After 1 h, the mixture was poured into water, neutralized with solid sodium bicarbonate, extracted into diethyl ether, washed with water, then brine, dried over magnesium sulfate, and concentrated to give 11.3 g (100%) as an oil. $^1$H-NMR (CDCl$_3$, 500 MHz) δ 7.56 (s, 1H), 7.23 (s, 1H), 4.36 (bs, 2H), 2.23 (s, 3H); $^{13}$C-NMR (CDCl$_3$, 126 MHz) δ 145.3, 127.7 (q, J=3.8 Hz), 126.4 (q, J=3.8 Hz), 124.0 (q, J=272 Hz), 120.6 (q, J=34 Hz), 108.2, 18.3. Mass spec.: 253.95 (MH)$^+$.

Intermediate 26

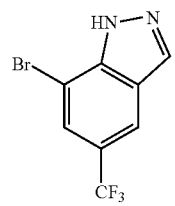

7-Bromo-5-(trifluoromethyl)-1H-indazole. To a suspension of 2-bromo-6-methyl-4-(trifluoromethyl)aniline (1 1.3 g, 44.5 mmol) in hydrochloric acid (8 M, 40 mL, 320 mmol) at −10° C. was added a solution of sodium nitrite (3.22 g, 46.7 mmol) in water (ca. 10 mL) dropwise. After 10 min, the resulting solution was neutralized by addition of solid sodium acetate. The resulting solution was added to a solution of 2-methyl-2-propanethiol (5.01 mL, 44.5 mmol) in ethanol (100 mL) at 0° C. The resulting mixture was stirred at 0° C. for 30 min. The resulting mixture was poured onto ice and the resulting mixture was extracted into diethyl ether (2×). The ethereal was washed with water, then brine, dried over magnesium sulfate, and concentrated. The resulting residue was dissolved in dimethylsulfoxide (25 mL) and transferred to a solution of potassium tert-butoxide (39.9 g, 356 mmol) in dimethylsulfoxide (250 mL) in a cool water bath (ca. 10° C.)

via canula. The bath was removed and stirring continued for 30 min. The reaction mixture was poured onto ice/concentrated hydrochloric acid to give a precipitate. After 30 min, the resulting solid was collected by filtration and air dried on the filter overnight to give 10.1 g (86%) as a tan solid. $^1$H-NMR (CDCl$_3$, 500 MHz) δ 8.24 (s, 1H), 8.01 (s, 1H), 7.73 (s, 1H), 2.83 (bs, 1H); $^{13}$C-NMR (CDCl$_3$, 126 MHz) δ 140.7, 136.3, 125.8 (q, J=2.9 Hz), 124.9 (q, J=33 Hz), 123.8 (q, J=273 Hz), 123.2, 118.4 (q, J=3.8 Hz), 104.1.

Intermediate 27

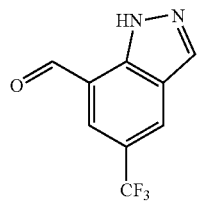

5-(Trifluoromethyl)-1H-indazole-7-carbaldehyde. To a solution of 7-bromo-5-(trifluoromethyl)-1H-indazole (9.05 g, 34.1 mmol) in tetrahydrofuran (120 mL) at 0° C. was added sodium hydride (0.901 g, 37.6 mmol). The ice bath was removed and stirring continued for 20 min. The solution was cooled to −78° C. and treated with tert-butyllithium (1.7 M in pentane, 41.2 mL, 70 mmol) dropwise. The reaction was stirred at −78° C. for 10 min, allowed to warm gradually in the dewar to −50° C., recooled to −78° C., and then treated with dimethylformamide (10.6 mL, 137 mmol). After 15 min, the ice bath was removed and stirring continued for 1 h. The reaction was poured onto ice/1 M hydrochloric acid (120 mL). The mixture was extracted with ethyl acetate (2×). The organics were washed with water, then brine, dried over magnesium sulfate, and concentrated to give a dark solid. The solid was triturated with a minimum of diethyl ether and filtered to give 5.25 g (72%) as a tan solid. $^1$H-NMR (CDCl$_3$, 500 MHz) δ 10.17 (s, 1H), 8.33 (s, 1H), 8.26 (s, 1H), 8.08 (s, 1H), 2.90 (s, 1H); $^{13}$C-NMR (CDCl$_3$, 126 MHz) δ 191.4, 137.2, 135.8, 129.7, 125.8, 124.2, 124.0 (q, J=272 Hz), 123.7 (q, J=34 Hz), 120.6. Mass spec.: 214.93 (MH)$^+$.

Intermediates 28 and 29

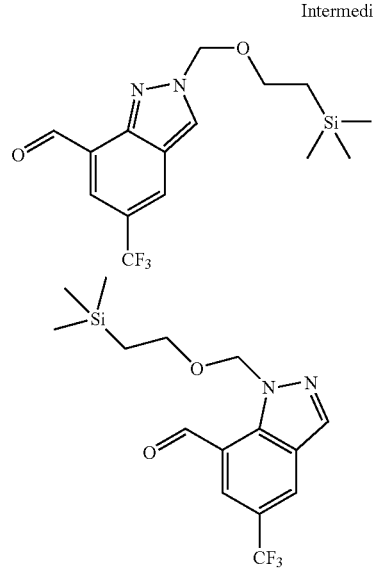

5-(Trifluoromethyl)-2-((2-(trimethylsilyl)ethoxy)methyl)-2H-indazole-7-carbaldehyde and 5-(Trifluoromethyl)-1-((2-(trimethylsilyl)ethoxy)methyl)-1H-indazole-7-carbaldehyde. To a solution of 5-(trifluoromethyl)-1H-indazole-7-carbaldehyde (3.87 g, 18.1 mmol) and N-methyldicyclohexylamine (6.19 mL, 28.9 mmol) in tetrahydrofuran (55 mL) at 0° C. was added (2-(chloromethoxy)ethyl)trimethylsilane (4.49 mL, 25.3 mmol). The ice bath was removed and stirring continued overnight. The reaction was poured into diethyl ether, washed with water (2×), then 1 M potassium bisulfate, then water, then brine, dried over magnesium sulfate, and concentrated. Column chromatography (12%→30% EtOAc/Hex) gave two fractions. The faster eluting fraction was concentrated to give 5-(trifluoromethyl)-1-((2-(trimethylsilyl)ethoxy)methyl)-1H-indazole-7-carbaldehyde (1.7 g, 27%). The second fraction was concentrated to give 5-(trifluoromethyl)-2-((2-(trimethylsilyl)ethoxy)methyl)-2H-indazole-7-carbaldehyde (3.85 g, 62%). 5-(Trifluoromethyl)-2-((2-(trimethylsilyl)ethoxy)methyl)-2H-indazole-7-carbaldehyde: $^1$H-NMR (CDCl$_3$, 500 MHz) δ 10.57 (s, 1H), 8.43 (s, 1H), 8.33 (s, 1H), 8.08 (d, J=1.8 Hz, 1H), 5.85 (s, 2H), 3.68 (m, 2H), 0.96 (m, 2H), −0.03 (s, 9H); $^{13}$C-NMR (CDCl$_3$, 126 MHz) δ 189.6, 146.1, 127.4, 126.3, 125.9, 125.4, 124.4 (q, J=34 Hz), 124.1 (q, J=273 Hz), 122.8, 82.6, 68.4, 18.1, −1.4. 5-(Trifluoromethyl)-1-((2-(trimethylsilyl)ethoxy)methyl)-1H-indazole-7-carbaldehyde: $^1$H-NMR (CDCl$_3$, 500 MHz) δ 10.41 (s, 1H), 8.31 (s, 1H), 8.24 (s, 1H), 88.21 (d, J=1.5 Hz, 1H), 6.12 (s, 2H), 3.48 (m, 2H), 0.83 (m, 2H), −0.10 (s, 9H); $^{13}$C-NMR (CDCl$_3$, 126 MHz) δ 189.1, 137.3, 135.8, 129.1, 127.4, 125.1, 124.2 (q, J=34 Hz), 124.0 (q, J=272 Hz), 122.4, 81.3, 66.5, 17.8, −1.5.

Intermediate 30

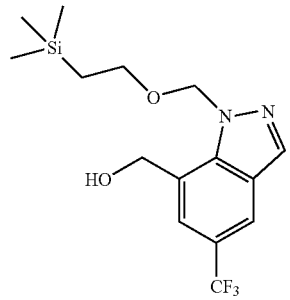

(5-(Trifluoromethyl)-1-((2-(trimethylsilyl)ethoxy)methyl)-1H-indazol-7-yl)methanol To a solution of 5-(trifluoromethyl)-1-((2-(trimethylsilyl)ethoxy)methyl)-1H-indazole-7-carbaldehyde (1 g, 2.9 mmol) in ethanol (15 mL) at 0° C. was added sodium borohydride (0.055 g, 1.45 mmol). The ice bath was removed and stirring continued for 15 min. The reaction was cooled to 0° C. and quenched by addition of saturated ammonium chloride. The reaction was concentrated to remove most of the ethanol and poured into diethyl ether. The ethereal was washed with water (2×), then brine, dried over magnesium sulfate, and concentrated to give 0.985 g (98%) as an oil which solidified upon standing. $^1$H-NMR (CDCl$_3$, 500 MHz) δ 8.08 (s, 1H), 8.00 (s, 1H), 7.57 (d, J=1.2 Hz, 1H), 5.96 (s, 2H), 5.07 (s, 2H), 3.53 (m, 2H), 3.34 (bs, 1H), 0.85 (m, 2H), −0.08 (s, 9H); $^{13}$C-NMR (CDCl$_3$, 126 MHz) δ 139.0, 135.1, 125.9, 125.3, 124.52 (q, J=272 Hz), 124.51, 124.2 (q,J=33 Hz), 119.3, 80.1, 66.7, 62.6, 17.8, −1.5.

Intermediate 31

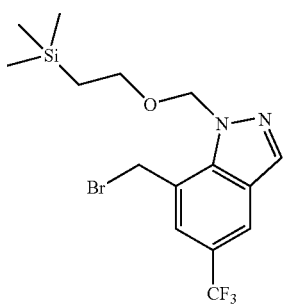

7-(Bromomethyl)-5-(trifluoromethyl)-1-((2-(trimethylsilyl)ethoxy)methyl)-1H-indazole. To a solution of (5-(trifluoromethyl)-1-((2-(trimethylsilyl)ethoxy)methyl)-1H-indazol-7-yl)methanol (980 mg, 2.83 mmol) and carbon tetrabromide (1.41 g, 4.24 mmol) in tetrahydrofuran (10 mL) at 0° C. was added triphenylphosphine (1.11 g, 4.24 mmol). The resulting solution was stirred at room temperature for 30 min. The reaction was diluted with several volumes of pentane and filtered to remove undissolved solids. The organics were concentrated and purified by column chromatography (4%→8% EtOAc/Hex) to give 1.155 g (100%) as a colorless oil. $^1$H-NMR (CDCl$_3$, 500 MHz) δ 8.12 (s, 1H), 8.03 (s, 1H), 7.61 (d, J=1.2 Hz, 1H), 6.05 (s, 2H), 5.01 (s, 2H), 3.52 (m, 2H), 0.87 (m, 2H), −0.08 (s, 9H); $^{13}$C-NMR (CDCl$_3$, 126 MHz) δ 138.4, 135.1, 126.4, 125.7, 124.4 (q, J=33 Hz), 124.3 (q, J=273 Hz), 122.5, 120.1, 80.5, 66.6, 29.7, 17.9, −1.4.

Intermediate 32

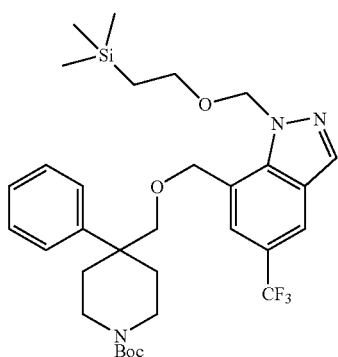

tert-Butyl 4-phenyl-4-((((5-(trifluoromethyl)-1-((2-(trimethylsilyl)ethoxy)methyl)-1H-indazol-7-yl)methoxy)methyl)piperidine-1-carboxylate. To a solution of tert-butyl 4-(hydroxymethyl)-4-phenylpiperidine-1-carboxylate (0.669 g, 2.3 mmol) and 7-(bromomethyl)-5-(trifluoromethyl)-1-((2-(trimethylsilyl)ethoxy)methyl)-1H-indazole (0.94 g, 2.3 mmol) in dimethylformamide (7 mL) at 0° C. was added sodium hydride (60% in mineral oil, 0.119 g, 3.0 mmol). The resulting solution was stirred at 0° C. for 30 min. The reaction was quenched by the cautious addition of saturated ammonium chloride and diluted with diethyl ether. The ethereal was washed with water (2×), then brine, dried over magnesium sulfate, and concentrated. Column chromatography (12% EtOAc/Hex) gave 1.13 g (79%) as an oil. $^1$H-NMR (CDCl$_3$, 500 MHz) δ 8.03 (s, 1H), 7.98 (s, 1H), 7.41 (d, J=0.9 Hz, 1H), 7.10-7.28 (m, 5H), 5.37 (s, 2H), 4.73 (s, 2H), 3.69 (bs, 2H), 3.45 (s, 2H), 3.39 (m, 2H), 3.01 (m, 2H), 2.13 (m, 2H), 1.77 (m, 2H), 1.41 (s, 9H), 0.77 (m, 2H), −0.11 (s, 9H); $^{13}$C-NMR (CDCl$_3$, 126 MHz) δ 155.0 142.7, 139.3, 134.7, 128.4, 127.1, 126.4, 125.6, 124.8, 124.6 (q, J=273 Hz), 123.5 (q, J=32 Hz), 122.1, 119.2, 79.4, 79.2, 79.0, 70.6, 66.1, 41.5, 40.3 (br), 32.2, 28.5, 17.8, −1.4. Mass spec.: 620.15 (MH)$^+$.

Intermediate 33

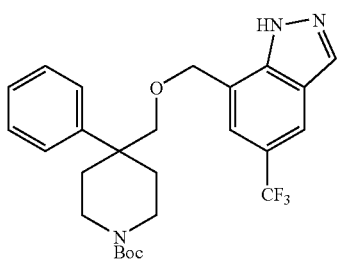

tert-Butyl 4-phenyl-4-(((5-(trifluoromethyl)-1H-indazol-7-yl)methoxy)methyl)piperidine-1-carboxylate. tert-Butyl 4-phenyl-4-((((5-(trifluoromethyl)-1-((2-(trimethylsilyl)ethoxy)methyl)-1H-indazol-7-yl)methoxy)methyl)piperidine-1-carboxylate (1.05 g, 1.7 mmol) was dissolved in trifluoroacetic acid (50% in dichloromethane, 10 mL). The reaction was stirred at room temperature for 3 h and concentrated. The crude trifluoroacetic acid salt was loaded onto a strong cation exchange cartridge in methanol and washed with several volumes of methanol which were discarded. The product was eluted with 2 M ammonia in methanol and concentrated to give 0.65 g. The crude amine was dissolved in dichloromethane (20 mL) and treated with di-tert-butyl dicarbonate (723 mg, 3.31 mmol). The reaction was stirred at room temperature for 1 h. The reaction was quenched by addition of 2 M ammonia in methanol and concentrated. The residue was purified by column chromatography (25%→40% EtOAc/Hex) to give 0.79 g (97%) as a viscous oil. $^1$H-NMR (CDCl$_3$, 500 MHz) δ 9.87 (bs, 1H), 8.03 (s, 1H), 7.91 (s, 1H), 7.46 (m, 2H), 7.37 (m, 3H), 7.25 (s, 1H), 4.71 (s, 2H), 3.71 (m, 2H), 3.56 (s, 2H), 3.08 (m, 2H), 2.23 (m, 2H), 1.80 (m, 2H), 1.42 (s, 9H); $^{13}$C-NMR (CDCl$_3$, 126 MHz) δ 156.5, 155.0, 142.7, 139.5, 135.3, 129.1, 127.2, 127.0, 124.7 (q, J=272 Hz), 123.2 (q, J=33 Hz), 122.9, 121.8, 120.3, 118.4, 80.5, 79.6, 71.8, 41.6, 40.2 (br), 32.4, 28.5, 28.3. Mass spec.: 490.06 (MH)$^+$.

Intermediates 34 and 35

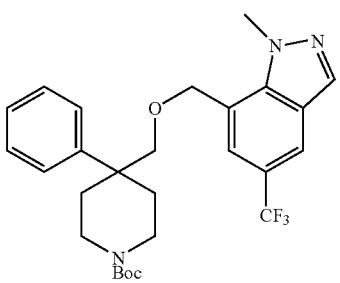

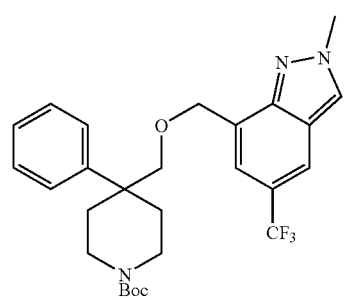

tert-Butyl 4-(((1-methyl-5-(trifluoromethyl)-1H-indazol-7-yl)methoxy)methyl)-4-phenylpiperidine-1-carboxylate and tert-Butyl 4-(((2-methyl-5-(trifluoromethyl)-2H-indazol-7-yl)methoxy)methyl)-4-phenylpiperidine-1-carboxylate. To a solution of tert-butyl 4-phenyl-4-(((5-(trifluoromethyl)-1H-indazol-7-yl)methoxy)methyl)piperidine-1-carboxylate (350 mg, 0.715 mmol) in dimethylformamide (4 mL) at 0° C. was added sodium hydride (60% in mineral oil, 57.2 mg, 1.43 mmol). After 5 min, the reaction was treated with iodomethane (0.089 mL, 1.43 mmol). After 30 min, the reaction was quenched by addition of saturated ammonium chloride and poured into diethyl ether. The organics were washed with water (3×), then brine, dried over magnesium sulfate, and concentrated. Column chromatography (25%→75% EtOAc/Hex) gave two fractions. The faster eluting fraction was concentrated to give tert-butyl 4-(((1-methyl-5-(trifluoromethyl)-1H-indazol-7-yl)methoxy)methyl)-4-phenylpiperidine-1-carboxylate (187 mg, 52%). The second fraction was concentrated to give tert-butyl 4-(((2-methyl-5-(trifluoromethyl)-2H-indazol-7-yl)methoxy)methyl)-4-phenylpiperidine-1-carboxylate (76.5 mg, 21%). tert-Butyl 4-(((1-methyl-5-(trifluoromethyl)-1H-indazol-7-yl)methoxy)methyl)-4-phenylpiperidine-1-carboxylate:
$^1$H-NMR (CDCl$_3$, 500 MHz) δ 7.98 (s, 1H), 7.93 (s, 1H), 7.30 (s, 1H), 7.22 (m, 4H), 7.17 (m, 1H), 4.66 (s, 2H), 3.91 (s, 3H), 3.67 (m, 2H), 3.45 (s, 2H), 3.00 (m, 2H), 2.13 (m, 2H), 1.77 (m, 2H), 1.41 (s, 9H); $^{13}$C-NMR (CDCl$_3$, 126 MHz) δ 155.0, 142.6, 139.4, 133.9, 128.5, 127.1, 126.5, 124.8, 124.7 (q, J=272 Hz), 124.5, 122.5 (q, J=33 Hz), 121.1, 119.7 (q, J=3.8 Hz), 79.4, 79.2, 70.7, 41.5, 40.0 (br), 38.2, 32.2, 28.5. tert-Butyl 4-(((2-methyl-5-(trifluoromethyl)-2H-indazol-7-yl)methoxy)methyl)-4-phenylpiperidine-1-carboxylate:
$^1$H-NMR (CDCl$_3$, 500 MHz) δ 7.98 (s, 1H), 7.88 (s, 1H), 7.42 (m, 2H), 7.37 (m, 2H), 7.29 (s, 1H), 7.25 (m, 1H), 4.85 (s, 2H), 4.22 (s, 3H), 3.76 (m, 2H), 3.58 (s, 2H), 3.09 (m, 2H), 2.24 (m, 2H), 1.97 (m, 2H), 1.46 (s, 9H); $^{13}$C-NMR (CDCl$_3$, 126 MHz) δ 155.1, 147.6, 142.9, 129.2, 128.5, 127.3, 126.4, 125.6, 124.9 (q, J=272 Hz), 124.1 (q, J=33 Hz), 120.7, 118.7, 117.6 (q, J=4.8 Hz), 79.9, 79.3, 68.7, 41.9, 40.7, 40.0 (br), 32.0, 28.6.

Intermediate 36

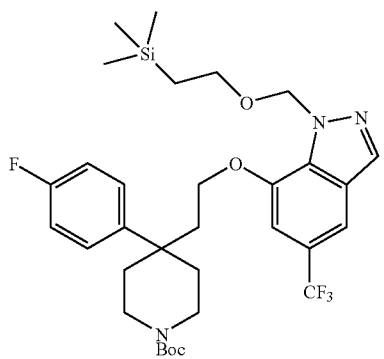

tert-Butyl 4-(4-fluorophenyl)-4-(((5-(trifluoromethyl)-1-((2-(trimethylsilyl)ethoxy)methyl)-1H-indazol-7-yl)methoxy)methyl)piperidine-1-carboxylate. To a solution of tert-butyl 4-(4-fluorophenyl)-4-(hydroxymethyl)piperidine-1-carboxylate (0.16 g, 0.517 mmol) and 7-(bromomethyl)-5-(trifluoromethyl)-1-((2-(trimethylsilyl)ethoxy)methyl)-1H-indazole (0.212 g, 0.517 mmol) in dimethylformamide (6 mL) at 0° C. was added sodium hydride (60% in mineral oil, 0.027 g, 0.672 mmol). The resulting solution was stirred at 0° C. for 30 min. The reaction was quenched by the cautious addition of saturated ammonium chloride and diluted with diethyl ether. The ethereal was washed with water (2×), then brine, dried over magnesium sulfate, and concentrated. Column chromatography (12% EtOAc/Hex) gave 280 mg (85%) as an oil. $^1$H-NMR (CDCl$_3$, 500 MHz) δ 8.16 (s, 1H), 8.10 (s, 1H), 7.51 (s, 1H), 7.24 (m, 2H), 6.98 (m, 2H), 5.58 (s, 2H), 4.86 (s, 2H), 3.78 (m, 2H), 3.55 (s, 2H), 3.52 (m, 2H), 3.11 (m, 2H), 2.19 (m, 2H), 1.87 (m, 2H), 1.53 (s, 9H), 0.89 (m, 2H), 0.00 (s, 9H); $^{13}$C-NMR (CDCl$_3$, 126 MHz) δ 162.3, 160.3, 155.0, 139.2, 138.4, 134.8, 128.63, 128.57, 125.7, 124.8, 124.6 (q, J=272 Hz), 123.5 (q, J=32 Hz), 121.9, 119.3 (q, J=3.8 Hz), 115.2, 115.0, 79.5, 79.2, 78.7, 70.5, 66.2, 41.1, 40.0 (br), 32.3, 28.5, 17.8, −1.4. Mass spec.: 638.12 (MH)$^+$.

Intermediate 37

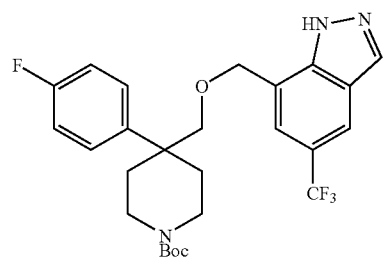

tert-Butyl 4-(4-fluorophenyl)-4-(((5-(trifluoromethyl)-1H-indazol-7-yl)methoxy)methyl)piperidine-1-carboxylate. tert-Butyl 4-(4-fluorophenyl)-4-(((5-(trifluoromethyl)-1-((2-(trimethylsilyl)ethoxy)methyl)-1H-indazol-7-yl)methoxy)methyl)piperidine-1-carboxylate (280 mg, 0.439 mmol) was dissolved in trifluoroacetic acid (50% in dichloromethane, 4 mL). The reaction was stirred at room temperature for 3 h and concentrated. The crude trifluoroacetic acid salt was loaded onto a strong cation exchange cartridge in methanol and washed with several volumes of methanol which were discarded. The product was eluted with 2 M ammonia in methanol and concentrated to give 170 mg. The crude amine was dissolved in dichloromethane (5 mL) and treated with di-tert-butyl dicarbonate (182 mg, 0.835 mmol). The reaction was stirred at room temperature for 1 h. The reaction was quenched by addition of 2 M ammonia in methanol and concentrated. The residue was purified by column chromatography (25%→40% EtOAc/Hex) to give 193 mg (86%) as a viscous oil. $^1$H-NMR (CDCl$_3$, 500 MHz) δ 10.11 (bs, 1H), 8.06 (s, 1H), 7.93 (s, 1H), 7.25-7.35 (m, 3H), 7.08 (m, 2H), 4.73 (s, 2H), 3.69 (m, 2H), 3.50 (s, 2H), 3.05 (m, 2H), 2.15 (m, 2H), 1.79 (m, 2H), 1.42 (s, 9H); $^{13}$C-NMR (CDCl$_3$, 126 MHz) δ 162.6, 160.7, 155.0, 139.6, 138.4, 135.4, 128.7, 128.6, 124.7 (q, J=272 Hz), 123.3 (q, J=32 Hz), 122.9, 121.7, 118.5 (q, J=3.8 Hz), 115.9, 115.8, 80.1, 79.7, 71.6, 41.2, 39.8 (br), 32.5, 28.5, 28.3. Mass spec.: 508.03 (MH)$^+$.

Intermediates 38 and 39

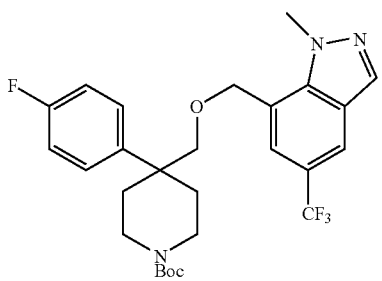

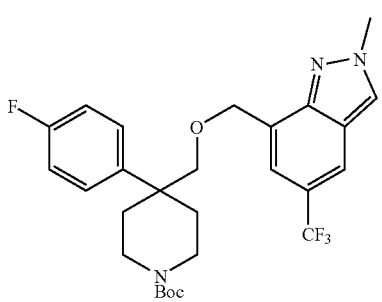

tert-Butyl 4-(4-fluorophenyl)-4-(((1-methyl-5-(trifluoromethyl)-1H-indazol-7-yl)methoxy)methyl)piperidine-1-carboxylate and tert-Butyl 4-(4-fluorophenyl)-4-(((2-methyl-5-(trifluoromethyl)-2H-indazol-7-yl)methoxy)methyl)piperidine-1-carboxylate. To a solution of tert-butyl 4-(4-fluorophenyl)-4-(((5-(trifluoromethyl)-1H-indazol-7-yl)methoxy)methyl)piperidine-1-carboxylate (115 mg, 0.227 mmol) in dimethylformamide (2 mL) at 0° C. was added sodium hydride (60% in mineral oil, 18.1 mg, 0.45 mmol). After 5 min, the reaction was treated with iodomethane (0.028 mL, 0.45 mmol). After 30 min, the reaction was quenched by addition of saturated ammonium chloride and poured into diethyl ether. The organics were washed with water (3×), then brine, dried over magnesium sulfate, and concentrated. Column chromatography (25%→75% EtOAc/Hex) gave two fractions. The faster eluting fraction was concentrated to give tert-butyl 4-(4-fluorophenyl)-4-(((1-methyl-5-(trifluoromethyl)-1H-indazol-7-yl)methoxy)methyl)piperidine-1-carboxylate (66 mg, 56%). The second fraction was concentrated to give tert-butyl 4-(4-fluorophenyl)-4-(((2-methyl-5-(trifluoromethyl)-2H-indazol-7-yl)methoxy)methyl)piperidine-1-carboxylate (26 mg, 22%). tert-Butyl 4-(4-fluorophenyl)-4-(((1-methyl-5-(trifluoromethyl)-1H-indazol-7-yl)methoxy)methyl)piperidine-1-carboxylate: $^1$H-NMR (CDCl$_3$, 500 MHz) δ 8.03 (s, 1H), 7.98 (s, 1H), 7.31 (s, 1H), 7.17 (m, 2H), 6.91 (m, 2H), 4.72 (s, 2H), 4.03 (s, 3H), 3.67 (m, 2H), 3.46 (s, 2H), 3.02 (m, 2H), 2.10 (m, 2H), 1.79 (m, 2H), 1.44 (s, 9H); $^{13}$C-NMR (CDCl$_3$, 126 MHz) δ 162.3, 160.3, 139.6, 135.4, 128.7, 128.6, 124.7 (q, J=272 Hz), 123.3 (q, J=32 Hz), 122.9, 121.8, 120.3 (q, J=2.9 Hz), 118.4 (q, J=4.8 Hz), 115.8, 115.6, 80.4, 71.9, 51.8, 46.3, 40.3, 32.9. tert-Butyl 4-(4-fluorophenyl)-4-(((2-methyl-5-(trifluoromethyl)-2H-indazol-7-yl)methoxy)methyl)piperidine-1-carboxylate: $^1$H-NMR (CDCl$_3$, 500 MHz) δ 8.01 (s, 1H), 7.89 (s, 1H), 7.35 (m, 2H), 7.24 (s, 1H), 7.03 (m, 2H), 4.85 (s, 2H), 4.24 (s, 3H), 3.72 (m, 2H), 3.55 (s, 2H), 3.10 (m, 2H), 2.18 (m, 2H), 1.94 (m, 2H), 1.46 (s, 9H); $^{13}$C-NMR (CDCl$_3$, 126 MHz) δ 162.4, 160.5, 155.1, 147.6, 138.7, 129.0, 128.9, 128.8, 125.6, 124.8 (q, J=273 Hz), 124.1 (q, J=32 Hz), 120.8, 118.8, 117.7 (q, J=4.8 Hz), 115.3, 115.1, 79.6, 79.4, 68.7, 41.4, 40.7, 40.2 (br), 32.2, 28.5.

Intermediate 40

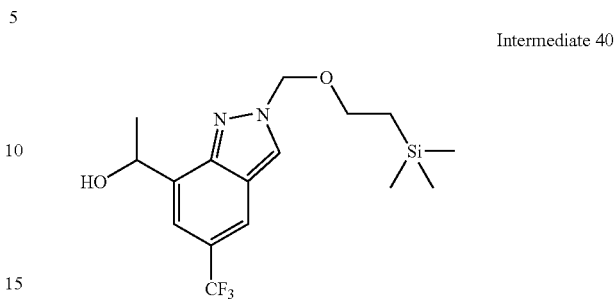

(±)-1-(5-(Trifluoromethyl)-2-((2-(trimethylsilyl)ethoxy)methyl)-2H-indazol-7-yl)ethanol. To a solution of 5-(trifluoromethyl)-2-((2-(trimethylsilyl)ethoxy)methyl)-2H-indazole-7-carbaldehyde (0.5 g, 1.45 mmol) in tetrahydrofuran (10 mL) at −78° C. was added methyl magnesiumbromide (3 M in diethyl ether, 0.97 mL, 2.90 mmol). The reaction was allowed to gradually warm in the ice bath (ca. 1 h) to 0° C. The reaction which had been a suspension became a solution. The reaction was quenched by addition of saturated ammonium chloride and poured into diethyl ether. The ethereal was washed with water (2×), then brine, dried over magnesium sulfate, and concentrated to give 444 mg (85%) as an oil. $^1$H-NMR (CDCl$_3$, 500 MHz) δ 8.23 (s, 1H), 7.93 (s, 1H), 7.39 (s, 1H), 5.73 (s, 2H), 5.38 (q, J=6.4 Hz, 1H), 3.65 (m, 2H), 3.52 (bs, 1H), 1.71 (d, J=6.7 Hz, 3H), 0.94 (m, 2H), −0.03 (s, 9H); $^{13}$C-NMR (CDCl$_3$, 126 MHz) δ 147.3, 136.6, 128.0, 124.8, 124.7 (q, J=273 Hz), 124.7 (q, J=32 Hz), 121.3, 118.4 (q, J=4.8 Hz), 117.4 (q, J=2.9 Hz), 82.1, 68.2, 68.0, 23.4, 17.9, −1.4.

Intermediate 41

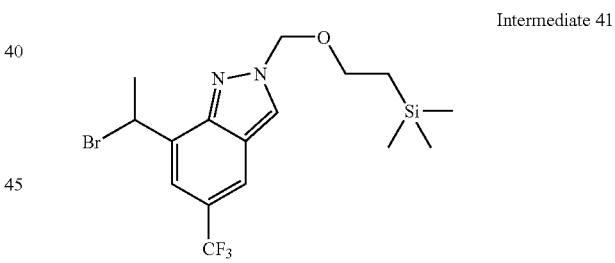

(±)-7-(1-Bromoethyl)-5-(trifluoromethyl)-2-((2-(trimethylsilyl)ethoxy)methyl)-2H-indazole. To a solution of (±)-1-(5-(trifluoromethyl)-2-((2-(trimethylsilyl)ethoxy)methyl)-2H-indazol-7-yl)ethanol (444 mg, 1.23 mmol) and carbon tetrabromide (613 mg, 1.85 mmol) in tetrahydrofuran (5 mL) at 0° C. was added triphenylphosphine (485 mg, 1.85 mmol). The resulting solution was stirred at room temperature for 30 min. The reaction was diluted with several volumes of pentane and filtered to remove undissolved solids. The organics were concentrated and purified by column chromatography (4%→6% EtOAc/Hex) to give 284 mg (55%) as a colorless oil. $^1$H-NMR (CDCl$_3$, 500 MHz) δ 8.27 (s, 1H), 8.00 (s, 1H), 7.58 (s, 1H), 5.90 (q, J=7.0 Hz, 1H), 5.77 (q$_{AB}$, J$_{AB}$=10.4 Hz, 2H), 3.68 (m, 2H), 2.23 (d, J=7.0 Hz, 3H), 0.95 (m, 2H), −0.03 (s, 9H); $^{13}$C-NMR (CDCl$_3$, 126 MHz) δ 146.4, 134.2, 124.9, 124.7 (q, J=32 Hz), 124.6 (q, J=273 Hz), 121.6, 119.7 (q, J=4.8 Hz), 119.3 (q, J=2.9 Hz), 82.2, 68.1, 43.7, 25.5, 18.0, −1.4.

Intermediate 42

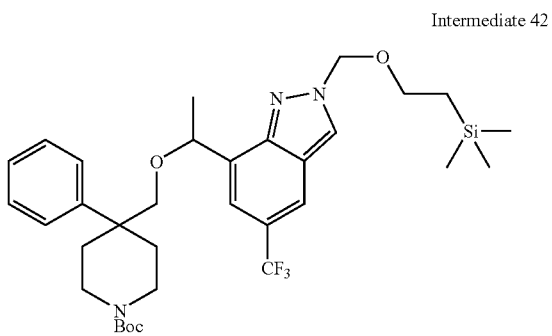

(±)-tert-Butyl 4-phenyl-4-((1-(5-(trifluoromethyl)-2-((2-(trimethylsilyl)ethoxy)methyl)-2H-indazol-7-yl)ethoxy)methyl)piperidine-1-carboxylate. To a solution of (±)-tert-butyl 4-(hydroxymethyl)-4-phenylpiperidine-1-carboxylate (193 mg, 0.66 mmol) and 7-(1-bromoethyl)-5-(trifluoromethyl)-2-((2-(trimethylsilyl)ethoxy)methyl)-2H-indazole (280 mg, 0.66 mmol) in dimethylformamide (2.5 mL) at 0° C. was added sodium hydride (60% in mineral oil, 34.4 mg, 0.86 mmol). The resulting solution was stirred at 0° C. for 30 min. The reaction was quenched by the cautious addition of saturated ammonium chloride and diluted with diethyl ether. The ethereal was washed with water (2×), then brine, dried over magnesium sulfate, and concentrated. Column chromatography (12%→20% EtOAc/Hex) gave 62 mg (15%) as an oil. $^1$H-NMR (CDCl$_3$, 500 MHz) δ 8.24 (s, 1H), 7.94 (s, 1H), 7.32-7.45 (m, 4H), 7.23-7.29 (m, 2H), 5.75 (m, 2H), 5.04 (q, J=6.4 Hz, 1H), 3.81 (m, 2H), 3.67 (m, 2H), 3.44 (q$_{AB}$, J$_{AB}$=9.2 Hz, 2H), 3.10 (m, 2H), 2.23 (m, 2H), 2.03 (m, 2H), 1.52 (d, J=6.4 Hz, 3H), 1.48 (s, 9H), 0.97 (m, 2H), 0.00 (s, 9H); $^{13}$C-NMR (CDCl$_3$, 126 MHz) δ 155.2, 147.4, 142.9, 135.5, 128.5, 127.3, 126.4, 124.8 (q, J=272 Hz), 124.7 (q, J=32 Hz), 124.6, 121.1, 117.9 (q, J=4.8 Hz), 117.3 (q, J=2.9 Hz), 82.0, 79.3, 78.2, 74.1, 67.8, 41.8, 40.3 (br), 31.8, 28.6, 22.8, 17.9, −1.4. Mass spec.: 634.17 (MH)$^+$.

Intermediate 43

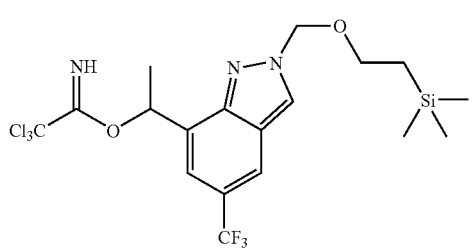

(±)-1-(5-(Trifluoromethyl)-2-((2-(trimethylsilyl)ethoxy)methyl)-2H-indazol-7-yl)ethyl 2,2,2-trichloroacetimidate. To a solution of (±)-1-(5-(trifluoromethyl)-2-((2-(trimethylsilyl)ethoxy)methyl)-2H-indazol-7-yl)ethanol (2.5 g, 6.94 mmol) and trichloroacetonitrile (6.95 mL, 69.4 mmol) in dichloromethane (50 mL) at room temperature was added 1,8-diazabicyclo[5.4.0]undec-7-ene (0.1 mL, 0.66 mmol). After stirring for 4 h, the reaction was concentrated and purified by column chromatography (12% EtOAc/Hex+0.1% Et3N) to give 3.1 g, (89%) as a white powder. $^1$H-NMR (CDCl$_3$, 500 MHz) δ 8.33 (s, 1H), 8.22 (s, 1H), 7.95 (s, 1H), 7.57 (s, 1H), 6.67 (q, J=6.6 Hz, 1H), 5.73 (s, 2H), 3.65 (t, J=8.4 Hz, 2H), 1.80 (d, J=6.6 Hz, 3H), 0.93 (m, 2H), −0.05 (s, 9H). Mass spec.: 526.90 (MH)$^+$.

Intermediate 44

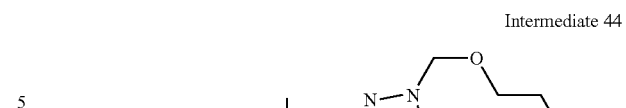
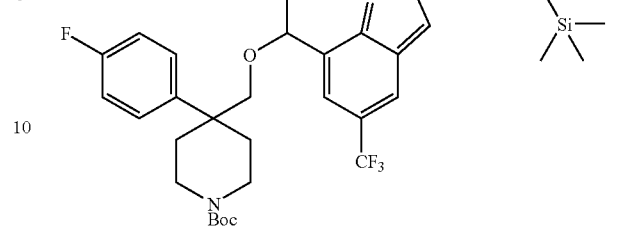

(±)-tert-Butyl 4-(4-fluorophenyl)-4-((1-(5-(trifluoromethyl)-2-((2-(trimethylsilyl)ethoxy)methyl)-2H-indazol-7-yl)ethoxy)methyl)piperidine-1-carboxylate. To a solution of (±)-1-(5-(trifluoromethyl)-2-((2-(trimethylsilyl)ethoxy)methyl)-2H-indazol-7-yl)ethyl 2,2,2-trichloroacetimidate (1.63 g, 3.23 mmol) and tert-butyl 4-(4-fluorophenyl)-4-(hydroxymethyl)piperidine-1-carboxylate (1 g, 3.23 mmol) in dichloromethane (10 mL) at 0° C. was added cyclohexane (10 mL) and tetrafluoroboric acid diethyl ether complex (0.044 mL, 0.323 mmol). The reaction was stirred at 0° C. for 1 h. The reaction was treated with an additional portion of tetrafluoroboric acid diethyl ether complex (25 μL, 0.184 mmol) and stirred at 0° C. for 30 min. The reaction was quenched by addition of triethylamine, diluted with diethyl ether, and poured into water. The ethereal was washed with 1M potassium bisulfate, then 10% sodium hydroxide, then brine, dried over magnesium sulfate, and concentrated. Column chromatography (12%→18% EtOAc/Hex) gave 720 mg, (34%) as a colorless film. $^1$H-NMR (CDCl$_3$, 500 MHz) δ 8.20 (s, 1H), 7.89 (s, 1H), 7.31 (m, 2H), 7.14 (s, 1H), 7.00 (m, 2H), 5.71 (q$_{AB}$, J$_{AB}$=10.4 Hz, 2H), 4.97 (q, J=6.4 Hz, 1H), 3.50-3.60 (m, 4H), 3.38 (q$_{AB}$, J$_{AB}$9.2 Hz, 2H), 3.06 (m, 2H), 2.13 (m, 2H), 1.90 (m, 2H), 1.46 (d, J=6.4 Hz, 3H), 1.43 (s, 9H), 0.92 (m, 2H), −0.05 (s, 9H); $^{13}$C-NMR (CDCl$_3$, 126 MHz) δ 163.7, 162.4, 160.5, 155.1, 147.4, 138.8, 135.4, 128.9, 128.8, 124.8 (q, J=272 Hz), 124.6, 121.1, 118.0 (q, J=5.8 Hz), 117.3, 115.2, 115.0, 82.0, 79.5, 77.9, 74.2, 67.8, 41.3, 40.0 (br), 32.2, 32.1, 28.6, 22.7, 17.9, −1.4. Mass spec.: 652.23 (MH)$^+$.

Intermediates 45 and 46

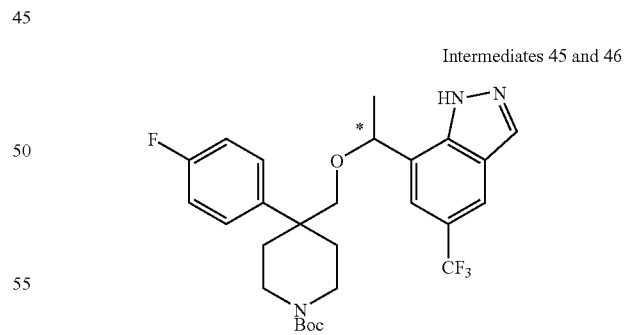

Enantiomers A and B of tert-Butyl 4-(4-fluorophenyl)-4-((1-(5-(trifluoromethyl)-1H-indazol-7-yl)ethoxy)methyl)piperidine-1-carboxylate. (±)-tert-Butyl 4-(4-fluorophenyl)-4-((1-(5-(trifluoromethyl)-2-((2-(trimethylsilyl)ethoxy)methyl)-2H-indazol-7-yl)ethoxy)methyl)piperidine-1carboxylate (600 mg, 0.921 mmol) was dissolved in trifluoroacetic acid (50% in dichloromethane, 10 mL) and stirred at room temperature for 3 h. The reaction was concentrated, loaded onto a strong cation exchange cartridge in methanol. The cartridge was flushed with several volumes of methanol which were discarded. The product was eluted with 2M ammonia in methanol and concentrated. The crude piperidine was dissolved in dichloromethane (10 mL), cooled to 0° C., and treated with di-tert-butyl dicarbonate (0.427 mL, 1.84 mmol). After stirring at 0° C. for 1 h, the reaction was quenched by addition of 2M ammonia in methanol (2 mL) and concentrated. The residue was dissolved in diethyl ether, washed with water, then brine, dried over magnesium sulfate, and concentrated. Column chromatography (25%→37% EtOAc/Hex) gave the racemate (400 mg, 83%) as a foam solid. $^1$H-NMR (CDCl$_3$, 500 MHz) δ 10.11 (bs, 1H), 8.05 (s, 1H), 7.92 (s, 1H), 7.26 (m, 2H), 7.05 (m, 2H), 4.59 (q, J=6.4 Hz, 1H), 3.71 (m, 2H), 3.33 (q$_{AB}$, J$_{AB}$=8.9 Hz, 2H), 3.06 (m, 1H), 2.97 (m, 1H), 2.25 (m, 1H), 2.06 (m, 1H), 1.85 (m, 1H), 1.83 (m, 1H), 1.40-1.46 (m, 12H); $^{13}$C-NMR (CDCl$_3$, 126 MHz) δ 162.7, 160.7, 156.5, 155.0, 138.1, 135.3, 128.72, 128.66, 127.1, 124.7 (q, J=272 Hz), 123.6, 123.3, 119.9 (q, J=2.9 Hz), 118.3 (q, J=4.8 Hz), 115.8, 115.6, 79.7, 79.6, 78.7, 78.4, 41.2, 40.0, 32.5, 32.2, 28.5, 28.3, 22.2. Mass spec.: 522.10 (MH)$^+$. Chiral HPLC (Chiralpak AD-H column, 4.6× 250 mm, 5 μm; Mobile phase=15% EtOH (w/0.1%DEA) in CO2; Temp: 35 C; Flow rate=2.0 mL/min. for 11 min) gave the two individual enantiomers. The faster eluting peak was concentrated to give Enantiomer A of tert-butyl 4-(4-fluorophenyl)-4-((1-(5-(trifluoromethyl)-1H-indazol-7-yl) ethoxy)methyl)piperidine-1-carboxylate (184 mg). The slower eluting peak was concentrated to give Enantiomer B of tert-butyl 4-(4-fluorophenyl)-4-((1-(5-(trifluoromethyl)-1H-indazol-7-yl)ethoxy)methyl)piperidine-1-carboxylate (188 mg).

treated with iodomethane (0.027 mL, 0.43 mmol). After 30 min, the reaction was quenched by addition of saturated ammonium chloride and poured into diethyl ether. The organics were washed with water (3×), then brine, dried over magnesium sulfate, and concentrated. Column chromatography (25%→75% EtOAc/Hex) gave two fractions. Concentration of the first fraction gave Enantiomer A of tert-butyl 4-(4-fluorophenyl)-4-((1-(1-methyl-5-(trifluoromethyl)-1H-indazol-7-yl)ethoxy)methyl)piperidine-1-carboxylate (49.5 mg, 43%). Concentration of the second fraction gave Enantiomer A of tert-butyl 4-(4-fluorophenyl)-4-((1-(2-methyl-5-(trifluoromethyl)-2H-indazol-7-yl)ethoxy)methyl)piperidine-1-carboxylate (61 mg, 53%). Enantiomer A of tert-butyl 4-(4-fluorophenyl)-4-((1-(1-methyl-5-(trifluoromethyl)-1H-indazol-7-yl)ethoxy)methyl)piperidine-1-carboxylate:
$^1$H-NMR (CDCl$_3$, 500 MHz) δ 8.02 (s, 1H), 7.90 (s, 1H), 7.35 (s, 1H), 7.23 (m, 2H), 6.97 (m, 2H), 4.88 (q, J=6.4 Hz, 1H), 4.09 (s, 3H), 3.71 (m, 2H), 3.28 (q$_{AB}$, J$_{AB}$=8.9 Hz, 2H), 3.02 (m, 2H), 2.11 (m, 2H), 1.83 (m, 2H), 1.49 (d, J=6.7 Hz, 3H), 1.43 (s, 9H); $^{13}$C-NMR (CDCl$_3$, 126 MHz) δ 162.5, 160.5, 155.0, 138.6, 138.4, 134.3, 128.8, 128.7, 127.5, 125.3, 124.7 (q, J=272 Hz), 123.1 (q, J=33 Hz), 120.9, 118.6 (q, J=4.8 Hz), 115.3, 115.1, 79.5, 77.7, 75.0, 41.2, 40.1 (br), 40.0, 32.3, 32.2, 28.5, 23.3. Mass spec.: 536.2 (MH)$^+$. Enantiomer A of tert-butyl 4-(4-fluorophenyl)-4-((1-(2-methyl-5-(trifluoromethyl)-2H-indazol-7-yl)ethoxy)methyl)piperidine-1-carboxylate: $^1$H-NMR (CDCl$_3$, 500 MHz) δ 7.98 (s, 1H), 7.83 (s, 1H), 7.30 (m, 2H), 7.14 (s, 1H), 6.99 (m, 2H), 4.94 (q, J=6.7 Hz, 1H), 4.21 (s, 3H), 3.69 (m, 2H), 3.36 (q$_{AB}$, J$_{AB}$=9.2 Hz, 2H), 3.06 (m, 2H), 2.12 (m, 2H), 1.92 (m, 2H), 1.46 (d, J=6.4 Hz, 3H), 1.43 (s, 9H); $^{13}$C-NMR (CDCl$_3$, 126 MHz) δ 162.4, 160.5, 155.1, 147.7, 138.9, 134.6, 128.9, 128.8, 125.5, 124.8 (q, J=272 Hz), 124.3 (q, J=32 Hz), 121.1, 117.4 (q, J=4.8 Hz), 117.0 (q, J=2.9 Hz), 115.1, 115.0, 79.4, 77.8, 74.2, 65.9, 41.3, 40.7, 40.2 (br), 32.3, 32.1, 28.5, 22.7, 15.3. Mass spec.: 536.20 (MH)$^+$.

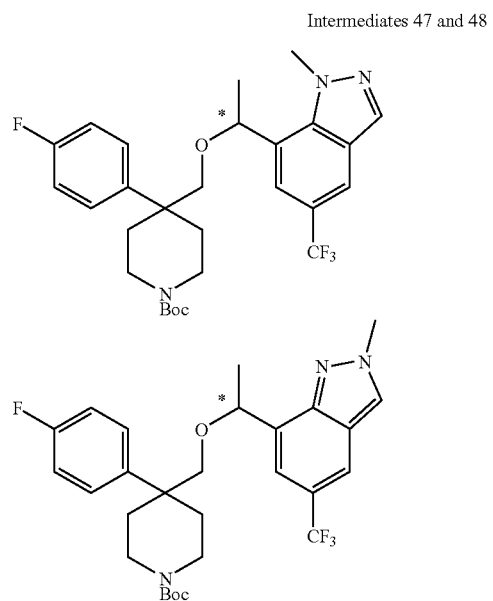

Intermediates 47 and 48

Enantiomer A of tert-Butyl 4-(4-fluorophenyl)-4-((1-(1-methyl-5-(trifluoromethyl)-1H-indazol-7-yl)ethoxy)methyl) piperidine-1-carboxylate and Enantiomer A of tert-Butyl 4-(4-fluorophenyl)-4-((1-(2-methyl-5-(trifluoromethyl)-2H-indazol-7-yl)ethoxy)methyl)piperidine-1-carboxylate. To a solution of Enantiomer A of tert-butyl 4-(4-fluorophenyl)-4-((1-(5-(trifluoromethyl)-1H-indazol-7-yl)ethoxy)methyl)piperidine-1-carboxylate (113 mg, 0.217 mmol) in dimethylformamide (2 mL) at 0° C. was added sodium hydride (60% in oil, 17 mg, 0.43 mmol). After 5 min, the reaction was

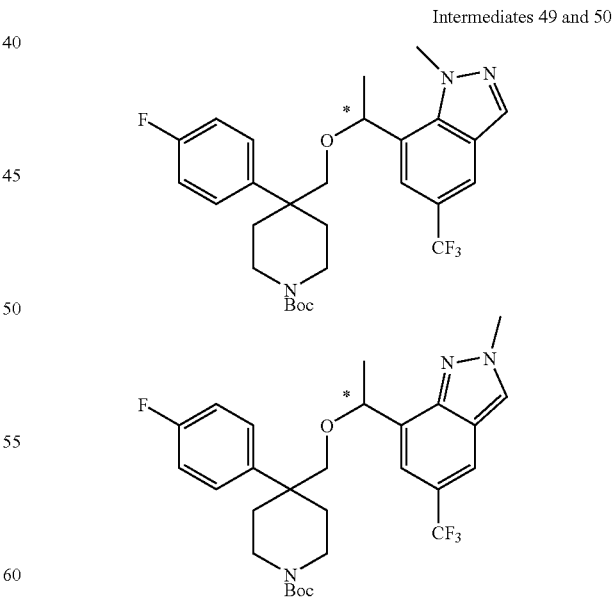

Intermediates 49 and 50

Enantiomer B of tert-Butyl 4-(4-fluorophenyl)-4-((1-(1-methyl-5-(trifluoromethyl)-1H-indazol-7-yl)ethoxy)methyl) piperidine-1-carboxylate and Enantiomer B of tert-Butyl 4-(4-fluorophenyl)-4-((1-(2-methyl-5-(trifluoromethyl)-2H-indazol-7-yl)ethoxy)methyl)piperidine-1-carboxylate. To a solution of Enantiomer B of tert-butyl 4-(4-fluorophenyl)-4-((1-(5-(trifluoromethyl)-1H-indazol-7-yl)ethoxy)methyl)piperidine-1-carboxylate (116 mg, 0.222 mmol) in dimethylformamide (2 mL) at 0° C. was added sodium hydride (60% in oil, 18 mg, 0.45 mmol). After 5 min, the reaction was treated with iodomethane (0.028 mL, 0.45 mmol). After 30 min, the reaction was quenched by addition of saturated ammonium chloride and poured into diethyl ether. The organics were washed with water (3×), then brine, dried over magnesium sulfate, and concentrated. Column chromatography (25%→75% EtOAc/Hex) gave two fractions. Concentration of the first fraction gave Enantiomer B of tert-butyl 4-(4-fluorophenyl)-4-((1-(1-methyl-5-(trifluoromethyl)-1H-indazol-7-yl)ethoxy)methyl)piperidine-1-carboxylate (52 mg, 44%). The second fraction was concentrated to give Enantiomer B of tert-butyl 4-(4-fluorophenyl)-4-((1-(2-methyl-5-(trifluoromethyl)-2H-indazol-7-yl)ethoxy)methyl)piperidine-1-carboxylate (64 mg, 54%). Enantiomer B of tert-butyl 4-(4-fluorophenyl)-4-((1-(1-methyl-5-(trifluoromethyl)-1H-indazol-7-yl)ethoxy)methyl)piperidine-1-carboxylate: $^1$H-NMR (CDCl$_3$, 500 MHz) δ 8.02 (s, 1H), 7.90 (s, 1H), 7.35 (s, 1H), 7.23 (m, 2H), 6.97 (m, 2H), 4.88 (q, J=6.4 Hz, 1H), 4.09 (s, 3H), 3.71 (m, 2H), 3.28 (q$_{AB}$, J$_{AB}$=8.9 Hz, 2H), 3.02 (m, 2H), 2.11 (m, 2H), 1.83 (m, 2H), 1.49 (d, J=6.7 Hz, 3H), 1.43 (s, 9H); $^{13}$C-NMR (CDCl$_3$, 126 MHz) δ 162.5, 160.5, 155.0, 138.6, 138.4, 134.3, 128.8, 128.7, 127.5, 125.3, 124.7 (q, J=272 Hz), 123.1 (q, J=33 Hz), 120.9, 118.6 (q, J=4.8 Hz), 115.3, 115.1, 79.5, 77.7, 75.0, 41.2, 40.1 (br), 40.0, 32.3, 32.2, 28.5, 23.3. Mass spec.: 536.2 (MH)$^+$. Enantiomer B of tert-butyl 4-(4-fluorophenyl)-4-((1-(2-methyl-5-(trifluoromethyl)-2H-indazol-7-yl)ethoxy)methyl)piperidine-1-carboxylate: $^1$H-NMR (CDCl$_3$, 500 MHz) δ 7.98 (s, 1H), 7.83 (s, 1H), 7.30 (m, 2H), 7.14 (s, 1H), 6.99 (m, 2H), 4.94 (q, J=6.7 Hz, 1H), 4.21 (s, 3H), 3.69 (m, 2H), 3.36 (q$_{AB}$, J$_{AB}$=9.2 Hz, 2H), 3.06 (m, 2H), 2.12 (m, 2H), 1.92 (m, 2H), 1.46 (d, J=6.4 Hz, 3H), 1.43 (s, 9H); $^{13}$C-NMR (CDCl$_3$, 126 MHz) δ 162.4, 160.5, 155.1, 147.7, 138.9, 134.6, 128.9, 128.8, 125.5, 124.8 (q, J=272 Hz), 124.3 (q, J=32 Hz), 121.1, 117.4 (q, J=4.8 Hz), 117.0 (q, J=2.9 Hz), 115.1, 115.0, 79.4, 77.8, 74.2, 65.9, 41.3, 40.7, 40.2 (br), 32.3, 32.1, 28.5, 22.7, 15.3. Mass spec.: 536.20 (MH)$^+$.

boxylate. tert-Butyl 4-(((5-bromo-1-((2-(trimethylsilyl)ethoxy)methyl)-1H-indazol-7-yl)methoxy)methyl)-4-phenylpiperidine-1-carboxylate (55 mg, 0.09 mmol) was dissolved in dry tetrahydrofuran (1.5 mL) and stirred at room temperature for 15 min. The stirred mixture was cooled to −78° C. and treated with a solution of tert-butyllithium (1.7M in pentane, 103 µL, 0.17 mmol) over several minutes. The mixture was stirred at −78° C. for 20 min, quenched by addition of a few drops of methanol and concentrated. Flash chromatography on silica gel (20% ethyl acetate/hexanes) afforded 34 mg (91%) as a clear oil. $^1$H-NMR (CDCl$_3$, 300 MHz) δ 7.93 (s, 1H), 7.66 (dd, J=7.0, 1.1 Hz, 1H), 7.04-7.23 (m, 7H), 5.38 (s, 2H), 4.70 (s, 2H), 3.39 (s, 2H), 3.35-3.41 (m, 2H), 2.94-3.03 (m, 2H), 2.05-2.09 (m, 2H), 1.71-1.80 (m, 2H), 1.39 (s, 9H), 0.72-0.78 (m, 2H), 0.14 (s, 9H). Mass spec.: 552.15 (MH)$^+$.

Intermediate 52

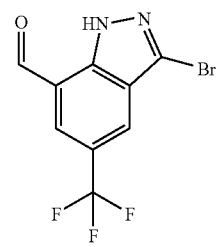

3-Bromo-5-(trifluoromethyl)-1H-indazole-7-carbaldehyde. To a mixture of 5-(trifluoromethyl)-1H-indazole-7-carbaldehyde (270 mg, 1.26 mmol) in acetic acid (5 mL) was added bromine (97 µL, 1.89 mmol) slowly over 5 min. After 1 h, the reaction mixture was diluted with methylene chloride, washed with water (2×), saturated sodium thiosulfate (2×), saturated sodium bicarbonate (2×), brine (2×), dried over sodium sulfate, and concentrated to afford 340 mg (92%) as a yellow powder. $^1$H-NMR (CDCl$_3$, 300 MHz) δ 10.18 (s, 1H), 8.22 (s, 1H), 8.15 (s, 1H). Mass spec.: 294.81 (MH)$^+$.

Intermediate 51

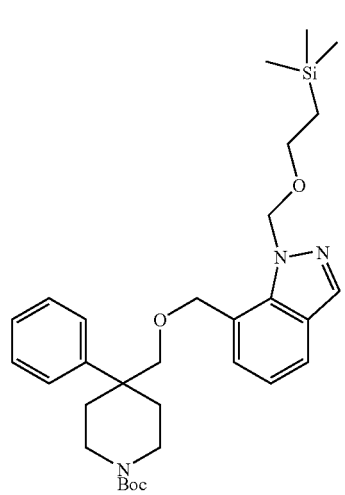

tert-Butyl 4-phenyl-4-(((1-((2-(trimethylsilyl)ethoxy)methyl)-1H-indazol-7-yl)methoxy)methyl)piperidine-1-car- Intermediate 53

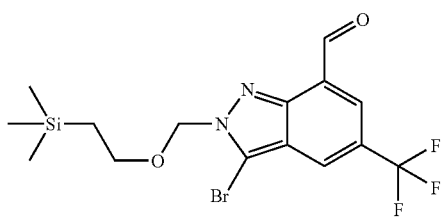

3-Bromo-5-(trifluoromethyl)-2-((2-(trimethylsilyl)ethoxy)methyl)-2H-indazole-7-carbaldehyde. 3-Bromo-5-(trifluoromethyl)-1H-indazole-7-carbaldehyde (340 mg, 1.16 mmol) and N-methyldicyclohexylamine (335 µL, 1.57 mmol) were suspended in tetrahydrofuran (6 mL), cooled to 0° C., and treated with (2-(chloromethoxy)ethyl)trimethylsilane (257 µL, 1.45 mmol). Cooling was removed and stirring continued for 4 h. The reaction was poured into ethyl acetate, washed with water (3×), 1M potassium bisulfate (2×), brine (2×), dried over sodium sulfate, and concentrated. Column chromatography on silica gel (10% ethyl acetate/hexanes)

gave 400 mg (81%) as a faint yellow oil. ¹H-NMR (CDCl₃, 300 MHz) δ 10.25 (s, 1H), 8.14 (s, 1H), 8.08 (s, 1H), 5.95 (s, 2H), 3.41-3.43 (m, 2H), 0.69-0.75 (m, 2H), 0.20 (s, 9H). Mass spec.: 446.87 (MNa)⁺.

Intermediate 54

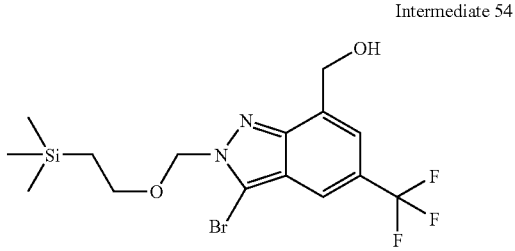

(3-Bromo-5-(trifluoromethyl)-2-((2-(trimethylsilyl)ethoxy)methyl)-2H-indazol-7-yl)methanol 3-Bromo-5-(trifluoromethyl)-2-((2-(trimethylsilyl)ethoxy)methyl)-2H-indazole-7-carbaldehyde (400 mg, 0.95 mmol) was suspended in ethanol (5 mL), cooled to 0° C., and treated sodium borohydride (18 mg, 0.47 mmol) in one portion. Cooling was removed and the reaction stirred at room temperature for 1 h. The reaction was cooled to 0° C. and treated with saturated aqueous ammonium chloride. The reaction was concentrated to remove most of the ethanol and diluted with ethyl acetate. The layers were separated and the organic layer washed with brine (2×), dried over sodium sulfate, filtered and concentrated. Flash chromatography on silica gel afforded 220 mg (55%) as a light yellow oil. ¹H-NMR (CDCl₃, 300 MHz) δ 7.86 (s, 1H), 7.61 (s, 1H), 5.86 (s, 2H), 5.02 (s, 2H), 3.51-3.56 (m, 2H), 0.79-0.85 (m, 2H), 0.09 (s, 9H). Mass spec.: 448.82 (MNa)⁺.

Intermediate 55

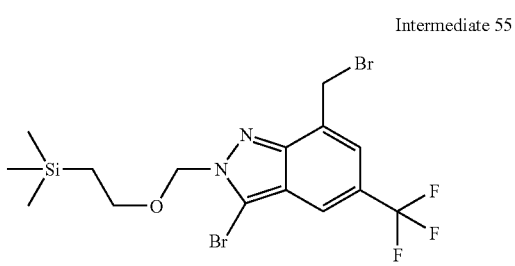

3-Bromo-7-(bromomethyl)-5-(trifluoromethyl)-2-((2-(trimethylsilyl)ethoxy)methyl)-2H-indazole. (3-Bromo-5-(trifluoromethyl)-2-((2-(trimethylsilyl)ethoxy)methyl)-2H-indazol-7-yl)methanol (198 mg, 0.48 mmol) and triphenylphosphine (253 mg, 0.96 mmol) were combined in tetrahydrofuran (3 mL) and cooled to 0° C. N-Bromosuccinimide (180 mg, 1.01 mmol) was introduced in portions and the reaction allowed to warm to room temperature. After 16 h, the reaction mixture was diluted with ethyl acetate, washed with sodium bicarbonate (2×), brine (2×), dried over sodium sulfate, and concentrated. Column chromatography on silica gel (5% ethyl acetate/hexanes) gave 140 mg (61%) as a light brown oil. ¹H-NMR (CDCl₃, 300 MHz) δ 7.90 (s, 1H), 7.64 (s, 1H), 5.94 (s, 2H), 4.95 (s, 2H), 3.51-3.57 (m, 2H), 0.82-0.87 (m, 2H), 0.08 (s, 9H).

Intermediate 56

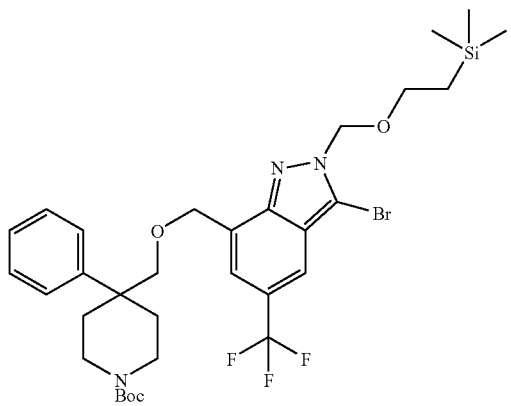

tert-Butyl 4-(((3-bromo-5-(trifluoromethyl)-2-((2-(trimethylsilyl)ethoxy)methyl)-2H-indazol-7-yl)methoxy)methyl)-4-phenylpiperidine-1-carboxylate. 3-Bromo-7-(bromomethyl)-5-(trifluoromethyl)-2-((2-(trimethylsilyl)ethoxy)methyl)-2H-indazole (140 mg, 0.29 mmol) and tert-butyl 4-(hydroxymethyl)-4-phenylpiperidine-1-carboxylate (75 mg, 0.26 mmol) were combined in dimethylformamide (2 mL) and cooled to 0° C. The reaction was treated with sodium hydride (14 mg, 0.57 mmol), stirred at 0° C. for 1 h, and at room temperature for 30 min. The reaction mixture was diluted with water and extracted with ethyl acetate (2×). The organic layers were pooled together, washed with brine (2×), dried over sodium sulfate, and concentrated. Column chromatography on silica gel (10%→20% ethyl acetate/hexanes) gave 101 mg (50%) as an oil. ¹H-NMR (CDCl₃, 500 MHz) δ 7.86 (s, 1H), 7.44 (s, 1H), 7.14-7.18 (m, 5H), 5.26 (s, 2H), 4.68 (s, 2H), 3.69 (m, 2H), 3.44 (s, 2H), 3.38-3.41 (m, 2H), 2.98-3.02 (m, 2H), 2.11-2.14 (m, 2H), 1.72-1.77 (m, 2H), 1.41 (s, 9H), 0.74-0.77 (m, 2H), 0.10 (s, 9H). Mass spec.: 700.11 (MH)⁺.

Intermediate 57

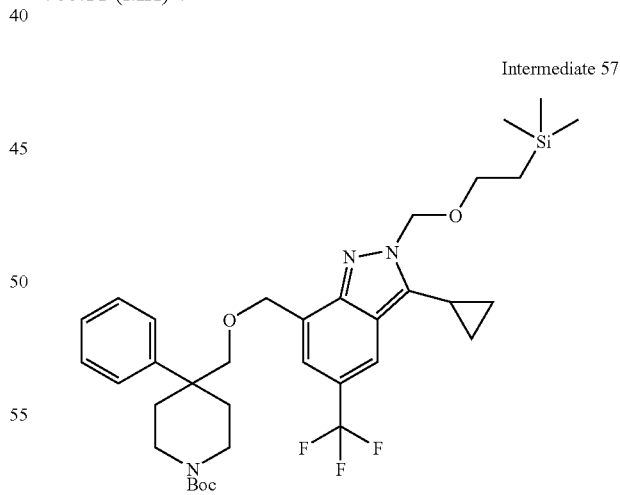

tert-Butyl 4-(((3-cyclopropyl-5-(trifluoromethyl)-2-((2-(trimethylsilyl)ethoxy)methyl)-2H-indazol-7-yl)methoxy)methyl)-4-phenylpiperidine-1-carboxylate. tert-Butyl 4-(((3-bromo-5-(trifluoromethyl)-2-((2-(trimethylsilyl)ethoxy)methyl)-2H-indazol-7-yl)methoxy)methyl)-4-phenylpiperidine-1-carboxylate (36 mg, 0.05 mmol), cyclopropylboronic acid (13 mg, 0.16 mmol), and tetrakis(triphenylphosphine) palladium(0) (6 mg, 0.005 mmol) were combined in dry tetrahydrofran (2 mL) in a microwave tube and sealed. The mixture was flushed with nitrogen then 180 μL of a 1 N potassium hydroxide aqueous solution was introduced. The mixture was heated at 100° C. for 1 h via microwave. After cooling to room temperature, the reaction mixture was diluted with ethyl acetate, washed with water (2×), then brine (2×), dried over sodium sulfate, and concentrated. Flash chromatography on silica gel (15% ethyl acetate/hexanes) gave 18 mg (53%). ¹H-NMR (CDCl₃, 500 MHz) δ 7.99 (s, 1H), 7.37 (s, 1H), 7.15-7.21 (m, 5H), 5.30 (s, 2H), 4.68 (s, 2H), 3.68 (m, 2H), 3.43 (s, 2H), 3.35-3.38 (m, 2H), 2.98-3.02 (m, 2H), 2.10-2.19 (m, 3H), 1.74-1.79 (m, 2H), 1.41 (s, 9H), 1.03-1.06 (m, 4H), 0.73-0.76 (m, 2H), 0.11 (s, 9H). Mass spec.: 660.31 (MH)⁺.

Intermediate 58

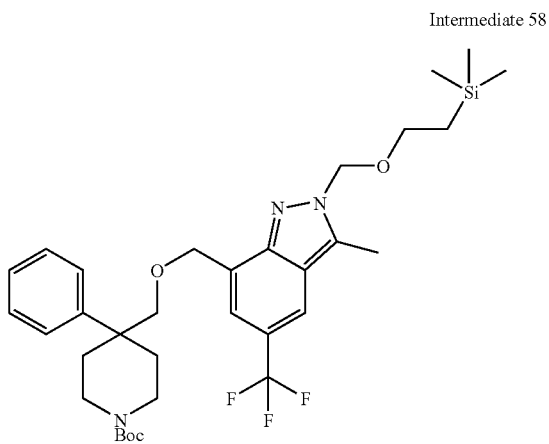

tert-Butyl 4-(((3-methyl-5-(trifluoromethyl)-2-((2-(trimethylsilyl)ethoxy)methyl)-2H-indazol-7-yl)methoxy)methyl)-4-phenylpiperidine-1-carboxylate. tert-Butyl 4-phenyl-4-(((5-(trifluoromethyl)-2-((2-(trimethylsilyl)ethoxy)methyl)-2H-indazol-7-yl)methoxy)methyl)piperidine-1-carboxylate (97 mg, 0.16 mmol) was dissolved in dry tetrahydrofuran (3 mL) and stirred at room temperature for 15 min. The stirred mixture was cooled to −78° C. and treated with a solution of tert-butyllithium (1.7 M in pentane, 190 μL, 0.33 mmol). The reaction was gradually warmed to −20° C. over 1 h, cooled to −78° C. and treated with iodomethane (10 μL, 0.19 mmol). The reaction was warmed to 0° C. over several hours then treated with saturated ammonium chloride. The reaction was diluted with ethyl acetate. The layers were separated and the organic layer washed with brine (2×), dried over sodium sulfate, filtered and concentrated to afford 100 mg (quant.) as a clear oil. LC/MS (HPLC method 1): t_R=3.70 min, 634.26(MH)⁺.

Intermediate 59

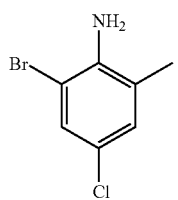

2-Bromo-4-chloro-6-methylaniline. 4-Chloro-2-methylaniline (1.0 g, 7.06 mmol), potassium bromide (1.01 g, 8.47 mmol), and ammonium heptamolybdate tetrahydrate (87 mg, 0.07 mmol) were suspended in acetic acid (7 mL, 122 mmol) and cooled to 0° C. The reaction was treated with sodium perborate tetrahydrate (1.2 g, 7.77 mmol), stirred at 0° C. for 30 min, and at room temperature for 2 h. The mixture was poured into water, neutralized with saturated sodium bicarbonate and extracted with ethyl acetate (2×). The organic layers were pooled together, washed with brine (2×), dried over sodium sulfate, and concentrated to afford 1.2 g (78%). ¹H-NMR (CDCl₃, 500 MHz) δ 7.28 (s, 1H), 6.97 (s, 1H), 4.03 (bs, 2H), 2.17 (s, 3) Mass spec.: 221.90 (MH)⁺.

Intermediate 60

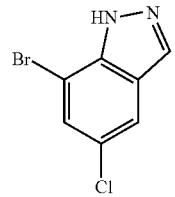

7-Bromo-5-chloro-1H-indazole. 2-Bromo-4-chloro-6-methylaniline (13.2 g, 59.90 mmol) was suspended in 24% hydrochloric acid (40 mL). The stirred mixture was cooled to 0° C. and treated with sodium nitrite (4.54 g, 65.90 mmol) in water (10 mL), dropwise over 30 min. The mixture was then buffered to ca. pH 5 with sodium acetate. This mixture was kept at 0° C. and added in portions to a stirred solution of 2-methyl-2-propanethiol (6.8 mL, 59.9 mmol) in ethanol (40 mL) at 0° C. over 30 min. After the addition, the mixture was stirred at 0° C. for 30 min then transferred to crushed ice, and extracted with ethyl acetate (2×). The organics were pooled together, washed with brine (2×), dried over sodium sulfate, filtered, and concentrated. The resulting residue was dissolved in dimethyl sulfoxide (50 mL) and transferred to a solution of potassium tert-butoxide (53.7 g, 479 mmol) in dimethyl sulfoxide (200 mL) at 0° C. via cannula. The ice-bath was removed and stirring continued for 30 min. The reaction was then poured into a mixture of crushed ice (400 mL) and 10% hydrochloric acid (200 mL) to give a precipitate which was collected by filtration. The resulting solid was triturated with hexanes to afford 7.5 g (54%) as a brown powder. ¹H-NMR (CDCl₃, 300 MHz) δ 7.97 (s, 1H), 7.60 (s, 1H), 7.44 (s, 1H). Mass spec.: 232.90 (MH)⁺.

Intermediate 61

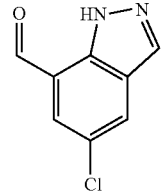

5-Chloro-1H-indazole-7-carbaldehyde. 7-Bromo-5-chloro-1H-indazole (0.44 g, 1.90 mmol) and sodium hydride were combined in tetrahydrofuran (5 mL) at 0° C. After 15 min, cooling was removed and the mixture stirred at room temperature for 20 min. The stirred mixture was cooled to −78° C. and treated with a solution of tert-butyllithium in pentane (1.7 M, 2.4 mL, 3.99 mmol) over several minutes. The mixture was allowed to gradually warm to −20° C. over 1 h, re-cooled to −78° C. and treated with dimethylformamide (220 μL, 2.85 mmol). The reaction was warmed to 0° C. over several hours, then treated with saturated ammonium chloride. The reaction was diluted with ethyl acetate. The layers were separated. The organic layer was washed with brine (2×), dried over sodium sulfate, filtered and concentrated to afford 0.3 g (87%) as a white powder. LC/MS (HPLC method 1): $t_R$=1.88 min, 181.02(MH)$^+$.

brown oil. $^1$H-NMR (CDCl$_3$, 300 MHz) δ 8.00 (s, 1H), 8.21 (s, 1H), 7.50 (d, J=1.8 Hz, 1H), 7.13 (m, 1H), 5.65 (s, 2H), 5.28 (q, J=6.2 Hz, 1H), 3.57-3.62 (m, 2H), 1.64 (d, J=6.2 Hz, 3H), 0.86-0.92 (m, 2H), 0.07 (s, 9H). Mass spec.: 327.04 (MH)$^+$.

Intermediate 62

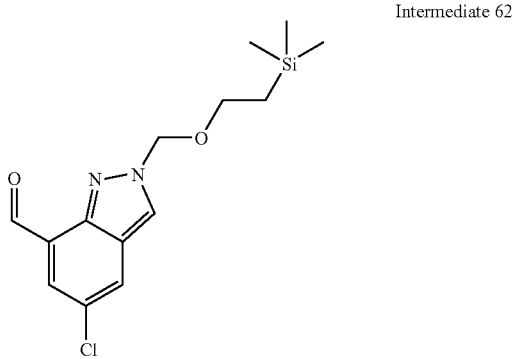

5-Chloro-2-((2-(trimethylsilyl)ethoxy)methyl)-2H-indazole-7-carbaldehyde. 5-Chloro-1H-indazole-7-carbaldehyde (5.6 g, 31.0 mmol) and N-methyldicyclohexylamine (9 mL, 41.9 mmol) were suspended in tetrahydrofuran (100 mL), cooled to 0° C., and treated with (2-(chloromethoxy)ethyl)trimethylsilane (8.3 mL, 46.5 mmol). Cooling was removed and stirring continued for 4 h. The reaction was poured into ethyl acetate, washed with water (3×), 1 M potassium bisulfate (2×), brine (2×), dried over sodium sulfate, and concentrated. Column chromatography on silica gel (25% ethyl acetate/hexanes) gave 5.6 g (58%) as a faint yellow oil. $^1$H-NMR (CDCl$_3$, 300 MHz) δ 10.50 (s, 1H), 8.21 (s, 1H), 7.94 (d, J=2.2 Hz, 1H), 7.82 (d, J=1.8 Hz, 1H), 5.78 (s, 2H), 3.62-3.67 (m, 2H), 0.90-0.96 (m, 2H), 0.05 (s, 9H). Mass spec.: 332.98 (MNa)$^+$.

Intermediate 64

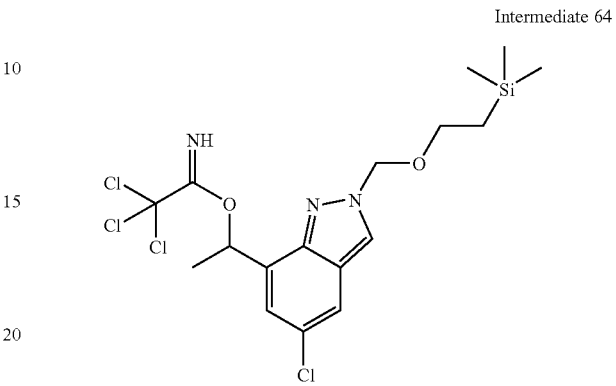

(±)-1-(5-Chloro-2-((2-(trimethylsilyl)ethoxy)methyl)-2H-indazol-7-yl)ethyl 2,2,2-trichloroacetimidate. (±)-1-(5-Chloro-2-((2-(trimethylsilyl)ethoxy)methyl)-2H-indazol-7-yl)ethanol (0.54 g, 1.65 mmol) was dissolved in diethyl ether (5 mL), cooled to 0° C. and treated with 1,8-diazabicyclo(5.4.0)undec-7-ene (50 µL, 0.33 mmol). The reaction was stirred for 10 min and treated with trichloroacetonitrile (250 µL, 2.48 mmol) dropwise over 10 min. The reaction was allowed to warm to room temperature overnight and concentrated. Flash chromatography on silica gel (5% ethyl acetate/hexanes) gave 600 mg (77%) as an oil. $^1$H-NMR (CDCl$_3$, 300 MHz) δ 8.34 (s, 1H), 8.02 (s, 1H), 7.56 (d, J =1.5 Hz, 1H), 7.33 (m, 1H), 6.62 (q, J=6.2 Hz, 1H), 5.68 (s, 2H), 3.59-3.65 (m, 2H), 1.79 (m, 3H), 0.88-0.94 (m, 2H), 0.05 (s, 9H).

Intermediate 63

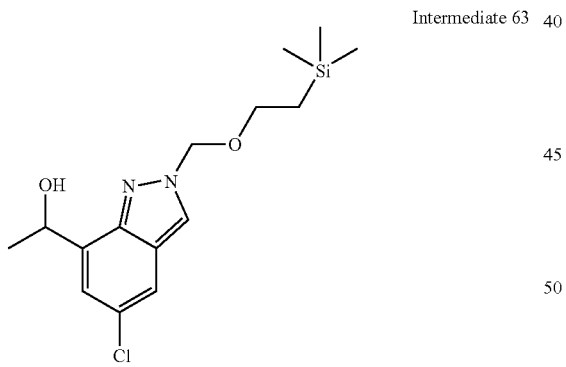

(±)-1-(5-Chloro-2-((2-(trimethylsilyl)ethoxy)methyl)-2H-indazol-7-yl)ethanol. 5-Chloro-2-((2-(trimethylsilyl)ethoxy)methyl)-2H-indazole-7-carbaldehyde (0.88 g, 2.83 mmol) was dissolved in tetrahydrofuran (10 mL), cooled to −78° C. and treated with methylmagnesium bromide (3.0 M in diethyl ether, 0.9 mL, 2.83 mmol) over several minutes. After 1 h, cooling was removed and stirring continued for 1 h at room temperature. The reaction was cooled to 0° C., treated with saturated ammonium chloride and diluted with ethyl acetate. The layers were separated. The organic layer was washed with water (2×), brine (2×), dried over sodium sulfate, filtered and concentrated. Flash chromatography on silica gel (30% ethyl acetate/hexanes) afforded 540 mg (58%) as a light Intermediate 65

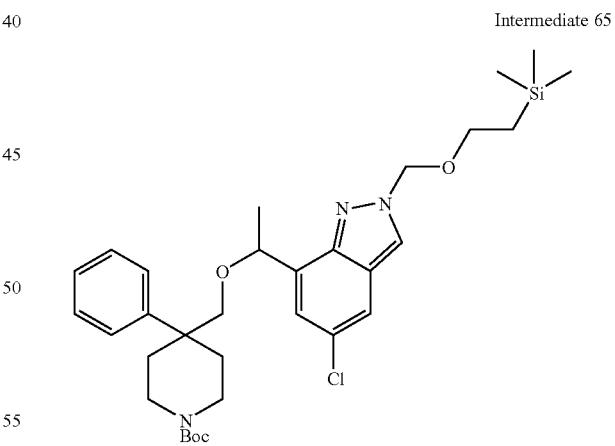

(±)-tert-Butyl 4-((1-(5-chloro-2-((2-(trimethylsilyl)ethoxy)methyl)-2H-indazol-7-yl)ethoxy)methyl)-4-phenylpiperidine-1-carboxylate. (±)-1-(5-Chloro-2-((2-(trimethylsilyl)ethoxy)methyl)-2H-indazol-7-yl)ethyl 2,2,2-trichloroacetimidate (600 mg, 1.27 mmol) and tert-butyl 4-(hydroxymethyl)-4-phenylpiperidine-1-carboxylate (0.41 g, 1.40 mmol) were combined in a dichloromethane/cyclohexane mixture (1:1, 8 mL) and cooled to 0° C. The reaction was treated with tetrafluoroboric acid-diethyl ether complex (40 µL, 0.26 mmol), stirred at 0° C. for 1 h, quenched by addition of saturated sodium bicarbonate, and diluted with diethyl ether. The layers were separated. The ethereal was washed with water (2×), 1M potassium bisulfate (2×), brine (2×), dried over sodium sulfate, and concentrated. Column chromatography on silica gel (18% ethyl acetate/hexanes) gave 380 mg (50%) as a yellow film. $^1$H-NMR (CDCl$_3$, 300 MHz) δ 7.96 (s, 1H), 7.45 (d, J=1.8 Hz, 1H), 7.28-7.35 (m, 4H), 7.17-7.23 (m, 1H), 6.86 (m, 1H), 5.62 (s, 2H), 4.93 (q, J=6.2 Hz, 1H), 3.72 (m, 2H), 3.55-3.60 (m, 2H), 3.38 (d, J=9.2 Hz, 1H), 3.34 (d, J=8.8 Hz, 1H), 2.97-3.08 (m, 2H), 2.10-2.21 (m, 2H), 1.91-1.97 (m, 2H), 1.42 (d, J=6.2 Hz, 3H), 1.41 (s, 9H), 0.82-0.87 (m, 2H), 0.08 (s, 9H). Mass spec.: 600.22 (MH)$^+$.

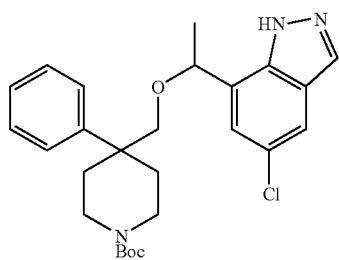

Intermediate 66

(±)-tert-Butyl 4-((1-(5-chloro-1H-indazol-7-yl)ethoxy)methyl)-4-phenylpiperidine-1-carboxylate. (±)-tert-Butyl 4-((1-(5-chloro-2-((2-(trimethylsilyl)ethoxy)methyl)-2H-indazol-7-yl)ethoxy)methyl)-4-phenylpiperidine-1-carboxylate (0.28 g, 0.06 mmol) was treated with a trifluoroacetic acid/methylene chloride mixture (1:1, 4 mL) for 3 h. The solvent was removed in vacuo and the resulting crude mixture passed through a strong cation exchange column. After washing the column with several volumes of methanol, the product was eluted by washing the column with 2 M ammonia in methanol. The solvent was concentrated to afford a crude product which was dissolved in dichloromethane (2 mL), cooled to 0° C., and treated with di-tert-butyl carbonate (204 mg, 0.93 mmol). After 1 h, the reaction was treated with a few drops of 2 M ammonia in methanol and concentrated. The residue was dissolved in ethyl acetate, washed with water (2×), brine (2×), dried over sodium sulfate, filtered and concentrated. Flash chromatography on silica gel (30% ethyl acetate/hexanes) afforded 170 mg (78%) as an oil. $^1$H-NMR (CDCl$_3$, 500 MHz) δ 7.85 (s, 1H), 7.52 (d, J=1.8 Hz, 1H), 7.28-7.39 (m, 5H), 6.95 (m, 1H), 4.49 (q, J=6.4 Hz, 1H), 3.72 (m, 2H), 3.36 (m, 2H), 3.36 (d, J=8.9 Hz, 1H), 3.27 (d, J=8.9 Hz, 1H), 2.97-3.06 (m, 2H), 2.07-2.29 (m, 2H), 1.72-1.85 (m, 2H), 1.40 (s, 9H), 1.39 (m, 3H). Mass spec.: 470.16 (MH)$^+$.

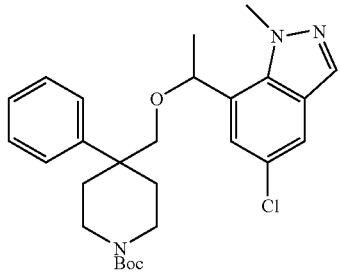

Intermediates 67 and 68

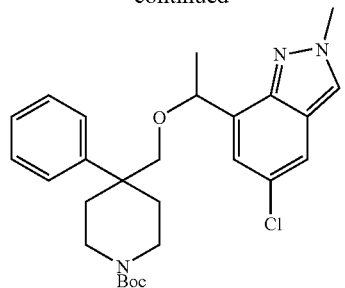

(±)-tert-Butyl 4-((1-(5-chloro-1-methyl-1H-indazol-7-yl)ethoxy)methyl)-4-phenylpiperidine-1-carboxylate and (±)-tert-Butyl 4-((1-(5-chloro-2-methyl-2H-indazol-7-yl)ethoxy)methyl)-4-phenylpiperidine-1-carboxylate. (±)-tert-Butyl 4-((1-(5-chloro-1H-indazol-7-yl)ethoxy)methyl)-4-phenylpiperidine-1-carboxylate (80 mg, 0.17 mmol), iodomethane (21.0 μL, 0.15 mmol) and sodium hydride (60% in mineral oil, 27 mg, 0.68 mmol) were combined in dimethylformamide (2 mL) at 0° C. After 30 min, the reaction was quenched by addition of concentrated ammonium chloride, poured into ethyl acetate and the layers separated. The organic layer was washed with water (2×), brine (2×), dried over sodium sulfate, filtered and concentrated. Flash chromatography on silica gel (30% ethyl acetate/hexanes) gave (±)-tert-butyl 4-((1-(5-chloro-2-methyl-2H-indazol-7-yl)ethoxy)methyl)-4-phenylpiperidine-1-carboxylate (27 mg, 33%) and (±)-tert-butyl 4-((1-(5-chloro-1-methyl-1H-indazol-7-yl)ethoxy)methyl)-4-phenylpiperidine-1-carboxylate (22 mg, 27%). (±)-tert-Butyl 4-((1-(5-chloro-2-methyl-2H-indazol-7-yl)ethoxy)methyl)-4-phenylpiperidine-1-carboxylate: $^1$H-NMR (CDCl$_3$, 500 MHz) δ 7.84 (s, 1H), 7.53 (d, J=2.1 Hz, 1H), 7.27-7.32 (m, 4H), 7.20-7.23 (m, 1H), 7.07 (d, J=1.8 Hz, 1H), 4.75 (q, J=6.4 Hz, 1H), 3.96 (s, 3H), 3.72 (m, 2H), 3.34 (d, J=9.2 Hz, 1H), 3.22 (d, J=9.5 Hz, 1H), 2.98-3.05 (m, 2H), 2.15 (m, 2H), 1.80-1.86 (m, 2H), 1.43 (m, 3H), 1.42 (s, 9H). Mass spec.: 484.13(MH)$^+$. (±)-tert-Butyl 4-((1-(5-chloro-1-methyl-1H-indazol-7-yl)ethoxy)methyl)-4-phenylpiperidine-1-carboxylate: LC/MS (HPLC method 1): $t_R$=3.39 min, 484.21(MH)$^+$.

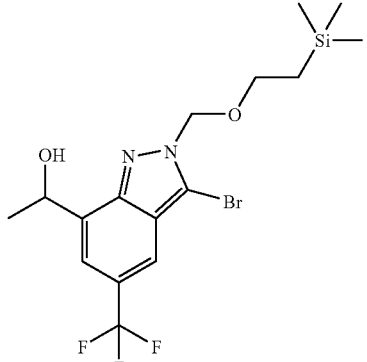

Intermediate 69

(±)-1-(3-Bromo-5-(trifluoromethyl)-2-((2-(trimethylsilyl)ethoxy)methyl)-2H-indazol-7-yl)ethanol 3-Bromo-5-(trifluoromethyl)-2-((2-(trimethylsilyl)ethoxy)methyl)-2H-indazole-7-carbaldehyde (1. 10 g, 2.60 mmol) was dissolved in tetrahydrofuran (10 mL), cooled to −78° C. and treated with a solution of methylmagnesium bromide (3.0 M in diethyl ether, 0.87 mL, 2.60 mmol) over several minutes. After 1 h, cooling was removed and stirring continued for 1 h at room temperature. The reaction was cooled to 0° C., treated with saturated ammonium chloride and diluted with ethyl acetate. The layers were separated and the organic layer washed with water (2×), brine (2×), dried over sodium sulfate, filtered and concentrated. Flash chromatography on silica gel (30% ethyl acetate/hexanes) afforded 1.07 g (94%) as a light brown oil. $^1$H-NMR (CDCl$_3$, 300 MHz) δ 7.86 (s, 1H), 7.80 (s, 1H), 5.94 (d, J=11.7 Hz, 1H), 5.83 (d, J=12.1 Hz, 1H), 5.61 (q, J=6.6 Hz, 1H), 3.51-3.57 (m, 2H), 1.69 (d, J=6.6 Hz, 3H), 0.80-0.86 (m, 2H), 0.09 (s, 9H). Mass spec.: 462.87 (MNa)$^+$.

Intermediate 70

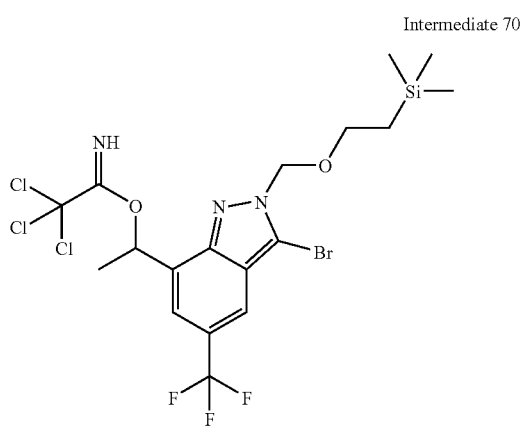

(±)-1-(3-Bromo-5-(trifluoromethyl)-2-((2-(trimethylsilyl)ethoxy)methyl)-2H-indazol-7-yl)ethyl 2,2,2-trichloroacetimidate. (±)-1-(3-Bromo-5-(trifluoromethyl)-2-((2-(trimethylsilyl)ethoxy)methyl)-2H-indazol-7-yl)ethanol (1.07 g, 2.44 mmol) was dissolved in diethyl ether (10 mL), cooled to 0° C. and treated with 1,8-diazabicyclo(5.4.0)undec-7-ene (70 μL, 0.49 mmol). The reaction was stirred for 10 min and treated with trichloroacetonitrile (370 μL, 3.65 mmol) dropwise over 10 min. The reaction was allowed to warm to room temperature overnight and concentrated. Flash chromatography on silica gel (5% ethyl acetate/hexanes) gave 1.29 g (91%) as an oil. $^1$H-NMR (CDCl$_3$, 300 MHz) δ 8.25 (s, 1H), 7.86 (s, 1H), 6.66 (q, J=6.6 Hz, 1H), 6.27 (d, J=11.7 Hz, 1H), 5.68 (d, J=11.7 Hz, 1H), 3.52-3.59 (m, 2H), 1.77 (d, J=6.6 Hz, 3H), 0.82-0.87 (m, 2H), 0.05 (s, 9H).

Intermediate 71

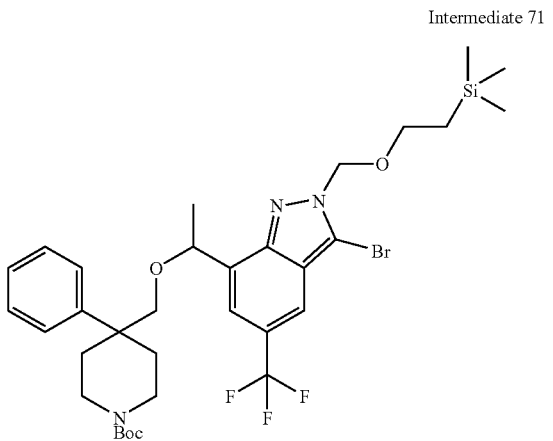

(±)-tert-Butyl 4-((1-(3-bromo-5-(trifluoromethyl)-2-((2-(trimethylsilyl)ethoxy)methyl)-2H-indazol-7-yl)ethoxy)methyl)-4-phenylpiperidine-1-carboxylate. (±)-1-(3-Bromo-5-(trifluoromethyl)-2-((2-(trimethylsilyl)ethoxy)methyl)-2H-indazol-7-yl)ethyl 2,2,2-trichloroacetimidate (1.29 g, 2.21 mmol) and tert-butyl 4-(hydroxymethyl)-4-phenylpiperidine-1-carboxylate (0.71 g, 2.43 mmol) were combined in a dichloromethane/cyclohexane mixture (1:1, 8 mL) and cooled to 0° C. The reaction was treated with tetrafluoroboric acid-diethyl ether complex (60 μL, 0.44 mmol), stirred at 0° C. for 1 h, quenched by addition of saturated sodium bicarbonate and diluted with diethyl ether and the layers separated. The ethereal was washed with water (2×), 1 M potassium bisulfate (2×), brine (2×), dried over sodium sulfate, and concentrated. Column chromatography on silica gel (10% ethyl acetate/hexanes) gave 840 mg (53%) as a yellow film. $^1$H-NMR (CDCl$_3$, 500 MHz) δ 7.82 (s, 1H), 7.54 (s, 1H), 7.24-7.27 (m, 2H), 7.18-7.22 (m, 3H), 5.51 (s, 2H), 5.07 (q, J=6.4 Hz, 1H), 3.74 (m, 2H), 3.44-3.51 (m, 2H), 3.27 (d, J=9.2 Hz, 1H), 3.24 (d, J=9.2 Hz, 1H), 2.99-3.03 (m, 2H), 2.11-2.16 (m, 2H), 1.82-1.88 (m, 2H), 1.50 (d, J=6.4 Hz, 3H), 1.43 (s, 9H), 0.70-0.83 (m, 2H), 0.08 (s, 9H). Mass spec.: 736.03 (MNa)$^+$.

Intermediate 72

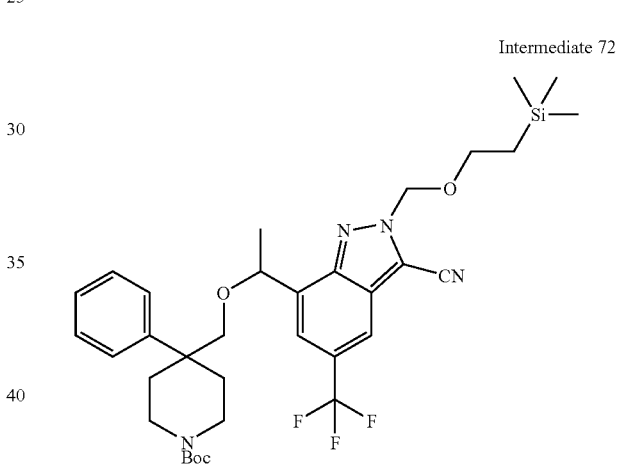

(±)-tert-Butyl 4-((1-(3-cyano-5-(trifluoromethyl)-2-((2-(trimethylsilyl)ethoxy)methyl)-2H-indazol-7-yl)ethoxy)methyl)-4-phenylpiperidine-1-carboxylate. A microwave tube was charged with (±)-tert-butyl 4-((1-(3-bromo-5-(trifluoromethyl)-2-((2-(trimethylsilyl)ethoxy)methyl)-2H-indazol-7-yl)ethoxy)methyl)-4-phenylpiperidine-1-carboxylate (290 mg, 0.41 mmol), tetrakis(triphenylphosphine) palladium(0) (47 mg, 0.04 mmol) and zinc cyanide (96 mg, 0.81 mmol). The tube was flushed with nitrogen and treated with dimethylformamide (3 mL). The tube was sealed and heated at 120° C. for 1 h via microwave. The reaction was cooled, poured into ethyl acetate, washed with water (2×), then brine (2×), dried over sodium sulfate, and concentrated. Column chromatography (15% ethyl acetate/hexanes) gave 95 mg (35%) as an oil. $^1$H-NMR (CDCl$_3$, 500 MHz) δ 8.04 (s, 1H), 7.58 (s, 1H), 7.16-7.23 (m, 5H), 5.54 (s, 2H), 5.12 (q, J=6.4 Hz, 1H), 3.73 (m, 2H), 3.42-3.46 (m, 2H), 3.27 (d, J=8.9 Hz, 1H), 3.23 (d, J=8.9 Hz, 1H), 2.96-3.01 (m, 2H), 2.09-2.16 (m, 2H), 1.79-1.84 (m, 2H), 1.53 (d, J=6.4 Hz, 3H), 1.43 (s, 9H), 0.71-0.84 (m, 2H), 0.08 (s, 9H). Mass spec.: 681.16 (MNa)$^+$.

Intermediate 73

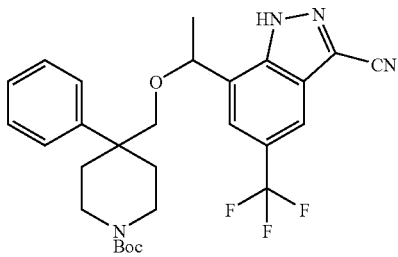

(±)-tert-Butyl 4-((1-(3-cyano-5-(trifluoromethyl)-1H-indazol-7-yl)ethoxy)methyl)-4-phenylpiperidine-1-carboxylate. (±)-tert-Butyl 4-((1-(3-cyano-5-(trifluoromethyl)-2-((2-(trimethylsilyl)ethoxy)methyl)-2H-indazol-7-yl)ethoxy)methyl)-4-phenylpiperidine-1-carboxylate (95 mg, 0.14 mmol) was treated with a trifluoroacetic acid/methylene chloride mixture (1:1, 2 mL) for 3 h. The solvent was removed in vacuo and the resulting crude mixture passed through a strong cation exchange column. After washing the column with several volumes of methanol, the product was eluted by washing the column with 2 M ammonia in methanol. The solvent was concentrated to afford a crude product which was dissolved in dichloromethane (3 mL), cooled to 0° C., and treated with di-tert-butyl carbonate (63 mg, 0.29 mmol) and triethylamine (30 μL, 0.22 mmol). After 1 h, the reaction was treated with a few drops of 2 M ammonia in methanol and concentrated. The residue was dissolved in ethyl acetate, washed with water (2×), brine (2×), dried over sodium sulfate, filtered and concentrated. Flash chromatography on silica gel (15% ethyl acetate/hexanes) afforded 40 mg (53%). $^1$H-NMR (CDCl$_3$, 500 MHz) δ 7.99 (s, 1H), 7.38-7.46 (m, 3H), 7.31-7.33 (m, 3H), 4.70 (q, J=6.7 Hz, 1H), 4.46 (m, 2H), 3.78-3.79 (m, 2H), 3.55 (d, J=8.9 Hz, 1H), 3.35 (d, J=8.9 Hz, 1H), 2.98-3.12 (m, 2H), 2.08-2.40 (m, 2H), 1.68-1.87 (m, 2H), 1.46 (m, 3H), 1.43 (s, 9H). Mass spec.: 529.19 (MH)$^+$.

Intermediate 74

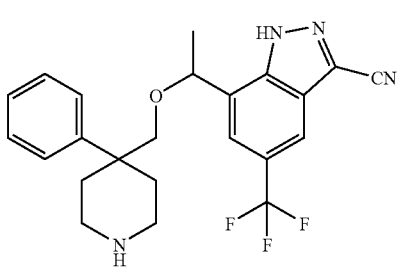

(±)-7-(1-((4-Phenylpiperidin-4-yl)methoxy)ethyl)-5-(trifluoromethyl)-1H-indazole-3-carbonitrile. (±)-tert-Butyl 4-((1-(3-cyano-5-(trifluoromethyl)-1H-indazol-7-yl)ethoxy)methyl)-4-phenylpiperidine-1-carboxylate (40 mg, 0.08 mmol) was treated with a trifluoroacetic acid/methylene chloride mixture (1:1, 2 mL) for 1 h. The solvent was removed in vacuo and the resulting crude mixture passed through a strong cation exchange column. After washing the column with several volumes of methanol, the product was eluted by washing the column with 2 M ammonia in methanol. The solvent was evaporated to afford 25 mg (77%) as a clear oil. $^1$H-NMR (CDCl$_3$, 500 MHz) δ 7.89 (s, 1H), 7.54 (d, J=1.8 Hz, 1H), 7.37-7.40 (m, 2H), 7.30-7.32 (m, 3H), 7.69 (m, 1H), 4.49 (q, J=6.7 Hz, 1H), 3.40 (q, J=9.2 Hz, 1H), 3.29 (d, J=9.2 Hz, 1H), 2.87-2.93 (m, 2H), 2.67-2.77 (m, 2H), 2.07-2.26 (m, 2H), 1.78-1.93 (m, 2H), 1.41 (m, 3H); $^{13}$C-NMR (126 MHz, CDCl$_3$) δ ppm 143.2, 138.4, 129.4, 129.1, 127.2, 127.0, 126.0 (q, J=32.6 Hz), 124.7, 124.1 (q, J=273 Hz), 121.0, 120.3, 116.6, 77.3, 50.6, 42.4, 41.7, 33.1, 22.3. Mass spec.: 429.13 (MH)$^+$.

Intermediate 75

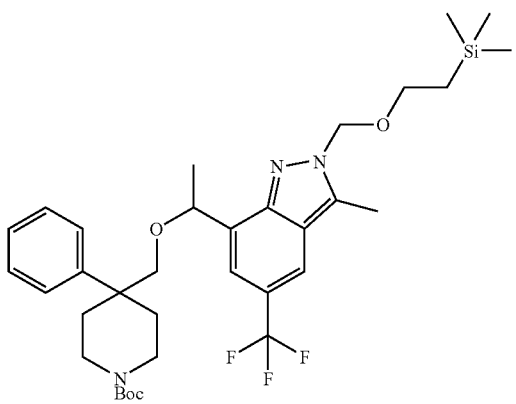

(±)-tert-Butyl 4-((1-(3-methyl-5-(trifluoromethyl)-2-((2-(trimethylsilyl)ethoxy)methyl)-2H-indazol-7-yl)ethoxy)methyl)-4-phenylpiperidine-1-carboxylate. A microwave tube was charged with (±)-tert-butyl 4-((1-(3-bromo-5-(trifluoromethyl)-2-((2-(trimethylsilyl)ethoxy)methyl)-2H-indazol-7-yl)ethoxy)methyl)-4-phenylpiperidine-1-carboxylate (170 mg, 0.24 mmol), tetrakis(triphenylphosphine) palladium(0) (28 mg, 0.02 mmol) and trimethylboroxine (100 μL, 0.72 mmol). The tube was flushed with nitrogen, treated with tetrahydrofuran (3 mL) and potassium hydroxide (2 M in water, 240 μL, 0.48 mmol). The tube was sealed and heated at 100° C. for 1 h via microwave. The reaction was cooled, poured into ethyl acetate, washed with water (2×), then brine (2×), dried over sodium sulfate, and concentrated. Column chromatography (15% ethyl acetate/hexanes) gave 98 mg (63%) as an oil. $^1$H-NMR (CDCl$_3$, 500 MHz) δ 7.82 (s, 1H), 7.49 (s, 1H), 7.25-7.30 (m, 4H), 7.18-7.21 (m, 1H), 5.52 (s, 2H), 5.07 (q, J=6.1 Hz, 1H), 3.71-3.73 (m, 2H), 3.40-3.47 (m, 2H), 3.27 (d, J=8.9 Hz, 1H), 3.23 (d, J=9.2 Hz, 1H), 2.98-3.03 (m, 2H), 2.55 (s, 3H), 2.12-2.14 (m, 2H), 1.85-1.91 (m, 2H), 1.47 (m, 3H), 1.43 (s, 9H), 0.72-0.82 (m, 2H), 0.09 (s, 9H). Mass spec.: 648.23 (MH)$^+$.

Intermediate 76

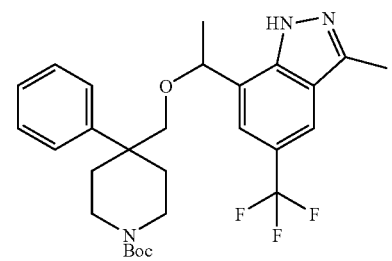

(±)-tert-Butyl 4-((1-(3-methyl-5-(trifluoromethyl)-1H-indazol-7-yl)ethoxy)methyl)-4-phenylpiperidine-1-carboxylate. (±)-tert-Butyl 4-((1-(3-methyl-5-(trifluoromethyl)-2-((2-(trimethylsilyl)ethoxy)methyl)-2H-indazol-7-yl)ethoxy)methyl)-4-phenylpiperidine-1-carboxylate (94 mg, 0.15 mmol) was treated with a trifluoroacetic acid/methylene chloride mixture (1:1, 2 mL) for 1 h. The solvent was removed in vacuo and the resulting crude mixture passed through a strong cation exchange column. After washing the column with several volumes of methanol, the product was eluted by washing the column with 2 M ammonia in methanol. The solvent was concentrated to afford a crude product which was dissolved in dichloromethane (3 mL), cooled to 0° C., and treated with di-tert-butyl carbonate (63 mg, 0.29 mmol) and triethylamine (30 μL, 0.22 mmol). After 1 h, the reaction was treated with a few drops of 2 M ammonia in methanol and concentrated. The residue was dissolved in ethyl acetate, washed with water (2×), brine (2×), dried over sodium sulfate, filtered and concentrated. Flash chromatography on silica gel (15% ethyl acetate/hexanes) afforded 62 mg (83%). $^1$H-NMR (CDCl$_3$, 500 MHz) δ 7.81 (s, 1H), 7.38-7.41 (m, 2H), 7.30-7.35 (m, 3H), 7.19 (m, 1H), 4.56 (q, J=6.4 Hz, 1H), 3.76 (m, 2H), 3.40 (d, J=9.2 Hz, 1H), 3.29 (d, J=8.9 Hz, 1H), 2.99-3.06 (m, 2H), 2.54 (s, 3H), 2.11-2.31 (m, 2H), 1.75-1.87 (m, 2H), 1.42 (s, 9H), 1.40 (m, 3H). Mass spec.: 518.28 (MH)$^+$.

Intermediate 77

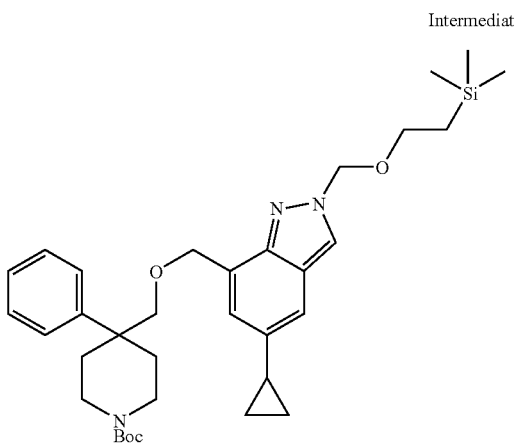

tert-Butyl 4-(((5-cyclopropyl-2-((2-(trimethylsilyl)ethoxy)methyl)-2H-indazol-7-yl)methoxy)methyl)-4-phenylpiperidine-1-carboxylate. tert-Butyl 4-(((5-bromo-2-((2-(trimethylsilyl)ethoxy)methyl)-2H-indazol-7-yl)methoxy)methyl)-4-phenylpiperidine-1-carboxylate (42 mg, 0.07 mmol), cyclopropyl boronic acid (17.2 mg, 0.2 mmol), and tetrakis(triphenylphosphine) palladium(0) (7.7 mg, 0.007 mmol) were combined in dry tetrahydrofran (2 mL) in a microwave tube and sealed. After flushing the mixture with nitrogen, 0.24 mL of a 1 N potassium hydroxide aqueous solution was introduced. The mixture was heated at 100° C. for 1 h via microwave. After cooling to room temperature, the reaction mixture was concentrated and purified by flash chromatography on silica gel to afford 34 mg (86%). $^1$H-NMR (CDCl$_3$, 300 MHz) δ 7.86 (s, 1H), 7.32 (m, 1H), 7.14-7.23 (m, 5H), 6.94 (m, 1H), 5.32 (s, 2H), 4.65 (s, 2H), 3.61-3.85 (m, 2H), 3.39 (s, 2H), 3.32-3.38 (m, 2H), 2.95-3.02 (m, 2H), 2.06-2.11 (m, 2H), 1.93-1.96 (m, 1H), 1.71-1.80 (m, 2H), 1.39 (s, 9H), 0.92-0.97 (m, 2H), 0.64-0.78 (m, 4H), 0.13 (s, 9H). Mass spec.: 592.24 (MH)$^+$.

Intermediate 78

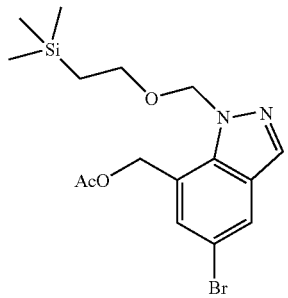

(5-Bromo-1-((2-(trimethylsilyl)ethoxy)methyl)-1H-indazol-7-yl)methyl acetate. To a solution of 5-bromo-7-(bromomethyl)-1-((2-(trimethylsilyl)ethoxy)methyl)-1H-indazole (940 mg, 2.237 mmol) in dimethylformamide (10 mL) at room temperature was added potassium acetate (659 mg, 6.71 mmol). After 10 min, the reaction was placed in a 40° C. bath and stirred for 1 h. The reaction was cooled to room temperature, diluted with diethyl ether, washed with water (2×), then brine, dried over magnesium sulfate, and concentrated to give 1.04 g (quant.) as a colorless oil. $^1$H-NMR (CDCl$_3$, 500 MHz) δ 7.95 (s, 1H), 7.86 (d, J=1.8, 1H), 7.55 (d, J=1.2, 1H), 5.81 (s, 2H), 5.52 (s, 2H), 3.49 (m, 2H), 2.08 (s, 3H), 0.84 (m, 2H), −0.09 (s, 9H; $^{13}$C NMR (126 MHz, CDCl$_3$) δ ppm 170.2, 137.1, 133.4, 132.2, 128.1, 124.1, 120.9, 114.1, 79.6, 66.3, 63.0, 21.1, 17.8, −1.4.

Intermediate 79

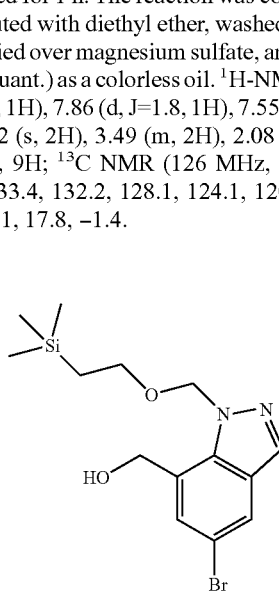

(5-Bromo-1-((2-(trimethylsilyl)ethoxy)methyl)-1H-indazol-7-yl)methanol. To a solution of (5-bromo-1-((2-(trimethylsilyl)ethoxy)methyl)-1H-indazol-7-yl)methyl acetate (1.04 g, 2.60 mmol) in methanol (15 mL, 371 mmol) at room temperature was added potassium carbonate (200 mg, 1.45 mmol). After 20 min, the reaction was concentrated and the resulting residue partitioned between water and diethyl ether. The ethereal was washed with water (2×), then brine, dried over magnesium sulfate, and concentrated. Column chromatography (12%→25% EtOAc/Hex) gave 0.73 g (78%) as a colorless oil that solidified to an amorphous white solid upon standing. $^1$H-NMR (CDCl$_3$, 500 MHz) δ 7.91 (s, 1H), 7.81 (d, J=1.5, 1H), 7.43 (d, J=1.8, 1H), 5.90 (s, 2H), 4.97 (d, J=6.4, 2H), 3.49 (m, 2H), 3.43 (t, J=6.4, 1H), 0.83 (m, 2H), −0.09 (s, 9H); $^{13}$C NMR(126 MHz, CDCl$_3$) δ ppm 136.7, 133.5, 131.1, 128.1, 125.9, 123.6, 114.4, 80.0, 66.6, 62.5, 17.8, −1.4.

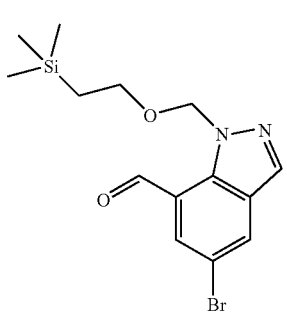

Intermediate 80

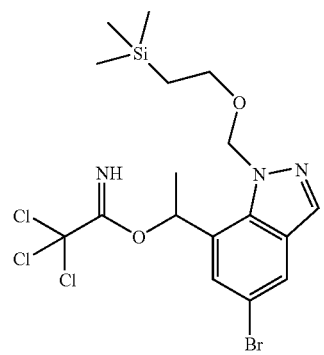

Intermediate 82

5-Bromo-1-((2-(trimethylsilyl)ethoxy)methyl)-1H-indazole-7-carbaldehyde. To a suspension of (5-bromo-1-((2-(trimethylsilyl)ethoxy)methyl)-1H-indazol-7-yl)methanol (675 mg, 1.889 mmol), 4-methylmorpholine 4-oxide (443 mg, 3.78 mmol), and molecular sieves (337 mg, 1.889 mmol) in dichloromethane (10 mL) at room temperature was added tetrapropylammonium perruthenate (19.9 mg, 0.057 mmol). After 1.5 h, the crude reaction mixture was loaded directly onto a pre-conditioned column of silica gel (silica gel/dichloromethane). The solvent was then switched directly to 12% EtOAc/Hex and the column run in that solvent system to give 565 mg (84%) as a colorless oil. $^1$H-NMR (CDCl$_3$, 500 MHz) δ 10.31 (s, 1H), 8.11 (d, J=1.8, 1H), 8.05 (s, 1H), 8.03 (d, J=1.8, 1H), 6.04 (s, 2H), 3.45 (m, 2H), 0.81 (m, 2H), −0.12 (s, 9H); $^{13}$C NMR (126 MHz, CDCl$_3$) δ ppm 188.9, 135.4, 135.0, 134.2, 130.0, 129.3, 123.0, 114.0, 81.2, 66.4, 17.8, −1.4.

(±)-1-(5-Bromo-1-((2-(trimethylsilyl)ethoxy)methyl)-1H-indazol-7-yl)ethyl 2,2,2-trichloroacetimidate. To a solution of (±)-1-(5-bromo-1-((2-(trimethylsilyl)ethoxy)methyl)-1H-indazol-7-yl)ethanol (575 mg, 1.55 mmol) and trichloroacetonitrile (1.55 mL, 15.5 mmol) in dichloromethane (15 mL) at room temperature was added diazabicycloundecene (50 μL, 0.33 mmol). After stirring 30 min, the reaction was concentrated and purified by column chromatography (10% EtOAc/Hex+0.5% Et$_3$N) to give 780 mg (98%) as a colorless film. $^1$H-NMR (CDCl$_3$, 500 MHz) δ 8.30 (s, 1H), 7.92 (d, J=2.4, 1H), 7.79 (d, J=1.5, 1H), 7.69 (d, J=1.8, 1H), 6.67 (q, J=6.4, 1H), 6.25 (d, J=11.6, 1H), 5.70 (d, J=11.6, 1H), 3.42-3.60 (m, 3H), 1.76 (d, J=6.4, 3H), 1.19 (m, 2H), 0.75-1.02 (m, 2H), −0.06 (s, 9H); $^{13}$C NMR (126 MHz, CDCl$_3$) δ ppm 161.2, 135.6, 133.1, 128.0, 127.9, 127.6, 123.2, 114.8, 91.4, 80.2, 72.7, 66.1, 22.5, 17.8, −1.4.

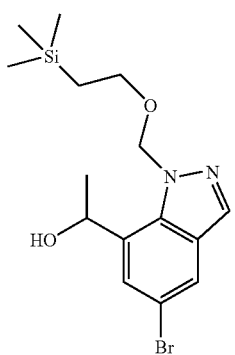

Intermediate 81

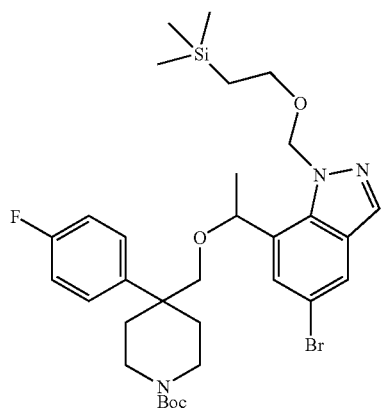

Intermediate 83

(±)-1-(5-Bromo-1-((2-(trimethylsilyl)ethoxy)methyl)-1H-indazol-7-yl)ethanol. To a solution of 5-bromo-1-((2-(trimethylsilyl)ethoxy)methyl)-1H-indazole-7-carbaldehyde (600 mg, 1.689 mmol) in tetrahydrofuran (10 mL) at −78° C. was added methylmagnesiumbromide (3M in diethyl ether, 1.13 mL, 3.38 mmol). After 5 min, the ice bath was removed and stirring continued for 30 min. The reaction was cooled to 0° C. and quenched by the cautious addition of saturated ammonium chloride. The mixture was poured into diethyl ether, washed with water (2×), then brine, dried over magnesium sulfate, and concentrated. Column chromatography (12%→25% EtOAc/Hex) gave 575 mg (92%) as a colorless oil. $^1$H-NMR (CDCl$_3$, 500 MHz) δ 7.89 (s, 1H), 7.76 (s, 1H), 7.61 (s, 1H), 5.92 (d, J=11.6, 1H), 5.80 (d, J=11.6, 1H), 5.56 (m, 1H), 3.46 (m, 2H), 3.26 (s, 1H), 1.64 (d, J=6.4, 3H), 0.80 (m, 2H), −0.11 (s, 9H); $^{13}$C NMR (126 MHz, CDCl$_3$) δ ppm 136.2, 133.5, 130.8, 128.1, 126.9, 122.9, 114.8, 80.3, 66.5, 64.6, 23.0, 17.8, −1.4.

(±)-tert-Butyl 4-((1-(5-bromo-1-((2-(trimethylsilyl)ethoxy)methyl)-1H-indazol-7-yl)ethoxy)methyl)-4-(4-fluorophenyl)piperidine-1-carboxylate. To a solution of (±)-1-(5-bromo-1-((2-(trimethylsilyl)ethoxy)methyl)-1H-indazol-7-yl)ethyl 2,2,2-trichloroacetimidate (780 mg, 1.512 mmol) and tert-butyl 4-(4-fluorophenyl)-4-(hydroxymethyl)piperidine-1-carboxylate (468 mg, 1.512 mmol) in dichloromethane (3 mL) at 0° C. was added cyclohexane (3 mL) and tetrafluoroboric acid diethyl etherate (0.041 mL, 0.302 mmol). After 15 min, the reaction was quenched by addition of triethylamine (ca. 0.05 mL). The reaction was diluted with diethyl ether, washed with water (2×), then brine, dried over magnesium sulfate, and concentrated. Column chromatography (12%→18% EtOAc/Hex) gave 543 mg (54%) as a colorless film. $^1$H-NMR (CDCl$_3$, 500 MHz) δ 7.87 (s, 1H), 7.71

(d, J=1.8, 1H), 7.21 (m, 2H), 7.18 (s, 1H), 6.97 (m, 2H), 5.58 (qAB, JAB, 11.6, 2H), 5.06 (q, J=6.1, 1H), 3.68 (m, 2H), 3.41 (m, 2H), 3.24 (qAB, JAB=8.9, 2H), 3.02 (m, 2H), 2.12 (m, 1H), 2.04 (m, 1H), 1.83 (m, 2H), 1.42 (s, 12H), 0.80 (m, 1H), 0.71 (m, 1H), −0.11 (s, 9H); $^{13}$C NMR (126 MHz, CDCl$_3$) δ ppm 162.4, 160.4, 155.0, 138.6, 136.1, 133.4, 129.3, 128.7 (d, J=7.7), 128.1, 127.4, 122.5, 115.3, 115.1, 114.8, 79.8, 79.4, 76.7, 72.8, 66.1, 41.1, 40.0 (br), 32.3, 32.1, 28.6, 22.8, 17.9, −1.4. Mass spec.: 662.02 (MH)$^+$.

Intermediate 84

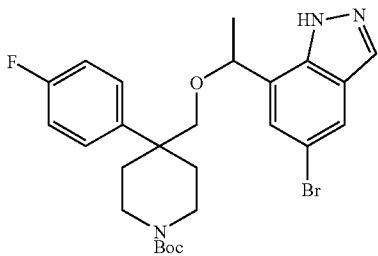

(±)-tert-Butyl 4-((1-(5-bromo-1H-indazol-7-yl)ethoxy)methyl)-4-(4-fluorophenyl)piperidine-1-carboxylate. (±)-tert-Butyl 4-((1-(5-bromo-1-((2-(trimethylsilyl)ethoxy)methyl)-1H-indazol-7-yl)ethoxy)methyl)-4-(4-fluorophenyl)piperidine-1-carboxylate (543 mg, 0.819 mmol) was dissolved in trifluoroacetic acid (50% in dichloromethane, 10 mL) and stirred at room temperature for 4 h. The reaction was concentrated and loaded onto a strong cation exchange cartridge in methanol. After washing with several volumes of methanol, the product was eluted with 2M ammonia in methanol. Concentration gave the crude piperidine. The piperidine was dissolved in dichloromethane (5 mL) and treated with di-tert-butyl dicarbonate (224 mg, 1.02 mmol). After 1 h, the reaction was quenched by addition of 2M ammonia in methanol and concentrated. The residue was suspended in water and extracted with diethyl ether. The ethereal was washed with water, then brine, dried over magnesium sulfate, and concentrated. Column chromatography (EtOAc/Hex) gave 420 mg (96%). $^1$H-NMR (CDCl$_3$, 500 MHz) δ 10.05 (bs, 1H), 7.89 (s, 1H), 7.71 (d, J=1.8, 1H), 7.23 (m, 2H), 7.08 (d, J=1.5, 1H), 7.02 (m, 2H), 4.48 (q, J=6.7, 1H), 3.70 (m, 2H), 3.34 (d, J=9.2, 1H), 3.23 (d, J=8.9, 1H), 3.03 (m, 1H), 2.95 (m, 1H), 2.21 (m, 1H), 2.03 (m, 1H), 1.82 (m, 1H), 1.72 (m, 1H), 1.41 (s, 9H), 1.40 (d, J=6.7, 3H); $^{13}$C NMR (126 MHz, CDCl$_3$) δ ppm 162.6, 160.6, 155.0, 138.1, 135.9, 133.7, 128.7 (d, J=7.7), 127.9, 126.5, 125.5, 122.3, 115.7, 115.6, 113.6, 79.6, 78.6, 78.0, 41.2, 40.1, 32.5, 32.1, 28.5, 22.2, 14.3.

Intermediate 85

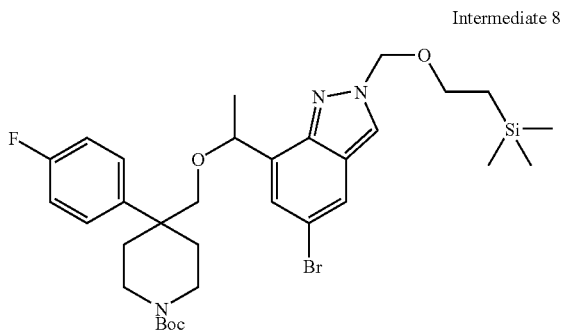

(±)-tert-Butyl 4-((1-(5-bromo-2-((2-(trimethylsilyl)ethoxy)methyl)-2H-indazol-7-yl)ethoxy)methyl)-4-(4-fluorophenyl)piperidine-1-carboxylate. To a solution of (±)-tert-butyl 4-((1-(5-bromo-1H-indazol-7-yl)ethoxy)methyl)-4-(4-fluorophenyl)piperidine-1-carboxylate (340 mg, 0.639 mmol) and N-methyldicyclohexylamine (0.205 mL, 0.958 mmol) in tetrahydrofuran (2 mL) at 0° C. was added (2-(chloromethoxy)ethyl)trimethylsilane (0.159 mL, 0.894 mmol). The ice bath was removed and the reaction stirred at room temperature overnight. The reaction was poured into diethyl ether, washed with water (2×), then brine, dried over magnesium sulfate, and concentrated. Column chromatography (12%→25% EtOAc/Hex) gave 383 mg (91%) as a foam. $^1$H-NMR (CDCl$_3$, 500 MHz) δ 7.99 (s, 1H), 7.66 (s, 1H), 7.30 (m, 2H), 7.02 (m, 2H), 6.89 (s, 1H), 5.64 (qAB, JAB=10.7, 2H), 4.92 (q, J=6.4, 1H), 3.71 (m, 2H), 3.59 (m, 2H), 3.35 (qAB, JAB=9.2, 2H), 3.05 (m, 2H), 2.18 (m, 1H), 2.06 (m, 1H), 1.93 (m, 1H), 1.86 (m, 1H), 1.42 (m, 12H), 0.90 (m, 2H), −0.07 (s, 9H); $^{13}$C NMR (126 MHz, CDCl$_3$) δ ppm 162.4, 160.5, 155.1, 145.6, 138.8, 135.9, 128.9 (d, J=7.7), 124.9, 123.6, 122.2, 121.1, 116.2, 115.3, 115.2, 81.9, 79.4, 77.9, 73.9, 67.6, 41.3, 40.3 (br), 32.3, 31.9, 28.6, 22.9, 17.9, −1.3.

Intermediate 86

(±)-5-Bromo-7-(1-((4-(4-fluorophenyl)piperidin-4-yl)methoxy)ethyl)-1H-indazole. (±)-tert-Butyl 4-((1-(5-bromo-2-((2-(trimethylsilyl)ethoxy)methyl)-2H-indazol-7-yl)ethoxy)methyl)-4-(4-fluorophenyl)piperidine-1-carboxylate (40 mg, 0.075 mmol) was dissolved in trifluoroacetic acid (20% in dichloromethane, 1.25 mL) and stirred at room temperature for 30 min. The reaction was concentrated and loaded onto a strong cation exchange cartridge in methanol. The cartridge was flushed with several volumes of methanol which were discarded. The product was eluted with 2M ammonia in methanol and concentrated. $^1$H-NMR (CDCl$_3$, 500 MHz) δ 10.05 (bs, 1H), 7.90 (s, 1H), 7.73 (d, J=1.5, 1H), 7.25 (m, 2H), 7.10 (d, J=1.5, 1H), 7.05 (m, 2H), 4.48 (q, J=6.4, 1H), 3.39 (d, J=8.9, 1H), 3.25 (d, J=8.9, 1H), 2.91 (m, 1H), 2.84 (m, 1H), 2.75 (m, 1H), 2.68 (m, 1H), 1.60-2.30 (bs, 1H), 2.20 (m, 1H), 2.04 (m, 1H), 1.89 (m, 1H), 1.80 (m, 1H), 1.42 (d, J=6.7, 3H); $^{13}$C NMR (126 MHz, CDCl$_3$) δ ppm 162.5, 160.6, 139.5, 135.9, 133.7, 128.7 (d, J=7.7), 128.0, 126.5, 125.5, 122.3, 115.6, 115.4, 113.5, 79.0, 78.2, 50.7, 42.6, 42.5, 41.4, 33.9, 33.6, 22.2.

Intermediate 87

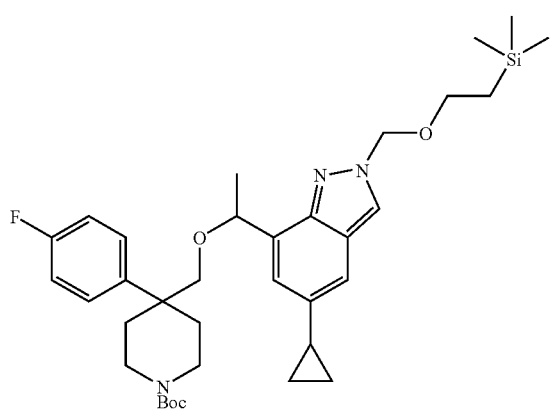

(±)-tert-Butyl 4-((1-(5-cyclopropyl-2-((2-(trimethylsilyl)ethoxy)methyl)-2H-indazol-7-yl)ethoxy)methyl)-4-(4-fluorophenyl)piperidine-1-carboxylate. (±)-tert-Butyl 4-((1-(5-bromo-2-((2-(trimethylsilyl)ethoxy)methyl)-2H-indazol-7-yl)ethoxy)methyl)-4-(4-fluorophenyl)piperidine-1-carboxylate (75 mg, 0. 113 mmol), cyclopropyl boronic acid (20 mg, 0.34 mmol), and tetrakis(triphenylphosphine) palladium(0) (13. 1 mg, 0.011 mmol) were combined in dry tetrahydrofuran (2 mL) followed by addition of 0.58 mL of a 1 N aqueous potassium hydroxide solution in a microwave tube and sealed. After flushing the mixture with nitrogen, the mixture was heated at 100° C. for 1 h via microwave. After cooling to room temperature, the reaction mixture was concentrated, dissolved in ethyl acetate and washed with water and brine, concentrated and purified by flash chromatography on silica gel (20% EtOAc/Hex) to afford 70.5 mg (100%) as an oil. LC/MS (HPLC method 2): $t_R$=3.738 min, 624.24(MH)$^+$.

Intermediate 88

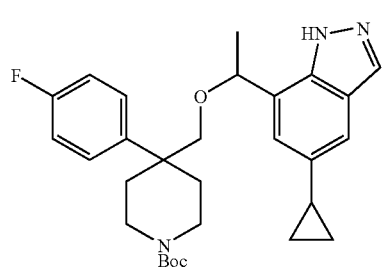

(±)-tert-Butyl 4-((1-(5-cyclopropyl-1H-indazol-7-yl)ethoxy)methyl)-4-(4-fluorophenyl)piperidine-1-carboxylate. (±)-tert-Butyl 4-((1-(5-cyclopropyl-2-((2-(trimethylsilyl)ethoxy)methyl)-2H-indazol-7-yl)ethoxy)methyl)-4-(4-fluorophenyl)piperidine-1-carboxylate(70.5 mg, 0. 113 mmol) was dissolved in trifluoroacetic acid (50% in dichloromethane, 1 mL) and stirred at room temperature overnight. The reaction was concentrated and loaded onto a strong cation exchange cartridge in methanol. The cartridge was flushed with several volumes of methanol which were discarded. The product was eluted with 2 M ammonia in methanol and concentrated to give 40.5 mg of (±)-5-cyclopropyl-7-(1-((4-(4-fluorophenyl)piperidin-4-yl)methoxy)ethyl)-2H-indazole (91%). The crude amine (40.5 mg, 0. 103 mmol) in dichloromethane (2 mL) was cooled to 0° C. and treated with di-tert-butyl dicarbonate (44.9 mg, 0.206 mmol). The reaction was stirred at 0° C. for 1 h and was quenched by addition of 2 M ammonia in methanol and concentrated. The residue was purified by column chromatography (1%→30% EtOAc/Hex) to give 30 mg (59%) as oil. LC/MS (HPLC method 3): $t_R$=3.15 min, 494.12(MH)$^+$.

Intermediate 89

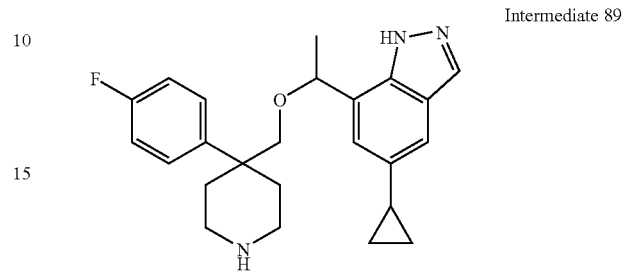

(±)-5-Cyclopropyl-7-(1-((4-(4-fluorophenyl)piperidin-4-yl)methoxy)ethyl)-1H-indazole. (±)-tert-Butyl 4-((1-(5-cyclopropyl-1H-indazol-7-yl)ethoxy)methyl)-4-(4-fluorophenyl)piperidine-1-carboxylate (30 mg, 0.061 mmol) was dissolved in trifluoroacetic acid (20% in dichloromethane, 2 mL) and stirred at room temperature for 30 min. The reaction was concentrated and loaded onto a strong cation exchange cartridge in methanol. The cartridge was flushed with several volumes of methanol which were discarded. The product was eluted with 2 M ammonia in methanol and concentrated to give 21.8 mg (91%). LC/MS (HPLC method 3): $t_R$=2.235 min, 394.10(MH)$^+$.

Intermediate 90

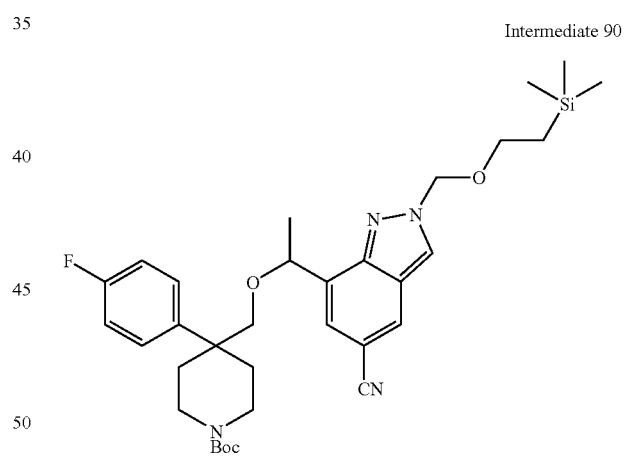

(±)-tert-Butyl 4-((1-(5-cyano-2-((2-(trimethylsilyl)ethoxy)methyl)-2H-indazol-7-yl)ethoxy)methyl)-4-(4-fluorophenyl)piperidine-1-carboxylate. (±)-tert-Butyl 4-((1-(5-bromo-2-((2-(trimethylsilyl)ethoxy)methyl)-2H-indazol-7-yl)ethoxy)methyl)-4-(4-fluorophenyl)piperidine-1-carboxylate (75 mg, 0. 113 mmol), tetrakis(triphenylphosphine) palladium(0) (13.1 mg, 0.011 mmol) and cyanozinc (20.7 mg, 0.226 mmol) were combined in dry N,N-dimethylformamide (2 mL) in a microwave tube and sealed. After flushing the mixture with nitrogen, the mixture was heated at 120° C. for 1 h via microwave. After cooling to room temperature, the reaction mixture was concentrated, dissolved in ethyl acetate and washed with water and brine, concentrated and purified by flash chromatography on silica gel (20% EtOAc/Hex) to afford 21 mg (30.5%) as an oil. LC/MS (HPLC method 2): $t_R$=3.265 min, 609.18(MH)⁺.

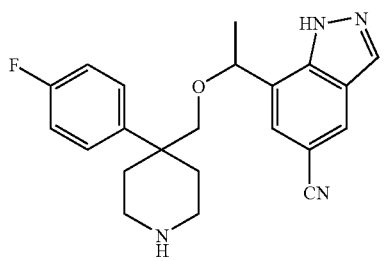

Intermediate 91

(±)-7-(-((4-(4-Fluorophenyl)piperidin-4-yl)methoxy)ethyl)-1H-indazole-5-carbonitrile. (±)-tert-Butyl 4-((1-(5-cyano-2-((2-(trimethylsilyl)ethoxy)methyl)-2H-indazol-7-yl)ethoxy)methyl)-4-(4-fluorophenyl)piperidine-1-carboxylate (21 mg, 0.034 mmol) was dissolved in trifluoroacetic acid (50% in dichloromethane, 2 mL) and stirred at room temperature for 4 h. The reaction was concentrated and loaded onto a strong cation exchange cartridge in methanol. The cartridge was flushed with several volumes of methanol which were discarded. The product was eluted with 2 M ammonia in methanol and concentrated to give 13.5 mg (quant.). LC/MS (HPLC method 3): $t_R$=1.717 min, 379.09 (MH)⁺.

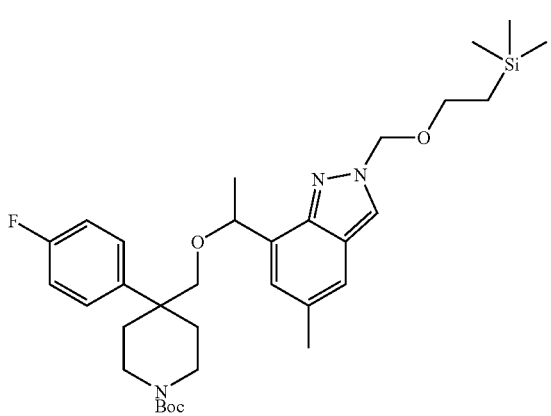

Intermediate 92

(±)-tert-Butyl 4-(4-fluorophenyl)-4-((1-(5-methyl-2-((2-(trimethylsilyl)ethoxy)methyl)-2H-indazol-7-yl)ethoxy)methyl)piperidine-1-carboxylate. (±)-tert-Butyl 4-((1-(5-bromo-2-((2-(trimethylsilyl)ethoxy)methyl)-2H-indazol-7-yl)ethoxy)methyl)-4-(4-fluorophenyl)piperidine-1-carboxylate (150 mg, 0.226 mmol), trimethylboroxine (0.063 mL, 0.453 mmol), and tetrakis(triphenylphosphine) palladium(0) (13.1 mg, 0.011 mmol) were combined in dry tetrahydrofuran (1.1 mL) and 4 M sodium carbonate (0.17 mL) in a microwave tube and sealed. After flushing the mixture with nitrogen, the mixture was heated at 110° C. for 2 h via microwave. After cooling to room temperature, the reaction mixture was concentrated, dissolved in diethyl ether and washed with water and brine, concentrated and purified by flash chromatography on silica gel (20-25% EtOAc/Hex) to afford 49 mg (36.2%) as an oil. ¹H-NMR (CDCl₃, 500 MHz) δ 7.93 (s, 1H), 7.32 (m, 2H), 7.24 (s, 1H), 7.02 (m, 2H), 6.66 (s, 1H), 5.65 (s, 2H), 4.96 (d, J=5 Hz, 1H), 3.33-3.75 (m, 6H), 3.0-3.15 (m, 2H), 2.29 (s, 3H), 1.85-2.2 (m, 4H), 1.43 (m, 12H), 0.89 (m, 2H), −0.06 (s, 9H); ¹³C-NMR (CDCl₃, 126 MHz) δ 161.4 (d, J=974 Hz), 155.1, 146.2, 139.2, 133.3, 131.7, 129.1, 129.0, 124.0, 122.8, 121.8, 117.1, 115.1, 114.9, 81.7, 79.4, 77.6, 74.1, 67.3, 65.9, 41.3, 28.6, 23.1, 21.9, 17.9, 15.4, −1.4; Mass spec.: 598.45(MH)⁺.

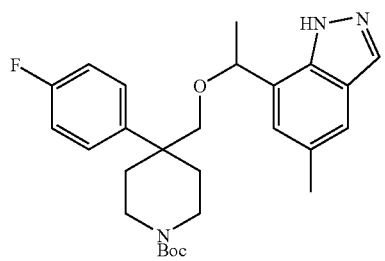

Intermediate 93

(±)-tert-Butyl 4-(4-fluorophenyl)-4-((1-(5-methyl-1H-indazol-7-yl)ethoxy)methyl)piperidine-1-carboxylate. (±)-tert-Butyl 4-(4-fluorophenyl)-4-((1-(5-methyl-2-((2-(trimethylsilyl)ethoxy)methyl)-2H-indazol-7-yl)ethoxy)methyl)piperidine-1-carboxylate (49 mg, 0.082 mmol) was dissolved in trifluoroacetic acid (50% in dichloromethane, 2 mL) and stirred at room temperature for 6 h. The reaction was concentrated and loaded onto a strong cation exchange cartridge in methanol. The cartridge was flushed with several volumes of methanol which were discarded. The product was eluted with 2 M ammonia in methanol and concentrated to give 28 mg of (±)-7-(1-((4-(4-fluorophenyl)piperidin-4-yl)methoxy)ethyl)5-5methyl-2H-indazole (93%). The crude amine (28 mg, 0.076 mmol) in dichloromethane (1 mL) was cooled to 0° C. and treated with di-tert-butyl dicarbonate (33.3 mg, 0.152 mmol). The reaction was stirred at 0° C. for 1 h and was quenched by addition of 2 M ammonia in methanol and concentrated. The residue was purified by column chromatography (1%→30% EtOAc/Hex) to give 35 mg (98%) as an oil. ¹H-NMR (CDCl₃, 400 MHz) δ 9.62 (bs, 1H), 7.87 (s, 1H), 7.35 (s, 1H), 7.24 (m, 2H), 7.05 (m, 2H), 6.82 (s, 1H), 4.46 (q, J=8 Hz, 1H), 3.6-3.8 (m, 2H), 3.32 (d, J=8 Hz, 1H), 3.23 (d, J=8 Hz, 1H), 2.95-3.06 (m, 2H), 2.37 (s, 3H), 2.2-2.27 (m, 1H), 2.03-2.1 (m, 1H), 1.7-1.87 (m, 2H), 1.42 (s, 9H), 1.40 (d, J=8 Hz, 3H); ¹³C-NMR (CDCl₃, 101 MHz) δ 162.8 (d, J=980 Hz), 154.9, 143.7, 135.6, 133.7, 130.0, 128.7, 128.6, 125.7, 125.6, 124.4, 118.9, 115.6, 115.4, 79.5, 78.9, 78.4, 41.2, 28.5, 22.3, 21.2; Mass spec.: 468.39 (MH)⁺.

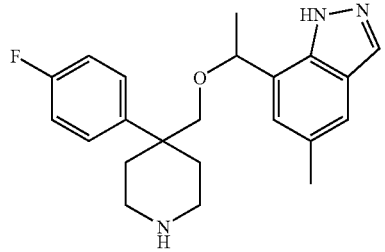

Intermediate 94

(±)-7-(1-((4-(4-Fluorophenyl)piperidin-4-yl)methoxy)ethyl)-5-methyl-1H-indazole. (±)-tert-Butyl 4-(4-fluorophenyl)-4-((1-(5-methyl-1H-indazol-7-yl)ethoxy)methyl)piperidine-1-carboxylate (35 mg, 0.075 mmol) was dissolved in trifluoroacetic acid (20% in dichloromethane, 2 mL) and stirred at room temperature for 30 min. The reaction was concentrated and loaded onto a strong cation exchange cartridge in methanol. The cartridge was flushed with several volumes of methanol which were discarded. The product was eluted with 2 M ammonia in methanol and concentrated to give 24 mg (87%). LC/MS (HPLC method 3): $t_R$=2.658 min, 368.38(MH)$^+$.

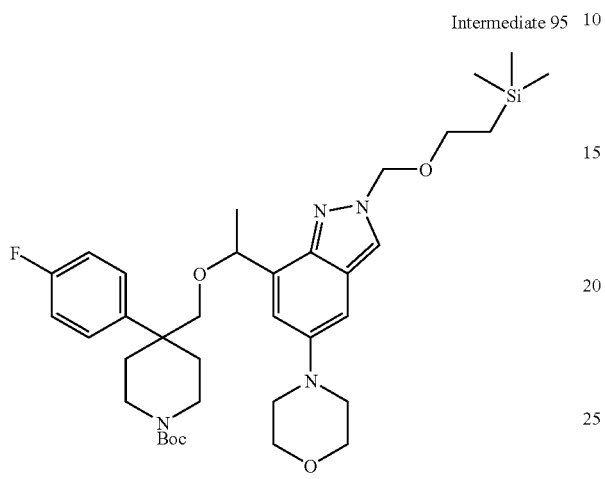

Intermediate 95

(±)-tert-Butyl 4-(4-fluorophenyl)-4-((1-(5-morpholino-2-((2-(trimethylsilyl)ethoxy)methyl)-2H-indazol-7-yl)ethoxy) methyl)piperidine-1-carboxylate. (±)-tert-Butyl 4-((1-(5-bromo-2-((2-(trimethylsilyl)ethoxy)methyl)-2H-indazol-7-yl)ethoxy)methyl)-4-(4-fluorophenyl)piperidine-1-carboxylate (75 mg, 0.113 mmol), sodium tert-butoxide (16.3 mg, 0.17 mmol), and palladium(II)acetate (1.02 mg, 4.53 μmol) were combined in toluene (2 mL) and treated with 2,8,9-triisobutyl-2,5,8,9-tetraaza-1-phosphabicyclo[3.3.3] undecane (3.1 mg, 9.05 μmol) and morpholine (0.012 mL, 0.136 mmol) in a microwave tube and sealed. After flushing the mixture with nitrogen, the mixture was heated at 100° C. for 1 h via microwave. After cooling to room temperature, the reaction mixture was concentrated, dissolved in ethyl acetate, washed with water and brine, concentrated, and purified by flash chromatography on silica gel (30% EtOAc/Hex) to afford 44 mg (58%) as an oil. LC/MS (HPLC method 2): $t_R$=3.185 min, 669.25(MH)$^+$.

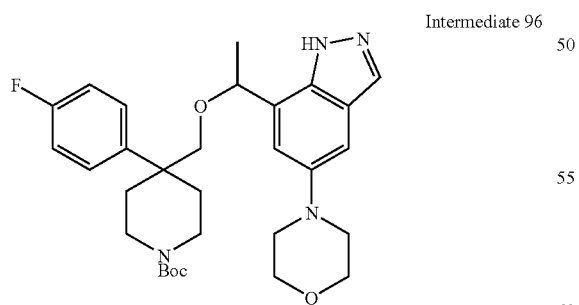

Intermediate 96

(±)-tert-Butyl 4-(4-fluorophenyl)-4-((1-(5-morpholino-1H-indazol-7-yl)ethoxy)methyl)piperidine-1-carboxylate. (±)-tert-Butyl 4-(4-fluorophenyl)-4-((1-(5-morpholino-2-((2-(trimethylsilyl)ethoxy)methyl)-2H-indazol-7-yl)ethoxy) methyl)piperidine-1-carboxylate (44 mg, 0.066 mmol) was dissolved in trifluoroacetic acid (50% in dichloromethane, 2 mL) and stirred at room temperature for 4 h. The reaction was concentrated and loaded onto a strong cation exchange cartridge in methanol. The cartridge was flushed with several volumes of methanol which were discarded. The product was eluted with 2 M ammonia in methanol and concentrated to give 30.5 mg of (±)-4-(7-(1-(((4-(4-fluorophenyl)piperidin-4-yl)methoxy)ethyl)-2H-indazole-5-yl)morpholino (quant.). The crude amine (30.5 mg, 0.07 mmol) in dichloromethane (2 mL) was cooled to 0° C. and treated with di-tert-butyl dicarbonate (30.4 mg, 0.139 mmol). The reaction was stirred at 0° C. for 1 h and was quenched by addition of 2 M ammonia in methanol and concentrated. The residue was purified by column chromatography (30% EtOAc/Hex) to give 32 mg (85%) as oil. LC/MS (HPLC method 3): $t_R$=1.592 min, 539.44(MH)$^+$.

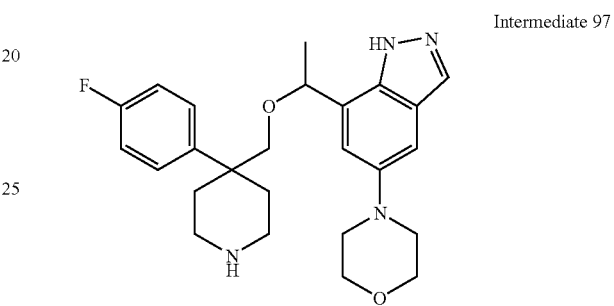

Intermediate 97

(±)-4-7-(-((4-(4-Fluorophenyl)piperidin-4-yl)methoxy) ethyl)-1H-indazole-5-yl)morpholino. (±)-tert-Butyl 4-(4-fluorophenyl)-4-((1-(5-morpholino-1H-indazol-7-yl) ethoxy)methyl)piperidine-1-carboxylate (32 mg, 0.059 mmol) was dissolved in trifluoroacetic acid (20% in dichloromethane, 2 mL) and stirred at room temperature for 30 min. The reaction was concentrated and loaded onto a strong cation exchange cartridge in methanol. The cartridge was flushed with several volumes of methanol which were discarded. The product was eluted with 2 M ammonia in methanol and concentrated to give 24.2 mg (93%). LC/MS (HPLC method 3): $t_R$=1.752 min, 439.10(MH)$^+$.

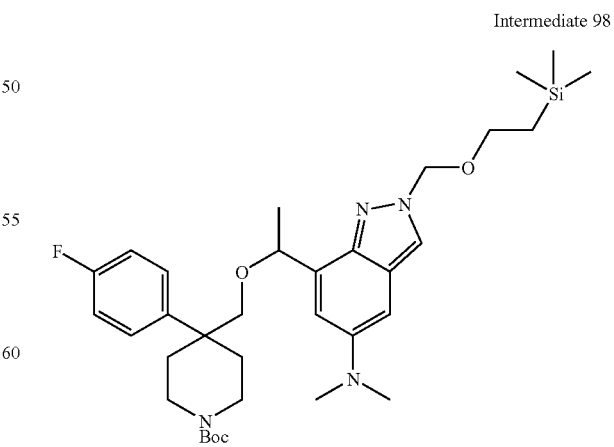

Intermediate 98

(±)-tert-Butyl 4-((1-(5-dimethylamino-2-((2-(trimethylsilyl)ethoxy)methyl)-2H-indazol-7-yl)ethoxy)methyl)-4-(4- fluorophenyl)piperidine-1-carboxylate. (±)-tert-Butyl 4-((1-(5-bromo-2-((2-(trimethylsilyl)ethoxy)methyl)-2H-indazol-7-yl)ethoxy)methyl)-4-(4-fluorophenyl)piperidine-1-carboxylate (150 mg, 0.226 mmol), trans-dichlorobis(tri-o-tolylphosphine)palladium (II) (17.79 mg, 0.023 mmol), and dimethylaminotri-n-butyltin (0.28 mL, 0.905 mmol) were combined in toluene (1.5 mL) in a microwave tube and sealed. After flushing the mixture with nitrogen, the mixture was heated at 120° C. for 1 h via microwave. After cooling to room temperature, the reaction mixture was concentrated, dissolved in ethyl acetate, washed with water and brine, concentrated and purified by flash chromatography on silica gel (15-30% EtOAc/Hex) to afford 115 mg (80.8%) as yellow oil. $^1$H-NMR (CDCl$_3$, 500 MHz) δ 7.81 (s, 1H), 7.30 (m, 2H), 6.97 (m, 2H), 6.84 (s, 1H), 5.54 (s, 1H), 5.59 (m, 2H), 4.94 (q, J=5 Hz, 1H), 3.6-3.75 (m, 2H), 3.54 (m, 2H), 3.43 (d, J=10 Hz, 1H), 3.31 (d, J=10 Hz, 2H), 3.00-3.10 (m, 2H), 2.81 (s, 6H), 2.03-2.12 (m, 2H), 1.85-1.95 (m, 2H), 1.43 (d, J=10 Hz, 3H), 1.41 (s, 9H), 0.85-0.90 (m, 2H), −0.09 (s, 9H); $^{13}$C-NMR (CDCl$_3$, 126 MHz) δ 171.1, 161.3 (d, J=975 Hz), 155.0, 147.0, 143.4, 139.2, 134.1, 128.9, 123.5, 120.9, 115.4, 115.1, 114.9, 97.2, 81.5, 79.3, 74.4, 67.0, 60.4, 41.9, 41.2, 32.3, 28.5, 27.9, 26.9, 23.1, 21.1, 17.8, 17.6, 14.3, 13.7, −1.36; Mass spec.: 627.60(MH)$^+$.

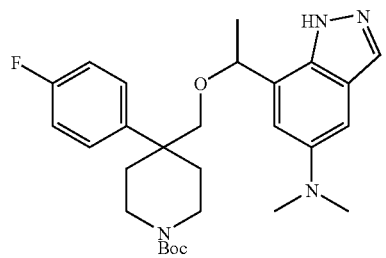

Intermediate 99

(±)-tert-Butyl 4-((1-(5-(dimethylamino)-1H-indazol-7-yl)ethoxy)methyl)-4-(4-fluorophenyl)piperidine-1-carboxylate. (±)-tert-Butyl 4-((1-(5-dimethylamino-2-((2-(trimethylsilyl)ethoxy)methyl)-2H-indazol-7-yl)ethoxy)methyl)-4-(4-fluorophenyl)piperidine-1-carboxylate (206 mg, 0.329 mmol) was dissolved in trifluoroacetic acid (50% in dichloromethane, 3.5 mL) and stirred at room temperature for 4 h. The reaction was concentrated and loaded onto a strong cation exchange cartridge in methanol. The cartridge was flushed with several volumes of methanol which were discarded. The product was eluted with 2 M ammonia in methanol and concentrated to give 124 mg of (±)-7-(1-((4-(4-fluorophenyl)piperidin-4-yl)methoxy)ethyl)-N,N-dimethyl-2H-indazol-5-amine (95%). The crude amine (124 mg, 0.313 mmol) in dichloromethane (2.7 mL) was cooled to 0° C. and treated with di-tert-butyl dicarbonate (137 mg, 0.625 mmol). The reaction was stirred at 0° C. for 1 h and was quenched by addition of 2 M ammonia in methanol and concentrated. The residue was purified by column chromatography (18%→45% EtOAc/Hex) to give 138 mg (89%) as clear oil. LC/MS (HPLC method 3): t$_R$=2.816 min, 497.50(MH)$^+$.

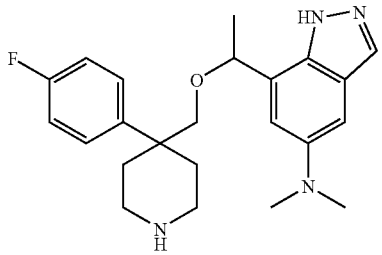

Intermediate 100

(±)-7-(1-((4-(4-Fluorophenyl)piperidin-4-yl)methoxy)ethyl)-N,N-dimethyl-1H-indazol-5-amine. (±)-tert-Butyl 4-((1-(5-(dimethylamino)-1H-indazol-7-yl)ethoxy)methyl)-4-(4-fluorophenyl)piperidine-1-carboxylate (138 mg, 0.278 mmol) was dissolved in trifluoroacetic acid (20% in dichloromethane, 7.5 mL) and stirred at room temperature for 30 min. The reaction was concentrated and loaded onto a strong cation exchange cartridge in methanol. The cartridge was flushed with several volumes of methanol which were discarded. The product was eluted with 2 M ammonia in methanol and concentrated to give 101 mg (92%). LC/MS (HPLC method 3): t$_R$=1.133 min, 397.42(MH)$^+$.

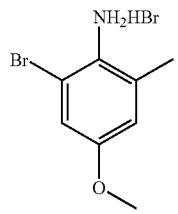

Intermediate 101

2-Bromo-4-methoxy-6-methylaniline hydrobromide. 4-Methoxy-2-methylaniline (9.30 ml, 72.9 mmol) in chloroform (250 ml ) at 0° C. was added a solution of bromine (3.76 ml, 72.9 mmol) in chloroform (60 ml) dropwise over ca. 3 h. The reaction mixture was concentrated, diluted with dichloromethane and concentrated, diluted again with diethyl ether and concentrated, and dried under high vacuum to give 18.5 g of 2-bromo-4-methoxy-6-methylaniline hydrobromide (85%). LC/MS (HPLC method 3): t$_R$=1.395 min, 216.03 (MH)$^+$.

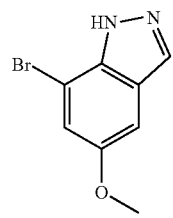

Intermediate 102

7-Bromo-5-methoxy-1H-indazole. To a suspension of 2-bromo-4-methoxy-6-methylaniline hydrobromide (18.5 g, 62.3 mmol) in hydrochloric acid (8 M, 56 mL, 448 mmol) at 0° C. was added a solution of sodium nitrite (4.51 g, 65.4 mmol) in water (ca. 14 mL) drop wise. After 10 min, the resulting solution was neutralized (pH 4-5) by addition of solid sodium acetate. The resulting solution was added to a solution of 2-methyl-2-propanethiol (7.02 mL, 62.3 mmol) in ethanol (140 mL) at 0° C. The resulting mixture was stirred at 0° C. for 30 min. The resulting mixture was poured onto ice and the resulting mixture was extracted into diethyl ether (2x). The ethereal was washed with water, then brine, dried over magnesium sulfate, and concentrated. The resulting residue was dissolved in dimethylsulfoxide (35 mL) and transferred to a solution of potassium tert-butoxide (55.9 g, 498 mmol) in dimethylsulfoxide (350 mL) in a cool water bath (ca. 10° C.) via canula. The bath was removed and stirring continued for 30 min. The reaction mixture was poured onto ice/concentrated hydrochloric acid. The resulting mixture was extracted with dichloromethane (2x), washed with water (3x), then brine, dried over magnesium sulfate and concentrated. Preparative HPLC gave 10.1 g (86%) as a tan solid. $^1$H-NMR (CDCl$_3$, 300 MHz) δ 8.05 (s, 1H), 7.24 (m, 1H), 7.04 (m, 1H), 3.82 (s, 3H); Mass spec.: 226.95 (MH)$^+$.

Intermediate 103

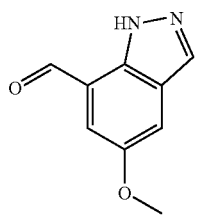

5-Methoxy-1H-indazole-7-carbaldehyde. To a solution of 7-bromo-5-methoxy-1H-indazole (1.32 g, 5.81 mmol) in tetrahydrofuran (27 mL) at 0° C. was added sodium hydride (0.465 g, 11.62 mmol). The ice bath was removed and stirring continued for 20 min. The solution was cooled to –78° C. and treated with tert-butyllithium (1.7 M in pentane, 6.84 mL, 11.63 mmol) dropwise. The reaction was stirred at –78° C. for 10 min, allowed to warm gradually in the dewar to –50° C., recooled to –78° C., and then treated with dimethylformamide (1.8 mL, 23.25 mmol). After 15 min, the ice bath was removed and stirring continued for 1 h. The reaction was poured onto ice/1 M hydrochloric acid (20 mL). The mixture was extracted with ethyl acetate (2x). The organics were washed with water, then brine, dried over magnesium sulfate, and concentrated to give 1.1 g of 5-methoxy-1H-indazole-7-carbaldehyde (100%) as a tan solid. $^1$H-NMR (CDCl$_3$, 300 MHz) δ 10.08 (s, 1H), 8.04 (s, 1H), 7.52 (s, 1H), 7.44 (m, 1H), 3.90 (s, 3H); Mass spec.: 177.09 (MH)$^+$.

Intermediates 104 and 105

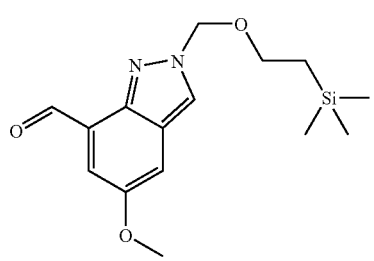

5-Methoxy-2-((2-(trimethylsilyl)ethoxy)methyl)-2H-indazole-7-carbaldehyde and 5-Methoxy-1-((2-(trimethylsilyl)ethoxy)methyl)-1H-indazole-7-carbaldehyde. To a solution of 5-methoxy-1H-indazole-7-carbaldehyde (1.1 g, 6.24 mmol) and N-methyldicyclohexylamine (2.14 mL, 9.99 mmol) in tetrahydrofuran (20 mL) at 0° C. was added (2-(chloromethoxy)ethyl)trimethylsilane (1.55 mL, 8.74 mmol). The ice bath was removed and stirring continued for 4 h. The reaction was poured into diethyl ether, washed with water (2x), then brine, dried over magnesium sulfate, and concentrated. Column chromatography (5%→25% EtOAc/Hex) gave 2 fractions. The faster eluting fraction was concentrated to give 5-methoxy-1-((2-(trimethylsilyl)ethoxy)methyl)-1H-indazole-7-carbaldehyde (0.12 g, 6.3%). The second fraction was concentrated to give 5-methoxy-2-((2-(trimethylsilyl)ethoxy)methyl)-2H-indazole-7-carbaldehyde (1.32 g, 69%). 5-methoxy-2-((2-(trimethylsilyl)ethoxy)methyl)-2H-indazole-7-carbaldehyde: $^1$H-NMR (CDCl$_3$, 500 MHz) δ 10.48 (s, 1H), 8.12 (s, 1H), 7.60 (s, 1H), 7.24 (s, 1H), 5.77 (s, 2H), 3.89 (s, 3H), 3.65 (m, 2H), 0.94 (m, 2H), -0.03 (s, 9H); $^{13}$C-NMR (CDCl$_3$, 126 MHz) δ 190.2, 154.9, 142.9, 126.8, 125.2, 124.1, 122.1, 104.9, 82.2, 67.8, 55.9, 18.0, –1.4; Mass spec.: 307.28 (MH)$^+$. 5-methoxy-1-((2-(trimethylsilyl)ethoxy)methyl)-1H-indazole-7-carbaldehyde: $^1$H-NMR (CDCl$_3$, 300 MHz) δ 10.3 (s, 1H), 7.99 (s, 1H), 7.62 (s, 1H), 7.38 (s, 1H), 6.02 (s, 2H), 3.88 (s, 3H), 3.44 (m, 2H), 0.79 (m, 2H), –0.14 (s, 9H); Mass spec.: 307.28 (MH)$^+$.

Intermediate 106

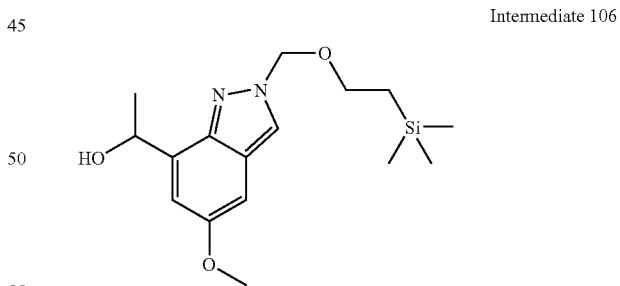

(±)-1-(5-Methoxy-2-((2-(trimethylsilyl)ethoxy)methyl)-2H-indazol-7-yl)ethanol. To a solution of 5-methoxy-2-((2-(trimethylsilyl)ethoxy)methyl)-2H-indazole-7-carbaldehyde (1.32 g, 4.31 mmol) in tetrahydrofuran (27 mL) at –78° C. was added methyl magnesiumbromide (3M in diethyl ether, 2.87 mL, 8.62 mmol). The reaction was allowed to gradually warm in the ice bath (ca. 1 h) to 0° C. The reaction which had been a suspension became a solution. The reaction was quenched by addition of saturated ammonium chloride and poured into diethyl ether. The ethereal was washed with water (2x), then brine, dried over magnesium sulfate, and concentrated to give 1.44 g (quant.) as oil. $^1$H-NMR (CDCl$_3$, 300 MHz) δ 7.92 (s, 1H), 6.88 (s, 1H), 6.75 (s, 1H), 5.63 (s, 2H), 5.26 (q, J=6 Hz, 1H), 3.8 (s, 3H), 3.6 (m, 2H), 1.65 (d, J=6 Hz, 3H), 0.9 (m, 2H), −0.06 (s, 9H); Mass spec.: 323.42 (MH)$^+$.

Intermediate 107

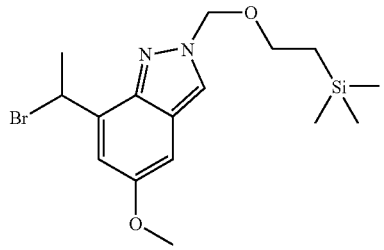

(±)-7-(1-Bromoethyl)-5-methoxy-2-((2-(trimethylsilyl)ethoxy)methyl)-2H-indazole. To a solution of (±)-1-(5-methoxy-2-((2-(trimethylsilyl)ethoxy)methyl)-2H-indazol-7-yl)ethanol (712 mg, 2.21 mmol) and carbon tetrabromide (1.10 g, 3.31 mmol) in tetrahydrofuran (10 mL) at 0° C. was added triphenylphosphine (869 mg, 3.31 mmol). The resulting solution was stirred at room temperature for 30 min. The reaction was diluted with several volumes of pentane and filtered to remove undissolved solids. The organics were concentrated and purified by column chromatography (5% 30% EtOAc/Hex) to give 240 mg (28.2%) as colorless oil. $^1$H-NMR (CDCl$_3$, 300 MHz) δ 7.95 (s, 1H), 7.15 (s, 1H), 6.82 (s, 1H), 5.84 (q, J=6.0 Hz, 1H), 5.67 (s, 2H), 3.8 (s, 3H), 3.62 (m, 2H), 2.94 (d, J=6.0 Hz, 2H), 0.9 (m, 2H), −0.06 (s, 9H).

Intermediate 108

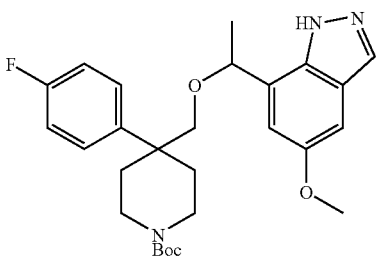

(±)-tert-Butyl 4-(4-fluorophenyl)-4-((1-(5-methoxy-2-((2-(trimethylsilyl)ethoxy)methyl)-2H-indazol-7-yl)ethoxy)methyl)piperidine-1-carboxylate. To a solution of (±)-tert-butyl 4-(4-fluorophenyl)-4-(hydroxymethyl)piperidine-1-carboxylate (193 mg, 0.66 mmol) and 7-(1-bromoethyl)-5-methoxy-2-((2-(trimethylsilyl)ethoxy)methyl)-2H-indazole (240 mg, 0.623 mmol) in dimethylformamide (2.5 mL) at 0° C. was added sodium hydride (60% in mineral oil, 32.4 mg, 0.81 mmol). The resulting solution was stirred at 0° C. for 30 min. The reaction was quenched by the cautious addition of saturated ammonium chloride and diluted with diethyl ether. The ethereal was washed with water (2×), then brine, dried over magnesium sulfate, and concentrated. Column chromatography (15%→25% EtOAc/Hex) gave 29 mg (7.6%) as oil. $^1$H-NMR (CDCl$_3$, 300 MHz) δ 7.88 (s, 1H), 7.25-7.30 (m, 2H), 6.95-7.00 (m, 2H), 6.6606.71 (m, 2H), 5.60 (s, 2H), 4.88 (q, J=6.0 Hz, 1H), 3.77 (s, 3H), 3.66-3.71 (m, 2H), 3.53-3.59 (m, 2H), 3.28-3.41 (m, 2H), 1.40 (m, 12H), 0.85-0.9 (m, 2H), −0.08 (s, 9H), $^{13}$C-NMR (CDCl$_3$, 76 MHz) δ 161.2 (d, J=972 Hz), 155.5, 154.9, 143.9, 138.8, 135.3, 128.8, 122.3, 121.5, 116.1, 115.0, 114.7, 94.9, 81.4, 79.2, 73.9, 67.0, 60.3, 55.1, 41.2, 31.8, 28.4, 22.6, 20.9, 17.7, 14.1, −1.6; Mass spec.: 614.63 (MH)$^+$.

Intermediate 109

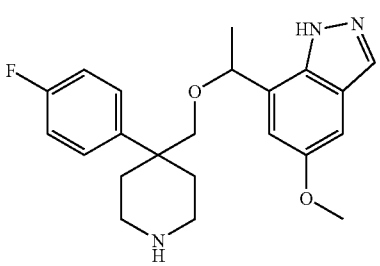

(±)-tert-Butyl 4-(4-fluorophenyl)-4-((1-(5-methoxy-1H-indazol-7-yl)methoxy)methyl)piperidine-1-carboxylate. (±)-tert-Butyl 4-(4-fluorophenyl)-4-((1-(5-methoxy-2-((2-(trimethylsilyl)ethoxy)methyl)-2H-indazol-7-yl)ethoxy)methyl)piperidine-1-carboxylate (29 mg, 0.047 mmol) was dissolved in trifluoroacetic acid (50% in dichloromethane, 2 mL) and stirred at room temperature for 4 h. The reaction was concentrated and loaded onto a strong cation exchange cartridge in methanol. The cartridge was flushed with several volumes of methanol which were discarded. The product was eluted with 2 M ammonia in methanol and concentrated to give 17 mg of (±)-7-(1-((4-(4-fliuorophenyl)piperidin-4-yl)methoxy)ethyl)-5-methoxy-1H-indazole (94%). The crude amine (17 mg, 0.044 mmol) in dichloromethane (1 mL) was cooled to 0° C. and treated with di-tert-butyl dicarbonate (19.4 mg, 0.089 mmol). The reaction was stirred at 0° C. for 1 h and was quenched by addition of 2 M ammonia in methanol and concentrated. The residue was purified by column chromatography (1%→30% EtOAc/Hex) to give 20 mg (93%) as oil. LC/MS (HPLC method 3): t$_R$=3.818 min, 484.49(MH)$^+$.

Intermediate 110

(±)-7-(1-((4-(4-Fluorophenyl)piperidin-4-yl)methoxy)methyl)-5-methoxy-1H-indazole. (±)-tert-Butyl 4-(4-fluorophenyl)-4-((1-(5-methoxy-1H-indazol-7-yl)methoxy)methyl)piperidine-1-carboxylate (20 mg, 0.041 mmol) was dissolved in trifluoroacetic acid (20% in dichloromethane, 1.5 mL) and stirred at room temperature for 30 min. The reaction was concentrated and loaded onto a strong cation exchange cartridge in methanol. The cartridge was flushed with several volumes of methanol which were discarded. The product was eluted with 2 M ammonia in methanol and concentrated to give 15 mg (95%). LC/MS (HPLC method 3): t$_R$=2.387 min, 384.41(MH)$^+$.

Intermediate 111

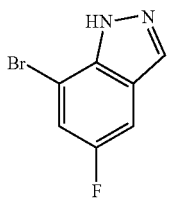

7-Bromo-5-fluoro-1H-indazole. To a suspension of 2-bromo-4-fluoro-6-methylaniline (5 g, 24.51 mmol) in hydrochloric acid (8 M, 22 mL, 176 mmol) at 0° C. was added a solution of sodium nitrite (1.78 g, 25.7 mmol) in water (ca. 5.5 mL) dropwise. After 10 min, the resulting solution was neutralized (pH 4-5) by addition of solid sodium acetate. The resulting solution was added to a solution of 2-methyl-2-propanethiol (2.76 mL, 24.5 mmol) in ethanol (57 mL) at 0° C. The resulting mixture was stirred at 0° C. for 30 min. The resulting mixture was poured onto ice and the resulting mixture was extracted into diethyl ether (2×). The ethereal was washed with water, then brine, dried over magnesium sulfate, and concentrated. The resulting residue was dissolved in dimethylsulfoxide (14 mL) and transferred to a solution of potassium tert-butoxide (22 g, 196 mmol) in dimethylsulfoxide (140 mL) in a cool water bath (ca. 10° C.) via canula. The bath was removed and stirring continued for 30 min. The reaction mixture was poured onto ice/concentrated hydrochloric acid. The resulting mixture was extracted with dichloromethane (2×), washed with water (3×), then brine, dried over magnesium sulfate and concentrated. Prep HPLC gave 1.66 g (31.5%) as a pale solid. LC/MS (HPLC method 3): $t_R$=2.337 min, 215.01(MH)+.

Intermediate 112

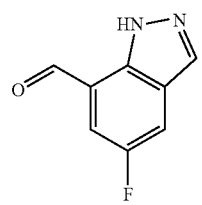

5-Fluoro-1H-indazole-7-carbaldehyde. To a solution of 7-bromo-5-fluoro-1H-indazole (1.66 g, 7.72 mmol) in tetrahydrofuran (35 mL) at 0° C. was added sodium hydride (0.618 g, 15.4 mmol). The ice bath was removed and stirring continued for 20 min. The solution was cooled to −78° C. and treated with tert-butyllithium (1.7 M in pentane, 9.08 mL, 15.4 mmol) dropwise. The reaction was stirred at −78° C. for 10 min, allowed to warm gradually in the dewar to −50° C., recooled to −78° C., and then treated with dimethylformamide (2.39 mL, 30.9 mmol). After 15 min, the ice bath was removed and stirring continued for 1 h. The reaction was poured onto ice/1 M hydrochloric acid (26.5 mL). The mixture was extracted with ethyl acetate (2×). The organics were washed with water, then brine, dried over magnesium sulfate, and concentrated to give 1.42 g of 5-fluoro-1H-indazole-7-carbaldehyde (quant.) as a light yellow solid. LC/MS (HPLC method 3): $t_R$=1.39 min, 165.17(MH)+.

Intermediates 113 and 114

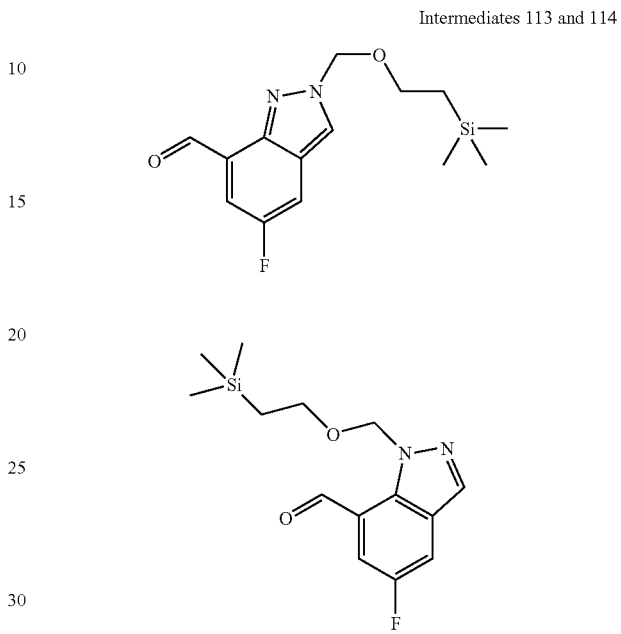

5-Fluoro-2-((2-(trimethylsilyl)ethoxy)methyl)-2H-indazole-7-carbaldehyde and 5-Fluoro-1-((2-(trimethylsilyl)ethoxy)methyl)-1H-indazole-7-carbaldehyde. To a solution of 5-fluoro-1H-indazole-7-carbaldehyde (1.27 g, 7.74 mmol) and N-methyldicyclohexylamine (2.56 mL, 12.38 mmol) in tetrahydrofuran (26 mL) at 0° C. was added (2-(chloromethoxy)ethyl)trimethylsilane (1.92 mL, 10.8 mmol). The ice bath was removed and stirring continued for 4 h. To this was added another portion of N-methyldicyclohexylamine (1.60 mL, 7.74 mmol) and (2-(chloromethoxy)ethyl)trimethylsilane (0.69 mL, 3.87 mmol) and the reaction stirred overnight. The reaction was poured into diethyl ether, washed with water (2×), then brine, dried over magnesium sulfate, and concentrated. Column chromatography (1%→22% EtOAc/Hex) gave 2 fractions. The faster eluting fraction was concentrated to give 5-fluoro-1-((2-(trimethylsilyl)ethoxy)methyl)-1H-indazole-7-carbaldehyde (0.104 g, 4.54%). The second fraction was concentrated to give 5-fluoro-2-((2-(trimethylsilyl)ethoxy)methyl)-2H-indazole-7-carbaldehyde (1.53 g, 67.2%). 5-methoxy-2-((2-(trimethylsilyl)ethoxy)methyl)-2H-indazole-7-carbaldehyde: $^1$H-NMR (CDCl$_3$, 500 MHz) δ 10.57 (s, 1H), 8.25 (s, 1H), 7.71 (m, 1H), 7.59 (m, 1H), 5.80 (s, 2H), 3.66(m, 2H), 0.96 (m, 2H), −0.03 (s, 9H); $^{13}$C-NMR (CDCl$_3$, 126 MHz) δ 189.3, 158.0 (d, J=960 Hz), 143.9, 126.9, 123.3, 120.7, 120.5, 110.6, 110.4, 82.4, 68.1, 18.0, −1.4; 5-methoxy-1-((2-(trimethylsilyl)ethoxy)methyl)-1H-indazole-7-carbaldehyde: $^1$H-NMR (CDCl$_3$, 300 MHz) δ 10.37 (s, 1H), 8.06 (s, 1H), 7.74 (m, 1H), 7.63 (m, 1H), 6.02 (s, 2H), 3.46 (m, 3H), 0.80 (m, 2H), −0.13 (s, 9H); $^{13}$C-NMR (CDCl$_3$, 76 MHz) δ 188.7, 157.3 (d, J=963 Hz), 134.5, 133.6, 122.4, 120.0, 119.7, 112.4, 112.1, 80.9, 66.2, 17.6, −1.6.

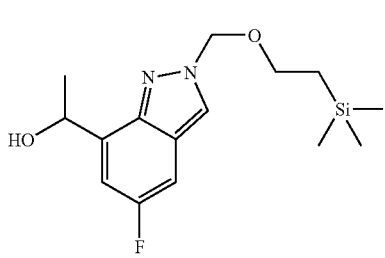

Intermediate 115

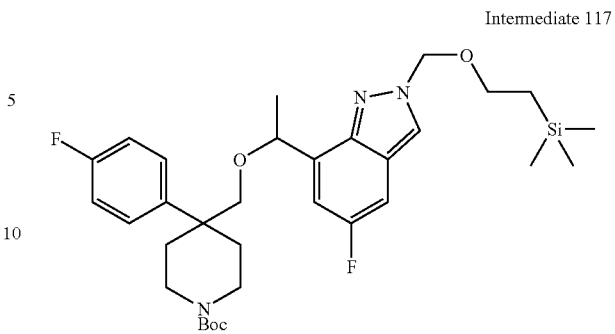

Intermediate 117

(±)-1-(5-Fluoro-2-((2-(trimethylsilyl)ethoxy)methyl)-2H-indazol-7-yl)ethanol. To a solution of 5-fluoro-2-((2-(trimethylsilyl)ethoxy)methyl)-2H-indazole-7-carbaldehyde (1.53 g, 5.2 mmol) in tetrahydrofuran (32 mL) at −78° C. was added methyl magnesiumbromide (3M in diethyl ether, 3.46 mL, 10.4 mmol). The reaction was allowed to gradually warm in the ice bath (ca. 2 h) to 0° C. The reaction which had been a suspension became a solution. The reaction was quenched by addition of saturated ammonium chloride and poured into diethyl ether. The ethereal was washed with water (2×), then brine, dried over magnesium sulfate, and concentrated to give 1.59 g (99%) as an yellow oil. $^1$H-NMR (CDCl$_3$, 500 MHz) δ 8.05(s, 1H), 7.15(m, 1H), 7.05(m, 1H), 5.68(s, 2H), 5.33(q, J=5 Hz, 1H), 3.63(m, 2H), 1.68 (d, J=10.0 Hz, 3H), 0.93(m, 2H), −0.03(s, 9H); $^{13}$C-NMR (CDCl$_3$, 126MHz) δ 58.7 (d, J=960 Hz), 144.4, 137.7, 122.9, 121.9, 113.5, 113.3, 101.6, 101.4, 81.9, 68.0, 67.6, 25.7, 23.3, 17.9, −1.38; Mass spec.: 311.33 (MH)$^+$.

(±)-tert-Butyl 4-((1-(5-fluoro-2-((2-(trimethylsilyl)ethoxy)methyl)-2H-indazol-7-yl)ethoxy)methyl)-4-(4-fluorophenyl)piperidine-1-carboxylate. To a solution of (±)-1-(5-fluoro-2-((2-(trimethylsilyl)ethoxy)methyl)-2H-indazole-7-yl)ethyl 2,2,2-trichloroacetimidate (1.121 g, 2.465 mmol) and tert-butyl 4-(4-fluorophenyl)-4-(hydroxymethyl)piperidine-1-carboxylate (0.839 g, 2.71 mmol) in dichloromethane (6 mL) at 0° C. was added cyclohexane (5.61 mL) and tetrafluoroboric acid diethyl ether complex (0.017 mL, 0.123 mmol). The reaction was stirred at 0° C. for 10 min. The reaction was treated with an additional portion of tetrafluoroboric acid diethyl ether complex (9 μL, 0.065 mmol) and stirred at 0° C. for 30 min. The reaction was quenched by addition of saturated sodium bicarbonate, diluted with diethyl ether, and poured into water. The ethereal was washed with water (2×), then brine, dried over magnesium sulfate, and concentrated. Column chromatography (15%→22% EtOAc/Hex) gave 922 mg (62.2%) as an amorphous foam solid. $^1$H-NMR (CDCl$_3$, 300 MHz) δ 7.98 (s, 1H), 7.26-7.32 (m, 2H), 6.97-7.08 (m, 3H), 6.64-6.68(m, 1H), 5.62 (s, 2H), 4.92 (q, J=6.0 Hz, 1H), 3.65-3.75 (m, 2H), 3.58 (m, 2H), 3.35 (m, 2H), 2.9-3.1 (m, 2H), 1.8-2.2 (m, 4H), 1.39-1.42(m, 12H), 0.88(m, 2H), −0.07 (s, 9H); Mass spec.: 602.54 (MH)$^+$.

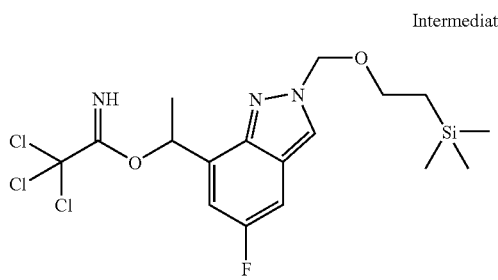

Intermediate 116

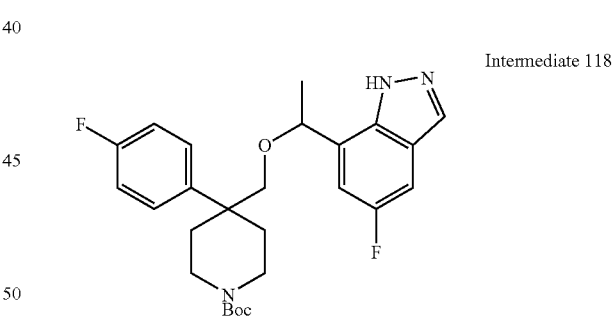

Intermediate 118

(±)-1-(5-Fluoro-2-((2-(trimethylsilyl)ethoxy)methyl)-2H-indazole-7-yl)ethyl 2,2,2-trichloroacetimidate. (±)-1-(5-Fluoro-2-((2-(trimethylsilyl)ethoxy)methyl)-2H-indazol-7-yl)ethanol (1.58 g, 5.09 mmol) was dissolved in dichloromethane (10 mL), cooled to 0° C. and treated with 1,8-diazabicyclo(5.4.0)undec-7-ene (153 μL, 1.018 mmol). The reaction was stirred for 10 min and treated with trichloroacetonitrile (5.1 mL, 50.9 mmol) dropwise over 10 min. The reaction was stirred at room temperature for 2 h and concentrated. The resulting residue was dissolved in diethyl ether. The resulting solution was decanted to separate it from the resulting dark tar which formed. The ethereal was concentrated to give 2.247 g (97%). $^1$H-NMR (CDCl$_3$, 300 MHz) δ 8.35 (s, 1H), 8.03 (s, 1H), 7.16 (m, 1H), 6.63 (q, J=6.0 Hz, 1H), 5.68 (s, 2H), 3.62 (m, 2H), 1.78 (d, J=6.0 Hz, 3H), 0.89-0.94 (m, 2H), −0.05 (s, 9H).

(±)-tert-Butyl 4-((1-(5-fluoro-1H-indazol-7-yl)ethoxy)methyl) 4-(4-fluorophenyl)piperidine-1-carboxylate. (±)-tert-Butyl 4-((1-(5-fluoro-2-((2-(trimethylsilyl)ethoxy)methyl)-2H-indazol-7-yl)ethoxy)methyl)-4-(4-fluorophenyl) piperidine-1-carboxylate (200 mg, 0.332 mmol) was dissolved in trifluoroacetic acid (50% in dichloromethane, 6 mL) and stirred at room temperature for 4 h. The reaction was concentrated and loaded onto a strong cation exchange cartridge in methanol. The cartridge was flushed with several volumes of methanol which were discarded. The product was eluted with 2 M ammonia in methanol and concentrated to give 92.5 mg of (±)-5-fluoro-7-(1-((4-(4-fluorophenyl)piperidin-4-yl)methoxy)ethyl)-2H-indazole (74.9%). The crude amine (92.5 mg, 0.249 mmol) in dichloromethane (2.5 mL) was cooled to 0° C. and treated with di-tert-butyl dicarbonate (109 mg, 0.498 mmol). The reaction was stirred at 0° C. for 1 h and was quenched by addition of 2 M ammonia in methanol and concentrated. The residue was purified by column chromatography (15%→30% EtOAc/Hex) to give 108 mg (92%) as white foam. $^1$H-NMR (CDCl$_3$, 300 MHz) δ 9.68(bs, 1H), 7.90(s, 1H), 7.17-7.28(m, 3H), 7.01-7.10(m, 2H), 6.80(m, 1H), 4.48(q, J=6.0 Hz, 1H), 3.60-3.80(m, 2H), 3.36 (d, J=9 Hz, 1H), 3.25 (d, J=9 Hz, 1H), 2.90-3.10(m, 2H), 2.01-2.25 (m, 2H), 1.68-1.87(m, 2H), 1.39-1.41(m, 12H); $^{13}$C-NMR (CDCl$_3$, 76MHz) δ 161.5 (d, J=981 Hz), 157.4 (d, J=948 Hz), 154.8, 137.9, 134.2, 133.8, 128.6, 127.4, 123.7, 115.7, 115.4, 113.2, 112.9, 103.7, 103.4, 79.4, 78.5, 78.2, 60.27, 41.0, 32.3, 32.0, 28.33, 22.0; Mass spec.: 472.51 (MH)$^+$.

Intermediate 119

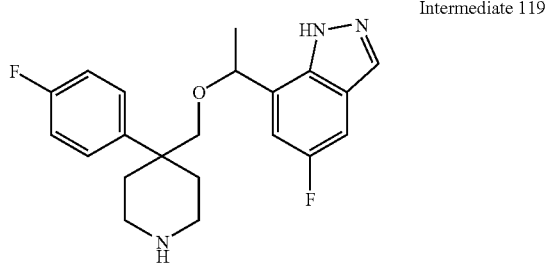

(±)-5-Fluoro-7-(1-((4-(4-fluorophenyl)piperidin-4-yl) methoxy)methyl)-1H-indazole. (±)-tert-Butyl 4-((1-(5-fluoro-1H-indazol-7-yl)ethoxy)methyl) 4-(4-fluorophenyl) piperidine-1-carboxylate(94 mg, 0.199 mmol) was dissolved in trifluoroacetic acid (20% in dichloromethane, 5.5 mL) and stirred at room temperature for 30 min. The reaction was concentrated and loaded onto a strong cation exchange cartridge in methanol. The cartridge was flushed with several volumes of methanol which were discarded. The product was eluted with 2 M ammonia in methanol and concentrated to give 64 mg (86%). LC/MS (HPLC method 3): t$_R$=2.478 min, 372.37(MH)$^-$.

Intermediate 120

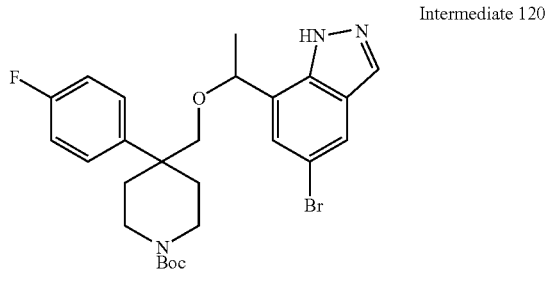

(±)-tert-Butyl 4-((1-(5-bromo-1H-indazol-7-yl)ethoxy) methyl)-4-(4-fluorophenyl)piperidine-1-carboxylate. (±)-tert-Butyl 4-((1-(5-bromo-2-((2-(trimethylsilyl)ethoxy)methyl)-2H-indazol-7-yl)ethoxy)methyl)-4-(4-fluorophenyl) piperidine-1-carboxylate(380 mg, 0.573 mmol) was dissolved in trifluoroacetic acid (50% in dichloromethane, 6 mL) and stirred at room temperature for 4 h. The reaction was concentrated and loaded onto a strong cation exchange cartridge in methanol. The cartridge was flushed with several volumes of methanol which were discarded. The product was eluted with 2 M ammonia in methanol and concentrated to give 200 mg of (±)-5-bromo-7-(1-((4-(4-fluorophenyl)piperidin-4-yl)methoxy)ethyl)-2H-indazole (81%). The crude amine (200 mg, 0.463 mmol) in dichloromethane (4 mL) was cooled to 0° C. and treated with di-tert-butyl dicarbonate (202 mg, 0.925 mmol). The reaction was stirred at 0° C. for 1 h and was quenched by addition of 2 M ammonia in methanol and concentrated. The residue was purified by column chromatography (1%→30% EtOAc/Hex) to give 200 mg (81%) as clear oil. LC/MS (HPLC method 3): t$_R$=4.046 min, 532.27 (MH)$^+$.

Intermediate 121

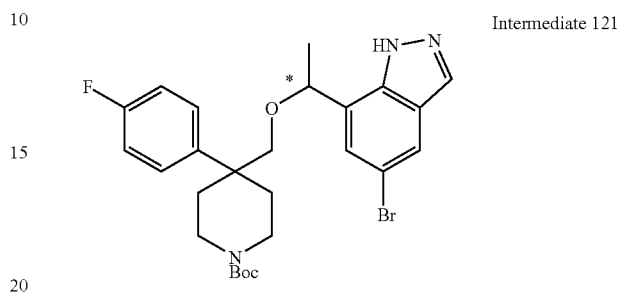

Enantiomer B of tert-Butyl 4-((1-(5-bromo-1H-indazol-7-yl)ethoxy)methyl)-4-(4-fluorophenyl)piperidine-1-carboxylate. (±)-tert-Butyl 4-((1-(5-bromo-1H-indazol-7-yl)ethoxy) methyl)-4-(4-fluorophenyl)piperidine-1-carboxylate (270 mg) resolved by chiral HPLC (OD-H column, 30×250 mm, 5 μm, 220 nm, eluting with 15% MeOH/0.1% DEA) to give 2 fractions. The faster eluting fraction was concentrated to give Enantiomer A of tert-butyl 4-((1-(5-bromo-1H-indazol-7-yl) ethoxy)methyl)-4-(4-fluorophenyl)piperidine-1-carboxylate (106 mg, 39.3%). The second fraction was concentrated to give Enantiomer B of tert-butyl 4-((1-(5-bromo-1H-indazol-7-yl)ethoxy)methyl)-4-(4-fluorophenyl)piperidine-1-carboxylate (108 mg, 40%).

Intermediate 122

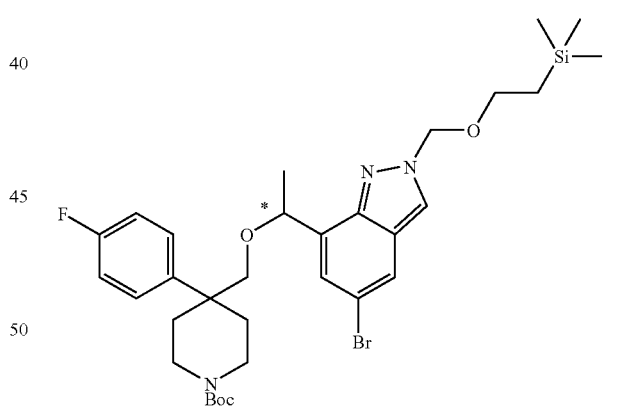

Enantiomer B of tert-Butyl 4-((1-(5-bromo-2-((2-(trimethylsilyl)ethoxy)methyl)-2H-indazol-7-yl)ethoxy)methyl)-4-(4-fluorophenyl)piperidine-1-carboxylate. To a solution of Enantiomer B of tert-Butyl 4-((1-(5-bromo-1H-indazol-7-yl) ethoxy)methyl)-4-(4-fluorophenyl)piperidine-1-carboxylate (108 mg, 0.203 mmol) and N-methyldicyclohexylamine (0.070 mL, 0.325 mmol) in tetrahydrofuran (tert-Butyl 4-((1-(5-bromo-1H-indazol-7-yl)ethoxy)methyl)-4-(4-fluorophenyl)piperidine-1-carboxylate ) at 0° C. was added (2-(chloromethoxy)ethyl)trimethylsilane (0.050 mL, 0.28 mmol). The ice bath was removed and stirring continued for 5 h. An additional portion of N-methyldicyclohexylamine (0.044 mL, 0.20 mmol) and (2-(chloromethoxy)ethyl)trimethylsilane (0.018 mL, 0.10 mmol) were added and the reaction mixture stirred at room temperature overnight. The reaction mixture was filtered and concentrated. Column chromatography (20% EtOAc/Hex) gave 107 mg (80%) as white foam. LC/MS (HPLC method 3): $t_R$=4.481 min, 662.46(MH)$^+$.

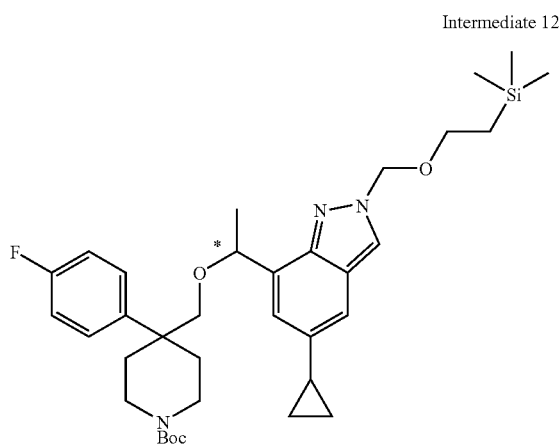

Intermediate 123

Enantiomer B of tert-Butyl 4-((1-(5-cyclopropyl-2-((2-(trimethylsilyl)ethoxy)methyl)-2H-indazol-7-yl)ethoxy)methyl)-4-(4-fluorophenyl)piperidine-1-carboxylate. Enantiomer B of tert-Butyl 4-((1-(5-bromo-2-((2-(trimethylsilyl)ethoxy)methyl)-2H-indazol-7-yl)ethoxy)methyl)-4-(4-fluorophenyl)piperidine-1-carboxylate (105 mg, 0.158 mmol), cyclopropyl boronic acid (40.8 mg, 0.475 mmol), and tetrakis(triphenylphosphine) palladium(0) (18.3 mg, 0.016 mmol) were combined in dry tetrahydrofuran (3 mL) followed by addition of 0.56 mL of a 1 N potassium hydroxide aqueous solution in a microwave tube and sealed. After flushing the mixture with nitrogen, the mixture was heated at 100° C. for 1 h via microwave. After cooling to room temperature, the reaction mixture was concentrated, dissolved in ethyl acetate and washed with water and brine, concentrated and purified by flash chromatography on silica gel (20% EtOAc/Hex) to afford 46 mg (46.5%). LC/MS (HPLC method 2): $t_R$=4.431 min, 624.63(MH)$^+$.

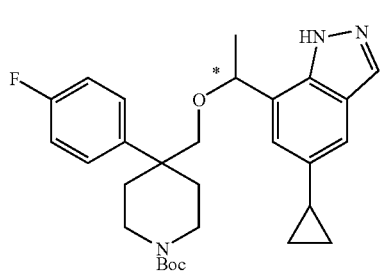

Intermediate 124

Enantiomer B of tert-Butyl 4-((1-(5-cyclopropyl-1H-indazol-7-yl)ethoxy)methyl)-4-(4-fluorophenyl)piperidine-1-carboxylate. Enantiomer B of tert-Butyl 4-((1-(5-cyclopropyl-2-((2-(trimethylsilyl)ethoxy)methyl)-2H-indazol-7-yl)ethoxy)methyl)-4-(4-fluorophenyl)piperidine-1-carboxylate (46 mg, 0.074 mmol) was dissolved in trifluoroacetic acid (50% in dichloromethane, 1.6 mL) and stirred at room temperature for 4 h. The reaction was concentrated and loaded onto a strong cation exchange cartridge in methanol. The cartridge was flushed with several volumes of methanol which were discarded. The product was eluted with 2 M ammonia in methanol and concentrated to give 30 mg of Enantiomer B of 5-cyclopropyl-7-(1-((4-(4-fluorophenyl)piperidin-4-yl)methoxy)ethyl)-1H-indazole (quant.). The crude amine (30 mg, 0.076 mmol) in dichloromethane (2 mL) was cooled to 0° C. and treated with di-tert-butyl dicarbonate (33.3 mg, 0.152 mmol). The reaction was stirred at 0° C. for 1 h and was quenched by addition of 2 M ammonia in methanol and concentrated. The residue was purified by column chromatography (25% EtOAc/Hex) to give 28 mg (74.4%) as oil. $^1$H-NMR (CDCl$_3$, 300 MHz) δ 7.85 (s, 1H), 7.23 (m,2H), 7.03 (m, 3H), 6.76 (s, 1H), 4.46 (q, J=6 Hz, 1H), 3.57-3.75 (m, 2H), 3.32 (d, J=9 Hz, 1H), 3.22 (d, J=9 Hz, 1H), 2.9-3.1(m, 2H), 2.01-2.22 (m,2H), 1.65-1.8 (m, 2H), 1.37-1.41 (m, 12H), 0.91 (m, 2H), 0.64 (m, 2H); Mass spec.: 494.48 (MH)$^+$.

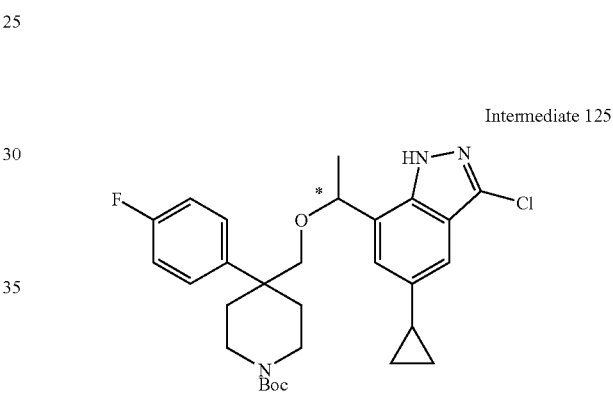

Intermediate 125

Enantiomer B of tert-Butyl 4-((1-(3-chloro-5-cyclopropyl-1H-indazol-7-yl)ethoxy)methyl)-4-(4-fluorophenyl)piperidine-1-carboxylate. To a solution of Enantiomer B of tert-Butyl 4-((1-(5-cyclopropyl-1H-indazol-7-yl)ethoxy)methyl)-4-(4-fluorophenyl)piperidine-1-carboxylate (28.0 mg, 0.057 mmol) and sodium hydroxide (4 M in water, 0.018 mL, 0.071 mmol) in ethanol (0.5 mL) at 0° C. was added N-chlorosuccinimide (15.2 mg, 0.113 mmol). After 30 min, the reaction showed clean, but partial, conversion to a less polar spot. It was treated with another 0.009 ml of 4 M sodium hydroxide and N-chlorosuccinimide (7.6 mg, 0.057 mmol). After 30 min, the reaction was again treated with 0.018 mL of 4 M sodium hydroxide and N-chlorosuccinimide (15.2 mg, 0.113 mmol). The reaction was stirred for another 30 min, and stored in the refrigerator overnight. The reaction was again treated with 0.018 mL of 4 M sodium hydroxide and N-chlorosuccinimide (15.2 mg, 0.113 mmol) and stirred for 30 min. The reaction was quenched by addition of aqueous ammonia and diluted with ether. The ethereal was washed with water (2×), then brine, dried over magnesium sulfate, and concentrated. Column chromatography (25% EtOAc/Hex) gave 23.5 mg (78%) as a clear oil. $^1$H-NMR (CDCl$_3$, 300 MHz) δ 7.23 (m, 2H), 7.16 (s, 1H), 7.04 (m, 2H), 6.81 (s, 1H), 4.46 (1, J=6.0 Hz, 1H), 3.64-3.74 (m, 2H), 3.33 (d, J=9 Hz, 1H), 3.23 (d, J=9 Hz, 2H), 2.92-3.1(m, 2H), 2.01-2.22 (m,2H), 1.70-1.90 (m, 2H), 1.41 (s, 9H), 1.37 (d, J=6 Hz, 3H), 0.91 (m, 2H), 0.65 (m, 2H); Mass spec.: 528.56 (MH)$^+$.

Intermediate 126

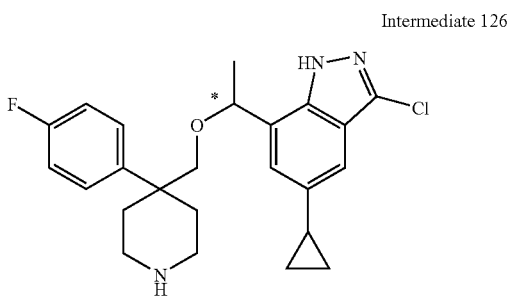

Enantiomer B of 3-Chloro-5-cyclopropyl-7-(1-((4-(4-fluorophenyl)piperidin-4-yl)methoxy)ethyl)-1H-indazole. Enantiomer B of tert-Butyl 4-((1-(3-chloro-5-cyclopropyl-1H-indazol-7-yl)ethoxy)methyl)-4-(4-fluorophenyl)piperidine-1-carboxylate (23.5 mg, 0.045 mmol) was dissolved in trifluoroacetic acid (20% in dichloromethane, 1.5 mL) and stirred at room temperature for 30 min. The reaction was concentrated and loaded onto a strong cation exchange cartridge in methanol. The cartridge was flushed with several volumes of methanol which were discarded. The product was eluted with 2 M ammonia in methanol and concentrated to give 17.2 mg (90%). $^1$H-NMR (CDCl$_3$, 300 MHz) δ 7.22-7.26 (m, 2H), 7.16 (s, 1H), 7.0-7.06 (m, 2H), 6.81 (s, 1H), 4.44 (q, J=9 Hz, 1H), 3.35 (d, J=9 Hz, 1H), 3.23 (d, J=9 Hz, 1H), 2.6-2.9 (m, 4H), 1.7-2.2 (m, 4H), 1.37 (d, J=4 Hz, 3H), 0.91 (m, 2H), 0.65 (m, 2H); Mass spec.: 528.56 (MH)$^+$.

Intermediate 127

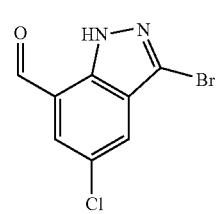

3-Bromo-5-chloro-1H-indazole-7-carbaldehyde. To a mixture of 5-chloro-1H-indazole-7-carbaldehyde (1.0 g, 5.54 mmol) in acetic acid (5 mL) was added bromine (0.43 mL, 8.31 mmol) slowly over 5 min. After 1 h, the reaction mixture was diluted with methylene chloride, washed with water (2×), saturated sodium thiosulfate (2×), saturated sodium bicarbonate (2×), then brine (2×), dried over sodium sulfate, and concentrated to afford 1.4 g (97%) as a yellow powder. LC/MS (HPLC method 1): t$_R$=2.49 min, 261.00(MH)$^+$.

Intermediate 128

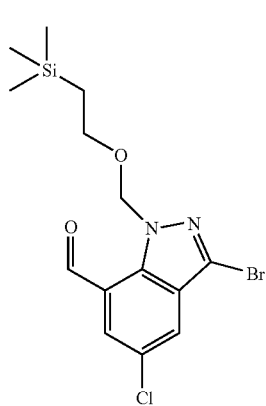

3-Bromo-5-chloro-1-((2-(trimethylsilyl)ethoxy)methyl)-1H-indazole-7-carbaldehyde. 3-Bromo-5-chloro-1H-indazole-7-carbaldehyde (1.4 g, 5.4 mmol) and N-methyldicyclohexylamine (1.6 mL, 7.28 mmol) were suspended in tetrahydrofuran (6 mL), cooled to 0° C., and treated with (2-(chloromethoxy)ethyl)trimethylsilane (2.0 mL, 6.74 mmol). The ice bath was removed and stirring continued for 4 h. The reaction was poured into ethyl acetate, washed with water (3×), 1M potassium bisulfate (2×), then brine (2×), dried over sodium sulfate, and concentrated. Column chromatography on silica gel (10% ethyl acetate/hexanes) gave 1.45 g (69%) as a faint yellow oil. $^1$H-NMR (CDCl$_3$, 500 MHz) δ 10.28 (s, 1H), 7.97 (d, J=1.83 Hz, 1H), 7.87 (d, J=2.14 Hz, 1H), 6.0(s, 2H), 3.48-3.51 (m, 2H), 0.80-0.83 (m, 2H), 0.10 (s, 9H).

Intermediate 129

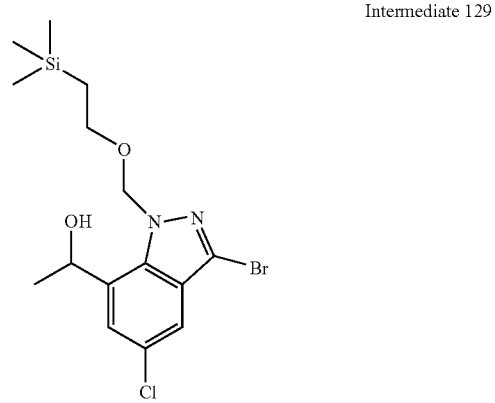

(±)-1-(3-Bromo-5-chloro-1-((2-(trimethylsilyl)ethoxy)methyl)-1H-indazol-7-yl)ethanol. 3-Bromo-5-chloro-1-((2-(trimethylsilyl)ethoxy)methyl)-1H-indazole-7-carbaldehyde (1.35 g, 3.46 mmol) was dissolved in tetrahydrofuran (10 mL), cooled to −78° C. and treated with methylmagnesium bromide (3.0 M in diethyl ether, 1.7 mL, 5.20 mmol) over several minutes. After 1 h, the ice bath was removed and stirring continued for 1 h at room temperature. The reaction was cooled to 0° C., treated with saturated ammonium chloride and diluted with ethyl acetate. The layers were separated. The organic layer was washed with water (2×), brine (2×), dried over sodium sulfate, filtered and concentrated. Flash chromatography on silica gel (30% ethyl acetate/hexanes) afforded 1.29 g (92%) as a brown oil. $^1$H-NMR (CDCl$_3$, 300 MHz) δ 7.51-7.53 (m, 2H), 5.91 (q$_{AB}$, J$_{AB}$=11.7 Hz, 2H), 5.52-5.54 (m, 1H), 3.49-3.54 (m, 2H), 1.63 (d, J=6.6 Hz, 3H), 0.78-0.83 (m, 2H), 0.09 (s, 9H). Mass spec.: 429.18 (MNa)$^+$.

Intermediate 130

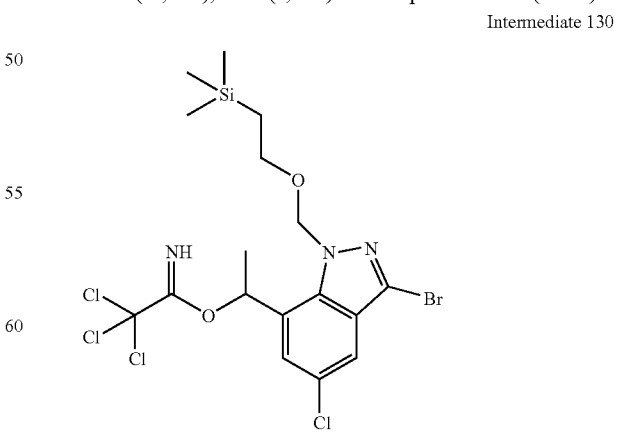

(±)-1-(3-Bromo-5-chloro-1-((2-(trimethylsilyl)ethoxy)methyl)-1H-indazol-7-yl)ethyl 2,2,2-trichloroacetimidate.

(±)-1-(3-Bromo-5-chloro-1-((2-(trimethylsilyl)ethoxy)methyl)-1H-indazol-7-yl)ethanol (1.29 g, 3.18 mmol) was dissolved in methylene chloride (10 mL), cooled to 0° C. and treated with 1,8-diazabicyclo(5.4.0)undec-7-ene (96 μL, 0.64 mmol). The reaction was stirred for 10 min and treated with trichloroacetonitrile (3.19 mL, 31.8 mmol) dropwise over 10 min. The ice bath was removed and the reaction stirred at room temperature for 1 h and concentrated. Flash chromatography on silica gel (5% ethyl acetate/hexanes) gave 1.69 g (77%) as an oil. $^1$H-NMR (CDCl$_3$, 300 MHz) δ 8.27 (s, 1H), 7.59 (d, J=1.8 Hz, 1H), 7.53 (d, J=1.8 Hz, 1H), 6.58 (q, J=6.6 Hz, 1H), 6.19 (q$_{AB}$, J$_{AB}$=11.4 Hz, 2H), 3.50-3.56 (m, 2H), 1.74 (m, 3H), 0.80-0.84 (m, 2H), 0.06 (s, 9H).

Intermediate 131

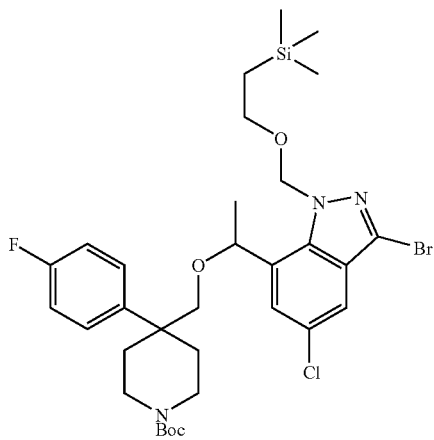

(±)-tert-Butyl 4-((1-(3-bromo-5-chloro-1-((2-(trimethylsilyl)ethoxy)methyl)-1H-indazol-7-yl)ethoxy)methyl)-4-(4-fluorophenyl)piperidine-1-carboxylate. (±)-1-(3-Bromo-5-chloro-1-((2-(trimethylsilyl)ethoxy)methyl)-1H-indazol-7-yl)ethyl 2,2,2-trichloroacetimidate (1.69 g, 3.07 mmol) and tert-butyl 4-(4-fluorophenyl)-4-(hydroxymethyl)piperidine-1-carboxylate (1.05 g, 3.38 mmol) were combined in a dichloromethane/cyclohexane mixture (1:1, 8 mL) and cooled to 0° C. The reaction was treated with tetrafluoroboric acid-diethyl ether complex (86 μL, 0.61 mmol), stirred at 0° C. for 1 h, quenched by addition of saturated sodium bicarbonate and diluted with diethyl ether. The layers were separated. The ethereal was washed with water (2x), brine (2x), dried over sodium sulfate, and concentrated. Column chromatography on silica gel (18% ethyl acetate/hexanes) gave 1.2 g (56%) as a white film. $^1$H-NMR (CDCl$_3$, 500 MHz) δ 7.48 (d, J=1.84 Hz, 1H), 7.19-7.21 (m, 2H), 7.08 (m, 1H), 6.97-7.00 (m, 2H), 5.49-5.56 (m, 2H), 5.01 (q, J=6.1 Hz, 1H), 3.70 (m, 2H), 3.43-3.47 (m, 2H), 3.22 (m, 2H), 3.00-3.05 (m, 2H), 2.04-2.14 (m, 2H), 1.76-1.87 (m, 2H), 1.43 (s, 9H), 1.42 (m, 3H), 0.72-0.82 (m, 2H), 0.08 (s,9H). Mass spec.: 720.42 (MNa)$^+$.

Intermediate 132

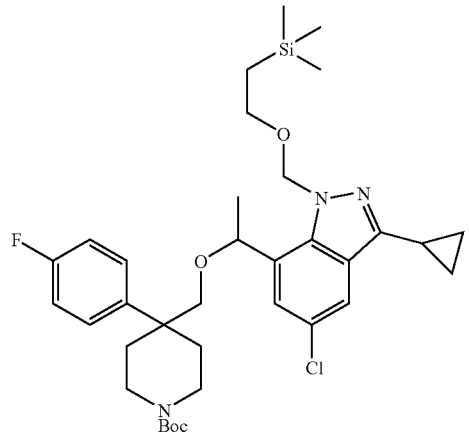

(±)-tert-Butyl 4-((1-(5-chloro-3-cyclopropyl-1-((2-(trimethylsilyl)ethoxy)methyl)-1H-indazol-7-yl)ethoxy)methyl)-4-(4-fluorophenyl)piperidine-1-carboxylate. (±)-tert-Butyl 4-((1-(3-bromo-5-chloro-1-((2-(trimethylsilyl)ethoxy)methyl)-1H-indazol-7-yl)ethoxy)methyl)-4-(4-fluorophenyl)piperidine-1-carboxylate (100 mg, 0.14 mmol), cyclopropylboronic acid (18.5 mg, 0.22 mmol), and tetrakis(triphenylphosphine) palladium(0) (16.6 mg, 0.01 mmol) were combined in dry tetrahydrofuran (3 mL) in a microwave tube and sealed. The mixture was flushed with nitrogen then 0.5 mL of a 1 N potassium hydroxide aqueous solution was introduced. The mixture was heated at 100° C. for 1 h via microwave. After cooling to room temperature, the reaction mixture was diluted with ethyl acetate, washed with water (2x), then brine (2x), dried over sodium sulfate, and concentrated. Flash chromatography on silica gel (15% ethyl acetate/hexanes) gave 65 mg (69%). $^1$H-NMR (CDCl$_3$, 500 MHz) δ 7.58 (d, J=1.8 Hz, 1H), 7.21-7.23 (m, 2H), 6.97-7.01 (m, 3H), 5.50 (q$_{AB}$, J$_{AB}$=11.9 Hz, 2H), 5.00 (q, J=6.4 Hz, 1H), 3.69 (m, 2H), 3.33-3.45 (m, 2H), 3.19-3.27 (m, 2H), 3.01-3.06 (m, 2H), 2.01-2.14 (m, 3H), 1.79-1.89 (m, 2H), 1.43 (s, 9H), 1.41 (m, 3H), 0.96-1.01 (m, 4H), 0.67-0.83 (m, 2H), 0.09 (s, 9H). Mass spec.: 658.67 (MH)$^+$.

Intermediate 133

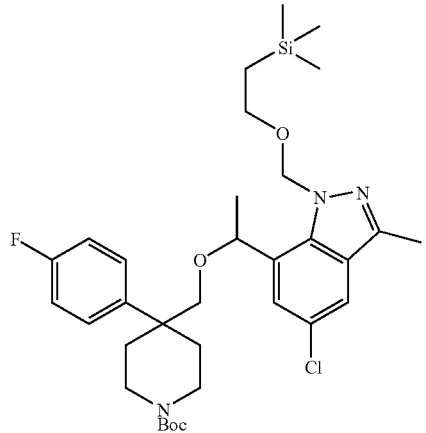

(±)-tert-Butyl 4-((1-(5-chloro-3-methyl-1-((2-(trimethylsilyl)ethoxy)methyl)-1H-indazol-7-yl)ethoxy)methyl)-4-(4- fluorophenyl)piperidine-1-carboxylate. A microwave tube was charged with (±)-tert-butyl 4-((1-(3-bromo-5-chloro-1-((2-(trimethylsilyl)ethoxy)methyl)-1H-indazol-7-yl)ethoxy)methyl)-4-(4-fluorophenyl)piperidine-1-carboxylate (100 mg, 0.14 mmol), tetrakis(triphenylphosphine) palladium(0) (16.6 mg, 0.01 mmol) and trimethylboroxine (60 µL, 0.43 mmol). The tube was flushed with nitrogen, treated with tetrahydrofuran (3 mL) and potassium hydroxide (2 M in water, 140 µL, 0.28 mmol). The tube was sealed and heated at 100° C. for 2 h via microwave. The reaction was cooled, poured into ethyl acetate, washed with water (2×), then brine (2×), dried over sodium sulfate, and concentrated. Column chromatography (20% ethyl acetate/hexanes) gave 70 mg (77%) as an oil. $^1$H-NMR (CDCl$_3$, 500 MHz) δ 7.47 (d, J=1.8 Hz, 1H), 7.20-7.23 (m, 2H), 7.02 (m, 1H), 6.96-6.99 (m, 2H), 5.53 (q$_{AB}$, J$_{AB}$=11.6 Hz, 2H), 5.02 (q, J=6.4 Hz, 1H), 3.69 (m, 2H), 3.39-3.45(m, 2H), 3.24 (q$_{AB}$, J$_{AB}$=9.2 Hz, 2H), 3.01-3.05 (m, 2H), 2.47 (s, 3H), 2.03-2.04 (m, 2H), 1.81-1.88 (m, 2H), 1.43 (s, 9H), 1.43 (m, 3H), 0.68-0.84 (m, 2H), 0.09 (s, 9H). Mass spec.: 632.62 (MH)$^+$.

Intermediate 134

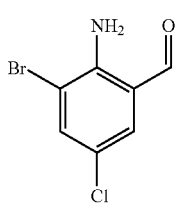

2-Amino-3-bromo-5-chlorobenzaldehyde. 2-Amino-5-chlorobenzaldehyde (2.1 g, 13.5 mmol) was dissolved in chloroform (20 mL) and treated with N-bromosuccinimide (2.6 g, 14.9 mmol). The reaction was stirred for 30 min at ambient temperature. The reaction was diluted with methylene chloride and washed with sodium thiosulfate (2×), 5% sodium bicarbonate (2×), water (2×), brine, dried over sodium sulfate, and concentrated to afford 3.0 g (95%) as a pale yellow powder. $^1$H-NMR (CDCl$_3$, 500 MHz) δ 9.75 (s, 1H), 7.60 (d, J=2.4 Hz, 1H), 7.45 (d, J=2.4 Hz, 1H). Mass spec.: 236.01 (MH)$^+$.

Intermediate 135

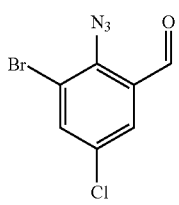

2-Azido-3-bromo-5-chlorobenzaldehyde. To a suspension of 2-amino-3-bromo-5-chlorobenzaldehyde (3.0 g, 12.8 mmol) in a water (4 mL) and hydrochloric acid (4 mL) mixture at 0° C. was added a solution of sodium nitrite (1.1 g, 16.0 mmol) in water (ca. 2 mL) dropwise. After 30 min, the ice bath was removed and the reaction stirred at room temperature for 30 min forming a white suspension. The solids were removed by filtration. The mother liquor was cooled to 0° C. and treated with sodium azide (0.8 g, 12.8 mmol) in water (2.0 mL). The ice bath was removed and stirring was continued for 30 min. The resulting solid was collected by filtration and dried in vacuo for several hours to afford 2.6 g (76%) as a white solid. $^1$H-NMR (CDCl$_3$, 500 MHz) δ 10.30 (s, 1H), 7.78 (d, J=2.4 Hz, 1H), 7.77 (d, J=2.5 Hz, 1H).

Intermediate 136

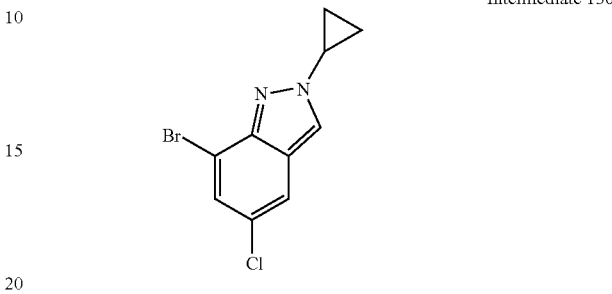

7-Bromo-5-chloro-2-cyclopropyl-2H-indazole. 2-Azido-3-bromo-5-chlorobenzaldehyde (1.38 g, 5.30 mmol) and cyclopropylamine (0.37 mL, 5.30 mmol) in methylene chloride (20 mL) were treated with molecular sieves (1.5 g). The reaction was stirred at room temperature for 2 h, filtered over celite and the resulting solution evaporated in vacuo. The resulting oil was suspended in toluene (15 mL) and heated at reflux for 2 h. After cooling to room temperature, the mixture was poured into ice water and extracted with diethyl ether (2×). The organic layers were pooled together, washed with brine (2×), dried over sodium sulfate, and concentrated. Column chromatography on silica gel (15% ethyl acetate/hexanes) gave 1.1 g (76%) as a light yellow solid. $^1$H-NMR (CDCl$_3$, 500 MHz) δ 8.7 (s, 1H), 7.81 (d, J=2.6 Hz, 1H), 7.53 (d, J=2.6 Hz, 1H), 3.05-3.09 (m, 1H), 0.95-0.99 (m, 4H). Mass spec.: 273.03 (MH)$^+$.

Intermediate 137

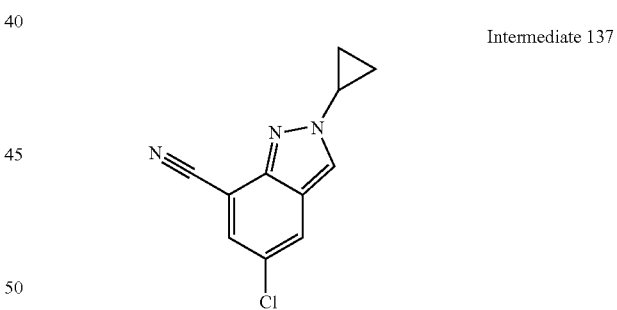

5-Chloro-2-cyclopropyl-2H-indazole-7-carbonitrile. A microwave tube was charged with 7-bromo-5-chloro-2-cyclopropyl-2H-indazole (0.97 g, 3.57 mmol), tetrakis(triphenylphosphine) palladium(0) (0.41 g, 0.36 mmol) and zinc cyanide (0.42 g, 3.57 mmol). The tube was flushed with nitrogen and treated with dimethylformamide (15 mL). The tube was sealed and heated at 120° C. for 1 h via microwave. The reaction was cooled, poured into ethyl acetate, washed with water (2×), then brine (2×), dried over sodium sulfate, and concentrated. Column chromatography (50% ethyl acetate/hexanes) gave 0.54 g (70%) as a white powder. $^1$H-NMR (CDCl$_3$, 500 MHz) δ 8.08 (s, 1H), 7.83 (d, J=1.8 Hz, 1H), 7.60 (d, J=1.8 Hz, 1H), 3.97-4.01 (m, 1H), 1.41-1.44 (m, 2H), 1.19-1.24 (m, 2H). Mass spec.: 220.05 (MH)$^+$.

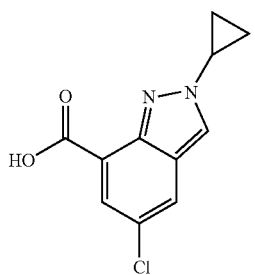

Intermediate 138

5-Chloro-2-cyclopropyl-2H-indazole-7-carboxylic acid. A microwave tube was charged 5-chloro-2-cyclopropyl-2H-indazole-7-carbonitrile (0.54 g, 2.5 mmol), methanol (8.0 mL) and a 4 N sodium hydroxide solution (5 mL, 20 mmol). The tube was sealed and heated at 110° C. for 3 h via microwave. After cooling to room temperature, the mixture was concentrated in vacuo to remove most of the methanol. The residue was poured into water/ethyl acetate. The product was extracted with water (2×) and the organics discarded. The aqueous layers were pooled together and acidified to pH 2.0 with 1 N hydrochloric acid. The resulting precipitate was filtered and dried in vacuo for several hours to afford 0.47 g (80%) as a white powder. $^1$H-NMR (CD$_3$OD, 300 MHz) δ 8.40 (s, 1H), 7.94-7.95 (m, 2H), 4.08-4.14 (m, 1H), 1.37-1.42 (m, 2H), 1.21-1.23 (m, 2H). Mass spec.: 237.16 (MH)$^+$.

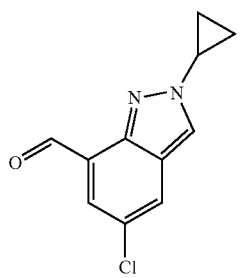

Intermediate 140

5-Chloro-2-cyclopropyl-2H-indazole-7-carbaldehyde. (5-Chloro-2-cyclopropyl-2H-indazol-7-yl)methanol (0.39 g, 1.75 mmol) and triethylamine (0.73 mL, 5.25 mmol) were combined in dimethyl sulfoxide (4 mL) and cooled to 0° C. The reaction was treated with sulfur trioxide pyridine complex (0.87 g, 5.25 mmol) in dimethyl sulfoxide (2 mL), stirred at 0° C. for 5 min, and at room temperature for 20 min. The reaction was poured into ice water and extracted with ethyl acetate (2×). The organic layers were pooled together, washed with 10% acetic acid (2×), water (2×), saturated sodium bicarbonate (2×), brine (2×), dried over sodium sulfate, and concentrated. Column chromatography on silica gel (30% ethyl acetate/hexanes) gave 298 mg (77%) as a yellow solid. $^1$H-NMR (CDCl$_3$, 300 MHz) δ 10.52 (s, 1H), 8.05 (s, 1H), 7.84 (d, J=2.2 Hz, 1H), 7.77 (d, J=1.8 Hz, 1H), 3.96-4.03 (m, 1H), 1.35-1.40 (m, 2H), 1.16-1.23 (m, 2H). Mass spec.: 221.30 (MH)$^+$.

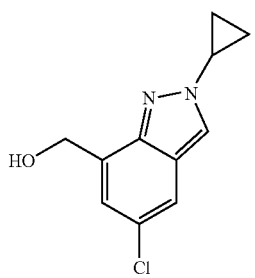

Intermediate 139

(5-Chloro-2-cyclopropyl-2H-indazol-7-yl)methanol. To a suspension of 5-chloro-2-cyclopropyl-2H-indazole-7-carboxylic acid (0.47 g, 2.0 mmol) in tetrahydrofuran (4 mL) at room temperature was added borane tetrahydrofuran complex (1 M in tetrahydrofuran, 4 mL, 4.0 mmol). The reaction was stirred at room temperature overnight. The reaction was cooled to 0° C. and quenched by the cautious addition of methanol. The reaction was diluted with diethyl ether, washed with water (2×), then brine, dried over sodium sulfate, and concentrated. Flash chromatography on silica gel (40% ethyl acetate/hexanes) gave 0.39 g (88%) as an oil. $^1$H-NMR (CDCl$_3$, 300 MHz) δ 7.89 (s, 1H), 7.46 (m, 1H), 7.12 (m, 1H), 4.99 (s, 2H), 3.85-3.89 (m, 1H), 1.26-1.32 (m, 2H), 1.09-1.18 (m, 2H). Mass spec.: 223.19 (MH)$^+$.

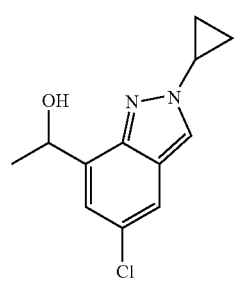

Intermediate 141

(±)-1-(5-Chloro-2-cyclopropyl-2H-indazol-7-yl)ethanol. To a solution of 5-chloro-2-cyclopropyl-2H-indazole-7-carbaldehyde (0.30 g, 1.35 mmol) in tetrahydrofuran (5 mL) at −78° C. was added methyl magnesiumbromide (3 M in diethyl ether, 0.68 mL, 2.03 mmol). The reaction was allowed to gradually warm in the ice bath (ca. 1 h) to 0° C. The reaction which had been a suspension became a solution. The reaction was quenched by addition of saturated ammonium chloride and poured into diethyl ether. The ethereal was washed with water (2×), then brine, dried over sodium sulfate, and concentrated to give 240 mg (77%) as an oil. $^1$H-NMR (CDCl$_3$, 300 MHz) δ 7.90 (s, 1H), 7.45 (m, 1H), 7.09 (m, 1H), 5.27 (q, J=6.6 Hz, 1H), 3.85-3.93 (m, 1H), 1.65 (d, J=6.6 Hz, 1H), 1.28-1.34 (m, 2H), 1.10-1.17 (m, 2H). Mass spec.: 237.28 (MH)$^+$.

Intermediate 142

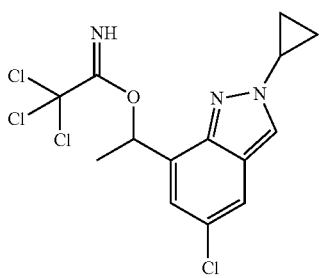

(±)-1-(5-Chloro-2-cyclopropyl-2H-indazol-7-yl)ethyl 2,2,2-trichloroacetimidate. (±)-1-(5-Chloro-2-cyclopropyl-2H-indazol-7-yl)ethanol (240 mg, 1.01 mmol) was dissolved in methylene chloride (5 mL), cooled to 0° C. and treated with 1,8-diazabicyclo(5.4.0)undec-7-ene (31 µL, 0.2 mmol). The reaction was stirred for 10 min and treated with trichloroacetonitrile (1 mL, 10.1 mmol) dropwise over 10 min. The ice bath was removed and the reaction stirred at room temperature for 1 h and concentrated to give a dark brown solid. The crude product was treated with diethyl ether and stirred vigorously for 10 min. The resulting mixture was filtered through a pad of cotton and the ethereal concentrated to afford 365 mg (94%) as an oil. ¹H-NMR (CDCl₃, 300 MHz) δ 8.33 (s, 1H), 7.89 (s, 1H), 7.48 (m, 1H), 7.29 (m, 1H), 6.59 (q, J=6.6 Hz, 1H), 3.86-3.94 (m, 1H), 1.77 (d, J=6.6 Hz, 1H), 1.30-1.35 (m, 2H), 1.10-1.20 (m, 2H).

Intermediate 143

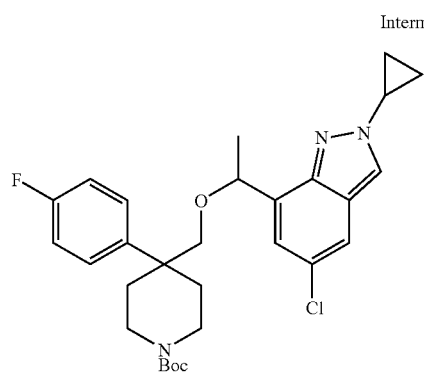

(±)-tert-Butyl 4-((1-(5-chloro-2-cyclopropyl-2H-indazol-7-yl)ethoxy)methyl)-4-(4-fluorophenyl)piperidine-1-carboxylate. (±)-1-(5-Chloro-2-cyclopropyl-2H-indazol-7-yl)ethyl 2,2,2-trichloroacetimidate (365 mg, 0.96 mmol) and tert-butyl 4-(4-fluorophenyl)-4-(hydroxymethyl)piperidine-1-carboxylate (366 mg, 1.05 mmol) were combined in a dichloromethane/cyclohexane mixture (1:1, 10 mL) and cooled to 0° C. The reaction was treated with tetrafluoroboric acid-diethyl ether complex (26 µL, 0.19 mmol), stirred at 0° C. for 1 h, quenched by addition of saturated sodium bicarbonate and diluted with diethyl ether. The layers were separated. The ethereal was washed with water (2×), brine (2×), dried over sodium sulfate, and concentrated. Column chromatography on silica gel (18% ethyl acetate/hexanes) gave 0.32 g (62%) as an oil. ¹H-NMR (CDCl₃, 500 MHz) δ 7.86 (s, 1H), 7.40 (m, 1H), 7.28-7.31 (m, 2H), 6.99-7.03 (m, 2H), 6.75 (m, 1H), 4.90 (q, J=6.4 Hz, 1H), 3.86-3.90(m, 2H), 3.32-3.36 (m, 2H), 3.00-3.09 (m, 2H), 2.04-2.17 (m, 2H), 1.84-1.95 (m, 2H), 1.43 (s, 9H), 1.41 (d, J=6.4 Hz, 3H), 1.26-1.30 (m, 2H), 1.12-1.16 (m, 2H); ¹³C-NMR (CDCl₃, 126 MHz) δ 163.7, 161.4 (d, J=244.7 Hz), 152.2, 145.3, 138.9, 135.1, 128.9, 127.7, 122.3, 117.2, 115.2, 115.1, 79.5, 77.8, 73.9, 60.5, 41.3, 34.7, 28.6, 22.7, 14.3, 7.4. Mass spec.: 528.62 (MH)⁺.

Intermediate 144

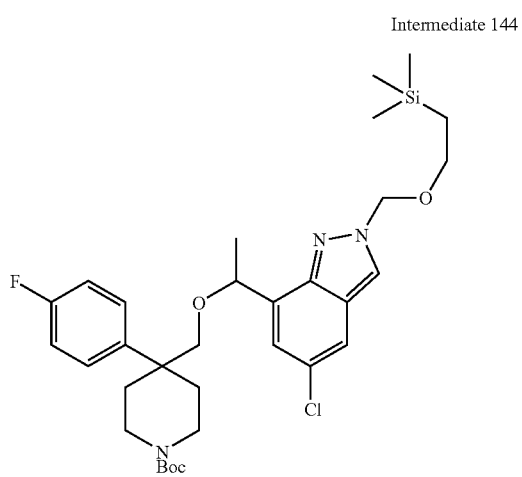

(±)-tert-Butyl 4-((1-(5-chloro-2-((2-(trimethylsilyl)ethoxy)methyl)-2H-indazol-7-yl)ethoxy)methyl)-4-(4-fluorophenyl)piperidine-1-carboxylate. (±)-1-(5-Chloro-2-((2-(trimethylsilyl)ethoxy)methyl)-2H-indazol-7-yl)ethyl 2,2,2-trichloroacetimidate (1.1 g, 2.33 mmol) and tert-butyl 4-(4-fluorophenyl)-4-(hydroxymethyl)piperidine-1-carboxylate (0.79 g, 2.57 mmol) were combined in a dichloromethane/cyclohexane mixture (1:1, 10 mL) and cooled to 0° C. The reaction was treated with tetrafluoroboric acid-diethyl ether complex (64 µL, 0.47 mmol), stirred at 0° C. for 1 h, quenched by addition of saturated sodium bicarbonate, and diluted with diethyl ether. The layers were separated. The ethereal was washed with water (2×), brine (2×), dried over sodium sulfate, and concentrated. Column chromatography on silica gel (20% ethyl acetate/hexanes) gave 0.81 g (56%) as a clear film. ¹H-NMR (CDCl₃, 500 MHz) δ 8.00 (s, 1H), 7.49 (d, J=1.8 Hz, 1H), 7.30-7.33 (m, 2H), 7.01-7.05 (m, 2H), 6.77 (m, 1H), 5.62-5.68 (s, 2H), 4.93 (q, J=6.4 Hz, 1H), 3.72 (m, 2H), 3.58-3.61 (m, 2H), 3.33-3.39 (m, 2H), 3.03-3.08 (m, 2H), 2.08-2.22 (m, 2H), 1.87-1.97 (m, 2H), 1.44 (s, 9H), 1.43 (d, J=6.4 Hz, 3H), 0.91-0.92 (m, 2H), 0.05 (s, 9H). Mass spec.: 618.86 (MH)⁺.

Intermediate 145

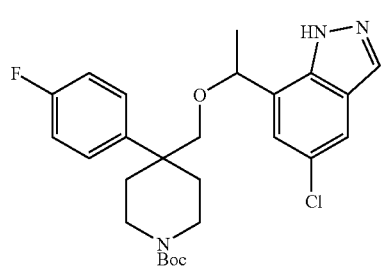

(±)-tert-Butyl 4-((1-(5-chloro-1H-indazol-7-yl)ethoxy)methyl)-4-(4-fluorophenyl)piperidine-1-carboxylate. (±)-tert-Butyl 4-((1-(5-chloro-2-((2-(trimethylsilyl)ethoxy)methyl)-2H-indazol-7-yl)ethoxy)methyl)-4-(4-fluorophenyl)piperidine-1-carboxylate (810 mg, 1.31 mmol) was dissolved in trifluoroacetic acid (50% in dichloromethane, 4 mL). The reaction was stirred at room temperature for 3 h and concentrated. The crude trifluoroacetic acid salt was loaded onto a strong cation exchange cartridge in methanol and washed with several volumes of methanol which were discarded. The product was eluted with 2 M ammonia in methanol and concentrated. The crude amine was dissolved in dichloromethane (5 mL) and treated with di-tert-butyl dicarbonate (572 mg, 2.62 mmol) and triethylamine (0.27 mL, 2.0 mmol). The reaction was stirred at room temperature for 1 h. The reaction was quenched by addition of 2 M ammonia in methanol and concentrated. The residue was purified by column chromatography (30% ethyl acetate/hexanes) to give 400 mg (63%) as a viscous oil. $^1$H-NMR (CDCl$_3$, 500 MHz) δ 9.90 (s, 1H), 7.89 (s, 1H), 7.55 (d, J=1.8 Hz, 1H), 7.22-7.25 (m, 2H), 7.02-7.06 (m, 2H), 6.96 (d, J=1.8 Hz, 1H, 1H), 4.49 (q, J=6.7 Hz, 1H), 3.62-3.72 (m, 2H), 3.23-3.36 (m, 2H), 2.94-3.06 (m, 2H), 2.05-2.24 (m, 2H), 1.70-1.86 (m, 2H), 1.44 (m, 3H), 1.41 (s, 9H); $^{13}$C-NMR (CDCl$_3$, 126 MHz) δ 171.1, 161.7 (d, J=246.6 Hz), 155.0 135.7, 133.8, 128.7, 127.5, 126.2, 124.8, 124.2, 119.0, 115.7, 79.6, 78.6, 78.2, 60.4, 41.2, 28.5, 22.2, 14.3. Mass spec.: 488.39 (MH)$^+$.

Intermediate 146

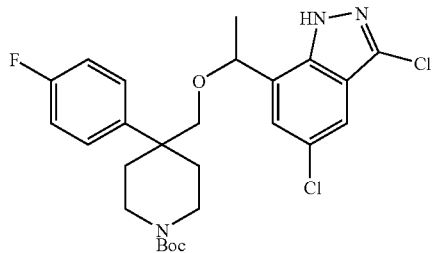

(±)-tert-Butyl 4-((1-(3, 5-dichloro-1H-indazol-7-yl) ethoxy)methyl)-4-(4-fluorophenyl)piperidine-1-carboxylate. To a solution of (±)-tert-butyl 4-((1-(5-chloro-1H-indazol-7-yl)ethoxy)methyl)-4-(4-fluorophenyl)piperidine-1-carboxylate (0.15 g, 0.31 mmol) and sodium hydroxide (4 N in water, 64 μL, 0.384 mmol) in ethanol (3 mL) at 0° C. was added N-chlorosuccinimide (82 mg, 0.615 mmol). The resulting solution was stirred at 0° C. for 30 min. The reaction was quenched by the cautious addition of ammonium hydroxide solution and diluted with diethyl ether. The layers were separated. The ethereal was washed with water (2×), then brine, dried over sodium sulfate, and concentrated. Column chromatography on silica gel (25% ethyl acetate/hexanes) gave 120 mg (75%) as an oil. $^1$H-NMR (CDCl$_3$, 500 MHz) δ 9.71 (s, 1H), 7.49 (d, J=1.5 Hz, 1H), 7.22-7.25 (m, 2H), 7.03-7.06 (m, 2H), 7.00 (d, J=1.8 Hz, 1H), 4.50 (q, J=6.4 Hz, 1H), 3.37 (q$_{AB}$, J$_{AB}$=9.2 Hz, 2H), 2.96-3.06 (m, 2H), 2.06-2.24 (m, 2H), 1.72-1.85 (m, 2H), 1.41 (s, 9H), 1.40 (m, 3H).; $^{13}$C-NMR (CDCl$_3$, 126 MHz) δ 171.1, 161.7 (d, J=246.6 Hz), 155.0 137.1, 134.3, 128.6, 128.2, 127.0, 125.3, 122.1, 117.8, 115.8, 79.6, 78.8, 78.0, 60.4, 41.2, 28.5, 22.1, 14.3.1 Mass spec.: 522.35 (MH)$^+$.

Intermediates 147 and 148

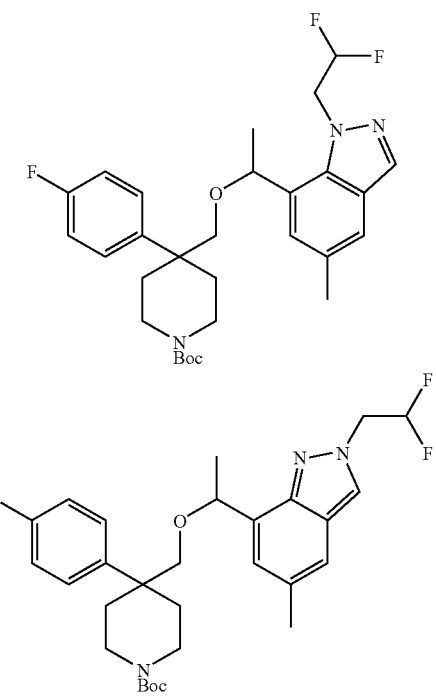

(±)-tert-Butyl 4-((1-(1-(2,2-difluoroethyl)-5-methyl-1H-indazol-7-yl)ethoxy)methyl)-4-(4-fluorophenyl)piperidine-1-carboxylate and (±)-tert-Butyl 4-((1-(2-(2,2-difluoroethyl)-5-methyl-2H-indazol-7-yl)ethoxy)methyl)-4-(4-fluorophenyl)piperidine-1-carboxylate. A microwave tube was charged with (±)-tert-butyl 4-(4-fluorophenyl)-4-((1-(5-methyl-1H-indazol-7-yl)ethoxy)methyl)piperidine-1-carboxylate (50 mg, 0.11 mmol) and 2-bromo-1,1-difluoroethane (31 mg, 0.21 mmol). The tube was flushed with nitrogen, treated with dimethylformamide (2 mL) and cesium carbonate (105 mg, 0.32 mmol). The tube was sealed and heated at 110° C. for 3 h via microwave. The reaction was cooled, poured into ethyl acetate, washed with water (2×), then brine (2×), dried over sodium sulfate, and concentrated. Column chromatography (10% ethyl acetate/hexanes) gave (±)-tert-butyl 4-((1-(1-(2,2-difluoroethyl)-5-methyl-1H-indazol-7-yl)ethoxy)methyl)-4-(4-fluorophenyl)piperidine-1-carboxylate (10 mg, 18%) and (±)-tert-butyl 4-((1-(2-(2,2-difluoroethyl)-5-methyl-2H-indazol-7-yl)ethoxy)methyl)-4-(4-fluorophenyl)piperidine-1-carboxylate (10 mg, 18%). (±)-tert-Butyl 4-((1-(1-(2,2-difluoroethyl)-5-methyl-1H-indazol-7-yl)ethoxy)methyl)-4-(4-fluorophenyl)piperidine-1-carboxylate: $^1$H-NMR (CDCl$_3$, 500 MHz) δ 7.95 (s, 1H), 7.37 (m, 1H), 7.21-7.24 (m, 2H), 6.98-7.02 (m, 2H), 6.92 (m, 1H), 5.98-6.22 (m, 1H), 4.82 (q, J=6.7 Hz, 1H), 4.62-4.72 (m, 2H), 3.68 (m, 2H), 3.29 (q$_{AB}$, J$_{AB}$=9.2 Hz, 2H), 2.98-3.03 (m, 2H), 2.35 (s, 3H), 2.04-2.12 (m, 2H), 1.77-1.87 (m, 2H), 1.48 (d, J=6.7 Hz, 3H), 1.43 (s, 9H). Mass spec.: 432.46(MH)$^+$. (±)-tert-Butyl 4-((1-(2-(2,2-difluoroethyl)-5-methyl-2H-indazol-7-yl)ethoxy)methyl)-4-(4-fluorophenyl)piperidine-1-carboxylate: $^1$H-NMR (CDCl$_3$, 500 MHz) δ 7.84 (s, 1H), 7.29-7.33 (m, 2H), 7.23 (m, 1H), 7.00-7.04 (m, 2H), 6.68 (m, 1H), 6.06-6.28 (m, 1H), 4.87 (q, J=6.4 Hz, 1H), 4.65-4.71 (m, 2H), 3.69 (m, 2H), 3.32-3.37 (m, 2H), 3.01-3.10 (m, 2H), 2.29 (s, 3H), 2.04-2.11 (m, 2H), 1.85-1.90 (m, 2H), 1.44 (m, 3H), 1.43 (s, 9H). Mass spec.: 432.47(MH)$^+$.).

Intermediates 149 and 150

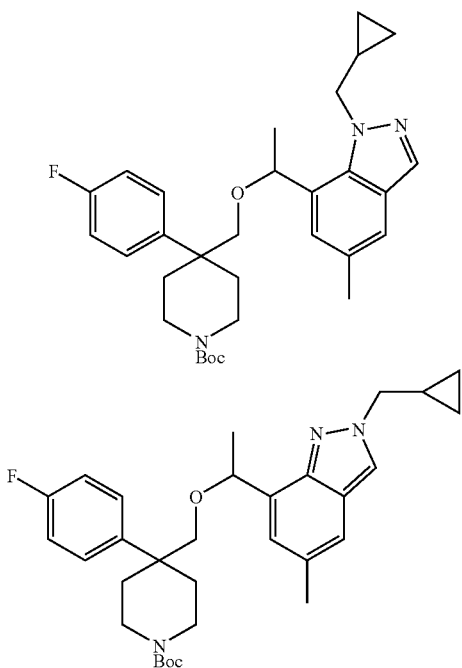

(±)-tert-Butyl 4-((1-(1-(cyclopropylmethyl)-5-methyl-1H-indazol-7-yl)ethoxy)methyl)-4-(4-fluorophenyl)piperidine-1-carboxylate and (±)-tert-Butyl 4-((1-(2-(cyclopropylmethyl)-5-methyl-2H-indazol-7-yl)ethoxy)methyl)-4-(4-fluorophenyl)piperidine-1-carboxylat. (±)-tert-Butyl 4-(4-fluorophenyl)-4-((1-(5-methyl-1H-indazol-7-yl)ethoxy) methyl)piperidine-1-carboxylate (50 mg, 0.11 mmol), (bromomethyl)cyclopropane (16.0 µL, 0.16 mmol) and cesium carbonate (105 mg, 0.32 mmol) were combined in dimethylformamide (2 mL) at room temperature. After 24 h, the reaction was diluted with ethyl acetate and washed with water (2×), then brine (2×), dried over sodium sulfate, filtered and concentrated. Column chromatography (10%→25% EtOAc/Hex) gave two fractions. Concentration of the first fraction gave (±)-tert-butyl 4-((1-(1-(cyclopropylmethyl)-5-methyl-1H-indazol-7-yl)ethoxy)methyl)-4-(4-fluorophenyl) piperidine-1-carboxylate (7 mg, 13%). Concentration of the second fraction gave (±)-tert-butyl 4-((1-(2-(cyclopropylmethyl)-5-methyl-2H-indazol-7-yl)ethoxy)methyl)-4-(4-fluorophenyl)piperidine-1-carboxylate (15 mg, 27%). (±)-tert-Butyl 4-((1-(1-(cyclopropylmethyl)-5-methyl-1H-indazol-7-yl)ethoxy)methyl)-4-(4-fluorophenyl)piperidine-1-carboxylate: $^1$H-NMR (CDCl$_3$, 500 MHz) δ 7.86 (s, 1H), 7.34 (m, 1H), 7.26-7.29 (m, 2H), 7.00-7.04 (m, 2H), 6.85 (m, 1H), 4.90 (q, J=6.4 Hz, 1H), 4.14-4.35 (m, 2H), 3.69 (m, 2H), 3.33 (q$_{AB}$, J$_{AB}$=9.2 Hz, 2H), 3.01-3.03 (m, 2H), 2.31 (s, 3H), 2.07-2.18 (m, 2H), 1.82-1.85 (m, 2H), 1.44 (m, 3H), 1.43 (s, 9H), 1.09-1.10 (m, 1H), 0.47-0.52 (m, 2H), 0.33-0.36 (m, 2H). Mass spec.: 522.52 (MH)$^+$. (±)-tert-Butyl 4-((1-(2-(cyclopropylmethyl)-5-methyl-2H-indazol-7-yl)ethoxy)methyl)-4-(4-fluorophenyl)piperidine-1-carboxylate: $^1$H-NMR (CDCl$_3$, 500 MHz) δ 7.89 (s, 1H), 7.30-7.33 (m, 2H), 7.24 (m, 1H), 7.00-7.03 (m, 2H), 6.66 (m, 1H), 4.95 (q, J=6.4 Hz, 1H), 4.23-4.24 (m, 2H), 3.67 (m, 2H), 3.38 (q$_{AB}$, J$_{AB}$=9.2 Hz, 2H), 3.02-3.09 (m, 2H), 2.29 (s, 3H), 1.96-2.17 (m, 4H), 1.85-1.91 (m, 1H), 1.45 (m, 3H), 1.43 (s, 9H), 0.65-0.68 (m, 2H), 0.40-0.43 (m, 2H). Mass spec.: 522.40 (MH)$^+$.

Intermediate 151

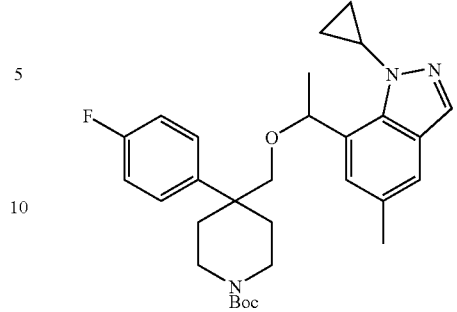

(±)-tert-Butyl 4-((1-(1-cyclopropyl-5-methyl-1H-indazol-7-yl)ethoxy)methyl)-4-(4-fluorophenyl)piperidine-1-carboxylate. A microwave tube was charged with (±)-tert-butyl 4-(4-fluorophenyl)-4-((1-(5-methyl-1H-indazol-7-yl) ethoxy)methyl)piperidine-1-carboxylate (45 mg, 0.1 mmol), cyclopropyl boronic acid (24.8 mg, 0.29 mmol) and copper (II) acetate (35 mg, 0.19 mmol). The tube was flushed with nitrogen and treated with tetrahydrofuran (2 mL). The tube was sealed and heated at 130° C. for 1 h via microwave. After cooling to room temperature, the reaction was poured into ethyl acetate, washed with water (2×), then brine (2×), dried over sodium sulfate, and concentrated. Column chromatography (40% ethyl acetate/hexanes) gave 10 mg (20%) as a clear oil. $^1$H-NMR (CDCl$_3$, 500 MHz) δ 7.76 (s, 1H), 7.28-7.30 (m, 3H), 7.00-7.04 (m, 2H), 6.89 (m, 1H), 5.39 (m, 1H), 3.69 (m, 3H), 3.29 (q$_{AB}$, J$_{AB}$=8.9 Hz, 2H), 2.89-3.07 (m, 2H), 2.31 (s, 3H), 2.07-2.10 (m, 2H), 1.81-1.93 (m, 2H), 1.45 (m, 3H), 1.43 (m, 9H), 1.25 (m, 2H), 1.02-1.08 (m, 2H), Mass spec.: 508.50(MH)$^1$.

Intermediate 152

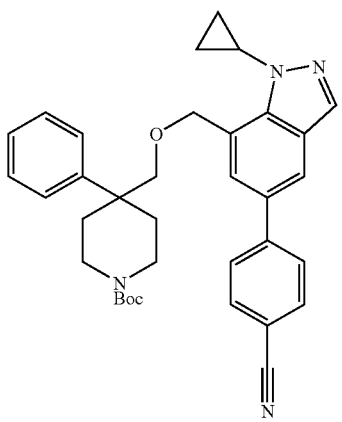

tert-Butyl 4-(((5-(4-cyanophenyl)-1-cyclopropyl-1H-indazol-7-yl)methoxy)methyl)-4-phenylpiperidine-1-carboxylate. A microwave tube was charged with tert-butyl 4-(((5-(4-cyanophenyl)-1H-indazol-7-yl)methoxy)methyl)-4-phenylpiperidine-1-carboxylate (75 mg, 0.14 mmol), cyclopropyl boronic acid (37 mg, 0.43 mmol), copper (II) acetate (52 mg, 0.29 mmol), triethylamine (0.1 mL, 0.72 mmol) and pyridine (93 µL, 1.15 mmol). The tube was flushed with nitrogen and treated with tetrahydrofuran (3 mL). The tube was sealed and heated at 130° C. for 1 h via microwave. After cooling to room temperature, the reaction was poured into ethyl acetate, washed with water (2×), then brine (2×), dried over sodium sulfate, and concentrated. Column chromatography (40% ethyl acetate/hexanes) gave 24 mg (30%) as a clear oil. ¹H-NMR (CDCl₃, 500 MHz) δ 7.92 (s, 1H), 7.82 (d, J=1.5 Hz, 1H), 7.72-7.73 (m, 2H), 7.65-7.67 (m, 2H), 7.40 (m, 1H), 7.27-7.29 (m, 4H), 7.18-7.21 (m, 1H), 4.94 (s, 2H), 3.69 (m, 2H), 3.52 (s, 2H), 3.49-3.51 (m, 1H), 2.99-3.03 (m, 2H), 2.15-2.17 (m, 2H), 1.79-1.85 (m, 2H), 1.41 (s, 9H), 1.22-1.26 (m, 2H), 0.90-0.94 (m, 2H). Mass spec.: 563.43 (MH)⁺.

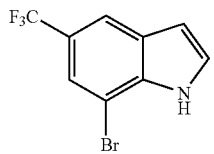

Intermediate 153

7-bromo-5-trifluoromethyl-1H-indole. The title compound was prepared according to the procedure in patent WO 2006/013048.

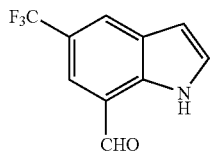

Intermediate 154

5-(Trifluoromethyl)-1H-indole-7-carbaldehyde. To a −78° C. solution of 7-bromo-5-(trifluoromethyl)-1H-indole (8.77 g, 33.2 mmol) in tetrahydrofuran (200 mL), n-BuLi (1.6 M in hexanes, 72.7 mL, 116 mmol) was added slowly. The reaction was warmed to 0° C. and stirred for 15 min. The reaction was recooled to −78° C., treated with dimethylformamide (12.9 mL, 166 mmol), warmed to ambient temperature, and stirred for 30 min. The reaction was quenched by slow addition of 1N hydrochloric acid (50 mL) and was then extracted with ethyl acetate (2×40 mL). The organic layers were dried (magnesium sulfate) and evaporated. The residue was purified by chromatography on silica gel with 15% ethyl acetate/hexanes. The product 5-(trifluoromethyl)-1H-indole-7-carbaldehyde (5.95 g, 27.9 mmol, 84% yield) was obtained as an orange solid. ¹H-NMR (CDCl₃, 400 MHz) δ 10.28 (bs, 1H), 10.16 (s, 1H), 8.20 (d, J=0.6 Hz, 1H), 7.90 (d, J=0.6 Hz), 7.45 (dd, J=3.2, 2.5 Hz, 1H), 6.72 (dd, J=3.2, 2.4 Hz, 1H).

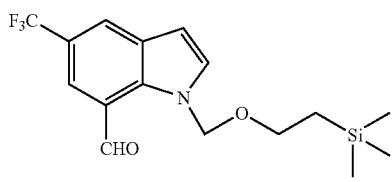

Intermediate 155

5-(Trifluoromethyl)-1-((2-trimethylsilyl)ethoxy)methyl-1H-indole-7-carbaldehyde. Sodium hydride (60% in oil, 0.225 g, 5.63 mmol) was added slowly in portions to a solution of 5-(trifluoromethyl)-1H-indole-7-carbaldehyde (1.0 g, 4.69 mmol) in tetrahydrofuran (50 ml). The reaction was stirred at ambient temperature for 20 min, treated with 2-(Trimethylsilyl)ethoxymethyl chloride (1.08 ml, 6.10 mmol), and the reaction stirred an additional 1 h. Water (20 mL) was added and the reaction diluted with ethyl acetate (30 mL). The layers were separated and the aqueous layer extracted with ethyl acetate (2×10 mL). The combined organic phases were dried with magnesium sulfate and evaporated. The residue was purified by chromatography on silica gel with 15% ethyl acetate/hexanes. The product 5-(trifluoromethyl)-1-((2-trimethylsilyl)ethoxy)methyl-1H-indole-7-carbaldehyde (1.12 g, 3.26 mmol, 69.5% yield) was obtained as a clear oil. ¹H-NMR (CDCl₃, 400 MHz) δ 10.10 (s, 1H), 8.14 (s, 1H), 8.02 (s, 1H), 7.34 (d, J=3.5 Hz, 1H), 6.72 (d, J=3.3 Hz), 5.82 (s, 2H), 3.41 (t, J=8.4 Hz, 2H), 0.81 (t, J=5.6 Hz, 2H), −0.10 (s, 9H); Mass spec.(M+Na): 366.12.

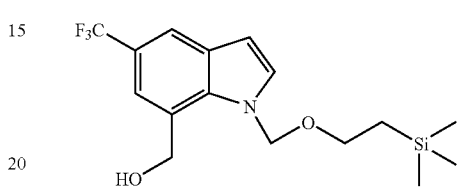

Intermediate 156

(5-(Trifluoromethyl)-1-((2-trimethylsilyl)ethoxy)methyl-1H-indole-7-yl)methanol. Sodium borohydride (0.112 g, 2.97 mmol) was added to a solution of 5-(trifluoromethyl)-1-((2-trimethylsilyl)ethoxy)methyl-1H-indole-7-carbaldehyde (1.02 g, 2.97 mmol) in methanol (50 ml) and stirred at ambient temperature for 30 min. The solvent was evaporated, the residue taken up in 1N hydrochloric acid (10 mL), and extracted with ethyl acetate (2×20 mL). The combined organic layers were dried with magnesium sulfate and evaporated. The residue was purified by chromatography on a silica gel column with ethyl acetate/hexanes 15%. The product (5-(trifluoromethyl)-1-((2-trimethylsilyl)ethoxy)methyl-1H-indol-7-yl)methanol (925 mg, 2.68 mmol, 90% yield) was obtained as a clear oil. ¹H-NMR (CDCl₃, 400 MHz) δ 7.88 (s, 1H), 7.39 (s, 1H), 7.20 (d, J=3.0 Hz, 1H), 6.61 (d, J=3.1 Hz, 1H), 5.70 (s, 2H), 5.04 (s, 2H), 3.47 (t, J=8.4 Hz, 2H), 0.87 (m, 2H), −0.06 (s, 9H); Mass spec. (MNa)⁺: 368.13.

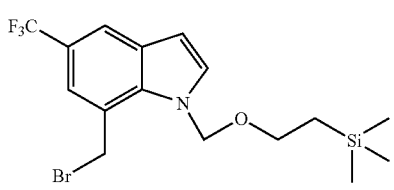

Intermediate 157

7-(Bromomethyl)-5-(trifluoromethyl)-1-((2-trimethylsilyl)ethoxy)methyl-1H-indole. A solution of (5-(trifluoromethyl)-1-((2-trimethylsilyl)ethoxy)methyl-1H-indol-7-yl)methanol (915 mg, 2.65 mmol) and triphenylphosphine (1.39 g, 5.30 mmol) in tetrahydrofuran (30 ml) were treated with N-bromosuccinimide (990 mg, 5.56 mmol) and stirred for 30 min at ambient temperature. The reaction became cloudy and orange in color. The reaction was filtered and the solvent evaporated. The residue was purified by chromatography on silica gel with a gradient of ethyl acetate/hexanes from 2% to 15%. The product 7-(bromomethyl)-5-(trifluoromethyl)-1-((2-trimethylsilyl)ethoxy)methyl-1H-indole (815 mg, 2.00 mmol, 75% yield) was obtained as a clear oil. ¹H-NMR (CDCl₃, 400 MHz) δ 7.88 (s, 1H), 7.43 (s, 1H), 7.22 (d, J=3.1 Hz, 1H), 6.61 (d, J=3.2 Hz, 1H), 5.75 (s, 2H), 5.03 (s, 2H), 3.46 (t, J=8.7 Hz, 2H), 0.86 (t, J=8.4 Hz, 2H), −0.07 (s, 9H).

Intermediate 158

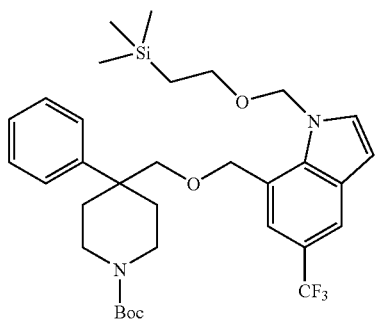

tert-Butyl 4-phenyl-4-((((5-(trifluoromethyl)-1-((2-trimethylsilyl)ethoxy)methyl)-1H-indol-7-yl)methoxy)methyl)piperidine-1-carboxylate. Potassium tert-butoxide (116 mg, 1.03 mmol) was added to a 0° C. solution of 7-(bromomethyl)-5-(trifluoromethyl)-1-((2-trimethylsilyl)ethoxy)methyl-1H-indole (252 mg, 0.618 mmol) and tert-butyl 4-(hydroxymethyl)-4-phenylpiperidine-1-carboxylate (150 mg, 0.515 mmol) in tetrahydrofuran (20 ml). The reaction was stirred at 0° C. for 30 min and warmed to ambient temperature. The reaction was diluted with brine (20 mL) and extracted with ethyl acetate (2×20 mL). The combined organic layers were dried with magnesium sulfate and evaporated. The residue was purified by chromatography on silica gel with a gradient of 5% to 50% ethyl acetate/hexanes. The product tert-butyl 4-phenyl-4-((((5-(trifluoromethyl)-1-((2-trimethylsilyl)ethoxy)methyl)-1H-indol-7-yl)methoxy)methyl)piperidine-1-carboxylate (266 mg, 0.430 mmol, 84% yield) was obtained as a clear oil. $^1$H-NMR (CDCl$_3$, 400 MHz) δ 7.85 (s, 1H), 7.13-7.25 (m, 6H), 7.06 (d, J=3.0 Hz, 1H), 6.54 (d, J=3.2 Hz, 1H), 5.07 (s, 2H), 4.70 (s, 2H), 3.64 (m, 2H), 3.40 (s, 2H), 3.29 (t, J=8.3 Hz, 2H), 3.00 (m, 1H), 2.11 (m, 2H), 1.76 (m, 2H), 1.40 (s, 9H), 0.76 (t, J=8.7 Hz, 2H), −0.11 (s, 9H); Mass spec. (MH)$^+$: 619.35.

Intermediate 159

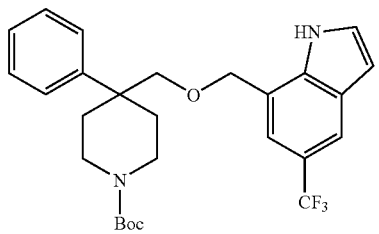

tert-Butyl 4-phenyl-4-(((5-(trifluoromethyl)-1H-indol-7-yl)methoxy)methyl)piperidine-1-carboxylate. A solution of tert-butyl 4-phenyl-4-((((5-(trifluoromethyl)-1-((2-trimethylsilyl)ethoxy)methyl)-1H-indol-7-yl)methoxy)methyl)piperidine-1-carboxylate (36 mg, 0.058 mmol) and tetrabutylammonium fluoride (1M in tetrahydrofuran, 0.349 ml, 0.349 mmol) in tetrahydrofuran (20 ml) was heated at reflux for 5 h. The solvent was evaporated, the residue taken up in brine (10 mL), and extracted with ethyl acetate (3×5 mL). The combined organic layers were dried with magnesium sulfate and evaporated. The residue was purified on silica gel with 20% ethyl acetate/hexanes. The product tert-butyl 4-phenyl-4-(((5-(trifluoromethyl)-1H-indol-7-yl)methoxy)methyl)piperidine-1-carboxylate (23 mg, 0.047 mmol, 81% yield) was obtained as a clear oil. $^1$H-NMR (CDCl$_3$, 400 MHz) δ 7.78 (s, 1H), 7.73 (bs, 1H), 7.34-7.48 (m, 5H), 7.08 (s, 1H), 6.78 (s, 1H), 6.44 (s, 1H), 4.72 (s, 2H), 3.70 (m, 2H), 3.52 (s, 2H), 3.09 (m, 2H), 2.22 (m, 2H), 1.78 (m, 2H), 1.42 (s, 9H); Mass spec. (MH)$^+$: 489.2.

Intermediate 160

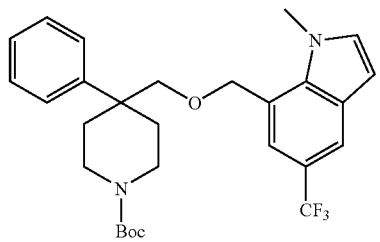

tert-Butyl 4-(((1-methyl-5-(trifluoromethyl)-1H-indol-7-yl)methoxy)methyl)-4-phenylpiperidine-1-carboxylate. Dimethyl sulfate (0.020 ml, 0.209 mmol) was added to a solution of tert-butyl 4-phenyl-4-(((5-(trifluoromethyl)-1H-indol-7-yl)methoxy)methyl)piperidine-1-carboxylate (93 mg, 0.190 mmol) and potassium tert-butoxide (23.5 mg, 0.209 mmol) in tetrahydrofuran (5 ml). The reaction was stirred 1 h at ambient temperature. The reaction was quenched with water (10 mL) and extracted with ethyl acetate (3×10 mL). The combined organic layers were dried with magnesium sulfate and evaporated. The residue was purified by chromatography on silica gel with a gradient of 8% to 66% ethyl acetate/hexanes. The product tert-butyl 4-(((1-methyl-5-(trifluoromethyl)-1H-indol-7-yl)methoxy)methyl)-4-phenylpiperidine-1-carboxylate (63 mg, 0.125 mmol, 65.9% yield) was obtained as a white solid. $^1$H-NMR (CDCl$_3$, 400 MHz) δ 7.83 (s, 1H), 7.22-7.36 (m, 6H), 6.95 (s, 1H), 6.50 (s, 1H), 4.66 (s, 2H), 3.66 (s, 3H), 3.62 (m, 2H), 3.41 (m, 2H), 2.99 (m, 2H), 2.09 (m, 2H), 1.77 (m, 2H), 1.40 (s, 9H); Mass spec.(MH)$^+$: 503.19.

Intermediate 161

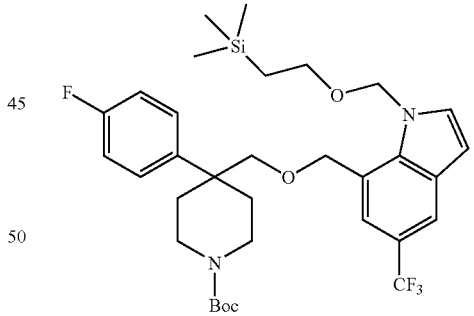

tert-Butyl 4-(4-fluorophenyl)-4-((((5-(trifluoromethyl)-1-((2-trimethylsilyl)ethoxy)methyl)-1H-indol-7-yl)methoxy)methyl)piperidine-1-carboxylate. Potassium tert-butoxide (264 mg, 2.35 mmol) was added to a 0° C. solution of 7-(bromomethyl)-5-(trifluoromethyl)-1-((2-trimethylsilyl)ethoxy)methyl-1H-indole (480 mg, 1.18 mmol) and tert-butyl 4-(hydroxymethyl)-4-(4-fluorophenyl)piperidine-1-carboxylate (364 mg, 1.18 mmol) in tetrahydrofuran (20 ml). The reaction was stirred at 0° C. for 30 min and warmed to ambient temperature. The reaction was diluted with brine (20 mL) and extracted with ethyl acetate (2×20 mL). The combined organic layers were dried with magnesium sulfate and evaporated. The residue was purified by chromatography on silica gel with a gradient of 5% to 50% ethyl acetate/hexanes to give 484 mg (65%) as a clear oil. ¹H-NMR (CDCl₃, 400 MHz) δ 7.85 (s, 1H), 7.23 (d, J=7.0 Hz, 1H), 7.10 (m, 2H), 6.85 (m, 2H), 6.54 (d, J=3.1 Hz, 1H), 5.11 (s, 2H), 4.71 (s, 2H), 3.64 (m, 2H), 3.37 (s, 2H), 3.29 (t, J=8.3 Hz, 2H), 3.00 (m, 1H), 2.03 (m, 2H), 1.74 (m, 2H), 1.40 (s, 9H), 0.76 (t, J=8.6 Hz, 2H), −0.11 (s, 9H).

Intermediate 162

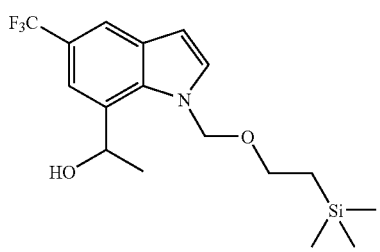

(±)-1-(5-(Trifluoromethyl)-1-((2-(trimethylsilyl)ethoxy)methyl)-1H-indol-7-yl)ethanol. Methylmagnesium bromide (0.582 ml, 1.747 mmol) was added dropwise to a 0° C. solution of 5-(trifluoromethyl)-1-((2-(trimethylsilyl)ethoxy)methyl)-1H-indole-7-carbaldehyde (500 mg, 1.456 mmol) in tetrahydrofuran (10 ml). The reaction was stirred 30 min at 0° C. An additional portion of methylmagnesium bromide (0.58 ml, 1.75 mmol) was added. The reaction was stirred another 30 min, quenched by addition of water (10 mL), and extracted with ethyl acetate (3×10 ml). The combined organic layers were dried with magnesium sulfate and evaporated. The residue was purified by chromatography on silica gel with a gradient of 5% to 40% ethyl acetate/hexanes to give 427 mg (82%) as a yellow liquid. ¹H-NMR (CDCl₃, 400 MHz) δ 7.84 (d, J=1.1 Hz, 1H), 7.62 (d, J=1.0 Hz, 1H), 7.18 (d, J=3.2 Hz, 1H), 6.59 (d, J=3.3 Hz, 1H), 5.74 (d, J=11.5 Hz, 1H), 5.68 (m, 1H), 5.59 (d, J=11.4 Hz, 1H), 3.44 (dd, J=8.4, 7.8 Hz, 2H), 1.69 (d, J=6.3 Hz, 3H), 0.87 (m, 2H), −0.10 (s, 9H); LC/MS (HPLC method 4): t_R=3.743 min, 382.12(MH)⁺.

Intermediate 163

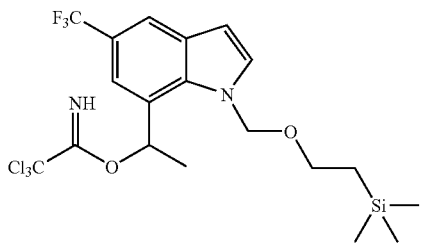

(±)-1-(5-(Trifluoromethyl)-1-((2-(trimethylsilyl)ethoxy)methyl)-1H-indol-7-yl)ethyl 2,2,2-trichloroacetimidate. Diazabicycloundecene (33.0 mg, 0.217 mmol) was added to a solution of (±)-1-(5-(trifluoromethyl)-1-((2-(trimethylsilyl)ethoxy)methyl)-1H-indol-7-yl)ethanol (390 mg, 1.09 mmol) in diethyl ether (10 ml) and stirred for 10 min. Trichloroacetonitrile (235 mg, 1.627 mmol) was then added and the reaction stirred 16 h at ambient temperature. The solvent was evaporated and the residue purified by chromatography on silica gel with a gradient of ethyl acetate/hexanes from 5% to 40% to give 290 mg (53%) as a brown oil. ¹H-NMR (CDCl₃, 400 MHz) δ 8.23 (s, 1H), 7.82 (s, 1H), 7.69 (s, 1H), 7.17 (d, J=33 Hz, 1H), 6.76 (q, J=6.5 Hz, 1H), 6.57 (d, J=3.2 Hz, 1H), 6.19 (d, J=11.5 Hz, 1H), 5.30 (d, J=11.5 Hz, 1H), 3.48 (dd, J=9.0, 8.0 Hz, 2H), 1.75 (d, J=6.4 Hz, 3H), 0.92 (m, 2H), −0.07 (s, 9H); LC/MS (HPLC method 4): t_R=4.31 min, 342.16(M-OC₂NHCl₃)⁺.

Intermediate 164

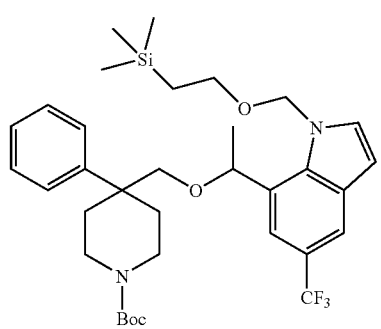

(±)-tert-Butyl 4-phenyl-4-((1-(5-(trifluoromethyl)-1-((2-(trimethylsilyl)ethoxy)methyl)-1H-indol-7-yl)ethoxy)methyl)piperidine-1-carboxylate. To a solution of (±)-1-(5-(trifluoromethyl)-1-((2-(trimethylsilyl)ethoxy)methyl)-1H-indol-7-yl)ethyl 2,2,2-trichloroacetimidate (290 mg, 0.576 mmol) and tert-butyl 4-(hydroxymethyl)-4-phenylpiperidine-1-carboxylate (184 mg, 0.633 mmol) in dichloromethane (2 mL) at 0° C. was added cyclohexane (2 ml) and fluoroboric acid diethyl ether complex (0.016 ml, 0.115 mmol). The reaction was stirred at 0° C. for 45 min and was judged complete by TLC. The reaction was quenched with aqueous sodium bicarbonate (5 mL) and extracted with ethyl acetate (3×5 mL). The combined organic layers were dried with magnesium sulfate and evaporated. The residue was purified by chromatography on silica gel with a gradient of ethyl acetate/hexanes from 12% to 100%. The product (173 mg, 0.273 mmol, 47.5% yield) was isolated as a clear oil. ¹H-NMR (CDCl₃, 400 MHz) δ 7.77 (m, 1H), 7.39 (m, 1H), 7.14-7.29 (m, 5H), 7.07 (m, 1H), 6.54 (m, 1H), 5.15 (m, 1H), 3.32 (m, 2H), 3.21 (m, 2H), 3.00 m, 2H), 2.11 (m, 2H), 1.88 (m, 2H), 1.45 (d, J=6.4 Hz, 3H), 1.42 (s, 9H), 0.75 (m, 2H), −0.09 (s, 9H); LC/MS (HPLC method 4): t_R=4.36 min, 655.20(MNa)⁺.

Intermediate 165

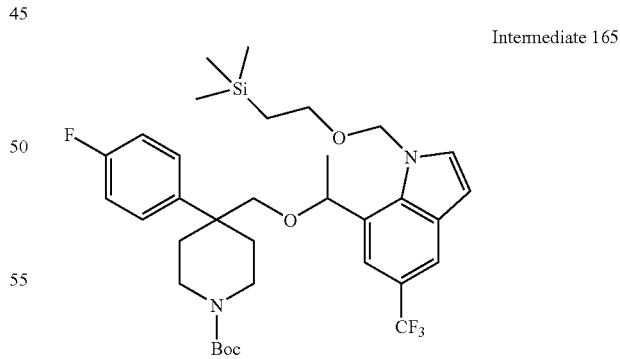

(±)-tert-Butyl 4-(4-fluorophenyl)-4-((1-(5-(trifluoromethyl)-1-((2-(trimethylsilyl)ethoxy)methyl)-1H-indol-7-yl)ethoxy)methyl)piperidine-1-carboxylate. To a solution of (±)-1-(5-(trifluoromethyl)-1-((2-(trimethylsilyl)ethoxy)methyl)-1H-indol-7-yl)ethyl 2,2,2-trichloroacetimidate (361 mg, 0.716 mmol) and tert-butyl 4-(4-fluorophenyl)-4-(hydroxymethyl)piperidine-1-carboxylate (244 mg, 0.788 mmol) at 0° C. was added cyclohexane (2 ml, 18.49 mmol)

and fluoroboric acid diethyl ether complex (0.019 ml, 0.143 mmol). The reaction was stirred at 0° C. for 45 min and was judged complete by TLC. The reaction was quenched with aqueous sodium bicarbonate (5 mL) and extracted with ethyl acetate (3×5 mL). The combined organic layers were dried with magnesium sulfate and evaporated. The residue was purified by chromatography on silica gel with a gradient of ethyl acetate/hexanes from 12% to 100%. The product (245 mg, 0.376 mmol, 52.5% yield) was isolated as a clear oil. $^1$H-NMR (CDCl$_3$, 400 MHz) δ 7.77 (m, 1H), 7.34 (s, 1H), 7.18 (m, 2H), 7.08 (d, J=3.7 Hz, 1H), 6.94 (m, 2H), 6.54 (m, 1H), 5.29 (m, 2H), 5.18 (m, 1H), 3.65 (m, 2H), 3.33 (m, 2H), 3.24 (m, 1H), 3.14 (m, 1H), 3.00 (m, 2H), 2.03 (m, 2H), 1.86 (m, 2H), 1.44 (d, J=6.4 Hz, 3H), 1.419 (s, 9H), 0.74 (m, 2H), −0.09 (s, 9H); LC/MS (HPLC method 4): t$_R$=4.871 min, 651.28(MH)$^+$.

Intermediate 166

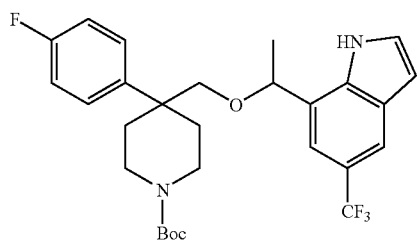

(±)-tert-Butyl 4-(4-fluorophenyl)-4-((1-(5-(trifluoromethyl)-1H-indol-7-yl)ethoxy)methyl)piperidine-1-carboxylate. A solution of (±)-tert-butyl 4-(4-fluorophenyl)-4-((1-(5-(trifluoromethyl)-1-((2-(trimethylsilyl)ethoxy)methyl)-1H-indol-7-yl)ethoxy)methyl)piperidine-1-carboxylate (240 mg, 0.369 mmol) and tetrabutylammonium fluoride (1 M in THF, 1.844 ml, 1.844 mmol) in tetrahydrofuran (10 ml) was held at reflux for 3 h. The solvent was evaporated and the residue was purified by chromatography on silica gel with a gradient of 8% to 66% ethyl acetate/hexanes. The product (51 mg, 0.098 mmol, 26.6% yield) was isolated as a clear oil. $^1$H-NMR (CDCl$_3$, 400 MHz) δ 7.92 (bs, 1H), 7.76 (m, 1H), 7.25 (m, 2H), 7.04 (m, 3H), 6.78 (d, J=2.1 Hz, 1H), 6.43 (d, J=2.0 Hz, 1H), 4.57 (m, 1H), 3.70 (m, 2H), 3.37 (d, J=8.7 Hz, 1H), 3.19 (d, J=8.8 Hz, 1H), 3.11 (m, 1H), 2.96 (m, 1H), 2.35 (m, 1H), 1.60-1.97 (m 3H), 1.44 (d, J=6.4 Hz, 3H), 1.42 (s, 9H); LC/MS (HPLC method 4): t$_R$=4.415 min, 521.20(MH)$^+$.

Intermediates 167 and 168

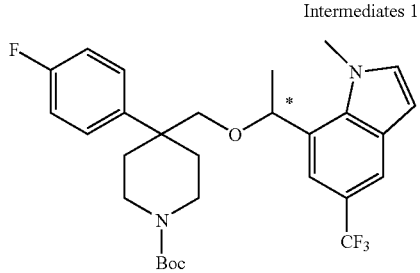

Enantiomers A and B of tert-butyl 4-(4-fluorophenyl)-4-((1-(1-methyl-5-(trifluoromethyl)-1H-indol-7-yl)ethoxy)methyl)piperidine-1-carboxylate. (±)-tert-butyl 4-(4-fluorophenyl)-4-((1-(1-methyl-5-(trifluoromethyl)-1H-indol-7-yl)ethoxy)methyl)piperidine-1-carboxylate (derived from tert-Butyl 4-(4-fluorophenyl)-4-((1-(5-(trifluoromethyl)-1H-indol-7-yl)ethoxy)methyl)piperidine-1-carboxylate by methylation) was subjected to chiral HPLC on a chiralcel OD-H column with a mobile phase of 95% CO2/5% ethanol/ 0.1% diethylamine. The early-eluting enantiomer is Enantiomer A of tert-butyl 4-(4-fluorophenyl)-4-((1-(1-methyl-5-(trifluoromethyl)-1H-indol-7-yl)ethoxy)methyl)piperidine-1-carboxylate and the late-eluting enantiomer is Enantiomer B of tert-butyl 4-(4-fluorophenyl)-4-((1-(1-methyl-5-(trifluoromethyl)-1H-indol-7-yl)ethoxy)methyl)piperidine-1-carboxylate.

Intermediate 169

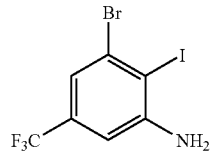

3-Bromo-2-iodo-5-(trifluoromethyl)aniline. 3-Bromo-5-(trifluoromethyl)aniline (20 g, 83 mmol) in acetic acid (150 ml) was treated portionwise with N-iodosuccinimide (20.62 g, 92 mmol). The reaction was stirred 24 h at ambient temperature. The reaction was diluted with ethyl acetate (600 mL) and was washed with aqueous sodium bisulfie (100 mL) and brine (100 mL). The organic layer was dried with magnesium sulfate and evaporated. The residue was purified on a silica gel column with a gradient of ethyl acetate/hexanes from 7% to 15% to give 23.5 g (77%) of slightly impure product. $^1$H-NMR (CDCl$_3$, 400 MHz) δ 7.21 (d, J=1.3 Hz, 1H), 6.82 (d, J=1.5 Hz, 1H), 4.57 (bs, 2H); LC/MS (HPLC method 4): t$_R$=3.578 min, 365.80(MH)$^+$.

Intermediate 170

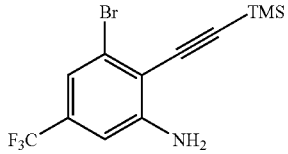

3-Bromo-5-(trifluoromethyl)-2-((trimethylsilyl)ethynyl) aniline. 3-Bromo-2-iodo-5-(trifluoromethyl)aniline (18.7 g, 51.1 mmol) was dissolved in triethylamine (400 mL). To this was added dichlorobis(triphenylphosphine)palladium(II) (3.59 g, 5.11 mmol), copper(I) iodide (0.973 g, 5.11 mmol), and trimethylsilylacetylene (5.52 g, 56.2 mmol). The reaction was stirred for 2 h at ambient temperature, at 80° C. for 2 h, and then evaporated. The residue was purified by chromatography on silica gel with 5% ethyl acetate/hexanes to give 10.67 g (62.1%) as a brown liquid. $^1$H-NMR (CDCl$_3$, 400 MHz) δ 7.13 (s, 1H), 6.82 (s, 1H), 4.52 (bs, 2H), 0.29 (s, 9H); LC/MS (HPLC method 4): t$_R$=4.208 min, 336.05(MH)$^+$.

Intermediate 171

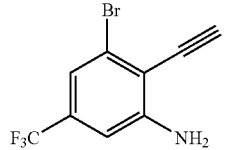

3-Bromo-2-ethynyl-5-(trifluoromethyl)aniline. Sodium hydroxide (3.17 mL, 31.7 mmol) was added to a solution of 3-bromo-5-(trifluoromethyl)-2-((trimethylsilyl)ethynyl)

aniline (10.67 g, 31.7 mmol) in methanol (200 mL) and was stirred for 30 min. The solvent was evaporated. The residue was taken up in brine (30 mL) and extracted with ethyl acetate (3×100 mL). The combined organic layers were dried with magnesium sulfate and evaporated. The residue was purified on silica gel with 10% ethyl acetate/hexanes to give 7.54 g (90%) as a tan solid. $^1$H-NMR (CDCl$_3$, 400 MHz) δ 7.15 (s, 1H), 6.85 (s, 1H), 4.58 (bs, 2H), 3.77 (s, 1H); LC/MS (HPLC method 4): t$_R$=3.186 min, 263.89(MH)$^+$.

Intermediate 172

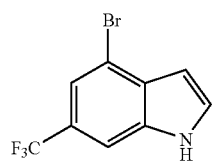

4-Bromo-6-(trifluoromethyl)-1H-indole. A solution of 3-bromo-2-ethynyl-5-(trifluoromethyl)aniline (7.54 g, 28.6 mmol) in N-methylpyrrollidinone (50 mL) was added dropwise to a 0° C. solution of potassium tert-butoxide (6.41 g, 57.1 mmol) in N-methylpyrrollidinone (200 mL). The reaction was stirred at ambient temperature for 4 h. The reaction was poured into brine (500 mL) and extracted with ethyl acetate (4×50 mL). The combined organic layers were washed with brine (100 mL), dried with magnesium sulfate and evaporated. The residue was purified by chromatography on silica gel with a gradient of 10% to 25% ethyl acetate/hexanes to give 7.16 g (95%) as a brown oil. $^1$H-NMR (CDCl$_3$, 400 MHz) δ 8.54 (bs, 1H), 7.63 (s, 1H), 7.53 (s, 1H), 7.40 (t, J=2.8 Hz, 1H), 6.66 (t, J=2.8 Hz, 1H); LC/MS (HPLC method 4): t$_R$=3.280 min, 264.12(MH)$^+$.

Intermediate 173

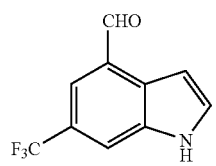

6-(Trifluoromethyl)-1H-indole-4-carbaldehyde. A solution of 4-bromo-6-(trifluoromethyl)-1H-indole (5.23 g, 19.81 mmol) in tetrahydrofuran (20 ml) was cooled to −78° C. and treated slowly with n-butyllithium (1.6 M solution in hexanes, 39.6 ml, 63.4 mmol). The solution was stirred for 15 min at −78° C., and then treated with dimethylformamide (7.67 ml, 99 mmol), and stirred for 30 minutes more, allowing the reaction to warm to ambient temperature. The resulting solution was poured into brine and extracted with ethyl acetate. The pooled organics were dried over sodium sulfate and concentrated to give an amber oil. Column chromatography (ethyl acetate/hexanes gradient elution) afforded 1.17 g, (32%). $^1$H-NMR (CDCl$_3$, 500 MHz) δ ppm 10.28 (s, 1H), 8.72 (br s, 1H), 7.93 (s, 1H), 7.88 (s, 1H), 7.58 (s, 1H), 7.42 (s, 1H). Mass spec.: 214.14 (MH)$^+$.

Intermediate 174

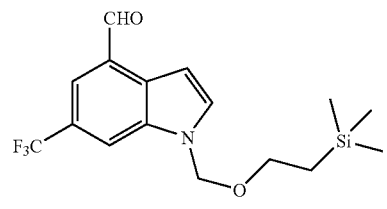

6-(Trifluoromethyl)-1-((2-(trimethylsilyl)ethoxy)methyl)-1H-indole-4-carbaldehyde. A solution of 6-(trifluoromethyl)-1H-indole-4-carbaldehyde (0.70 g, 3.28 mmol) in tetrahydrofuran (20 ml) at 25° C. was treated with sodium hydride (60 % mineral oil dispersion, 0.158 g, 3.94 mmol) and stirred for 30 minutes. (2-(chloromethoxy)ethyl)trimethylsilane (0.756 ml, 4.27 mmol) was added and the reaction stirred an additional hour at 25° C. The mixture was poured into brine and extracted several times with ethyl acetate. The pooled organics were dried over sodium sulfate, filtered, and concentrated. Column chromatography (ethyl acetate/hexanes gradient) afforded 1.01 g (89%) as a clear oil. $^1$H-NMR (CDCl$_3$, 500 MHz) δ ppm 10.28 (s, 1H), 8.03 (s, 1H), 7.90 (s, 1H), 7.51 (s, 1H), 7.37 (s, 1H), 5.57 (s, 2H), 3.47 (m, 2H), 0.88 (m, 2H), −0.08 (s, 9H). Mass spec.: 344.16 (MH)$^+$.

Intermediate 175

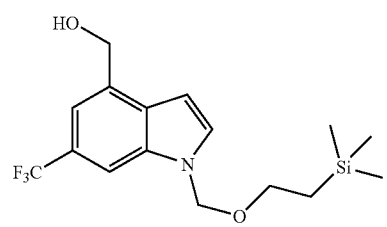

(6-(Trifluoromethyl)-1-((2-(trimethylsilyl)ethoxy)methyl)-1H-indol-4-yl)methanol. A solution of 6-(trifluoromethyl)-1-((2-(trimethylsilyl)ethoxy)methyl)-1H-indole-4-carbaldehyde (0.95 g, 2.77 mmol) in methanol (20 ml) at 25° C. was treated with sodium borohydride (0.209 g, 5.53 mmol) and stirred for 1 h. The resulting solution was concentrated in vacuo, taken up in ethyl acetate, washed with brine, dried over sodium sulfate and re-concentrated to a light yellow oil. Column chromatography (ethyl acetate/hexanes gradient elution) afforded 0.91 g (95%) as a colorless oil. $^1$H-NMR (CDCl$_3$, 500 MHz) δ ppm 7.74 (s, 1H), 7.41 (m, 2H), 6.73 (m, 1H), 5.46 (s, 2H), 5.10 (s, 2H), 3.46 (m, 2H), 0.88 (m, 2H), −0.07 (s, 9H). Mass spec.: 346.17 (MH)$^+$.

Intermediate 176

4-(Bromomethyl)-6-(trifluoromethyl)-1-((2-(trimethylsilyl)ethoxy)methyl)-1H-indole. A solution of (6-(trifluoromethyl)-1-((2-(trimethylsilyl)ethoxy)methyl)-1H-indol-4-yl)

methanol and triphenylphosphine in tetrahydrofuran (30 ml) at 25° C. was treated with N-bromosuccinimide and stirred for 30 minutes. The mixture was filtered through sand and celite and concentrated. Column chromatography (ethyl acetate/hexanes gradient) afforded 0.73 g (69%) as a colorless oil. $^1$H-NMR (CDCl$_3$, 500 MHz) δ ppm 7.74 (s, 1H), 7.39 (m, 2H), 6.72 (s, 1H), 5.51 (s, 2H), 4.79 (s, 2H), 3.45 (m, 2H), 0.88 (m, 2H), −0.07 (s, 9H). Mass spec.: 408.34 (MH)$^+$.

Intermediate 177

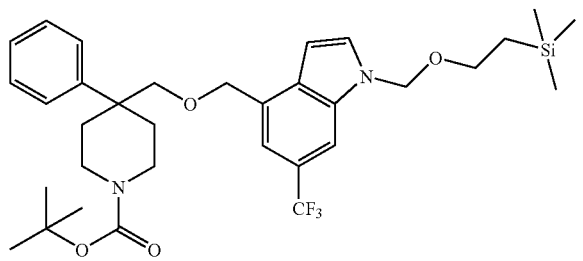

tert-Butyl 4-phenyl-4-(((6-(trifluoromethyl)-1-((2-(trimethylsilyl)ethoxy)methyl)-1H-indol-4-yl)methoxy)methyl)piperidine-1-carboxylate. A solution of 4-(bromomethyl)-6-(trifluoromethyl)-1-((2-(trimethylsilyl)ethoxy)methyl)-1H-indole (300 mg, 0.735 mmol), tert-butyl 4-(hydroxymethyl)-4-phenylpiperidine-1-carboxylate (214 mg, 0.735 mmol), and tetrahydrofuran (10 ml) at 0° C. was treated with potassium tert-butoxide (165 mg, 1.469 mmol) and stirred for 3 h. The resulting mixture was poured into brine and extracted several times with ethyl acetate. The pooled organics were dried over sodium sulfate and concentrated in vacuo. Column chromatography (ethyl acetate/hexanes gradient) afforded 151 mg (33%) as an oil. $^1$H-NMR (CDCl$_3$, 500 MHz) δ ppm 7.66 (s, 1H), 7.18-7.41 (m, 7H), 6.54 (s, 1H), 5.42 (s, 2H), 4.99 (s, 2H), 3.74 (m, 2H), 3.53 (s, 2H), 3.43 (m, 2H), 3.02 (m, 2H), 2.18 (m, 2H), 1.92 (m, 2H), 1.41 (s, 9H), 0.87 (m, 2H), −0.07 (s, 9H). Mass spec.: 641.63 (MNa)$^+$.

Intermediate 178

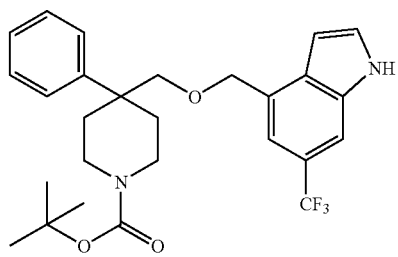

tert-Butyl 4-phenyl-4-(((6-(trifluoromethyl)-1H-indol-4-yl)methoxy)methyl)piperidine-1-carboxylate. A solution of tert-butyl 4-phenyl-4-(((6-(trifluoromethyl)-1-((2-(trimethylsilyl)ethoxy)methyl)-1H-indol-4-yl)methoxy)methyl)piperidine-1-carboxylate (150 mg, 0.242 mmol) in tetrahydrofuran (5 ml) was treated with tetrabutylammonium fluoride (1.0 M solution in tetrahydrofuran, 1.45 ml, 1.45 mmol) and heated at 90° C. for 6 h. The solvent was evaporated and the remaining residue partitioned between ethyl acetate and brine. The layers were separated and the aqueous layer was extracted with additional ethyl acetate. The pooled organics were dried over sodium sulfate and concentrated to a dark oil. Column chromatography (ethyl acetate/hexanes gradient) afforded 69 mg (58%) as a clear oil. $^1$H-NMR (CDCl$_3$, 500 MHz) δ ppm 8.41 (s, 1H), 7.58 (s, 1H), 7.21-7.37 (m, 7H), 6.45 (s, 1H), 4.66 (s, 2H), 3.66 (m, 2H), 3.43 (s, 2H), 3.02 (m, 2H), 2.26 (m, 2H), 1.87 (m, 2H), 1.41 (s, 9H). Mass spec.: 489.32 (MH)$^+$.

Intermediate 179

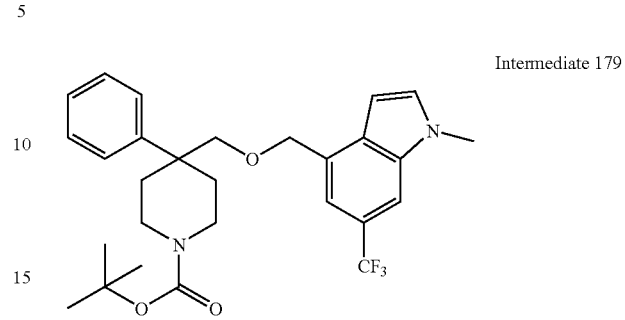

tert-Butyl 4-(((1-methyl-6-(trifluoromethyl)-1H-indol-4-yl)methoxy)methyl)-4-phenylpiperidine-1-carboxylate. A solution of tert-butyl 4-phenyl-4-(((6-(trifluoromethyl)-1H-indol-4-yl)methoxy)methyl)piperidine-1-carboxylate (59 mg, 0.121 mmol) in tetrahydrofuran (5 ml) at 25° C. was treated with potassium tert-butoxide (13.6 mg, 0.121 mmol) and stirred for 5 minutes. Dimethyl sulfate (0.012 ml, 0.121 mmol) was added, the solution was stirred at 25° C. for 1 h, and then concentrated in vacuo. Column chromatography (ethyl acetate/hexanes gradient elution) afforded 45 mg (90%) as a colorless oil. Mass spec.: 503.17 (MH)$^+$.

Intermediate 180

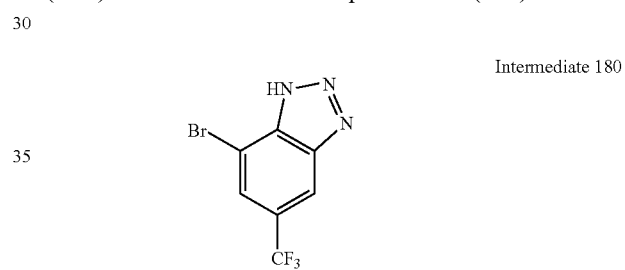

7-Bromo-5-(trifluoromethyl)-1H-benzo[d][1,2,3]triazole. To a cooled (15° C.) solution of 3-bromo-5-(trifluoromethyl)benzene-1,2-diamine (1.82 g, 7.14 mmol) in acetic acid (20 mL) was added a solution of sodium nitrite (0.517 g, 7.49 mmol) in water (10 mL). After 15 min, the product was collected by filtration and washed with 65% HOAc in water and air dried to give 1.5 g (79%) as a faint pink powder. $^1$H-NMR (4:1 CDCl$_3$/CD$_3$OD, 500 MHz) δ 8.08 (s, 1H), 7.71 (s, 1H), 4.23 (bs, 1H); $^{13}$C-NMR (4:1 CDCl$_3$/CD$_3$OD, 126 MHz) δ 139.9, 129.0 (q, J=33 Hz), 125.3, 123.3 (q, J=273 Hz), 113.4, 108.2. Mass spec.: 265.82 (MH)$^+$.

Intermediate 181

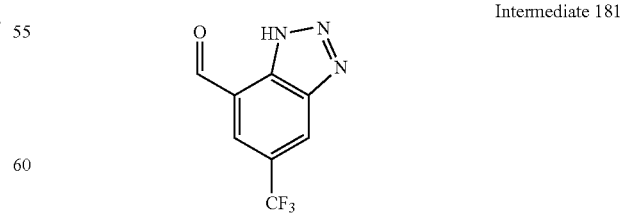

5-(Trifluoromethyl)-1H-benzo[d][1,2,3]triazole-7-carbaldehyde. To a solution of 7-bromo-5-(trifluoromethyl)-1H-benzo[d][1,2,3]triazole (0.95 g, 3.57 mmol) in tetrahydrofuran (9 mL) at 0° C. was added sodium hydride (0.090 g, 3.75 mmol). The ice bath was removed and stirring continued for 20 min. The solution was cooled to −78° C. and treated with tert-butyllithium (1.7M in pentane, 4.20 mL, 7.14 mmol) dropwise. The reaction was stirred at −78° C. for 10 min, allowed to warm gradually in the dewar to −50° C., recooled to −78° C., and then treated with dimethylformamide (0.69 mL, 8.9 mmol). After 15 min, the ice bath was removed and stirring continued for 1 h. The reaction was poured onto ice/1 M hydrochloric acid (40 mL). The product was collected by filtration to give 0.655 g (85%) as a light tan solid. $^1$H-NMR (4:1 CDCl$_3$/CD$_3$OD, 500 MHz) δ 10.18 (s, 1H), 8.60 (s, 1H), 8.18 (s, 1H), 4.19 (bs, 1H); $^{13}$C-NMR (4:1 CDCl$_3$/CD$_3$OD, 126 MHz) δ 189.9, 131.6, 129.4, 126.9 (q, J=34 Hz), 124.6, 123.6, 122.44, 122.35.

Intermediates 182, 183 and 184

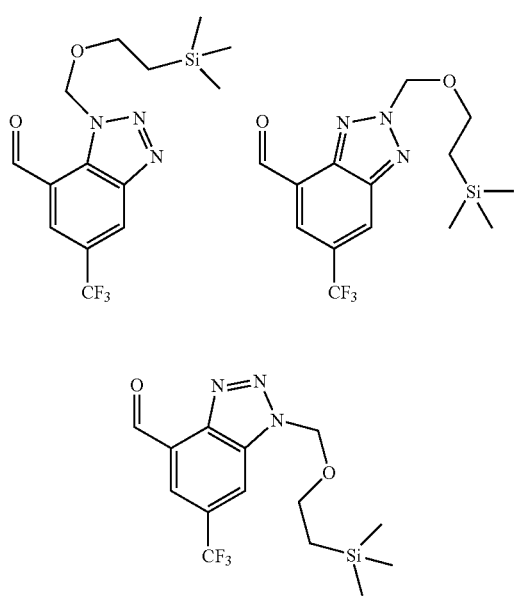

5-(Trifluoromethyl)-1-((2-(trimethylsilyl)ethoxy)methyl)-1H-benzo[d][1,2,3]triazole-7-carbaldehyde and 6-(Trifluoromethyl)-2-((2-(trimethylsilyl)ethoxy)methyl)-2H-benzo[d][1,2,3]triazole-4-carbaldehyde and 6-(Trifluoromethyl)-1-((2-(trimethylsilyl)ethoxy)methyl)-1H-benzo[d][1,2,3]triazole-4-carbaldehyde. To a solution of 5-(trifluoromethyl)-1H-benzo[d][1,2,3]triazole-7-carbaldehyde (700 mg, 2.027 mmol) and N-methyldicyclohexylamine (0.59 mL, 2.74 mmol) in tetrahydrofuran (6 mL) at 0° C. was added (2-(chloromethoxy)ethyl)trimethylsilane (0.45 mL, 2.53 mmol). After 30 min, the ice bath was removed and stirring continued for an additional 30 min. The reaction was poured into ether, washed with water (2×), then 1M potassium bisulfate, then water, then brine, dried over magnesium sulfate, and concentrated. Column chromatography (5%→25% ethyl acetate/hexanes) gave two fractions. Concentration of the first fraction gave a mixture of 5-(trifluoromethyl)-1-((2-(trimethylsilyl)ethoxy)methyl)-1H-benzo[d][1,2,3]triazole-7-carbaldehyde and 6-(trifluoromethyl)-2-((2-(trimethylsilyl)ethoxy)methyl)-2H-benzo[d][1,2,3]triazole-4-carbaldehyde (600 mg) as an oil. Concentration of the second fraction gave 6-(trifluoromethyl)-1-((2-(trimethylsilyl)ethoxy)methyl)-1H-benzo[d][1,2,3]triazole-4-carbaldehyde (165 mg) as a tan solid. 6-(Trifluoromethyl)-1-((2-(trimethylsilyl)ethoxy)methyl)-1H-benzo[d][1,2,3]triazole-4-carbaldehyde: $^1$H-NMR (CDCl$_3$, 500 MHz) δ 10.92 (s, 1H), 8.29 (s, 1H), 8.21 (s, 1H), 6.12 (s, 2H), 3.59 (m, 2H), 0.91 (m, 2H), −0.07 (s, 9H); $^{13}$C-NMR (CDCl$_3$, 126 MHz) δ 187.9, 146.2, 133.3, 130.4 (q, J=34 Hz), 127.4, 123.4 (q, J=274 Hz), 121.5 (q, J=2.9 Hz), 113.8 (q, J=4.8 Hz), 68.0, 17.7, −1.4.

Intermediate 185

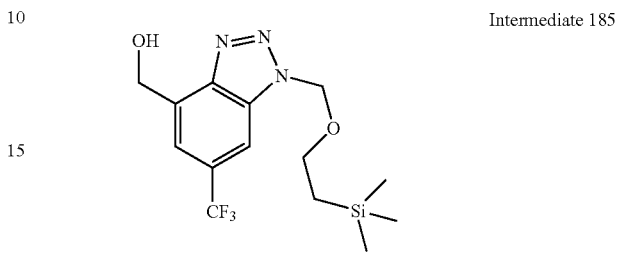

(6-(Trifluoromethyl)-1-((2-(trimethylsilyl)ethoxy)methyl)-1H-benzo[d][1,2,3]triazol-4-yl)methanol. To a solution of 6-(trifluoromethyl)-1-((2-(trimethylsilyl)ethoxy)methyl)-1H-benzo[d][1,2,3]triazole-4-carbaldehyde (165 mg, 0.478 mmol) in ethanol (5 mL) at 0° C. was added sodium borohydride (18.1 mg, 0.48 mmol). The ice bath was removed. After 15 min, the reaction was recooled to 0° C., quenched by the cautious addition of saturated ammonium chloride, and poured into ether. The ethereal was washed with water (2×), then brine, dried over magnesium sulfate, and concentrated to give 165 mg (99%) as a colorless oil. $^1$H-NMR (CDCl$_3$, 500 MHz) δ 7.91 (s, 1H), 7.67 (s, 1H), 6.02 (s, 2H), 5.30 (s, 2H), 3.70 (s, 1H), 3.56 (m, 2H), 0.89 (m, 2H), −0.09 (s, 9H); $^{13}$C-NMR (CDCl$_3$, 126 MHz) δ 145.6, 135.1, 132.3, 130.4 (q, J=33 Hz), 124.0 (q, J=273 Hz), 118.5 (q, J=2.9 Hz), 107.4 (q, J=4.8 Hz), 77.3, 67.6, 61.0, 17.7, −1.5.

Intermediate 186

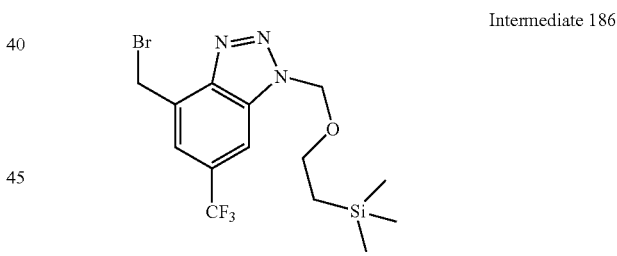

4-(Bromomethyl)-6-(trifluoromethyl)-1-((2-(trimethylsilyl)ethoxy)methyl)-1H-benzo[d][1,2,3]triazole. To a solution of (6-(trifluoromethyl)-1-((2-(trimethylsilyl)ethoxy)methyl)-1H-benzo[d][1,2,3]triazol-4-yl)methanol (165 mg, 0.475 mmol) and carbon tetrabromide (236 mg, 0.712 mmol) in tetrahydrofuran (2 mL) at 0° C. was added triphenylphosphine (187 mg, 0.712 mmol). The ice bath was removed and stirring continued at room temperature for 30 min. The reaction was diluted with several volumes of pentane and filtered to remove undissolved solids which were discarded. The organics were concentrated and purified by column chromatography (4→8% ethyl acetate/hexanes) to give 159 mg (82%) as a colorless oil. $^1$H-NMR (CDCl$_3$, 500 MHz) δ 7.96 (s, 1H), 7.67 (s, 1H), 6.03 (s, 2H), 5.04 (s, 2H), 3.59 (m, 2H), 0.90 (m, 2H), −0.07 (s, 9H); $^{13}$C-NMR (CDCl$_3$, 126 MHz) δ 145.9, 132.6, 131.6, 130.4 (q, J=33 Hz), 123.7 (q, J=273 Hz), 121.6 (q, J=2.9 Hz), 108.6 (q, J=4.8 Hz), 67.7, 25.9, 17.7, −1.5.

Intermediate 187

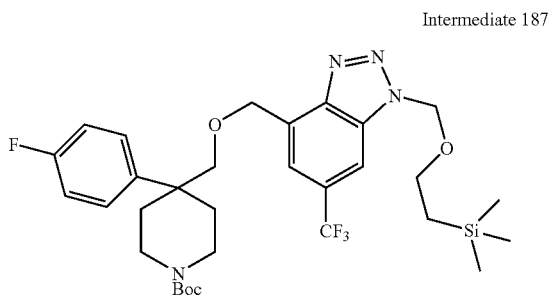

tert-Butyl 4-(4-fluorophenyl)-4-(((6-(trifluoromethyl)-1-((2-(trimethylsilyl)ethoxy)methyl)-1H-benzo[d][1,2,3]triazol-4-yl)methoxy)methyl)piperidine-1-carboxylate. To a solution of tert-butyl 4-(4-fluorophenyl)-4-(hydroxymethyl)piperidine-1-carboxylate (0.132 g, 0.426 mmol) and 4-(bromomethyl)-6-(trifluoromethyl)-1-((2-(trimethylsilyl)ethoxy)methyl)-1H-benzo[d][1,2,3]triazole (0.159 g, 0.388 mmol) in dimethylformamide (2 mL) at 0° C. was added sodium hydride (95%, 0.014 g, 0.58 mmol). The resulting solution was stirred at 0° C. for 5 min. The reaction was immediately quenched by the cautious addition of saturated ammonium chloride and diluted with ether. The ethereal was washed with water (2×), then brine, dried over magnesium sulfate, and concentrated. Column chromatography (12→25% ethyl acetate/hexanes) gave 122 mg (49%) as a foam. $^1$H-NMR (CDCl$_3$, 500 MHz) δ 7.87 (s, 1H), 7.38 (s, 1H), 7.33 (m, 2H), 7.00 (m, 2H), 6.00 (s, 2H), 5.01 (s, 2H), 3.72 (m, 2H), 3.56 (s, 2H), 3.55 (m, 2H), 3.04 (m, 2H), 2.18 (m, 2H), 1.88 (m, 2H), 1.42 (s, 9H), 0.88 (m, 2H), −0.09 (s, 9H); $^{13}$C-NMR (CDCl$_3$, 126 MHz) δ 162.5, 160.5, 155.0, 145.5, 138.5, 132.8, 132.1, 130.2 (q, J=33 Hz), 128.9, 128.8, 124.0 (q, J=273 Hz), 118.6 (q, J=2.9 Hz), 115.3, 115.1, 107.1 (q, J=4.8 Hz), 80.1, 79.4, 77.2, 68.0, 67.6, 41.5, 40.1 (br), 32.2, 28.5, 17.7, −1.5.

Intermediate 188

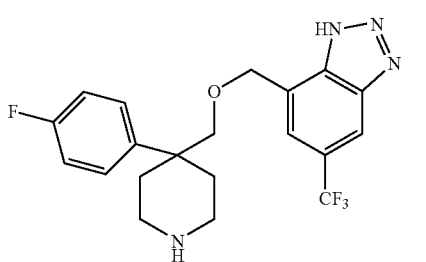

7-(((4-(4-Fluorophenyl)piperidin-4-yl)methoxy)methyl)-5-(trifluoromethyl)-1H-benzo[d][1,2,3]triazole. tert-Butyl 4-(4-fluorophenyl)-4-(((6-(trifluoromethyl)-1-((2-(trimethylsilyl)ethoxy)methyl)-1H-benzo[d][1,2,3]triazol-4-yl)methoxy)methyl)piperidine-1-carboxylate (120 mg, 0.188 mmol) was dissolved in trifluoroacetic acid (50% in dichloromethane, 2 mL) and stirred at room temperature for 4 h. The reaction was concentrated and loaded onto a strong cation exchange cartridge. The cartridge was flushed with several volumes of methanol which were discarded. The product was eluted using 2M ammonia in methanol and concentrated to give 75 mg (98%) as an amorphous solid. LC/MS (HPLC method 4): t$_R$=2.28 min, 409.15(MH)$^+$.

Intermediate 189

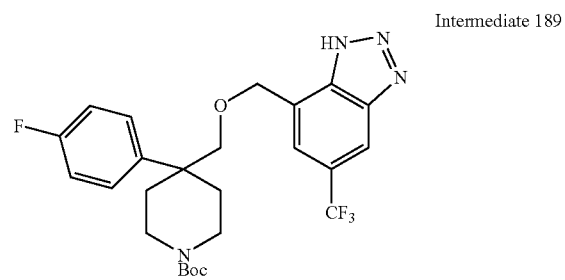

tert-Butyl 4-(4-fluorophenyl)-4-(((5-(trifluoromethyl)-1H-benzo[d][1,2,3]triazol-7-yl)methoxy)methyl)piperidine-1-carboxylate. To a suspension of 7-(((4-(4-fluorophenyl)piperidin-4-yl)methoxy)methyl)-5-(trifluoromethyl)-1H-benzo[d][1,2,3]triazole (69 mg, 0.169 mmol) in dimethylformamide (2 mL) was added di-tert-butyl dicarbonate (74 mg, 0.338 mmol). After stirring for 10 min, the reaction was gently warmed with a heat gun (to ca. 50° C.). The reaction was allowed to cool to room temperature with stirring. The reaction was quenched by addition of 2M ammonia in methanol, again warmed to ca. 50° C. with a heat gun, and allowed to cool to room temperature with stirring. The reaction was diluted with ether, washed with water (2×), then brine, dried over magnesium sulfate, and concentrated. Column chromatography (25% ethyl acetate/hexanes 100% ethyl acetate) gave 79 mg (92%) as a white foam. $^1$H-NMR (CDCl$_3$, 500 MHz) δ 12.2 (bs, 1H), 8.22 (bs, 1H), 7.38 (s, 1H), 7.34 (m, 2H), 7.11 (bs, 2H), 4.83 (bs, 2H), 3.74 (bs, 2H), 3.56 (s, 2H), 3.08 (m, 2H), 2.19 (m, 2H), 1.84 (m, 2H), 1.44 (s, 9H). Mass spec.: 509.13 (MH)$^+$.

Intermediates 190, 191 and 192

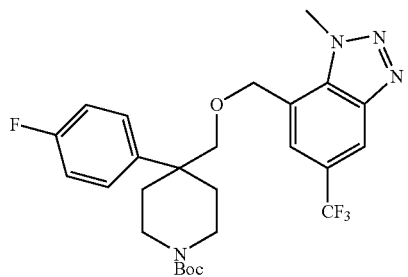

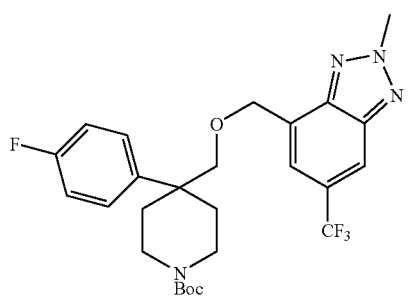

-continued

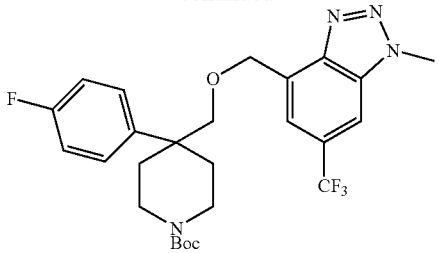

tert-Butyl 4-(4-fluorophenyl)-4-(((1-methyl-5-(trifluoromethyl)-1H-benzo[d][1,2,3]triazol-7-yl)methoxy)methyl)piperidine-1-carboxylate and tert-Butyl 4-(4-fluorophenyl)-4-(((2-methyl-6-(trifluoromethyl)-2H-benzo[d][1,2,3]triazol-4-yl)methoxy)methyl)piperidine-1-carboxylate and tert-Butyl 4-(4-fluorophenyl)-4-(((1-methyl-6-(trifluoromethyl)-1H-benzo[d][1,2,3]triazol-4-yl)methoxy)methyl)piperidine-1-carboxylate. To a solution of tert-butyl 4-(4-fluorophenyl)-4-(((5-(trifluoromethyl)-1H-benzo[d][1,2,3]triazol-7-yl)methoxy)methyl)piperidine-1-carboxylate (75 mg, 0.147 mmol) in dimethylformamide (1 mL) at 0° C. was added sodium hydride (95%, 8.9 mg, 0.22 mmol). After 5 min, the reaction was treated with iodomethane (0.018 mL, 0.30 mmol). After stirring for 30 min at 0° C., the reaction was quenched by the cautious addition of saturated ammonium chloride. The reaction was diluted with ether, washed with water (2×), then brine, dried over magnesium sulfate, concentrated, and purified by column chromatography (18% ethyl acetate/hexanes→37% ethyl acetate/hexanes). Concentration of the first fraction gave tert-Butyl 4-(4-fluorophenyl)-4-(((2-methyl-6-(trifluoromethyl)-2H-benzo[d][1,2,3]triazol-4-yl)methoxy)methyl)piperidine-1-carboxylate (22 mg, 29%). Concentration of the second fraction gave a mixture of tert-butyl 4-(4-fluorophenyl)-4-(((1-methyl-5-(trifluoromethyl)-1H-benzo[d][1,2,3]triazol-7-yl)methoxy)methyl)piperidine-1-carboxylate and tert-butyl 4-(4-fluorophenyl)-4-(((1-methyl-6-(trifluoromethyl)-1H-benzo[d][1,2,3]triazol-4-yl)methoxy)methyl)piperidine-1-carboxylate.
Concentration of the third faction gave tert-butyl 4-(4-fluorophenyl)-4-(((1-methyl-5-(trifluoromethyl)-1H-benzo[d][1,2,3]triazol-7-yl)methoxy)methyl)piperidine-1-carboxylate (17 mg, 22%). The second fraction was loaded onto a silica gel plate (25 cm×25 cm×1 mm) and eluted several times with 25% ethyl acetate/hexanes. The faster eluting fraction was cut from the plate, eluted with ethyl acetate, and concentrated to give tert-butyl 4-(4-fluorophenyl)-4-(((1-methyl-6-(trifluoromethyl)-1H-benzo[d][1,2,3]triazol-4-yl)methoxy)methyl)piperidine-1-carboxylate (14 mg, 18%). tert-Butyl 4-(4-fluorophenyl)-4-(((1-methyl-5-(trifluoromethyl)-1H-benzo[d][1,2,3]triazol-7-yl)methoxy)methyl)piperidine-1-carboxylate: $^1$H-NMR (CDCl$_3$, 500 MHz) δ 8.29 (s, 1H), 7.42 (s, 1H), 7.13 (m, 2H), 6.91 (m, 2H), 4.70 (s, 2H), 4.10 (s, 3H), 3.68 (m, 2H), 3.43 (s, 2H), 2.99 (m, 2H), 2.08 (m, 2H), 1.74 (m, 2H), 1.41 (s, 9H). Mass spec.: 523.06 (MH)$^+$. tert-Butyl 4-(4-fluorophenyl)-4-(((2-methyl-6-(trifluoromethyl)-2H-benzo [d][1,2,3]triazol-4-yl)methoxy)methyl)piperidine-1-carboxylate: $^1$H-NMR (CDCl$_3$, 500 MHz) δ 8.06 (s, 1H), 7.31 (m, 3H), 7.00 (m, 2H), 4.81 (s, 2H), 4.51 (s, 3H), 3.72 (m, 2H), 3.51 (s, 2H), 3.05 (m, 2H), 2.16 (m, 2H), 1.89 (m, 2H), 1.43 (s, 9H). Mass spec.: 523.06 (MH)$^+$. tert-Butyl 4-(4-fluorophenyl)-4-(((1-methyl-6-(trifluoromethyl)-1H-benzo[d][1,2,3]triazol-4-yl)methoxy)methyl)piperidine-1-carboxylate: $^1$H-NMR (CDCl$_3$, 500 MHz) δ 7.71 (s, 1H), 7.36 (s, 1H), 7.32 (m, 2H), 7.00 (m, 2H), 5.01 (s, 2H), 4.34 (s, 3H), 3.72 (m, 2H), 3.55 (s, 2H), 3.04 (m, 2H), 2.18 (m, 2H), 1.88 (m, 2H), 1.43 (s, 9H). Mass spec.: 523.06 (MH)$^+$.

Intermediate 193

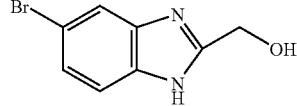

5-Bromo-1H-benzo[d]imidazol-2-yl)methanol. The title compound was prepared from the corresponding phenylenediamine following literature procedure described for the synthesis of 2-hydroxymethylbenzimidazole (Philips, J. Chem. Soc. 1928, 2393).

Intermediate 194

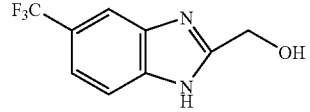

5-(Trifluoromethyl)-1H-benzo[d]imidazol-2-yl)methanol. The title compound was prepared from the corresponding phenylenediamine following literature procedure described for the synthesis of 2-hydroxymethylbenzimidazole (Philips, J. Chem. Soc. 1928, 2393).

Intermediates 195 and 196

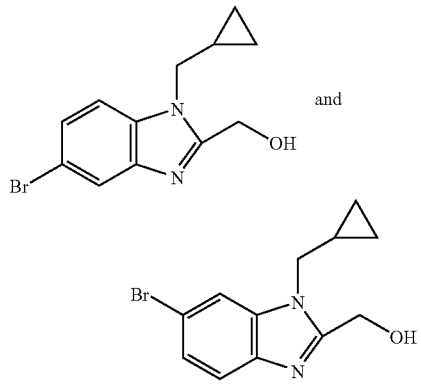

5-Bromo-1-(cyclopropylmethyl)-1H-benzo[d]imidazol-2-yl)methanol and 6-bromo-1-(cyclopropylmethyl)-1H-benzo[d]imidazol-2-yl)methanol. A 0.1 M solution of 5-Bromo-1H-benzo[d]imidazol-2-yl)methanol (630 mg, 2.8 mmol) in dimethylformamide was stirred with 2.4 equiv of cesium carbonate and (0.3 mL, 1.2 equiv) of cyclopropylmethyl bromide at 50° C. for 19 h. At the end dimethylformamide was evaporated in vacuo. The residue was partitioned between ethyl acetate (70 mL) and water (30 mL). Organic layer was dried (sodium sulfate) and evaporated in vacuo to give 800 mg of crude product which by LC-MS was 75% pure. LC/MS (HPLC method 1): $t_R$=2.1 min, 281(MH)$^+$. Silica gel TLC (ethyl acetate:hexane=4: 1) revealed two major products with R$_f$=0.29 and 0.20, which without separation were used in the next step.

Intermediates 197 and 198

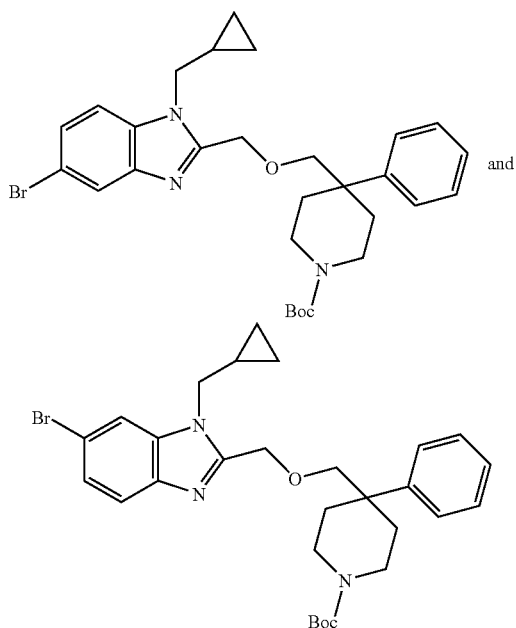

tert-Butyl 4-(((5-bromo-1-(cyclopropylmethyl)-1H-benzo[d]imidazol-2-yl)methoxy)methyl)-4-phenylpiperidine-1-carboxylate and tert-butyl 4-(((6-bromo-1-(cyclopropylmethyl)-1H-benzo[d]imidazol-2-yl)methoxy)methyl)-4-phenylpiperidine-1-carboxylate. An amber colored solution of crude 5-Bromo-1-(cyclopropylmethyl)-1H-benzo[d]imidazol-2-yl)methanol and 6-bromo-1-(cyclopropylmethyl)-1H-benzo[d]imidazol-2-yl)methanol (800 mg, 2.8 mmol, 75% purity) in dichloromethane was treated with thionyl chloride (1.0 mL, 4.8 equiv) and the resulting solution was kept at ambient temperature for 19 h. The reaction was concentrated. LC-MS analysis of the residue indicated complete conversion to the required chloromethyl derivative (LC/MS (HPLC method 5): $t_R$=2.8 min, 299(MH)$^+$). The residue was combined with tert-butyl 4-(hydroxymethyl)-4-phenylpiperidine-1-carboxylate (832 mg, 1.0 equiv), sodium hydride (3 equiv) and tetrahydrofuran (50 mL) and stirred under nitrogen. After 27 h, the suspension was warmed to 50° C. After another 24 h, LC-MS analysis revealed mostly the two starting materials. To the suspension was added tert-butyl 4-(hydroxymethyl)-4-phenylpiperidine-1-carboxylate (832 mg, 1.0 equiv) and 3 equiv of sodium hydride and continued stirring. LC-MS anlaysis after another 18 h indicated complete conversion to the required regioisomeric products. The reaction mixture was poured into saturated aqueous ammonium chloride (150 mL) and was extracted with ethyl acetate (2×75 mL). The organic layer was dried (sodium sulfate) and evaporated in vacuo. The residue was purified by preparative HPLC (HPLC method 11). Immediately after collection the pH of the fractions was adjusted to 10 using ammonium hydroxide to prevent any loss of Boc group. Methanol was evaporated in vacuo from the pooled fractions and the residue was extracted with ethyl acetate (200 mL). The ethyl acetate layer was dried (sodium sulfate) and evaporated in vacuo and the residue was purified by silica gel chromatography using a linear gradient of 8-100% ethyl acetate in hexane. Fractions containing the two regioisomers were separately combined and evaporated in vacuo to give faster eluting tert-butyl 4-(((5-bromo-1-(cyclopropylmethyl)-1H-benzo[d]imidazol-2-yl)methoxy)methyl)-4-phenylpiperidine-1-carboxylate (0.34 g, 21.5% yield) and its regio-isomer tert-butyl 4-(((6-bromo-1-(cyclopropylmethyl)-1H-benzo[d]imidazol-2-yl)methoxy)methyl)-4-phenylpiperidine-1-carboxylate (0.19 g, 12.0% yield). tert-Butyl 4-(((5-bromo-1-(cyclopropylmethyl)-1H-benzo[d]imidazol-2-yl)methoxy)methyl)-4-phenylpiperidine-1-carboxylate: $^1$H-NMR (CD$_3$OD, 500 MHz) δ7.75 (s, 1H), 7.37 (s, 2H), 7.30-7.24 (m, 4H), 7.16 (m, 1H), 4.64 (s, 2H), 3.73, (d, J=7.0 Hz, 2H), 3.69 (m, 2H), 3.52 (s, 2H), 3.00 (m, 2H), 2.14 (m, 2H), 1.79 (m, 2H), 1.42 (s, 9H), 0.95 (m, 1H), 0.45-0.41 (m, 2H), 0.27-0.24 (m, 2H); $^{13}$C NMR (CD$_3$OD, 126 MHz,) δ 155.6, 151.9, 143.1, 142.9, 134.8, 128.6, 127.3, 126.5, 126.3, 121.8, 115.3, 112.4, 79.9, 65.6, 41.6, 32.0, 27.8, 11.0, 3.8. LC/MS (HPLC method 6): $t_R$=2.8 min, 554(MH)$^+$. tert-Butyl 4-(((6-bromo-1-(cyclopropylmethyl)-1H-benzo[d]imidazol-2-yl)methoxy)methyl)-4-phenylpiperidine-1-carboxylate: $^1$H-NMR (CD$_3$OD, 500 MHz) 67.66 (s, 1H), 7.51 (d, J=8.3 Hz, 2H), 7.33 (m, 1H), 7.30-7.24 (m, 4H), 7.16 (m, 1H), 4.64 (s, 2H), 3.72, (d, J=7.0 Hz, 2H), 3.68 (m, 2H), 3.52 (s, 2H), 3.00 (m, 2H), 2.14 (m, 2H), 1.79 (m, 2H), 1.42 (s, 9H), 0.95 (m, 1H), 0.45-0.41 (m, 2H), 0.26-0.24 (m, 2H); $^{13}$C NMR (CD$_3$OD, 126 MHz,) δ 155.6, 151.6, 143.1, 140.6, 136.9, 128.6, 127.3, 126.5, 125.8, 120.5, 116.5, 114.0, 79.9, 65.6, 41.6, 32.1, 27.8, 11.0, 3.8. LC/MS (HPLC method 6): $t_R$=2.8 min, 554(MH)$^+$.

Intermediate 199

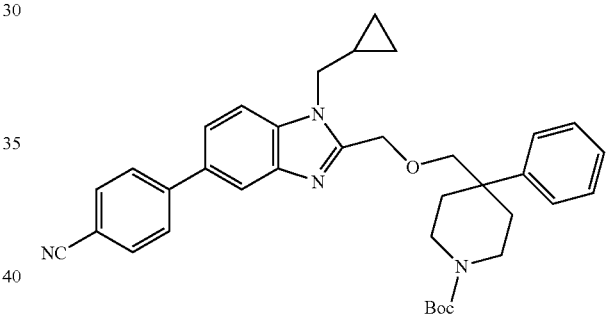

tert-Butyl 4-(((5-(4-cyanophenyl)-1-(cyclopropylmethyl)-1H-benzo[d]imidazol-2-yl)methoxy)methyl)-4-phenylpiperidine-1-carboxylate. Following the procedure is described in the literature (Lee, S. H. et. al. J. Org. Chem. 2004, 69, 8829-8835). tert-Butyl 4-(((5-bromo-1-(cyclopropylmethyl)-1H-benzo-[d]imidazol-2-yl)methoxy)methyl)-4-phenylpiperidine-1-carboxylate (48 mg, 0.087 mmol) was subjected to Suzuki coupling reaction in toluene (1.0 mL) at 110° C. with p-cyanophenylboronic acid (3 equiv) and cesium carbonate (3 equiv) using Pd (dppf) (0.08 equiv) as catalyst. The crude product was purified by silica gel chromatography using a 50 min linear gradient of 12% -100% ethyl acetate in hexane. Fractions containing the required product were combined and evaporated in vacuo to give 23 mg (46%) as a gum. $^1$H-NMR (CD$_3$OD, 500 MHz) δ 7.91 (s, 1H), 7.85 (d, J$_{AB}$=8.5 Hz, 2H), 7.80 (d, J$_{AB}$=8.5 Hz, 2H), 7.65-7.60 (m, 2H), 7.36-7.29 (m, 4H), 7.21 (m, 1H), 4.71 (s, 2H), 3.82, (d, J=7.0 Hz, 2H), 3.72 (m, 2H), 3.58 (s, 2H), 3.04 (m, 2H), 2.20 (m, 2H), 1.84 (m, 2H), 1.42 (s, 9H), 1.04 (m, 1H), 0.50-0.47 (m, 2H), 0.33-0.30 (m, 2H); $^{13}$C NMR (CD$_3$OD, 126 MHz,) δ 155.7, 151.9, 146.5, 143.1, 142.2, 136.2, 134.3, 132.8, 128.5, 128.0, 127.3, 126.4, 122.9, 118.9, 117.6, 111.6, 110.4, 80.0, 79.9, 65.6, 41.6, 32.1, 27.7, 11.0, 3.6. Mass Spec.: 577(MH)$^+$.

Intermediate 200

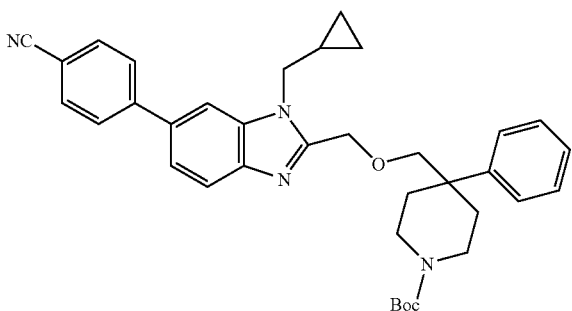

tert-Butyl 4-(((6-(4-cyanophenyl)-1-(cyclopropylmethyl)-1H-benzo[d]imidazol-2-yl)methoxy)methyl)-4-phenylpiperidine-1-carboxylate. This compound was prepared from tert-butyl 4-(((6-bromo-1-(cyclopropylmethyl)-1H-benzo[d]imidazol-2-yl)methoxy)methyl)-4-phenylpiperidine-1-carboxylate (52 mg) following the same procedure described for the synthesis of tert-butyl 4-(((5-(4-cyanophenyl)-1-(cyclopropylmethyl)-1H-benzo [d]imidazol-2-yl)methoxy)methyl)-4-phenylpiperidine-1-carboxylate in 72% yield. $^1$H-NMR (CD$_3$OD, 500 MHz) δ 7.85 (d, $J_{AB}$=8.5 Hz, 2H), 7.78 (m, 3H), 7.72 (d, J=8.5 Hz, 1H), 7.57 (m, 1H), 7.35-7.26 (m, 4H), 7.19 (m, 1H), 4.70 (s, 2H), 3.87, (d, J=6.7 Hz, 2H), 3.70 (m, 2H), 3.57 (s, 2H), 3.03 (m, 2H), 2.17 (m, 2H), 1.83 (m, 2H), 1.44 (s, 9H), 1.06 (m, 1H), 0.50-0.45 (m, 2H), 0.34-0.29 (m, 2H); $^{13}$C NMR (CD$_3$OD, 126 MHz,) δ 155.6, 152.0, 146.5, 143.1, 142.0, 136.4, 135.0, 132.8, 128.5, 128.2, 127.3, 126.4, 122.2, 119.6, 118.9, 110.6, 109.7, 80.0, 79.9, 65.6, 41.6, 32.1, 27.7, 11.1, 3.7. LC/MS (HPLC method 7): $t_R$=2.8 min, 577(MH)$^+$.

Intermediates 201 and 202

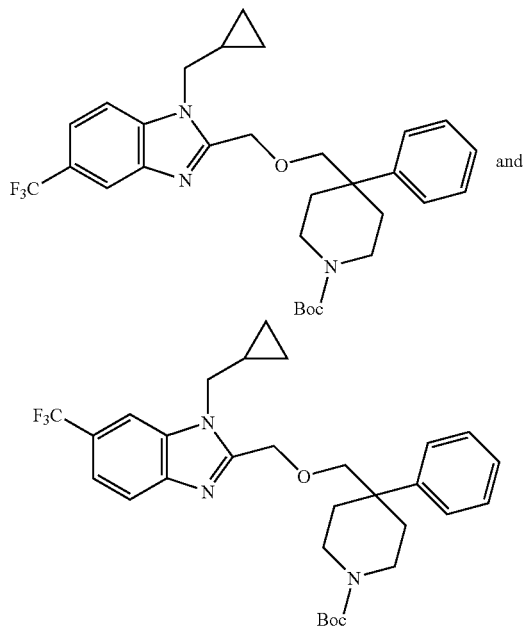

and tert-Butyl 4-(((1-(cyclopropylmethyl)-5-(trifluoromethyl)-1H-benzo[d]imidazol-2-yl)methoxy)methyl)-4-phenylpiperidine-1-carboxylate and tert-Butyl 4-(((1-(cyclopropylmethyl)-6-(trifluoromethyl)-1H-benzo[d]imidazol-2-yl)methoxy)methyl)-4-phenylpiperidine-1-carboxylate. 5-(Trifluoromethyl)-1H-benzo[d]imidazol-2-yl)methanol (665 mg, 1.77 mmol as TFA salt) was alkylated cyclopropylmethyl bromide following the procedure described for the synthesis of 5-Bromo-1-(cyclopropylmethyl)-1H-benzo[d]imidazol-2-yl)methanol and 6-bromo-1-(cyclopropylmethyl)-1H-benzo[d]imidazol-2-yl)methanol. After work up the crude product obtained was subjected to alkylation reaction with tert-butyl 4-(hydroxymethyl)-4-phenylpiperidine-1-carboxylate as described in the synthesis of tert-butyl 4-(((5-bromo-1-(cyclopropylmethyl)-1H-benzo[d]imidazol-2-yl)methoxy)methyl)-4-phenylpiperidine-1-carboxylate and tert-butyl 4-(((6-bromo-1-(cyclopropylmethyl)-1H-benzo[d]imidazol-2-yl)methoxy)methyl)-4-phenylpiperidine-1-carboxylate. The crude product obtained was purified silica gel chromatography using a step gradient of ethyl acetate in hexane from 10% to 100%. After pooling and evaporating the fractions three major fractions were obtained. Fraction 1 (204 mg, tert-butyl 4-(((1-(cyclopropylmethyl)-5-(trifluoromethyl)-1H-benzo[d]imidazol-2-yl)methoxy)methyl)-4-phenylpiperidine-1-carboxylate containing phenylpiperidinyl alcohol as contaminant), Fraction 2 (513 mg, mixture of tert-butyl 4-(((1-(cyclopropylmethyl)-5-(trifluoromethyl)-1H-benzo[d]imidazol-2-yl)methoxy)methyl)-4-phenylpiperidine-1-carboxylate and tert-butyl 4-(((1-(cyclopropylmethyl)-6-(trifluoromethyl)-1H-benzo[d]imidazol-2-yl)methoxy)methyl)-4-phenylpiperidine-1-carboxylate and fraction 3 (tert-butyl 4-(((1-(cyclopropylmethyl)-6-(trifluoromethyl)-1H-benzo[d]imidazol-2-yl)methoxy)methyl)-4-phenylpiperidine-1-carboxylate containing more polar impurities). Fraction 1 was purified further by preparative HPLC (HPLC method 11) and tert-butyl 4-(((1-(cyclopropylmethyl)-5-(trifluoromethyl)-1 H-benzo [d]imidazol-2-yl) methoxy)methyl)-4-phenylpiperidine-1-carboxylate (190 mg) was isolated as free base after extractive work up using ethyl acetate and aqueous ammonium hydroxide as described in the synthesis of 5. tert-Butyl 4-(((1-(cyclopropylmethyl)-5-(trifluoromethyl)-1H-benzo[d]imidazol-2-yl)methoxy) methyl)-4-phenylpiperidine-1-carboxylate: $^1$H NMR (500 MHz, CD$_3$OD) δ 7.93 (s, 1 H), 7.69 (d, J=8.5 Hz, 1 H), 7.62-7.58 (m, 1 H), 7.38-7.34 (m, 2 H), 7.30 (m, 2 H), 7.20 (m, 1 H), 4.73 (s, 2 H), 3.83 (d, J=7.0 Hz, 2 H), 3.73 (m, 2 H), 3.59 (s, 2 H), 3.05 (m, 2 H), 2.20 (m, 2 H), 1.84 (m, 2 H), 1.45 (s, 9 H), 1.04 (m, 1 H), 0.52-0.46 (m, 2 H), 0.35-0.29 (m, 2 H). $^{19}$F NMR (471 MHz, CD$_3$OD) δ −68.9, −84.5.

Fraction 2 was also purified in the same manner to give tert-butyl 4-(((1-(cyclopropylmethyl)-6-(trifluoromethyl)-1H-benzo[d]imidazol-2-yl)methoxy)methyl)-4-phenylpiperidine-1-carboxylate (160 mg). $^1$H-NMR (500 MHz, CD$_3$OD) δ 7.87 (s, 1 H), 7.79 (d, J=8.5 Hz, 1 H), 7.56 (d, J=8.5 Hz, 1 H), 7.36-7.18 (3×m, 5 H), 4.73 (s, 2 H), 3.87 (d, J=7.0 Hz, 2 H), 3.73 (m, 2 H), 3.59 (s, 2 H), 3.04 (m, 2 H), 2.20 (m, 2 H), 1.84 (m, 2 H), 1.45 (s, 9 H), 1.06-0.98 (m, 1 H), 0.52-0.46 (m, 2 H), 0.34-0.29 (m, 2 H). $^{19}$F NMR (471 MHz, CD$_3$OD) δ −69.0, −84.5.

Intermediate 203

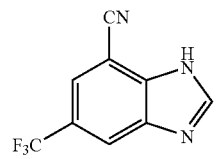

5-(Trifluoromethyl)-1H-benzo[d]imidazole-7-carbonitrile. A red suspension of 7-Bromo-5-(trifluoromethyl)-1H- benzo[d]imidazole (270 mg, 1.02 mmol), zinc cyanide (1.12 mmol), and PdCl$_2$(dppf) (0.06 mmol) in Water (3 ml) and dimethylformamide (10 ml) was heated with stirring under argon for 2 h. At the end, LC-MS analysis revealed completion of the reaction. The reaction mixture was cooled to ambient temperature and was subjected to preparative HPLC (8 injections using HPLC method 14). Fractions containing the required product were combined and evaporated in vacuo to give 97 mg (45% yield). $^1$H NMR (CD$_3$OD, 500 MHz) δ 7.88 (s, 1H), 8.21 (s, 1H), 8.54 (s, 1H); IR (KBr) 2229 (CN stretching); LC/MS (HPLC method 9): t$_R$=1.8 min, 212(MH)$^+$.

Intermediate 204

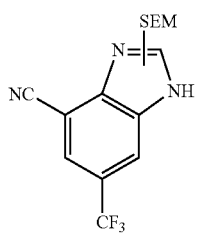

6-(Trifluoromethyl)-1-((2-(trimethylsilyl)ethoxy)methyl)-1H-benzo[d]imidazole-4-carbonitrile. The procedure used for the synthesis of this compound is as described in the literature for the synthesis of SEM ethers (Lipshutz, B. H. et al. Tetrahedron Lett. 1980, 21, 3343). The synthesis was carried out on a 0.28 mmol in 95% yield. $^1$H-NMR (500 MHz, CDCl$_3$) δ 8.31 (s, 1 H), 8.07 (s, 1 H), 7.88 (s, 1 H), 5.65 (s, 2 H), 3.54 (t, J=8.1 Hz, 2 H), 0.91 (t, J=8.1 Hz, 2 H), −0.06 (s, 9 H); $^{19}$F NMR (471 MHz, CDCl$_3$) δ−61.6, −76.4; LC/MS (HPLC method 7): t$_R$=3.1 min, 364(MNa)$^+$.

Intermediate 205

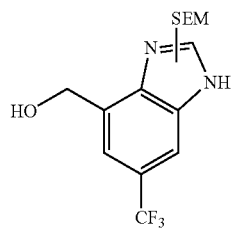

(6-(Trifluoromethyl)-1-((2-(trimethylsilyl)ethoxy)methyl)-1H-benzo[d]imidazol-4-yl)methanol. A 0.05 M solution of 6-(Trifluoromethyl)-1-((2-(trimethylsilyl)ethoxy)methyl)-1 H-benzo[d]imidazole-4-carbonitrile (124 mg, 0.363 mmol) in dichloromethane (7 mL) at −78° C. was treated with diisobutylaluminum hydride (1 M in tetrahydrofuran, 0.8 mL, 2.2 equiv). After 2 h, acetone (3 mL) was added followed by the addition of a 20% aqueous sodium potassium tartrate solution (5 mL). The mixture was warmed to ambient temperature and then extracted with dichloromethane (3×20 mL). The combined organic layer washed with water, brine and dried (sodium sulfate). The organic layer was evaporated in vacuo and the residue obtained was dissolved in tetrahydrofuran (3 mL) and treated with lithium borohydride (27 mg, 3.4 equiv). After 18 h, acetone (3 mL) was added. After 1 h, the reaction was concentrated. Extractive work up with ethyl acetate (3×20 mL) and water (15 mL) followed by evaporation of the dried (sodium sulfate) organic layer gave the crude product which was purified by preparative HPLC (HPLC method 13). Pooled fractions containing the required product were evaporated in vacuo to give 25 mg (20% yield). $^1$H-NMR (CD$_3$OD, 500 MHz) δ 9.14 (s, 1H), 8.12 (s, 1H), 7.83 (s, 1H), 5.87 (s, 2H), 5.13 (s, 2H), 3.67 (t, J=7.94 Hz, 2H), 0.95 (t, J=7.94 Hz, 2H), −0.03 (s, 9H); $^{19}$F NMR (471 MHz, CD$_3$OD) −63.1, −77.8; LC/MS (HPLC method 7): t$_R$=2.4 min, 347(MH)$^+$.

Intermediate 206

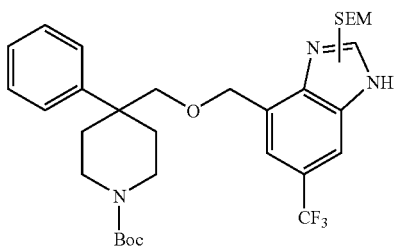

tert-Butyl 4-phenyl-4-(((6-(trifluoromethyl)-1-((2-(trimethylsilyl)ethoxy)methyl)-1H-benzo[d]imidazol-4-yl)methoxy)methyl)piperidine-1-carboxylate. The conversion of the alcohol to chloromethyl derivative and the subsequent alkylation were done using similar procedure as described in the synthesis of tert-butyl 4-(((5-bromo-1-(cyclopropylmethyl)-1H-benzo[d]imidazol-2-yl)methoxy)methyl)-4-phenylpiperidine-1-carboxylate (5) and tert-butyl 4-(((6-bromo-1-(cyclopropylmethyl)-1H-benzo[d]imidazol-2-yl)methoxy)methyl)-4-phenylpiperidine-1-carboxylate. (6-(Trifluoromethyl)-1-((2-(trimethylsilyl)ethoxy)methyl)-1H-benzo[d]imidazol-4-yl)methanol (25 mg, 0.072 mmol) was converted to chloromethyl derivative as described in the synthesis of tert-butyl 4-(((5-bromo-1-(cyclopropylmethyl)-1H-benzo[d]imidazol-2-yl)methoxy)methyl)-4-phenylpiperidine-1-carboxylate and tert-butyl 4-(((6-bromo-1-(cyclopropylmethyl)-1H-benzo[d]imidazol-2-yl)methoxy)methyl)-4-phenylpiperidine-1-carboxylate using thionyl chloride (0.030 mL, 5.7 eq) and the crude chloromethyl derivative was alkylated with tert-butyl 4-(hydroxymethyl)-4-phenylpiperidine-1-carboxylate (25.2 mg, 1.2 eq) using sodium hydride (9 equiv) in tetrahydrofuran (3 mL) at ambient temperature for 3 days. The crude product was purified by silica gel chromatography using a gradient of 10%-80% ethyl acetate in dichloromethane. Fractions containing required compound were combined and evaporated in vacuo to give tert-butyl 4-phenyl-4-(((6-(trifluoromethyl)-1-((2-(trimethylsilyl)ethoxy)methyl)-1H-benzo[d]imidazol-4-yl)methoxy)methyl)piperidine-1-carboxylate (25 mg) containing required product and piperidinyl alcohol reagent in the ratio of 2:3 by proton NMR. Material used without additional purification. LC/MS (HPLC method 8): t$_R$=3.8 min, 642(MNa)$^+$.

Intermediate 207

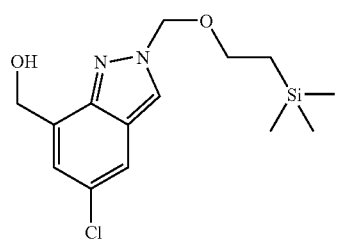

(5-Chloro-2-((2-(trimethylsilyl)ethoxy)methyl)-2H-indazol-7-yl)methanol. To a suspension of 5-chloro-2-((2-(trimethylsilyl)ethoxy)methyl)-2H-indazole-7-carbaldehyde (3 g, 9.65 mmol) in ethanol (20 mL) at 0° C. was added sodium borohydride (0.183 g, 4.83 mmol). The ice bath was removed and stirring continued for 1 h. The reaction was recooled to 0° C. and quenched by the cautious addition of saturated ammonium chloride. The reaction was concentrated to remove most of the ethanol. The resulting residue was dissolved in water and extracted with diethyl ether (2×). The ethereal was washed with water, then brine, dried over magnesium sulfate, and concentrated to give 3.3 g (quant.) as a viscous oil. $^1$H-NMR (CDCl$_3$, 500 MHz) δ 8.04 (s, 1H), 7.55 (d, J=1.5 Hz, 1H), 7.19 (d, J=1.2 Hz, 1H), 5.67 (s, 2H), 5.04 (d, J=4.9 Hz, 2H), 3.61 (t, J=8.2 Hz, 2H), 3.31 (m, 1H), 0.92 (t, J=8.2 Hz, 2H), −0.04 (s, 9H); $^{13}$C NMR (126 MHz, CDCl$_3$) δ ppm 145.9, 132.4, 128.0, 124.7, 122.7, 122.6, 118.3, 81.9, 67.8, 62.3, 17.9, −1.4. Mass spec.: 313.12 (MH)$^+$.

Intermediate 208

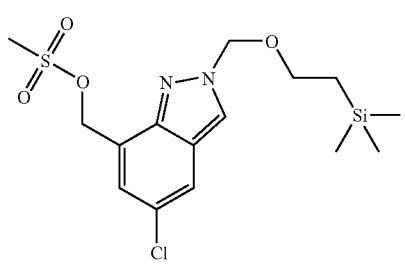

(5-Chloro-2-((2-(trimethylsilyl)ethoxy)methyl)-2H-indazol-7-yl)methyl methanesulfonate. To a solution of (5-chloro-2-((2-(trimethylsilyl)ethoxy)methyl)-2H-indazol-7-yl)methanol (2.5 g, 8 mmol) and triethylamine (3.34 mL, 24 mmol) in dichloromethane (120 mL) at 0° C. was added methanesulfonyl chloride (1.25 mL, 16 mmol). The reaction was stirred at 0° C. for 1 h. The reaction was quenched by addition of water, stirred 5 min, and poured into water. The layers were separated and the organics washed with brine, dried over magnesium sulfate, and concentrated to give 3.25 g (quant.). $^1$H-NMR (CDCl$_3$, 500 MHz) δ 8.09 (s, 1H), 7.66 (d, J=1.8 Hz, 1H), 7.31 (d, J=0.9 Hz, 1H), 5.68 (s, 2H), 5.59 (s, 2H), 3.60 (t, J=8.2 Hz, 2H), 3.06 (s, 3H), 0.91 (t, J=8.2 Hz, 2H), −0.05 (s, 9H); $^{13}$C NMR (126 MHz, CDCl$_3$) δ ppm 145.4, 127.5, 127.4, 125.0, 123.0, 122.8, 120.5, 82.1, 67.8, 67.4, 38.0, 17.9, −1.4. Mass spec.: 391.14 (MH)$^+$.

Intermediate 209

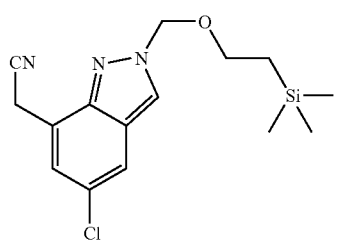

2-(5-Chloro-2-((2-(trimethylsilyl)ethoxy)methyl)-2H-indazol-7-yl)acetonitrile. To a solution of (5-chloro-2-((2-(trimethylsilyl)ethoxy)methyl)-2H-indazol-7-yl)methyl methanesulfonate (3.25 g, 8.3 mmol) in dimethylformamide (10 mL) at room temperature was added sodium cyanide (0.815 g, 16.6 mmol). The reaction was placed in a 60° C. oil bath and allowed to stir for 30 min. The reaction was cooled, diluted with diethyl ether, washed with water (2×), then brine, dried over magnesium sulfate, and concentrated to give 2.33 g (87%). $^1$H-NMR (CDCl$_3$, 500 MHz) δ 8.07 (s, 1H), 7.62 (d, J=1.2 Hz, 1H), 7.32 (d, J=1.2 Hz, 1H), 5.68 (s, 2H), 4.09 (s, 2H), 3.62 (t, J=8.2 Hz, 2H), 0.93 (t, J=7.9 Hz, 2H), −0.04 (s, 9H), $^{13}$C NMR (126 MHz, CDCl$_3$) δ ppm 145.7, 127.7, 126.4, 123.2, 122.4, 121.8, 119.5, 117.0, 82.1, 67.9, 19.4, 17.9, −1.4.

Intermediate 210

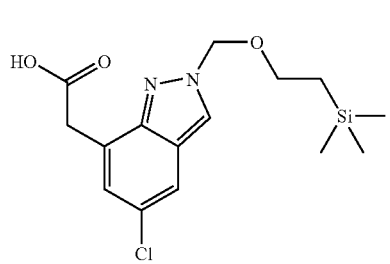

2-(5-Chloro-2-((2-(trimethylsilyl)ethoxy)methyl)-2H-indazol-7-yl)acetic acid. To a solution of 2-(5-chloro-2-((2-(trimethylsilyl)ethoxy)methyl)-2H-indazol-7-yl)acetonitrile (2.47 g, 7.25 mmol) in methanol (36 mL) was added sodium hydroxide (25% in water, 12 mL). The reaction was warmed to reflux and held there overnight. The reaction was cooled to room temperature, concentrated to remove the methanol. The resulting residue was diluted with diethyl ether (20 mL), cooled to 0° C., and made acidic by the cautious addition of concentrated hydrochloric acid with stirring. The resulting suspension was extracted with 1:1 diethyl ether/ethyl acetate (2×). The organics were washed with brine, dried over magnesium sulfate, and concentrated to give 2.47 g (100%) as an off white solid. $^1$H-NMR (CDCl$_3$, 500 MHz) δ 9.98 (bs, 1H), 8.04 (s, 1H), 7.57 (d, J=1.5 Hz, 1H), 7.17 (d, J=0.9 Hz, 1H), 5.70 (s, 2), 4.04 (s, 2H), 3.61 (t, J=8.2 Hz, 2H), 0.91 (t, J=8.2 Hz, 2H), −0.05 (s, 9H), $^{13}$C NMR (126 MHz, CDCl$_3$) δ ppm 174.5, 146.7, 128.4, 128.0, 125.1, 123.2, 122.5, 118.6, 81.9, 67.9, 36.9, 17.9, −1.4. Mass spec.: 341.11 (MH)$^+$.

Intermediate 211

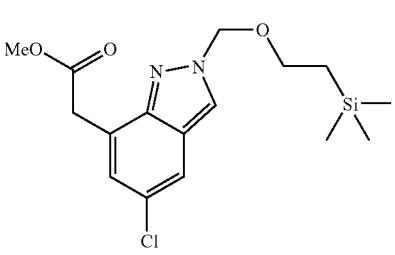

Methyl 2-(5-chloro-2-((2-(trimethylsilyl)ethoxy)methyl)-2H-indazol-7-yl)acetate. To a heterogeneous mixture of sodium hydroxide (4M in water, 25 mL) and diethyl ether (75 mL) at 0° C. was added N-methyl-N'-nitro-N-nitrosoguanidine (2.24 g, 15.3 mmol) with swirling (no stirbar). After addition was complete, the mixture was allowed to stand at 0° C. for 15 min with occasional swirling. The ethereal was transferred in portions to a suspension of 2-(5-chloro-2-((2-(trimethylsilyl)ethoxy)methyl)-2H-indazol-7-yl)acetic acid (2.6 g, 7.63 mmol) in diethyl ether (50 mL) until the yellow color persisted and all of the starting material had gone into solution. The reaction was allowed to rest at room temperature for 5 min before bubbling nitrogen through the solution to remove most of the unreacted diazomethane. Column chromatography (25% ethyl acetate/n-hexane) gave 2.28 g (84%) as a colorless oil. $^1$H-NMR (CDCl$_3$, 500 MHz) δ 8.02 (s, 1H), 7.56 (d, J=1.5 Hz, 1H), 7.14 (d, J=0.9 Hz, 1H), 5.67 (s, 2H), 4.01 (s, 2H), 3.70 (s, 3H), 3.61 (t, J=8.2 Hz, 2H), 0.92 (t, J=8.3 Hz, 2H), −0.04 (s, 9H); $^{13}$C NMR (126 MHz, CDCl$_3$) δ ppm 171.3, 146.9, 127.7, 127.5, 126.0, 122.61, 122.57, 118.3, 82.0, 67.7, 52.1, 36.1, 17.9, −1.4.

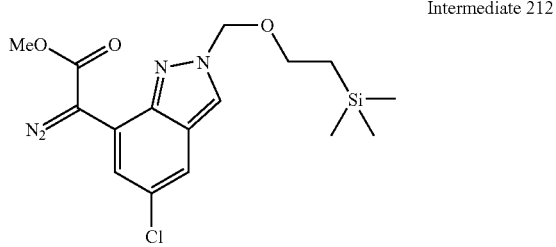

Intermediate 212

Methyl 2-(5-chloro-2-((2-(trimethylsilyl)ethoxy)methyl)-2H-indazol-7-yl)-2-diazoacetate. To a solution of methyl 2-(5-chloro-2-((2-(trimethylsilyl)ethoxy)methyl)-2H-indazol-7-yl)acetate (1.95 g, 5.49 mmol) and 4-acetamidobenzenesulfonyl azide (1.52 g, 6.32 mmol) in acetonitrile (11 mL) at 0° C. was added 1,8-Diazabicyclo[5.4.0]undec-7-ene (1.04 mL, 6.87 mmol) dropwise over 20 min. The ice bath was removed and stirring continued at room temperature for 1 h. The reaction was partitioned between water and ethyl acetate. The organics were washed with saturated sodium bicarbonate, dried over sodium sulfate, and concentrated. The resulting residue was purified by column chromatography (8%→25% ethyl acetate/n-hexane) to give 1.39 g (66%) as a yellow oil. $^1$H-NMR (CDC13, 500 MHz) δ 8.01 (s, 1H), 7.79 (d, J=1.5 Hz, 1H), 7.45 (d, J=1.8 Hz, 1H), 5.64 (s, 2H), 3.89 (s, 3H), 3.64 (t, J=8.2 Hz, 2H), 0.93 (t, J=8.4 Hz, 2H), −0.03 (s,9H; $^{13}$C NMR (126 MHz, CDCl$_3$) δ ppm 165.9, 143.2, 128.7, 125.3, 123.1, 122.7, 122.5, 116.5, 116.4, 81.8, 67.9, 52.1, 17.8, −1.4.

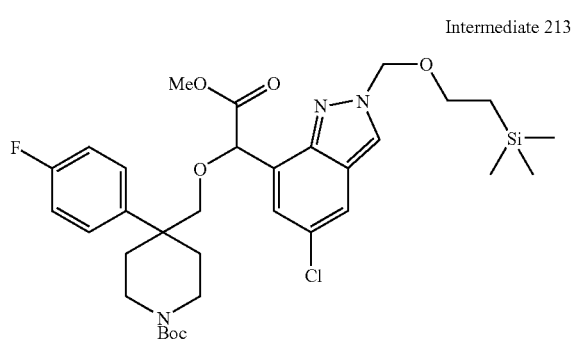

Intermediate 213 tert-Butyl 4-((1-(5-chloro-2-((2-(trimethylsilyl)ethoxy)methyl)-2H-indazol-7-yl)-2-methoxy-2-oxoethoxy)methyl)-4-(4-fluorophenyl)piperidine-1-carboxylate. To a suspension of tert-butyl 4-(4-fluorophenyl)-4-(hydroxymethyl)piperidine-1-carboxylate (2.26 g, 7.30 mmol) and rhodium (II) acetate dimer (4.84 mg, 11 μmol) in benzene (4 mL) at reflux was added a solution of methyl 2-(5-chloro-2-((2-(trimethylsilyl)ethoxy)methyl)-2H-indazol-7-yl)-2-diazoacetate (1.39 g, 3.65 mmol) in benzene (3 mL) via syringe pump over 60 h. After addition was complete, the reaction was cooled. It became a very viscous solution. The reaction mixture was diluted with 20% ethyl acetate/n-hexane and loaded onto a column. Column chromatography (20% ethyl acetate/n-hexane→25% ethyl acetate/n-hexane) gave 1.88 g (78%) as a yellow foam solid. $^1$H-NMR (CDCl$_3$, 500 MHz) δ 8.03 (s, 1H), 7.58 (d, J=1.8 Hz, 1H), 7.29 (dd, J=8.5, 5.2 Hz, 2H), 7.06 (s, 1H), 6.97 (dd, J=8.9, 8.5 Hz, 2H), 5.68 (d, J=10.7 Hz, 1H), 5.65 (d, J=10.7 Hz, 1H), 5.42 (s, 1H), 3.71 (bs, 2H), 3.61 (s, 3H), 3.60 (t, J=8.6 Hz, 2H), 3.39 (d, J=8.9 Hz, 1H), 3.03 (m, 2H), 2.16 (m, 1H), 2.08 (m, 1H), 1.93 (m, 2H), 1.42 (s, 9H), 0.91 (t, J=8.2 Hz, 2H), −0.05 (s, 9H); $^{13}$C NMR (126 MHz, CDCl$_3$) δ ppm 170.5, 161.5 (d, J=246 Hz), 155.0, 145.6, 138.3, 128.9 (d, J=7.7 Hz), 127.9, 125.5, 122.8, 122.5, 119.5, 115.2 (d, J=21 Hz), 82.1, 79.4, 78.6, 76.4, 67.7, 52.3, 41.4, 40.0 (br), 32.1, 31.9, 28.6, 17.9, −1.4. Mass spec.: 662.53 (MH)$^+$.

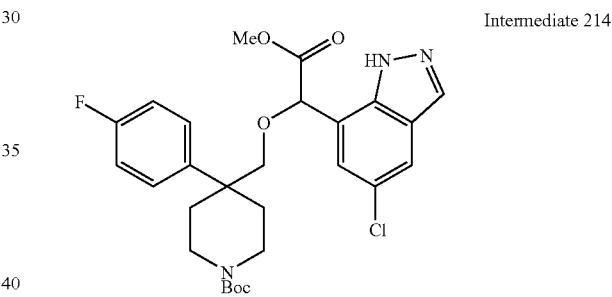

Intermediate 214 tert-Butyl 4-((1-(5-chloro-1H-indazol-7-yl)-2-methoxy-2-oxoethoxy)methyl)-4-(4-fluorophenyl)piperidine-1-carboxylate. tert-Butyl 4-((1-(5-chloro-2-((2-(trimethylsilyl) ethoxy)methyl)-2H-indazol-7-yl)-2-methoxy-2-oxoethoxy) methyl)-4-(4-fluorophenyl)piperidine-1-carboxylate (25 mg) was stirred in trifluoroacetic acid (50% in dichloromethane, 1.5 mL) for 4 h and concentrated. The residue was loaded onto a strong cation exchange cartridge and washed with several volumes of methanol. The product was eluted with 2M ammonia in methanol and concentrated. The crude piperidine was dissolved in dichloromethane (1 mL) and treated with di-tert-butyldicarbonate (17 mg). After 15 min, the reaction was quenched by addition of 2 M ammonia in methanol and concentrated. Column chromatography (ethyl acetate/n-hexane) gave the title compound. $^1$H-NMR (CDCl$_3$, 500 MHz) δ 10.14 (bs, 1H), 7.93 (s, 1H), 7.66 (d, J=1.8, 1H), 7.29 (dd, J=8.2, 5.2, 2H), 7.07 (dd, J=8.9, 8.5, 2H), 4.85 (s, 1H), 3.50-3.80 (m, 6H), 3.36 (d, J=8.5, 1H), 3.02 (m, 2H), 2.15 (m, 2H), 1.81 (m, 2H), 1.42 (s, 9H); $^{13}$C NMR (126 MHz, CDCl$_3$) δ ppm 169.8, 161.7 (d, J=247 Hz), 155.0, 137.82, 137.79, 136.0, 133.7, 128.8 (d, J=7.7 Hz), 126.2, 126.1, 125.0, 120.8, 119.5, 115.7 (d,J=21 Hz), 80.7, 79.6, 79.0, 52.7, 41.3, 39.9 (br), 32.3, 32.2, 28.5.

Intermediate 215

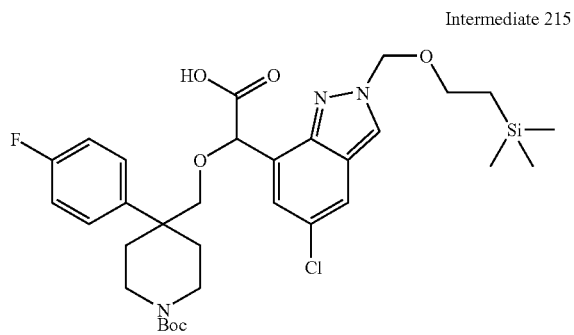

2-((1-(tert-Butoxycarbonyl)-4-(4-fluorophenyl)piperidin-4-yl)methoxy)-2-(5-chloro-2-((2-(trimethylsilyl)ethoxy)methyl)-2H-indazol-7-yl)acetic acid. To a solution of tert-butyl 4-((1-(5-chloro-2-((2-(trimethylsilyl)ethoxy)methyl)-2H-indazol-7-yl)-2-methoxy-2-oxoethoxy)methyl)-4-(4-fluorophenyl)piperidine-1-carboxylate (150 mg, 0.226 mmol) in tetrahydrofuran (1 mL) and methanol (1 mL) at 0° C. was added a solution of lithium hydroxide monohydrate (28.5 mg, 0.679 mmol) in water (0.5 mL). After 1 h, the reaction was concentrated to remove most of the solvent. The resulting residue was dissolved in a minimum of water, and acidified with 1N hydrochloric acid to give a white solid which was collected by filtration. $^1$H-NMR (CDCl$_3$, 500 MHz) δ 8.83 (bs, 1H), 8.05 (s, 1H), 7.59 (d, J=1.8 Hz, 1H), 7.28 (dd, J=8.9, 5.5 Hz, 2H), 7.10 (s, 1H), 6.98 (dd, J=8.9, 8.6 Hz, 2H), 5.65 (s, 2H), 5.23 (s, 1H), 3.62-3.82 (m, 3H), 3.58 (t, J=8.2 Hz, 2H), 3.37 (d, J=8.9 Hz, 1H), 3.02 (m, 2H), 2.17 (m, 1H), 2.08 (m, 1H), 1.92 (m, 1H), 1.84 (m, 1H), 1.41 (s, 9H), 0.91 (m, 2H), −0.05 (s, 9H); $^{13}$C NMR (126 MHz, CDCl$_3$) δ ppm 170.7, 161.5 (d, J=246 Hz), 155.1, 145.3, 138.1, 128.9 (d, J=7.7 Hz), 128.2, 126.5, 126.4, 123.3, 122.7, 119.9, 115.3 (d, J=20.2 Hz), 82.0, 79.7, 78.7, 77.7, 68.0, 41.3, 39.8, 32.1, 31.9, 28.5, 17.9, −1.4.

Intermediate 216

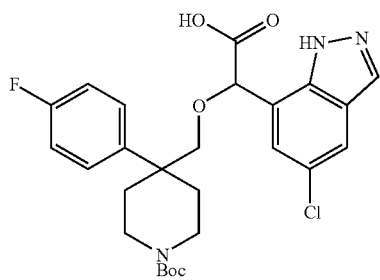

2-((1-(tert-Butoxycarbonyl)-4-(4-fluorophenyl)piperidin-4-yl)methoxy)-2-(5-chloro-1H-indazol-7-yl)acetic acid. Prepared according to the procedure used to prepare tert-butyl 4-((1-(5-chloro-1H-indazol-7-yl)-2-methoxy-2-oxoethoxy)methyl)-4-(4-fluorophenyl)piperidine-1-carboxylate using 2-((1-(tert-butoxycarbonyl)-4-(4-fluorophenyl)piperidin-4-yl)methoxy)-2-(5-chloro-2-((2-(trimethylsilyl)ethoxy)methyl)-2H-indazol-7-yl)acetic acid as the starting material and using dichloromethane/methanol in its purification. t$_R$=3.03 min (Phenomenex C18 3.0×50 mm, A=90% H$_2$O/10% methanol, B=90% methanol/10% H$_2$O, Modifier 0.1% TFA, 0.00 min=0% B, 3.0 min=100% B, 5.0 min=100% B, Flow rate=4 mL/min). Mass spec.: 518.22 (MH)$^+$.

Intermediate 217

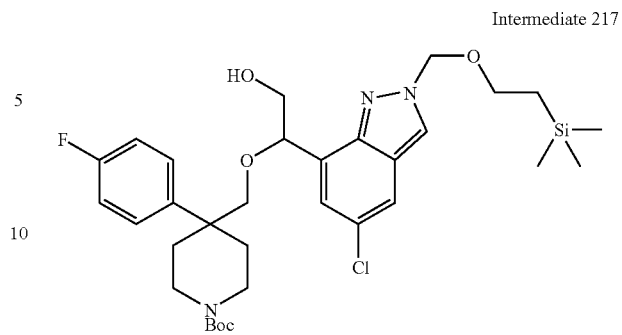

tert-Butyl 4-((1-(5-chloro-2-((2-(trimethylsilyl)ethoxy)methyl)-2H-indazol-7-yl)-2-hydroxyethoxy)methyl)-4-(4-fluorophenyl)piperidine-1-carboxylate. To a solution of tert-butyl 4-((1-(5-chloro-2-((2-(trimethylsilyl)ethoxy)methyl)-2H-indazol-7-yl)-2-methoxy-2-oxoethoxy)methyl)-4-(4-fluorophenyl)piperidine-1-carboxylate (850 mg, 1.28 mmol) in tetrahydrofuran (7.4 mL) and methanol (0.37 mL) at 0° C. was added lithium borohydride (55.9 mg, 2.57 mmol). The ice bath was removed and stirring continued for 30 min. The reaction was diluted with diethyl ether and quenched by addition of saturated ammonium chloride. The ethereal was washed with water, then brine, dried over magnesium sulfate, and concentrated. Column chromatography (25%→50% ethyl acetate/n-hexane) gave 794 mg (98%) as a foam solid. $^1$H-NMR (CDCl$_3$, 500 MHz) δ 8.01 (s, 1H), 7.52 (d, J=1.5 Hz, 1H), 7.33 (dd, J=8.6, 5.2 Hz, 2H), 7.05 (dd, J=8.6, 8.5 Hz, 2H), 6.75 (s, 1H), 5.65 (d, J=10.7 Hz, 1H), 5.62 (d, J=10.7 Hz, 1H), 4.95 (dd, J=7.0, 3.4 Hz, 1H), 3.55-3.85 (m, 6H), 3.52 (d, J=8.9 Hz, 1H), 3.41 (d, J=8.9 Hz, 1H), 3.06 (m, 2H), 2.10-2.35 (m, 3H), 1.88 (m, 2H), 1.43 (s, 9H), 0.90 (t, J=8.2 Hz, 2H), −0.06 (s, 9H); $^{13}$C NMR (126 MHz, CDCl$_3$) δ ppm 161.5 (d, J=246 Hz), 155.0, 145.7, 138.6, 130.2, 128.8 (d, J=7.7 Hz), 128.1, 124.2, 122.8, 122.5, 118.5, 115.4 (d, J=21 Hz), 81.9, 79.5, 79.1, 78.6, 67.7, 66.2, 41.5, 40.0, 32.3, 32.2, 28.6, 17.9, −1.4. Mass spec.: 634.38 (MH)$^+$.

Intermediate 218

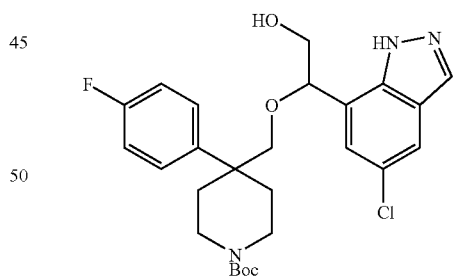

tert-Butyl 4-((1-(5-chloro-1H-indazol-7-yl)-2-hydroxyethoxy)methyl)-4-(4-fluorophenyl)piperidine-1-carboxylate. Prepared according to the procedure used to prepare tert-butyl 4-((1-(5-chloro-1H-indazol-7-yl)-2-methoxy-2-oxoethoxy)methyl)-4-(4-fluorophenyl)piperidine-1-carboxylate using tert-butyl 4-((1-(5-chloro-2-((2-(trimethylsilyl)ethoxy)methyl)-2H-indazol-7-yl)-2-hydroxyethoxy)methyl)-4-(4-fluorophenyl)piperidine-1-carboxylate as the starting material. $^1$H-NMR (CDCl$_3$, 500 MHz) δ 10.20 (bs, 1H), 7.93 (s, 1H), 7.62 (d, J=1.5 Hz, 1H), 7.25 (dd, J=8.5 Hz, 5.2, 2H), 7.06 (dd, J=8.6, 8.5 Hz, 2H), 7.02 (d, J=1.8 Hz, 1H), 4.46 (dd, J=7.0, 4.3 Hz, 1H), 3.76 (dd, J=11.9, 7.3 Hz, 1H), 3.67 (dd, J=11.9, 4.3 Hz, 1H), 3.40 (m, 2H), 3.00 (m, 2H), 2.23 (m, 1H), 2.10 (m, 1H), 1.84 (m, 1H), 1.75 (m, 1H), 1.42 (s, 9H); $^{13}$C NMR (126 MHz, CDCl$_3$) δ ppm 171.2, 161.7 (d, J=247 Hz), 155.0, 137.8, 136.4, 133.9, 128.7 (d, J=7.7 Hz), 126.3, 125.6, 124.9, 122.6, 119.9, 115.8 (d, J=21 Hz), 83.0, 79.7, 79.4, 65.7, 41.4, 39.9 (br), 32.5, 32.2, 28.5.

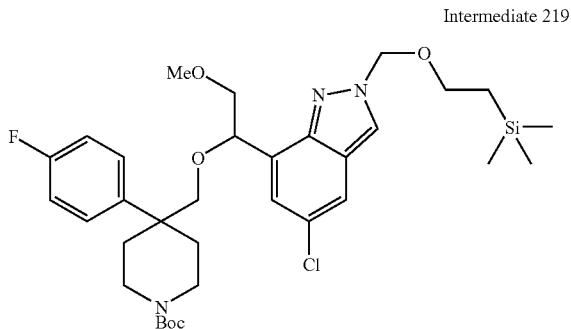

Intermediate 219 tert-Butyl 4-((1-(5-chloro-2-((2-(trimethylsilyl)ethoxy)methyl)-2H-indazol-7-yl)-2-methoxyethoxy)methyl)-4-(4-fluorophenyl)piperidine-1-carboxylate. To a solution of tert-butyl 4-((1-(5-chloro-2-((2-(trimethylsilyl)ethoxy)methyl)-2H-indazol-7-yl)-2-hydroxyethoxy)methyl)-4-(4-fluorophenyl)piperidine-1-carboxylate (25 mg, 0.039 mmol) in dimethylformamide (0.5 mL) at 0° C. was added sodium hydride (60%, 3.15 mg, 0.079 mmol). After 5 min, the reaction was treated with iodomethane (4.93 μL, 0.079 mmol). The ice bath was removed and stirring continued for 1 h. The reaction was cooled to 0° C. and quenched by the cautious addition of saturated ammonium chloride. The reaction was diluted with diethyl ether and the layers separated. The ethereal was washed with water (2×). then brine, dried over magnesium sulfate, and concentrated. Column chromatography (25% ethyl acetate/n-hexane) gave 22 mg (86%) as a colorless film. $^1$H-NMR (CDCl$_3$, 500 MHz) δ 8.00 (s, 1H), 7.51 (d, J=1.8 Hz, 1H), 7.31 (dd, J=8.9, 5.2 Hz, 2H), 7.02 (dd, J=8.9, 8.5 Hz, 2H), 6.74 (s, 1H), 5.67 (d, J=10.7 Hz, 1H), 5.63 (d, J=10.7 Hz, 1H), 5.06 (dd, J=7.3, 2.7 Hz, 1H), 3.50-3.80 (m, 6H), 3.48 (d, J=9.2 Hz, 1H), 3.41 (d, J=9.2 Hz, 1H), 3.33 (s, 3H), 3.06 (m, 2H), 2.23 (m, 1H), 2.07 (m, 1H), 1.97 (m, 1H), 1.87 (m, 1H), 1.69 (bs, 1H), 1.44 (s, 9H), 0.91 (t, J=8.2 Hz, 2H), −0.05 (s, 9H); $^{13}$C NMR (126 MHz, CDCl$_3$) δ ppm 161.5 (d, J=245 Hz), 155.1, 145.7, 138.84, 138.82, 130.8, 128.9 (d, J=7.7 Hz), 128.1, 124.3, 122.8, 122.2, 118.3, 115.2 (d, J=21), 81.9, 79.4, 78.7, 77.9, 76.1, 67.7, 59.4, 41.4, 40.2 (br), 32.4, 32.0, 28.6, 17.9, −1.4. Mass spec.: 648.38 (MH)$^+$.

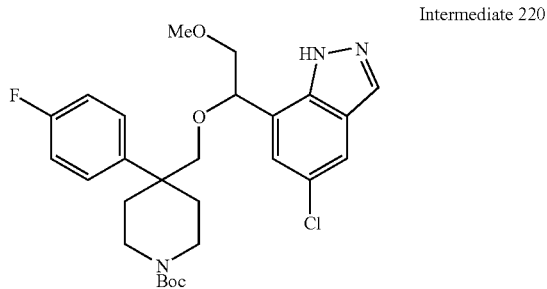

Intermediate 220 tert-Butyl 4-((1-(5-chloro-1H-indazol-7-yl)-2-methoxyethoxy)methyl)-4-(4-fluorophenyl)piperidine-1-carboxylate. Prepared according to the procedure used to prepare tert-butyl 4-((1-(5-chloro-1H-indazol-7-yl)-2-methoxy-2-oxoethoxy)methyl)-4-(4-fluorophenyl)piperidine-1-carboxylate using tert-butyl 4-((1-(5-chloro-2-((2-(trimethylsilyl)ethoxy)methyl)-2H-indazol-7-yl)-2-methoxyethoxy)methyl)-4-(4-fluorophenyl)piperidine-1-carboxylate as the starting material. $^1$H-NMR (CDCl$_3$, 500 MHz) δ 10.01 (bs, 1H), 7.90 (s, 1H), 7.60 (d, J=1.5 Hz, 1H), 7.25 (dd, J=8.9, 5.2 Hz, 2H), 7.04 (dd, J=8.6, 8.5 Hz, 2H), 6.99 (d, J=1.5 Hz, 1H), 4.46 (t, J=5.1 Hz, 1H), 3.60-3.85 (m, 2H), 3.56 (m, 2H), 3.44 (d, J=8.9 Hz, 1H), 3.32 (d, J=8.9 Hz, 1H), 3.27 (s, 3H), 3.05 (m, 1H), 2.98 (m, 1H), 2.23 (m, 1H), 2.05 (m, 1H), 1.86 (m, 1H), 1.76 (m, 1H), 1.43 (s, 9H); $^{13}$C NMR (126 MHz, CDCl$_3$) δ ppm 161.6 (d, J=247 Hz), 155.0, 138.12, 138.09, 136.6, 133.7, 128.7 (d, J=7.7 Hz), 126.1, 125.3, 124.7, 123.6, 119.6, 115.6 (d, J=20), 81.6, 79.6, 79.4, 76.0, 59.5, 41.4, 40.0 (br), 32.4, 32.1, 28.5.

Intermediate 221 tert-Butyl 4-((1-(5-chloro-2-((2-(trimethylsilyl)ethoxy)methyl)-2H-indazol-7-yl)-2-(dimethylamino)-2-oxoethoxy)methyl)-4-(4-fluorophenyl)piperidine-1-carboxylate. To a solution of 2-((1-(tert-butoxycarbonyl)-4-(4-fluorophenyl)piperidin-4-yl)methoxy)-2-(5-chloro-2-((2-(trimethylsilyl)ethoxy)methyl)-2H-indazol-7-yl)acetic acid (25 mg, 0.039 mmol) and dimethylamine (40% in water, 0.024 mL) in dimethylformamide (1 mL) at 0° C. was added PyBOP® (24.08 mg, 0.046 mmol). The ice bath was removed and stirring continued for 1 h. The reaction was quenched by addition of water and diluted with diethyl ether. The ethereal was washed with water (2×), then brine, dried over magnesium sulfate, and concentrated. Column chromatography (50%→85% ethyl acetate/n-hexane) gave 21 mg (81%) as a foam solid. $^1$H-NMR (CDCl$_3$, 500 MHz) δ 8.01 (s, 1H), 7.57 (d, J=1.8 Hz, 1H), 7.31 (dd, J=8.5, 5.5 Hz, 2H), 7.09 (d, J=1.8 Hz, 1H), 6.99 (dd, J=8.6, 8.5 Hz, 2H), 5.66 (d, J=10.7 Hz, 1H), 5.62 (d, J=10.7 Hz, 1H), 3.70 (m, 2H), 3.57 (m, 3H), 3.44 (d, J=8.9 Hz, 1H), 3.05 (m, 2H), 2.88 (s, 3H), 2.80 (s, 3H), 2.13 (m, 2H), 1.91 (m, 2H), 1.42 (s, 9H), 0.91 (t, J=8.3 Hz, 2H), −0.04 (s, 9H); $^{13}$C NMR (126 MHz, CDCl$_3$) δ ppm 169.0, 161.5 (d, J=245 Hz), 155.0, 145.8, 138.7, 129.0 (d, J=7.7 Hz), 128.3, 125.9, 122.7, 122.5, 119.2, 115.2 (d, J=21 Hz), 82.1, 79.4, 78.4, 75.7, 67.7, 41.4, 40.1 (br), 36.8, 36.1, 32.1, 28.6, 17.9, −1.3. Mass spec.: 675.38 (MH)$^+$.

Intermediate 222

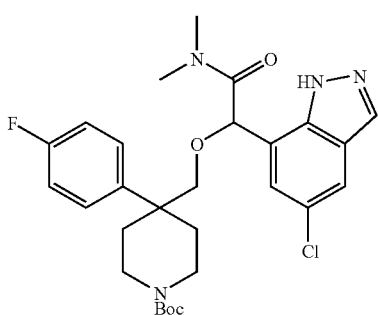

tert-Butyl 4-((1-(5-chloro-1H-indazol-7-yl)-2-(dimethylamino)-2-oxoethoxy)methyl)-4-(4-fluorophenyl)piperidine-1-carboxylate. Prepared according to the procedure used to prepare tert-butyl 4-((1-(5-chloro-1H-indazol-7-yl)-2-methoxy-2-oxoethoxy)methyl)-4-(4-fluorophenyl)piperidine-1-carboxylate using tert-butyl 4-((1-(5-chloro-2-((2-(trimethylsilyl)ethoxy)methyl)-2H-indazol-7-yl)-2-(dimethylamino)-2-oxoethoxy)methyl)-4-(4-fluorophenyl)piperidine-1-carboxylate as the starting material. $^1$H-NMR (CDCl$_3$, 500 MHz) δ 10.84 (bs, 1H), 7.94 (s, 1H), 7.65 (d, J=1.8 Hz, 1H), 7.31 (m, 2H), 7.00-7.10 (m, 3H), 5.12 (s, 1H), 3.72 (m, 2H), 3.59 (d, J=8.9 Hz, 1H), 3.38 (d, J=8.9 Hz, 1H), 3.02 (m, 2H), 2.87 (s, 3H), 2.77 (s, 3H), 2.17 (m, 2H), 1.85 (m, 2H), 1.42 (s, 9H); $^{13}$C NMR (126 MHz, CDCl$_3$) δ ppm 168.9, 161.6 (d, J=247 Hz), 155.0, 138.1, 136.3, 133.7, 128.8 (d, J=7.7 Hz), 125.9, 124.9, 124.5, 120.3, 119.8, 115.6 (d, J=21 Hz), 80.6, 79.6, 79.1, 41.3, 40.0 (br), 36.6, 36.5, 32.4, 32.2, 28.5.

Intermediate 223

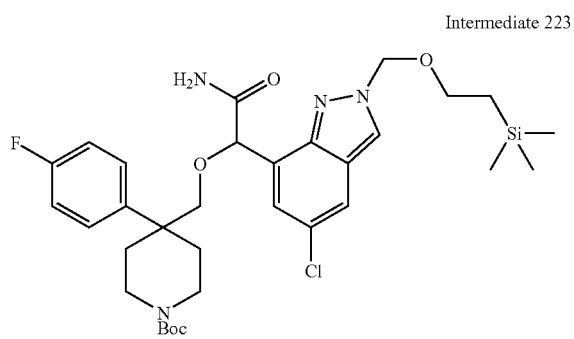

tert-Butyl 4-((2-amino-1-(5-chloro-2-((2-(trimethylsilyl)ethoxy)methyl)-2H-indazol-7-yl)-2-oxoethoxy)methyl)-4-(4-fluorophenyl)piperidine-1-carboxylate. To a solution of 2-((1-(tert-butoxycarbonyl)-4-(4-fluorophenyl)piperidin-4-yl)methoxy)-2-(5-chloro-2-((2-(trimethylsilyl)ethoxy)methyl)-2H-indazol-7-yl)acetic acid (100 mg, 0.154 mmol) and ammonia (7 M in methanol, 0.110 mL, 0.771 mmol) in dimethylformamide (2 mL) at 0° C. was added PyBOP (96 mg, 0.19 mmol). The ice bath was removed and stirring continued for 1 h. The reaction was quenched by addition of water and diluted with diethyl ether. The ethereal was washed with water (2×), then brine, dried over magnesium sulfate, and concentrated. Column chromatography (50%→85% ethyl acetate/n-hexane) gave 89 mg (89%) as a foam solid. $^1$H-NMR (CDCl$_3$, 500 MHz) δ 8.02 (s, 1H), 7.57 (d, J=1.8 Hz, 1H), 7.27 (dd, J=8.9, 5.2 Hz, 2H), 7.00 (dd, J=8.6, 8.5 Hz, 2H), 6.95 (d, J=1.5 Hz, 1H), 6.48 (d, J=2.7 Hz, 1H), 6.05 (d, J=2.4 Hz, 1H), 5.65 (s, 2H), 5.23 (s, 1H), 3.66 (m, 2H), 3.60 (t, J=8.1 Hz, 2H), 3.51 (d, J=8.9 Hz, 1H), 3.41 (d, J=8.9 Hz, 1H), 3.01 (m, 2H), 2.10 (m, 2H), 1.80 (m, 2H), 1.40 (s, 9H), 0.91 (m, 2H), −0.05 (s, 9H); $^{13}$C NMR (126 MHz, CDCl$_3$) δ ppm 172.5, 161.5 (d, J=246 Hz), 155.0, 146.1, 138.42, 138.39, 128.7 (d, J=7.7 Hz), 128.5, 127.8, 125.5, 122.9, 122.6, 119.7, 115.4 (d, J=21 Hz), 82.1, 79.5, 78.3, 67.8, 41.2, 40.0 (br), 32.2, 32.1, 28.5, 17.9, −1.3. Mass spec.: 647.35 (MH)$^+$.

Intermediate 224

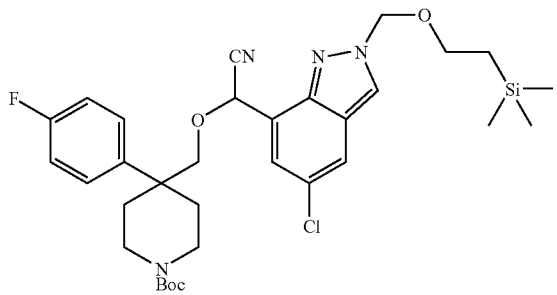

tert-Butyl 4-(((5-chloro-2-((2-(trimethylsilyl)ethoxy)methyl)-2H-indazol-7-yl)(cyano)methoxy)methyl)-4-(4-fluorophenyl)piperidine-1-carboxylate. To a solution of tert-butyl 4-((2-amino-1-(5-chloro-2-((2-(trimethylsilyl)ethoxy)methyl)-2H-indazol-7-yl)-2-oxoethoxy)methyl)-4-(4-fluorophenyl)piperidine-1-carboxylate (64 mg, 0.099 mmol) in dimethylformamide (0.7 mL) at 0° C. was added cyanuric chloride (18.2 mg, 0.10 mmol). The ice bath was removed and stirring continued for 5 h. The reaction was diluted with diethyl ether and quenched by addition of water. After stirring for 10 min, the ethereal was washed with water (2×), then brine, dried over magnesium sulfate, and concentrated. Column chromatography (18%→25% ethyl acetate/n-hexane) gave 31 mg (50%) as a colorless oil. $^1$H-NMR (CDCl$_3$, 500 MHz) δ0 8.08 (s, 1H), 7.68 (d, J=1.2 Hz, 1H), 7.29 (dd, J=8.6, 5.2 Hz, 2H), 7.24 (s, 1H), 7.00 (dd, J=8.9, 8.5 Hz, 2H), 5.71 (s, 1H), 5.69 (d, J=10.7 Hz, 1H), 5.64 (d, J=10.7 Hz, 1H), 3.76 (m, 3H), 3.61 (t, J=8.2 Hz, 2H), 3.58 (d, J=8.9 Hz, 1H), 3.03 (m, 2H), 2.14 (m, 2H), 1.90 (m, 2H), 1.43 (s, 9H), 0.92 (m, 2H), −0.03 (s, 9H); $^{13}$C NMR (126 MHz, CDCl$_3$) δ ppm 161.5 (d, J=246 Hz), 155.0, 144.3, 137.6, 128.9 (d, J=8.6 Hz), 127.6, 125.9, 124.4, 122.92, 122.87, 121.0, 116.6, 115.4(d, J=21 Hz), 82.1, 79.6, 78.6, 68.0, 66.5, 41.2, 40.0 (br), 32.0, 28.5, 17.9, −1.3. Mass spec.: 629.35 (MH)$^+$ Intermediate 225

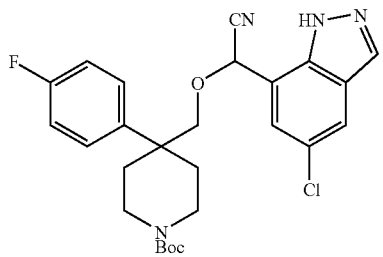

tert-Butyl 4-(((5-chloro-1H-indazol-7-yl)(cyano)methoxy)methyl)-4-(4-fluorophenyl)piperidine-1-carboxylate. Prepared according to the procedure used to prepare tert-butyl 4-((1-(5-chloro-1H-indazol-7-yl)-2-methoxy-2-oxoethoxy)methyl)-4-(4-fluorophenyl)piperidine-1-carboxylate using tert-butyl 4-(((5-chloro-2-((2-(trimethylsilyl)ethoxy)methyl)-2H-indazol-7-yl)(cyano)methoxy)methyl)-4-(4-fluorophenyl)piperidine-1-carboxylate as the starting material. ¹H-NMR (CDCl₃, 500 MHz) δ 9.66 (bs, 1H), 7.98 (s, 1H), 7.74 (d, J=1.5 Hz, 1H), 7.31 (m, 3H), 7.13 (dd, J=8.6, 8.6 Hz, 2H), 5.46 (s, 1H), 3.60-3.90 (m, 4H), 3.07 (m, 2H), 2.18 (m, 2H), 1.82 (m, 2H), 1.43 (s, 9H); ¹³C NMR (126 MHz, CDCl₃) δ ppm 171.2, 161.9 (d, J=248 Hz), 154.9, 137.4, 135.6, 134.4, 128.6 (d, J=7.7 Hz), 126.3, 125.5, 125.4, 122.0, 116.2 (d, J=21 Hz), 79.9, 78.9, 69.5, 41.1, 39.9 (br), 32.5, 32.3, 28.5.

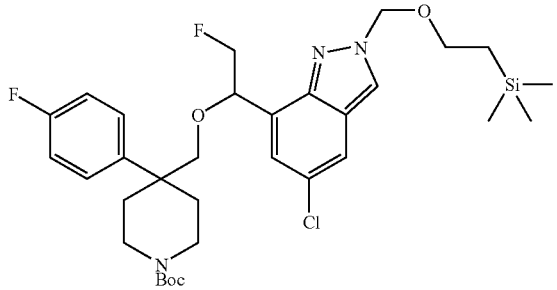

Intermediate 226 tert-Butyl 4-((1-(5-chloro-2-((2-(trimethylsilyl)ethoxy)methyl)-2H-indazol-7-yl)-2-fluoroethoxy)methyl)-4-(4-fluorophenyl)piperidine-1-carboxylate. To a solution of tert-butyl 4-((1-(5-chloro-2-((2-(trimethylsilyl)ethoxy)methyl)-2H-indazol-7-yl)-2-hydroxyethoxy)methyl)-4-(4-fluorophenyl)piperidine-1-carboxylate (50 mg, 0.079 mmol) in acetonitrile (0.1 mL) at room temperature was added diisopropylethylamine (0.062 mL, 0.355 mmol), diisopropylethylamine trihydrofluoride (22.4 mg, 0.118 mmol), and perfluoro-1-butanesulfonyl fluoride (0.028 mL, 0.16 mmol). The reaction was stirred at room temperature overnight. The reaction was poured into saturated sodium bicarbonate, and diluted with diethyl ether. The ethereal was washed with water, then brine, dried over magnesium sulfate, and concentrated. Column chromatography (15%→20% ethyl acetate/n-hexane) gave 40 mg (80%) as a colorless film. ¹H-NMR (CDCl₃, 500 MHz) δ 8.01 (s, 1H), 7.54 (d, J=1.8 Hz, 1H), 7.33 (dd, J=9.2, 5.5 Hz, 2H), 7.03 (dd, J=8.9, 8.5 Hz, 2H), 6.73 (bs, 1H), 5.66 (d, J=10.7 Hz, 1H), 5.63 (d, J=10.7 Hz, 1H), 5.16 (m, 1H), 4.62 (ddd, J=46.7, 9.5, 2.4 Hz, 1H), 4.42 (ddd, J=48.2, 9.8, 7.3 Hz, 1H), 3.75 (bs, 2H), 3.60 (m, 2H), 3.52 (d, J=9.2 Hz, 1H), 3.45 (d, J=9.2 Hz, 1H), 3.10 (bs, 1H), 3.03 (m, 1H), 2.27 (m, 1H), 2.07 (m, 1H), 1.99 (m, 1H), 1.87 (m, 1H), 1.44 (s, 9H), 0.92 (m, 2H), −0.05 (s, 9H); ¹³C NMR (126 MHz, CDCl₃) δ ppm 161.5 (d, J=246 Hz), 155.1, 145.4, 138.5, 128.9 (d, J=7.7 Hz), 128.2, 128.11, 128.07, 124.9, 122.7, 122.6, 118.9, 115.3 (d, J=21 Hz), 85.9, 84.4, 81.9, 79.5, 78.8, 77.3, 77.1, 67.8, 41.5, 40.5, 39.7, 32.2, 31.8, 28.6, 17.9, −1.4. Mass spec.: 636.43 (MH)⁺.

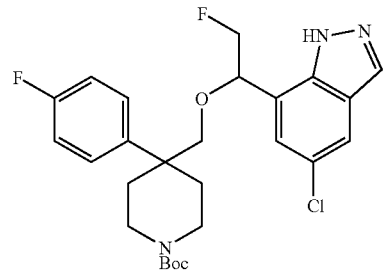

Intermediate 227 tert-Butyl 4-((1-(5-chloro-1H-indazol-7-yl)-2-fluoroethoxy)methyl)-4-(4-fluorophenyl)piperidine-1-carboxylate. tert-Butyl 4-((1-(5-chloro-2-((2-(trimethylsilyl)ethoxy)methyl)-2H-indazol-7-yl)-2-fluoroethoxy)methyl)-4-(4-fluorophenyl)piperidine-1-carboxylate (40 mg, 0.063 mmol) was dissolved in tetrabutylammonium fluoride (1M in tetrahydrofuran, 0.8 mL, 0.8 mmol). The flask was sealed and placed in a 55° C. bath. After 1.5 h, the reaction was cooled to room temperature, diluted with diethyl ether, washed with water, then brine, dried over magnesium sulfate, and concentrated. Column chromatography (50%→60% ethyl acetate/n-hexane) gave 29 mg (91%) as a colorless oil. ¹H-NMR (CDCl₃, 500 MHz) δ 9.82 (bs, 1H), 7.91 (s, 1H), 7.63 (d, J=1.8 Hz, 1H), 7.27 (dd, J=89., 5.5 Hz, 2H), 7.07 (dd, J=8.9, 8.5 Hz, 2H), 7.03 (d, J=1.5 Hz, 1H), 4.61 (ddd, J=18.0, 5.2, 4.6 Hz, 1H), 4.53 (d, J=4.6 Hz, 1H), 4.44 (d, J=4.9 Hz, 1H), 3.74 (m, 2H), 3.49 (d, J=9.2 Hz, 1H), 3.39 (d, J=9.2 Hz, 1H), 3.06 (m, 1H), 2.97 (m, 1H), 2.30 (m, 1H), 2.06 (m, 1H), 1.87 (m, 1H), 1.75 (m, 1H), 1.43 (s, 9H); ¹³C NMR (126 MHz, CDCl₃) δ ppm 161.7 (d, J=247 Hz), 155.0, 137.7, 136.4, 133.8, 128.8 (d, J=7.7 Hz), 126.2, 125.6, 124.9, 121.0, 120.9, 120.2, 115.8 (d, J=21 Hz), 85.8, 84.4, 81.3, 81.1, 79.8, 79.7, 41.4, 40.3, 39.6, 32.4, 32.1, 28.5. Mass spec.: 506.23 (MH)⁺.

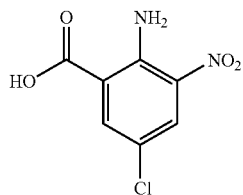

Intermediate 228

2-Amino-5-chloro-3-nitrobenzoic acid. To a solution of 2-amino-3-nitrobenzoic acid (1 g, 5.5 mmol) in acetic acid (5 mL) at room temperature was added N-chlorosuccinimide (0.953 g, 7.14 mmol). The reaction was sealed and heated via microwave for 2 h at 80° C. The resulting mixture was poured into water (ca. 20 mL), cooled to 0° C., and the product collected by filtration. ¹H-NMR (2:1 CDCl₃/CD₃OD, 500 MHz) δ 8.24 (d, J=2.7 Hz, 1H), 8.14 (d, J=2.8 Hz, 1H); ¹³C NMR (126 MHz, 2:1 CDCl₃/CD₃OD) δ ppm 167.8, 145.7, 139.6, 132.8, 130.9, 118.5, 116.1. Mass spec.: 215.18 (M−H)⁻.

Intermediate 229

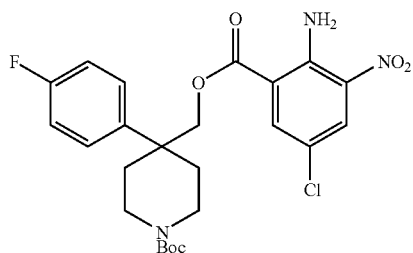

tert-Butyl 4-((2-amino-5-chloro-3-nitrobenzoyloxy)methyl)-4-(4-fluorophenyl)piperidine-1-carboxylate. To a suspension of 2-amino-5-chloro-3-nitrobenzoic acid (500 mg, 2.3 mmol), tert-butyl 4-(4-fluorophenyl)-4-(hydroxymethyl)piperidine-1-carboxylate (714 mg, 2.3 mmol), and dimethylaminopyridine (282 mg, 2.3 mmol) in dichloromethane (6.6 mL) was added 1-ethyl-3-[3-dimethylaminopropyl]carbodiimide hydrochloride (664 mg, 3.46 mmol) in one portion. The suspension was stirred overnight. The reaction was poured into water and diluted with diethyl ether. The ethereal was washed with water, then saturated sodium bicarbonate, then water. The ethereal was washed with brine, dried over magnesium sulfate, and concentrated. Column chromatography (15%→30% ethyl acetate/n-hexane) gave 0.88 g (75%) as a yellow foam solid. $^1$H-NMR (CDCl$_3$, 500 MHz) δ 8.31 (d, J=2.4 Hz, 1H), 8.27 (bs, 2H), 7.87 (d, J=2.8 Hz, 1H), 7.36 (dd, J=8.9, 5.2 Hz, 2H), 7.09 (dd, J=8.9, 8.6 Hz, 2H), 4.25 (s, 2H), 3.81 (m, 2H), 3.06 (m, 2H), 2.25 (m, 2H), 1.86 (m, 2H), 1.43 (s, 9H); $^{13}$C NMR (126 MHz, CDCl$_3$) δ ppm 165.5, 161.8 (d, J=248 Hz), 154.9, 145.8, 138.6, 136.8, 133.5, 131.6, 128.8 (d, J=7.7 Hz), 118.9, 115.8 (d, J=21 Hz), 115.4, 79.8, 73.2, 40.8, 39.9, 32.2, 28.5.

Intermediate 230

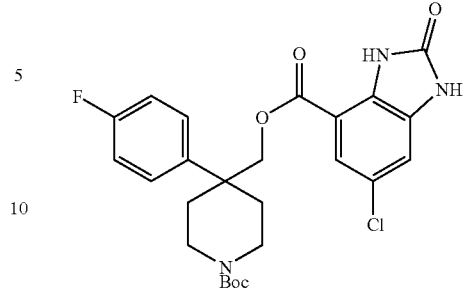

tert-Butyl 4-((2,3-diamino-5-chlorobenzoyloxy)methyl)-4-(4-fluorophenyl)piperidine-1-carboxylate. To a solution of tert-butyl 4-((2-amino-5-chloro-3-nitrobenzoyloxy)methyl)-4-(4-fluorophenyl)piperidine-1-carboxylate (700 mg, 1.4 mmol) in ethyl acetate (20 mL) under nitrogen was added palladium (10% on carbon, 140 mg). The flask was flushed with hydrogen and shaken under 60 psi of hydrogen overnight. The reaction was filtered through celite and concentrated to give 715 mg (quant.) as a foam semi-solid which was used without purification. $t_R$=3.19 (Sunfire C18 4.6×50 mm, A=90% H$_2$O/10% ACN, B=90% ACN/10% H$_2$O, Modifier 0.1% TFA, 0.00 min=0% B, 4.0 min=100% B, 5.0 min=100% B, Flow rate=4 mL/min. Mass spec.: 377.88 (MH-Boc)$^+$.

Intermediate 231

(1-(tert-Butoxycarbonyl)-4-(4-fluorophenyl)piperidin-4-yl)methyl 6-chloro-2-oxo-2,3-dihydro-1H-benzo[d]imidazole-4-carboxylate. To a solution of tert-butyl 4-((2,3-diamino-5-chlorobenzoyloxy)methyl)-4-(4-fluorophenyl)piperidine-1-carboxylate (714 mg, 1.5 mmol) in tetrahydrofuran (10 mL) at 0° C. was added carbonyldiimidazole (242 mg, 1.5 mmol). The ice bath was removed and stirring continued for 1 h. The reaction was treated with a second portion of carbonyldiimidazole (242 mg, 1.5 mmol) and stirred for 1 h at room temperature. The solution was transferred to a microwave vial and heated at 70° C. for 1 h via microwave. The reaction was poured into diethyl ether, washed with water, then brine, dried over magnesium sulfate, and concentrated. Column chromatography (25%→100 ethyl acetate/n-hexane) gave 0.52 g (69%) as a brown solid. $^1$H-NMR (CDCl$_3$, 500 MHz) δ 9.69 (bs, 1H), 9.05 (bs, 1H), 7.42 (d, J=1.8 Hz, 1H), 7.38 (dd, J=8.6, 5.2 Hz, 2H), 7.19 (d, J=1.5 Hz, 1H), 7.11 (dd, J=8.6, 8.5 Hz, 2H), 4.32 (s, 2H), 3.81 (m, 2H), 3.09 (m, 2H), 2.24 (m, 2H), 1.89 (m, 2H), 1.44 (s, 9H); $^{13}$C NMR (126 MHz, CDCl$_3$) δ ppm 164.6, 162.6, 160.6, 157.4, 155.1, 136.5, 131.1, 128.8 (d, J=7.7 Hz), 126.0, 121.1, 115.7 (d, J=21 Hz), 114.7, 111.8, 79.8, 73.1, 40.6, 39.9, 31.8, 28.6. Mass spec.: 525.87 (MNa)$^+$.

Intermediate 232

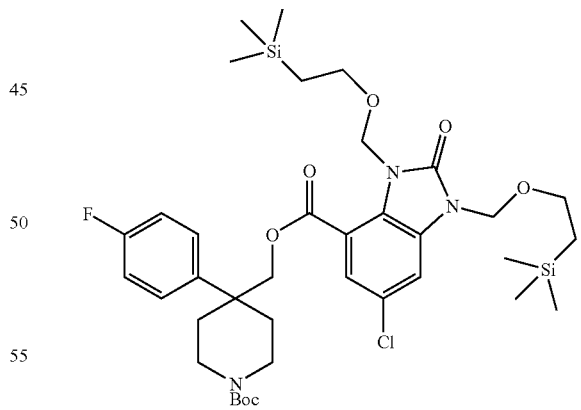

(1-(tert-Butoxycarbonyl)-4-(4-fluorophenyl)piperidin-4-yl)methyl 6-chloro-2-oxo-1,3-bis((2-(trimethylsilyl)ethoxy)methyl)-2,3-dihydro-1H-benzo[d]imidazole-4-carboxylate. To a solution of (1-(tert-butoxycarbonyl)-4-(4-fluorophenyl)piperidin-4-yl)methyl 6-chloro-2-oxo-2,3-dihydro-1H-benzo[d]imidazole-4-carboxylate (0.5 g, 0.99 mmol) and N-cyclohexyl-N-methylcyclohexanamine (0.70 mL, 3.3 mmol) in tetrahydrofuran (6.5 mL) at 0° C. was added (2-(chloromethoxy)ethyl)trimethylsilane (0.56 mL, 3.2 mmol).

After 5 min, the ice bath was removed and stirring continued at room temperature for 24 h. The reaction was allowed to stir overnight. The reaction was diluted with diethyl ether, washed with water, then 1M potassium bisulfate, then water, then brine, dried over magnesium sulfate, and concentrated. Column chromatography (12%→25% ethyl acetate/n-hexane) gave 580 mg (76%) as an amorphous white foam solid. $^1$H-NMR (CDCl$_3$, 500 MHz) δ 7.37 (dd, J=8.9, 5.2 Hz, 2H), 7.27 (d, J=2.1 Hz, 1H), 7.08 (m, 3H), 5.43 (s, 2H), 5.27 (s, 2H), 4.26 (s, 2H), 3.78 (m, 2H), 3.55 (t, J=8.1 Hz, 2H), 3.27 (t, J=8.1 Hz, 2H), 3.08 (m, 2H), 2.23 (m, 2H), 1.88 (m, 2H), 1.42 (s, 9H), 0.89 (t, J=8.2 Hz, 2H), 0.71 (t, J=8.1 Hz, 2H), −0.05 (s, 9H), −0.12 (s, 9H); $^{13}$C NMR (126 MHz, CDCl$_3$) δ ppm 164.6, 161.7 (d, J=247 Hz), 154.9, 154.7, 137.1 (d, J=3.8 Hz), 131.3, 128.9 (d, J=7.7 Hz), 127.1, 125.4, 122.8, 116.9, 115.7 (d, J=20 Hz), 112.3, 79.7, 73.3, 71.9, 70.9, 66.5, 65.6, 40.6, 39.9, 32.2, 28.5, 17.8, 17.7, −1.3, "1.4. Mass spec.: 786.00 (MNa)$^+$.

Intermediate 233

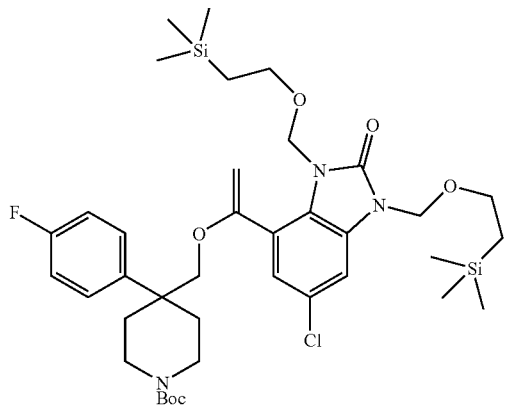

tert-Butyl 4-((1-(6-chloro-2-oxo-1,3-bis((2-(trimethylsilyl)ethoxy)methyl)-2,3-dihydro-1H-benzo[d]imidazol-4-yl)vinyloxy)methyl)-4-(4-fluorophenyl)piperidine-1-carboxylate. General Note: The reaction was run in such a way as to minimize exposure to light. Reactions were run under a layer of foil to block light and the lab lights were turned off while manipulating the reaction mixtures. To a suspension of titanocenedichloride (0.560 g, 2.198 mmol) in toluene (18 mL) at 0° C. was added methyllithium (1.6 M in diethyl ether, 3.4 mL, 5.5 mmol) dropwise. The reaction was stirred at 0° C. for 1 h. The reaction was quenched by addition of 9 mL of a 6% ammonium chloride solution. The heterogeneous mixture was filtered through a course frit and added to the sep funnel. The layers were separated and the organic layer dried over magnesium sulfate. The solution was filtered and treated with (1-(tert-butoxycarbonyl)-4-(4-fluorophenyl)piperidin-4-yl)methyl 6-chloro-2-oxo-1,3-bis((2-(trimethylsilyl)ethoxy)methyl)-2,3-dihydro-1H-benzo[d]imidazole-4-carboxylate (0.560 g, 0.733 mmol) and N-cyclohexyl-N-methylcyclohexanamine (0.078 mL, 0.366 mmol) and the mixture concentrated to ca. ⅓ its volume. The bath temperature was maintained at 30° C. while the reaction mixture was being concentrated. The reaction flask was flushed with a stream of nitrogen and fitted with a reflux condenser and the resulting solution was placed in an oil bath preheated to 80° C. The bath temperature was set to 80° C. and stirred at that temperature for 2 h. The reaction was diluted with ~20 mL of hexanes to precipitate some of the titanocenes with stirring. To decompose the remaining titanocene, silica gel (excess) was added as a solid with vigorous stirring to the suspension at 0° C. The ice bath was removed and stirring continued for 15 min. The resulting suspension was filtered and the resulting pad washed with 25% ethyl acetate/n-hexane. The mother liquor was concentrated and loaded onto a silica gel column (10% ethyl acetate/n-hexane). After several volumes at 10%, the gradient was ramped to 25% ethyl acetate/n-hexane to give 470 mg (84%) as a very faint yellow solid. $^1$H-NMR (CD$_3$OD, 500 MHz) δ 7.36 (dd, J=8.9, 5.2 Hz, 2H), 7.19 (d, J=2.1 Hz, 1H), 7.02 (m, 2H), 6.84 (d, J=2.1 Hz, 1H), 5.24 (s, 2H), 4.59 (s, 2H), 4.43 (d, J=2.7 Hz, 1H), 4.22 (d, J=2.5 Hz, 1H), 3.78 (s, 2H), 3.69 (m, 2H), 3.54 (t, J=7.8 Hz, 2H), 3.26 (m, 2H), 2.94 (bs, 2H), 2.19 (m, 2H), 1.78 (m, 2H), 1.36 (s, 9H), 0.85 (t, J=7.9 Hz, 2H), 0.66 (t, J=7.9 Hz, 2H), −0.10 (s, 9H), −0.16 (s, 9H); $^{13}$C NMR (126 MHz, CD$_3$OD) δ ppm 163.0 (d, J=245 Hz), 158.7, 156.5 (d, J=14 Hz), 139.4 (d, J=3.8 Hz), 131.8, 130.6 (d, J=7.7 Hz), 128.3, 125.6, 125.1, 124.1, 116.3 (d, J=21 Hz), 110.7, 89.2, 81.1, 77.8, 71.6, 67.4, 66.9, 41.8, 33.2, 28.7, 18.63, 18.58, −1.29, −1.32. Mass spec.: 784.01 (MNa)$^+$.

Intermediate 234

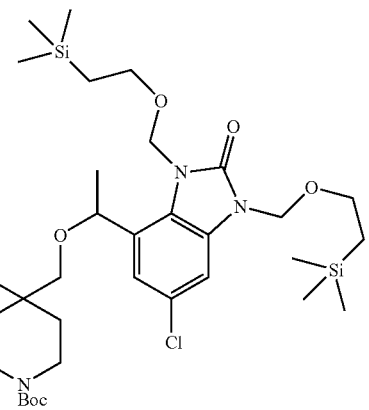

tert-Butyl 4-((1-(6-chloro-2-oxo-1,3-bis((2-(trimethylsilyl)ethoxy)methyl)-2,3-dihydro-1H-benzo[d]imidazol-4-yl)ethoxy)methyl)-4-(4-fluorophenyl)piperidine-1-carboxylate. A solution of tert-butyl 4-((1-(6-chloro-2-oxo-1,3-bis((2-(trimethylsilyl)ethoxy)methyl)-2,3-dihydro-1H-benzo[d]imidazol-4-yl)vinyloxy)methyl)-4-(4-fluorophenyl)piperidine-1-carboxylate (470 mg, 0.616 mmol) in 1,2-dichloroethane (20 mL) was degassed by passing a stream of nitrogen through the solution for 1 h. The reaction was quickly treated with (−)-1,2-Bis((2R,5R)-2,5-diethylphospholano)benzene(cyclooctadiene)rhodium(1)tetrafluoroborate (50 mg, 0.076 mmol) and flushed with nitrogen for 10 minutes longer. The vessel was pressurized to 60 psi of hydrogen and shaken for 24 h. The mixture was concentrated and the crude mixture purified by column chromatography (8%→25% ethyl acetate/n-hexane) to give 420 mg (89%) as a foam semi-solid. $^1$H-NMR (CDCl$_3$, 500 MHz) δ 7.21 (dd, 8.9, 5.2 Hz, 2H), 7.02 (d, J=1.8 Hz, 1H), 6.98 (dd, J=8.9, 8.6 Hz, 2H), 6.78 (d, J=2.1 Hz, 1H), 5.35 (d, J=11.6 Hz, 1H), 5.23 (m, 2H), 5.03 (d, J=11.6 Hz, 1H), 4.94 (q, J=6.4 Hz, 1H), 3.69 (m, 2H), 3.57 (t, J=8.1 Hz, 2H), 3.51 (m, 2H), 3.18 (m, 2H), 3.01 (m, 2H), 2.07 (m, 2H), 1.84 (m, 2H), 1.42 (s, 9H), 1.34 (d, J=6.7 Hz, 3H), 0.70-0.97 (m, 4H), −0.05 (s, 9H), −0.06 (s, 9H); $^{13}$C NMR (126 MHz, CDCl$_3$) δ ppm 161.4 (d, J=246 Hz), 155.0, 154.8, 138.6, 130.3, 128.7 (d, J=7.7 Hz), 128.5, 128.3, 124.5, 120.0, 115.1 (d, J=21 Hz), 108.3, 79.4, 76.8, 71.5, 71.4, 70.9, 66.5, 66.0, 41.1, 40.2, 40.1, 32.2, 32.0, 28.6, 23.3, 18.0, 17.9, −1.4. Mass spec.: 786.01 (MNa)+.

55.9, 48.3, 42.5, 41.3, 33.5, 33.4, 23.2, 23.0, 18.0, 17.9, 15.3, −1.4. Mass spec.: 678.10 (MH)+.

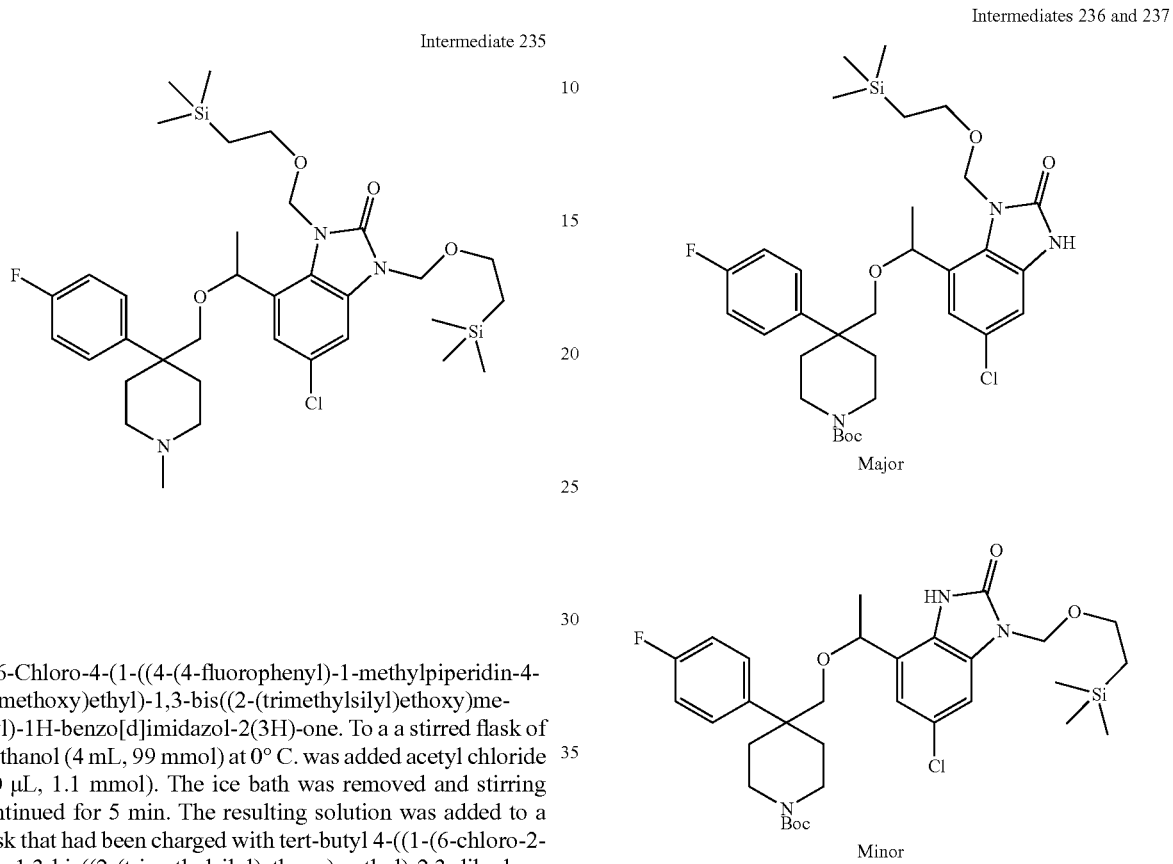

6-Chloro-4-(1-((4-(4-fluorophenyl)-1-methylpiperidin-4-yl)methoxy)ethyl)-1,3-bis((2-(trimethylsilyl)ethoxy)methyl)-1H-benzo[d]imidazol-2(3H)-one. To a a stirred flask of methanol (4 mL, 99 mmol) at 0° C. was added acetyl chloride (80 µL, 1.1 mmol). The ice bath was removed and stirring continued for 5 min. The resulting solution was added to a flask that had been charged with tert-butyl 4-((1-(6-chloro-2-oxo-1,3-bis((2-(trimethylsilyl)ethoxy)methyl)-2,3-dihydro-1H-benzo[d]imidazol-4-yl)ethoxy)methyl)-4-(4-fluorophenyl)piperidine-1-carboxylate (110 mg, 0.144 mmol). After 8 h, the reaction was concentrated by blowing it down under a stream of nitrogen. The crude residue was loaded onto a strong cation exchange cartridge, flushed with several volumes of methanol which were discarded. The crude product was eluted with 2 M ammonia in methanol and concentrated. The resulting residue was dissolved in a couple of drops of tetrahydrofuran, diluted with acetonitrile (2 mL), and treated with formalin (100 µL), followed quickly by the addition of sodium cyanoborohydride (18.1 mg, 0.29 mmol). The reaction was treated with two small drops of acetic acid over 10 min, and concentrated. The reaction was concentrated, extracted into ethyl acetate, washed with saturated sodium bicarbonate, washed with brine, and dried over magnesium sulfate, and concentrated. The resulting residue was dissolved in ethanol (10 mL) and heated at reflux overnight. The reaction was concentrated, and purified by column chromatography (methanol/ethyl acetate) to give 58 mg (59%). 1H-NMR (CDCl3, 500 MHz) δ 7.10-7.40 (m, 4H), 6.87-7.10 (m, 5H), 6.65-6.85 (m, 2H), 5.10-5.40 (m, 4H), 4.75-5.10 (m, 3H), 3.40-3.65 (m, 6H), 3.10-3.37 (m, 6H), 2.88 (m, 3H), 2.45-2.80 (m, 4H), 1.70-2.20 (m, 7H), 1.33 (m, 5H), 1.18 (t, J=7.0 Hz, 2H), 0.70-1.00 (m, 4H), −0.05 (s, 9H), −0.06 (s, 9H); 13C NMR (126 MHz, CDCl3) δ ppm 161.2 (d, J=245 Hz), 154.8, 139.8, 130.3, 128.7 (d, J=7.7 Hz), 128.3, 124.5, 120.2, 115.0 (d, J=21 Hz), 108.3, 73.3, 72.9, 71.4, 70.9, 66.5, 65.9, 56.6, tert-Butyl 4-((1-(6-chloro-2-oxo-1-((2-(trimethylsilyl) ethoxy)methyl)-2,3-dihydro-1H-benzo[d]imidazol-4-yl) ethoxy)methyl)-4-(4-fluorophenyl)piperidine-1-carboxylate and tert-Butyl 4-((1-(6-chloro-2-oxo-3-((2-(trimethylsilyl) ethoxy)methyl)-2,3-dihydro-1H-benzo[d]imidazol-4-yl) ethoxy)methyl)-4-(4-fluorophenyl)piperidine-1-carboxylate (2:1). tert-Butyl 4-((1-(6-chloro-2-oxo-1,3-bis((2-(trimethylsilyl)ethoxy)methyl)-2,3-dihydro-1H-benzo[d]imidazol-4-yl)ethoxy)methyl)-4-(4-fluorophenyl)piperidine-1-carboxylate (110 mg, 0.144 mmol) was dissolved in tetrabutylammonium fluoride (1M in tetrahydrofuran) (1 mL, 1 mmol) and immersed in an oil bath which was pre-heated to 60° C. After 6.5 h, the crude reaction mixture was diluted with diethyl ether and poured into water. The mixture was extracted with diethyl ether (2×), dried over magnesium sulfate, and concentrated. The resulting residue was purified by column chromatography (25%→50% ethyl acetate/n-hexane) to give 84.5 mg (93%) as a 2:1 mixture of isomers (by 1H-NMR) as a colorless film. $t_R$=4.21 min (Sunfire C18 4.6→50 mm, A=90% H2O/10% ACN, B=90% ACN/10% H2O, Modifier 0.1% TFA, 0.00 min=0% B, 4.0 min=100% B, 5.0 min=100% B, Flow rate=4 mL/min). Mass spec.: 656.09 (MNa)+.

Intermediates 238 and 239

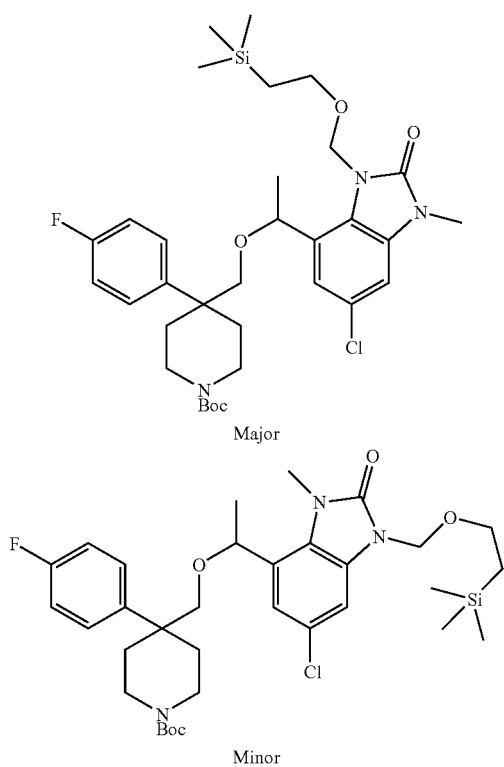

Major

Minor tert-Butyl 4-((1-(6-chloro-1-methyl-2-oxo-3-((2-(trimethylsilyl)ethoxy)methyl)-2,3-dihydro-1H-benzo[d]imidazol-4-yl)ethoxy)methyl)-4-(4-fluorophenyl)piperidine-1-carboxylate and tert-Butyl 4-((1-(6-chloro-3-methyl-2-oxo-1-((2-(trimethylsilyl)ethoxy)methyl)-2,3-dihydro-1H-benzo[d]imidazol-4-yl)ethoxy)methyl)-4-(4-fluorophenyl)piperidine-1-carboxylate (2:1). To a solution of tert-Butyl 4-((1-(6-chloro-2-oxo-1-((2-(trimethylsilyl)ethoxy)methyl)-2,3-dihydro-1H-benzo[d]imidazol-4-yl)ethoxy)methyl)-4-(4-fluorophenyl)piperidine-1-carboxylate and tert-Butyl 4-((1-(6-chloro-2-oxo-3-((2-(trimethylsilyl)ethoxy)methyl)-2,3-dihydro-1H-benzo[d]imidazol-4-yl)ethoxy)methyl)-4-(4-fluorophenyl)piperidine-1-carboxylate (2:1) (84 mg, 0.066 mmol) in dimethylformamide (1 mL) at 0° C. was added sodium hydride (9.5 mg, 0.40 mmol). To this was quickly added iodomethane (0.033 mL, 0.53 mmol). After stirring at 0° C. for 15 min, the reaction was quenched by addition of saturated ammonium chloride. The mixture was diluted with diethyl ether and water and the layers separated. The ethereal was washed with water (2×), then brine, dried over magnesium sulfate, and concentrated. Column chromatography (25%→37% ethyl acetate/n-hexane) gave separation of the two isomers. The first to elute was tert-butyl 4-((1-(6-chloro-1-methyl-2-oxo-3-((2-(trimethylsilyl) ethoxy)methyl)-2,3-dihydro-1H-benzo[d]imidazol-4-yl) ethoxy)methyl)-4-(4-fluorophenyl)piperidine-1-carboxylate (major) (53 mg, 0.082 mmol, 62%). The second to elute was tert-Butyl 4-((1-(6-chloro-3-methyl-2-oxo-1-((2-(trimethylsilyl)ethoxy)methyl)-2,3-dihydro-1H-benzo[d]imidazol-4-yl)ethoxy)methyl)-4-(4-fluorophenyl)piperidine-1-carboxylate (minor) (26 mg, 0.040 mmol, 30%). tert-Butyl 4-((1-(6-chloro-1-methyl-2-oxo-3-((2-(trimethylsilyl)ethoxy) methyl)-2,3-dihydro-1H-benzo[d]imidazol-4-yl)ethoxy) methyl)-4-(4-fluorophenyl)piperidine-1-carboxylate:

$^1$H-NMR (CDCl$_3$, 500 MHz) δ 7.21 (dd, J=8.9, 5.2 Hz, 2H), 6.97 (dd, J=8.9, 8.5 Hz, 2H), 6.81 (d, J=2.1 Hz, 1H), 6.75 (d, J=1.2 Hz, 1H), 5.36 (d, J=11.6 Hz, 1H), 5.04 (d, J=11.3 Hz, 1H), 4.95 (q, J=6.4 Hz, 1H), 3.68 (m, 2H), 3.51 (t, J=8.2 Hz, 2H), 3.35 (s, 2H), 3.20 (d, J=9.2 Hz, 1H), 3.18 (d, J=9.2 Hz, 1H), 3.01 (m, 2H), 2.07 (m, 2H), 1.83 (m, 2H), 1.42 (s, 9H), 1.34 (d, J=6.4 Hz, 3H), 0.72-0.92 (m, 2H), −0.05 (s, 9H); $^{13}$C NMR (126 MHz, CDCl$_3$) δ ppm 161.4 (d, J=245 Hz), 155.0, 154.9, 138.7, 138.6, 131.7, 128.7 (d, J=7.7 Hz), 128.3, 128.0, 124.4, 119.4, 115.1 (d, J=21 Hz), 106.9, 104.2, 79.4, 76.7, 71.5, 71.4, 65.9, 41.1, 40.1, 32.2, 32.1, 28.5, 27.4, 23.2, 18.1, −1.4. tert-Butyl 4-((1-(6-chloro-3-methyl-2-oxo-1-((2-(trimethylsilyl)ethoxy)methyl)-2,3-dihydro-1H-benzo[d]imidazol-4-yl)ethoxy)methyl)-4-(4-fluorophenyl)piperidine-1-carboxylate: $^1$H-NMR (CDCl$_3$, 500 MHz) δ 7.24 (dd, J=8.9, 5.2 Hz, 2H), 7.01 (m, 3H), 6.76 (d, J=2.1 Hz, 1H), 5.23 (s, 2H), 4.75 (q, J=6.4 Hz, 1H), 3.72 (bs, 2H), 3.58 (t, J=8.2 Hz, 2H), 3.43 (s, 3H), 3.27 (d, J=8.9 Hz, 1H), 3.17 (d, J=9.2 Hz, 1H), 3.00 (m, 2H), 2.11 (m, 2H), 1.83 (m, 2H), 1.43 (s, 9H), 1.38 (d, J=6.4 Hz, 3H), 1.25 (m, 2H), 0.91 (m, 2H), −0.04 (s, 9H); $^{13}$C NMR (126 MHz, CDCl$_3$) δ ppm 161.5 (d, J=246 Hz), 155.0, 154.7, 138.43, 138.41, 130.3, 128.7 (d, J=7.7 Hz), 127.4, 127.2, 125.7, 120.0, 115.2 (d, J=21 Hz), 108.4, 104.3, 79.5, 77.6, 73.1, 71.0, 66.5, 41.2, 40.1 (br), 32.3, 32.1, 30.6, 28.6, 23.8, 17.9, −1.4.

Intermediate 240

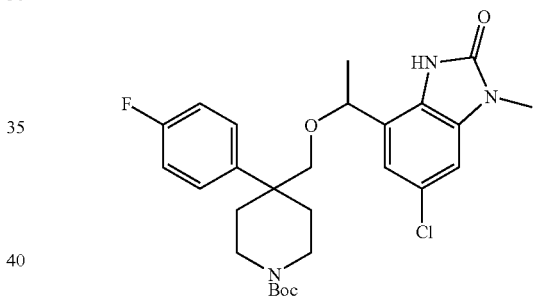

tert-Butyl 4-((1-(6-chloro-1-methyl-2-oxo-2,3-dihydro-1H-benzo[d]imidazol-4-yl)ethoxy)methyl)-4-(4-fluorophenyl)piperidine-1-carboxylate. tert-Butyl 4-((1-(6-chloro-1-methyl-2-oxo-3-((2-(trimethylsilyl)ethoxy)methyl)-2,3-dihydro-1H-benzo[d]imidazol-4-yl)ethoxy)methyl)-4-(4-fluorophenyl)piperidine-1-carboxylate (53 mg, 0.082 mmol) was dissolved in tetrabutylammonium fluoride (1M in tetrahydrofuran, 1 mL, 1 mmol) and immersed in an oil bath which was pre-heated to 60° C. After 1.5 h, the temperature was increased to 65° C. and stirred at that temperature for 5 h. The reaction was sealed and heated at 70° C. overnight. The crude reaction mixture was diluted with diethyl ether and poured into water. The ethereal was washed with water (2×), then brine, dried over magnesium sulfate and concentrated. Column chromatography (25%→75% ethyl acetate/n-hexane) gave 26 mg (61%) as a colorless film. $^1$H-NMR (CDCl$_3$, 500 MHz) δ 7.66 (bs, 1H), 7.25 (dd, J=8.6, 5.5 Hz, 2H), 7.05 (dd, J=8.9, 8.6 Hz, 2H), 6.80 (d, J=1.5 Hz, 1H), 6.66 (d, J=1.8 Hz, 1H), 4.29 (q, J=6.7 Hz, 1H), 3.73 (m, 2H), 3.32 (d, J=9.2 Hz, 1H), 3.31 (s, 3H), 3.27 (d, J=9.2 Hz, 1H), 2.87-3.12 (m, 2H), 2.20 (m, 1H), 2.06 (m, 1H), 1.81 (m, 1H), 1.74 (bs, 1H), 1.43 (s, 9H), 1.32 (d, J=6.4 Hz, 3H). Mass spec.: 540.10 (MNa)$^+$.

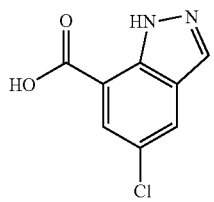

Intermediate 241

5-Chloro-1H-indazole-7-carboxylic acid. To a suspension of 7-bromo-5-chloro-1H-indazole (23.7 g, 102 mmol) in tetrahydrofuran (400 mL) at 0° C. was added sodium hydride (2.70 g, 113 mmol) in portions to control the release of hydrogen. The ice bath was removed and the reaction was stirred at room temperature for 20 min. The reaction was then cooled to −78° C. and treated with tert-butyllithium (1.7 M, 126 mL, 215 mmol) dropwise over 20 min. The reaction was allowed to gradually warm to −40° C. in the icebath over 1 h. The reaction was re-cooled to −78° C. and treated with an excess of freshly crushed pellets of dry ice. The ice bath was removed and the reaction allowed to gradually warm to room temperature. The reaction was diluted with diethyl ether, and washed with water until most of the insoluble solid was dissolved. The ethereal was washed once more with 1M sodium hydroxide, which was combined with the other aqueous layers. The ethereal was discarded. The combined aqueous washings were cooled to 0° C., and made acidic by the cautious addition of concentrated hydrochloric acid to give a precipitate. The resulting solid was collected by filtration to give the product as a light tan solid. The product was air dried overnight and then pumped under high vaccuum to remove any trace of water to give 15.9 g (79%) which was used without purification. $^{1}$H-NMR (d$_{6}$-DMSO, 500 MHz) δ 13.29 (bs, 1H), 8.18 (s, 1H), 8.14 (d, J=1.8 Hz, 1H), 7.86 (d, J=2.1 Hz, 1H); $^{13}$C NMR (126 MHz, d$_{6}$-DMSO) δ ppm 165.6, 136.5, 133.6, 128.0, 125.5, 124.8, 123.9, 115.5. Mass spec.: 196.97 (MH)$^{+}$.

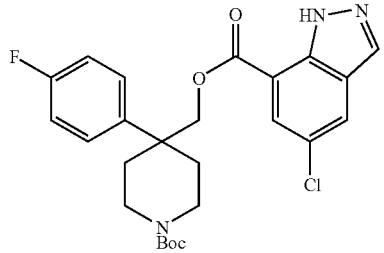

Intermediate 242

(1-(tert-Butoxycarbonyl)-4-(4-fluorophenyl)piperidin-4-yl) methyl 5-chloro-1H-indazole-7-carboxylate. To a suspension of 5-chloro-1H-indazole-7-carboxylic acid (13.8 g, 70 mmol), tert-butyl 4-(4-fluorophenyl)-4-(hydroxymethyl)piperidine-1-carboxylate (21.64 g, 69.9 mmol), and dimethylaminopyridine (8.54 g, 69.9 mmol) in dichloromethane (200 mL) was added 1-ethyl-3-[3-dimethylaminopropyl]carbodiimide hydrochloride (20.1 g, 105 mmol) in one portion. Stirring was continued at room temperature overnight. The reaction was poured into water and diluted with diethyl ether. The ethereal was washed with water, then saturated sodium bicarbonate, then water. The ethereal was washed with brine, dried over magnesium sulfate, and concentrated. Column chromatography (20%→30% ethyl acetate/n-hexane) gave the product (37 g) as a tan foam solid. The resulting product was triturated with diethyl ether (ca. 200 mL) and filtered to give 21.3 g. Concentration of the mother liquor and trituration in a minimum of diethyl ether gave a second crop of product which was filtered to give 5.4 g. $^{1}$H-NMR (CDCl$_{3}$, 500 MHz) δ 11.32 (bs, 1H), 8.03 (s, 1H), 7.89 (d, J=1.5 Hz, 1H), 7.80 (d, J=1.5 Hz, 1H), 7.41 (dd, J=8.9, 5.2 Hz, 2H), 7.09 (dd, J=8.6, 8.5 Hz, 2H), 4.42 (s, 2H), 3.79 (bs, 2H), 3.11 (m, 2H), 2.26 (m, 2H), 1.92 (m, 2H), 1.43 (s, 9H); $^{13}$C NMR (126 MHz, CDCl$_{3}$) δ ppm 164.9, 161.8 (d, J=247 Hz), 155.0, 137.3, 134.4, 129.1, 128.8 (d, J=7.7 Hz), 126.04, 125.97, 125.5, 115.9 (d, J=21 Hz), 113.3, 79.8, 73.0, 39.8, 32.3, 28.5. Mass spec.: 488.21 (MH)$^{+}$.

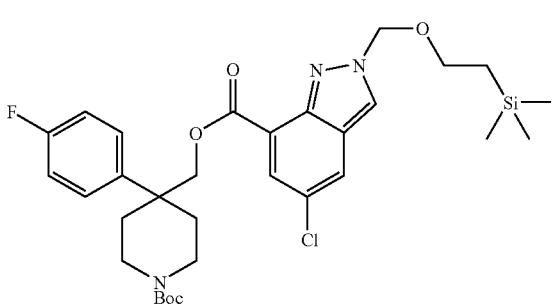

Intermediate 243

(1-(tert-Butoxycarbonyl)-4-(4-fluorophenyl)piperidin-4-yl)methyl 5-chloro-2-((2-(trimethylsilyl)ethoxy)methyl)-2H-indazole-7-carboxylate. To a solution of (1-(tert-butoxycarbonyl)-4-(4-fluorophenyl)piperidin-4-yl)methyl 5-chloro-1H-indazole-7-carboxylate (15 g, 30.7 mmol) and N-cyclohexyl-N-methylcyclohexanamine (10.86 mL, 50.7 mmol) in tetrahydrofuran (100 mL) at 0° C. was added (2-(chloromethoxy)ethyl)trimethylsilane (8.7 mL, 49 mmol). After 5 min, the ice bath was removed and stirring continued at room temperature for 24 h. The reaction was treated with 25 mL of 2M ammonia in methanol and allowed to stir at room temperature for 20 min. The reaction was diluted with diethyl ether, washed with water, then 1M potassium bisulfate, then water, then brine, dried over magnesium sulfate, and concentrated. TLC shows a slightly less polar impurity. The product was purified by column chromatography. The column was begun with 25% ethyl acetate/n-hexane and continued with that solvent system until the less polar impurity had been removed. The polarity was then ramped to 30% ethyl acetate/n-hexane to give nearly perfect separation. All absolutely pure fractions (by TLC) were combined to give 17.6 g (93%) as an amorphous white foam solid. $^{1}$H-NMR (CDCl$_{3}$, 500 MHz) δ 8.18 (s, 1H), 7.86 (d, J=2.1 Hz, 1H), 7.82 (d, J=1.8 Hz, 1H), 7.44 (dd, J=8.6, 5.6 Hz, 2H), 7.03 (dd, J=8.9, 8.6 Hz, 2H), 5.77 (s, 2H), 4.33 (s, 2H), 3.80 (br, 2H), 3.63 (t, J=8.2 Hz, 2H), 3.07 (m, 2H), 2.28 (m, 2H), 2.05 (m, 2H), 1.42 (s, 9H), 0.93 (t, J=8.2 Hz, 2H), −0.05 (s, 9H); $^{13}$C NMR (126 MHz, CDCl$_{3}$) δ ppm 164.5, 161.7 (d, J=247 Hz), 155.0, 144.4, 137.5, 131.8, 129.1 (d, J=7.7 Hz), 126.8, 125.0, 124.4, 122.7, 121.1, 115.5 (d, J=21 Hz), 82.6, 79.6, 72.7, 68.0, 40.8, 40.1 (br), 32.1, 28.5, 18.1, −1.3. Mass spec.: 618.28 (MH)$^{+}$.

Intermediate 244

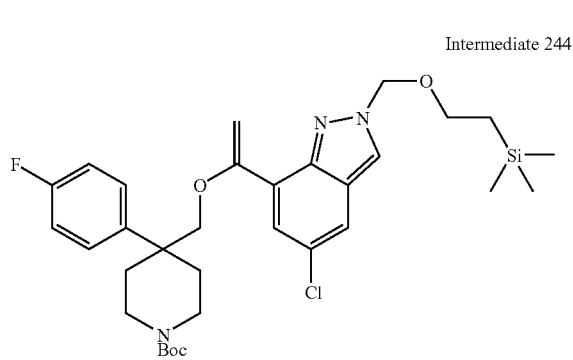

tert-Butyl 4-((1-(5-chloro-2-((2-(trimethylsilyl)ethoxy)methyl)-2H-indazol-7-yl)vinyloxy)methyl)-4-(4-fluorophenyl)piperidine-1-carboxylate. General Note: The reaction was run in such a way as to minimize exposure to light. Reactions were run under a layer of foil to block light and the lab lights were turned off while manipulating the reaction mixtures. To a suspension of titanocenedichloride (4.33 g, 17 mmol) in toluene (141 mL) at 0° C. was added methyllithium (1.6M in diethyl ether, 26.5 mL, 42.5 mmol) dropwise. The reaction was stirred at 0° C. for 1 h. The reaction was quenched by addition of 70 mL of a 6% ammonium chloride solution. The resulting heterogeneous mixture was vigorously stirred for 15 min at 0° C. prior to separation of the layers. The heterogeneous mixture was filtered through a course frit and added to the sep funnel. The layers were separated and the organic layer dried over magnesium sulfate. The solution was filtered and treated with (1-(tert-butoxycarbonyl)-4-(4-fluorophenyl)piperidin-4-yl)methyl 5-chloro-2-((2-(trimethylsilyl)ethoxy)methyl)-2H-indazole-7-carboxylate (3.5 g, 5.7 mmol) and N-cyclohexyl-N-methylcyclohexanamine (0.61 mL, 2.8 mmol) and the mixture concentrated to ~⅓ its volume. The bath temperature was maintained at 30° C. while reaction mixture was being concentrated. The reaction flask was flushed with a stream of nitrogen and fitted with a reflux condenser (which had also been flushed with a stream of nitrogen for some time) and the resulting solution was placed in an oil bath preheated to 80° C. The bath temperature was set to 80° C. and stirred at that temperature (start=11 AM). After 9 h, heating was discontinued and the reaction allowed to stir at room temperature overnight. The reaction was concentrated to remove ~½ of the toluene. The reaction was diluted with 100 mL of hexanes to precipitate some of the titanocenes with stirring. To decompose the remaining titanocene, silica gel (10 g) was added as a solid with vigorous stirring to the suspension at 0° C. The ice bath was removed and stirring continued for 15 min. The resulting suspension was filtered and the resulting pad washed with 25% ethyl acetate/n-hexane. The mother liquor was concentrated and loaded onto a silica gel column (10% ethyl acetate/n-hexane). After several volumes at 10%, the gradient was ramped to 25% ethyl acetate/n-hexane to give the product with significant levels of titanocene byproducts by TLC. All of the fractions that contained product were concentrated and repurified by column chromatography (10% ethyl acetate/n-hexane→25% ethyl acetate/n-hexane) to give 3.06 g (88%) as a very faint yellow solid. $^1$H-NMR (CDCl$_3$, 500 MHz) δ 8.05 (s, 1H), 7.58 (d, J=1.8 Hz, 1H), 7.44 (dd, J=8.9, 5.5 Hz, 2H), 7.33 (d, J=1.8 Hz, 1H), 7.10 (dd, J=8.9, 8.5 Hz, 2H), 5.95 (d, J=2.1 Hz, 1H), 5.69 (s, 2H), 4.59 (d, J=2.1 Hz, 1H), 3.83 (s, 2H), 3.80 (bs, 2H), 3.64 (t, J=8.6 Hz, 2H), 3.10 (m, 2H), 2.31 (m, 2H), 1.99 (m, 2H), 1.45 (s, 9H), 0.93 (t, J=8.2 Hz, 2H), −0.04 (s, 9H); $^{13}$C NMR (126 MHz, CDCl$_3$) δ ppm 161.6 (d, J=246 Hz), 155.0, 144.3, 138.21, 138.19, 128.9 (d, J=8.6 Hz), 127.8, 126.9, 124.7, 123.6, 122.4, 119.2, 115.5 (d, J=20 Hz), 90.0, 82.0, 79.6, 75.8, 67.8, 41.1, 40.2 (br), 32.5, 28.6, 17.9, −1.4. Mass spec.: 616.36 (MH)$^+$.

Intermediate 245

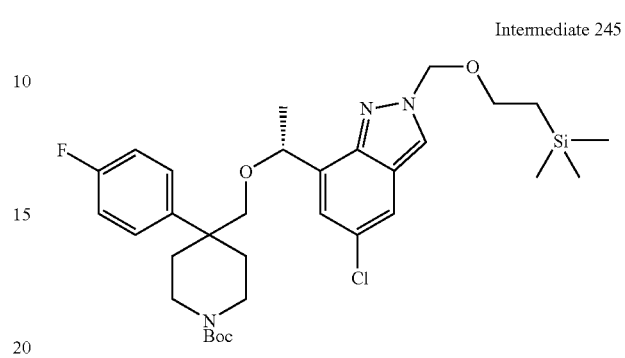

(R)-tert-Butyl 4-((1-(5-chloro-2-((2-(trimethylsilyl)ethoxy)methyl)-2H-indazol-7-yl)ethoxy)methyl)-4-(4-fluorophenyl)piperidine-1-carboxylate. tert-Butyl 4-((1-(5-chloro-2-((2-(trimethylsilyl)ethoxy)methyl)-2H-indazol-7-yl)vinyloxy)methyl)-4-(4-fluorophenyl)piperidine-1-carboxylate (1 g, 1.62 mmol) was transferred to a parr bottle (pre-purged with nitrogen) and dissolved in dichloroethane (40 mL). The resulting solution was purged by bubbling nitrogen through it for 45 min. To the bottle was quickly added diacetato[(S)-(−)-2,2'-bis(di-p-tolylphosphino)-1,1'-binaphthyl]ruthenium(II) (233 mg, 0.259 mmol). The bottle was purged for 10 additional min, and quickly affixed to the parr shaker. After 3 vaccuum/pressurize cycles, the shaker was pressurized to 65 psi and shaken overnight. The crude reaction mixture was loaded onto a pre-conditioned column of 12% ethyl acetate/n-hexane. After several volumes, the polarity was increased to 25% ethyl acetate/n-hexane to give 850 mg (85%) as a viscous amber oil. $^1$H-NMR (CDCl$_3$, 500 MHz) δ 8.00 (s, 1H), 7.48 (d, J=1.8 Hz, 1H), 7.31 (dd, J=8.5, 5.2 Hz, 2H), 7.03 (dd, J=8.9, 8.6 Hz, 2H), 6.77 (s, 1H), 5.67 (d, J=10.7 Hz, 1H), 5.64 (d, J=10.7 Hz, 1H), 4.93 (q, J=6.4 Hz, 1H), 3.72 (m, 2H), 3.59 (t, J=8.4 Hz, 2H), 3.37 (d, J=9.2 Hz, 1H), 3.34 (d, J=9.2 Hz, 1H), 3.05 (m, 2H), 2.19 (m, 1H), 2.08 (m, 1H), 1.94 (m, 1H), 1.87 (m, 1H), 1.44 (s, 9H), 1.43 (d, J=6.4 Hz, 3H), 0.91 (dd, J=9.2, 7.3 Hz, 2H), −0.06 (s, 9H); $^{13}$C NMR (126 MHz, CDCl$_3$) δ ppm 161.5 (d, J=245 Hz), 155.1, 145.6, 138.9, 135.8, 128.9 (d, J=7.7 Hz), 128.3, 122.82, 122.76, 122.2, 117.6, 115.2 (d, J=21 Hz), 81.9, 79.4, 77.9, 73.9, 67.6, 41.3, 40.3, 32.3, 32.0, 28.6, 22.8, 17.9, −1.4. Mass spec.: 618.39 (MH)$^+$.

Intermediate 246

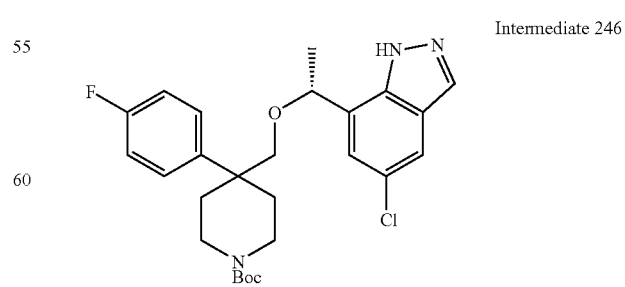

(R)-tert-Butyl 4-((1-(5-chloro-1H-indazol-7-yl)ethoxy)methyl)-4-(4-fluorophenyl)piperidine-1-carboxylate. (R)- tert-Butyl 4-((1-(5-chloro-2-((2-(trimethylsilyl)ethoxy)methyl)-2H-indazol-7-yl)ethoxy)methyl)-4-(4-fluorophenyl)piperidine-1-carboxylate (850 mg, 1.375 mmol) was dissolved in trifluoroacetic acid (50% in dichloromethane, 30 mL) and stirred at room temperature for 4 h. The reaction was concentrated, loaded onto a strong cation exchange cartridge (4×2 g cartridges) in methanol, and flushed with several volumes of methanol which were discarded. The product was eluted with 2M ammonia in methanol and concentrated. The crude piperidine was dissolved in dichloromethane (10 mL), and treated with di-tert-butyl dicarbonate(0.48 mL, 2.062 mmol). The reaction was quenched by addition of ethylene diamine (200 mg) in dichloromethane (2 mL). The reaction was concentrated and purified by column chromatography (25%→37% ethyl acetate/n-hexane) to give 650 mg (97%) as a white foam solid. $^1$H-NMR (CDCl$_3$, 500 MHz) δ 9.66 (bs, 1H), 7.90 (s, 1H), 7.57 (d, J=1.8 Hz, 1H), 7.26 (dd, J=8.9, 5.5 Hz, 2H), 7.07 (dd, J=8.9, 8.6 Hz, 2H), 6.98 (d, J=1.5 Hz, 1H), 4.49 (q, J=6.4 Hz, 1H), 3.74 (m, 2H), 3.38 (d, J=9.2 Hz, 1H), 3.25 (d, J=9.2 Hz, 1H), 3.22 (bs, 2H), 3.05 (m, 1H), 2.97 (m, 1H), 2.26 (m, 1H), 2.06 (m, 1H), 1.84 (m, 1H), 1.73 (m, 1H), 1.43 (m. 12H); $^{13}$C NMR (75 MHz, CDCl$_3$) δ ppm 171.0, 161.5 (d, J=247 Hz), 154.8, 137.9, 137.8, 135.4, 133.7, 128.5 (d, J=7.5 Hz), 127.3, 125.9, 124.6, 124.0, 118.9, 115.5 (d, J=21 Hz), 79.4, 78.5, 78.1, 60.3, 41.0, 39.8 (br), 32.3, 32.0, 28.3, 22.0, 20.9, 14.1. Mass spec.: 488.17 (MH)$^+$.

Intermediate 247

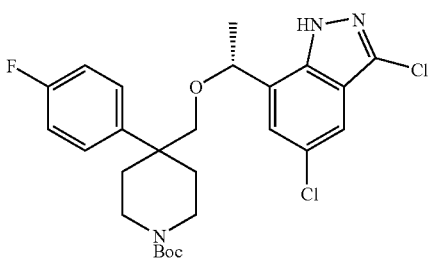

(R)-tert-Butyl 4-((1-(3,5-dichloro-1H-indazol-7-yl)ethoxy)methyl)-4-(4-fluorophenyl)piperidine-1-carboxylate. To a solution of (R)-tert-butyl 4-((1-(5-chloro-1H-indazol-7-yl)ethoxy)methyl)-4-(4-fluorophenyl)piperidine-1-carboxylate (2.65 g, 5.43 mmol) and sodium hydroxide (4M in water, 2.7 mL, 10.9 mmol) in ethanol (50 mL) at 0° C. was added N-chlorosuccinimide (0.725 g, 5.43 mmol). After 10 min, an additional portion of N-chlorosuccinimide (0.725 g, 5.43 mmol) was added. To the reaction was added another portion of sodium hydroxide (4M in water, 1.36 mL) and N-chlorosuccinimide (150 mg). The reaction was quenched by the addition of aqueous ammonia and diluted with diethyl ether. The ethereal was washed with water (3×), then brine, dried over magnesium sulfate, and concentrated. Column chromatography (25% ethyl acetate/n-hexane) gave 2.44 g (86%) as a colorless film. $^1$H-NMR (CDCl$_3$, 500 MHz) δ 9.49 (bs, 1H), 7.51 (d, J=1.5 Hz, 1H), 7.25 (m, 2H), 7.08 (dd, J=8.6, 8.5 Hz, 2H), 7.01 (d, J=1.5 Hz, 1H), 4.50 (q, J=6.7 Hz, 1H), 3.73 (m, 2H), 3.40 (d, J=9.2 Hz, 1H), 3.27 (d, J=8.9 Hz, 1H), 3.05 (m, 1H), 2.98 (m, 1H), 2.25 (m, 1H), 2.06 (m, 1H), 1.83 (m, 1H), 1.73 (m, 1H), 1.43 (s, 9H), 1.41 (d, J=6.4 Hz, 3H); $^{13}$C NMR (126 MHz, CDCl$_3$) δ ppm 171.1, 161.7 (d, J=247 Hz), 155.0, 138.0, 137.0, 134.4, 128.6 (d, J=7.7 Hz), 128.2, 127.0, 125.4, 122.1, 117.9, 115.8 (d, J=20 Hz), 79.7, 78.9, 78.2, 41.2, 40.1 (br), 32.6, 32.2, 28.5, 22.1. Mass spec.: 522.11 (MH)$^+$.

Intermediates 248 and 249

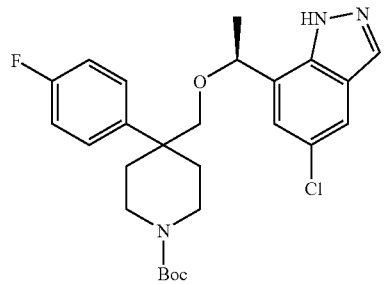

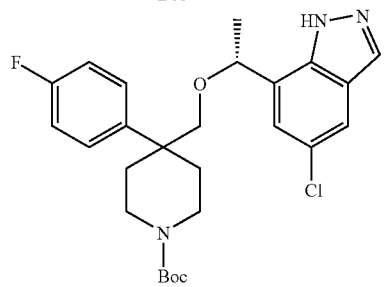

Chiral separation of tert-butyl 4-((1-(5-chloro-1H-indazole-7-yl)ethoxy)methyl)-4-(4-fluorophenyl)piperidine-1-carboxylate (8.1 g) to give 3.57 g of (S)-tert-butyl 4-((1-(5-chloro-1H-indazole-7-yl)ethoxy)methyl)-4-(4-fluorophenyl)piperidine-1-carboxylate (peak #1, 8.53 min), and 3.54 g of (R)-tert-butyl 4-((1-(5-chloro-1H-indazole-7-yl)ethoxy)methyl)-4-(4-fluorophenyl)piperidine-1-carboxylate (peak #2, 12.14 min). Chiral SFC Method: Chiral OD-H analytical column, 4.6×250 mm, 5 μm; Mobile Phase: 12% MeOH (0.1% DEA) in CO2; Temp: 35° C.; Flow rate: 2.0 mL/min. for 16 min; UV monitored @ 220 nm; Injection: 5 μL of 2 mg/mL solution in MeOH.

Intermediates 250 and 251

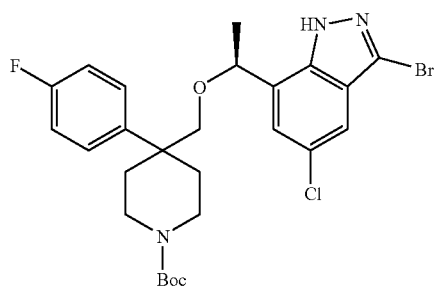

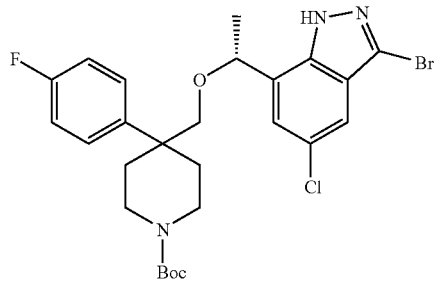

Chiral separation of tert-butyl 4-((1-(3-bromo-5-chloro-1H-indazole-7yl)ethoxy)methyl)-4-(4-fluorophenyl)piperidine-carboxylate (222 mg) to give 97 mg of (S)-tert-butyl 4-((1-(5-chloro-1H-indazole-7-yl)ethoxy)methyl)-4-(4- fluorophenyl)piperidine-1-carboxylate (peak #1, 15.09 min), and 97 mg of (R)-tert-butyl 4-((1-(3-bromo-5-chloro-1H-indazole-7yl)ethoxy)methyl)-4-(4-fluorophenyl)piperidinecarboxylate (peak #2, 17.89 min). Chiral SFC Method: Chiral OD-H analytical column, 4.6×250 mm, 5 μm; Mobile Phase: 12% MeOH (0.1% DEA) in CO2; Temp: 35° C.; Flow rate: 2.0 mL/min. for 30 min; UV monitored @ 220nm; Injection: 5 μL of 1 mg/mL solution in MeOH.

Intermediate 252

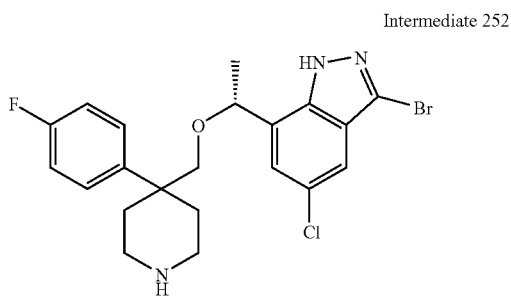

(R)-3-bromo-5-chloro-7-(1-((4-(4-fluorophenyl)piperidine-4-yl)methoxy)ethyl)-1H-indazole. $^1$H-NMR (CDCl$_3$, 300 MHz) δ 7.43 (d, J=1.83 Hz, 1H), 7.26-7.22 (m, 2H), 7.07-7.0 (m, 3H), 4.47 (q, J=6.59 Hz, 1H), 3.4 (d, J=8.8 Hz, 1H), 3.25 (d, J=9.15 Hz, 1H), 2.91-2.62 (m, 4H), 2.20-2.10 (m, 1H), 2.04-1.99 (m, 1H), 1.88-1.73 (m, 2H), 1.38 (d, J=6.69 Hz, 3H). LC/MS (HPLC method 3): $t_R$=3.09 min, 468.06(MH)$^+$.

Intermediate 253

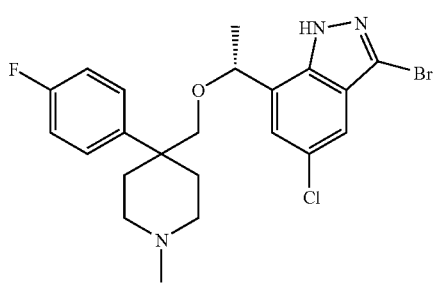

(R)-3-bromo-5-chloro-7-(1-((4-(4-fluorophenyl)-1-methylpiperidin-4-yl)methoxy)ethyl)-1H-indazole. $^1$H-NMR (CDCl$_3$, 500 MHz) δ 7.44 (d, J=1.83 Hz, 1H), 7.26-7.22 (m, 2H), 7.06-7.03 (m, 2H), 7.0 (m, 1H), 4.49 (q, J=6.41 Hz, 1H), 3.39 (d, J=8.85 Hz, 1H), 3.25 (d, J=8.85 Hz, 1H), 2.59-2.51 (m, 2H), 2.19 (s, 3H), 2.26-2.04 (m, 4H), 2.01-1.94 (m, 1H), 1.93-1.88 (m, 1H), 1.39 (d, J=6.71 Hz, 3H). $^{13}$C-NMR (CDCl$_3$, 126 MHz) δ 161.55 (d, J=246.6 Hz), 136.9, 128.73, 128.66, 128.3, 127.0, 125.3, 124.6, 121.8, 118.4, 115.7, 115.5, 78.0, 65.9, 51.8, 51.7. LC/MS (HPLC method 3): $t_R$=3.05 min, 482.05(MH)$^+$.

Intermediates 254 and 255

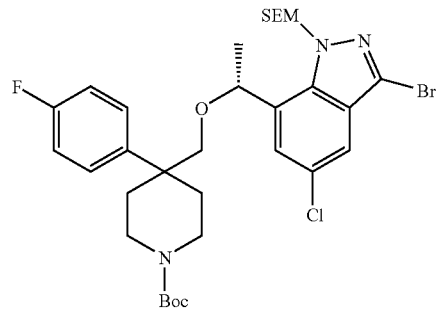

(R)-tert-butyl 4-((1-(5-chloro-3-bromo-1-((2-(trimethylsilyl)ethoxy)methyl)-1H-indazol-7-yl)ethoxy)methyl)-4-(4-fluorophenyl)piperidine-1-carboxylate and (R)-tert-butyl 4-((1-(5-chloro-3-bromo-2-((2-(trimethylsilyl)ethoxy)methyl)-2H-indazol-7-yl)ethoxy)methyl)-4-(4-fluorophenyl)piperidine-1-carboxylate. HPLC Method (Phenomenex C18 10u 3.0×50 mm, A=90% H$_2$O/10% MeOH, B=90% MeOH/10% H$_2$O, Modifier 0.1% TFA, 0.00 min=0% B, 4.0 min=100% B, Flow rate=4 mL/min.): $t_R$=4.83 min, 698.2 (MH)$^+$.

Intermediates 256 and 257

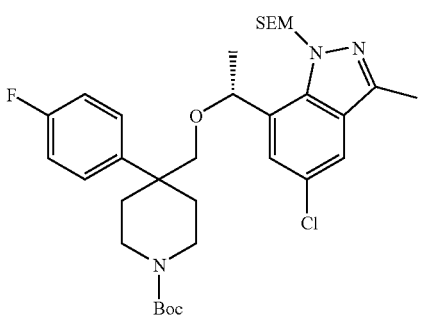

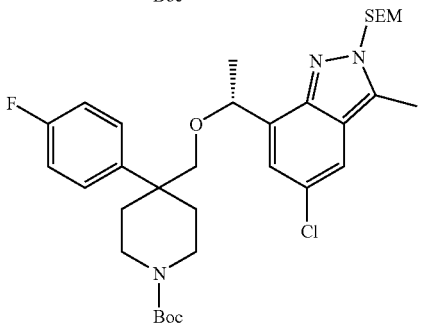

(R)-tert-butyl 4-((1-(5-chloro-3-methyl-1-((2-(trimethylsilyl)ethoxy)methyl)-1H-indazole-7-yl)ethoxy)methyl)-4-(4-fluorophenyl)piperidine-1-carboxylate and (R)-tert-butyl 4-((1-(5-chloro-3-methyl-2-((2-(trimethylsilyl)ethoxy)methyl)-2H-indazole-7-yl)ethoxy)methyl)-4-(4-fluorophenyl)piperidine-1-carboxylate. A pressure tube was flushed with nitrogen. To this was added a mixture of (R)-tert-butyl 4-((1-(5-chloro-3-bromo-1-((2-(trimethylsilyl)ethoxy)methyl)-1H-indazole-7-yl)ethoxy)methyl)-4-(4-fluorophenyl)piperidine-1-carboxylate and (R)-tert-butyl 4-((1-(5-chloro-3-bromo-2-((2-(trimethylsilyl)ethoxy)methyl)-2H-indazole-7-yl)ethoxy)methyl)-4-(4-fluorophenyl)piperidine-1-carboxylate (1.28 g, 1.836 mmol) in thf (30 mL, 366 mmol). The solution was degassed by bubbling nitrogen through the solution for 20 min. To this was added Tetrakis (0.085 g, 0.073 mmol), KOH (4M) (1.377 mL, 5.51 mmol), and Trimethylboroxine (0.770 mL, 5.51 mmol). After bubbling nitrogen for 10 min longer, the tube was sealed and placed in an oil bath which was pre-heated to 100 C. The reaction was stirred for 2 h, cooled to room temperature, diluted with ether, washed with water (2×), then brine, dried over MgSO4, filtered and concentrated. Column chromatography (12%-20% EtOAc/Hex) gave the title compounds (1.05 g, 1.661 mmol, 90% yield) as a mixture of regioisomers. HPLC Method (Phenomenex C18 10u 3.0×50 mm, A=90% H$_2$O/10% MeOH, B=90% MeOH/10% H$_2$O, Modifier 0.1% TFA, 0.00 min=0% B, 4.0 min=100% B, Flow rate=4 mL/min.): $t_R$=4.49 min, 632.4(MH)$^+$.

Intermediate 258

Intermediates 259 and 260

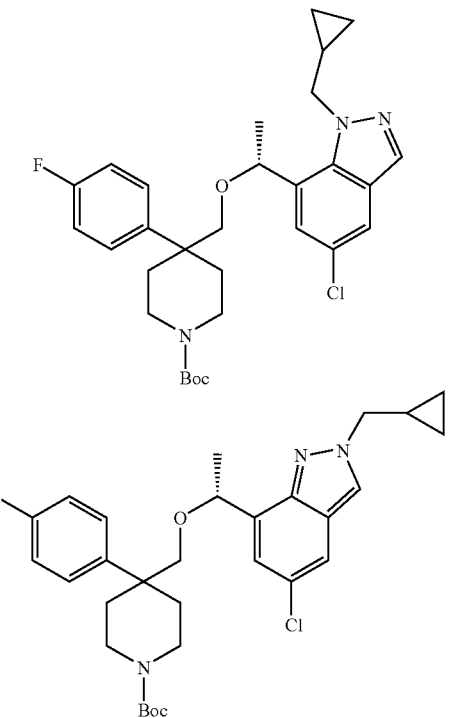

(R)-tert-butyl 4-((1-(5-chloro-3-methyl-1H-indazol-7-yl)ethoxy)methyl)-4-(4-fluorophenyl)piperidine-1-carboxylate. $^1$H-NMR (CDCl$_3$, 500 MHz) δ 7.48 (d, J=1.83 Hz, 1H), 7.25-7.22 (m, 2H), 7.04-7.0 (m, 2H), 6.94 (d, J=1.53 Hz, 1H), 4.49 (q, J=6.41 Hz, 1H), 3.8-3.58 (m, 2H), 3.32 (d, J=9.16 Hz, 1H), 3.24 (d, J=9.16 Hz, 1H), 3.04-2.92 (m, 2H), 2.49 (s, 3H), 2.18 (m, 1H), 2.07 (m, 1H), 1.85-1.67 (m, 2H), 1.42(s, 9H), 1.39 (d, J=6.41 Hz, 3H). $^{13}$C-NMR (CDCl$_3$, 126 MHz) δ 161.6 (d, J=245.7 Hz), 154.99, 142.4, 138.1, 136.7, 128.7, 162.59, 160.64, 128.6, 127.4, 125.4, 124.1, 118.6, 115.7, 115.5, 79.6, 78.2, 41.2, 32.1, 28.5, 22.1, 11.9. HPLC Method (Phenomenex C18 10u 3.0×50 mm, A=90% H$_2$O/10% MeOH, B=90% MeOH/10% H$_2$O, Modifier 0.1% TFA, 0.00 min=0% B, 3.0 min=100% B, Flow rate=4 mL/min.): $t_R$=3.17 min, 502.29(MH)$^+$.

(R)-tert-butyl 4-((1-(5-chloro-1-(cyclopropylmethyl)-1H-indazol-7-yl)ethoxy)methyl)-4-(4-fluorophenyl)piperidine-1-carboxylate and (R)-tert-butyl 4-((1-(5-chloro-2-(cyclopropylmethyl)-2H-indazol-7-yl)ethoxy)methyl)-4-(4-fluorophenyl)piperidine-1-carboxylate. (R)-tert-butyl 4-((1-(5-chloro-1H-indazol-7-yl)ethoxy)methyl)-4-(4-fluorophenyl)piperidine-1-carboxylate (75 mg, 0.154 mmol) and (bromomethyl)cyclopropane (0.022 ml, 0.231 mmol) in DMF (2.0 ml) were treated with cesium carbonate (150 mg, 0.461 mmol). The reaction was allowed to stir at room temperature for four hours, then poured into ice water and extracted with ether (2×). The organics were pooled together and washed with brine (2×), dried over MgSO4, filtered and concentrated. The crude product was purified by Biotage LC (1-25% EtOAc/Hexanes) to afford (R)-tert-butyl 4-((1-(5-chloro-1-(cyclopropylmethyl)-1H-indazol-7-yl)ethoxy)methyl)-4-(4-fluorophenyl)piperidine-1-carboxylate (17.5 mg, 0.032 mmol, 21.01% yield), and (R)-tert-butyl 4-((1-(5-chloro-2-(cyclopropylmethyl)-2H-indazol-7-yl)ethoxy)methyl)-4-(4-fluorophenyl)piperidine-1-carboxylate (50 mg, 0.092 mmol, 60.0% yield). LC/MS (HPLC method 3): $t_R$=4.14 min, 542.3(MH)$^+$.

(R)-tert-butyl 4-((1-(5-chloro-1-(cyclopropylmethyl)-1H-indazol-7-yl)ethoxy)methyl)-4-(4-fluorophenyl)piperidine-1-carboxylate. $^1$H-NMR (CDCl$_3$, 500 MHz) δ 7.89 (s, 1H), 7.54 (d, J=1.83 Hz, 1H), 7.28-7.25 (m, 2H), 7.04-7.0 (m, 2H), 6.98 (d, J=1.83 Hz, 1H), 4.87 (q, J=6.41 Hz, 1H), 4.32-4.28 (m, 1H), 4.19-4.15 (m, 1H), 3.77-3.65 (m, 2H), 3.34 (d, J=8.85 Hz, 1H), 3.20 (d, J=8.85 Hz, 1H), 3.05-2.97 (m, 2H), 2.18-2.09 (m, 2H), 1.87-1.81 (m, 2H), 1.43 (m, 12), 1.11-1.06 (m, 1H), 0.55-0.47 (m, 2H), 0.37-0.32 (m, 2H).

(R)-tert-butyl 4-((1-(5-chloro-2-(cyclopropylmethyl)-2H-indazol-7-yl)ethoxy)methyl)-4-(4-fluorophenyl)piperidine-1-carboxylate. $^1$H-NMR (CDCl$_3$, 500 MHz) δ 7.95 (s, 1H), 7.46 (d, J=1.83 Hz, 1H), 7.32-7.29 (m, 2H), 7.04-7.0 (m, 2H), 6.77 (bs, 1H), 4.9 (q, J=6.41 Hz, 1H), 4.23 (d, J=7.32 Hz, 2H), 3.78-3.6 (m, 2H), 3.39-3.33 (m, 2H), 3.1-3.0 (m, 2H), 2.18-2.05 (m, 2H), 1.96-1.87 (m, 2H), 1.42 (m, 12H), 1.25 (m, 1H), 0.7-0.67 (m, 2H), 0.44-0.41 (m, 2H).

(m, 1H), 5.29 (s, 2H), 4.79 (q, J=6.59 Hz, 1H), 3.73-3.65 (m, 2H), 3.1-2.95 (m, 2H), 2.18-2.03 (m, 2H), 1.94-1.84 (m, 2H), 1.4 (m, 12H).

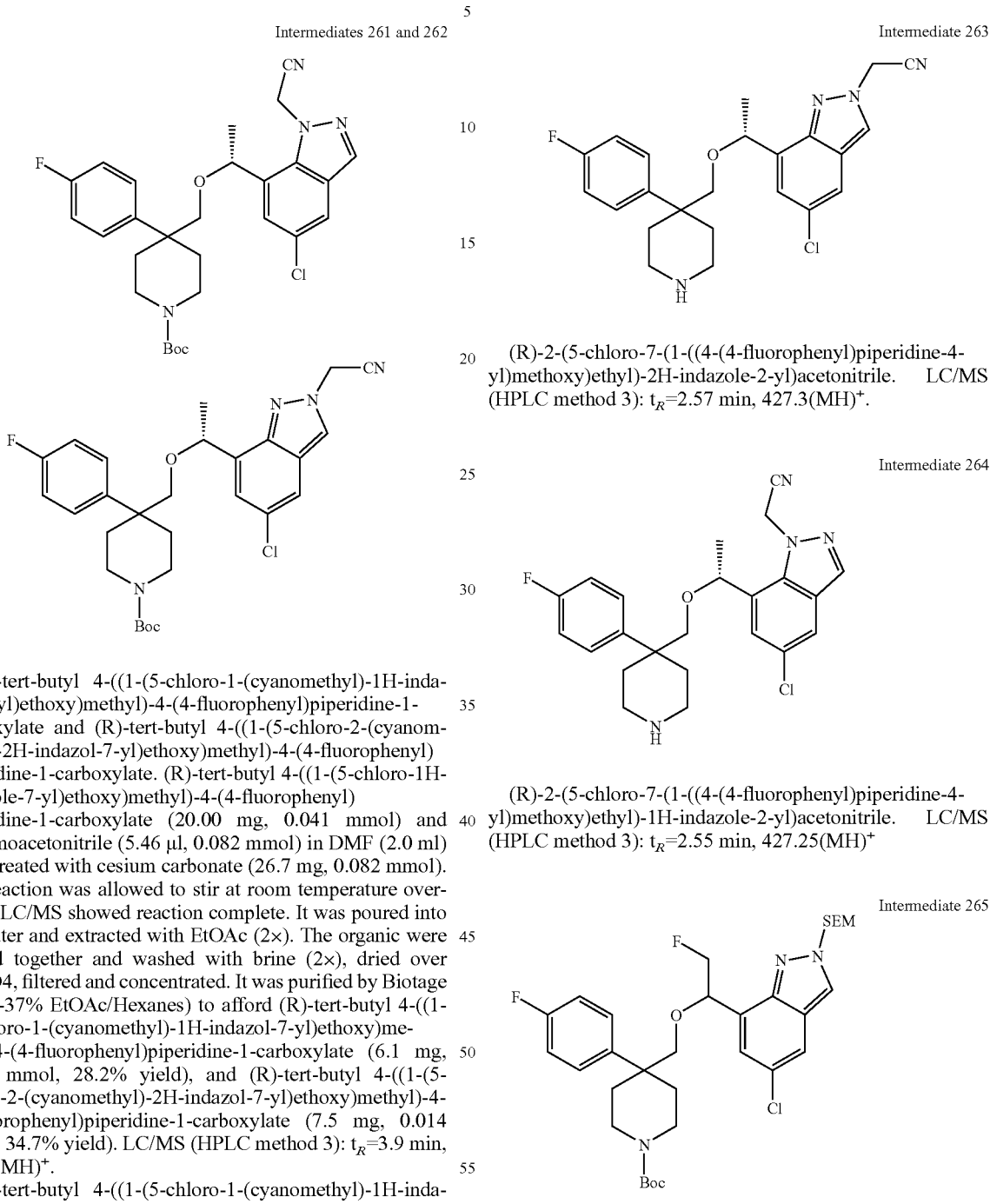

Intermediates 261 and 262

Intermediate 263

(R)-tert-butyl 4-((1-(5-chloro-1-(cyanomethyl)-1H-indazol-7-yl)ethoxy)methyl)-4-(4-fluorophenyl)piperidine-1-carboxylate and (R)-tert-butyl 4-((1-(5-chloro-2-(cyanomethyl)-2H-indazol-7-yl)ethoxy)methyl)-4-(4-fluorophenyl)piperidine-1-carboxylate. (R)-tert-butyl 4-((1-(5-chloro-1H-indazole-7-yl)ethoxy)methyl)-4-(4-fluorophenyl)piperidine-1-carboxylate (20.00 mg, 0.041 mmol) and 2-bromoacetonitrile (5.46 µl, 0.082 mmol) in DMF (2.0 ml) were treated with cesium carbonate (26.7 mg, 0.082 mmol). The reaction was allowed to stir at room temperature overnight. LC/MS showed reaction complete. It was poured into ice water and extracted with EtOAc (2×). The organic were pooled together and washed with brine (2×), dried over MgSO4, filtered and concentrated. It was purified by Biotage LC (1-37% EtOAc/Hexanes) to afford (R)-tert-butyl 4-((1-(5-chloro-1-(cyanomethyl)-1H-indazol-7-yl)ethoxy)methyl)-4-(4-fluorophenyl)piperidine-1-carboxylate (6.1 mg, 0.012 mmol, 28.2% yield), and (R)-tert-butyl 4-((1-(5-chloro-2-(cyanomethyl)-2H-indazol-7-yl)ethoxy)methyl)-4-(4-fluorophenyl)piperidine-1-carboxylate (7.5 mg, 0.014 mmol, 34.7% yield). LC/MS (HPLC method 3): $t_R$=3.9 min, 527.3(MH)$^+$.

(R)-tert-butyl 4-((1-(5-chloro-1-(cyanomethyl)-1H-indazol-7-yl)ethoxy)methyl)-4-(4-fluorophenyl)piperidine-1-carboxylate. $^1$H-NMR (CDCl$_3$, 300 MHz) δ 7.98 (s, 1H), 7.61 (d, J=1.83 Hz, 1H), 7.16-7.1 (m, 3H), 6.99-6.93 (m, 2H), 5.33 (d, J=17.57 Hz, 1H), 4.88 (d, J=17.93 Hz, 1H), 4.7-4.63 (m, 1H), 3.68-3.62 (m, 2H), 3.32-3.2 (m, 2H), 3.07-2.94 (m, 2H), 2.13-1.98 (m, 2H), 1.75-1.69 (m, 2H), 1.56 (d, J=6.95 Hz, 3H), 1.4 (s, 9H).

(R)-tert-butyl 4-((1-(5-chloro-1-(cyanomethyl)-2H-indazol-7-yl)ethoxy)methyl)-4-(4-fluorophenyl)piperidine-1-carboxylate. $^1$H-NMR (CDCl$_3$, 300 MHz) δ 7.98 (s, 1H), 7.45 (d, J=1.83 Hz, 1H), 7.3-7.26 (m, 2H), 7.03-7.26 (m, 2H), 6.79

(R)-2-(5-chloro-7-(1-((4-(4-fluorophenyl)piperidine-4-yl)methoxy)ethyl)-2H-indazole-2-yl)acetonitrile. LC/MS (HPLC method 3): $t_R$=2.57 min, 427.3(MH)$^+$.

Intermediate 264

(R)-2-(5-chloro-7-(1-((4-(4-fluorophenyl)piperidine-4-yl)methoxy)ethyl)-1H-indazole-2-yl)acetonitrile. LC/MS (HPLC method 3): $t_R$=2.55 min, 427.25(MH)$^+$ Intermediate 265

Tert-butyl 4-((1-(5-chloro-2-((2-(trimethylsilyl)ethoxy)methyl)-2H-indazol-7-yl)-2-fluoroethoxy)methyl)-4-(4-fluorophenyl)piperidine-1-carboxylate. To a solution of tert-butyl 4-((1-(5-chloro-2-((2-(trimethylsilyl)ethoxy)methyl)-2H-indazol-7-yl)-2-hydroxyethoxy)methyl)-4-(4-fluorophenyl)piperidine-1-carboxylate (440 mg, 0.694 mmol) in ACETONITRILE (0.1 mL, 1.915 mmol) at room temperature was added diisopropylethylamine (0.545 mL, 3.12 mmol), Diisopropylethylamine trihydrofluoride (197 mg, 1.041 mmol), and perfluoro-1-butanesulfonyl fluoride (0.249 mL, 1.387 mmol). The reaction was stirred at room temperature overnight. It was then poured into sat'd NaHCO3 and diluted with ether. The ether layer was washed with water and brine, dried over MgSO4, filtered and concentrated. The crude product was purified by silica gel column chromatography (15%-20% EtOAc/Hex) to give title compound (420 mg, 0.660 mmol, 95% yield) as a colorless film. LC/MS (HPLC method 3): $t_R$=4.33 min, 636.3(MH)$^+$.

Intermediate 266

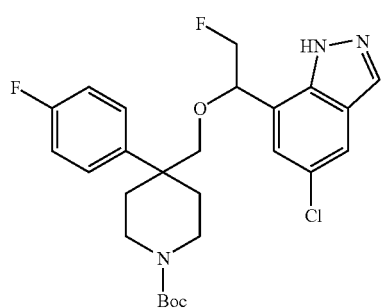

Tert-butyl 4-((1-(5-chloro-1H-indazol-7-yl)-2-fluoroethoxy)methyl)-4-(4-fluorophenyl)piperidine-1-carboxylate. Tert-butyl 4-((1-(5-chloro-2-((2-(trimethylsilyl)ethoxy)methyl)-1H-indazol-7-yl)-2-fluoroethoxy)methyl)-4-(4-fluorophenyl)piperidine-1-carboxylate (420 mg, 0.660 mmol) was dissolved in TBAF (1M in THF) (8.5 mL, 8.50 mmol). The flask was sealed and heated at 55° C. for 1.5 h. The reaction was cooled to room temperature and diluted with ether, washed with water then brine, dried over MgSO4, filtered and concentrated. The crude product was purified by silica gel column chromatography (30%-40% EtOAc/Hex) to give title compound (286 mg, 0.565 mmol, 86% yield) as a colorless oil. LC/MS (HPLC method 3): $t_R$=3.78 min, 506.3 (MH)$^+$.

Intermediates 267 and 268

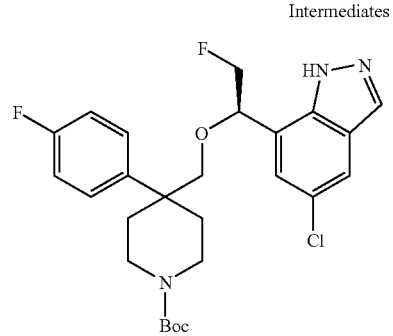

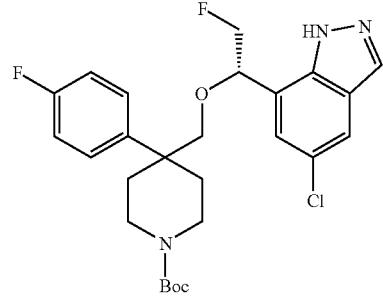

Chiral separation of tert-butyl 4-((1-(5-chloro-1H-indazol-7-yl)-2-fluoroethoxy)methyl)-4-(4-fluorophenyl)piperidine-1-carboxylate (200 mg) to give 81 mg of (S)-tert-butyl 4-((1-(5-chloro-1H-indazol-7-yl)-2-fluoroethoxy)methyl)-4-(4-fluorophenyl)piperidine-1-carboxylate (peak #1, 11.21 min), and 90 mg of (R)-tert-butyl 4-((1-(5-chloro-1H-indazol-7-yl)-2-fluoroethoxy)methyl)-4-(4-fluorophenyl)piperidine-1-carboxylate (peak #2, 13.51 min). Chiral SFC Method: Chiral OD-H analytical column, 4.6×250 mm, 5 µm; Mobile Phase: 10% MeOH (0.1% DEA) in CO2; Temp: 35° C.; Flow rate: 2.0 mL/min. for 18 min; UV monitored @ 220 nm; Injection: 5 µL of 1 mg/mL solution in MeOH.

Intermediate 269

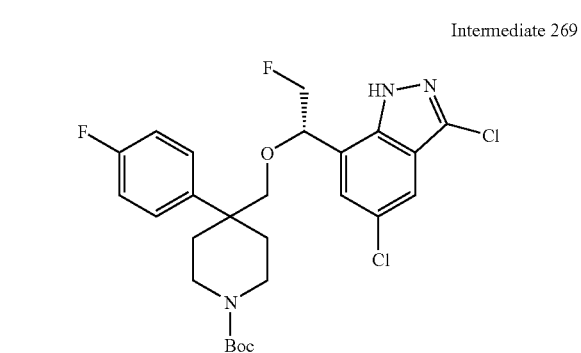

(S)-tert-butyl 4-((1-(3,5-dichloro-1H-indazol-7-yl)-2-fluoroethoxy)methyl)-4-(4-fluorophenyl)piperidine-1-carboxylate. To a solution of tert-butyl 4-((1-(5-chloro-1H-indazol-7-yl)-2-fluoroethoxy)methyl)-4-(4-fluorophenyl) piperidine-1-carboxylate (90 mg, 0.178 mmol) and sodium hydroxide (4N in water) (0.056 mL, 0.222 mmol) in ethanol (1.7 mL, 29.1 mmol) at 0 C was added NCS (47.5 mg, 0.356 mmol), it was stirred at 0 C for 2 h when most S.M. converted to product. The reaction was treated with 0.03 ml of 4 N NaOH, 1 eq. of NCS and was stirred at 0 C for another 2 h., there is still some unreacted SM by TLC. The reaction was quenched by addition of aqueous ammonia and diluted with Et2O. The organic layer was washed with water (2×) then brine, dried over MgSO4, filtered and concentrated. The crude product was purified by silica gel column chromatography (25% EtOAc/Hex) to give title compound (72 mg, 74.9% yield) as clear oil. $^1$H-NMR (CDCl$_3$, 500 MHz) δ 7.57 (d, J=1.83, 1H), 7.28-7.25 (m, 2H), 7.09-7.06 (m, 3H), 4.6-4.4 (m, 3H), 3.77-3.6 (m, 2H), 3.51 (d, J=9.16 Hz, 1H), 3.39 (d, J=9.16 Hz, 1H), 3.08-2.95 (m, 2H), 2.27 (m, 1H), 2.05 (m, 1H), 1.86 (m, 1H), 1.74 (m, 1H), 1.43 (s, 9H); $^{13}$C-NMR (CDCl$_3$, 126 MHz) δ 161.8 (d, J=247.6 Hz), 154.9, 137.8, 137.6, 134.4, 128.73, 127.67, 126.7, 122.2, 121.8, 119.0, 115.9, 115.8, 85.7, 84.3, 81.1, 80.9, 79.7, 42.5, 41.4, 32.4, 32.1, 31.7, 28.5, 22.7, 14.2. LC/MS (HPLC method 3): $t_R$=4.12 min, 540.1(MH)$^+$.

Intermediate 270

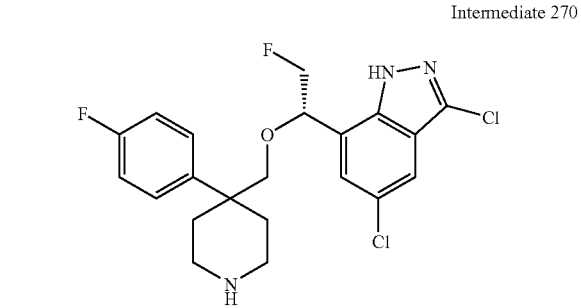

(S)-3,5-dichloro-7-(2-fluoro-1-((4-(4-fluorophenyl)piperidine-4-yl)methoxy)ethyl)-1H-indazole. LC/MS (HPLC method 3): $t_R$=2.96 min, 440.1 (MH)$^+$.

Intermediate 271

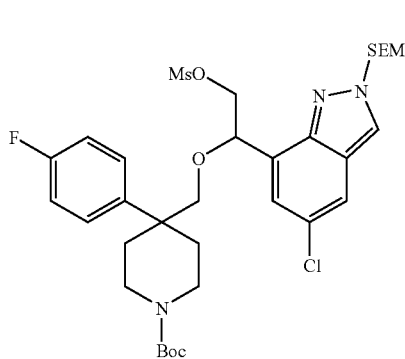

tert-butyl 4-((1-(5-chloro-2-((2-(trimethylsilyl)ethoxy)methyl)-2H-indazol-7-yl)-2-(methylsulfonyloxy)ethoxy)methyl)-4-(4-fluorophenyl)piperidine-1-carboxylate. To a solution of tert-butyl 4-((1-(5-chloro-2-((2-(trimethylsilyl)ethoxy)methyl)-2H-indazol-7-yl)-2-hydroxyethoxy)methyl)-4-(4-fluorophenyl)piperidine-1-carboxylate (150 mg, 0.236 mmol) and Et3N (0.099 mL, 0.709 mmol) in DCM (3 mL, 46.6 mmol) at 0 C was added Methanesulfonyl chloride (0.037 mL, 0.473 mmol). The ice bath was removed and stirring continued for 1 h. The reaction was cooled to 0 , quenched by addition of saturated NaHCO3 and diluted with ether, the layers were separated and the ether layer was washed with brine, dried over MgSO4, filtered and concentrated. The crude product was purified by Biotage LC (30% EtOAc/Hex) to give 155 mg of title product as white foam (92% yield). LC/MS (HPLC method 3): $t_R$=4.15 min, 712.3 (MH)$^+$.

Intermediate 272

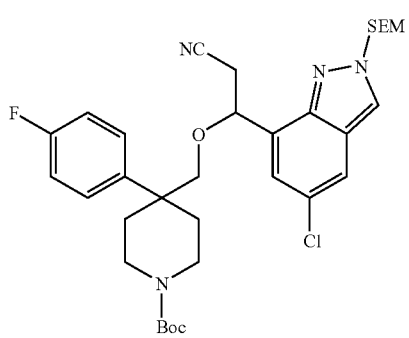

tert-butyl 4-((1-(5-chloro-2-((2-(trimethylsilyl)ethoxy)methyl)-2H-indazol-7-yl)-2-cyanoethoxy)methyl)-4-(4-fluorophenyl)piperidine-1-carboxylate. Tert-butyl 4-((1-(5-chloro-2-((2-(trimethylsilyl)ethoxy)methyl)-2H-indazol-7-yl)-2-(methylsulfonyloxy)ethoxy)methyl)-4-(4-fluorophenyl)piperidine-1-carboxylate (155 mg, 0.218 mmol) in DMF was added NaCN (21.37 mg, 0.436 mmol) and the reaction was stirred at R.T for 1 h. LC/MS showed no reaction. The reaction was heated at 50 C for another hour, LC/MS showed no reaction either. The reaction was again heated at 80 C for another hour, no reaction was observed. It was stirred at 80 C over the weekend. LC/MS showed product along with staring material. It was stirred at 80 C for 6 h, LC/MS showed the reaction was complete. The reaction was then partitioned between Et2O and H2O, the phase was separated and the aqueous phase was extracted with Et2O, the combined organic phases were washed with water and brine, dried over magnesium sulfate, filtered and concentrated under reduced pressure. It was purified by Biotage LC (30% EtOAc/Hex) to title compound (52.2 mg, 0.081 mmol, 37.3% yield). $^1$H-NMR (CDCl$_3$, 300 MHz) δ 8.0 (s, 1H),), 7.53 (m, 1H), 7.32 (m, 2H), 7.05 (m, 2H), 6.63 (s, 1H), 5.61 (s, 2H), 5.04 (m, 1H), 3.68 (m, 2H), 3.57 (t, J=8.05 Hz, 2H), 3.45 (m, 2H), 3.05-2.96 (m, 3H), 2.74 (m, 1H), 2.28 (m, 1H), 1.98 (m, 1H), 1.96 (m, 1H), 1.83 (m, 1H), 1.42 (s, 9H), 0.9 (t, J=8.42 Hz, 2H); $^{13}$C-NMR (CDCl$_3$, 126 MHz) δ 161.63 (d, J=245.7 Hz), 155.0, 144.8, 129.9, 128.9, 128.0, 124.0, 122.8, 119.3, 117.2, 115.5, 115.4, 81.9, 79.5, 79.0, 73.4, 67.8, 42.5, 41.4, 32.4, 28.6, 25.3, 17.9, 1.35. LC/MS (HPLC method 3): $t_R$=4.16 min, 643.1 (MH)$^+$.

Intermediate 273

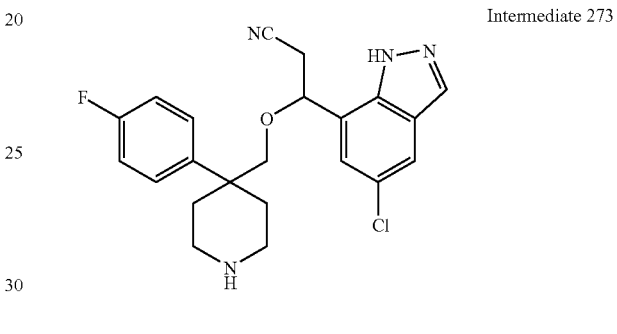

3-(5-chloro-1H-indazol-7-yl)-3-((4-(4-fluorophenyl)piperidine-4-yl)methoxy)propanenitrile. LC/MS (HPLC method 3): $t_R$=2.36 min, 413.1(MH)$^+$.

Intermediate 274 tert-butyl 4-((1-(5-chloro-2-((2-(trimethylsilyl)ethoxy)methyl)-2H-indazol-7-yl)-2-(dimethylamino)ethoxy)methyl)-4-(4-fluorophenyl)piperidine-1-carboxylate. To a solution of tert-butyl 4-((1-(5-chloro-2-((2-(trimethylsilyl)ethoxy)methyl)-2H-indazol-7-yl)-2-oxoethoxy)methyl)-4-(4-fluorophenyl)piperidine-1-carboxylate (40.0 mg, 0.063 mmol)and DIMETHYLAMINE (0.040 mL, 0.316 mmol) in Acetonitrile (1.5 mL) at 0° C. was added SODIUM CYANOBOROHYDRIDE (3.98 mg, 0.063 mmol). To this was added 1 drop of HOAc, and a second drop of HOAc after 5 min. The reaction was then stirred at R.T. for another hour. LC/MS showed reaction complete. It was concentrated, diluted with ether and washed with 0.5M NaOH, then loaded onto an SCX cartridge in methanol. The cartridge was flushed with several volumes of methanol which were discarded, and eluted with 2M NH3 in MeOH, the solvent was concentrated to give the title product (27 mg, 0.041 mmol, 64.5% yield). ¹H-NMR (CDCl₃, 500 MHz) δ 7.99 (s, 1H),), 7.48 (d, J=1.83 Hz, 1H), 7.29 (m, 2H), 7.03 (m, 2H), 6.61 (d, J=19.8 Hz, 1H), 5.64 (m, 2H), 5.05 (m, 1H), 3.63 (m, 2H), 3.60 (t, c), 3.4 (m, 1H), 3.31 (m, 1H), 3.04 (m, 2H), 2.9 (m, 1H), 2.7 (m, 1H), 2.6 (m,2H), 2.25 (d, J=2.44 Hz, 6H), 2.2 (m, 1H), 2.05 (m, 1H), 1.9 (m, 1H), 1.8 (m, 1H), 1.43 (s, 9H), 0.9 (t, J=8.55 Hz, 2H), 0.06 (s, 9H). LC/MS (HPLC method 3): $t_R$=3.53 min, 661.5 (MH)⁺.

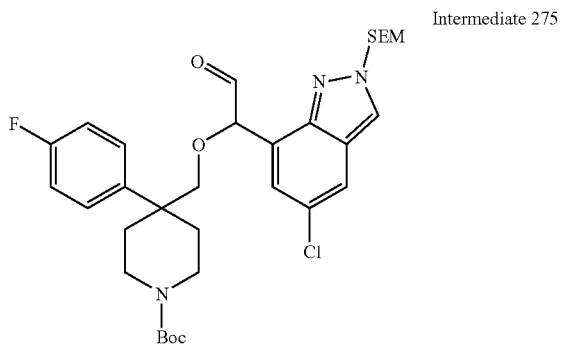

Intermediate 275

Tert-butyl 4-((1-(5-chloro-2-((2-(trimethylsilyl)ethoxy)methyl)-2H-indazol-7-yl)-2-oxoethoxy)methyl)-4-(4-fluorophenyl)piperidine-1-carboxylate. To solution of Methyl Sulfoxide (0.197 ml, 2.77 mmol) in DCM (12 ml) at −78° C. was added oxalyl chloride (0.694 ml, 1.387 mmol) dropwise. The solution was stirred at −78° C. for 0.5 h. A solution of Tert-butyl 4-((1-(5-chloro-2-((2-(trimethylsilyl)ethoxy)methyl)-2H-indazol-7-yl)-2-hydroxyethoxy)methyl)-4-(4-fluorophenyl)piperidine-1-carboxylate (400 mg, 0.631 mmol) in DCM (12 ml) was then added dropwise. The slurry was stirred at −78° C. for 2 h before addition of N,N-Diisopropylethylamine (0.549 ml, 3.15 mmol) dropwise. The solution was slowly warmed up and stirred at room temperature for 3 h. It was then washed with iced 1M HCl and brine, dried over MgSO4, filtered and concentrated. The residual light yellow oil was purified by Biotage LC (35% EtOAc/Hexane) to afford title compound (286.3 mg, 0.453 mmol, 71.8% yield) as yellow foam solid. ¹H-NMR (CDCl₃, 500 MHz) δ 9.61 (s, 1H), 8.05, s, 1H), 7.60 (d, J=1.8 Hz, 1H), 7.33 (m, 2H), 7.04 (m, 2H), 7.02 (buried, 1H), 5.67 (m, 2H), 3.60 (app t, J=8.3 Hz, 2H), 3.45-3.85 (m, 3H), 3.45 (d, J=9.1 Hz, 1H), 2.18 (m, 2H), 1.95 (m, 2H), 1.75 (m, 1H), 1.43 (s, 9H), 0.91 (app t, J=8.2 Hz, 2H), −0.04 (s, 9H). LC/MS (HPLC method 3): $t_R$=4.11 min, 632.3(MH)⁺.

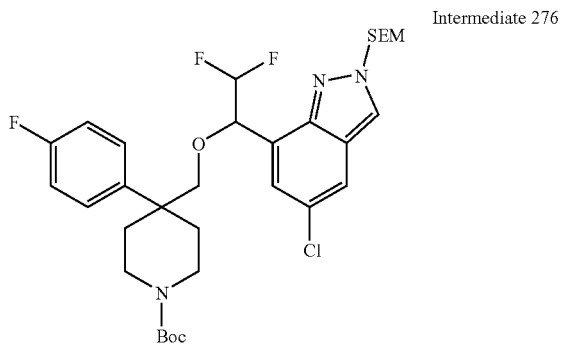

Intermediate 276 tert-butyl 4-((1-(5-chloro-2-((2-(trimethylsilyl)ethoxy)methyl)-2H-indazol-7-yl)-2,2-difluoroethoxy)methyl)-4-(4-fluorophenyl)piperidine-1-carboxylate. To a well-stirred solution of tert-butyl 4-((1-(5-chloro-2-((2-(trimethylsilyl)ethoxy)methyl)-2H-indazol-7-yl)-2-oxoethoxy)methyl)-4-(4-fluorophenyl)piperidine-1-carboxylate (85 mg, 0.134 mmol) in dry DCM (4 ml) was slowly added DAST (0.019 ml, 0.1428 mmol). It was stirred at room temperature for 24 h. The reaction mixture was quenched with 10% sodium bicarbonate solution, the aqueous layer was extracted with dichloromethane (×2), the combined organics were dried with anhydrous magnesium sulfate, filtered and concentrated. It was purified by Biotage LC (15-32% EtOAc/Hex) to afford 36.6 mg (42%) of title compound as clear oil. LC/MS (HPLC method 3): $t_R$=4.28 min, 654.28(MH)⁺.

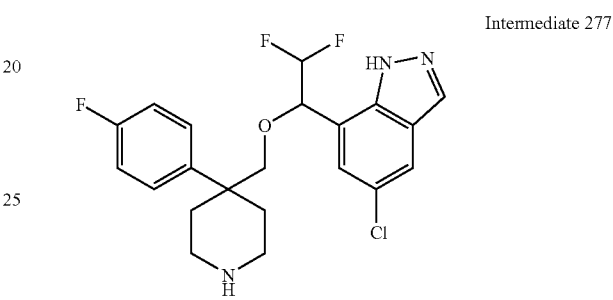

Intermediate 277

5-chloro-7-(2,2-difluoro-1-((4-(4-fluorophenyl)piperidin-4-yl)methoxy)ethyl)-1H-indazole. LC/MS (HPLC method 3): $t_R$=2.52 min, 424.17(MH)⁺.

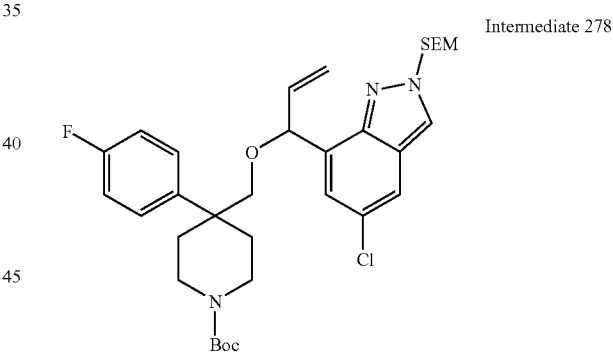

Intermediate 278 tert-butyl 4-((1-(5-chloro-2-((2-(trimethylsilyl)ethoxy)methyl)-2H-indazol-7-yl)allyloxy)methyl)-4-(4-fluorophenyl)piperidine-1-carboxylate. To a suspension of methyltriphenylphosphoniumbromide (470 mg, 1.314 mmol) in THF (17 ml) was added N-BUTYLLITHIUM (0.526 ml, 1.314 mmol). The ice bath was removed and the suspension was stirred for 10 min. To this was added tert-butyl 4-((1-(5-chloro-2-((2-(trimethylsilyl)ethoxy)methyl)-2H-indazol-7-yl)-2-oxoethoxy)methyl)-4-(4-fluorophenyl)piperidine-1-carboxylate (277 mg, 0.438 mmol) in 2.5 mL THF. The reaction was allowed to stir 1 hour before diluted with ether (100 mL) and filtered out the solid, the ether layer was washed with water, brine and dried over magnesium sulfate, filtered and concentrated. It was then purified by Biotage LC (20-25% EtOAc/Hex) to give title compound (84 mg, 0.133 mmol, 30.4% yield) as light yellow foam solid. ¹H-NMR (CDCl₃, 500 MHz) δ 7.98 (s, 1H), 7.49 (d, J=1.8 Hz, 1H), 7.29 (m, 2H), 7.00 T, J=8.8 Hz, 2H), 6.85 (s, 1H), 5.88 (ddd, J=17.2, 10.6, 5.9 Hz, 1H), 5.63(d, J=4.0 Hz, 1H), 5.60 (d, J=3.7 Hz, 1H), 5.30 (d, J=5.5 Hz, 1H), 5.23 (d, J=17.2 Hz, 1H), 5.02 (d, J=10.3 Hz, 1H), 3.69 (m, 2H), 3.58 (t, J=8.4 Hz, 2H), 3.42 (AB, Δν=28.5 Hz, J=8.8 Hz, 2H), 3.04 (m, 2H), 1.80-2.25 (m,4H), 1.41 (s, 9H), 0.88 (t, J=9.2 Hz, 2H), −0.07 (s, 9H). LC/MS (HPLC method 3): $t_R$=4.43 min, 630.3(MH)$^+$.

Intermediate 279

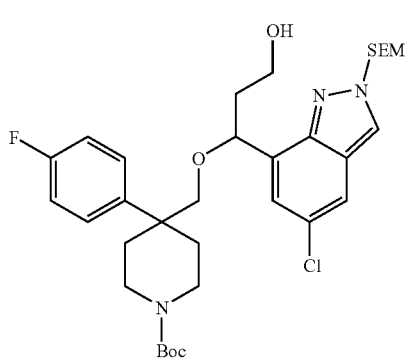

tert-butyl 4-((1-(5-chloro-2-((2-(trimethylsilyl)ethoxy)methyl)-2H-indazol-7-yl)-3-hydroxypropoxy)methyl)-4-(4-fluorophenyl)piperidine-1-carboxylate. To a solution of tert-butyl 4-((1-(5-chloro-2-((2-(trimethylsilyl)ethoxy)methyl)-2H-indazol-7-yl)allyloxy)methyl)-4-(4-fluorophenyl)piperidine-1-carboxylate (84 mg, 0.133 mmol) in tetrahydrofuran (2 mL, 0.133 mmol) at 0 C was added Borane-THF (0.267 mL, 0.267 mmol). The reaction was allowed to slowly warm to room temperature over 1.5 h. The reaction was recooled to 0 C and treated with hydrogen peroxide (30%) (1.3 mL, 0.133 mmol) followed by sodium hydroxide (0.6 mL, 2.400 mmol). After stirring for 30 min, the reaction was diluted with ether and quenched by addition of sat'd ammonium chloride. The mixture was extracted with ether, washed with brine, dried over magnesium sulfate, filtered and concentrated. It was purified by column chromatography (30% to 47% EtOAc/Hex) to give title compound (61 mg, 0.094 mmol, 70.6% yield) as white foam solid. $^1$H-NMR (CDCl$_3$, 500 MHz) δ 8.02 (s, 1H), 7.52 (d, J=1.5 Hz, 1H), 7.30 (m, 2H), 7.06 (t, J=8.8 Hz, 2H), 6.70 (bs, 1H), 5.64 (AB, Δν=17.1 Hz, J=10.7 Hz, 2H), 5.07 (t, J=6.7 Hz, 1H), 3.75 (m, 2H), 3.57 (m 2H), 3.38 (m, 2H), 2.95-3.25 (m, 2H), 2.05-2.25 (m, 2H), 1.85 (m, 2H), 1.43 (s, 9H), 0.90 (t, J=8.5 Hz, 2H), −0.06 (s, 9H). LC/MS (HPLC method 3): $t_R$=4.29 min, 648.2(MH)$^+$.

Intermediate 280

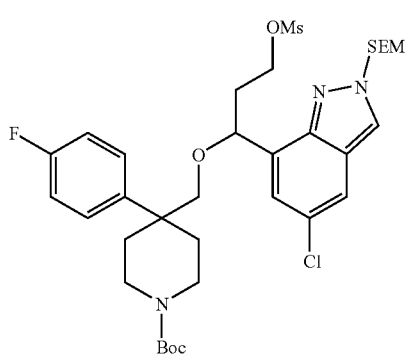

tert-butyl 4-((1-(5-chloro-2-((2-(trimethylsilyl)ethoxy)methyl)-2H-indazol-7-yl)-3-(methylsulfonyloxy)propoxy)methyl)-4-(4-fluorophenyl)piperidine-1-carboxylate. To a solution of tert-butyl 4-((1-(5-chloro-2-((2-(trimethylsilyl)ethoxy)methyl)-2H-indazol-7-yl)-3-hydroxypropoxy)methyl)-4-(4-fluorophenyl)piperidine-1-carboxylate (56 mg, 0.086 mmol) and TRIETHYLAMINE (0.036 ml, 0.259 mmol) in DCM (1.5 ml) at 0 C was added METHANESULFONYL CHLORIDE (0.013 ml, 0.173 mmol). The ice bath was removed and stirring continued for 1 h. The reaction was cooled to 0 C and quenched by addition of sat'd sodium bicarbonate. The reaction was diluted with ether and the layers separated. The ethereal was washed with brine, dried over magnesium sulfate, filtered and concentrated to give 69 mg title compound (quantitative yield). LC/MS (HPLC method 1): $t_R$=4.42 min, 726.2(MH)$^+$.

Intermediate 281

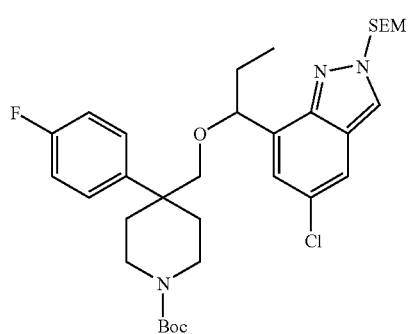

tert-butyl 4-((1-(5-chloro-2-((2-(trimethylsilyl)ethoxy)methyl)-2H-indazol-7-yl)propoxy)methyl)-4-(4-fluorophenyl)piperidine-1-carboxylate. Tert-butyl 4-((1-(5-chloro-2-((2-(trimethylsilyl)ethoxy)methyl)-2H-indazol-7-yl)-3-(methylsulfonyloxy)propoxy)methyl)-4-(4-fluorophenyl)piperidine-1-carboxylate (28.5 mg, 0.039 mmol) in THF (1 ml) at 0° C. was added Superhydride (0.059 ml, 0.059 mmol). It was stirred at R.T. over three hours, LC/MS showed no reaction. Another 1.5 eq of super hydride was added and it was stirred at R.T. overnight. LC/MS showed partial conversion to product, another 1.5eq of superhydride was added and it was stirred at R.T. overweekend. LC/MS showed the reaction was complete. The reaction was cooled to 0° C. and diluted with ether, water was added and layer separated, the organics were washed with brine and dried over magnesium sulfate, filtered and concentrated. It was purified by Biotage LC eluting with 25% EtOAc/Hex to afford title compound (15 mg, 0.024 mmol, 60.5% yield) as clear oil. $^1$H-NMR (CDCl$_3$, 500 MHz) δ 7.99 (s, 1H), 7.48 (d, J=1.6 Hz, 1H), 7.48 (d, J=1.6 Hz, 1H), 7.31 (m, 2H), 7.03 (t, J=8.9 Hz, 2H), 6.68 (s, 1H), 5.66 (AB, Δν=17.4 Hz, J=10.7 Hz, 2H), 4.77 (m, 1H), 3.72 (m, 2H), 3.59 (t, J=8.2 Hz, 2H), 3.34 (AB, Δν=23.5 Hz, J=8.8 Hz, 2H), 3.09 (m, 2H), 2.40 (m, 1H), 2.12 (m, 1H), 1.96 (m, 1H), 1.84 (m, 2H), 1.70 (m, 1H), 1.44 (s, 9H), 0.91 (m, 2H), 0.84 (t, J=7.3 Hz, 3H), −0.06 (s, 9H). LC/MS (HPLC method 4): $t_R$=4.99 min, 632.2(MH)$^+$.

Intermediates 282 and 283

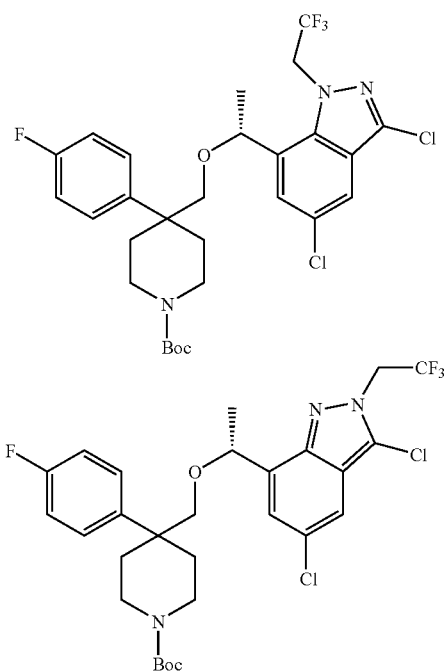

(R)-tert-butyl 4-((1-(3,5-dichloro-1-(2,2,2-trifluoroethyl)-1H-indazole-7-yl)ethoxy)methyl)-4-(4-fluorophenyl)piperidine-1-carboxylate and (R)-tert-butyl 4-((1-(3,5-dichloro-1-(2, 2,2-trifluoroethyl)-2H-indazole-7-yl)ethoxy)methyl)-4-(4-fluorophenyl)piperidine-1-carboxylate. (R)-tert-butyl 4-((1-(3,5-dichloro-1H-indazol-7-yl)ethoxy)methyl)-4-(4-fluorophenyl)piperidine-1-carboxylate (50.0 mg, 0.096 mmol) in THF (2 mL) was added POTASSIUM CARBONATE (132 mg, 0.957 mmol) and stirred at room temperature for 20 min. Trifluoromethanesulfonic acid 2,2,2-trifluoroethyl ester (0.028 mL, 0.191 mmol) was then added and the mixture was stirred at room temperature for five hours, LC/MS showed no reaction. The reaction was again stirred at rt over the weekend. LC/MS showed major product along with S.M. Ice water was added to the reaction mixture and extracted with EtOAc. The organics were washed with brine, dried over MgSO4, filtered and concentrated. The crude product was purified by prep plate (silica gel 60 $F_{254}$, 20×20 cm, 0.5 mm) eluting with 7% EtOAc/DCM to afford (R)-tert-butyl 4-((1-(3,5-dichloro-1-(2,2,2-trifluoroethyl)-1H-indazole-7-yl)ethoxy)methyl)-4-(4-fluorophenyl)piperidine-1-carboxylate (21 mg, 0.035 mmol, 36.3% yield) as clear oil, and (R)-tert-butyl 4-((1-(3,5-dichloro-1-(2,2,2-trifluoroethyl)-2H-indazole-7-yl)ethoxy)methyl)-4-(4-fluorophenyl)piperidine-1-carboxylate (21 mg, 0.035 mmol, 36.3% yield) as clear oil. LC/MS (HPLC method 1): $t_R$=4.58 min, 604.4 (MH)+. (R)-tert-butyl 4-((1-(3,5-dichloro-1-(2,2,2-trifluoroethyl)-1H-indazole-7-yl)ethoxy)methyl)-4-(4-fluorophenyl)piperidine-1-carboxylate. $^1$H-NMR (CDCl$_3$, 500 MHz) δ 7.58 (d, J=1.8 Hz, 1H), 7.15 (m, 3H), 6.98 (t, J=8.5 Hz, 2H), 4.80 (m, 2H), 4.65 (m, 1H), 3.68 (bs, 2H), 3.29 (d, J=9.1 Hz, 1H), 3.08 (d, J=8.8 Hz, 1H), 3.01 (m, 2H), 2.08 (m, 2H), 1.73 (m, 2H), 1.50 (d, J=6.7 Hz, 3H), 1.43 (s, 9H).

(R)-tert-butyl 4-((1-(3,5-dichloro-1-(2,2,2-trifluoroethyl)-2H-indazole-7-yl)ethoxy)methyl)-4-(4-fluorophenyl)piperidine-1-carboxylate. $^1$H-NMR (CDCl$_3$, 500 MHz) δ 7.39 (d, J=1.8 Hz, 1H), 7.30 (m, 2H), 7.03 (t, J=8.6 Hz, 2H), 6.78 (s, 1H), 4.98 (q, J=8.0 Hz, 2H), 4.82 (q, J=6.4 Hz, 1H), 3.72 (bs, 2H), 3.35 (AB, Δv=14.0 Hz, J=9.1 Hz, 2H), 2.95-3.12 (m, 2H), 2.19 (m, 1H), 2.08 (m, 1H), 1.92 (m, 1H), 1.85 (m, 1H), 1.44 (s, 9H), 1.41 (d, J=6.4 Hz).

Intermediate 284

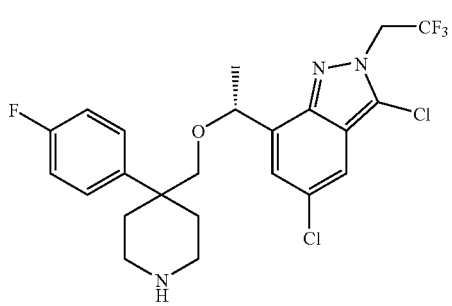

(R)-3,5-dichloro-7-(1-((4-(4-fluorophenyl)piperidine-4-yl)methoxy)ethyl)-2-(2,2,2-trifluoroethyl)-2H-indazole. LC/MS (HPLC method 1): $t_R$=2.34 min, 503.93(MNa).

Intermediate 285

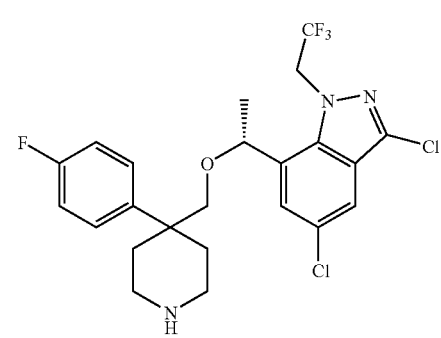

(R)-3,5-dichloro-7-(1-((4-(4-fluorophenyl)piperidine-4-yl)methoxy)ethyl)-2-(2,2,2-trifluoroethyl)-1H-indazole. LC/MS (HPLC method 1): $t_R$=2.4 min, 503.92(MNa).

Intermediate 286

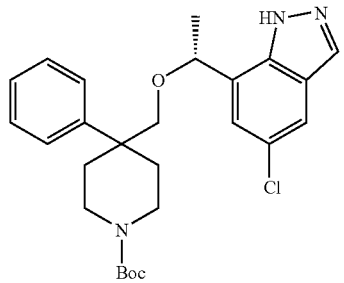

Chiral separation of tert-butyl 4-((1-(5-chloro-1H-indazole-7-yl)ethoxy)methyl)-4-phenylpiperidine-1-carboxylate (430 mg) to give 210 mg of (S)-tert-butyl 4-((1-(5-chloro-1H-indazole-7-yl)ethoxy)methyl)-4-phenylpiperidine-1-carboxylate (peak #1, 10.67 min), and 220 mg of (R)-tert-butyl 4-((1-(5-chloro-1H-indazole-7-yl)ethoxy)methyl)-4-phenylpiperidine-1-carboxylate (peak #2, 14.7 min). Chiral separation Method: Chiral OD-H analytical column, 4.6×250 mm, 5 μm; Mobile Phase: 10% MeOH (0.1% DEA) in CO2;

Temp: 35° C.; Flow rate: 2.0 mL/min. for 20 min; UV monitored @ 220 nm; Stacked Injection: 5 μL of ~2 mg/mL solution in MeOH.

Intermediate 287

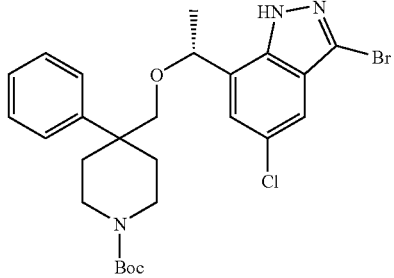

(R)-tert-butyl 4-((3-bromo-5-chloro-1H-indazol-7-yl)ethoxy)methyl)-4-phenylpiperidine-1-carboxylate. To a solution of (R)-tert-butyl 4-((1-(5-chloro-1H-indazole-7-yl)ethoxy)methyl)-4-phenylpiperidine-1-carboxylate (101 mg, 0.215 mmol) and NBS (40.2 mg, 0.226 mmol) in CHLOROFORM (2.5 mL, 31.0 mmol) at 0 C was added silica gel (65 mg). The ice bath was removed and stirring continued for 2 h. LC/MS showed the reaction complete. The reaction was filtered to remove the silica gel and treated with sat'd sodium thiosulfate. The reaction was stirred for 15 min and poured into ether. The ethereal was washed with saturated NaHCO3 then brine, dried over MgSO4, filtered and concentrated. The crude product was purified by silica gel column chromatography (18%-30% EtOAc/Hex) to give title compound (104 mg, 0.189 mmol, 88% yield) as clear oil. $^1$H-NMR (CDCl$_3$, 500 MHz) δ 7.43 (d, J=1.53 Hz, 1H), 7.40 (m, 2H), 7.36 (m, 1H), 7.30 (m, 2H), 7.0 (d, J=1.53 Hz, 1H), 4.5 (q, J=6.71 Hz, 1H), 3.85-3.66 (m, 2H), 3.43 (d, J=8.85 Hz, 1H), 3.29 (d, J=8.85 Hz, 1H), 3.09-2.97 (m, 2H), 2.32 (m, 1H), 2.11 (m, 1H), 1.81 (m, 1H), 1.80 (m, 1H), 1.43 (s, 9H), 1.39 (d, J=6.41 Hz, 3H); $^{13}$C-NMR (CDCl$_3$, 126 MHz) δ 155.0, 142.2, 136.9, 129.0, 128.3, 127.3, 127.0, 125.3, 124.7, 121.8, 118.4, 79.5, 79.0, 78.0, 60.44, 41.5, 32.38, 32.18, 28.55, 22.1, 21.1, 12.3. LC/MS (HPLC method 1): $t_R$=3.73 min, 571.8(MNa).

Intermediate 288

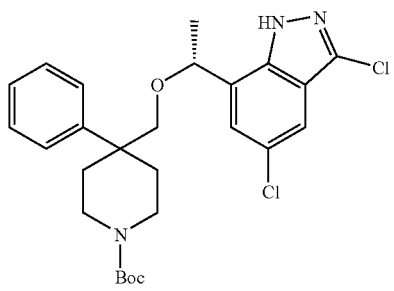

(R)-tert-butyl 4-((3,5-dichloro-1H-indazol-7-yl)ethoxy)methyl)-4-phenylpiperidine-1-carboxylate. $^1$H-NMR (CDCl$_3$, 500 MHz) δ 7.48 (d, J=1.53 Hz, 1H), 7.40 (m, 2H), 7.35 (m, 1H), 7.30 (m, 2H), 7.0 (d, J=1.83 Hz, 1H), 4.51 (q, J=6.71 Hz, 1H), 3.76 (m, 2H), 3.43 (d, J=8.85 Hz, 1H), 3.30 (d, J=8.85 Hz, 1H), 3.09-2.97 (m, 2H), 2.32 (m, 1H), 2.10 (m, 1H), 1.82 (m, 1H), 1.80 (m, 1H), 1.43 (s, 9H), 1.40 (d, J=6.41 Hz, 3H); $^{13}$C-NMR (CDCl$_3$, 126 MHz) δ 155.04, 142.2, 137.0, 134.2, 129.0, 128.4, 127.2, 127.0, 125.2, 122.1, 117.7, 79.5, 79.0, 60.4, 41.5, 32.4, 32.2, 28.6, 22.1, 21.1, 14.3. LC/MS (HPLC method 1): $t_R$=3.73 min, 525.8(MH)$^+$.

Intermediate 289

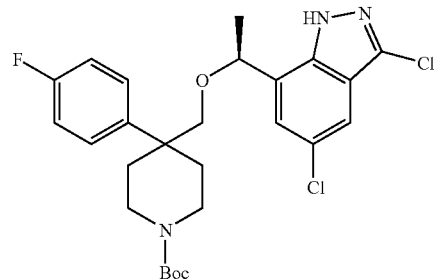

(S)-tert-butyl 4-((1-(3,5-dichloro-1H-indazole-7-yl)ethoxy)methyl)-4-(4-fluorophenyl)piperidine-1-carboxylate. $^1$H-NMR (CDCl$_3$, 500 MHz) δ 9.40 (bs, 1H), 7.50 (d, J=1.8 Hz, 1H), 7.23 (m, 2H), 7.06 (t, J=8.4 Hz, 2H), 7.00 (d, J=1.8 Hz, 1H), 4.47 (q, J=6.6 Hz, 1H), 3.72 (m, 2H), 3.31 (AB, Δv=40.3 Hz, J=8.8 Hz, 2H), 3.00 (m, 2H), 2.23 (m, 1H), 2.07 (m, 1H), 1.70-1.85 (m, 2H), 1.40 (s, 9H), 1.40 (buried, 1H). LC/MS (HPLC method 3): $t_R$=4.25 min, 522.1(MH)$^+$.

Intermediate 290

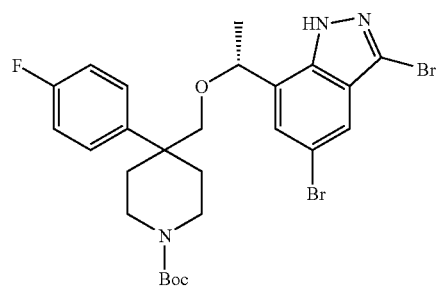

Chiral separation of tert-butyl 4-((1-(3,5-dibromo-1H-indazole-7-yl)ethoxy)methyl)-4-(4-fluorophenyl)piperidine-1-carboxylate (231 mg) to gave 92 mg of (S)-tert-butyl 4-((1-(3,5-dibromo-1H-indazole-7-yl)ethoxy)methyl)-4-(4-fluorophenyl)piperidine-1-carboxylate (peak #1, 17.73 min), and 99 mg of (R)-tert-butyl 4-((1-(3,5-dibromo-1H-indazole-7-yl)ethoxy)methyl)-4-(4-fluorophenyl)piperidine-1-carboxylate (peak #2, 21.3 min). Chiral separation Method: Chiral OD-H analytical column, 4.6×250 mm, 5 μm; Mobile Phase: 10% MeOH in CO2; Temp: 35° C.; Flow rate: 2.0 mL/min. for 26 min; UV monitored @ 220 nm; Stacked Injection: 5 μL of ~1 mg/mL solution in MeOH.

Intermediate 291

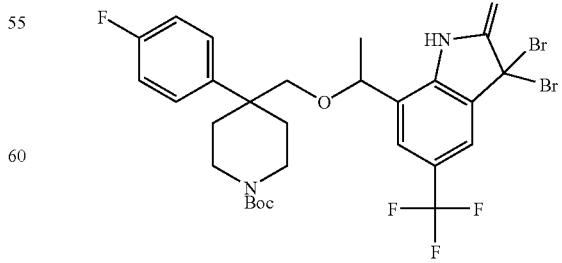

(±)-tert-butyl 4-((1-(3, 3-dibromo-2-oxo-5-(trifluoromethyl)indolin-7-yl)ethoxy)methyl)-4-(4-fluorophenyl)piperidine-1-carboxylate. To a solution of tert-butyl 4-(4-fluorophenyl)-4-((1-(5-(trifluoromethyl)-1H-indol-7-yl)ethoxy)methyl)piperidine-1-carboxylate (intermediate 166) (71.3 mg, 0.137 mmol) in tert-butanol (2 mL) and water (0.800 mL) was added NBS (60.9 mg, 0.342 mmol). The mixture was stirred at room temperature. After 17 hours LC/MS showed desired as major product. The mixture was concentrated to an orange glass that was purified on SiO2 (4 g) eluting with 20% ethyl acetate/hexane. The product was obtained as a slightly reddish clear oil (36.5 mg, 0.053 mmol, 38%). $^1$H-NMR (CDCl$_3$, 400 MHz) δ 7.68 (s, 1H), 7.38-7.44 (m, 1H), 7.22-7.29 (m, 2H), 7.17 (s, 1H), 7.09 (t, J=8.56 Hz, 2H), 4.36 (q, J=6.55 Hz, 1H), 3.63-3.80 (m, 2H), 3.40 (d, J=9.07 Hz, 1H), 3.29 (t, J=8.81 Hz, 1H), 3.02-3.11 (m, 1H), 2.91-3.02 (m, 1H), 2.23-2.32 (m, 1H), 2.01-2.10 (m, 1H), 1.79 (ddd, J=14.04, 10.89, 4.03 Hz, 1H), 1.63-1.73 (m 1H), 1.42 (s, 9H), 1.32 (d, J=6.55 Hz, 3H); Mass spec. (M-H)$^-$: 693.5.

Intermediate 292

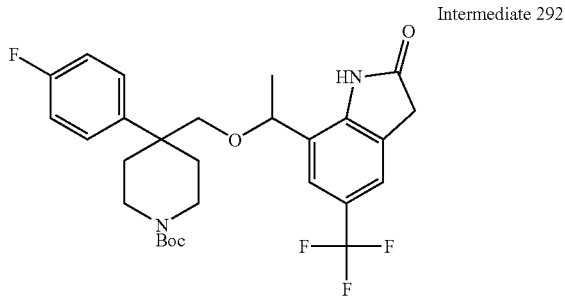

(±)-tert-butyl 4-(4-fluorophenyl)-4-((1-(2-oxo-5-(trifluoromethyl)indolin-7-yl)ethoxy)methyl)piperidine-1-carboxylate. To a solution of tert-butyl 4-((1-(3,3-dibromo-2-oxo-5-(trifluoromethyl)indolin-7-yl)ethoxy)methyl)-4-(4-fluorophenyl)piperidine-1-carboxylate (27.9 mg, 0.040 mmol) in acetic acid (500 µL) cooled briefly in a cold water bath was added zinc dust <10 micron (18 mg, 0.275 mmol). TLC (30% ethyl acetate/hexanes) after 15 minutes showed complete conversion of starting material. After 45 minutes the mixture was filtered through celite with ethyl acetate and concentrated. The crude material was purified on SiO$_2$ eluting with 30% ethyl acetate/hexanes to give the product (13.3 mg, 0.025 mmol, 62%) as a clear oil. $^1$H-NMR (CDCl$_3$, 400 MHz) δ 7.55-7.62 (m, 2H), 7.32 (s, 1H), 7.20-7.28 (m, 2H), 7.11 (s, 1H), 7.04 (t, J=8.69 Hz, 2H), 4.28 (q, J=6.55 Hz, 1H), 3.64-3.81 (m, 2H), 3.42 (s, 2H), 3.23-3.36 (m 2H), 2.88-3.08 (m, 2H), 2.16-2.25 (m, 1H), 2.04-2.12 (m, 1H), 1.67-1.85 (m, 1H), 1.57-1.64 (m, 1H), 1.42 (s, 9H), 1.29 (d, J=6.55 Hz, 3H); Mass spec. (M-H)$^-$: 535.6.

Intermediate 293

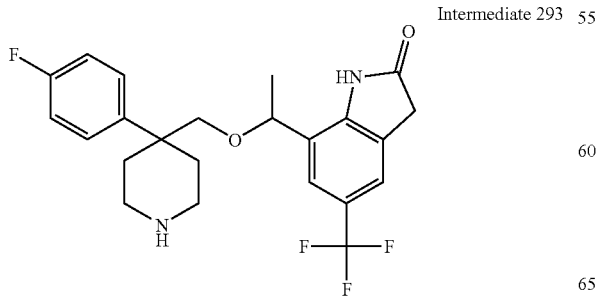

(±)-7-(1-((4-(4-fluorophenyl)piperidin-4-yl)methoxy)ethyl)-5-(trifluoromethyl)indolin-2-one. To a solution of tert-butyl 4-(4-fluorophenyl)-4-((1-(2-oxo-5-(trifluoromethyl)indolin-7-yl)ethoxy)methyl)piperidine-1-carboxylate (13 mg, 0.024 mmol) in dichloromethane (1.5 mL) at ice bath temperature was added TFA (200 µL, 2.60 mmol). The mixture was stirred at this temperature for 1 hour. TLC (30% ethyl acetate/hexanes) indicated complete conversion of starting material. The mixture was concentrated and the crude residue was loaded onto an SCX cartridge (Phenomenex Strata X-C 200mg) with methanol then the resin was washed with methanol and the compound eluted with 2N NH$_3$ in methanol to give the product (10.2 mg, 0.023 mmol, 96%) as a clear pale yellow film. $^1$H-NMR (CDCl$_3$, 400 MHz) δ 7.57-7.88 (m, 1H), 7.32 (s, 1H), 7.21-7.29 (m, 2H), 7.11 (s, 1H), 7.03 (t, J=8.69 Hz, 2H), 4.28 (q, J=6.55 Hz, 1H), 3.42 (s, 2H), 3.31-3.36 (m, 1H), 3.24-3.30 (m, 1H), 2.83-2.96 (m, 2H), 2.63-2.80 (m, 2H), 2.17 (ddd, J=13.72, 2.27 Hz, 1H), 2.06 (dt, J=13.60, 2.27 Hz, 1H), 1.74-1.91 (m, 2H), 1.29 (d, J=6.55 Hz, 3H). Mass spec. (M-H)$^-$: 435.5, (MH)$^+$: 437.3.

Intermediate 294

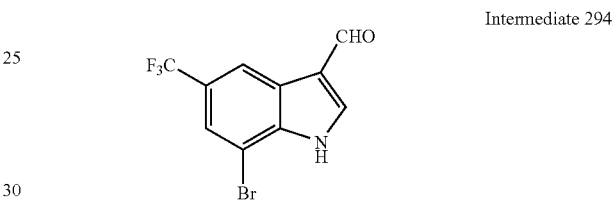

7-bromo-5-(trifluoromethyl)-1H-indole-3-carbaldehyde. Phosphorus oxychloride (1.029 ml, 11.04 mmol) was added dropwise to DMF (8 ml) at 0° C. The mixture was stirred 30 min at 0° C. and 7-bromo-5-(trifluoromethyl)-1H-indole (2.65 g, 10.04 mmol) in DMF (2 mL) was added dropwise. The cooling bath was removed and the reaction was stirred at ambient temperature for 3 hours. The reaction was quenched with ice (5 g) and aqueous sodium hydroxide (1N, 20 mL). The reaction was extracted with ethyl acetate (2×30 mL) and the organic phase was dried with MgSO$_4$ and evaporated. The residue was purified by chromatography on SiO$_2$ with a 5%-60% gradient of ethyl acetate/hexanes. The product 7-bromo-5-(trifluoromethyl)-1H-indole-3-carbaldehyde (2.17 g, 7.43 mmol, 74.0% yield) was obtained as a white solid. $^1$H-NMR (CDCl$_3$, 400 MHz) δ 10.09 (s, 1H), 9.06 (s, 1H), 8.59 (s, 1H), 8.00 (d, J=3.2 Hz, 1H), 7.72 (d, J=3.0 Hz, 1H). LC/MS (HPLC method 4): t$_R$=3.29 min, 292.06(MH)$^+$.

Intermediate 295

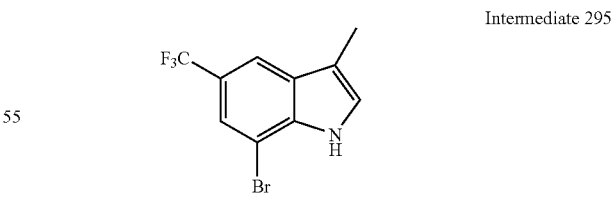

7-bromo-3-methyl-5-(trifluoromethyl)-1H-indole. Lithium aluminum hydride (16.98 ml, 16.98 mmol) was added to a −40° C. solution of 7-bromo-5-(trifluoromethyl)-1H-indole-3-carbaldehyde (1.24 g, 4.25 mmol) in THF (10 ml). The reaction was stirred between −30° C and −10° C. for 40 min and was quenched with saturated aqueous ammonium chloride (1 mL) and filtered through celite and washed with ethyl acetate (20 mL). The filtrate was evaporated and the residue was purified by chromatography on SiO$_2$ with a gradient of 4% to 30% ethyl acetate/hexanes. The product 7-bromo-3-methyl-5-(trifluoromethyl)-1H-indole (677 mg, 2.435 mmol, 57.3% yield) was obtained as a white solid. $^1$H-NMR (CDCl$_3$, 400 MHz) δ 8.35 (s, 1H), 7.80(d, J=1.2 Hz, 1H), 7.57 (d, J=0.9 Hz, 1H), 7.12,(q, J=1.2 Hz, 1H), 2.33(d, J=1.2 Hz, 3H). LC (HPLC method 4): t$_R$=3.45 min.

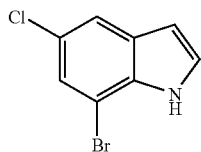

Intermediate 296

7-bromo-5-chloro-1H-indole. Made from 2-bromo-4-chloroaniline using the method for 7-bromo-5-(trifluoromethyl)-1H-indole. $^1$H-NMR (CDCl$_3$, 400 MHz) δ 8.32 (bs, 1H), 7.55 (d, J=1.2 Hz, 1H), 7.55 (d, J=1.8 Hz, 1H), 7.27 (t, J=3.0 Hz, 1H), 6.56 (dd, J=3.3, 2.3 Hz, 1H). LC/MS (HPLC method 4): t$_R$=3.07 min, 229.95(MH)$^+$.

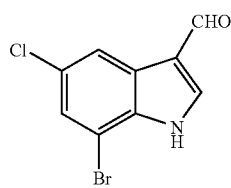

Intermediate 297

7-bromo-5-chloro-1H-indole-3-carbaldehyde. Phosphorus oxychloride (3.11 mL, 33.4 mmol) was added dropwise to a 0° C sample of DMF (30 mL). The reaction was stirred 30 min at 0° C., then 7-bromo-5-chloro-1H-indole (7.0 g, 30.4 mmol) in DMF (5 mL)was added and the reaction was warmed to ambient temperature and stirred 20 hours. Ice water (300 mL) was added, and the resulting thick solid was filtered. The product was detected by TLC in both filtrate and cake. Cake and filtrate were combined, and sodium hydroxide (10N) was added until most solids disappeared, then the mixture was extracted with ethyl acetate (4×100 mL). The organic layers were dried with MgSO$_4$ and evaporated to a solid that weighed 10.5 g. The residue was dissolved in 400 mL boiling ethyl acetate, the insoluble material was filtered away and the filtrate was evaporated. 7-bromo-5-chloro-1H-indole-3-carbaldehyde (6.45 g, 24.95 mmol, 82% yield) was obtained as an off-white solid. $^1$H-NMR (CDCl$_3$, 400 MHz) δ 9.99 (s, 1H), 8.35 (s, 1H), 8.32 (s, 1H), 7.92 (s, 1H), 7.47 (d, J=2.0 Hz, 1H). LC/MS (HPLC method 4): t$_R$=2.87 min, 257.91(MH)$^+$.

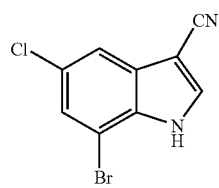

Intermediate 298

7-bromo-5-chloro-1H-indole-3-carbonitrile. A mixture of 7-bromo-5-chloro-1H-indole-3-carbaldehyde (0.80 g, 3.09 mmol), Ammonium phosphate, dibasic (1.269 mL, 15.47 mmol), and 1-nitropropane (0.276 mL, 3.09 mmol) in Acetic Acid (20 mL) was heated at reflux. The solvent was evaporated, the residue was taken up in aqueous sodium bicarbonate (300 mL) and extracted with ethyl acetate (3×20 mL). The organic layers were dried with MgSO$_4$ and evaporated. The residue was purified by chromatography on SiO$_2$ with 20%-25% ethyl acetate/hexanes to give 7-bromo-5-chloro-1H-indole-3-carbonitrile (0.43 g, 1.683 mmol, 54.4% yield) as a yellow solid. $^1$H-NMR (CDCl$_3$, 400 MHz) δ 8.27 (bs, 1H), 7.79 (s, 1H), 7.72 (d, J=1.8 Hz, 1H), 7.49 (d, J=1.8 Hz, 1H). LC/MS (HPLC method 4): t$_R$=3.12 min, 255.01(MH)$^+$.

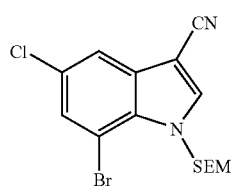

Intermediate 299

7-bromo-5-chloro-1-((2-(trimethylsilyl)ethoxy)methyl)-1H-indole-3-carbonitrile. Sodium hydride (0.081 g, 2.020 mmol) (60% in oil) was added slowly to a 0° C. solution of 7-bromo-5-chloro-1H-indole-3-carbonitrile (0.43 g, 1.683 mmol) in THF (10 mL). Bubbling occurred, and the reaction was stirred at 0° C. for 30 min, then 2-(Trimethylsilyl)ethoxymethyl chloride (0.418 mL, 2.356 mmol) was added. After stirring 30 min at ambient temperature, the reaction was quenched with aqueous sodium bicarbonate (10 mL) and extracted with ethyl acetate (2×20 mL). The organic layer was dried with MgSO$_4$ and evaporated, and the residue was purified by chromatography on SiO$_2$ with 5% ethyl acetate/hexanes to give 7-bromo-5-chloro-1-((2-(trimethylsilyl)ethoxy)methyl)-1H-indole-3-carbonitrile (620 mg, 1.607 mmol, 95% yield) as a yellow solid. $^1$H-NMR (CDCl$_3$, 400 MHz) δ 7.71 (s, 1H), 7.69 (d, J=2.0 Hz, 1H), 7.53 (d, J=2.0 Hz, 1H), 5.82 (s, 2H), 3.52 (app T, J=8.1 Hz, 2H), 0.90 (app t, J=8.2 Hz, 2H), −0.05 (s, 9H). LC/MS (HPLC method 4): t$_R$=4.07 min, 385.4(MH)+.

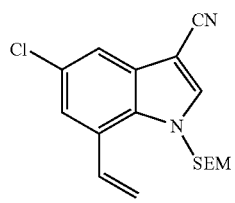

Intermediate 300

5-chloro-1-((2-(trimethylsilyl)ethoxy)methyl)-7-vinyl-1H-indole-3-carbonitrile. A solution of 7-bromo-5-chloro-1-((2-(trimethylsilyl)ethoxy)methyl)-1H-indole-3-carbonitrile (620 mg, 1.607 mmol), Potassium vinyltrifluoroborate (237 mg, 1.768 mmol), and triethylamine (0.672 mL, 4.82 mmol) in 2-Propanol (50 mL) and Water (25 mL) was degassed with nitrogen for 10 min, then 1,1'-Bis(diphenylphosphino)ferrocene-palladium(II)dichloride dichloromethane complex (66.1 mg, 0.080 mmol) was added and the reaction was sealed and heated at 90° C. for 2.5 hours. TLC indicated starting material was consumed and one major product plus byproducts were produced. The reaction was evaporated to remove most of the solvent, then the reaction was taken up in brine (10 mL) and extracted with ethyl acetate (3×10 mL). The organic layer was dried with MgSO₄ and evaporated. The residue was purified by chromatography on SiO₂ with 10% ethyl acetate/hexanes to give product 5-chloro-1-((2-(trimethylsilyl)ethoxy)methyl)-7-vinyl-1H-indole-3-carbonitrile (389 mg, 1.169 mmol, 72.7% yield) as a yellow oil which crystallized to a yellow solid. $^1$H-NMR (CDCl₃, 400 MHz) δ 7.65 (d, J=2.0 Hz, 1H), 7.60 (s, 1H), 7.42 (dd, J=17.1, 10.8 Hz, 1H), 7.33 (d, 2.0 Hz, 1H), 5.71 (dd, J=17.2, 1.3 Hz, 1H), 5.48 (s, 2H), 5.47 (dd, J=10.8, 1.3 Hz, 1H), 3.51 (app t, J=8.0 Hz, 2H), 0.90 (app t, J=8.0 Hz, 2H), −0.05 (s, 9H). LC/MS (HPLC method 4): $t_R$=4.30 min, 333.13(MH)+.

with ethyl acetate (3×20 mL). The organic layers were washed with brine (20 mL), dried with MgSO₄ and evaporated. The residue was purified by chromatography on SiO₂ with 20% ethyl acetate/hexanes to provide (±)-5-chloro-7-(1-hydroxyethyl)-1-((2-(trimethylsilyl)ethoxy)methyl)-1H-indole-3-carbonitrile (224 mg, 0.638 mmol, 70.1% yield) as a clear oil. $^1$H-NMR (CDCl₃, 400 MHz) δ 7.66 (d, J=2.0 Hz, 1H), 7.62 (s, 1H), 7.47 (d, J=2.0 Hz, 1H), 5.83 (d, J=11.3 Hz, 1H), 5.56 (pentet, J=6.3 Hz, 1H), 5.48 (d, J=11.3 Hz, 1H), 3.46 (app t, J=8.5 Hz, 2H), 2.27 (d, J=6.1 Hz, 1H), 1.66 (d, J=6.5 Hz, 3H), 0.86 (app t, J=8.3 Hz, 2H), −0.07 (s, 9H). LC/MS (HPLC method 4): $t_R$=3.57 min, 373.16(MNa)+.

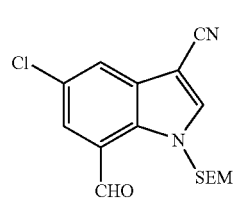

Intermediate 301

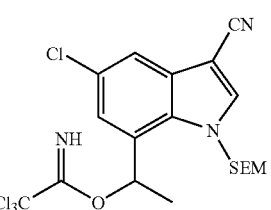

Intermediate 303

5-chloro-7-formyl-1-((2-(trimethylsilyl)ethoxy)methyl)-1H-indole-3-carbonitrile. Osmium tetroxide (0.1 mL, 0.013 mmol) (4% in water) was added to a solution of 5-chloro-1-((2-(trimethylsilyl)ethoxy)methyl)-7-vinyl-1H-indole-3-carbonitrile (385 mg, 1.157 mmol) and NMO (271 mg, 2.313 mmol) in Acetone (20 mL) and Water (5 mL). The reaction was stirred at ambient temperature for 2 hours and then THF (10 mL) and sodium periodate (742 mg, 3.47 mmol) were added. The reaction was stirred for 1 hour, and precipitate formed. The solvent was evaporated and the residue was taken up in water (100 mL) and extracted with ethyl acetate (3×20 mL). The organic layers were dried with MgSO₄ and evaporated. The residue was purified by chromatography on SiO₂ with 10% to 15% ethyl acetate/hexanes to give 5-chloro-7-formyl-1-((2-(trimethylsilyl)ethoxy)methyl)-1H-indole-3-carbonitrile (310 mg, 0.926 mmol, 80% yield) as a white solid. $^1$H-NMR (CDCl₃, 400 MHz) δ 10.22 (s, 1H), 8.0 (d, J=2.0 Hz, 1H), 7.84 (d, J=2.0 Hz, 1H), 7.79 (s, 1H), 5.80 (s, 2H), 3.43 (app T, J=8.2 Hz, 2H), 0.84 (app t, J=8.2 Hz, 2H), −0.07 (s, 9H). LC (HPLC method 4): $t_R$=3.68 min.

(±)-1-(5-chloro-3-cyano-1-((2-(trimethylsilyl)ethoxy)methyl)-1H-indol-7-yl)ethyl 2,2,2-trichloroacetimidate. DBU (0.020 mL, 0.130 mmol) was added to a solution of (±)-5-chloro-7-(1-hydroxyethyl)-1-((2-(trimethylsilyl)ethoxy)methyl)-1H-indole-3-carbonitrile (456 mg, 1.299 mmol) and Trichloroacetonitrile (0.391 mL, 3.90 mmol) in THF (10 mL) and the reaction was stirred for one hour. The solvent was evaporated and the reaction was purified by chromatography on SiO₂ with 10:89:1 ethyl acetate/hexanes/triethylamine to give (±)-1-(5-chloro-3-cyano-1-((2-(trimethylsilyl)ethoxy)methyl)-1H-indol-7-yl)ethyl 2,2,2-trichloroacetimidate (472 mg, 0.953 mmol, 73.3% yield) as a clear oil. $^1$H-NMR (CDCl₃, 400 MHz) δ 8.22 (s, 1H), 7.66 (d, J=2.0 Hz, 1H), 7.61 (s, 1H), 7.52 (d, J=2.0 Hz, 1H), 6.60 (q, J=6.3 Hz, 1H), 6.27 (d, J=11.3 Hz, 1H), 5.25 (d, J=11.3 Hz, 1H), 3.48 (m, 2H), 1.72 (d, J=6.3 Hz, 3H), 0.80-1.05 (m, 2H), −0.02 (s, 9H).

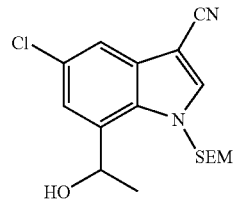

Intermediate 302

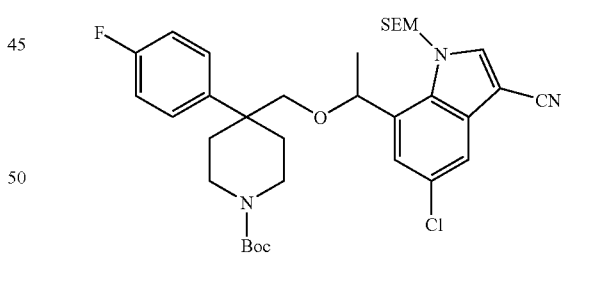

Intermediate 304

(±)-5-chloro-7-(1-hydroxyethyl)-1-((2-(trimethylsilyl)ethoxy)methyl)-1H-indole-3-carbonitrile. Methylmagnesium bromide (0.334 mL, 1.002 mmol) was added to a −20° C. solution of 5-chloro-7-formyl-1-((2-(trimethylsilyl)ethoxy)methyl)-1H-indole-3-carbonitrile (305 mg, 0.911 mmol) in THF (10 mL). The reaction was stirred 1 hour at −20° C., and TLC indicated that reaction was about 50% complete and no longer progressing. More methylmagnesium bromide (0.304 mL, 0.911 mmol) was added and the reaction was stirred an additional 1 hour at −20° C. The reaction was quenched by addition of HCL(1N, 10 mL) and then water (30 mL) was added and the reaction was extracted (±)-tert-butyl 4-((1-(5-chloro-3-cyano-1-((2-(trimethylsilyl)ethoxy)methyl)-1H-indol-7-yl)ethoxy)methyl)-4-(4-fluorophenyl)piperidine-1-carboxylate. Fluoroboric acid diethylether complex (0.015 g, 0.095 mmol) was added to a 0° C. solution of (±)-1-(5-chloro-3-cyano-1-((2-(trimethylsilyl)ethoxy)methyl)-1H-indol-7-yl)ethyl 2,2,2-trichloroacetimidate (0.945 g, 1.907 mmol) and tert-butyl 4-(4-fluorophenyl)-4-(hydroxymethyl)piperidine-1-carboxylate (0.59 g, 1.907 mmol) in Dichloromethane (10 mL) and was stirred for 20 min at 0° C. TLC indicated the reaction was complete, and the reaction was quenched with aqueous sodium bicarbonate (10 mL). The reaction was extracted with ethyl acetate (3×10 mL) and the organic phase was dried with MgSO₄ and evaporated. The residue was purified by chromatography on SiO$_2$ with 15%-20% ethyl acetate/hexanes to give (±)-tert-butyl 4-((1-(5-chloro-3-cyano-1-((2-(trimethylsilyl)ethoxy)methyl)-1H-indol-7-yl)ethoxy)methyl)-4-(4-fluorophenyl)piperidine-1-carboxylate (466 mg, 0.726 mmol, 38.0% yield) as a white solid. $^1$H-NMR (CDCl$_3$, 400 MHz) δ 7.60 (d, J=2.0 Hz, 1H), 7.49 (s, 1H), 7.15 (m, 2H), 7.05 (d, J=2.0 Hz, 1H), 6.94 (app t, J=8.6 Hz, 2H), 5.22 (m, 2H), 5.07 (m, 1H), 3.66 (m, 2H), 3.33 (app t, J=8.3 Hz, 2H), 3.22 (d, J=8.8 Hz, 1H), 3.11 (d, J=8.8 Hz, 1H), 3.02 (m, 2H), 2.07 (m, 2H), 1.79 (m, 2H), 1.42 (d, J=6.3 Hz, 3H), 0.65-0.90 (m, 2H), −0.08 (s, 9H).

Intermediate 305

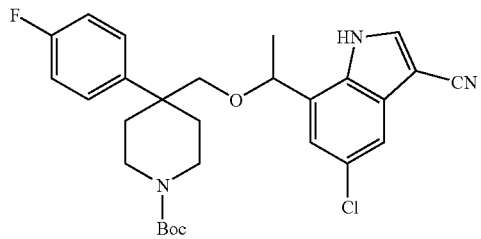

(±)-tert-butyl 4-((1-(5-chloro-3-cyano-1H-indol-7-yl)ethoxy)methyl)-4-(4-fluorophenyl)piperidine-1-carboxylate. A solution of (±)-tert-butyl 4-((1-(5-chloro-3-cyano-1-((2-(trimethylsilyl)ethoxy)methyl)-1H-indol-7-yl)ethoxy)methyl)-4-(4-fluorophenyl)piperidine-1-carboxylate (406 mg, 0.632 mmol) and TBAF (4 mL, 4.00 mmol) (1M in THF) in THF (10 mL) was heated at reflux for 8 hours then cooled to ambient temperature and the solvent was evaporated. Purified on SiO$_2$ column with 50% ethyl acetate/hexanes to obtain (±)-tert-butyl 4-((1-(5-chloro-3-cyano-1H-indol-7-yl)ethoxy)methyl)-4-(4-fluorophenyl)piperidine-1-carboxylate (231 mg, 0.451 mmol, 71.4% yield) as a clear foam. $^1$H-NMR (CDCl$_3$, 400 MHz) δ 8.11 (bs, 1H), 7.57 (d, J=1.9 Hz, 1H), 7.27 (m, 2H), 7.11 (m, 2H), 7.10 (s, 1H), 4.54 (q, J=6.5 Hz, 1H), 3.7 (m, 2H), 3.43 (d, J=8.8 Hz, 1H), 3.20 (d, J=8.6 Hz, 1H), 3.10 (t, J=7.5 Hz, 1H), 2.97 (t, J=10.1 Hz, 1H), 2.38 (m, 2H), 1.80-2.00 (m, 2H), 1.64 (m, 1H), 1.40 (s, 3H). LC/MS (HPLC method 4): $t_R$=4.02 min, 534.13(MNa)+.

Intermediate 306

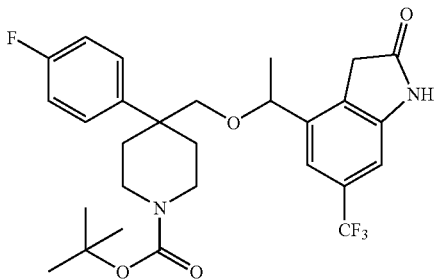

(±)-tert-butyl 4-(4-fluorophenyl)-4-((1-(2-oxo-6-(trifluoromethyl)indolin-4-yl)ethoxy)methyl)piperidine-1-carboxylate. To a 7 mL vial was added tert-butyl 4-(4-fluorophenyl)-4-((1-(6-(trifluoromethyl)-1H-indol-4-yl)ethoxy)methyl) piperidine-1-carboxylate (29 mg, 0.056 mmol) in t-butanol (0.5 mL) and water (0.2 mL). The solution was stirred at rt and then N-BROMOSUCCINIMIDE (9.92 mg, 0.056 mmol) was added and the reaction was allowed to stir at rt for 72 hr. The reaction mixture was diluted with ethyl acetate and washed with water. The organic layer was separated, washed with brine and dried over Na2SO4. The solvent was evaporated in vacuo and the resulting crude oil was purified by silica gel chromatography 4:1 Hexanes:Ethyl Acetate affording 11 mg (37% yield) of the desired oxindole. $^1$H-NMR (CDCl$_3$, 400 MHz) δ ppm 8.33 (s, 1H), 7.24-7.21 (m, 3H), 7.02-6.97 (m, 3H), 4.20 (q, J=4 Hz, 1H), 3.72 (m, 2H), 3.33-2.92 (m, 6H), 2.10 (m, 2H), 1.80 (m, 2H), 1.42 (s, 9H), 1.28 (d, J=4 Hz, 3H). Mass spec.: 537.28 (MH)+.

Intermediate 307

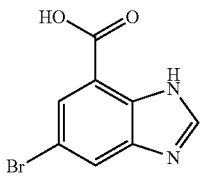

5-Bromo-1H-benzo[d]imidazole-7-carboxylic acid. This compound was prepared according to the procedure reported by Lopez-Rodreguez, M. L. et. al. (J. Med. Chem. 1999, 42, 5020-5028 and the referenced cited therein.) and had the following spectral characteristics as HCl salt. $^1$H NMR (500 MHz, DMSO-d6) δ ppm 13.61 (s, 1 H), 12.68 (s,1 H), 8.29 (s, 1 H), 8.14 (s, 1 H), 7.87 (s, 1 H). 241(MH)+.

Intermediate 308

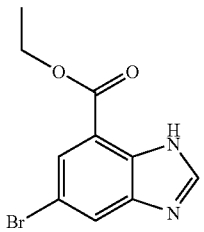

Ethyl 5-bromo-1H-benzo[d]imidazole-7-carboxylate. To a suspension of crude 5-Bromo-1H-benzo[d]imidazole-7-carboxylic acid (247 mg, 0.81 mmol, 77% pure) in dichloroethane under N$_2$ with stirring was added oxalyl chloride (0.5 mL, 5.6 equiv). Added one drop of DMF as catalyst. After 10 min, the suspension was treated with another 0.5 mL of oxalyl chloride. After 2.5 h, when effervescence ceased, added another 0.5 mL portion of oxalyl chloride and 2 drops of DMF and continued the reaction for another 1.5 h. The reaction mixture was added to 50 mL of ethanol carefully. The ethanol solution was maintained at ambient temperature for 30 min. It was then evaporated in vacuo. The residue was partitioned between EtOAc (75 mL) and satd aqueous bicarbonate (100 mL). The organic layer was washed with water (50 mL), dried (Na$_2$SO$_4$) and evaporated in vacuo. The crude product was coevaporated with hexane (50 mL). A suspension of the residual solid in hexane (50 mL) was filtered and washed with another 20 mL more hexane to give 200 mg. The crude product itself was used for subsequent reactions. $^1$H NMR (500 MHz, DMSO-d6) δ ppm 8.53 (s, 1 H), 8.20 (s, 1 H), 7.93 (s, 1 H), 4.45 (q, J=7.0 Hz, 2H), 1.39 (t, J=7.0 Hz, 3H). 269(MH)+.

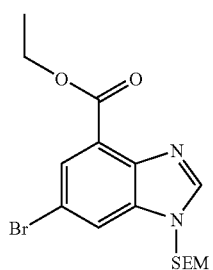

Intermediate 309

Ethyl 6-bromo-1-((2-(trimethylsilyl)ethoxy)methyl)-1H-benzo[d]imidazole-4-carboxylate. To a suspension of ethyl 5-bromo-1H-benzo[d]imidazole-7-carboxylate (I) (0.62 g, 1.67 mmol, 73% pure crude product) in dichloroethane (10 mL) was added sequentially diisopropylethylamine (0.9 mL, 3.1 equiv) and SEM-Cl (0.6 mL, 2.0 equiv). After 3 h volatiles were evaporated and a solution of the residue in DMF MeOH (1:1, 24 mL) was purified by prep HPLC (HPLC Method 16). Fractions containing the required product were combined and evaporated in vacuo to give 306 mg (63% yield). $^1$H NMR (500 MHz, DMSO-d6) δ ppm 8.55 (s, 1 H), 8.20 (d, J=1.8 Hz, 1 H), 7.86 (d, J=1.8 Hz, 1 H), 5.70 (s, 2 H), 4.38 (q, J=7.0 Hz, 2H), 3.49 (t, J=7.9 Hz, 2H), 1.36 (t, J=7.0 Hz, 3H), 0.83 (t, J=7.9 Hz, 2H), 0.09 (s, 1 H). 399(MH)$^+$.

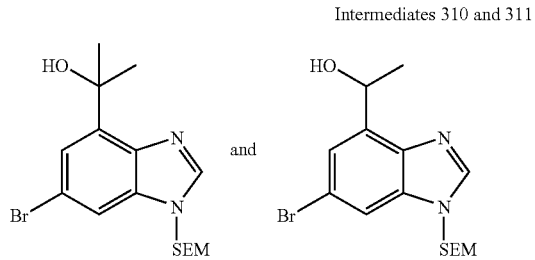

Intermediates 310 and 311

2-(6-bromo-1-((2-(trimethylsilyl)ethoxy)methyl)-1H-benzo[d]imidazol-4-yl)propan-2-ol and 1-(6-Bromo-1-((2-(trimethylsilyl)ethoxy)methyl)-1H-benzo[d]imidazol-4-yl)ethanol. To a stirred ice cold solution of 1M methylmagnesium bromide in butylether (4.9 mL) under argon was added triethylamine (2.1 mL, 6 equiv) followed by a solution of ethyl 6-bromo-1-((2-(trimethylsilyl)ethoxy)methyl)-1H-benzo[d]imidazole-4-carboxylate (974 mg, 2.44 mmol) in THF (5 mL). After stirring for 1 h, saturated aqueous ammonium chloride (50 mL) was added and the reaction mixture was subjected to extractive work up using EtOAc (50 mL). Organic layer was dried (Na$_2$SO$_4$), evaporated in vacuo. The residue was purified by SiO$_2$ chromatography using a linear gradient of EtOAc:hexane (7:93) to EtOAc (1:1) on biotage instrument on a 40M cartridge. The required ketone and the byproduct tertiary alcohol co-eluted and fractions containing the two compounds were combined and evaporated in vacuo to give 0.72 g of the mixture. Integration of the methylene singlet from the SEM residue in both compounds at δ 5.71 and δ 5.64 ppm in the proton NMR indicated that the ratio of the ketone to tertiary alcohol was 10:7. This mixture was subjected to reduction of the ketone as follows: The crude product (0.72 g) was dissolved in THF (10 mL) and treated with LiBH4 (130 mg, 6 mmol). After 5 h, the reaction mixture was cooled in ice-water bath and acetone (15 mL) was added carefully. The reaction mixture was warmed up to ambient temperature and volatiles were removed in vacuo. The residue was partitioned between EtOAc (40 mL) and water (30 mL). Organic layer was dried (Na$_2$SO$_4$) and evaporated in vacuo. The residue was purified by SiO$_2$ chromatography using a linear gradient of EtOAc:CH$_2$Cl$_2$ (3:22) to EtOAc on biotage instrument on a 25M cartridge. Fractions containing the less polar tertiary alcohol were combined and evaporated in vacuo to give 2-(6-bromo-1-((2-(trimethylsilyl)ethoxy)methyl)-1H-benzo[d]imidazol-4-yl)propan-2-ol (308 mg, 33% yield). $^1$H NMR (500 MHz, MeOD) δ ppm 8.24 (s, 1 H), 7.73 (d, J=1.8 Hz, 1 H), 7.59 (d, J=1.8 Hz, 1 H), 5.64 (s, 2 H), 3.58 (t, J=7.8 Hz, 2 H), 1.77 (s, 6 H), 0.90 (t, J=7.9 Hz, 2 H), −0.05 (s, 10 H). 385(MH)$^+$. Fractions containing the more polar secondary alcohol were combined and evaporated in vacuo to give 1-(6-Bromo-1-((2-(trimethylsilyl)ethoxy)methyl)-1H-benzo[d]imidazol-4-yl)ethanol (344 mg, 38% yield). 1H NMR (500 MHz, MeOD) δ ppm 8.30 (s, 1 H), 7.74 (d, J=1.8 Hz, 1 H), 7.57 (d, J=1.2 Hz, 1 H), 5.65 (s, 2 H), 5.54 (q, J=6.4 Hz, 1 H), 3.56-3.60 (m, 2 H), 1.56 (d, J=6.4 Hz, 3 H), 0.90 (t, J=7.9 Hz, 2 H), −0.05 (s, 9 H). 371(MH)$^+$.

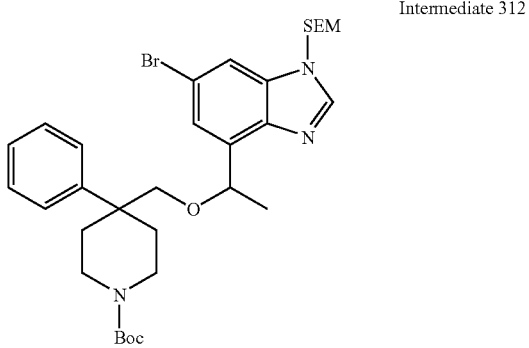

Intermediate 312 tert-Butyl 4-((1-(6-bromo-1-((2-(trimethylsilyl)ethoxy)methyl)-1H-benzo[d]imidazol-4-yl)ethoxy)methyl)-4-phenylpiperidine-1-carboxylate. 1-(6-Bromo-1-((2-(trimethylsilyl)ethoxy)methyl)-1H-benzo[d]imidazol-4-yl)ethanol (336 mg, 0.91 mmol) was converted to the corresponding trichloroacetimidate ester using trichloroacetonitrile (0.15 mL), DBU (0.02 mL) in CH$_2$Cl$_2$:cyclohexane (1:3, 2 mL) following a reported procedure (Kuethe, J. T. et. al. J. Org. Chem. 2006, 71, 7378-7390). TLC analysis (SiO$_2$, EtOAc:hexane, 7:3) indicated approximately 10% of starting material with the formation of a less polar product. The reaction mixture was worked up as described in the cited reference. The crude product was purified by SiO$_2$ chromatography using a linear gradient of EtOAc:hexane (3:22) to EtOAc on biotage instrument on a 25M cartridge. Fractions containing the less polar imidate ester were combined and evaporated in vacuo. The residue obtained weighed (363 mg, 78%). This was used in the next step as follows: Azeotropically dried (heptane) sample of imidate (354 mg, 0.69 mmol) was dissolved in dichloroethane (2 mL) and to this tert-butyl 4-(hydroxymethyl)-4-phenylpiperidine-1-carboxylate (200 mg, 1.0 equiv) and heptane (0.5 mL) were added. The clear solution was cooled to −15° C. (dry ice-ethyleneglycol bath) under N2 and to the resulting suspension HBF$_4$ (3 drops ~10-15 μL) was added. After stirring for 5 min, the cooling bath was changed to Ice-water bath and stirring continued for another 1 h. The reaction mixture was warmed to room temperature for 1 h. At the end 0.71 mL of 1N aq. NaOH was added and stirred for 10 min. Diluted with EtOAc (40 mL) and more water (30 mL) and extracted. Organic layer was dried (Na2SO4) and evaporated. The crude product was purified by SiO$_2$ chromatography using a linear gradient of EtOAc:hexane (3:22) to EtOAc on biotage instrument on a 25M cartridge. Fractions containing required product and tert-butyl 4-(hydroxymethyl)-4-phenylpiperidine-1-carboxylate as contaminant were purified by preparative HPLC (Method 17). Fractions containing the required product were combined and evaporated in vacuo. The residue was converted to free base using ammonium hydroxide to give tert-butyl 4-((1-(6-bromo-1-((2-(trimethylsilyl)ethoxy)methyl)-1H-benzo[d]imidazol-4-yl)ethoxy)methyl)-4-phenylpiperidine-1-carboxylate (34 mg) as racemate. $^1$H NMR (500 MHz, MeOD) δ ppm 8.28 (s, 1 H), 7.70 (d, J=1.8 Hz, 1 H), 7.33-7.41 (m, 4 H), 7.21-7.28 (m, 1 H), 7.08 (d, J=1.5 Hz, 1 H), 5.62 (s, 2 H), 5.01 (q, J=6.4 Hz, 1 H), 3.66-3.78 (m, 2 H), 3.55 (t, J=7.9 Hz, 2 H), 3.40 (d, J=9.2 Hz, 1 H), 3.31 (d, 1 H, partial overlap with solvent signal), 2.96-3.15 (m, 2 H), 2.12-2.27 (m, 2 H), 1.83-1.98 (m, 2 H), 1.46 (s, 9 H), 1.40 (d, J=6.4 Hz, 3 H), 0.88 (t, J=7.9 Hz, 2 H), −0.07 (s, 9 H). 644(MH)$^+$.

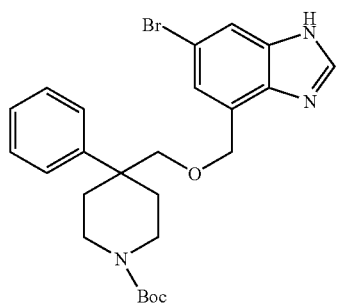

Intermediate 314 tert-Butyl 4-(((6-bromo-1H-benzo[d]imidazol-4-yl)methoxy)methyl)-4-phenylpiperidine-1-carboxylate. The protected intermediate (121 mg, 0.192 mmol) in DMF (1.9 mL) was combined with CsF (11 equiv) and heated at 80° C. for 76 h. At the end, DMF was evaporated in vacuo. The residue was partitioned between EtOAc (20 mL) and water (10 mL), EtOAc layer dried (Na2SO4) and evaporated. The residue was purified by SiO$_2$ chromatography using ethylacetate dichloromethane gradient to afford 43 mg of pure product. LC-MS (Method 7) t$_R$=2.5 min, 400 (MH)$^+$.

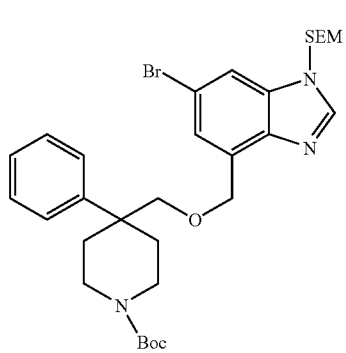

Intermediate 313 tert-Butyl 4-(((6-bromo-1-((2-(trimethylsilyl)ethoxy)methyl)-1H-benzo[d]imidazol-4-yl)methoxy)methyl)-4-phenylpiperidine-1-carboxylate. LiBH4 (153 mg) was added to an ice-cold solution of ethyl 6-bromo-1-((2-(trimethylsilyl)ethoxy)methyl)-1H-benzo[d]imidazole-4-carboxylate (517 mg, 1.3 mmol) in THF (15 mL). After 18 h the reaction mixture was cooled and treated with acetone 10 mL. Volatiles were evaporated and the residue was subjected to extractive work up as described in the synthesis of intermediate. The crude hydroxymethyl derivative which was 90% pure by LC-MS [HPLC method 7, t$_R$=2.3 min, 357 (MH)$^+$] was used as is for the preparation of chloromethyl derivative. The preparation of chloromethyl derivative and its coupling to phenylpipperidinyl alcohol were carried out on a 1.3 mmol scale in an analogous manner as described for other examples resulting in 71% yield of the required product with the following characteristics. 1H NMR (500 MHz, MeOD) δ ppm 8.28 (s, 1 H), 7.74 (d, J=1.8 Hz, 1 H), 7.41-7.45 (m, 2 H), 7.36 (t, J=7.8 Hz, 2 H), 7.21-7.26 (m, 2 H), 5.63 (s, 2 H), 4.79 (s, 2 H), 3.73 (td, J=8.9, 4.1 Hz, 2 H), 3.52-3.58 (m, 4 H), 3.05 (s, 2 H), 2.21 (d, J=14.0 Hz, 2 H), 1.92 (ddd, J=14.2, 10.5, 4.0 Hz, 2H), 1.46 (s, 9 H), −0.05 (s, 9 H). 630 (MH)$^+$.

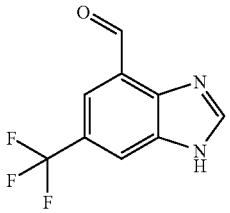

Intermediate 315

6-(Trifluoromethyl)-1H-benzo[d]imidazole-4-carbaldehyde. This compound was prepared from the corresponding commercially available 6-bromoderivative following similar procedure used for the synthesis of other intermediates on a 3 mmol scale (89% yield). $^1$H-NMR (DMSO-d$_6$, 500 MHz) δ 13.39 (br s, 1H), 10.33 (s, 1H), 8.56 (s, 1H), 8.39 (s, 1H), 8.24 (s, 1H); 215.12 (MH)$^+$.

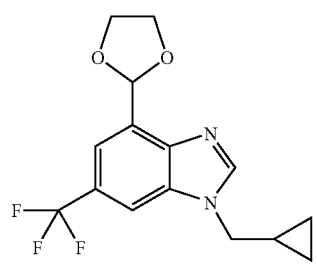

Intermediate 316

1-(Cyclopropylmethyl)-4-(1,3-dioxolan-2-yl)-6-(trifluoromethyl)-1H-benzo[d]imidazole. The ketal derivative was prepared by a procedure similar to a reported method [R. A. Daignault and E. L. Eliel, Org. Synth. Collect. Vol. V, 303 (1973)] on a 5 mmol scale. Instead of Benzene toluene was used as solvent. Without further purification the crude product was used for alkylation. LC/MS analysis (HPLC method 9): t$_R$=1.8 min, 259.15(MH)$^+$. Alkylation of the crude product by (bromomethyl)cyclopropane as described in the synthesis of other intermediates on a 5 mmol scale provided the required 1-(cyclopropylmethyl)-4-(1,3-dioxolan-2-yl)-6-(trifluoromethyl)-1H-benzo[d]imidazole (25% overall yield). ¹H-NMR (500 MHz, CHLOROFORM-D) δ ppm 8.15 (s, 1 H), 7.76 (s, 1 H), 7.72 (s, 1 H), 6.56 (s, 1 H), 4.19-4.27 (m, 2 H), 4.13-4.19 (m, 2 H), 4.06 (d, J=7.0 Hz, 2 H), 1.28-1.37 (m, 1 H), 0.68-0.78 (m, 2 H), 0.43 (q, J=5.2 Hz, 2 H). 313.13 (MH)$^+$.

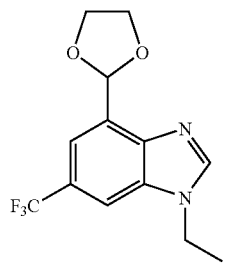

Intermediate 317

4-(1,3-Dioxolan-2-yl)-1-ethyl-6-(trifluoromethyl)-1H-benzo[d]imidazole. To the ketal derivative (3.873 g, 15 mmol) was mixed with cesium carbonate (7.82 g, 24 mmol) and anhydrous DMF (150ml) was added under N$_2$. After stirring for 15 min, bromoethane (1.696 ml, 22.5 mmol) was added to the suspension. The mixture was stirred at ambient temperature for 72 h. At the end DMF was evaporated under high vacuum and the residue was extracted with ethyl acetate (300 mL). The organic layer was combined, washed with water (2×100 mL), brine (100 mL) and dried (Na$_2$SO$_4$). The solvent was evaporated in vacuo and the residue was purified by flash chromatography (DCM:EtOAc=1:1) to give desired product 1.995 g (yield 46.5%) as yellow oil and its regioisomer as side product 1.10 g (yield 25.6%). Spectral characteristics: ¹H-NMR (500 MHz, CHLOROFORM-D) δ ppm 8.06 (s, 1 H), 7.76 (s, 1 H), 7.69 (s, 1 H), 6.54 (s, 1 H), 4.04-4.35 (m, 6 H), 1.55 (t, J=7.3 Hz, 3 H), 287.16 (MH)$^+$. Spectral characteristics for the regioisomer: ¹H-NMR (500 MHz, CHLOROFORM-D) δ ppm 8.08 (s, 1 H), 8.00 (s, 1 H), 7.78 (s, 1 H), 6.34 (s, 1 H), 4.50 (q, J=7.3 Hz, 2 H), 4.08-4.19 (m, 4 H), 1.52 (t, 3 H). 287.16 (MH)$^+$.

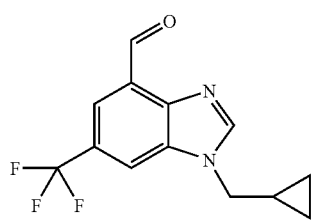

Intermediate 318

1-(Cyclopropylmethyl)-6-(trifluoromethyl)-1H-benzo[d]imidazole-4-carbaldehyde. 4-(1,3-dioxolan-2-yl)-6-(trifluoromethyl)-1H-benzo[d]imidazole (372 mg, 1.19 mmol) was dissolved in TFA:H$_2$O (9:1, 4 ml) and the mixture was stirred for 1 h at ambient temperature. Volatiles were removed in vacuo and the residue was basified with sat. NaHCO$_3$. The product was extracted with ethyl acetate (3×30 mL). Organic layer was washed with H$_2$O (30 mL), brine (30 mL) and dried (Na$_2$SO$_4$). The Ethyl acetate solution was evaporated in vacuo to give 320 mg crude aldehyde (quantitative yield). ¹H NMR (500 MHz, CHLOROFORM-D) δ ppm 10.84 (s, 1 H), 8.31 (s, 1 H), 8.11 (s, 1 H), 7.94 (s, 1 H), 4.13 (d, J=7.0 Hz, 2 H), 1.30-1.41 (m, 1 H), 0.75-0.83 (m, 2 H), 0.48 (q, J=5.2 Hz, 2 H). 269.14 (MH)$^+$.

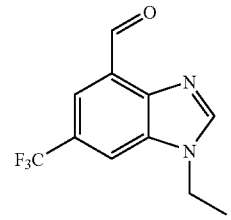

Intermediate 319

1-Ethyl-6-(trifluoromethyl)-1H-benzo[d]imidazole-4-carbaldehyde. The preparation of was analogous to that of the analogous compound and was carried out on a 7 mmol scale in quantitative yield. ¹H-NMR (500 MHz, CHLOROFORM-D) δ ppm 10.83 (s, 1 H), 8.25 (s, 1 H), 8.13 (s, 1 H), 7.93 (s, 1 H), 4.37 (q, J=7.3 Hz, 2 H), 1.63 (t, J=7.3 Hz, 3 H). 243.2 (MH)$^+$.

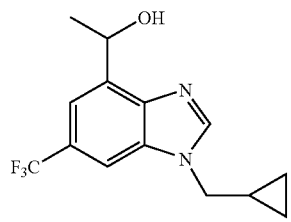

Intermediate 320

(±)-1-(1-(Cyclopropylmethyl)-6-(trifluoromethyl)-1H-benzo[d]imidazol-4-yl)ethanol. 1-(Cyclopropylmethyl)-6-(trifluoromethyl)-1H-benzo[d]imidazole-4-carbaldehyde (0.323 g, 1.2 mmol) was dissolved in tetrahydrofuran (6 mL), cooled down to 0° C. and to it was added methylmagnesium bromide (1.0 M in dibutyl ether, 2.2 mL, 2.2 mmol) dropwise. After 1.5 h, saturated aqueous ammonium chloride was added and the mixture was extracted with ethyl acetate (3×30 mL). The organic layer was washed with water (20 mL), brine (20 mL) and dried (Na$_2$SO$_4$). The crude product obtained after evaporation of solvent was purified by flash chromatography on silica gel (2% MeOH/CH$_2$Cl$_2$) affording 286 mg (84%) of product as light yellow oil. ¹H NMR (500 MHz, CHLOROFORM-D) δ ppm 8.11 (s, 1 H), 7.62 (s, 1 H), 7.46 (s, 1 H), 5.38-5.49 (m, 1 H), 4.16 (d, J=6.1 Hz, 1 H), 4.06 (d, J=7.0 Hz, 2 H), 1.70 (d, J=6.7 Hz, 3 H), 1.29-1.40 (m, 1 H), 0.69-0.80 (m, 2 H), 0.45 (q, J=5.2 Hz, 2 H). 308.17 (MNa)$^+$.

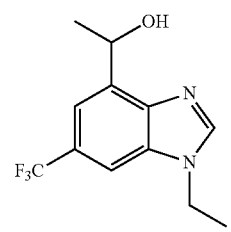

Intermediate 321

1-(1-Ethyl-6-(trifluoromethyl)-1H-benzo[d]imidazol-4-yl)ethanol. The preparation of this compound was analogous to the other analog followed the same procedure on a 7 mmol scale to give the product 1.41 g as a white solid, 78% yield. ¹H-NMR (500 MHz, CHLOROFORM-D) δ ppm 8.01 (s, 1 H), 7.60 (s, 1 H), 7.46 (s, 1 H), 5.36-5.49 (m, 1 H), 4.28 (q, J=7.3 Hz, 2 H), 4.14 (d, J=6.1 Hz, 1 H), 1.70 (d, J=6.4 Hz, 3 H), 1.57 (t, J=7.3 Hz, 3 H). 259.18 (MH)⁺.

Intermediate 322

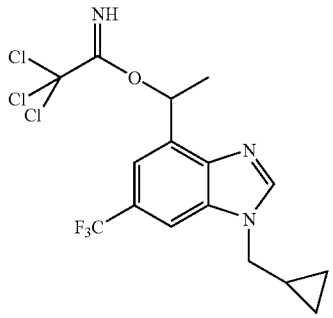

(±)-1-(1-(Cyclopropylmethyl)-6-(trifluoromethyl)-1H-benzo[d]imidazol-4-yl)ethyl 2,2,2-trichloroacetimidate. (±)-1-(1-(Cyclopropylmethyl)-6-(trifluoromethyl)-1H-benzo[d]imidazol-4-yl)ethanol (0.283 g, 0.996 mmol) was dissolved in diethyl ether (13 mL), cooled to 0° C. and treated with 1,8-diazabicyclo(5.4.0)undec-7-ene (341 µL, 2.27 mmol). The reaction was stirred for 10 min and treated with trichloroacetonitrile (300 µL, 2.93 mmol) dropwise over 10 min. The reaction was allowed to warm up to room temperature overnight and concentrated. Flash chromatography on silica gel (50% ethyl acetate/hexanes) gave 195 mg (45.6%) as an light yellow oil. ¹H-NMR (500 MHz, CHLOROFORM-D) δ ppm 8.33 (s, 1 H), 8.15 (s, 1 H), 7.69 (s, 1 H), 7.64 (s, 1 H), 6.81 (q, J=6.4 Hz, 1 H), 4.05 (d, J=7.0 Hz, 2 H), 1.82 (d, J=6.4 Hz, 3 H), 1.29-1.39 (m, 1 H), 0.70-0.80 (m, 2 H), 0.40-0.50 (m, 2 H); ¹⁹F-NMR (470 MHz, CHLOROFORM-D) δ ppm −61.19.

Intermediate 323

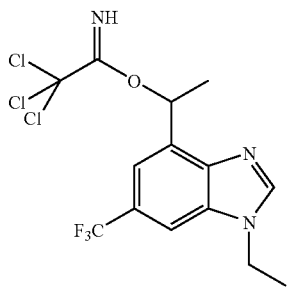

(±)-1-(1-Ethyl-6-(trifluoromethyl)-1H-benzo[d]imidazol-4-yl)ethyl 2,2,2-trichloroacetimidate. 5.42 mmol scale to give 1.34 g as brown oil (61.4% yield). ¹H-NMR (500 MHz, CHLOROFORM-D) δ ppm 8.33 (s, 1 H), 8.06 (s, 1 H), 7.69 (s, 1 H), 7.62 (s, 1 H), 6.79 (q, J=6.4 Hz, 1 H), 4.28 (q, J=7.4 Hz, 2 H), 1.81 (d, J=6.4 Hz, 3 H) 1.52-1.64 (t, J=7.4 Hz, 3 H). ¹⁹F-NMR (470 MHz, CHLOROFORM-D) δ ppm −61.19.

Intermediate 324

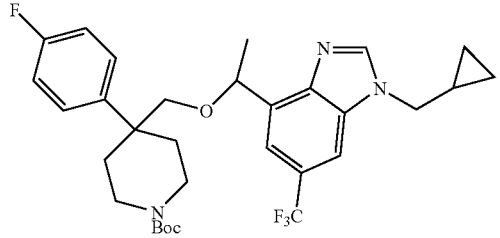

tert-Butyl 4-((1-(1-(cyclopropylmethyl)-6-(trifluoromethyl)-1H-benzo[d]imidazol-4-yl)ethoxy)methyl)-4-(4-fluorophenyl)piperidine-1-carboxylate. (±)-1-(1-(Cyclopropylmethyl)-6-(trifluoromethyl)-1H-benzo[d]imidazol-4-yl) ethyl 2,2,2-trichloroacetimidate (600 mg, 1.40 mmol) and tert-butyl 4-(4-fluorophenyl)-4-(hydroxymethyl)piperidine-1-carboxylate (650 mg, 2.10 mmol) were combined in a dichloroethane/cyclohexane mixture (3:2, 5 mL) and cooled to 0° C. The reaction mixture was treated with tetrafluoroboric acid-diethyl ether complex (76 µL, 0.56 mmol), and was slowly allowed to attain ambient temperature during 14 h. At the end 1 N NaOH (0.56 ml) was added the mixture was extracted with ethyl acetate (120 mL). The organic layer was washed with water (30 mL), brine (30 mL), dried (Na₂SO₄), filtered and evaporated in vacuo. Flash silica gel chromatography (50% ethyl acetate/hexanes) gave 214 mg (26.6%) as white foam-like solid. ¹H-NMR (500 MHz, CHLOROFORM-D) δ ppm 8.07 (s, 1 H), 7.56 (s, 1 H), 7.26-7.32 (m, 3 H), 7.00 (t, J=8.7 Hz, 2 H), 5.11 (q, J=6.4 Hz, 1 H), 4.03 (d, J=7.0 Hz, 2 H), 3.64-3.74 (m, 2 H), 3.27-3.38 (m, 2 H), 2.95-3.11 (m, 2 H), 2.03-2.18 (m, 2 H), 1.82-1.98 (m, 2 H), 1.45 (d, J=6.4 Hz, 3 H), 1.43 (s, 9 H), 1.28-1.36 (m, 1 H), 0.70-0.77 (m, 2 H), 0.43 (q, J=5.2 Hz, 2 H). 576.38 (MH)⁺.

Intermediate 325

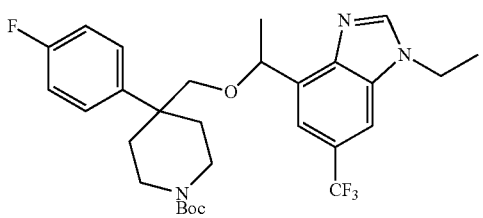

tert-Butyl 4-((1-(1-ethyl-6-(trifluoromethyl)-1H-benzo[d]imidazol-4-yl)ethoxy)methyl)-4-(4-fluorophenyl)piperidine-1-carboxylate. (±)-1-(1-Ethyl-6-(trifluoromethyl)-1H-benzo[d]imidazol-4-yl)ethyl 2,2,2-trichloroacetimidate (670 mg, 1.7 mmol) and tert-butyl 4-(4-fluorophenyl)-4-(hydroxymethyl)piperidine-1-carboxylate (772 mg, 2.5 mmol) were combined in a dichloroethane/cyclohexane mixture (4:2, 6 mL) and cooled to 0° C. The reaction mixture was treated with tetrafluoroboric acid-diethyl ether complex (91 µL, 0.67 mmol), and subsequent processing including extractive work up and purification were carried out as described in example 8 to give 281 mg (30.7%) as white foam-like solid. ¹H-NMR (500 MHz, CHLOROFORM-D) δ ppm 7.97 (s, 1 H), 7.54 (s, 1 H), 7.20-7.33 (m, 3 H), 7.00 (t, J=8.7 Hz, 2 H), 5.10 (q, J=6.6 Hz, 1 H), 4.17-4.30 (m, 2 H), 3.56-3.78 (m, 2 H), 3.24-3.40 (m, 2 H), 2.93-3.12 (m, 2 H), 2.02-2.21 (m, 2 H), 1.80-1.99 (m, 2 H), 1.56 (t, 3 H), 1.37-1.47 (m, 12 H). 550.40 (MH)⁺.

Intermediate 326

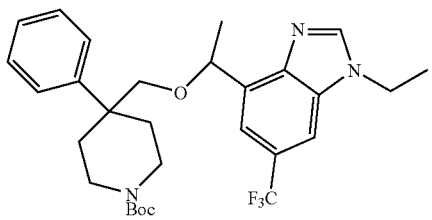

tert-Butyl 4-((1-(1-ethyl-6-(trifluoromethyl)-1H-benzo[d]imidazol-4-yl)ethoxy)methyl)-4-phenylpiperidine-1-carboxylate. (±)-(1-(1-Ethyl-6-(trifluoromethyl)-1H-benzo[d]imidazol-4-yl)ethyl 2,2,2-trichloroacetimidate (670 mg, 1.664 mmol) and tert-butyl 4-(hydroxymethyl)-4-phenylpiperidine-1-carboxylate (727 mg, 2.496 mmol) were combined in a dichloroethane/cyclohexane mixture (4:2, 6 mL) and cooled to 0° C. The reaction mixture was treated with tetrafluoroboric acid-diethyl ether complex (91 μL, 0.67 mmol), and subsequent processing including extractive work up and purification were carried out as described in example 8 to give 274 mg (30.7%) as white foam-like solid. $^1$H-NMR (500 MHz, CHLOROFORM-D) δ ppm 7.97 (s, 1 H), 7.54 (s, 1 H), 7.29-7.37 (m, 5 H), 7.16-7.24 (m, 1 H), 5.11 (q, J=6.4 Hz, 1 H), 4.20-4.29 (m, 2 H), 3.64-3.80 (m, J=13.1 Hz, 2 H), 3.29-3.37 (m, 2 H), 2.93-3.10 (m, 2 H), 2.09-2.22 (m, 2 H), 1.87-2.03 (m, 2 H), 1.56 (t, 3 H), 1.39-1.48 (m, 12 H). 532.40 (MH)$^+$.

EXAMPLE 1

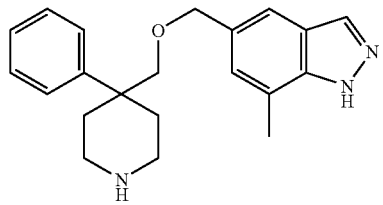

7-Methyl-5-(((4-phenylpiperidin-4-yl)methoxy)methyl)-1H-indazole. tert-Butyl 4-(((7-methyl-2-((2-(trimethylsilyl)ethoxy)methyl)-2H-indazol-5-yl)methoxy)methyl)-4-phenylpiperidine-1-carboxylate (170 mg, 0.300 mmol) was dissolved in trifluoroacetic acid (50% in dichloromethane, 5 mL) and stirred at room temperature for 2 h. The reaction was concentrated and loaded onto a strong cation exchange cartridge in methanol. The cartridge was flushed with several volumes of methanol which were discarded. The product was eluted with 2M ammonia in methanol and concentrated to give 95 mg (94%) as an amorphous solid. $^1$H-NMR (CDCl$_3$, 500 MHz) δ 7.98 (s, 1H), 7.31-7.40 (m, 4H), 7.29 (s, 1H), 7.24 (m, 1H), 6.88 (s, 1H), 4.42 (s, 2H), 3.45 (s, 1H), 3.41 (s, 2H), 2.95 (m, 2H), 2.77 (m, 2H), 2.46 (s, 3H), 2.17 (m, 2H), 1.97 (m, 2H); $^{13}$C NMR (126 MHz, CDCl$_3$) δ ppm 144.3, 140.3, 134.8, 131.5, 128.4, 127.4, 126.8, 126.1, 122.8, 120.0, 117.0, 79.2, 73.6, 50.4, 42.6, 41.9, 33.3, 17.1. Mass spec.: 336.31 (MH)$^+$. Accurate mass spec.: m/z 336.2090 [MH]$^+$, Δ=4.2 ppm.

EXAMPLE 2

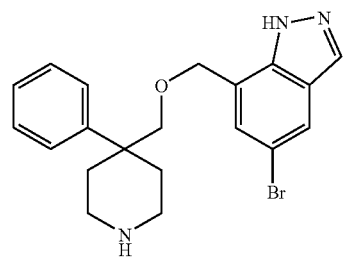

5-Bromo-7-(((4-phenylpiperidin-4-yl)methoxy)methyl)-1H-indazole. tert-Butyl 4-(((5-bromo-1-((2-(trimethylsilyl)ethoxy)methyl)-1H-indazol-7-yl)methoxy)methyl)-4-phenylpiperidine-1-carboxylate (40 mg, 0.064 mmol) was dissolved in trifluoroacetic acid (50% in dichloromethane, 3 mL) and stirred at room temperature for 4 h. The reaction was concentrated and loaded onto a strong cation exchange cartridge in methanol. The cartridge was washed with several volumes of methanol which were discarded. The product was eluted with 2 M ammonia in methanol and concentrated. Column chromatography (90:8:4 dichloromethane/methanol/2 M ammonia in methanol) gave 19 mg (75%) as a colorless film. $^1$H-NMR (CDCl$_3$, 500 MHz) δ 7.87 (s, 1H), 7.74 (d, J=1.8 Hz, 1H), 7.47 (m, 2H), 7.38 (m, 3H), 7.14 (d, J=1.2 Hz, 1H), 4.65 (s, 2H), 3.56 (s, 2H), 2.95 (m, 2H), 2.78 (m, 2H), 2.28 (bs, 1H), 2.22 (m, 2H), 1.88 (m, 2H); $^{13}$C-NMR (CDCl$_3$, 126 MHz) δ 143.8, 137.4, 133.6, 129.0, 127.0, 126.8, 125.2, 122.6, 122.5, 113.3, 80.7, 71.7, 42.5, 41.7, 33.5. Mass spec.: 400.01 (MH)$^+$. Accurate mass spec.: m/z 400.1035 [MH]$^+$, Δ=2.6 ppm.

EXAMPLE 3

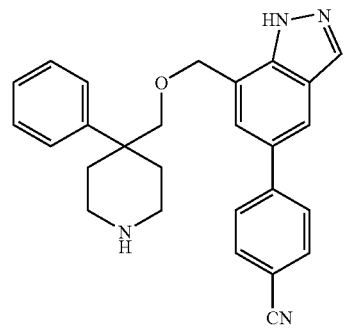

4-(7-(((4-Phenylpiperidin-4-yl)methoxy)methyl)-1H-indazol-5-yl)benzonitrile. tert-Butyl 4-(((5-(4-cyanophenyl)-2-((2-(trimethylsilyl)ethoxy)methyl)-2H-indazol-7-yl)methoxy)methyl)-4-phenylpiperidine-1-carboxylate (391 mg, 0.60 mmol) was dissolved in trifluoroacetic acid (50% in dichloromethane, 10 mL) and stirred at room temperature for 2 h. The reaction was concentrated and loaded onto a strong cation exchange cartridge in methanol. The cartridge was washed with several volumes of methanol which were discarded. The product was eluted with 2 M ammonia in methanol and concentrated to give 241 mg (95%) as an amorphous solid. $^1$H-NMR (CDCl$_3$, 500 MHz) δ 8.02 (s, 1H), 7.79 (s, 1H), 7.64 (m, 4H), 7.22-7.50 (m, 7H), 4.73 (s, 2H), 3.57 (s, 2H), 3.41 (s, 1H), 2.90 (m, 2H), 2.75 (m, 2H), 2.19 (m, 2H), 1.88 (m, 2H); $^{13}$C-NMR (CDCl$_3$, 126 MHz) δ 145.9, 144.1, 138.6, 134.9, 132.7, 132.0, 129.0, 127.9, 127.1, 126.8, 124.4, 123.7, 121.8, 119.1, 119.0, 110.4, 80.6, 72.0, 42.6, 41.7, 33.6. Mass spec.: 423.18 (MH)$^+$. Accurate mass spec.: m/z 423.2206 [MH]$^+$, Δ=5.0 ppm.

EXAMPLE 4

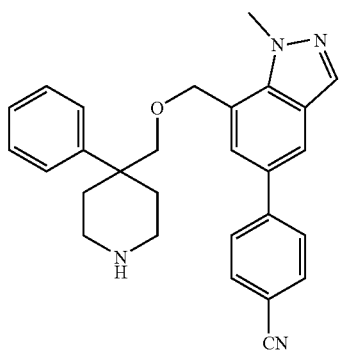

4-(1-Methyl-7-(((4-phenylpiperidin-4-yl)methoxy)methyl)-1H-indazol-5-yl)benzonitrile. tert-Butyl 4-(((5-(4-cyanophenyl)-1-methyl-1H-indazol-7-yl)methoxy)methyl)-4-phenylpiperidine-1-carboxylate (63 mg, 0.117 mmol) was dissolved in trifluoroacetic acid (25% in dichloromethane, 4 mL) and stirred at room temperature for 45 min. The reaction was concentrated, and loaded onto a strong cation exchange cartridge in methanol. The cartridge was flushed with several volumes of methanol which were discarded. The product was eluted with 2 M ammonia in methanol to give 47.3 mg (92%) as a colorless film. $^1$H-NMR (CDCl$_3$, 500 MHz) δ 7.98 (s, 1H), 7.85 (d, J=1.5 Hz, 1H), 7.70 (m, 4H), 7.35 (d, J=1.5 Hz, 1H), 7.25 (m, 4H), 7.17 (m, 1H), 4.72 (s, 2H), 3.93 (s, 3H), 3.48 (s, 2H), 2.83 (m, 2H), 2.69 (m, 2H), 2.11 (m, 2H), 1.81 (m, 2H), 1.78 (bs, 1H); $^{13}$C-NMR (CDCl$_3$, 126 MHz) δ 145.7, 144.2, 138.5, 133.5, 132.7, 131.4, 128.4, 127.9, 127.8, 127.2, 126.24, 126.20, 121.2, 120.2, 119.1, 110.5, 79.5, 71.1, 42.7, 41.7, 38.2, 33.7. Mass spec.: 437.19 (MH)$^+$. Accurate mass spec.: m/z 437.2354 [MH]$^+$, Δ=2.9 ppm.

EXAMPLE 5

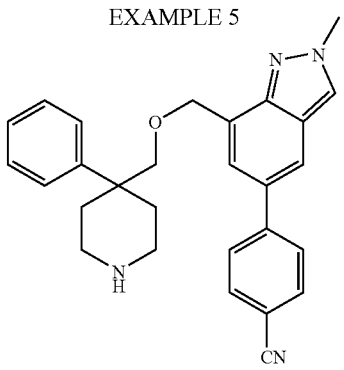

4-(2-Methyl-7-(((4-phenylpiperidin-4-yl)methoxy)methyl)-2H-indazol-5-yl)benzonitrile. tert-Butyl 4-(((5-(4-cyanophenyl)-2-methyl-2H-indazol-7-yl)methoxy)methyl)-4-phenylpiperidine-1-carboxylate (29 mg, 0.054 mmol) was dissolved in trifluoroacetic acid (25% in dichloromethane, 4 mL) and stirred at room temperature for 45 min. The reaction was concentrated, and loaded onto a strong cation exchange cartridge in methanol. The cartridge was flushed with several volumes of methanol which were discarded. The product was eluted with 2 M ammonia in methanol to give 20 mg (85%) as a colorless film. $^1$H-NMR (CDCl$_3$, 500 MHz) δ 7.94 (s, 1H), 7.71 (m, 3H), 7.61 (m, 2H), 7.41 (m, 2H), 7.30 (m, 3H), 7.18 (m, 1H), 4.89 (s, 2H), 4.21 (s, 3H), 3.60 (s, 2H), 2.90 (m, 2H), 2.75 (m, 2H), 2.19 (m, 2H), 1.95 (m, 2H), 1.92 (bs, 1H); $^{13}$C-NMR (CDCl$_3$, 126 MHz) δ 147.0, 146.4, 144.6, 132.9, 132.6, 128.8, 128.3, 127.8, 127.4, 126.0, 124.8, 122.5, 122.3, 119.3, 117.5, 110.3, 80.2, 68.9, 42.8, 42.0, 40.7, 33.7. Mass spec.: 437.17 (MH)$^+$. Accurate mass spec.: m/z 437.2339 [MH]$^+$, Δ=0.5 ppm.

EXAMPLE 6

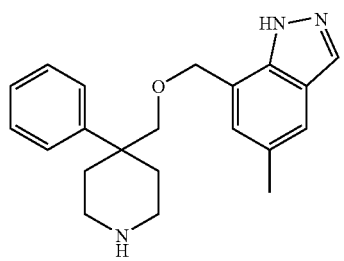

5-Methyl-7-(((4-phenylpiperidin-4-yl)methoxy)methyl)-1H-indazole. tert-Butyl 4-(((5-methyl-1H-indazol-7-yl)methoxy)methyl)-4-phenylpiperidine-1-carboxylate (12 mg, 0.028 mmol) was dissolved in trifluoroacetic acid (25% in dichloromethane, 4 mL) and stirred at room temperature for 45 min. The reaction was concentrated, and loaded onto a strong cation exchange cartridge in methanol. The cartridge was flushed with several volumes of methanol which were discarded. The product was eluted with 2 M ammonia in methanol to give 9.4 mg (quant.) as a colorless film. $^1$H-NMR (CDCl$_3$, 500 MHz) δ 9.43 (bs, 1H), 7.85 (s, 1H), 7.47 (m, 2H), 7.39 (m, 4H), 7.25 (m, 1H), 6.89 (s, 1H), 4.65 (s, 2H), 3.56 (s, 2H), 2.91 (m, 2H), 2.77 (m, 2H), 2.38 (s, 3H), 2.21 (m, 2H), 1.99 (bs, 1H), 1.86 (m, 2H); $^{13}$C-NMR (CDCl$_3$, 126 MHz) δ 144.2, 137.3, 133.8, 129.9, 128.9, 127.1, 126.8, 126.0, 124.1, 120.5, 119.1, 80.6, 72.4, 42.7, 41.7, 33.9, 21.3. Mass spec.: 336.13 (MH)$^+$. Accurate mass spec.: m/z 336.2066 [MH]$^+$, Δ=2.9 ppm.

EXAMPLE 7

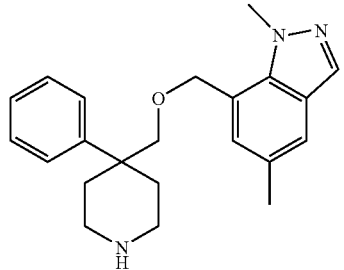

1,5-Dimethyl-7-(((4-phenylpiperidin-4-yl)methoxy)methyl)-1H-indazole. tert-Butyl 4-(((1,5-dimethyl-2H-indazol- 7-yl)methoxy)methyl)-4-phenylpiperidine-1-carboxylate (24 mg, 0.053 mmol) was dissolved in trifluoroacetic acid (25% in dichloromethane, 1.5 mL) and stirred at room temperature for 45 min. The reaction was concentrated, and loaded onto a strong cation exchange cartridge in methanol. The cartridge was flushed with several volumes of methanol which were discarded. The product was eluted with 2 M ammonia in methanol to give 18.8 mg (quant.) as a colorless film. $^1$H-NMR (CDCl$_3$, 500 MHz) δ 7.81 (s, 1H), 7.39 (s, 1H), 7.26 (m, 4H), 7.18 (m, 1H), 6.94 (s, 1H), 4.63 (s, 2H), 3.89 (s, 3H), 3.42 (s, 2H), 2.80 (m, 2H), 2.69 (m, 2H), 2.39 (s, 3H), 2.08 (m, 2H), 1.81 (m, 2H), 1.50-2.00 (bs, 1H); $^{13}$C-NMR (CDCl$_3$, 126 MHz) δ 144.3, 137.4, 132.0, 130.8, 129.3, 128.3, 127.2, 126.1, 126.0, 120.5, 119.9, 79.0, 71.2, 42.7, 41.7, 38.0, 33.7, 21.1. Mass spec.: 350.05 (MH)$^+$. Accurate mass spec.: m/z 350.2222 [MH]$^+$, Δ=3.0 ppm.

EXAMPLE 8

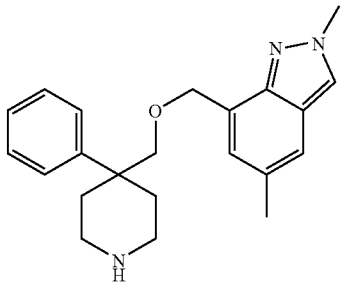

2,5-Dimethyl-7-(((4-phenylpiperidin-4-yl)methoxy)methyl)-2H-indazole. tert-Butyl 4-(((2,5-dimethyl-2H-indazol-7-yl)methoxy)methyl)-4-phenylpiperidine-1-carboxylate (8 mg, 0.018 mmol) was dissolved in trifluoroacetic acid (25% in dichloromethane, 1.5 mL) and stirred at room temperature for 45 min. The reaction was concentrated, and loaded onto a strong cation exchange cartridge in methanol. The cartridge was flushed with several volumes of methanol which were discarded. The product was eluted with 2 M ammonia in methanol to give 6.8 mg (quant.) as a colorless film. $^1$H-NMR (CDCl$_3$, 500 MHz) δ 7.73 (s, 1H), 7.41 (m, 2H), 7.35 (m, 2H), 7.22 (m, 2H), 6.84 (s, 1H), 4.82 (s, 2H), 4.15 (s, 3H), 3.54 (s, 2H), 2.91 (m, 2H), 2.75 (m, 2H), 2.33 (s, 3H), 2.18 (m, 2H), 1.98 (m, 2H), 1.50-2.30 (bs, 1H); $^{13}$C-NMR (CDCl$_3$, 126 MHz) δ 146.3, 144.6, 131.1, 128.3, 127.4, 127.3, 126.0, 125.7, 122.8, 122.5, 116.9, 79.8, 69.1, 42.8, 42.0, 40.3, 33.5, 21.9. Mass spec.: 350.04 (MH)$^+$. Accurate mass spec.: m/z 350.2230 [MH]$^+$, Δ=0.7 ppm.

EXAMPLE 9

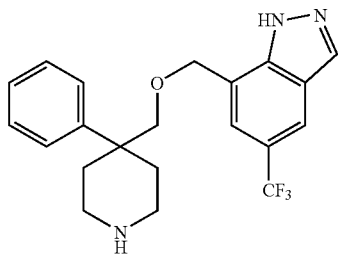

7-(((4-Phenylpiperidin-4-yl)methoxy)methyl)-5-(trifluoromethyl)-1H-indazole. tert-Butyl 4-phenyl-4-(((5-(trifluoromethyl)-1H-indazol-7-yl)methoxy)methyl)piperidine-1-carboxylate (120 mg, 0.245 mmol) was dissolved in trifluoroacetic acid (25% in dichloromethane, 1 mL) and stirred at room temperature for 15 min. The reaction was concentrated and loaded onto a strong cation exchange cartridge in methanol. The cartridge was flushed with several volumes of methanol which were discarded. The product was eluted with 2 M ammonia in methanol and concentrated to give 71 mg (74%). $^1$H-NMR (CDCl$_3$, 500 MHz) δ 8.04 (s, 1H), 7.92 (s, 1H), 7.45 (m, 2H), 7.32-7.42 (m, 3H), 7.26 (s, 1H), 4.70 (s, 2H), 3.57 (s, 2H), 2.90 (m, 2H), 2.76 (m, 2H), 2.20 (m, 2H), 1.86 (m, 2H); $^{13}$C-NMR (CDCl$_3$, 126 MHz) δ 144.1, 139.6, 135.2, 129.0, 127.0, 126.9, 124.7 (q, J=272 Hz), 123.1 (q, J=33 Hz), 122.9, 121.9, 120.3, 118.4, 80.7, 71.8, 50.4, 42.6, 41.7, 33.8. Mass spec.: 390.08 (MH)$^+$. Accurate mass spec.: m/z 390.1801 [MH]$^+$, Δ=2.0 ppm.

EXAMPLE 10

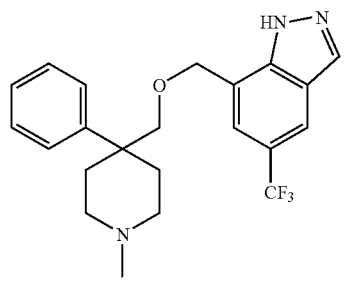

7-(((1-Methyl-4-phenylpiperidin-4-yl) methoxy) methyl)-5-(trifluoromethyl)-1H-indazole. To a solution of 7-(((4-phenylpiperidin-4-yl)methoxy)methyl)-5-(trifluoromethyl)-1H-indazole (62 mg, 0.159 mmol) and sodium cyanoborohydride (10 mg, 0.159 mmol) in acetonitrile (1 mL) at room temperature was added formalin (25 μL). To this was added 1 drop of acetic acid. After 5 min, a second drop of acetic acid was added and the reaction stirred at room temperature for 15 min. The reaction was concentrated and loaded onto a strong cation exchange cartridge in methanol. The cartridge was washed with several volumes of methanol which were discarded. The product was eluted with 2 M ammonia in methanol and concentrated. The product was purified by preparative HPLC. The trifluoroacetic acid salt was loaded onto a strong cation exchange cartridge in methanol. The cartridge was washed with several volumes of methanol which were discarded. The product was eluted with 2 M ammonia in methanol and concentrated to give 37 mg (58%). $^1$H-NMR (CDCl$_3$, 500 MHz) δ 9.60 (bs, 1H), 8.02 (s, 1H), 7.91 (s, 1H), 7.49 (m, 2H), 7.41 (m, 3H), 7.25 (s, 1H), 4.71 (s, 2H), 3.61 (s, 2H), 2.57 (m, 2H), 2.10-2.40 (m, 4H), 2.22 (s, 3H), 1.96 (m, 2H); $^{13}$C-NMR (CDCl$_3$, 126 MHz) δ 143.9, 139.5, 135.2, 129.0, 127.1, 126.9, 124.7 (q, J=272 Hz), 123.2 (q, J=32 Hz), 121.9, 120.1, 118.3, 80.8, 72.0, 52.0, 46.3, 40.7, 32.9. Mass spec.: 404.01 (MH)$^+$. Accurate mass spec.: m/z [MH]$^+$, Δ=4.4 ppm.

EXAMPLE 11

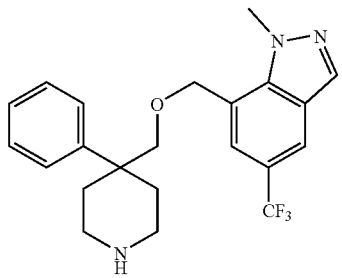

1-Methyl-7-(((4-phenylpiperidin-4-yl)methoxy)methyl)-5-(trifluoromethyl)-1H-indazole. tert-Butyl 4-(((1-methyl-5-(trifluoromethyl)-1H-indazol-7-yl)methoxy)methyl)-4-phenylpiperidine-1-carboxylate (187 mg, 0.371 mmol) was dissolved in trifluoroacetic acid (25% in dichloromethane, 2 mL) and stirred at room temperature for 15 min. The reaction was concentrated and loaded onto a strong cation exchange cartridge in methanol. The cartridge was flushed with several volumes of methanol which were discarded. The product was eluted with 2 M ammonia in methanol and concentrated to 151 mg (quant.) as a colorless film. $^1$H-NMR (CDCl$_3$, 500 MHz) δ 7.97 (s, 1H), 7.92 (s, 1H), 7.31 (s, 1H), 7.21 (m, 4H), 7.14 (m, 1H), 4.64 (s, 2H), 3.90 (s, 3H), 3.46 (s, 2H), 2.82 (m, 2H), 2.69 (m, 2H), 2.09 (m, 2H), 1.79 (m, 2H), 1.60 (bs, 1H); $^{13}$C-NMR (CDCl$_3$, 126 MHz) δ 144.2, 139.5, 133.8, 128.3, 127.1, 126.2, 124.8, 124.7 (q, J=272 Hz), 124.5, 122.5 (q, J=33 Hz), 121.3, 119.6 (q, J=4.8 Hz), 79.4, 70.6, 42.7, 41.7, 38.2, 33.8. Mass spec.: 404.14 (MH)$^+$. Accurate mass spec.: m/z 404.1947 [MH]$^+$, Δ=0.7 ppm.

EXAMPLE 12

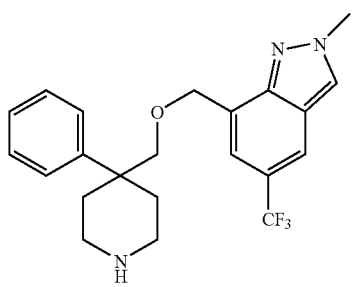

2-Methyl-7-(((4-phenylpiperidin-4-yl)methoxy)methyl)-5-(trifluoromethyl)-2H-indazole. tert-Butyl 4-(((2-methyl-5-(trifluoromethyl)-2H-indazol-7-yl)methoxy)methyl)-4-phenylpiperidine-1-carboxylate (76 mg, 0.151 mmol) was dissolved in trifluoroacetic acid (25% in dichloromethane, 2 mL) and stirred at room temperature for 15 min. The reaction was concentrated and loaded onto a strong cation exchange cartridge in methanol. The cartridge was flushed with several volumes of methanol which were discarded. The product was eluted with 2 M ammonia in methanol and concentrated to give 64 mg (quant.) as a colorless film. $^1$H-NMR (CDCl$_3$, 500 MHz) δ 7.94 (s, 1H), 7.84 (s, 1H), 7.41 (m, 2H), 7.34 (m, 2H), 7.28 (s, 1H), 7.21 (m, 1H), 4.83 (s, 2H), 4.18 (s, 3H), 3.57 (s, 2H), 2.90 (m, 2H), 2.76 (m, 2H), 2.20 (m, 2H), 1.95 (m, 2H), 1.85 (bs, 1H); $^{13}$C-NMR (CDCl$_3$, 126 MHz) δ 147.6, 144.4, 129.4, 128.3, 127.3, 126.1, 125.5, 124.9 (q, J=272 Hz), 124.2 (q, J=32 Hz), 120.7, 118.7, 117.5 (q, J=4.8 Hz), 80.2, 68.7, 42.9, 42.0, 40.7, 33.7. Mass spec.: 404.10 (MH)$^+$. Accurate mass spec.: m/z 404.1936 [MH]$^+$, Δ=3.4 ppm.

EXAMPLE 13

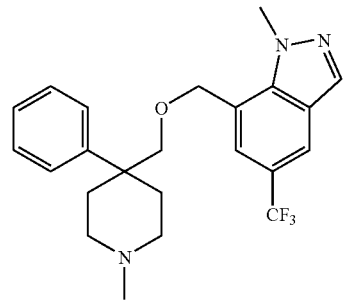

1-Methyl-7-(((1-methyl-4-phenylpiperidin-4-yl)methoxy)methyl)-5-(trifluoromethyl)-1H-indazole. To a solution of 1-methyl-7-(((4-phenylpiperidin-4-yl)methoxy)methyl)-5-(trifluoromethyl)-1H-indazole (65 mg, 0.161 mmol) and sodium cyanoborohydride (20 mg, 0.322 mmol) in acetonitrile (1 mL) at room temperature was added formalin (50 µL). To this was added 1 drop of acetic acid. After 5 min, a second drop of acetic acid was added and the reaction stirred at room temperature for 15 min. The reaction was concentrated and loaded onto a strong cation exchange cartridge in methanol. The cartridge was washed with several volumes of methanol which were discarded. The product was eluted with 2 M ammonia in methanol and concentrated to give 19 mg (28%). $^1$H-NMR (CDCl$_3$, 500 MHz) δ 7.99 (s, 1H), 7.95 (s, 1H), 7.31 (s, 1H), 7.23 (m, 4H), 7.17 (m, 1H), 4.66 (s, 2H), 3.90 (s, 3H), 3.47 (s, 2H), 2.51 (m, 2H), 2.18 (s, 3H), 2.05-2.25 (m, 4H), 1.91 (m, 2H); $^{13}$C-NMR (CDCl$_3$, 126 MHz) δ 143.7, 139.5, 135.1, 133.8, 128.3, 127.2, 126.2, 124.74, 124.67 (q, J=272 Hz), 124.6, 122.6 (q, J=33 Hz), 121.3, 119.6 (q, J=3.8 Hz), 79.2, 70.6, 51.9, 46.2, 40.6, 38.2, 32.5. Mass spec.: 418.15 (MH)$^+$. Accurate mass spec.: m/z 418.2119 [MH]$^+$, Δ=3.1 ppm.

EXAMPLE 14

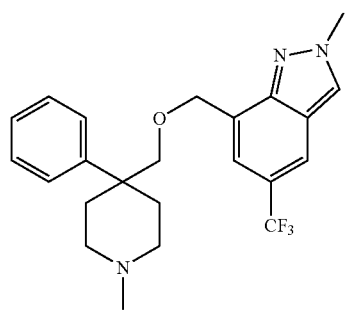

2-Methyl-7-(((1-methyl-4-phenylpiperidin-4-yl)methoxy)methyl)-5-(trifluoromethyl)-2H-indazole. To a solution of 2-methyl-7-(((4-phenylpiperidin-4-yl)methoxy)methyl)-5-(trifluoromethyl)-2H-indazole (58 mg, 0.144 mmol) and sodium cyanoborohydride (18 mg, 0.288 mmol) in acetonitrile (1 mL) at room temperature was added formalin (50 μL). To this was added 1 drop of acetic acid. After 5 min, a second drop of acetic acid was added and the reaction stirred at room temperature for 15 min. The reaction was concentrated and loaded onto a strong cation exchange cartridge in methanol. The cartridge was washed with several volumes of methanol which were discarded. The product was eluted with 2 M ammonia in methanol and concentrated to give 15 mg (25%). $^{1}$H-NMR (CDCl$_{3}$, 500 MHz) δ 7.97 (s, 1H), 7.85 (s, 1H), 7.41 (m, 2H), 7.34 (m, 2H), 7.22 (m, 1H), 4.82 (s, 2H), 4.21 (s, 3H), 3.58 (s, 2H), 2.60 (m, 2H), 2.20-2.33 (m, 4H), 2.22 (s, 3H), 2.06 (m, 2H); $^{13}$C-NMR (CDCl$_{3}$, 126 MHz) δ 147.6, 135.1, 129.3, 128.3, 127.4, 126.1, 125.5, 124.9 (q, J=272 Hz), 124.2 (q, J=32 Hz), 120.7, 118.7, 117.5 (q, J=4.8 Hz), 79.9, 68.7, 52.1, 46.2, 40.9, 40.7, 32.4. Mass spec.: 418.15 (MH)$^{+}$. Accurate mass spec.: m/z 418.2019 [MH]$^{+}$, Δ=0.7 ppm.

EXAMPLE 15

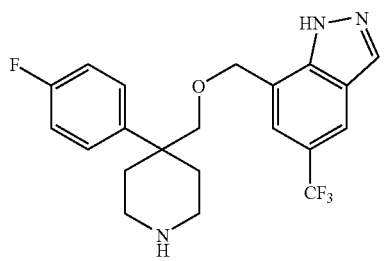

7-(((4-(4-Fluorophenyl)piperidin-4-yl)methoxy)methyl)-5-(trifluoromethyl)-1H-indazole. tert-Butyl 4-(4-fluorophenyl)-4-(((5-(trifluoromethyl)-1H-indazol-7-yl)methoxy)methyl)piperidine-1-carboxylate (75 mg, 0.148 mmol) was dissolved in trifluoroacetic acid (25% in dichloromethane, 1 mL) and stirred at room temperature for 15 min. The reaction was concentrated and loaded onto a strong cation exchange cartridge in methanol. The cartridge was flushed with several volumes of methanol which were discarded. The product was eluted with 2 M ammonia in methanol and concentrated to give 59 mg (98%). $^{1}$H-NMR (CDCl$_{3}$, 500 MHz) δ 8.06 (s, 1H), 7.94 (s, 1H), 7.20-7.40 (m, 3H), 7.07 (m, 2H), 4.71 (s, 2H), 3.50 (s, 2H), 3.43 (s, 2H), 2.88 (m, 2H), 2.72 (m, 2H), 2.12 (m, 2H), 1.85 (m, 2H); $^{13}$C-NMR (CDCl$_{3}$, 126 MHz) δ 162.5, 160.5, 139.6, 139.5, 135.3, 128.64, 128.58, 124.7 (q, J=272 Hz), 123.2 (q, J=32 Hz), 122.9, 121.8, 120.6, 118.5 (q, J=3.8 Hz), 115.8, 115.6, 80.3, 71.6, 50.5, 42.4, 41.4, 33.7. Mass spec.: 408.09 (MH)$^{+}$. Accurate mass spec.: m/z 408.1680 [MH]$^{+}$, Δ=4.7 ppm.

EXAMPLE 16

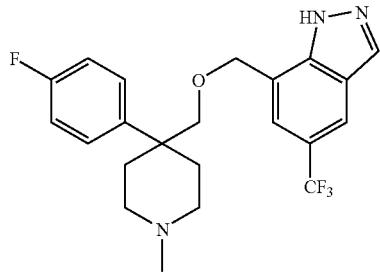

7-(((4-(4-Fluorophenyl)-1-methylpiperidin-4-yl)methoxy)methyl)-5-(trifluoromethyl)-1H-indazole. To a solution of 7-(((4-(4-fluorophenyl)piperidin-4-yl)methoxy)methyl)-5-(trifluoromethyl)-1H-indazole (50 mg, 0.123 mmol) and sodium cyanoborohydride (7.7 mg, 0.123 mmol) in acetonitrile (1 mL) at room temperature was added formalin (25 μL). To this was added 1 drop of acetic acid. After 5 min, a second drop of acetic acid was added and the reaction stirred at room temperature for 15 min. The reaction was concentrated and loaded onto a strong cation exchange cartridge in methanol. The cartridge was washed with several volumes of methanol which were discarded. The product was eluted with 2 M ammonia in methanol and concentrated. The product was purified by preparative HPLC. The trifluoroacetic acid salt was loaded onto a strong cation exchange cartridge in methanol. The cartridge was washed with several volumes of methanol which were discarded. The product was eluted with 2 M ammonia in methanol and concentrated to give 28 mg (54%). $^{1}$H-NMR (CDCl$_{3}$, 500 MHz) δ 9.81 (bs, 1H), 8.06 (s, 1H), 7.94 (s, 1H), 7.33 (m, 2H), 7.26 (s, 1H), 7.12 (m, 2H), 4.73 (s, 2H), 3.54 (s, 2H), 2.55 (m, 2H), 2.22 (m, 7H), 1.96 (m, 2H); $^{13}$C-NMR (CDCl$_{3}$, 126 MHz) δ 162.6, 160.6, 139.6, 135.4, 128.7, 128.6, 124.7 (q, J=272 Hz), 123.3 (q, J=32 Hz), 122.9, 121.8, 120.3 (q, J=2.9 Hz), 118.4 (q, J=4.8 Hz), 115.8, 115.6, 80.4, 71.9, 51.8, 46.3, 40.3, 32.9. Mass spec.: 422.13 (MH)$^{+}$. Accurate mass spec.: m/z 422.1836 [MH]$^{+}$, Δ=4.6 ppm.

EXAMPLE 17

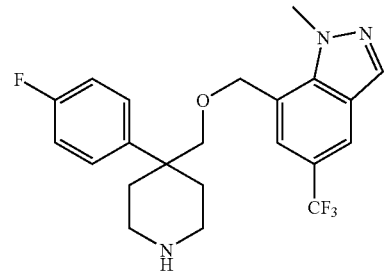

7-(((4-(4-Fluorophenyl)piperidin-4-yl)methoxy)methyl)-1-methyl-5-(trifluoromethyl)-1H-indazole. tert-Butyl 4-(4-fluorophenyl)-4-(((1-methyl-5-(trifluoromethyl)-1H-indazol-7-yl)methoxy)methyl)piperidine-1-carboxylate (66 mg, 0.127 mmol) was dissolved in trifluoroacetic acid (25% in dichloromethane, 2 mL) and stirred at room temperature for 15 min. The reaction was concentrated, and loaded onto a strong cation exchange cartridge in methanol. The cartridge was flushed with several volumes of methanol which were discarded. The product was eluted with 2 M ammonia in methanol and concentrated to give 53.5 mg (100%) as a colorless film. $^{1}$H-NMR (CDCl$_{3}$, 500 MHz) δ 8.00 (s, 1H), 7.94 (s, 1H), 7.30 (s, 1H), 7.15 (m, 2H), 6.87 (m, 2H), 4.68 (s, 2H), 3.99 (s, 3H), 3.44 (s, 2H), 2.82 (m, 2H), 2.67 (m, 2H), 2.04 (m, 2H), 1.60-1.95 (m, 3H); $^{13}$C-NMR (CDCl$_{3}$, 126 MHz) δ 162.2, 160.2, 139.8, 139.4, 133.9, 128.6, 128.5, 124.8, 124.6 (q, J=272 Hz), 124.5 (q, J=2.9 Hz), 122.6 (q, J=33 Hz), 121.2, 119.7 (q, J=4.8 Hz), 115.0, 114.8, 79.0, 70.5, 42.6, 41.3, 38.3, 33.9. Mass spec.: 422.08 (MH)⁺. Accurate mass spec.: m/z 422.1837 [MH]⁺, Δ=4.4 ppm.

EXAMPLE 18

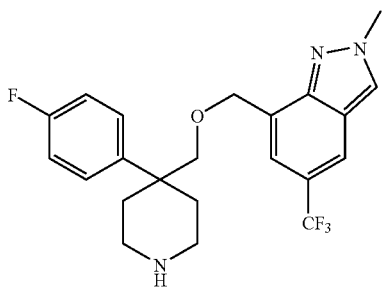

7-(((4-(4-Fluorophenyl)piperidin-4-yl)methoxy)methyl)-2-methyl-5-(trifluoromethyl)-2H-indazole. tert-Butyl 4-(4-fluorophenyl)-4-(((2-methyl-5-(trifluoromethyl)-2H-indazol-7-yl)methoxy)methyl)piperidine-1-carboxylate (26 mg, 0.050 mmol) was dissolved in trifluoroacetic acid (25% in dichloromethane, 2 mL) and stirred at room temperature for 15 min. The reaction was concentrated, and loaded onto a strong cation exchange cartridge in methanol. The cartridge was flushed with several volumes of methanol which were discarded. The product was eluted with 2 M ammonia in methanol and concentrated to give 20.6 mg (98%) as a colorless film. $^1$H-NMR (CDCl₃, 500 MHz) δ 7.98 (s, 1H), 7.86 (s, 1H), 7.35 (m, 2H), 7.23 (s, 1H), 7.00 (m, 2H), 4.82 (s, 2H), 4.21 (s, 3H), 3.54 (s, 2H), 2.90 (m, 2H), 2.74 (m, 2H), 2.14 (m, 2H), 1.60-2.05 (m, 3H); $^{13}$C-NMR (CDCl₃, 126 MHz) δ 162.3, 160.3, 147.6, 140.2, 129.2, 128.9, 128.8, 125.6, 124.9 (q, J=272 Hz), 124.2 (q, J=32 Hz), 120.8, 118.8 (q, J=2.9 Hz), 117.6 (q, J=5.8 Hz), 115.0, 114.9, 79.9, 68.7, 42.7, 41.6, 40.7, 33.9. Mass spec.: 422.12 (MH)⁺. Accurate mass spec.: m/z 422.1836 [MH]⁺, Δ=4.6 ppm.

EXAMPLE 19

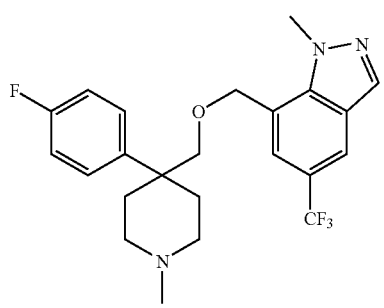

7-(((4-(4-Fluorophenyl)-1-methylpiperidin-4-yl)methoxy)methyl)-1-methyl-5-(trifluoromethyl)-1H-indazole. To a solution of 7-(((4-(4-fluorophenyl)piperidin-4-yl)methoxy)methyl)-1-methyl-5-(trifluoromethyl)-1H-indazole (35 mg, 0.083 mmol) and sodium cyanoborohydride (10.4 mg, 0.166 mmol) in acetonitrile (1 mL) at room temperature was added formalin (50 μL). To this was added 1 drop of acetic acid. After 5 min, a second drop of acetic acid was added and the reaction stirred at room temperature for 15 min. The reaction was concentrated and loaded onto a strong cation exchange cartridge in methanol. The cartridge was washed with several volumes of methanol which were discarded. The product was eluted with 2 M ammonia in methanol and concentrated to give 15 mg (42%). $^1$H-NMR (CDCl₃, 500 MHz) δ 8.01 (s, 1H), 7.95 (s, 1H), 7.29 (s, 1H), 7.14 (m, 2H), 6.87 (m, 2H), 4.68 (s, 2H), 3.98 (s, 3H), 3.44 (s, 2H), 2.50 (m, 2H), 2.00-2.25 (m, 7H), 1.91 (m, 2H); $^{13}$C-NMR (CDCl₃, 126 MHz) δ 162.2, 160.2, 139.4, 133.9, 128.62, 128.56, 124.8, 124.6 (q, J=272 Hz), 124.5 (q, J=2.9 Hz), 122.6 (q, J=33 Hz), 121.1, 119.7 (q, J=4.8 Hz), 115.0, 114.9, 78.7, 70.5, 51.8, 46.2, 40.2, 38.3, 32.6. Mass spec.: 436.15 (MH)⁺. Accurate mass spec.: m/z 436.2008 [MH]⁺, Δ=0.9 ppm.

EXAMPLE 20

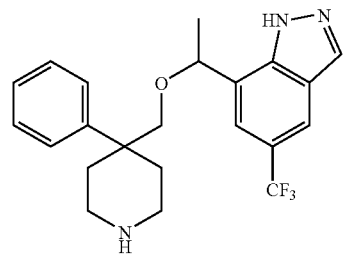

(±)-7-(1-((4-Phenylpiperidin-4-yl)methoxy)ethyl)-5-(trifluoromethyl)-1H-indazole. (±)-tert-Butyl 4-phenyl-4-((1-(5-(trifluoromethyl)-2-((2-(trimethylsilyl)ethoxy)methyl)-2H-indazol-7-yl)ethoxy)methyl)piperidine-1-carboxylate (62 mg, 0.098 mmol) was dissolved in trifluoroacetic acid (50% in dichloromethane, 1.5 mL) and stirred at room temperature for 3 h. The reaction was concentrated and loaded onto a strong cation exchange cartridge in methanol. The cartridge was flushed with several volumes of methanol which were discarded. The product was eluted with 2 M ammonia in methanol and concentrated to give 41 mg (quant.). $^1$H-NMR (CDCl₃, 500 MHz) δ 10.03 (bs, 1H), 8.08 (m, 1H), 7.95 (m, 1H), 7.32-7.55 (m, 5H), 7.26 (m, 1H), 4.66 (m, 1H), 3.54 (m, 2H), 3.36 (m, 2H), 2.72-3.06 (m, 4H), 2.36 (m, 1H), 2.16 (m, 1H), 1.97 (m, 1H), 1.85 (m, 1H), 1.49 (m, 3H); $^{13}$C-NMR (CDCl₃, 126 MHz) δ 143.8, 138.1, 135.2, 128.8, 127.5, 127.1, 126.8, 124.7 (q, J=272 Hz), 123.3, 119.7 (q, J=3.8 Hz), 118.1 (q, J=3.8 Hz), 79.2, 78.3, 42.8, 42.6, 41.7, 33.8, 33.7, 22.2. Mass spec.: 404.19 (MH)⁺. Accurate mass spec.: m/z 404.1960 [MH]⁺, Δ=2.5 ppm.

EXAMPLE 21

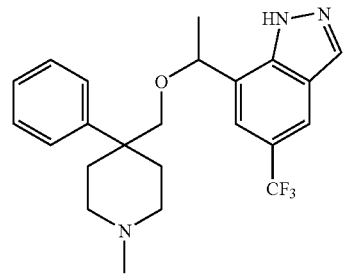

(±)-7-(1-((1-Methyl-4-phenylpiperidin-4-yl)methoxy)ethyl)-5-(trifluoromethyl)-1H-indazole. To a solution of (±)-

7-(1-((4-phenylpiperidin-4-yl)methoxy)ethyl)-5-(trifluoromethyl)-1H-indazole (35 mg, 0.087 mmol) and sodium cyanoborohydride (5.5 mg, 0.087 mmol) in acetonitrile (1 mL) at room temperature was added formalin (25 μL). To this was added 1 drop of acetic acid. After 5 min, a second drop of acetic acid was added and the reaction stirred at room temperature for 15 min. The reaction was concentrated and loaded onto a strong cation exchange cartridge in methanol. The cartridge was washed with several volumes of methanol which were discarded. The product was eluted with 2 M ammonia in methanol and concentrated to give 21 mg (58%). $^1$H-NMR (CDCl$_3$, 500 MHz) δ 9.78 (bs, 1H), 8.02 (s, 1H), 7.90 (s, 1H), 7.28-7.49 (m, 5H), 7.21 (s, 1H), 4.62 (q, J=6.7 Hz, 1H), 3.48 (s, 3H), 3.45-3.51 (m, 3H), 3.31 (d, J=8.9 Hz, 1H), 2.62 (m, 2H), 2.39 (m, 1H), 2.12-2.31 (m, 7H), 2.06 (m, 1H), 1.95 (m, 1H), 1.44 (d, J=6.7 Hz, 3H); $^{13}$C-NMR (CDCl$_3$, 126 MHz) δ 138.1, 135.2, 128.9, 127.5, 127.1, 126.9, 124.7 (q, J=272 Hz), 123.3, 119.8 (q, J=2.9 Hz), 118.1 (q, J=3.8 Hz), 79.0 (br), 78.4, 52.0, 51.8, 50.8, 46.1, 40.7, 32.5, 32.3, 22.2. Mass spec.: 418.18 (MH)$^+$. Accurate mass spec.: m/z 418.2101 [MH]$^+$, Δ=1.2 ppm.

EXAMPLE 22

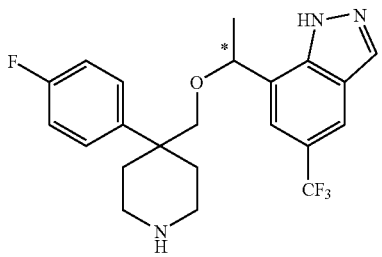

Enantiomer A of 7-(1-((4-(4-Fluorophenyl)piperidin-4-yl)methoxy)ethyl)-5-(trifluoromethyl)-1H-indazole. Enantiomer A of tert-Butyl 4-(4-fluorophenyl)-4-((1-(5-(trifluoromethyl)-1H-indazol-7-yl)ethoxy)methyl)piperidine-1-carboxylate (75 mg, 0.144 mmol) was dissolved in trifluoroacetic acid (20% in dichloromethane, 1 mL) and stirred at room temperature for 30 min. The reaction was concentrated, and loaded onto a strong cation exchange cartridge in methanol. The cartridge was flushed with several volumes of methanol which were discarded. The product was eluted with 2M ammonia in methanol and concentrated to give 59 mg (97%). $^1$H-NMR (CDCl$_3$, 500 MHz) δ 10.21 (bs, 1H), 8.06 (s, 1H), 7.92 (s, 1H), 7.28 (m, 2H), 7.22 (s, 1H), 7.06 (m, 2H), 4.59 (q, J=6.4 Hz, 1H), 3.36 (q$_{AB}$, J$_{AB}$=8.9 Hz, 2H), 2.92 (m, 1H), 2.85 (m, 1H), 2.76 (m, 1H), 2.69 (m, 1H), 2.22 (m, 1H), 2.05 (m, 1H), 1.91 (m, 1H), 1.81 (m, 1H), 1.44 (d, J=6.4 Hz, 3H); $^{13}$C-NMR (CDCl$_3$, 126 MHz) δ 162.5, 160.6, 139.5, 138.2, 135.3, 128.70, 128.65, 127.3, 124.7 (q, J=272 Hz), 123.5, 123.3, 119.8 (q, J=2.9 Hz), 118.2 (q, J=3.8 Hz), 115.6, 115.4, 79.0, 78.4, 42.6, 42.5, 41.4, 33.9, 33.7, 22.2. Mass spec.: 422.17 (MH)$^+$.

EXAMPLE 23

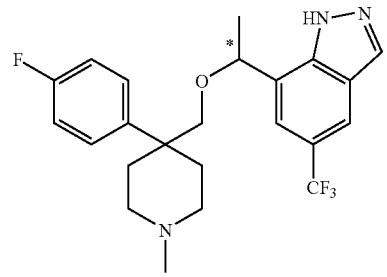

Enantiomer A of 7-(1-((4-(4-Fluorophenyl)-1-methylpiperidin-4-yl)methoxy)ethyl)-5-(trifluoromethyl)-1H-indazole. To a suspension of Enantiomer A of 7-(1-((4-(4-fluorophenyl)piperidin-4-yl)methoxy)ethyl)-5-(trifluoromethyl)-1H-indazole (53 mg, 0.126 mmol) and sodium cyanoborohydride (16 mg, 0.252 mmol) in acetonitrile (2 mL) at 0° C. was added formalin (0.15 mL). The ice bath was removed and stirring continued for 1 h. The reaction was diluted with diethyl ether and washed with 1M sodium hydroxide. The ethereal was concentrated and loaded onto a strong cation exchange cartridge in methanol. The cartridge was flushed with several volumes of methanol which was discarded. The product was eluted with 2 M ammonia and concentrated to give 35.5 mg (65%) as a colorless film. $^1$H-NMR (CDCl$_3$, 500 MHz) δ 9.95 (bs, 1H), 8.05 (s, 1H), 7.92 (s, 1H), 7.27 (m, 2H), 7.21 (s, 1H), 7.06 (m, 2H), 4.60 (q, J=6.4 Hz, 1H), 3.47 (s, 1H), 3.43 (d, J=8.9 Hz, 1H), 3.26 (d, J=8.9 Hz, 1H), 2.59 (m, 1H), 2.53 (m, 1H), 2.30 (m, 1H), 2.20 (s, 3H), 1.85-2.25 (m, 5H), 1.44 (d, J=6.7 Hz, 3H); $^{13}$C-NMR (CDCl$_3$, 126 MHz) δ 162.6, 160.6, 139.2, 138.1, 135.3, 128.8, 128.7, 127.3, 124.7 (q, J=272 Hz), 123.5, 123.3, 119.8 (q, J=2.9 Hz), 118.1 (q, J=4.8 Hz), 115.6, 115.5, 78.8, 78.5, 51.9, 51.7, 46.2, 40.3, 32.8, 32.5, 22.2. Mass spec.: 436.07 (MH)$^+$.

EXAMPLE 24

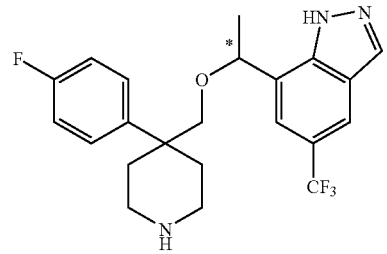

Enantiomer B of 7-(1-((4-(4-Fluorophenyl)piperidin-4-yl)methoxy)ethyl)-5-(trifluoromethyl)-1H-indazole. Enantiomer B of tert-Butyl 4-(4-fluorophenyl)-4-((1-(5-(trifluoromethyl)-1H-indazol-7-yl)ethoxy)methyl)piperidine-1-carboxylate (75 mg, 0.144 mmol) was dissolved in trifluoroacetic acid (20% in dichloromethane, 1 mL) and stirred at room temperature for 30 min. The reaction was concentrated and loaded onto a strong cation exchange cartridge in methanol. The cartridge was flushed with several volumes of methanol which were discarded. The product was eluted with 2M ammonia in methanol and concentrated to give 53 mg (87%). $^1$H-NMR (CDCl$_3$, 500 MHz) δ 10.21 (bs, 1H), 8.06 (s, 1H), 7.92 (s, 1H), 7.28 (m, 2H), 7.22 (s, 1H), 7.06 (m, 2H), 4.59 (q, J=6.4 Hz, 1H), 3.36 (q$_{AB}$, J$_{AB}$=8.9 Hz, 2H), 2.92 (m, 1H), 2.85 (m, 1H), 2.76 (m, 1H), 2.69 (m, 1H), 2.22 (m, 1H), 2.05 (m, 1H), 1.91 (m, 1H), 1.81 (m, 1H), 1.44 (d, J=6.4 Hz, 3H); $^{13}$C-NMR (CDCl$_3$, 126 MHz) δ 162.5, 160.6, 139.5, 138.2, 135.3, 128.70, 128.65, 127.3, 124.7 (q, J=272 Hz), 123.5, 123.3, 119.8 (q, J=2.9 Hz), 118.2 (q, J=3.8 Hz), 115.6, 115.4, 79.0, 78.4, 42.6, 42.5, 41.4, 33.9, 33.7, 22.2. Mass spec.: 422.17 (MH)$^+$.

(q, J=2.9 Hz), 118.1 (q, J=4.8 Hz), 115.6, 115.5, 78.8, 78.5, 51.9, 51.7, 46.2, 40.3, 32.8, 32.5, 22.2. Mass spec.: 436.07 (MH)$^+$.

EXAMPLE 26

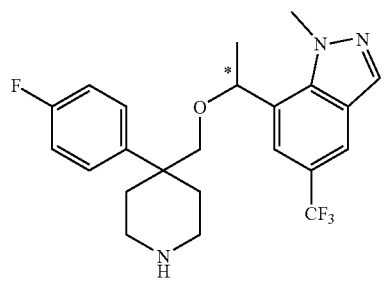

Enantiomer A of 7-(1-((4-(4-Fluorophenyl)piperidin-4-yl)methoxy)ethyl)-1-methyl-5-(trifluoromethyl)-1H-indazole. Enantiomer A of tert-Butyl 4-(4-fluorophenyl)-4-((1-(1-methyl-5-(trifluoromethyl)-1H-indazol-7-yl)ethoxy)methyl)piperidine-1-carboxylate (50 mg, 0.093 mmol) was dissolved in trifluoroacetic acid (20% in dichloromethane, 1 mL) and stirred at room temperature for 30 min. The reaction was concentrated and loaded onto a strong cation exchange cartridge in methanol. The cartridge was flushed with several volumes of methanol which were discarded. The product was eluted with 2M ammonia in methanol and concentrated to give 38 mg (94%). $^1$H-NMR (CDCl$_3$, 500 MHz) δ 8.01 (s, 1H), 7.89 (s, 1H), 7.36 (s, 1H), 7.23 (m, 2H), 6.96 (m, 2H), 4.86 (q, J=7.6 Hz, 1H), 4.08 (s, 3H), 3.44 (s, 1H), 3.28 (q$_{AB}$, J$_{AB}$=8.9 Hz, 2H), 2.85 (m, 2H), 2.70 (m, 2H), 2.08 (m, 2H), 1.85 (m, 4H), 1.48 (d, J=6.7 Hz, 3H); $^{13}$C-NMR (CDCl$_3$, 126 MHz) δ 162.3, 160.3, 139.7, 138.6, 134.3, 128.8, 128.7, 127.7, 125.2, 124.7 (q, J=272 Hz), 123.1 (q, J=33 Hz), 120.9, 118.6 (q, J=3.8 Hz), 115.1, 115.0, 78.0, 74.9, 50.7, 42.6, 41.3, 40.0, 33.7, 33.6, 23.4. Mass spec.: 436.10 (MH)$^+$.

EXAMPLE 25

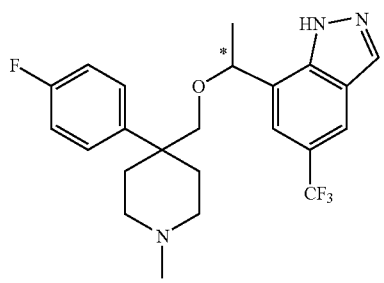

Enantiomer B of 7-(1-((4-(4-Fluorophenyl)-1-methylpiperidin-4-yl)methoxy)ethyl)-5-(trifluoromethyl)-1H-indazole. To a suspension of Enantiomer B of 7-(1-((4-(4-fluorophenyl)piperidin-4-yl)methoxy)ethyl)-5-(trifluoromethyl)-1H-indazole (46 mg, 0.109 mmol) and sodium cyanoborohydride (14 mg, 0.218 mmol) in acetonitrile (2 mL) at 0° C. was added formalin (0.15 mL). The ice bath was removed and stirring continued for 1 h. The reaction was diluted with diethyl ether and washed with 1M sodium hydroxide. The ethereal was concentrated and loaded onto a strong cation exchange cartridge in methanol. The cartridge was flushed with several volumes of methanol which was discarded. The product was eluted with 2 M ammonia and concentrated to give 36 mg (76%) as a colorless film. $^1$H-NMR (CDCl$_3$, 500 MHz) δ 9.95 (bs, 1H), 8.05 (s, 1H), 7.92 (s, 1H), 7.27 (m, 2H), 7.21 (s, 1H), 7.06 (m, 2H), 4.60 (q, J=6.4 Hz, 1H), 3.47 (s, 1H), 3.43 (d, J=8.9 Hz, 1H), 3.26 (d, J=8.9 Hz, 1H), 2.59 (m, 1H), 2.53 (m, 1H), 2.30 (m, 1H), 2.20 (s, 3H), 1.85-2.25 (m, 5H), 1.44 (d, J=6.7 Hz, 3H); $^{13}$C-NMR (CDCl$_3$, 126 MHz) δ 162.6, 160.6, 139.2, 138.1, 135.3, 128.8, 128.7, 127.3, 124.7 (q, J=272 Hz), 123.5, 123.3, 119.8

EXAMPLE 27

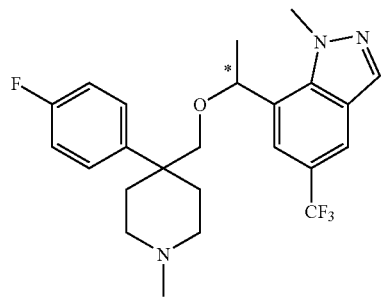

Enantiomer A of 7-(1-((4-(4-Fluorophenyl)-1-methylpiperidin-4-yl)methoxy)ethyl)-1-methyl-5-(trifluoromethyl)-1H-indazole. To a suspension of Enantiomer A of 7-(1-((4-(4-fluorophenyl)piperidin-4-yl)methoxy)ethyl)-1-methyl-5-(trifluoromethyl)-1H-indazole (30 mg, 0.069 mmol) and sodium cyanoborohydride (8.7 mg, 0.14 mmol) in acetonitrile (1.5 mL) at 0° C. was added formalin (0.1 mL). The reaction was treated with 1 drop of acetic acid. The ice bath was removed and stirring continued for 1 h. The reaction was diluted with diethyl ether and washed with 1M sodium hydroxide. The ethereal was concentrated and loaded onto a strong cation exchange cartridge in methanol. The cartridge was flushed with several volumes of methanol which was discarded. The product was eluted with 2 M ammonia and concentrated to give 23 mg (75%) as a colorless film. $^1$H-NMR (CDCl$_3$, 500 MHz) δ 8.05 (s, 1H), 7.93 (s, 1H), 7.39 (s, 1H), 7.27 (m, 2H), 6.99 (m, 2H), 4.90 (q, J=6.1 Hz, 1H), 4.11 (s, 3H), 3.31 (q$_{AB}$, J$_{AB}$=8.9 Hz, 2H), 2.55 (m, 2H), 2.22 (s, 3H), 2.18 (m, 4H), 2.00 (m, 2H), 1.51 (d, J=6.7 Hz, 3H); $^{13}$C-NMR (CDCl$_3$, 126 MHz) δ 162.3, 160.3, 139.5, 138.6, 134.3, 128.83, 128.77, 127.7, 125.2, 124.7 (q, J=272 Hz), 123.1 (q, J=33 Hz), 120.9, 118.6 (q, J=3.8 Hz), 115.1, 114.9, 77.7, 75.0, 51.8, 46.3, 40.3, 40.0, 32.7, 32.5, 23.4. Mass spec.: 449.99 (MH)$^+$.

EXAMPLE 28

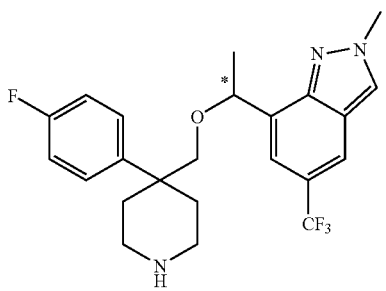

Enantiomer A of 7-(1-((4-(4-Fluorophenyl)piperidin-4-yl)methoxy)ethyl)-2-methyl-5-(trifluoromethyl)-2H-indazole. Enantiomer A of tert-Butyl 4-(4-fluorophenyl)-4-((1-(2-methyl-5-(trifluoromethyl)-2H-indazol-7-yl)ethoxy)methyl)piperidine-1-carboxylate (61 mg, 0.11 mmol) was dissolved in trifluoroacetic acid (20% in dichloromethane, 1 mL) and stirred at room temperature for 30 min. The reaction was concentrated and loaded onto a strong cation exchange cartridge in methanol. The cartridge was flushed with several volumes of methanol which were discarded. The product was eluted with 2M ammonia in methanol and concentrated to give 43 mg (87%). $^1$H-NMR (CDCl$_3$, 500 MHz) δ 8.00 (s, 1H), 7.86 (s, 1H), 7.34 (m, 2H), 7.19 (s, 1H), 7.01 (m, 2H), 4.96 (q, J=6.4 Hz, 1H), 4.23 (s, 3H), 3.46 (s, 1H), 3.39 (q$_{AB}$, J$_{AB}$=9.2 Hz, 2H), 2.91 (m, 2H), 2.75 (m, 2H), 2.13 (m, 2H), 1.96 (m, 4H), 1.48 (d, J=6.4 Hz, 3H); $^{13}$C-NMR (CDCl$_3$, 126 MHz) δ 162.2, 160.3, 147.7, 140.1, 134.7, 128.9, 128.8, 125.6, 124.9 (q, J=272 Hz), 124.2 (q, J=32 Hz), 121.0, 117.3 (q, J=4.8 Hz), 117.0 (q, J=2.9 Hz), 115.0, 114.8, 78.2, 74.1, 50.6, 42.7, 42.6, 41.5, 40.8, 33.7, 33.6, 22.8. Mass spec.: 436.01 (MH)$^+$.

EXAMPLE 29

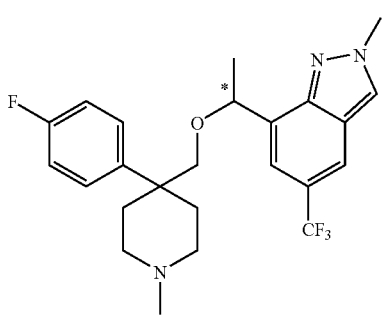

Enantiomer A of 7-(1-((4-(4-Fluorophenyl)-1-methylpiperidin-4-yl)methoxy)ethyl)-2-methyl-5-(trifluoromethyl)-2H-indazole. To a suspension of Enantiomer A of 7-(1-((4-(4-fluorophenyl)piperidin-4-yl)methoxy)ethyl)-2-methyl-5-(trifluoromethyl)-2H-indazole (32 mg, 0.073 mmol) and sodium cyanoborohydride (9.2 mg, 0.15 mmol) in acetonitrile (1.5 mL) at 0° C. was added formalin (0.1 mL). The reaction was treated with 1 drop of acetic acid. The ice bath was removed and stirring continued for 1 h. The reaction was diluted with diethyl ether and washed with 1M sodium hydroxide. The ethereal was concentrated and loaded onto a strong cation exchange cartridge in methanol. The cartridge was flushed with several volumes of methanol which was discarded. The product was eluted with 2 M ammonia and concentrated to give 25 mg (77%) as a colorless film. $^1$H-NMR (CDCl$_3$, 500 MHz) δ 8.01 (s, 1H), 7.87 (s, 1H), 7.35 (m, 2H), 7.18 (s, 1H), 7.02 (m, 2H), 4.97 (q, J=6.4 Hz, 1H), 4.24 (s, 3H), 3.40 (q$_{AB}$, J$_{AB}$=8.9 Hz, 2H), 2.57 (m, 2H), 2.23 (s, 3H), 2.14-2.30 (m, 4H), 2.07 (m, 2H), 1.48 (d, J=6.4 Hz, 3H); $^{13}$C-NMR (CDCl$_3$, 126 MHz) δ 162.2, 160.3, 147.7, 140.0, 134.7, 128.92, 128.86, 125.5, 124.9 (q, J=273 Hz), 124.3 (q, J=32 Hz), 121.0, 117.3 (q, J=5.8 Hz), 117.0 (q, J=2.9 Hz), 114.9, 114.8, 77.7, 74.0, 52.03, 51.97, 46.3, 40.8, 40.4, 32.7, 32.5, 22.9. Mass spec.: 449.99 (MH)$^+$.

EXAMPLE 30

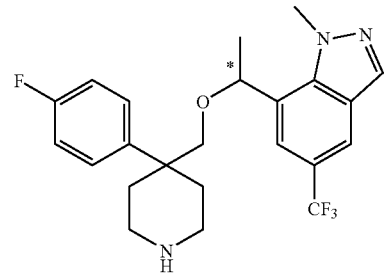

Enantiomer B of 7-(1-((4-(4-Fluorophenyl)piperidin-4-yl)methoxy)ethyl)-1-methyl-5-(trifluoromethyl)-1H-indazole. Enantiomer B of tert-Butyl 4-(4-fluorophenyl)-4-((1-(1-methyl-5-(trifluoromethyl)-1H-indazol-7-yl)ethoxy)methyl)piperidine-1-carboxylate (52 mg, 0.097 mmol) was dissolved in trifluoroacetic acid (20% in dichloromethane, 1 mL) and stirred at room temperature for 30 min. The reaction was concentrated and loaded onto a strong cation exchange cartridge in methanol. The cartridge was flushed with several volumes of methanol which were discarded. The product was eluted with 2M ammonia in methanol and concentrated to give 41 mg (97%). $^1$H-NMR (CDCl$_3$, 500 MHz) δ 8.01 (s, 1H), 7.89 (s, 1H), 7.36 (s, 1H), 7.23 (m, 2H), 6.96 (m, 2H), 4.86 (q, J=7.6 Hz, 1H), 4.08 (s, 3H), 3.44 (s, 1H), 3.28 (q$_{AB}$, J$_{AB}$=8.9 Hz, 2H), 2.85 (m, 2H), 2.70 (m, 2H), 2.08 (m, 2H), 1.85 (m, 4H), 1.48 (d, J=6.7 Hz, 3H); $^{13}$C-NMR (CDCl$_3$, 126 MHz) δ 162.3, 160.3, 139.7, 138.6, 134.3, 128.8, 128.7, 127.7, 125.2, 124.7 (q, J=272 Hz), 123.1 (q, J=33 Hz), 120.9, 118.6 (q, J=3.8 Hz), 115.1, 115.0, 78.0, 74.9, 50.7, 42.6, 41.3, 40.0, 33.7, 33.6, 23.4. Mass spec.: 436.10 (MH)+.

EXAMPLE 31

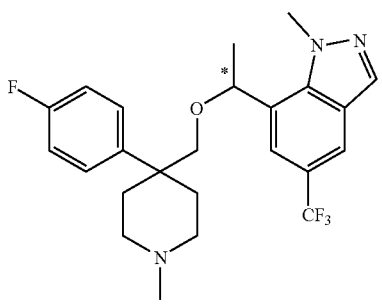

Enantiomer B of 7-(1-((4-(4-Fluorophenyl)-1-methylpiperidin-4-yl)methoxy)ethyl)-1-methyl-5-(trifluoromethyl)-1H-indazole. To a suspension of Enantiomer B of 7-(1-((4-(4-fluorophenyl)piperidin-4-yl)methoxy)ethyl)-1-methyl-5-(trifluoromethyl)-1H-indazole (33 mg, 0.076 mmol) and sodium cyanoborohydride (9.5 mg, 0.15 mmol) in acetonitrile (1.5 mL) at 0° C. was added formalin (0.1 mL). The reaction was treated with 1 drop of acetic acid. The ice bath was removed and stirring continued for 1 h. The reaction was diluted with diethyl ether and washed with 1M sodium hydroxide. The ethereal was concentrated and loaded onto a strong cation exchange cartridge in methanol. The cartridge was flushed with several volumes of methanol which was discarded. The product was eluted with 2 M ammonia and concentrated to give 18.5 mg (54%) as a colorless film. $^1$H-NMR (CDCl$_3$, 500 MHz) δ 8.05 (s, 1H), 7.93 (s, 1H), 7.39 (s, 1H), 7.27 (m, 2H), 6.99 (m, 2H), 4.90 (q, J=6.1 Hz, 1H), 4.11 (s, 3H), 3.31 (q$_{AB}$, J$_{AB}$=8.9 Hz, 2H), 2.55 (m, 2H), 2.22 (s, 3H), 2.18 (m, 4H), 2.00 (m, 2H), 1.51 (d, J=6.7 Hz, 3H); $^{13}$C-NMR (CDCl$_3$, 126 MHz) δ 162.3, 160.3, 139.5, 138.6, 134.3, 128.83, 128.77, 127.7, 125.2, 124.7 (q, J=272 Hz), 123.1 (q, J=33 Hz), 120.9, 118.6 (q, J=3.8 Hz), 115.1, 114.9, 77.7, 75.0, 51.8, 46.3, 40.3, 40.0, 32.7, 32.5, 23.4. Mass spec.: 449.99 (MH)+.

EXAMPLE 32

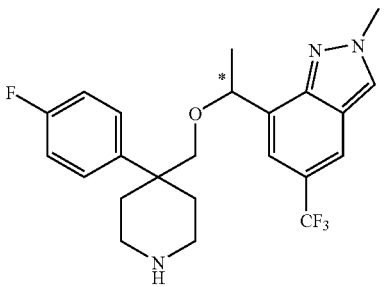

Enantiomer B of 7-(1-((4-(4-Fluorophenyl)piperidin-4-yl)methoxy)ethyl)-2-methyl-5-(trifluoromethyl)-2H-indazole. Enantiomer B of tert-Butyl 4-(4-fluorophenyl)-4-((1-(2-methyl-5-(trifluoromethyl)-2H-indazol-7-yl)ethoxy)methyl)piperidine-1-carboxylate (64 mg, 0.12 mmol) was dissolved in trifluoroacetic acid (20% in dichloromethane, 1 mL) and stirred at room temperature for 30 min. The reaction was concentrated and loaded onto a strong cation exchange cartridge in methanol. The cartridge was flushed with several volumes of methanol which were discarded. The product was eluted with 2M ammonia in methanol and concentrated to give 51 mg (98%). $^1$H-NMR (CDCl$_3$, 500 MHz) δ 8.00 (s, 1H), 7.86 (s, 1H), 7.34 (m, 2H), 7.19 (s, 1H), 7.01 (m, 2H), 4.96 (q, J=6.4 Hz, 1H), 4.23 (s, 3H), 3.46 (s, 1H), 3.39 (q$_{AB}$, J$_{AB}$=9.2 Hz, 2H), 2.91 (m, 2H), 2.75 (m, 2H), 2.13 (m, 2H), 1.96 (m, 4H), 1.48 (d, J=6.4 Hz, 3H); $^{13}$C-NMR (CDCl$_3$, 126 MHz) δ 162.2, 160.3, 147.7, 140.1, 134.7, 128.9, 128.8, 125.6, 124.9 (q, J=272 Hz), 124.2 (q, J=32 Hz), 121.0, 117.3 (q, J=4.8 Hz), 117.0 (q, J=2.9 Hz), 115.0, 114.8, 78.2, 74.1, 50.6, 42.7, 42.6, 41.5, 40.8, 33.7, 33.6, 22.8. Mass spec.: 436.01 (MH)+.

EXAMPLE 33

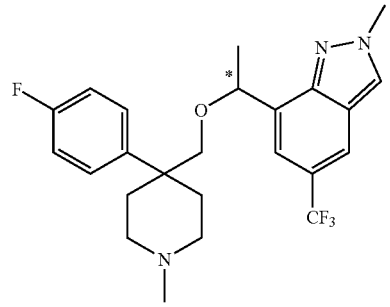

Enantiomer B of 7-(1-((4-(4-Fluorophenyl)-1-methylpiperidin-4-yl)methoxy)ethyl)-2-methyl-5-(trifluoromethyl)-2H-indazole. To a suspension of Enantiomer B of 7-(1-((4-(4-fluorophenyl)piperidin-4-yl)methoxy)ethyl)-2-methyl-5-(trifluoromethyl)-2H-indazole (42 mg, 0.096 mmol) and sodium cyanoborohydride (12 mg, 0.19 mmol) in acetonitrile (1.5 mL) at 0° C. was added formalin (0.1 mL). The reaction was treated with 1 drop of acetic acid. The ice bath was removed and stirring continued for 1 h. The reaction was diluted with diethyl ether and washed with 1M sodium hydroxide. The ethereal was concentrated and loaded onto a strong cation exchange cartridge in methanol. The cartridge was flushed with several volumes of methanol which was discarded. The product was eluted with 2 M ammonia and concentrated to give 22.8 mg (53%) as a colorless film. $^1$H-NMR (CDCl$_3$, 500 MHz) δ 8.01 (s, 1H), 7.87 (s, 1H), 7.35 (m, 2H), 7.18 (s, 1H), 7.02 (m, 2H), 4.97 (q, J=6.4 Hz, 1H), 4.24 (s, 3H), 3.40 (q$_{AB}$, J$_{AB}$=8.9 Hz, 2H), 2.57 (m, 2H), 2.23 (s, 3H), 2.14-2.30 (m, 4H), 2.07 (m, 2H), 1.48 (d, J=6.4 Hz, 3H); $^{13}$C-NMR (CDCl$_3$, 126 MHz) δ 162.2, 160.3, 147.7, 140.0, 134.7, 128.92, 128.86, 125.5, 124.9 (q, J=273 Hz), 124.3 (q, J=32 Hz), 121.0, 117.3 (q, J=5.8 Hz), 117.0 (q, J=2.9 Hz), 114.9, 114.8, 77.7, 74.0, 52.03, 51.97, 46.3, 40.8, 40.4, 32.7, 32.5, 22.9. Mass spec.: 449.99 (MH)+.

EXAMPLE 34

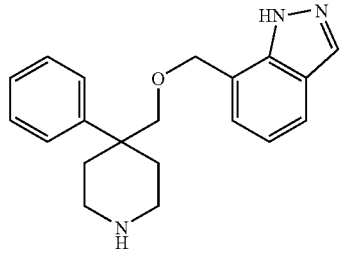

7-(((4-Phenylpiperidin-4-yl)methoxy)methyl)-1H-indazole. tert-Butyl 4-phenyl-4-(((1-((2-(trimethylsilyl)ethoxy)methyl)-1H-indazol-7-yl)methoxy)methyl)piperidine-1-carboxylate (34 mg, 0.06 mmol) was treated with a trifluoroacetic acid/methylene chloride mixture (1:1, 2 mL) for 4 h. The solvent was removed in vacuo and the resulting crude mixture passed through a strong cation exchange column. After washing the column with several volumes of methanol, the product was eluted by washing the column with 2 M ammonia in methanol. The solvent was evaporated and the compound purified by reverse phase HPLC to afford 11 mg (56%) as a clear oil. $^1$H-NMR (CDCl$_3$, 500 MHz) δ 8.91 (s, 1H), 8.24 (m, 1H), 7.76 (d, J=8.2 Hz, 1H), 7.40-7.43 (m, 2H), 7.28-7.35 (m, 4H), 7.22-7.25 (m, 1H), 4.81 (s, 2H), 3.48 (s, 2H), 3.38-3.41 (m, 2H), 2.96-2.97 (m, 2H), 2.39-2.41 (m, 4H). Mass spec.: 322.08 (MNa)+. Accurate mass spec.: m/z 322.1909 [MH]+, Δ=3.2 ppm.

EXAMPLE 35

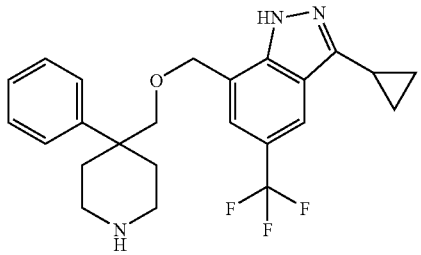

3-Cyclopropyl-7-(((4-phenylpiperidin-4-yl)methoxy)methyl)-5-(trifluoromethyl)-1H-indazole. tert-Butyl 4-(((3-cyclopropyl-5-(trifluoromethyl)-2-((2-(trimethylsilyl)ethoxy)methyl)-2H-indazol-7-yl)methoxy)methyl)-4-phenylpiperidine-1-carboxylate (18 mg, 0.03 mmol) was treated with a trifluoroacetic acid/methylene chloride mixture (1:1, 2 mL) for 4 h. The solvent was removed in vacuo and the resulting crude mixture passed through a strong cation exchange column. After washing the column with several volumes of methanol, the product was eluted by washing the column with 2 M ammonia in methanol. The solvent was evaporated to afford 9 mg (77%) as a clear oil. $^1$H-NMR (CDCl$_3$, 500 MHz) δ 7.92 (s, 1H), 7.31-7.45 (m, 5H), 7.22-7.33 (m, 1H), 4.67 (s, 2H), 3.52 (s, 2H), 2.95-2.99 (m, 2H), 2.76-2.81 (m, 2H), 2.15-2.24 (m, 3H), 1.89-1.95 (m, 2H), 1.04-1.02 (m, 4H). Mass spec.: 430.16 (MH)+. Accurate mass spec.: m/z 430.2097 [MH]+, Δ=2.1 ppm.

EXAMPLE 36

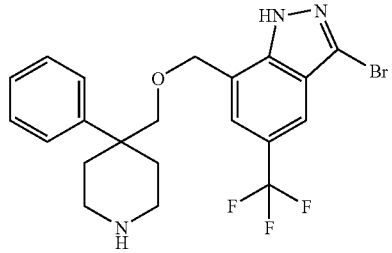

3-Bromo-7-(((4-phenylpiperidin-4-yl)methoxy)methyl)-5-(trifluoromethyl)-1H-indazole. tert-Butyl 4-(((3-bromo-5-(trifluoromethyl)-2-((2-(trimethylsilyl)ethoxy)methyl)-2H-indazol-7-yl)methoxy)methyl)-4-phenylpiperidine-1-carboxylate (34 mg, 0.06 mmol) was treated with a trifluoroacetic acid/methylene chloride mixture (1:1, 2 mL) for 4 h. The solvent was removed in vacuo and the resulting crude mixture passed through a strong cation exchange column. After washing the column with several volumes of methanol, the product was eluted by washing the column with 2 M ammonia in methanol. The solvent was evaporated and the compound purified by reverse phase HPLC to afford 5 mg (27%) as a clear oil. $^1$H-NMR (CD$_3$OD, 500 MHz) δ 7.87 (s, 1H), 7.53 (s, 1H), 7.37-7.43 (m, 4H), 7.29-7.30 (m, 1H), 4.77 (s, 2H), 3.56 (s, 2H), 3.27-3.31 (m, 2H), 2.90-2.95 (m, 2H), 2.50-2.53 (m, 2H), 2.14-2.20 (m, 2H). Mass spec.: 468.08 (MH)+. Accurate mass spec.: m/z 468.1322 [MH]+, Δ=0.5 ppm.

EXAMPLE 37

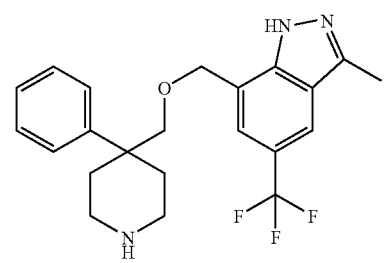

3-Methyl-7-(((4-phenylpiperidin-4-yl)methoxy)methyl)-5-(trifluoromethyl)-1H-indazole. tert-Butyl 4-(((3-methyl-5-(trifluoromethyl)-2-((2-(trimethylsilyl)ethoxy)methyl)-2H-indazol-7-yl)methoxy)methyl)-4-phenylpiperidine-1-carboxylate (100 mg, 0.16 mmol) was treated with a trifluoroacetic acid/methylene chloride mixture (1:1, 3 mL) for 4 h. The solvent was removed in vacuo and the resulting crude mixture passed through a strong cation exchange column. After washing the column with several volumes of methanol, the product was eluted by washing the column with 2 M ammonia in methanol. The solvent was evaporated and the compound purified by reverse phase HPLC to afford 24 mg (38%) as a clear oil. $^1$H-NMR (CD$_3$OD, 500 MHz) δ 8.02 (s, 1H), 7.39-7.45 (m, 5H), 7.29-7.45 (m, 1H), 4.76 (s, 2H), 3.56 (s, 2H), 3.27-3.31 (m, 2H), 2.89-2.96 (m, 2H), 2.60 (s, 3H), 2.49-2.52 (m, 2H), 2.16-2.22 (m, 2H). Mass spec.: 404.14 (MH)+. Accurate mass spec.: m/z 404.1930 [MH]+, Δ=4.9 ppm.

EXAMPLE 38

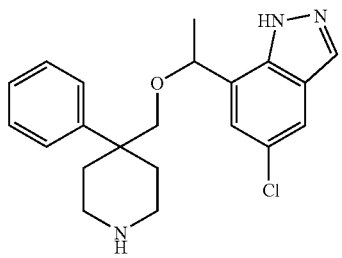

(±)-5-Chloro-7-(1-((4-phenylpiperidin-4-yl)methoxy)ethyl)-1H-indazole. (±)-tert-Butyl 4-((1-(5-chloro-1H-indazol-7-yl)ethoxy)methyl)-4-phenylpiperidine-1-carboxylate (80 mg, 0.17 mmol) was treated with a trifluoroacetic acid/methylene chloride mixture (1:1, 2 mL) for 1 h. The solvent was removed in vacuo and the resulting crude mixture passed through a strong cation exchange column. After washing the column with several volumes of methanol, the product was eluted by washing the column with 2 M ammonia in methanol. The solvent was evaporated to afford 50 mg (79%) as a clear oil. $^1$H-NMR (CDCl$_3$, 500 MHz) δ 7.89 (s, 1H), 7.54 (d, J=1.8 Hz, 1H), 7.37-7.40 (m, 2H), 7.30-7.32 (m, 3H), 7.69 (m, 1H), 4.49 (q, J=6.7 Hz, 1H), 3.40 (d, J=9.2 Hz, 1H), 3.29 (d, J=9.2 Hz, 1H), 2.87-2.93 (m, 2H), 2.67-2.77 (m, 2H), 2.07-2.26 (m, 2H), 1.78-1.93 (m, 2H), 1.41 (m, 3H); $^{13}$C-NMR (126 MHz, CDCl$_3$) δ ppm 143.7, 135.7, 133.6, 128.8, 127.9, 127.1, 126.7, 126.0, 124.8, 124.1, 118.9, 78.0, 50.4, 42.6, 41.9, 33.5, 22.1. Mass spec.: 370.17 (MH)+.

EXAMPLE 39

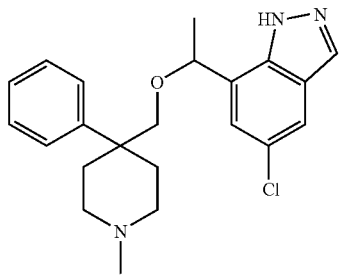

(±)-5-Chloro-7-(1-((1-methyl-4-phenylpiperidin-4-yl)methoxy)ethyl)-1H-indazole. (±)-5-Chloro-7-(1-((4-phenylpiperidin-4-yl)methoxy)ethyl)-1H-indazole (40 mg, 0.11 mmol) and formaldehyde (37 wt. % solution in water, 156 μL) were combined in acetonitrile (2 mL) and cooled to 0° C. The reaction was treated with sodium cyanoborohydride (34 mg, 0.54 mmol) and a few drops of acetic acid. The reaction was stirred at 0° C. for 30 min and at room temperature for 1 h. The solvent was removed in vacuo and the resulting crude mixture passed through a strong cation exchange column. After washing the column with several volumes of methanol, the product was eluted by washing the column with 2 M ammonia in methanol. The solvents were evaporated to afford 30 mg (72%). $^1$H-NMR (CDCl$_3$, 500 MHz) δ 7.89 (s, 1H), 7.55 (d, J=1.8 Hz, 1H), 7.39-7.42 (m, 2H), 7.34-7.37 (m, 1H), 7.27 (m, 2H), 6.97 (d, J=1.5 Hz, 1H), 4.52 (q, J=6.7 Hz, 1H), 3.35 (d, J=9.2 Hz, 1H), 3.23 (d, J=8.9 Hz, 1H), 3.11-3.26 (m, 2H), 2.45-2.53 (m, 2H), 2.49 (s, 3H), 2.38-2.40 (m, 2H), 2.25-2.30 (m, 2H), 1.46 (d, J=6.7 Hz, 3H); $^{13}$C-NMR (126 MHz, CDCl$_3$) δ ppm 135.5, 133.6, 129.3, 127.5, 127.4, 126.9, 126.0, 124.9, 124.4, 119.1, 78.2, 51.5, 51.4, 44.4, 40.5, 30.2, 22.0. Mass spec.: 384.16 (MH)+.

EXAMPLE 40

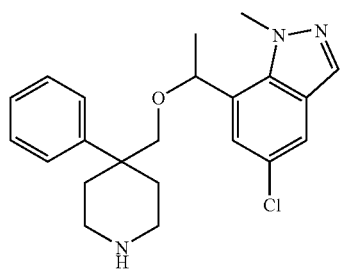

(±)-5-Chloro-1-methyl-7-(1-((4-phenylpiperidin-4-yl)methoxy)ethyl)-1H-indazole. (±)-tert-Butyl 4-((1-(5-chloro-1-methyl-1H-indazol-7-yl)ethoxy)methyl)-4-phenylpiperidine-1-carboxylate (22 mg, 0.06 mmol) was treated with a trifluoroacetic acid/methylene chloride mixture (1:1, 2 mL) for 1 h. The solvent was removed in vacuo and the resulting crude mixture passed through a strong cation exchange column. After washing the column with several volumes of methanol, the product was eluted by washing the column with 2 M ammonia in methanol. The solvent was evaporated to afford 17 mg (97%) as a clear oil. $^1$H-NMR (CDCl$_3$, 500 MHz) δ 7.78 (s, 1H), 7.44 (d, J=1.8 Hz, 1H), 7.31-7.37 (m, 4H), 7.20-7.23 (m, 1H), 6.89 (m, 1H), 4.91 (q, J=6.4 Hz, 1H), 4.16 (s, 3H), 3.40 (d, J=9.2 Hz, 1H), 3.35 (d, J=9.2 Hz, 1H), 2.89-2.95 (m, 2H), 2.71-2.79 (m, 2H), 2.12-2.20 (m, 2H), 1.94-2.03 (m, 2H), 1.44 (d, J=6.4 Hz, 3H); $^{13}$C-NMR (126 MHz, CDCl$_3$) δ ppm 145.7, 144.3, 135.4, 128.3, 127.8, 127.3, 126.1, 123.2, 122.7, 122.4, 117.1, 78.4, 74.0, 42.8, 42.0, 40.5, 33.4, 22.6. Mass spec.: 384.17 (MH)+.

EXAMPLE 41

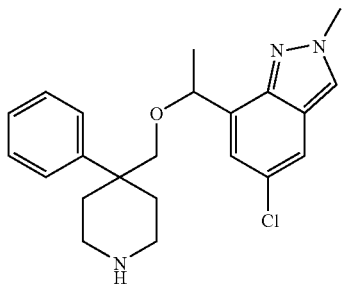

(±)-5-Chloro-2-methyl-7-(1-((4-phenylpiperidin-4-yl)methoxy)ethyl)-2H-indazole. (±)-tert-Butyl 4-((1-(5-chloro- 1-methyl-1H-indazol-7-yl)ethoxy)methyl)-4-phenylpiperidine-1-carboxylate (27 mg, 0.06 mmol) was treated with a trifluoroacetic acid/methylene chloride mixture (1:1, 2 mL) for 1 h. The solvent was removed in vacuo and the resulting crude mixture passed through a strong cation exchange column. After washing the column with several volumes of methanol, the product was eluted by washing the column with 2 M ammonia in methanol. The solvent was evaporated to afford 18 mg (79%) as a clear oil. $^1$H-NMR (CDCl$_3$, 500 MHz) δ 7.86 (s, 1H), 7.54 (d, J=1.8 Hz, 1H), 7.28-7.32 (m, 4H), 7.19-7.23 (m, 1H), 7.10 (d, J=1.8 Hz, 1H), 4.74 (q, J=6.4 Hz, 1H), 3.97 (s, 3H), 3.36 (d, J=9.2 Hz, 1H), 3.23 (d, J=9.2 Hz, 1H), 2.87-2.89 (m, 2H), 2.70-2.76 (m, 2H), 2.13-2.16 (m, 2H), 1.83-1.90 (m, 2H), 1.44 (d, J=6.4 Hz, 3H); $^{13}$C-NMR (126 MHz, CDCl$_3$) δ ppm 144.1, 136.3, 132.5, 128.4, 128.3, 127.2, 126.8, 126.2, 126.1, 125.2, 119.4, 78.2, 42.7, 41.8, 39.9, 33.6, 33.4, 23.4. Mass spec.: 384.17 (MH)$^+$.

EXAMPLE 42

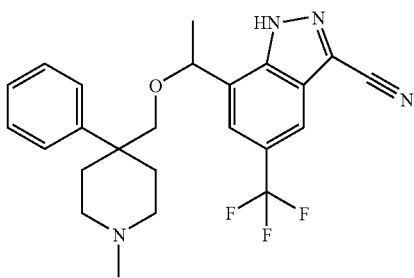

(±)-7-(1-((1-methyl-4-phenylpiperidin-4-yl)methoxy)ethyl)-5-(trifluoromethyl)-1H-indazole-3-carbonitrile. (±)-7-(1-((4-Phenylpiperidin-4-yl)methoxy)ethyl)-5-(trifluoromethyl)-1H-indazole-3-carbonitrile (24 mg, 0.06 mmol) and formaldehyde (37 wt. % solution in water, 77 μL) were combined in acetonitrile (2 mL) and cooled to 0° C. The reaction was treated with sodium cyanoborohydride (18 g, 0.28 mmol) and a few drops of acetic acid. The reaction was stirred at 0° C. for 30 min and at room temperature for 1 h. The solvent was removed in vacuo and the resulting crude mixture passed through a strong cation exchange column. After washing the column with several volumes of methanol, the product was eluted by washing the column with 2 M ammonia in methanol. The solvents were evaporated and the compound purified by flash chromatography on silica gel (1% aq. methanolic ammonia/8% methanol/methylene chloride) to afford 15 mg (59%). $^1$H-NMR (CDCl$_3$, 500 MHz) δ 8.05 (s, 1H), 7.37-7.40 (m, 2H), 7.31-7.34 (m, 2H), 7.22-7.23 (m, 2H), 4.66 (q, J=6.7 Hz, 1H), 3.36-3.43 (m, 2H), 3.34 (q, J=9.2 Hz, 1H), 3.17 (d, J=9.2 Hz, 1H), 2.73-2.84 (m, 2H), 2.59 (s, 3H), 2.53-2.58 (m, 2H), 2.13-2.29 (m, 2H), 1.59 (m, 3H). Mass spec.: 442.48 (MH)$^+$.

EXAMPLE 43

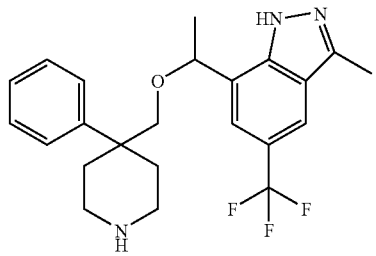

(±)-3-Methyl-7-(1-((4-phenylpiperidin-4-yl)methoxy)ethyl)-5-(trifluoromethyl)-1H-indazole. (±)-tert-Butyl 4-((1-(3-methyl-5-(trifluoromethyl)-1H-indazol-7-yl)ethoxy)methyl)-4-phenylpiperidine-1-carboxylate (62 mg, 0.12 mmol) was treated with a trifluoroacetic acid/methylene chloride mixture (1:1, 2 mL) for 1 h. The solvent was removed in vacuo and the resulting crude mixture passed through a strong cation exchange column. After washing the column with several volumes of methanol, the product was eluted by washing the column with 2 M ammonia in methanol. The solvent was evaporated to afford 42 mg (77%) as a clear oil. $^1$H-NMR (CDCl$_3$, 500 MHz) δ 7.82 (s, 1H), 7.37-7.40 (m, 2H), 7.29-7.32 (m, 3H), 7.19 (m, 1H), 4.55 (q, J=6.7 Hz, 1H), 3.41 (q, J=8.9 Hz, 1H), 3.30 (d, J=8.9 Hz, 1H), 2.87-2.93 (m, 2H), 2.68-2.84 (m, 2H), 2.55 (s, 3H), 2.10-2.25 (m, 2H), 1.81-1.93 (m, 2H), 1.42 (m, 3H); $^{13}$C-NMR (126 MHz, CDCl$_3$) δ ppm 143.8, 143.6, 139.2, 128.7, 127.3, 127.1, 126.7, 124.9 (q, J=272 Hz), 122.9, 122.4 (q, J=32.6 Hz), 119.8, 117.4, 78.3, 50.5, 42.6, 41.5, 33.5, 22.0, 11.9. Mass spec.: 418.19 (MH)$^+$.

EXAMPLE 44

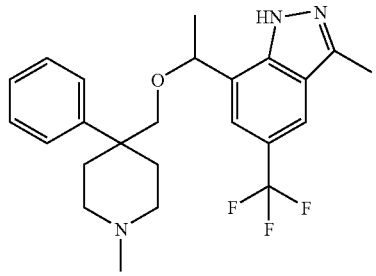

(±)-3-Methyl-7-(1-((1-methyl-4-phenylpiperidin-4-yl)methoxy)ethyl)-5-(trifluoromethyl)-1H-indazole. (±)-3-Methyl-7-(1-((4-phenylpiperidin-4-yl)methoxy)ethyl)-5-(trifluoromethyl)-1H-indazole (32 mg, 0.08 mmol) and formaldehyde (37 wt. % solution in water, 120 μL) were combined in acetonitrile (2 mL) and cooled to 0° C. The reaction was treated with sodium cyanoborohydride (24 mg, 0.38 mmol) and a few drops of acetic acid. The reaction was stirred at 0° C. for 30 min and at room temperature for 1 h. The solvent was removed in vacuo and the resulting crude mixture passed through a strong cation exchange column. After washing the column with several volumes of methanol, the product was eluted by washing the column with 2 M ammonia in methanol. The solvents were evaporated and the compound purified by flash chromatography on silica gel (1% ammonia/8% methanol/methylene chloride) to afford 20 mg (61%). $^1$H-NMR (CDCl$_3$, 500 MHz) δ 7.95 (s, 1H), 7.30-7.40 (m, 5H), 7.21-7.44 (m, 1H), 4.40 (q, J=6.7 Hz, 1H), 3.39 (q, J=9.2 Hz, 1H), 3.33 (d, J=9.2 Hz, 1H), 2.59 (s, 3H), 2.54 (m, 2H), 2.19-2.26 (m, 4H), 2.03-2.07 (m, 2H), 1.46 (m, 3H); $^{13}$C-NMR (126 MHz, CDCl$_3$) δ ppm 143.7, 139.0, 128.7, 127.3, 127.2, 126.7, 124.9 (q, J=272 Hz), 122.9, 122.6 (q, J=32.6 Hz), 119.7, 117.4, 78.4, 52.0, 51.9, 46.6, 40.7, 32.6, 22.0, 11.9. Mass spec.: 418.19 (MH)$^+$. Mass spec.: 432.09 (MH)$^+$.

EXAMPLE 45

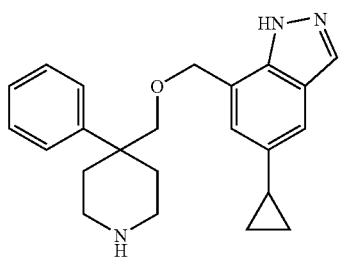

5-Cyclopropyl-7-(((4-phenylpiperidin-4-yl)methoxy)methyl)-1H-indazole. tert-Butyl 4-(((5-cyclopropyl-2-((2-(trimethylsilyl)ethoxy)methyl)-2H-indazol-7-yl)methoxy)methyl)-4-phenylpiperidine-1-carboxylate (34 mg, 0.06 mmol) was treated with a trifluoroacetic acid/methylene chloride mixture (1:1, 2 mL) for 4 h. The solvent was removed in vacuo and the resulting crude mixture passed through a strong cation exchange column. After washing the column with several volumes of methanol, the product was eluted by washing the column with 2 M ammonia in methanol. The solvent was evaporated and the product purified by reverse phase HPLC to afford 10 mg (48%) as a clear oil. $^1$H-NMR (CD$_3$OD, 500 MHz) δ 7.96 (s, 1H), 7.42-7.47 (m, 5H), 7.31-7.34 (m, 1H), 7.01 (m, 1H), 4.71 (s, 2H), 3.51 (s, 2H), 3.24-3.28 (m, 2H), 2.89-2.95 (m, 2H), 2.46-2.49 (m, 2H), 2.16-2.21 (m, 2H), 1.98-2.02 (m, 2H); $^{13}$C-NMR (126 MHz, CD$_3$OD) δ ppm 141.1, 138.1, 136.8, 133.5, 129.1, 127.2, 127.0, 125.6, 124.1, 120.1, 116.5, 78.9, 70.4, 41.1, 41.0, 28.9, 15.1, 8.1. Mass spec.: 362.22 (MH)$^+$. Accurate mass spec.: m/z 362.2217 [MH]$^+$, Δ=4.2 ppm.

EXAMPLE 46

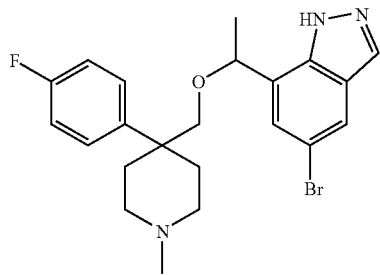

(±)-5-Bromo-7-(1-((4-(4-fluorophenyl)-1-methylpiperidin-4-yl)methoxy)ethyl)-1H-indazole. To a suspension (±)-5-bromo-7-(1-((4-(4-fluorophenyl)piperidin-4-yl)methoxy)ethyl)-1H-indazole (33 mg, 0.076 mmol) and sodium cyanoborohydride (9.6 mg, 0.15 mmol) in acetonitrile (1 mL) was added formalin (50 µl) and one drop of acetic acid. The reaction was stirred at room temperature for 1 h, poured into water/diethyl ether, washed with 1M sodium hydroxide, then water, and concentrated. The crude residue was loaded onto a strong cation exchange cartridge in methanol. The cartridge was flushed with several volumes of methanol which were discarded. The product was eluted with 2M ammonia in methanol and concentrated. $^1$H-NMR (CDCl$_3$, 500 MHz) δ 9.78 (bs, 1H), 7.89 (s, 1H), 7.73 (d, J=1.5, 1H), 7.25 (m, 2H), 7.10 (d, J=1.2, 1H), 7.05 (m, 2H), 4.49 (q, J=6.7, 1H), 3.39 (d, J=9.2, 1H), 3.25 (d, J=9.2, 1H), 2.60 (m, 1H), 2.53 (m, 1H), 1.95-2.32 (m, 5H), 2.21 (s, 3H), 1.92 (m, 1H), 1.41 (d, J=6.7, 3H); $^{13}$C NMR (126 MHz, CDCl$_3$) δ ppm 162.5, 160.6, 135.9, 133.7, 128.7 (d, J=7.7), 128.0, 126.5, 125.5, 122.2, 115.6, 115.4, 113.5, 78.2, 51.9, 51.7, 46.2, 40.3, 32.8, 32.5, 22.2. Mass spec.: 445.93 (MH)$^+$.

EXAMPLE 47

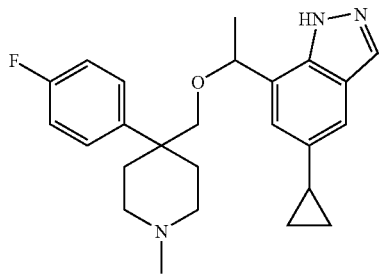

(±)-5-Cyclopropyl-7-(1-((4-(4-fluorophenyl)-1-methylpiperidin-4-yl)methoxy)ethyl)-1H-indazole. To a suspension of (±)-5-cyclopropyl-7-(1-((4-(4-fluorophenyl)piperidin-4-yl)methoxy)ethyl)-1H-indazole (13.5 mg, 0.036 mmol) and sodium cyanoborohydride (11.2 mg, 0.178 mmol) in acetonitrile (1 mL) at 0° C. was added formalin (0.027 mL). The reaction was treated with 1 drop of acetic acid. After 5 min, a second drop of acetic acid was added and the ice bath was removed, stirring continued for another hour. The reaction was diluted with diethyl ether and washed with 1 M sodium hydroxide. The ethereal was concentrated and loaded onto a strong cation exchange cartridge in methanol. The cartridge was flushed with several volumes of methanol which were discarded. The product was eluted with 2 M ammonia in methanol and concentrated. It was then purified by column chromatography (10% 2 M ammonia in MeOH/CH$_2$Cl$_2$) to give 10.5 mg (46.5%) as clear oil. $^1$H-NMR (CDCl$_3$, 500 MHz) δ 9.63 (bs, 1H), 7.86 (s, 1H), 7.23-7.27 (m, 3H), 7.03-7.07 (m, 2H), 6.78 (s, 1H), 4.47 (q, J=5.0 Hz, 1H), 3.35 (d, J=10 Hz, 1H), 3.24 (d, J=5 Hz, 1H), 2.55-2.70 (m, 2H), 1.91-2.30 (m, 9H), 1.40 (d, J=10.0 Hz, 3H), 0.9-0.94 (m, 2H), 0.62-0.68 (m, 2H); $^{13}$C-NMR (CDCl$_3$, 126 MHz) δ 161.5 (d, J=978 Hz), 136.2, 135.9, 133.9, 128.8, 125.9, 124.3, 123.3, 115.8, 115.6, 115.4, 78.9, 51.9, 51.7, 46.1, 40.3, 32.4, 32.3, 22.4, 15.4, 8.7; Mass spec.: 408.09 (MH)+.

EXAMPLE 48

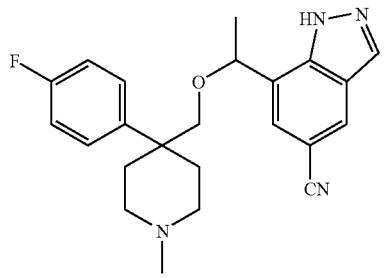

(±)-7-(1-((4-(4-Fluorophenyl)-1-methylpiperidin-4-yl)methoxy)ethyl)-1H-indazole-5-carbonitrile. To a suspension of (±)-5-cyclopropyl-7-(1-((4-(4-fluorophenyl)piperidin-4-yl)methoxy)ethyl)-1H-indazole (21.8 mg, 0.055 mmol) and sodium cyanoborohydride (17.4 mg, 0.277 mmol) in acetonitrile (1 mL) at 0° C. was added formalin (0.041 mL). The reaction was treated with 1 drop of acetic acid. After 5 min, a second drop of acetic acid was added. The ice bath was removed and stirring continued for another hour. The reaction was diluted with diethyl ether and washed with 1 M sodium hydroxide. The ethereal was concentrated and loaded onto a strong cation exchange cartridge in methanol. The cartridge was flushed with several volumes of methanol which were discarded. The product was eluted with 2 M ammonia in methanol and concentrated. It was then purified by preparative HPLC to give 7.8 mg (55.7%). LC/MS (HPLC method 3): $t_R$=1.742 min, 393.07(MH)+.

EXAMPLE 49

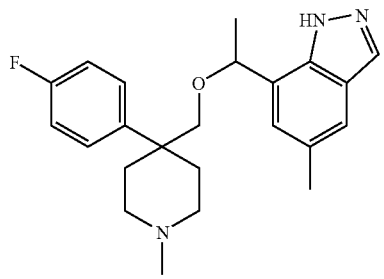

(±)-7-(1-((4-(4-Fluorophenyl)-1-methylpiperidin-4-yl)methoxy)ethyl)-5-methyl-1H-indazole. To a suspension of (±)-7-(1-((4-(4-Fluorophenyl)piperidin-4-yl)methoxy)ethyl)-5-methyl-1H-indazole (24 mg, 0.065 mmol) and sodium cyanoborohydride (20.5 mg, 0.327 mmol) in acetonitrile (1.5 mL) at 0° C. was added formalin (0.053 mL). The reaction was treated with 1 drop of acetic acid. After 5 min, a second drop of acetic acid was added. The ice bath was removed and stirring continued for another 2 h. The reaction was diluted with diethyl ether and washed with 1 M sodium hydroxide. The ethereal was concentrated and purified by column chromatography (10% 2 M ammonia in MeOH/CH$_2$Cl$_2$) to give 12.5 mg (50.2%) as clear oil. $^1$H-NMR (CDCl$_3$, 500 MHz) δ 9.67 (bs, 1H), 7.87 (s, 1H), 7.35 (s, 1H), 7.23-7.27 (m, 2H), 7.03-7.07 (m, 2H), 6.83 (s, 1H), 4.47 (q, J=10 Hz, 1H), 3.35 (d, J=10 Hz, 1H), 3.25 (d, J=10 Hz, 1H), 2.55-2.65 (m, 2H), 2.38 (s, 3H), 2.25-2.29 (m, 1H), 2.21(s, 3H), 1.9-2.2 (m, 5H), 1.40 (d, J=5.0 Hz, 3H); $^{13}$C-NMR (CDCl$_3$, 126 MHz) δ 161.49 (d, J=980 Hz), 135.7, 133.9, 130.0, 128.8, 125.8, 125.7, 124.4, 118.9, 115.5, 115.3, 78.9, 51.9, 51.8, 50.9, 46.2, 32.7, 32.4, 22.4, 21.3; Mass spec.: 382.4 (MH)+.

EXAMPLE 50

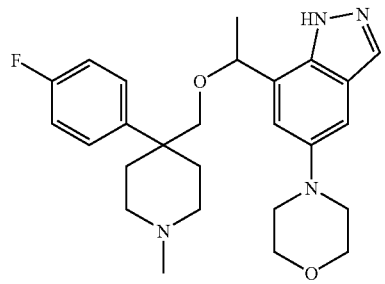

(±)-4-7-(1-((4-(4-Fluorophenyl)-1-methylpiperidin-4-yl)methoxy)ethyl)-1H-indazole-5-yl)morpholino. To a suspension of (±)-4-7-(1-((4-(4-Fluorophenyl)piperidin-4-yl)methoxy)ethyl)-1H-indazole-5-yl)morpholino (24.2 mg, 0.055 mmol) and sodium cyanoborohydride (17.34 mg, 0.276 mmol) in acetonitrile (1 mL) at 0° C. was added formalin (0.041 mL). The reaction was treated with 1 drop of acetic acid. After 5 min, a second drop of acetic acid was added and the ice bath was removed, stirring continued for another hour. The reaction was diluted with diethyl ether and washed with 1 M sodium hydroxide. The ethereal was concentrated and loaded onto a strong cation exchange cartridge in methanol. The cartridge was flushed with several volumes of methanol which were discarded. The product was eluted with 2 M ammonia in methanol and concentrated. It was then purified by preparative HPLC to give 18.5 mg (74%). $^1$H-NMR (MeOD, 500 MHz) δ 8.11 (s, 1H), 7.76 (s, 1H), 7.44 (m, 2H), 7.29 (s, 1H), 7.11 (m, 2H), 4.70 (q, J=10 Hz, 1H), 4.0-4.04 (m, 4H), 3.49-3.51 (m, 4H), 3.40-3.47 (m, 2H), 3.35 (d, J=10 Hz, 1H), 3.24 (d, J=10 Hz, 1H), 2.75-2.85 (m, 2H), 2.74 (s, 3H), 2.55-2.57 (m, 2H), 2.07-2.18 (m, 2H), 1.50 (d, J=5.0 Hz, 3H); $^{13}$C-NMR (MeOD, 126 MHz) δ 161.8 (d, J=975 Hz), 134.1, 129.1, 129.0, 116.4, 115.5, 115.3, 110.0, 78.6, 76.3, 64.9, 54.2, 51.0, 42.3, 40.1, 29.3, 29.2, 20.7; Mass spec.: 453.08 (MH)+.

EXAMPLE 51

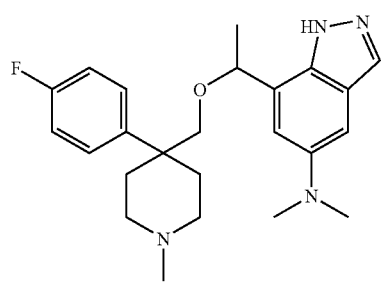

7-(1-((4-(4-Fluorophenyl)-1-methylpiperidin-4-yl)methoxy)ethyl)-N,N-dimethyl-1H-indazol-5-amine. To a suspension of (±)-7-(1-((4-(4-fluorophenyl)piperidin-4-yl)methoxy)ethyl)-N,N-dimethyl-1H-indazol-5-amine (101 mg, 0.255 mmol) and sodium cyanoborohydride (80 mg, 1.27 mmol) in acetonitrile (6 mL) at 0° C. was added formalin (0.053 mL). The reaction was treated with 5 drops of acetic acid and the ice bath was removed, stirring continued for 2 h. The reaction was concentrated and purified by preparative HPLC to give 78.5 mg (75%). $^1$H-NMR (CDCl$_3$, 500 MHz) δ 8.17 (s, 1H), 7.90 (s, 1H), 7.38 (s, 1H), 7.23 (m, 3H), 7.10 (m, 2H), 4.66 (q, J=5.0 Hz, 1H), 3.50-3.57 (m, 2H), 3.39 (d, J=10 Hz, 1H), 3.27 (s, 6H), 3.18 (d, J=10 Hz, 1H), 2.74 (s, 3H), 2.50-2.73 (m, 4H), 2.35-2.45 (m,2H), 1.51 (d, J=5.0 Hz, 3H); Mass spec.: 411.45 (MH)$^+$.

127.4, 124.3, 115.9, 115.4, 98.9, 78.6, 55.7, 51.9, 51.7, 46.1, 40.3, 32.6, 32.3, 22.2; Mass spec.: 398.45 (MH)$^+$.

EXAMPLE 53

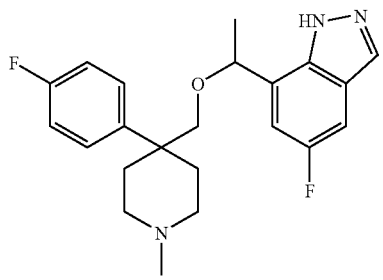

(±)-5-Fluoro-7-(1-((4-(4-fluorophenyl)-1-methylpiperidin-4-yl)methoxy)ethyl)-1H-indazole. To a suspension of (±)-5-fluoro-7-(1-((4-(4-fluorophenyl)piperidin-4-yl)methoxy)methyl)-1H-indazole (64 mg, 0.172 mmol) and sodium cyanoborohydride (21.7 mg, 0.345 mmol) in acetonitrile (4.5 mL) at 0° C. was added formalin (0.128 mL). The reaction was treated with 1 drop of acetic acid. After 5 min, a second drop of acetic acid was added. The ice bath was removed and stirring continued for another hour. The reaction mixture was concentrated and purified by preparative HPLC. The crude product was dissolved in diethyl ether, washed with saturated sodium bicarbonate, dried over magnesium sulfate and concentrated. Column chromatography (10% 2 M ammonia in MeOH/CH$_2$Cl$_2$) gave 26.5 mg (40%) as an clear oil. $^1$H-NMR (CDCl$_3$, 300 MHz) δ 9.72 (bs, 1H), 7.89 (s, 1H), 7.15-7.28 (m, 3H), 7.0-7.07 (m, 2H), 6.78 (m, 1H), 4.48 (q, J=6.0 Hz, 1H), 3.38 (d, J=9 Hz, 1H), 3.25 (d, J=9 Hz, 2H), 2.47-2.60 (m, 2H), 1.86-2.30 (m, 9H), 1.39 (d, J=9 Hz, 3H); $^{13}$C-NMR (CDCl$_3$, 76 MHz) δ 161.4 (d, J=978 Hz), 157.4 (d, J=945 Hz), 134.0, 133.8, 128.6, 128.5, 127.6, 123.7, 115.5, 115.2, 113.2, 112.8, 103.5, 103.2, 78.1, 51.7, 51.5, 46.0, 40.1, 32.6, 32.3, 22.0; Mass spec.: 386.22 (MH)$^+$.

EXAMPLE 52

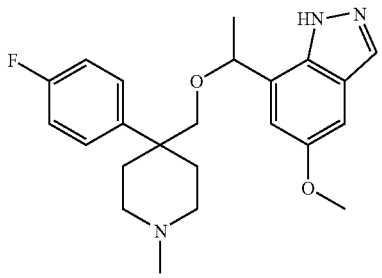

(±)-7-(1-((4-(4-Fluorophenyl)-1-methylpiperidin-4-yl)methoxy)ethyl)-5-methoxy-1H-indazole. To a suspension of (±)-7-(1-((4-(4-fluorophenyl)piperidin-4-yl)methoxy)methyl)-5-methoxy-1H-indazole (15 mg, 0.039 mmol) and sodium cyanoborohydride (4.92 mg, 0.078 mmol) in acetonitrile (1 mL) at 0° C. was added formalin (0.029 mL). The reaction was treated with 1 drop of acetic acid. After 5 min, a second drop of acetic acid was added and the ice bath was removed, stirring continued for another hour. The reaction was concentrated and loaded onto a strong cation exchange cartridge in methanol. The cartridge was flushed with several volumes of methanol which were discarded. The product was eluted with 2 M ammonia in methanol and concentrated. It was then purified by column chromatography (10% 2 M ammonia in MeOH/CH$_2$Cl$_2$) to give 12 mg (77%) as clear oil. $^1$H-NMR (CDCl$_3$, 500 MHz) δ 9.64 (bs, 1H), 7.86 (s, 1H), 7.24-7.27 (m, 2H), 7.04-7.07 (m, 2H), 6.93 (s, 1H), 6.70 (s, 1H), 4.46 (q, J=10 Hz, 1H), 3.80 (s, 3H), 3.36 (d, J=10 Hz, 1H), 3.27 (d, J=10 Hz, 1H), 2.50-2.70 (m, 2H), 2.23 (s, 3H), 1.95-2.30 (m, 6H), 1.41 (d, J=5.0 Hz, 3H); $^{13}$C-NMR (CDCl$_3$, 126 MHz) δ 161.5 (d, J=975 Hz), 154.5, 133.9, 133.1, 128.8,

EXAMPLE 54

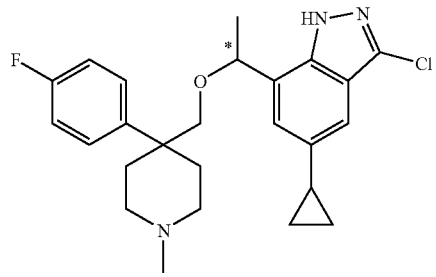

Enantiomer B of 5-Cyclopropyl-7-(1-((4-(4-fluorophenyl)-1-methylpiperidin-4-yl)methoxy)ethyl)-1H-indazole. To a suspension of Enantiomer B of 3-chloro-5-cyclopropyl-7-(1-((4-(4-fluorophenyl)piperidin-4-yl)methoxy)ethyl)-1H-indazole (17.2 mg, 0.04 mmol) and sodium cyanoborohydride (5.1 mg, 0.08 mmol) in acetonitrile (2 mL) at 0° C. was added formalin (0.03 mL). The reaction was treated with 1 drop of acetic acid. After 5 min, a second drop of acetic acid was added. The ice bath was removed and stirring continued for another hour. The reaction was diluted with diethyl ether and washed with 1 M sodium hydroxide. The ethereal was concentrated and loaded onto a strong cation exchange cartridge in methanol. The cartridge was flushed with several volumes of methanol which were discarded. The product was eluted with 2 M ammonia in methanol and concentrated. It was then purified by column chromatography (10% 2 M ammonia in MeOH/CH$_2$Cl$_2$) to give 17.4 mg (98%) as clear oil. $^1$H-NMR (CDCl$_3$, 300 MHz) δ 9.42 (s, 1H), 7.22-7.25 (m, 2H), 7.21 (s, 1H), 7.0-7.07 (m, 2H), 6.78 (s, 1H), 4.45 (q, J=6.0 Hz, 1H), 3.35 (d, J=9.0 Hz, 1H), 3.23 (d, J=9.0 Hz, 1H), 2.45-2.61 (m, 2H), 1.87-2.25 (m, 9H), 1.37 (d, J=6.0 Hz, 3H), 0.93 (m, 2H), 0.66 (m, 2H); $^{13}$C-NMR (CDCl$_3$, 76 MHz) δ 161.3 (d, J=975 Hz), 137.1, 134.1, 128.5, 126.4, 124.2, 121.3, 115.4, 115.17, 114.1, 78.5, 51.6, 46.0, 40.2, 32.5, 32.3, 22.15, 15.2, 8.7, 8.63; Mass spec.: 442.57 (MH)$^+$.

EXAMPLE 55

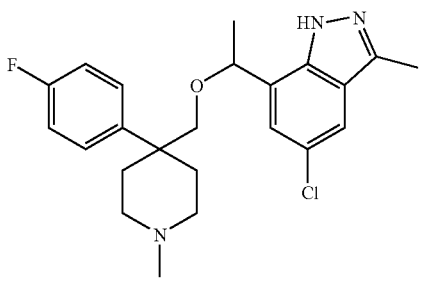

(±)-5-Chloro-7-(1-((4-(4-fluorophenyl)-1-methylpiperidin-4-yl)methoxy)ethyl)-3-methyl-1H-indazole. (±)-tert-Butyl 4-((1-(5-chloro-3-methyl-1-((2-(trimethylsilyl)ethoxy)methyl)-1H-indazol-7-yl)ethoxy)methyl)-4-(4-fluorophenyl)piperidine-1-carboxylate (70 mg, 0.11 mmol) was dissolved in trifluoroacetic acid (50% in dichloromethane, 2 mL) and stirred at room temperature for 3 h. The reaction was concentrated, loaded onto a strong cation exchange cartridge in methanol, and flushed with several volumes of methanol which were discarded. The crude secondary amine was eluted in 2 M ammonia in methanol and concentrated. The resulting residue was dissolved in acetonitrile (2 mL), cooled to 0° C., and treated with sodium cyanoborohydride (34.8 mg, 0.55 mmol) and formalin (0.4 mL). After 5 min, the reaction was treated with a few drops of acetic acid. The ice bath was removed and stirring continued for 1 h. The reaction was concentrated and purified by reverse phase HPLC to give 38 mg (65%) as the TFA salt. $^1$H-NMR (CD$_3$OD, 500 MHz) δ 7.59 (d, J=1.8 Hz, 1H), 7.32-7.45 (m, 2H), 6.99-7.15 (m, 2H), 6.94-6.99 (m, 1H), 4.66 (q, J=6.6 Hz, 1H), 3.43-3.52 (m, 2H), 3.22 (m, 2H), 2.81-2.85 (m, 2H), 2.76 (s, 3H), 2.58-2.68 (m, 2H), 2.51 (s, 3H), 2.07-2.21 (m, 2H), 1.47 (d, J=6.6 Hz, 3H). Mass spec.: 416.44 (MH)$^+$.

EXAMPLE 56

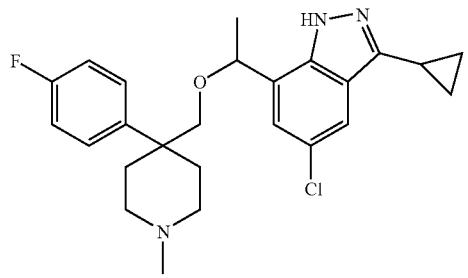

(±)-5-Chloro-3-cyclopropyl-7-(1-((4-(4-fluorophenyl)-1-methylpiperidin-4-yl)methoxy)ethyl)-1H-indazole. (±)-tert-Butyl 4-((1-(5-chloro-3-cyclopropyl-1-((2-(trimethylsilyl)ethoxy)methyl)-1H-indazol-7-yl)ethoxy)methyl)-4-(4-fluorophenyl)piperidine-1-carboxylate (65 mg, 0.1 mmol) was dissolved in trifluoroacetic acid (50% in dichloromethane, 2 mL) and stirred at room temperature for 3 h. The reaction was concentrated, loaded onto a strong cation exchange cartridge in methanol, and flushed with several volumes of methanol which were discarded. The crude secondary amine was eluted in 2 M ammonia in methanol and concentrated. The resulting residue was dissolved in acetonitrile (2 mL), cooled to 0° C., and treated with sodium cyanoborohydride (31.0 mg, 0.55 mmol) and formalin (0.36 mL). After 5 min, the reaction was treated with a few drops of acetic acid. The ice bath was removed and stirring continued for 1 h. The reaction was concentrated and purified by reverse phase HPLC to give 38 mg (67%) as the TFA salt. $^1$H-NMR (CD$_3$OD, 500 MHz) δ 7.64-6.65 (m, 1H), 7.33-7.44 (m, 2H), 7.01-7.14 (m, 2H), 6.92-6.95 (m, 1H), 4.65 (q, J=6.4 Hz, 1H), 3.42-3.51 (m, 2H), 3.22-3.36 (m, 2H), 2.80-2.89 (m, 2H), 2.76 (s, 3H), 2.60-2.67 (m, 2H), 2.08-2.21 (m, 3H), 1.46 (m, 3H), 0.97-1.06 (m, 4H). Mass spec.: 442.44 (MH)$^+$.

EXAMPLE 57

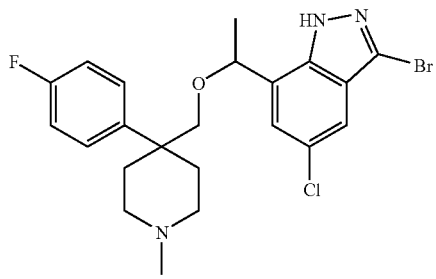

(±)-3-Bromo-5-chloro-7-(1-((4-(4-fluorophenyl)-1-methylpiperidin-4-yl)methoxy)ethyl)-1H-indazole. (±)-tert-Butyl 4-((1-(3-bromo-5-chloro-1-((2-(trimethylsilyl)ethoxy)methyl)-1H-indazol-7-yl)ethoxy)methyl)-4-(4-fluorophenyl)piperidine-1-carboxylate (70 mg, 0.1 mmol) was dissolved in trifluoroacetic acid (50% in dichloromethane, 2 mL) and stirred at room temperature for 3 h. The reaction was concentrated, loaded onto a strong cation exchange cartridge in methanol, and flushed with several volumes of methanol which were discarded. The crude secondary amine was eluted in 2 M ammonia in methanol and concentrated. The resulting residue was dissolved in acetonitrile (2 mL), cooled to 0° C., and treated with sodium cyanoborohydride (31.5 mg, 0.5 mmol) and formalin (0.36 mL). After 5 min, the reaction was treated with a few drops of acetic acid. The ice bath was removed and stirring continued for 1 h. The reaction was concentrated and purified by reverse phase HPLC to give 38 mg (67%) as the TFA salt. $^{1}$H-NMR (CD$_{3}$OD, 500 MHz) δ 7.46 (d, J=1.8 Hz, 1H), 7.32-7.44 (m, 2H), 7.01-7.14 (m, 3H), 4.66 (q, J=6.4 Hz, 1H), 3.41-3.52 (m, 2H), 3.37 (q$_{AB}$, J$_{AB}$=9.5 Hz, 2H), 2.81-2.88 (m, 2H), 2.76 (s, 3H), 2.61-2.68 (m, 2H), 2.07-2.18 (m, 2H), 1.48 (d, J=6.4 Hz, 3H). Mass spec.: 482.27 (MH)$^{+}$.

EXAMPLE 58

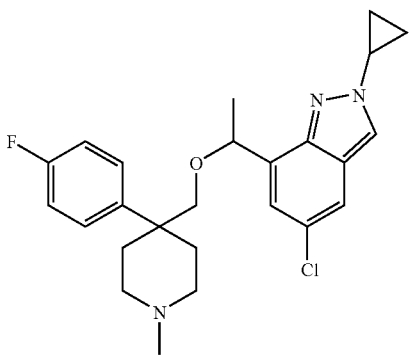

(±)-5-Chloro-2-cyclopropyl-7-(1-((4-(4-fluorophenyl)-1-methylpiperidin-4-yl)methoxy)ethyl)-2H-indazole. (±)-tert-Butyl 4-((1-(5-chloro-2-cyclopropyl-2H-indazol-7-yl)ethoxy)methyl)-4-(4-fluorophenyl)piperidine-1-carboxylate (65 mg, 0.12 mmol) was dissolved in trifluoroacetic acid (50% in dichloromethane, 2 mL) and stirred at room temperature for 1 h. The reaction was concentrated, loaded onto a strong cation exchange cartridge in methanol, and flushed with several volumes of methanol which were discarded. The crude secondary amine was eluted in 2 M ammonia in methanol and concentrated. The resulting residue was dissolved in acetonitrile (2 mL), cooled to 0° C., and treated with sodium cyanoborohydride (38.7 mg, 0.62 mmol) and formalin (0.45 mL). After 5 min, the reaction was treated with a few drops of acetic acid. The ice bath was removed and stirring continued for 1 h. The reaction was concentrated and loaded onto a strong cation exchange cartridge in methanol. The cartridge was flushed with several volumes of methanol which were discarded. The product was eluted with 2 M ammonia in methanol and concentrated to give 16 mg (29%) as a clear oil. $^{1}$H-NMR (CDCl$_{3}$, 500 MHz) δ 7.86 (s, 1H), 7.41 (m, 1H), 7.30-7.33 (m, 2H), 6.99-7.03 (m, 2H), 6.78 (m, 1H), 4.92 (q, J=6.4 Hz, 1H), 3.86-3.90 (m, 2H), 3.33-3.38 (m, 2H), 2.52-2.53 (m, 2H), 2.20 (s, 3H), 1.97-2.24(m, 6H), 1.41 (d, J=6.4 Hz, 3H), 1.25-1.28 (m, 2H), 1.13-1.17 (m, 2H); $^{13}$C-NMR (CDCl$_{3}$, 126 MHz) δ 161.3 (d, J=243.8 Hz), 145.4 135.2, 129.0, 128.9, 127.9, 122.3, 122.1, 117.0, 115.0, 114.9, 73.8, 52.1, 50.8, 46.4, 40.5, 34.7, 32.8, 22.8. Mass spec.: 442.44 (MH)$^{+}$.

EXAMPLE 59

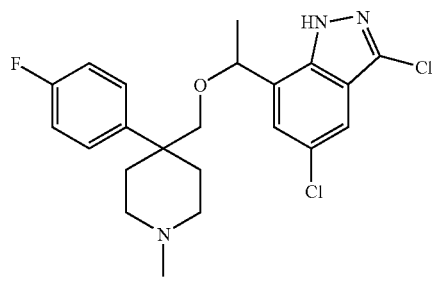

(±)-3,5-Dichloro-7-(1-((4-(4-fluorophenyl)-1-methylpiperidin-4-yl)methoxy)ethyl)-1H-indazole. (±)-tert-Butyl 4-((1-(3,5-dichloro-1H-indazol-7-yl)ethoxy)methyl)-4-(4-fluorophenyl)piperidine-1-carboxylate (120 mg, 0.23 mmol) was dissolved in trifluoroacetic acid (50% in dichloromethane, 2 mL) and stirred at room temperature for 1 h. The reaction was concentrated, loaded onto a strong cation exchange cartridge in methanol, and flushed with several volumes of methanol which were discarded. The crude secondary amine was eluted in 2 M ammonia in methanol and concentrated. The resulting residue was dissolved in acetonitrile (2 mL), cooled to 0° C., and treated with sodium cyanoborohydride (72 mg, 1.15 mmol) and formalin (0.84 mL). After 5 min, the reaction was treated with a drop of acetic acid. The ice bath was removed and stirring continued for 1 h. The reaction was concentrated and purified by preparative HPLC to afford 30 mg (30%) as a clear oil. $^{1}$H-NMR (CD$_{3}$OD, 500 MHz) δ 7.53 (d, J=1.8 Hz, 1H), 7.33-7.45 (m, 2H), 6.99-7.14 (m, 3H), 4.66 (q, J=6.7 Hz, 1H), 3.41-3.52 (m, 2H), 3.38 (q$_{AB}$, J$_{AB}$=9.2 Hz, 2H), 2.81-2.90 (m, 2H), 2.77(s, 3H), 2.61-2.69(m, 2H), 2.07-2.18 (m, 2H), 1.48 (m, 3H). Mass spec.: 442.44 (MH)$^{+}$.

EXAMPLE 60

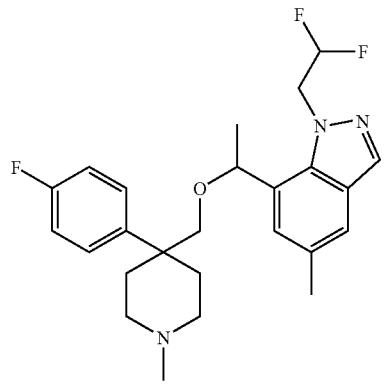

(±)-1-(2,2-Difluoroethyl)-7-(1-((4-(4-fluorophenyl)-1-methylpiperidin-4-yl)methoxy)ethyl)-5-methyl-1H-indazole. (±)-tert-Butyl 4-((1-(1-(2,2-difluoroethyl)-5-methyl-1H-indazol-7-yl)ethoxy)methyl)-4-(4-fluorophenyl)

piperidine-1-carboxylate (10 mg, 0.02 mmol) was dissolved in trifluoroacetic acid (50% in dichloromethane, 1 mL) and stirred at room temperature for 1 h. The reaction was concentrated, loaded onto a strong cation exchange cartridge in methanol, and flushed with several volumes of methanol which were discarded. The crude secondary amine was eluted in 2 M ammonia in methanol and concentrated. The resulting residue was dissolved in acetonitrile (1 mL), cooled to 0° C., and treated with sodium cyanoborohydride (5.9 mg, 0.01 mmol) and formalin (0.52 mL). After 5 min, the reaction was treated with a few drops of acetic acid. The ice bath was removed and stirring continued for 1 h. The reaction was concentrated and purified by column chromatography (10% methanolic ammonia/methylene chloride) to afford 4 mg (47%) as a clear oil. LC/MS (HPLC method 1): $t_R$=2.35 min, 446.56(MH)$^+$.

EXAMPLE 61

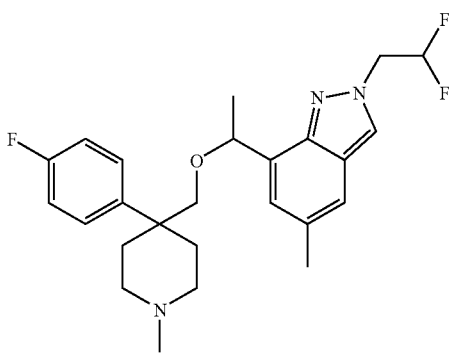

(±)-2-(2,2-Difluoroethyl)-7-(1-((4-(4-fluorophenyl)-1-methylpiperidin-4-yl)methoxy)ethyl)-5-methyl-2H-indazole. (±)-tert-Butyl 4-((1-(2-(2,2-difluoroethyl)-5-methyl-2H-indazol-7-yl)ethoxy)methyl)-4-(4-fluorophenyl)piperidine-1-carboxylate (10 mg, 0.02 mmol) was dissolved in trifluoroacetic acid (50% in dichloromethane, 1 mL) and stirred at room temperature for 1 h. The reaction was concentrated, loaded onto a strong cation exchange cartridge in methanol, and flushed with several volumes of methanol which were discarded. The crude secondary amine was eluted in 2 M ammonia in methanol and concentrated. The resulting residue was dissolved in acetonitrile (1 mL), cooled to 0° C., and treated with sodium cyanoborohydride (5.9 mg, 0.01 mmol) and formalin (0.52 mL). After 5 min, the reaction was treated with a few drops of acetic acid. The ice bath was removed and stirring continued for 1 h. The reaction was concentrated and purified by column chromatography (10% methanolic ammonia/methylene chloride) to afford 4.5 mg (54%) as a clear oil. $^1$H-NMR (CDCl$_3$, 500 MHz) δ 7.83 (s, 1H), 7.30-7.34 (m, 2H), 7.22 (m, 1H), 6.99-7.02 (m, 2H), 6.67 (m, 1H), 6.05-6.29 (m, 1H), 4.86 (q, J=6.4 Hz, 1H), 4.64-4.71 (m, 2H), 3.33-3.38 (m, 2H), 2.57 (m, 2H), 2.28 (s, 3H), 2.20 (s, 3H), 2.15-2.24 (m, 6H), 1.44 (d, J=6.4 Hz, 3H). Mass spec.: 446.63(MH)$^+$.

EXAMPLE 62

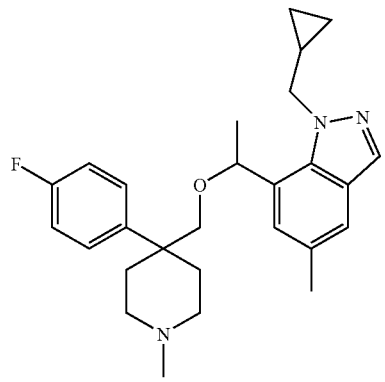

(±)-1-(Cyclopropylmethyl)-7-(1-((4-(4-fluorophenyl)-1-methylpiperidin-4-yl)methoxy)ethyl)-5-methyl-1H-indazole. (±)-tert-Butyl 4-((1-(1-(cyclopropylmethyl)-5-methyl-1H-indazol-7-yl)ethoxy)methyl)-4-(4-fluorophenyl)piperidine-1-carboxylate (7 mg, 0.01 mmol) was dissolved in trifluoroacetic acid (50% in dichloromethane, 1 mL) and stirred at room temperature for 1 h. The reaction was concentrated, loaded onto a strong cation exchange cartridge in methanol, and flushed with several volumes of methanol which were discarded. The crude secondary amine was eluted in 2 M ammonia in methanol and concentrated. The resulting residue was dissolved in acetonitrile (1 mL), cooled to 0° C., and treated with sodium cyanoborohydride (4.2 mg, 0.07 mmol) and formalin (37 µL). After 5 min, the reaction was treated with a few drops of acetic acid. The ice bath was removed and stirring continued for 1 h. The reaction was concentrated and purified by flash chromatography on silica gel (10% methanolic ammonia/methylene chloride) to afford 4 mg (68%). LC/MS (HPLC method 1): $t_R$=2.49 min, 436.59 (MH)$^+$.

EXAMPLE 63

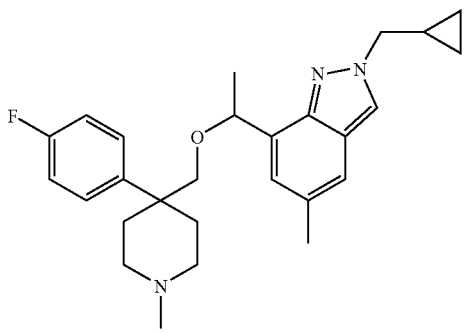

(±)-2-(Cyclopropylmethyl)-7-(1-((4-(4-fluorophenyl)-1-methylpiperidin-4-yl)methoxy)ethyl)-5-methyl-2H-indazole. (±)-tert-Butyl 4-((1-(2-(cyclopropylmethyl)-5-methyl-2H-indazol-7-yl)ethoxy)methyl)-4-(4-fluorophenyl)piperidine-1-carboxylate (15 mg, 0.03 mmol) was dissolved in trifluoroacetic acid (50% in dichloromethane, 1 mL) and stirred at room temperature for 1 h. The reaction was concentrated, loaded onto a strong cation exchange cartridge in methanol, and flushed with several volumes of methanol which were discarded. The crude secondary amine was eluted in 2 M ammonia in methanol and concentrated. The resulting residue was dissolved in acetonitrile (1 mL), cooled to 0° C., and treated with sodium cyanoborohydride (9 mg, 0.14 mmol) and formalin (79 μL). After 5 min, the reaction was treated with a few drops of acetic acid. The ice bath was removed and stirring continued for 1 h. The reaction was concentrated and purified by flash chromatography on silica gel (10% methanolic ammonia/methylene chloride) to afford 5 mg (40%) as a clear oil. $^1$H-NMR (CDCl$_3$, 500 MHz) δ 7.89 (s, 1H), 7.32-7.34 (m, 2H), 7.23 (m, 1H), 6.99-7.02 (m, 2H), 6.66 (m, 1H), 4.94 (q, J=6.4 Hz, 1H), 4.22-4.24 (m, 2H), 3.34-3.41 (m, 2H), 2.57 (m, 2H), 2.29 (s, 3H), 2.21 (s, 3H), 2.09-2.25 (m, 6H), 2.01-2.04 (m, 1H), 1.44 (d, J=6.4 Hz, 3H), 0.64 (m, 2H), 0.40-0.43 (m, 2H). Mass spec.: 436.53(MH)$^+$.

EXAMPLE 64

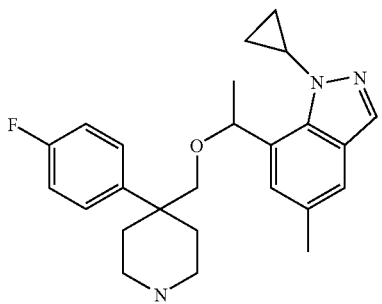

(±)-1-Cyclopropyl-7-(1-((4-(4-fluorophenyl)-1-methylpiperidin-4-yl)methoxy)ethyl)-5-methyl-1H-indazole. (±)-tert-Butyl 4-((1-(1-cyclopropyl-5-methyl-1H-indazol-7-yl)ethoxy)methyl)-4-(4-fluorophenyl)piperidine-1-carboxylate (10 mg, 0.02 mmol) was dissolved in trifluoroacetic acid (50% in dichloromethane, 1 mL) and stirred at room temperature for 1 h. The reaction was concentrated, loaded onto a strong cation exchange cartridge in methanol, and flushed with several volumes of methanol which were discarded. The crude secondary amine was eluted in 2 M ammonia in methanol and concentrated. The resulting residue was dissolved in acetonitrile (1 mL), cooled to 0° C., and treated with sodium cyanoborohydride (6.2 mg, 0.1 mmol) and formalin (54 μL). After 5 min, the reaction was treated with a few drops of acetic acid. The ice bath was removed and stirring continued for 1 h. The reaction was concentrated and purified by flash chromatography on silica gel (10% methanolic ammonia/methylene chloride) to afford 3 mg (36%) as a clear oil. LC/MS (HPLC method 1): t$_R$=2.46 min, 422.37(MH)$^+$.

EXAMPLE 65

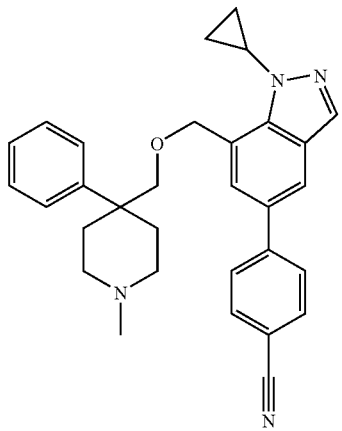

4-(1-Cyclopropyl-7-(((1-methyl-4-phenylpiperidin-4-yl)methoxy)methyl)-1H-indazol-5-yl)benzonitrile. tert-Butyl 4-(((5-(4-cyanophenyl)-1-cyclopropyl-1H-indazol-7-yl)methoxy)methyl)-4-phenylpiperidine-1-carboxylate (23 mg, 0.04 mmol) was dissolved in trifluoroacetic acid (50% in dichloromethane, 2 mL) and stirred at room temperature for 1 h. The reaction was concentrated, loaded onto a strong cation exchange cartridge in methanol, and flushed with several volumes of methanol which were discarded. The crude secondary amine was eluted in 2 M ammonia in methanol and concentrated. The resulting residue was dissolved in acetonitrile (2 mL), cooled to 0° C., and treated with sodium cyanoborohydride (12.8 mg, 0.2 mmol) and formalin (152 μL). After 5 min, the reaction was treated with a few drops of acetic acid. The ice bath was removed and stirring continued for 1 h. The reaction was concentrated and purified by flash chromatography on silica gel (10% methanolic ammonia/methylene chloride) to afford 23 mg (95%) as a clear oil. $^1$H-NMR (CDCl$_3$, 500 MHz) δ 7.91 (s, 1H), 7.81 (d, J=1.5 Hz, 1H), 7.71-7.73 (m, 2H), 7.65-7.67 (m, 2H), 7.40 (m, 1H), 7.24-7.30 (m, 4H), 7.16-7.19 (m, 1H), 4.93 (s, 2H), 3.49-3.52 (m, 1H), 3.46 (s, 2H), 2.51-253 (m, 2H), 2.16 (s, 3H), 2.12-2.22 (m, 4H), 1.91-1.96 (m, 2H), 1.21-1.24 (m, 2H), 0.88-0.92 (m, 2H), $^{13}$C-NMR (CDCl$_3$, 126 MHz) δ 171.1, 161.7 (d, J=246.6 Hz), 145.8 139.1, 133.0, 132.7, 131.9, 128.3, 127.8, 127.3, 127.1, 126.5, 126.1, 122.3, 119.6, 119.1, 110.6, 70.9, 52.0, 50.8, 46.3, 40.8, 32.7, 32.1, 8.2. Mass spec.: 477.41 (MH)$^+$.

EXAMPLE 66

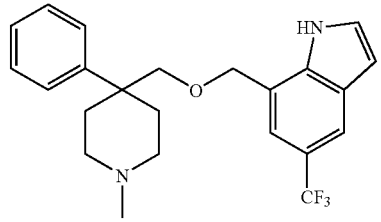

7-(((1-Methyl-4-phenylpiperidin-4-yl)methoxy)methyl)-5-(trifluoromethyl)-1H-indole. Lithium aluminum hydride (1M in tetrahydrofuran, 1.71 ml, 1.71 mmol) was added to a solution of tert-butyl 4-phenyl-4-(((5-(trifluoromethyl)-1H-indol-7-yl)methoxy)methyl)piperidine-1-carboxylate (93 mg, 0.19 mmol) in tetrahydrofuran (5 ml). The reaction was heated at reflux for 3 h. The reaction was quenched by sequential dropwise addition of water (0.2 mL), 1N sodium hydroxide (0.6 mL), and more water (0.2 mL). The mixture was filtered and the filtrate evaporated. The residue was chromatographed on silica gel with 15% methanol in dichloromethane. The product 7-(((1-methyl-4-phenylpiperidin-4-yl)methoxy)methyl)-5-(trifluoromethyl)-1H-indole (52 mg, 0.129 mmol, 67.9% yield) was isolated as a clear oil. $^1$H-NMR (CDCl$_3$, 400 MHz) δ 7.92 (bs, 1H), 7.78 (s, 1H), 7.32-7.48 (m, 5H), 7.08 (s, 1H), 6.85 (s, 1H), 6.45 (s, 1H), 4.72 (s, 2H), 3.52 (s, 2H), 2.73 (m, 2H), 2.31 (s, 3H), 2.22-2.40 (m, 4H), 2.12 (m, 2H); Mass spec. (MH)$^+$: 403.11.

EXAMPLE 67

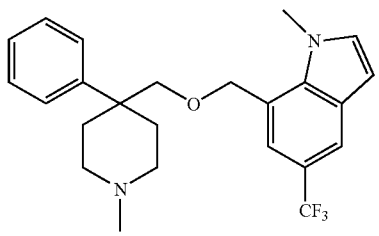

1-Methyl-7-(((1-methyl-4-phenylpiperidin-4-yl)methoxy)methyl)-5-(trifluoromethyl)-1H-indole. Lithium aluminum hydride (1M in tetrahydrofuran, 1.07 ml, 1.07 mmol) was added to a solution of tert-butyl 4-(((1-methyl-5-(trifluoromethyl)-1H-indol-7-yl)methoxy)methyl)-4-phenylpiperidine-1-carboxylate (60 mg, 0.119 mmol) in tetrahydrofuran (5 ml). The reaction was heated at reflux for 3 h. The reaction was quenched by sequential dropwise addition of water (0.2 mL), 1N sodium hydroxide (0.6 mL), and more water (0.2 mL). The mixture was filtered and the filtrate evaporated. The residue was purified by chromatography on silica gel with a gradient from 5% to 10% 2M ammonia in methanol/dichloromethane. The product 1-methyl-7-(((1-methyl-4-phenylpiperidin-4-yl)methoxy)methyl)-5-(trifluoromethyl)-1H-indole (45 mg, 0.108 mmol, 91% yield) was isolated as a clear oil. $^1$H-NMR (CDCl$_3$, 400 MHz) δ 7.82 (s, 1H), 7.22-7.36 (m, 6H), 6.93 (s, 1H), 6.49 (s, 1H), 4.65 (s, 2H), 3.63 (s, 3H), 3.42 (s, 2H), 2.53 (m, 2H), 2.20 (s, 3H), 2.13-2.25 (m, 4H), 1.94 (m, 2H); Mass spec. (MH)$^+$: 417.13.

EXAMPLE 68

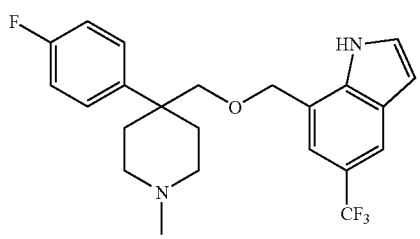

7-(((1-Methyl-4-(4-fluorophenyl)piperidin-4-yl)methoxy)methyl)-5-(trifluoromethyl)-1H-indole. The product was obtained from tert-Butyl 4-(4-fluorophenyl)-4-(((((5-(trifluoromethyl)-1-((2-trimethylsilyl)ethoxy)methyl)-1H-indol-7-yl)methoxy)methyl)piperidine-1-carboxylate using the route used for previous indole examples. The product 7-(((1-methyl-4-(4-fluorophenyl)piperidin-4-yl)methoxy)methyl)-5-(trifluoromethyl)-1H-indole was isolated as a clear oil. $^1$H-NMR (CDCl$_3$, 400 MHz) δ 8.01 (bs, 1H), 7.80 (s, 1H), 7.30 (m, 2H), 7.09 (m, 3H), 6.93 (t, J=2.5 Hz, 1H), 6.49 (m, 1H), 4.73 (s, 2H), 3.46 (s, 2H), 2.71 (m, 2H), 2.30 (s, 3H), 2.07-2.40 (m, 6H); LC/MS (HPLC method 4): t$_R$=2.993 min, 421.10(MH)$^+$.

EXAMPLE 69

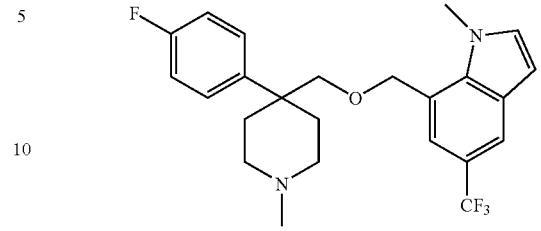

1-Methyl-7-(((1-methyl-4-(4-fluorophenyl)piperidin-4-yl)methoxy)methyl)-5-(trifluoromethyl)-1H-indole. The product was obtained from tert-Butyl 4-(4-fluorophenyl)-4-(((((5-(trifluoromethyl)-1-((2-trimethylsilyl)ethoxy)methyl)-1H-indol-7-yl)methoxy)methyl)piperidine-1-carboxylate using the route used for previous indole examples. The product 1-methyl-7-(((1-methyl-4-(4-fluorophenyl)piperidin-4-yl)methoxy)methyl)-5-(trifluoromethyl)-1H-indole was isolated as a clear oil. $^1$H-NMR (CDCl$_3$, 400 MHz) δ 7.83 (s, 1H), 7.11 (m, 3H), 6.94 (d, J=2.8 Hz, 1H), 6.86 (t J=8.7 Hz, 2H), 6.50 (d, J=3.2 Hz, 1H), 4.67 (s, 2H), 3.67 (s, 3H), 3.40 (s, 2H), 2.53 (m, 2H), 2.21 (s, 3H), 2.08-2.30 (m, 4H), 1.94 (m, 2H); LC/MS (HPLC method 4): t$_R$=2.731 min, 435.16(MH)$^+$.

EXAMPLE 70

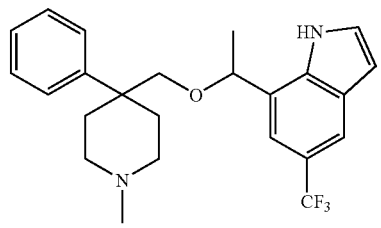

(±)-7-(1-((1-Methyl-4-phenylpiperidin-4-yl)methoxy)ethyl)-5-(trifluoromethyl)-1H-indole. The product was obtained from (±)-tert-Butyl 4-phenyl-4-((1-(5-(trifluoromethyl)-1-((2-(trimethylsilyl)ethoxy)methyl)-1H-indol-7-yl)ethoxy)methyl)piperidine-1-carboxylate using the route used for previous indole examples. The product was isolated as a clear oil. $^1$H-NMR (CDCl$_3$, 400 MHz) δ 8.05 (bs, 1H), 7.74 (s, 1H), 7.26-7.42 (m, 5H), 7.03 (s, 1H), 6.73 (s, 1H), 6.41 (dd, J=3.2, 2.5 Hz, 1H), 4.59 (q, J=7.0 Hz, 1H), 3.42 (m, 1H), 3.23 (d, J=8.3 Hz, 1H), 2.70 (m, 2H), 2.28 (s, 3H), 1.90-2.50 (m, 6H), 1.44 (d, J=6.5 Hz, 3H); LC/MS (HPLC method 4): t$_R$=3.150 min, 417.17(MH)$^+$.

EXAMPLE 71

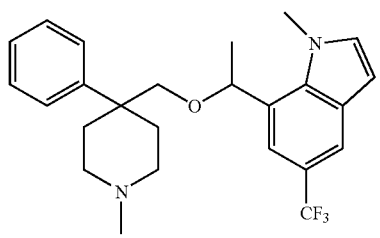

(±)-1-Methyl-7-(1-((1-methyl-4-phenylpiperidin-4-yl)methoxy)ethyl)-5-(trifluoromethyl)-1H-indole. The product was obtained from (±)-tert-Butyl 4-phenyl-4-((1-(5-(trifluoromethyl)-1-((2-(trimethylsilyl)ethoxy)methyl)-1H-indol-7-yl)ethoxy)methyl)piperidine-1-carboxylate using the route used for previous indole examples. $^1$H-NMR (CDCl$_3$, 400 MHz) δ 7.75 (s, 1H), 7.16-7.45 (m, 6H), 6.96 (d, J=3.0 Hz, 1H), 6.51 (d, J=3.0 Hz, 1H), 4.96 (m, 1H), 3.77 (s, 3H), 3.36 (m, 1H), 3.17 (m, 1H), 2.94 (m, 2H), 2.40 (s, 3H), 1.98-2.52 (m, 6H), 1.46 (d, J=6.8 Hz, 3H); LC/MS (HPLC method 4): $t_R$=3.223 min, 431.22(MH)$^+$.

EXAMPLE 72

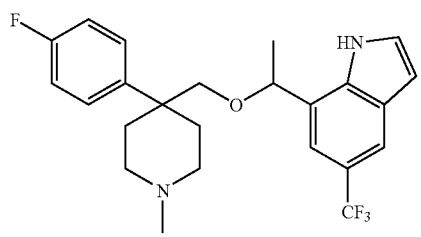

(±)-7-(1-((4-(4-Fluorophenyl)-1-methylpiperidin-4-yl)methoxy)ethyl)-5-(trifluoromethyl)-1H-indole. The product was obtained from (±)-tert-Butyl 4-(4-fluorophenyl)-4-((1-(5-(trifluoromethyl)-1H-indol-7-yl)ethoxy)methyl)piperidine-1-carboxylate using the method for previous indole examples. $^1$H-NMR (CDCl$_3$, 400 MHz) δ 8.13 (bs, 1H), 7.76 (s, 1H), 7.25 (m, 2H), 7.07 (m, 3H), 6.84 (s, 1H), 6.45 (m, 1H), 4.58 (q, J=7.0 Hz, 1H), 3.40 (m, 1H), 3.19 (d, J=8.6 Hz, 1H), 2.71 (m, 2H), 2.21 (s, 3H), 1.97-2.42 (m, 6H), 1.44 (d, J=6.9 Hz, 3H); LC/MS (HPLC method 4): $t_R$=3.235 min, 435.16 (MH)$^+$.

EXAMPLE 73

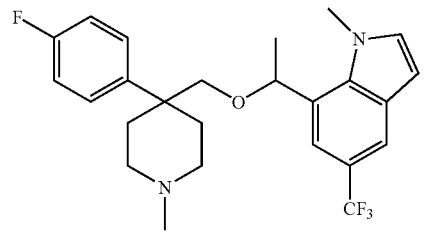

(±)-7-(1-((4-(4-Fluorophenyl)-1-methylpiperidin-4-yl)methoxy)ethyl)-1-methyl-5-(trifluoromethyl)-1H-indole. The product was obtained from (±)-tert-Butyl 4-(4-fluorophenyl)-4-((1-(5-(trifluoromethyl)-1H-indol-7-yl)ethoxy)methyl)piperidine-1-carboxylate using the route used for previous indole examples. $^1$H-NMR (CDCl$_3$, 400 MHz) δ 7.75 S, 1H), 7.22 (m, 3H), 6.96 (m, 3H), 6.51 (d, J=2.7 Hz, 1H), 4.96 (m, 1H), 3.78 (s, 3H), 3.34 (d, J=8.4 Hz, 1H), 3.14 (d, J=9.0 Hz, 1H), 2.60 (m, 2H), 2.23 (s, 3H), 1.93-2.30 (m, 6H), 1.45 (d, J=6.4 Hz, 3H); LC/MS (HPLC method 4): $t_R$=3.245 min, 449.18(MH)$^+$.

EXAMPLES 74 AND 75

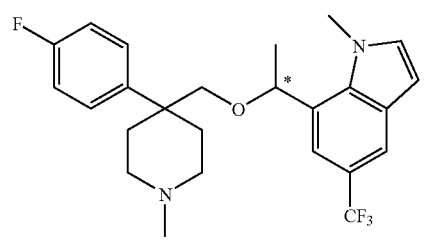

Enantiomers A and B of 7-(1-((4-(4-Fluorophenyl)-1-methylpiperidin-4-yl)methoxy)ethyl)-1-methyl-5-(trifluoromethyl)-1H-indole. Enantiomer A was derived from Enantiomer A of tert-butyl 4-(4-fluorophenyl)-4-((1-(1-methyl-5-(trifluoromethyl)-1H-indol-7-yl)ethoxy)methyl)piperidine-1-carboxylate by reduction as for previous indole examples. Enantiomer B was derived from Enantiomer B of tert-butyl 4-(4-fluorophenyl)-4-((1-(1-methyl-5-(trifluoromethyl)-1H-indol-7-yl)ethoxy)methyl)piperidine-1-carboxylate by the same method.

EXAMPLE 76

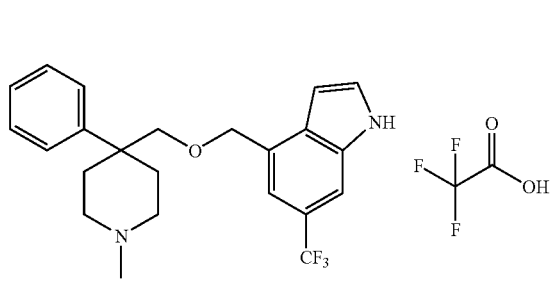

4-(((1-Methyl-4-phenylpiperidin-4-yl)methoxy)methyl)-6-(trifluoromethyl)-1H-indole 2,2,2-trifluoroacetate. Lithium aluminum hydride (1.0 M solution in tetrahydrofuran, 1.1 ml, 1.1 mmol) was added to a solution of tert-butyl 4-phenyl-4-(((6-(trifluoromethyl)-1H-indol-4-yl)methoxy)methyl)piperidine-1-carboxylate (69 mg, 0.141 mmol) in tetrahydrofuran (5 ml) at ambient temperature. The solution was heated at 90° C. for 3 h and then cooled and quenched by sequential addition of water (0.1 ml), 1 N sodium hydroxide (0.3 ml), and additional water (0.1 ml). The mixture was filtered through celite and sand and the solids were rinsed with warm ethanol. The filtrate was evaporated and the residue purified by preparative HPLC using a Phenomenex-Luna C18 column and methanol/water/trifluoroacetic acid gradient elution to afford 26 mg (36%). $^1$H-NMR (CDCl$_3$, 500 MHz) δ ppm 8.52 (s, 1H), 7.58 (s, 1H), 7.21-7.42 (m, 5H), 7.03 (s, 1H), 6.44 (s, 1H), 4.65 (s, 2H), 3.47 (m, 2H), 3.35 (s, 2H), 2.64 (m, 4H), 2.46 (m, 2H), 2.29-2.34 (m, 4H). Mass spec.: 403.50 (MH)$^+$.

EXAMPLE 77

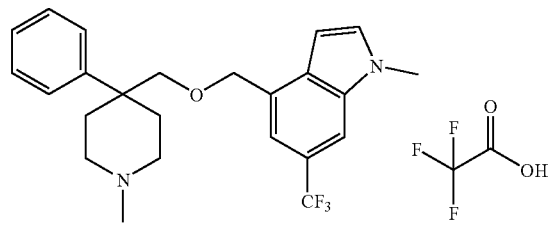

1-Methyl-4-(((1-methyl-4-phenylpiperidin-4-yl)methoxy)methyl)-6-(trifluoromethyl)-1H-indole 2,2,2-trifluoroacetate. $^1$H-NMR (CDCl$_3$, 500 MHz) δ ppm 7.49 (s, 1H), 7.37 (m, 2H), 7.25-7.30 (m, 4H), 7.13 (m, 1H), 7.01 (m, 1H), 6.38 (m, 1H), 4.65 (s, 2H), 3.81 (s, 3H), 3.48 (m, 2H), 3.36 (s, 2H), 2.63-2.70 (m, 4H), 2.46 (m, 2H), 2.33 (m, 2H). Mass spec.: 417.53 (MH)$^+$.

EXAMPLE 78

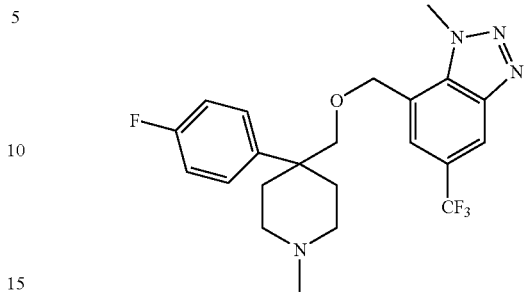

7-(((4-(4-Fluorophenyl)-1-methylpiperidin-4-yl)methoxy)methyl)-1-methyl-5-(trifluoromethyl)-1H-benzo[d][1,2,3]triazole. tert-Butyl 4-(4-fluorophenyl)-4-(((1-methyl-5-(trifluoromethyl)-1H-benzo[d][1,2,3]triazol-7-yl)methoxy)methyl)piperidine-1-carboxylate (17 mg, 0.033 mmol) was dissolved in trifluoroacetic acid (25% in dichloromethane, 1 mL) and stirred at room temperature for 30 min. The reaction was concentrated, loaded onto a strong cation exchange cartridge in methanol, and flushed with several volumes of methanol which were discarded. The crude secondary amine was eluted in 2M ammonia and concentrated. The resulting residue was dissolved in acetonitrile (1 mL), cooled to 0° C., treated with sodium cyanoborohydride (4.1 mg, 0.065 mmol) and formalin (75 µl). After 5 min, the reaction was treated with 1 drop of acetic acid. The ice bath was removed and stirring continued for 1 h. The reaction was diluted with ether and washed with 1M sodium hydroxide. The ethereal was concentrated and loaded onto a strong cation exchange cartridge in methanol. The cartridge was flushed with several volumes of methanol which was discarded. The product was eluted with 2 M ammonia and concentrated to give 10.4 mg (73%) as a colorless film. $^1$H-NMR (CDCl$_3$, 500 MHz) δ 8.28 (s, 1H), 7.42 (s, 1H), 7.12 (m, 2H), 6.89 (m, 2H), 4.69 (s, 2H), 4.08 (s, 3H), 3.44 (s, 2H), 2.51 (m, 2H), 2.19 (s, 3H), 2.12 (m, 4H), 1.89 (m, 2H). Mass spec.: 437.14 (MH)$^+$.

EXAMPLE 79

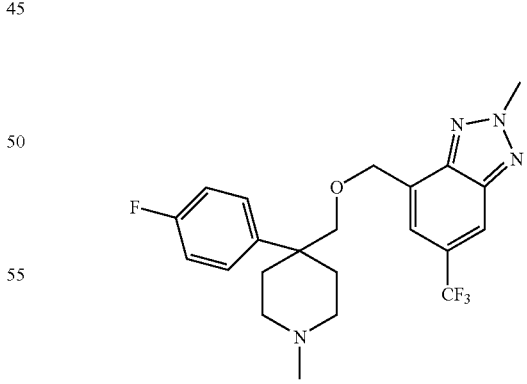

4-(((4-(4-Fluorophenyl)-1-methylpiperidin-4-yl)methoxy)methyl)-2-methyl-6-(trifluoromethyl)-2H-benzo[d][1,2,3]triazole. tert-Butyl 4-(4-fluorophenyl)-4-(((2-methyl-6-(trifluoromethyl)-2H-benzo[d][1,2,3]triazol-4-yl)methoxy)methyl)piperidine-1-carboxylate (22 mg, 0.042 mmol) was dissolved in trifluoroacetic acid (25% in dichloromethane, 1 mL) and stirred at room temperature for 30 min. The reaction was concentrated, loaded onto a strong cation exchange cartridge in methanol, and flushed with several volumes of methanol which were discarded. The crude secondary amine was eluted in 2M ammonia and concentrated. The resulting residue was dissolved in acetonitrile (1 mL), cooled to 0° C., and treated with sodium cyanoborohydride (5.3 mg, 0.084 mmol) and formalin (75 µl). After 5 min, the reaction was treated with 1 drop of acetic acid. The ice bath was removed and stirring continued for 1 h. The reaction was diluted with ether and washed with 1M sodium hydroxide. The ethereal was concentrated and loaded onto a strong cation exchange cartridge in methanol. The cartridge was flushed with several volumes of methanol which was discarded. The product was eluted with 2 M ammonia and concentrated to 13 mg (71%) as a colorless film. $^1$H-NMR (CDCl$_3$, 500 MHz) δ 8.05 (s, 1H), 7.32 (m, 2H), 7.30 (s, 1H), 6.99 (m, 2H), 4.80 (s, 2H), 4.51 (s, 3H), 3.53 (s, 2H), 2.57 (m, 2H), 2.21 (m, 7H), 2.00 (m, 2H). Mass spec.: 437.08 (MH)$^+$.

EXAMPLE 80

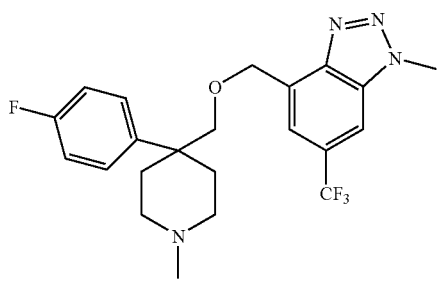

4-(((4-(4-Fluorophenyl)-1-methylpiperidin-4-yl)methoxy)methyl)-1-methyl-6-(trifluoromethyl)-1H-benzo[d][1,2,3]triazole. tert-Butyl 4-(4-fluorophenyl)-4-(((1-methyl-6-(trifluoromethyl)-1H-benzo[d][1,2,3]triazol-4-yl)methoxy)methyl)piperidine-1-carboxylate (14 mg, 0.027 mmol) was dissolved in trifluoroacetic acid (25% in dichloromethane, 1 mL) and stirred at room temperature for 30 min. The reaction was concentrated, loaded onto a strong cation exchange cartridge in methanol, and flushed with several volumes of methanol which were discarded. The crude secondary amine was eluted in 2M ammonia and concentrated. The resulting residue was dissolved in acetonitrile (1 mL), cooled to 0° C., and treated with sodium cyanoborohydride (3.4 mg, 0.054 mmol) and formalin (75 µl). After 5 min, the reaction was treated with 1 drop of acetic acid. The ice bath was removed and stirring continued for 1 h. The reaction was diluted with ether and washed with 1M sodium hydroxide. The ethereal was concentrated and loaded onto a strong cation exchange cartridge in methanol. The cartridge was flushed with several volumes of methanol which was discarded. The product was eluted with 2 M ammonia and concentrated to give 8 mg (68%) as a colorless film. $^1$H-NMR (CDCl$_3$, 500 MHz) δ 7.70 (s, 1H), 7.36 (s, 1H), 7.33 (m, 2H), 6.99 (m, 2H), 5.01 (s, 2H), 4.34 (s, 3H), 3.57 (s, 2H), 2.59 (m, 2H), 2.22 (m, 7H), 2.02 (m, 2H). Mass spec.: 437.16 (MH)$^+$.

EXAMPLE 81

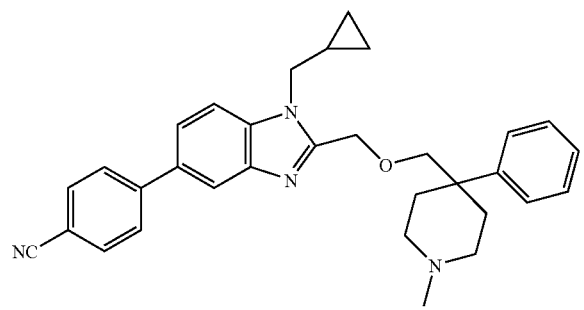

4-(1-(Cyclopropylmethyl)-2-(((1-methyl-4-phenylpiperidin-4-yl)methoxy)methyl)-1H-benzo[d]imidazol-5-yl)benzonitrile. tert-Butyl 4-(((5-(4-cyanophenyl)-1-(cyclopropylmethyl)-1H-benzo[d]imidazol-2-yl)methoxy)methyl)-4-phenylpiperidine-1-carboxylate (23 mg, 0.04 mmol) was combined with aqueous formaldehyde (37%, 0.5 mL, 168 equiv) and formic acid (0.5 mL, 329 equiv) and heated at 70° C. for 64 h. At the end, after adjusting the pH of the reaction mixture to 6.0 extractive work up with ethyl acetate followed by evaporation of the organic layer in vacuo gave the crude product. The crude product was purified by preparative HPLC (HPLC method 12). Fractions containing the required product were combined and evaporated in vacuo. The residue obtained was purified by silica gel chromatography using a linear gradient of 1.2%-20% methanol in dichloromethane to obtain 12 mg (50% yield) as a TFA salt. $^1$H-NMR (500 MHz, CD$_3$OD) δ 7.92 (s, 1H), 7.86 (d, J$_{AB}$=8.5 Hz, 2 H), 7.81 (d, J$_{AB}$=8.5 Hz, 2 H), 7.67-7.65 (m, 1 H), 7.63 (d, J=8.2 Hz, 1 H), 7.39-7.32 (m, 4 H), 7.24 (m, 1 H), 4.75 (s, 2 H), 3.84 (d, J=6.7 Hz, 2 H), 3.60 (s, 2 H), 3.08 (m, 2 H), 2.67 (m, 2 H), 2.55 (s, 3H), 2.42 (m, 2 H), 2.12 (m, 2 H), 1.05 (m, 1 H), 0.51-0.48 (m, 2 H), 0.35-0.32 (m, 2 H). $^{13}$C NMR (126 MHz, CD$_3$OD) δ 151.8, 146.5, 142.2, 136.1, 134.4, 132.8, 128.8, 128.0, 127.2, 126.8, 123.0, 118.9, 117.6, 111.6, 110.4, 65.5, 51.5, 43.7, 40.4, 30.6, 11.0, 3.6. Mass Spec.: 491(MH)$^+$.

EXAMPLE 82

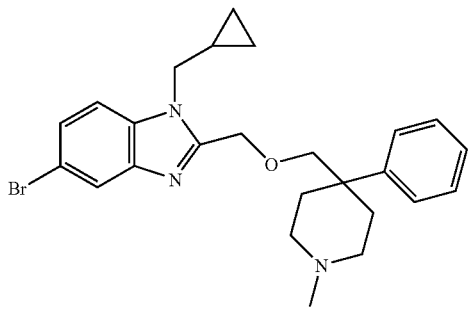

5-Bromo-1-(cyclopropylmethyl)-2-(((1-methyl-4-phenylpiperidin-4-yl)methoxy)methyl)-1H-benzo[d]imidazole. tert-Butyl 4-(((5-bromo-1-(cyclopropylmethyl)-1H-benzo[d]imidazol-2-yl)methoxy)methyl)-4-phenylpiperidine-1- carboxylate (291 mg, 0.525 mmol) was converted to the title compound in an analogous manner as described in the synthesis of 4-(1-(Cyclopropylmethyl)-2-(((1-methyl-4-phenylpiperidin-4-yl)methoxy)methyl)-1H-benzo[d]imidazol-5-yl)benzonitrile (204 mg, 83% yield). $^1$H-NMR (500 MHz, CD$_3$OD) δ 7.76 (bs, 1 H), 7.44-7.40 (m, 2 H), 7.33-7.26 (m, 4 H), 7.17 (m, 1 H), 4.66 (s, 2 H), 3.75 (d, J=7.0 Hz, 2 H), 3.56 (s, 2 H), 2.61 (m, 2 H), 2.23 (m, 2 H), 2.19 (s, 3H) 1.97 (m, 2 H), 0.99 (m, 1 H), 0.48-0.44 (m, 2 H), 0.29-0.26 (m, 2 H). $^{13}$C NMR (126 MHz, CD$_3$OD) δ 151.9, 142.9, 134.8, 128.4, 127.3, 126.3, 121.7, 115.3, 112.4, 65.6, 51.7, 45.3, 40.6, 31.9, 11.0, 3.7. Mass spec.: 468, 470 (Br pattern) (MH)$^+$.

EXAMPLE 83

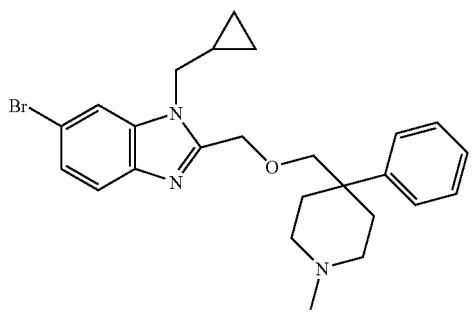

6-Bromo-1-(cyclopropylmethyl)-2-(((1-methyl-4-phenylpiperidin-4-yl)methoxy)methyl)-1H-benzo[d]imidazole. tert-Butyl 4-(((6-bromo-1-(cyclopropylmethyl)-1H-benzo[d]imidazol-2-yl)methoxy)methyl)-4-phenylpiperidine-1-carboxylate (138 mg, 0.25 mmol) was converted to the title compound in an analogous manner as described in the synthesis of 4-(1-(Cyclopropylmethyl)-2-(((1-methyl-4-phenylpiperidin-4-yl)methoxy)methyl)-1H-benzo[d]imidazol-5-yl)benzonitrile to give 104 mg (89% yield). $^1$H-NMR (500 MHz, CD$_3$OD) δ 7.68 (s, 1 H), 7.52 (d, J=8.5 Hz, 1 H), 7.36-7.15 (3×m, 7 H), 4.65 (s, 2 H), 3.72 (d, J=7.0 Hz, 2 H), 3.54 (s, 2 H), 2.59 (m, 2 H), 2.22 (m, 4 H), 2.18 (s, 3 H), 1.95 (m, 2 H), 0.96 (m, 1 H), 0.46-0.42 (m, 2 H), 0.27-0.24 (m, 2 H). $^{13}$C NMR (126 MHz, CD$_3$OD) δ 151.6, 140.6, 136.9, 128.4, 127.3, 126.3, 125.8, 120.4, 116.5, 113.9, 65.6, 51.7, 45.2, 40.5, 31.9, 10.9, 3.7. LC/MS (HPLC method 1): t$_R$=2.5 min, 468(MH)$^+$.

EXAMPLE 84

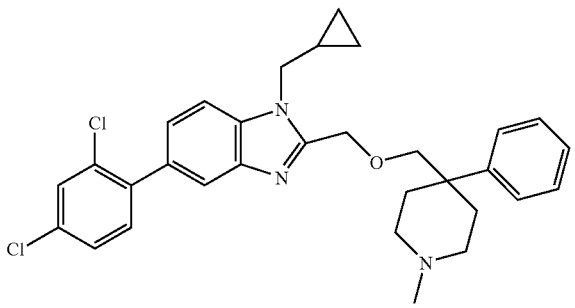

1-(Cyclopropylmethyl)-5-(2,4-dichlorophenyl)-2-(((1-methyl-4-phenylpiperidin-4-yl)methoxy)methyl)-1H-benzo[d]imidazole. Suzuki coupling reaction of 5-Bromo-1-(cyclopropylmethyl)-2-(((1-methyl-4-phenylpiperidin-4-yl)methoxy)methyl)-1H-benzo[d]imidazole (25 mg, 0.053 mmol) with 2,4-dicholrophenylboronic acid (3 equiv.) following the procedure described for the synthesis of tert-butyl 4-(((5-(4-cyanophenyl)-1-(cyclopropylmethyl)-1H-benzo[d]imidazol-2-yl)methoxy)methyl)-4-phenylpiperidine-1-carboxylate, gave 27 mg of the title compound as a TFA salt (79% yield). $^1$H-NMR (500 MHz, CD$_3$OD) δ 8.01 (d, J=8.5 Hz, 1 H), 7.89 (bs, 1 H), 7.72-7.67 (m, 2 H), 7.52-7.52-7.39 (m, 6 H), 7.28 (m, 1 H), 5.01 (s, 2 H), 4.21 (d, J=7.3 Hz, 2 H), 3.72 (s, 2 H), 3.49 (m, 2 H), 2.86 (m, 2 H), 2.77 (s, 3 H), 2.74 (m, 2 H), 2.26 (m, 2 H), 1.21 (m, 1 H), 0.66-0.62 (m, 2 H), 0.52-0.47 (m, 2 H). LC/MS (HPLC method 9): t$_R$=2.7 min, 534(MH)$^-$.

EXAMPLE 85

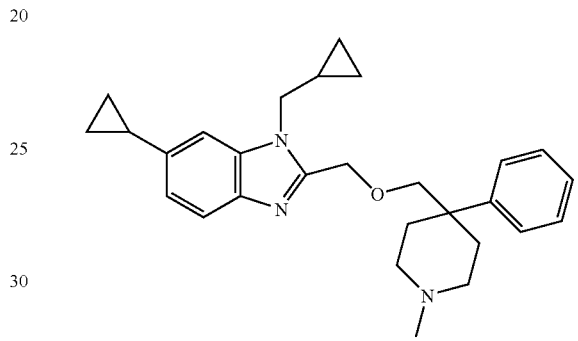

6-Cyclopropyl-1-(cyclopropylmethyl)-2-(((1-methyl-4-phenylpiperidin-4-yl)methoxy)methyl)-1H-benzo[d]imidazole. Suzuki coupling reaction of 6-Bromo-1-(cyclopropylmethyl)-2-(((1-methyl-4-phenylpiperidin-4-yl)methoxy)methyl)-1H-benzo[d]imidazole (12 mg, 0.026 mmol) with cyclopropylboronic acid (3 equiv.) following the procedure described for the synthesis of tert-butyl 4-(((5-(4-cyanophenyl)-1-(cyclopropylmethyl)-1H-benzo[d]imidazol-2-yl)methoxy)methyl)-4-phenylpiperidine-1-carboxylate, gave 13 mg of the title compound (92% yield). LC/MS (HPLC method 8): t$_R$=0.8 min, 430(MH)$^+$.

EXAMPLE 86

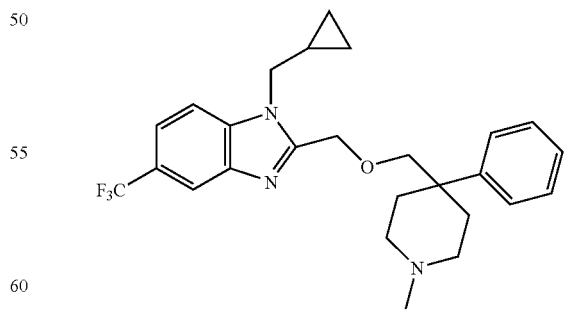

1-(Cyclopropylmethyl)-2-(((1-methyl-4-phenylpiperidin-4-yl)methoxy)methyl)-5-(trifluoromethyl)-1H-benzo[d]imidazole. N-Methylation of tert-butyl 4-(((1-(cyclopropylmethyl)-5-(trifluoromethyl)-1H-benzo[d]imidazol-2-yl)methoxy)methyl)-4-phenylpiperidine-1-carboxylate (35 mg, 0.064 mmol) was carried out as described in the preparation of 4-(1-(Cyclopropylmethyl)-2-(((1-methyl-4-phenylpiperidin-4-yl)methoxy)methyl)-1H-benzo[d]imidazol-5-yl)benzonitrile obtain the title compound (9 mg, 31%) as a free base. $^1$H-NMR (500 MHz, CD$_3$OD) δ 7.93 (s, 1 H), 7.71 (d, J=8.5 Hz, 1 H), 7.60 (d, J=8.5 Hz, 1 H), 7.40-7.25 (m, 5 H), 4.77 (s, 2 H), 3.88 (d, J=6.4 Hz, 2 H), 3.62 (bs, 2 H), 3.41 (m, 2 H), 2.93 (m, 2 H), 2.78 (s, 3 H), 2.54 (m, 2 H), 2.21 (m, 2 H), 1.04 (m, 1 H), 0.53-0.46 (m, 2 H), 0.33-0.29 (m, 2 H). $^{19}$F NMR (471 MHz, CD$_3$OD) δ −69.0.

EXAMPLE 87

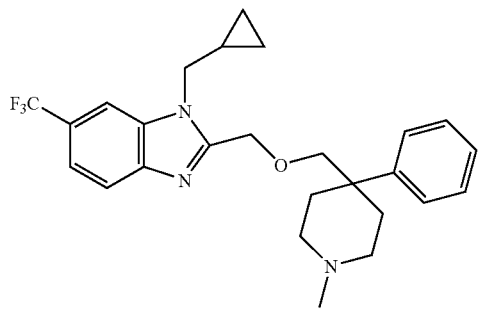

1-(Cyclopropylmethyl)-2-(((1-methyl-4-phenylpiperidin-4-yl)methoxy)methyl)-6-(trifluoromethyl)-1H-benzo[d]imidazole. N-Methylation of tert-butyl 4-(((1-(cyclopropylmethyl)-6-(trifluoromethyl)-1H-benzo[d]imidazol-2-yl)methoxy)methyl)-4-phenylpiperidine-1-carboxylate (35 mg, 0.064 mmol) was carried out as described in previous examples to obtain 15 mg (51%) as free base. $^1$H-NMR (500 MHz, CD$_3$OD) δ 7.87 (s, 1 H), 7.79 (d, J=8.5 Hz, 1 H), 7.56 (m, 1 H), 7.34-7.16 (3×m, 5 H), 4.72 (s, 2 H), 3.86 (d, J=7.0 Hz, 2 H), 3.58 (s, 2 H), 2.62 (s, 2 H), 2.24 (m, 4 H), 2.20 (s, 3 H), 1.98 (m, 2 H), 1.02 (m, 1 H), 0.52-0.45 (m, 2 H), 0.33-0.29 (m, 2 H). $^{19}$F NMR (471 MHz, CD$_3$OD) δ −68.9.

EXAMPLE 88

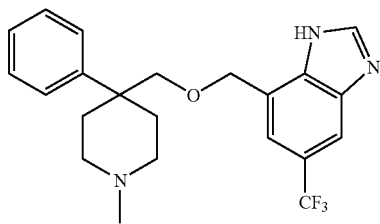

4-(((1-Methyl-4-phenylpiperidin-4-yl)methoxy)methyl)-6-(trifluoromethyl)-1H-benzo[d]imidazole. tert-Butyl 4-phenyl-4-(((6-(trifluoromethyl)-1-((2-(trimethylsilyl)ethoxy)methyl)-1H-benzo[d]imidazol-4-yl)methoxy)methyl) piperidine-1-carboxylate was treated with trifluoroacetic acid: water (9:1, 3 ml) at ambient temperature for 15 min at which time LC-MS analysis revealed completion of the reaction (HPLC method 10: $t_R$=2.5 min, 520(MH)$^+$). The volatiles were evaporated and dried under vacuo. The residue was treated with formaldehyde (0.1 mL, 3.6 mmol), acetic acid (cat.) and sodium cyanoborohydride (25 mg, 0.4 mmol) at ambient temperature for 2 h. The reaction was complete by LC-MS analysis (HPLC method 9: $t_R$=2.7 min, 534(MH)$^+$). The solvent was evaporated and the residue was treated with trifluoroacetic acid /dichloromethane (1:1, 4 ml) at ambient temperature for 3 h. LC-MS analysis (HPLC method 1: $t_R$=2.0 min, 404(MH)$^+$). The solvent was evaporated and the residue was purified by Prep HPLC (HPLC method 15). Fractions containing required product were combined and evaporated to give the title compound as a TFA salt. (6 mg, yield for 5 steps from (6-(trifluoromethyl)-1-((2-(trimethylsilyl)ethoxy)methyl)-1H-benzo[d]imidazol-4-yl)methanol, 13.2% yield). $^1$H-NMR (CD$_3$OD, 500 MHz) δ 8.85 (s, 1H), 7.99 (s, 2H), 7.57 (s, 1H), 7.43-7.27 (m, 5H), 4.85 (s, 2H), 3.52 (s, 2H), 3.45 (m, 2H), 2.85 (m, 2H), 2.75 (s, 3H), 2.69-2.66 (m, 2H), 2.19 (m, 2H); $^{19}$F NMR (471 MHz, CD$_3$OD) δ −62.9, −77.6; LC/MS (HPLC method 1): $t_R$=2.1 min, 404 (MH)$^+$.

EXAMPLE 89

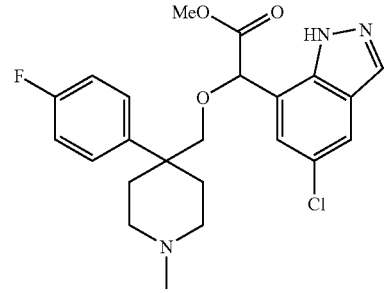

Methyl 2-(5-chloro-1H-indazol-7-yl)-2-((4-(4-fluorophenyl)-1-methylpiperidin-4-yl)methoxy)acetate trifluoroacetic acid salt. tert-butyl 4-((1-(5-chloro-1H-indazol-7-yl)-2-methoxy-2-oxoethoxy)methyl)-4-(4-fluorophenyl)piperidine-1-carboxylate (20 mg) was dissolved in trifluoroacetic acid (20% in dichloromethane, 1.5 mL) and stirred for 20 min at room temperature. The reaction was concentrated and the resulting residues loaded onto a strong cation exchange cartridge. The cartridge was flushed with several volumes of methanol which were discarded. The amine was eluted with 2M ammonia in methanol and concentrated. The unprotected piperidine was dissolved in acetonitrile (1 mL) and treated with formalin (50 μL) and sodium cyanoborohydride (2.4 mg) and one drop of acetic acid. The reaction was stirred at room temperature for 1 h. The reaction was concentrated. The resulting residue was dissolved in trifluoroacetic acid (25% in dichloromethane, 2 mL), stirred for 5 min, and concentrated. The resulting residue was purified by preparative HPLC to afford the title compound. $^1$H-NMR (CD$_3$OD, 500 MHz) δ 8.05 (m, 1H), 7.78 (m, 1H), 7.44 (m, 2H), 7.22 (m, 0.75H), 7.13 (m, 1.8H), 7.03 (m, 0.6H), 5.34 (s, 0.3H), 5.27 (s, 0.7H), 3.69 (m, 4H), 3.47 (m, 4H), 2.55-3.00 (m, 7H), 2.00-2.55 (m, 2.5H). Mass spec.: 446.24 (MH)+.

EXAMPLE 90

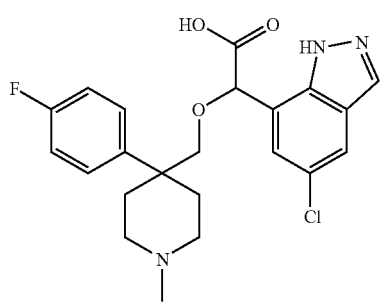

2-(5-Chloro-1H-indazol-7-yl)-2-((4-(4-fluorophenyl)-1-methylpiperidin-4-yl)methoxy)acetic acid trifluoroacetic acid salt. Prepared according to the procedure used to prepare methyl 2-(5-chloro-1H-indazol-7-yl)-2-((4-(4-fluorophenyl)-1-methylpiperidin-4-yl)methoxy)acetate trifluoroacetic acid salt using 2-((1-(tert-butoxycarbonyl)-4-(4-fluorophenyl)piperidin-4-yl)methoxy)-2-(5-chloro-1H-indazol-7-yl) acetic acid as the starting material. ¹H-NMR (CD₃OD, 500 MHz) δ 8.06 (m, 1H), 7.78 (m, 1H), 7.35-7.53)m, 2H), 7.27 (d, J=1.5 Hz, 0.8H), 7.20 (d, J=1.5 Hz, 0.2H), 7.14 (m, 1.5H), 7.04 (m, 0.5H), 5.20 (s, 1H), 4.05 (d, J=9.5 Hz, 0.2H), 3.66 (d, J=9.2 Hz, 1H), 3.35-3.55 (m, 5H), 2.60-2.97 (m, 8H), 2.00-2.40 (m, 2.6H). Mass spec.: 432.21 (MH)+.

EXAMPLE 91

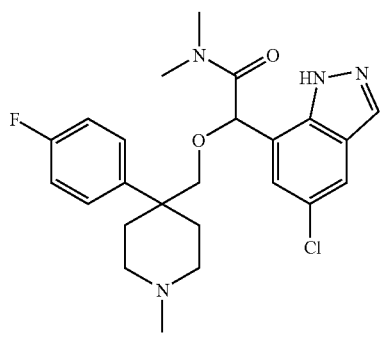

2-(5-Chloro-1H-indazol-7-yl)-2-((4-(4-fluorophenyl)-1-methylpiperidin-4-yl)methoxy)-N,N-dimethylacetamide trifluoroacetic acid salt. Prepared according to the procedure used to prepare methyl 2-(5-chloro-1H-indazol-7-yl)-2-((4-(4-fluorophenyl)-1-methylpiperidin-4-yl)methoxy)acetate trifluoroacetic acid salt using tert-butyl 4-((1-(5-chloro-1H-indazol-7-yl)-2-(dimethylamino)-2-oxoethoxy)methyl)-4-(4-fluorophenyl)piperidine-1-carboxylate as the starting material. ¹H-NMR (CD₃OD, 500 MHz) δ 8.53 (m, 0.1H), 8.07 (m, 0.8H), 7.98 (m, 0.1H), 7.81 (m, 0.8H), 7.45 (m, 1.7H), 7.36 (m, 0.5H), 7.29 (m, 0.9H), 7.14 (dd, J=8.9, 8.5 Hz, 1.6H), 7.03 (dd, J=8.9, 8.9 Hz, 0.5H), 5.52 (s, 1H), 3.91 (d, J=9.2 Hz, 0.2H), 3.35-3.66 (m, 4H), 2.50-3.00 (m, 14H), 1.90-2.25 (m, 2H). Mass spec.: 459.26 (MH)+.

EXAMPLE 92

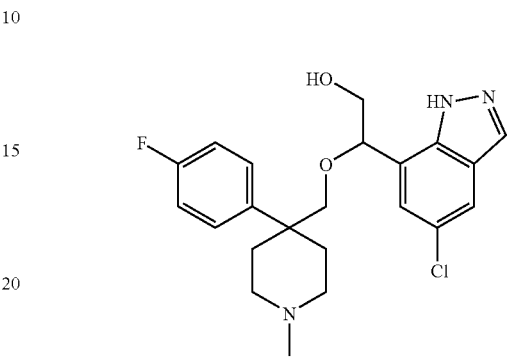

2-(5-Chloro-1H-indazol-7-yl)-2-((4-(4-fluorophenyl)-1-methylpiperidin-4-yl)methoxy)ethanol trifluoroacetic acid salt. Prepared according to the procedure used to prepare methyl 2-(5-chloro-1H-indazol-7-yl)-2-((4-(4-fluorophenyl)-1-methylpiperidin-4-yl)methoxy)acetate trifluoroacetic acid salt using tert-butyl 4-((1-(5-chloro-1H-indazol-7-yl)-2-hydroxyethoxy)methyl)-4-(4-fluorophenyl)piperidine-1-carboxylate as the starting material. ¹H-NMR (CD₃OD, 500 MHz) δ 8.05 (m, 1H), 7.73 (m, 1H), 7.40 (m, 2H), 6.85-7.20 (m, 3H), 4.65 (m, 1H), 3.77 (m, 1.6H), 3.49 (m, 3.8H), 2.40-3.00 (m, 7H), 2.13 (m, 2H). Mass spec.: 418.24 (MH)+.

EXAMPLE 93

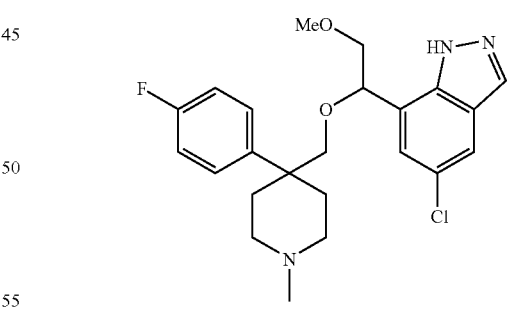

5-Chloro-7-(1-((4-(4-fluorophenyl)-1-methylpiperidin-4-yl)methoxy)-2-methoxyethyl)-1H-indazole trifluoroacetic acid salt. Prepared according to the procedure used to prepare methyl 2-(5-chloro-1H-indazol-7-yl)-2-((4-(4-fluorophenyl)-1-methylpiperidin-4-yl)methoxy)acetate trifluoroacetic acid salt using tert-butyl 4-((1-(5-chloro-1H-indazol-7-yl)-2-methoxyethoxy)methyl)-4-(4-fluorophenyl)piperidine-1-carboxylate as the starting material. ¹H-NMR (CD₃OD, 500 MHz) δ 8.48 (s, 0.1H), 8.03 (s, 0.8H), 7.88 (s, 0.1H), 7.70 (m, 0.8H), 7.42 (m, 2H), 6.90-7.40 (m, 3H), 4.77 (m, 1H), 3.87

(m, 0.3H), 3.68 (m, 1H), 3.40-3.63 (m, 4.8H), 2.40-3.00 (m, 7H), 2.12 (m, 2H). Mass spec.: 432.26 (MH)+.

EXAMPLE 94

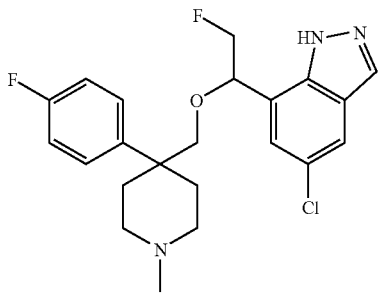

5-Chloro-7-(2-fluoro-1-((4-(4-fluorophenyl)-1-methylpiperidin-4-yl)methoxy)ethyl)-1H-indazole. tert-Butyl 4-((1-(5-chloro-1H-indazol-7-yl)-2-fluoroethoxy)methyl)-4-(4-fluorophenyl)piperidine-1-carboxylate (29 mg, 0.057 mmol) was dissolved in trifluoroacetic acid (20% in dichloromethane, 3 mL) and stirred at room temperature for 20 min. The reaction was concentrated. The residue was loaded onto a strong cation exchange cartridge in methanol and flushed with several volumes of methanol. The unprotected piperidine was eluted with 2M ammonia in methanol and concentrated. The crude piperidine was dissolved in acetonitrile (1 mL) and treated with sodium borohydride (2.2 mg, 0.057 mmol) and formalin (50 µL) and one drop of acetic acid. The reaction was treated with an additional portion of formalin (50 µL). To a rapidly stirred suspension was added several additional portions of sodium borohydride (until effervescence subsided). The reaction was quenched by addition of saturated ammonium chloride and diluted with diethyl ether. The aqueous was made basic by addition of 4M sodium hydroxide and the layers separated. The ethereal was dried over magnesium sulfate and concentrated. Column chromatography (1%→10% 2M ammonia in methanol/dichloromethane) gave 15.8 mg. $^1$H-NMR (CDCl$_3$, 500 MHz) δ 10.5 (bs, 1H), 9.90 (bs, 1H), 7.91 (s, 1H), 7.62 (s, 1H), 7.28 (dd, J=8.9, 5.5 Hz, 2H), 7.06 (dd, J=8.9, 8.5 Hz, 2H), 7.03 (d, J=1.8 Hz, 1H), 4.60 (dt, J=18.0, 4.9 Hz, 1H), 4.53 (d, J=4.9 Hz, 1H), 4.44 (d, J=5.2 Hz, 1H), 3.51 (m, 1H), 3.39 (m, 1H), 2.57 (m, 2H), 2.31 (m, 1H), 2.20 (s, 3H), 2.08 (m, 5H), 1.93 (m, 1H); $^{13}$C NMR (126 MHz, CDCl$_3$) δ ppm 161.6 (d, J=247 Hz), 136.5, 133.7, 128.8 (d, J=7.8), 126.1, 125.5, 124.9, 121.2 (d, J=6.7 Hz), 120.2, 115.7, 115.5, 85.8, 84.4, 81.2, 81.1, 51.8, 51.7, 46.2, 40.5, 32.6, 32.3. Mass spec.: 420.27 (MH)+.

EXAMPLE 95

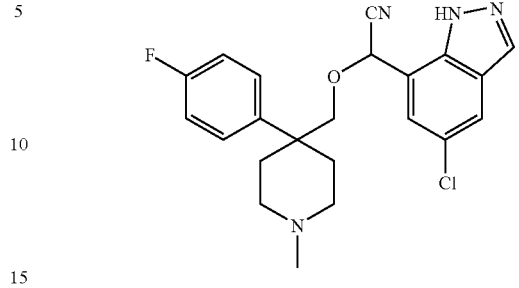

2-(5-Chloro-1H-indazol-7-yl)-2-((4-(4-fluorophenyl)-1-methylpiperidin-4-yl)methoxy)acetonitrile. Prepared according to the procedure used to prepare methyl 2-(5-chloro-1H-indazol-7-yl)-2-((4-(4-fluorophenyl)-1-methylpiperidin-4-yl)methoxy)acetate trifluoroacetic acid salt using tert-butyl 4-(((5-chloro-1H-indazol-7-yl)(cyano)methoxy)methyl)-4-(4-fluorophenyl)piperidine-1-carboxylate as the starting material. After preparative HPLC, the product was still impure. The product was re-purified by column chromatography (2M ammonia in methanol/dichloromethane) to give the title compound as the freebase. $^1$H-NMR (CDCl$_3$, 500 MHz) δ 9.51 (bs, 1H), 7.97 (s, 1H), 7.73 (d, J=1.8 Hz, 1H), 7.34 (dd, J=8.9, 5.2 Hz, 2H), 7.31 (s, 1H), 7.14 (m, 2H), 5.43 (s, 1H), 3.84 (d, J=8.6 Hz, 1H), 3.68 (d, J=8.5 Hz, 1H), 2.56 (m, 2H), 2.22 (m, 8H), 1.99 (m, 3H), 1.67 (bs, 6H). Mass spec.: 413.22 (MH)+.

EXAMPLE 96

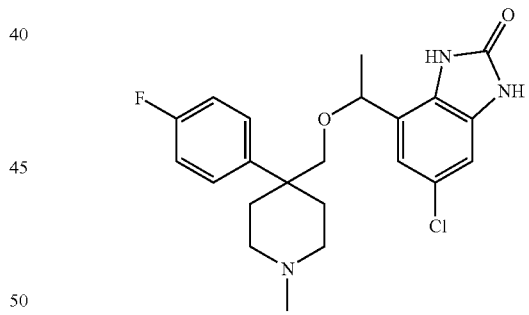

6-Chloro-4-(1-((4-(4-fluorophenyl)-1-methylpiperidin-4-yl)methoxy)ethyl)-1H-benzo[d]imidazol-2(3H)-one trifluoroacetic acid salt. 6-Chloro-4-(1-((4-(4-fluorophenyl)-1-methylpiperidin-4-yl)methoxy)ethyl)-1,3-bis((2-(trimethylsilyl)ethoxy)methyl)-1H-benzo[d]imidazol-2 (3H)-one (58 mg, 0.085 mmol) was dissolved in TFA (40% in dichloromethane, 1 mL) and stirred at room temperature for 1 h. The reaction was concentrated, loaded onto a strong cation exchange cartridge, and flushed with several volumes of methanol which were discarded. The crude product was eluted with 2M ammonia in methanol and concentrated. preparative HPLC (29% B, isocratic method, ACN/TFA) gave 12.5 mg (27%) as a colorless film. $^1$H-NMR (CD$_3$OD, 500 MHz) δ 7.30-7.60 (m, 2H), 7.00-7.25 (m, 2H), 6.92 (s, 1H), 6.60-6.70 (m, 1H), 4.49 (q, J=6.4 Hz, 1H), 3.46 (m, 2.4H), 3.23 (m, 1H), 2.40-3.00 (m, 7H), 1.90-2.25 (m, 2H), 1.38 (d, J=6.1 Hz, 3H). Mass spec.: 418.15 (MH)+.

EXAMPLE 97

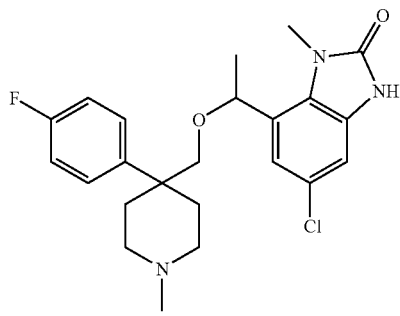

5-Chloro-7-(1-((4-(4-fluorophenyl)-1-methylpiperidin-4-yl)methoxy)ethyl)-1-methyl-1H-benzo[d]imidazol-2(3H)-one trifluoroacetic acid salt. tert-Butyl 4-((1-(6-chloro-3-methyl-2-oxo-1-((2-(trimethylsilyl)ethoxy)methyl)-2,3-dihydro-1H-benzo[d]imidazol-4-yl)ethoxy)methyl)-4-(4-fluorophenyl)piperidine-1-carboxylate (26 mg, 0.040 mmol) was dissolved in trifluoroacetic acid (40% in dichloromethane, 1 mL) and stirred at room temperature for 1 h. The reaction was concentrated and loaded onto a strong cation exchange cartridge in methanol. The cartridge was flushed with several volumes of methanol which were discarded. The crude piperidine was eluted with 2M ammonia in methanol and concentrated. The crude product was dissolved in acetonitrile (1 mL) and treated with formalin (50 µL) followed quickly by sodium cyanoborohydride (5.0 mg, 0.08 mmol). To this was added two small drops of acetic acid over 5 minutes. The reaction was concentrated and the residue taken up in ethyl acetate, washed with saturated sodium bicarbonate, then brine, dried over magnesium sulfate, and concentrated. The crude product was dissolved in ethanol (10 mL) and heated at reflux overnight. The reaction was concentrated and purified by preparative HPLC (28% B isocratic method, TFA/ACN) to give 10.3 mg (47%). $^1$H-NMR (CD$_3$OD, 500 MHz) δ 7.44 (m, 1.5H), 7.35 (m, 0.5H), 7.14 (m, 1.5H), 7.06 (m, 0.5H), 6.90-7.20 (m, 1H), 6.78 (d, J=2.1 Hz, 0.6H), 6.68 (m, 0.3H), 4.99 (m, 1H), 3.35-3.52 (m, 5H), 3.30 (d, J=9.2 Hz, 1H), 2.55-3.00 (m, 6H), 2.05 (m, 2H), 1.30-1.50 (m, 3H). Mass spec.: 432.1 (MH)+.

EXAMPLE 98

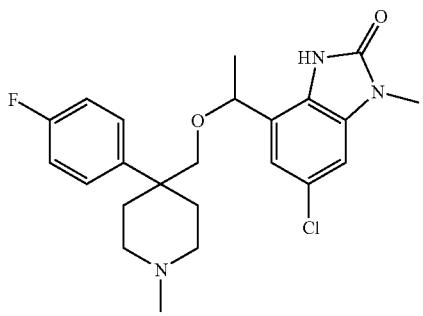

6-Chloro-4-(1-((4-(4-fluorophenyl)-1-methylpiperidin-4-yl)methoxy)ethyl)-1-methyl-1H-benzo[d]imidazol-2(3H)-one trifluoroacetic acid salt. tert-Butyl 4-((1-(6-chloro-1-methyl-2-oxo-3-((2-(trimethylsilyl)ethoxy)methyl)-2,3-dihydro-1H-benzo[d]imidazol-4-yl)ethoxy)methyl)-4-(4-fluorophenyl)piperidine-1-carboxylate (16.5 mg, 0.025 mmol) was dissolved in trifluoroacetic acid (40% in dichloromethane, 1 mL) and stirred at room temperature for 1 h. The reaction was concentrated and loaded onto a strong cation exchange cartridge in methanol. The cartridge was flushed with several volumes of methanol which were discarded. The crude piperidine was eluted with 2M ammonia in methanol and concentrated. The crude product was dissolved in acetonitrile (1 mL) and treated with formalin (50 µL) followed quickly by sodium cyanoborohydride (3.2 mg, 0.05 mmol). To this was added two small drops of acetic acid over 5 minutes. The reaction was concentrated and the residue taken up in ethyl acetate, washed with saturated sodium bicarbonate, then brine, dried over magnesium sulfate, and concentrated. The crude product was dissolved in ethanol (10 mL) and heated at reflux overnight. The reaction was concentrated and purified by preparative HPLC (28% B isocratic method, TFA/ACN) to give 9.0 mg (64%) as a colorless film. $^1$H-NMR (CD$_3$OD, 500 MHz) δ 7.43 (dd, J=8.9, 4.9 Hz, 1.5H), 7.33 (dd, J=8.9, 5.2 Hz, 0.5H), 7.13 (m, 1.5H), 7.04 (m, 1.5H), 6.72 (d, J=1.8 Hz, 0.7H), 6.67 (d, J=1.8 Hz, 0.3H), 4.5 1 (q, J=6.4 Hz, 1H), 3.15-3.52 (m, 9H), 2.40-3.00 (m, 7H), 2.08 (m, 2H), 1.38 (d, J=6.4 Hz, 3H). Mass spec.: 432.1 (MH)+.

EXAMPLE 99

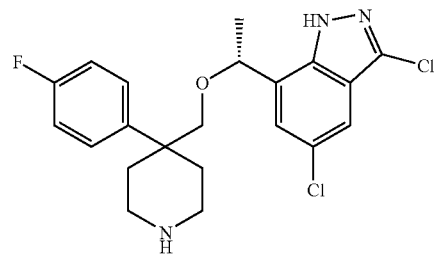

(R)-3,5-Dichloro-7-(1-((4-(4-fluorophenyl)piperidin-4-yl)methoxy)ethyl)-1H-indazole. (R)-tert-Butyl 4-((1-(3,5-dichloro-1H-indazol-7-yl)ethoxy)methyl)-4-(4-fluorophenyl)piperidine-1-carboxylate (4.6 g, 8.80 mmol) was dissolved in trifluoroacetic acid (20% in dichloromethane, 40 mL) and stirred at room temperature for 30 min. The reaction was concentrated and loaded onto a 20 g phenomenex strata giga tube strong cation exchange cartridge. After flushing the cartridge with several volumes of methanol (which were discarded), the product was eluted with 2M ammonia in methanol to give 3.75 g (100%) as a foam solid. $^1$H-NMR (CDCl$_3$, 500 MHz) δ 9.88 (bs, 1H), 7.51 (d, J=1.1 Hz, 1H), 7.26 (dd, J=8.9, 5.5 Hz, 2H), 7.06 (dd, J=8.5, 8.5 Hz, 2H), 7.01 (d, J=1.1 Hz, 1H), 4.49 (q, J=6.4 Hz, 1H), 3.41 (d, J=8.9 Hz, 1H), 3.27 (d, J=8.9 Hz, 1H), 2.91 (m, 2H), 2.73 (m, 2H), 2.20 (m, 1H), 2.05 (m, 1H), 1.87 (m, 2H), 1.42 (d, J=6.6 Hz, 3H); $^{13}$C NMR (126 MHz, CDCl$_3$) δ ppm 161.4 (d, J=246 Hz), 139.0, 136.9, 134.1, 128.5 (d, J=7.8 Hz), 128.3, 126.8, 125.2, 121.9, 117.7, 115.5 (d, J=21 Hz), 79.0, 77.9, 42.4, 42.3, 41.2, 33.5, 33.2, 22.0. Mass spec.: 328.12 (MH)+.

EXAMPLE 100

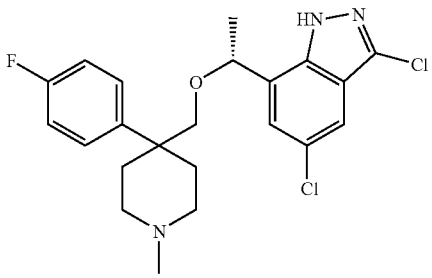

(R)-3,5-Dichloro-7-(1-((4-(4-fluorophenyl)-1-methylpiperidin-4-yl)methoxy)ethyl)-1H-indazole. (R)-3,5-Dichloro-7-(1-((4-(4-fluorophenyl)piperidin-4-yl)methoxy)ethyl)-1H-indazole was suspended in acetonitrile (40 mL) and treated with formalin (1 mL). The reaction was treated with sodium cyanoborohydride (0.83 g, 13.2 mmol). The reaction was treated with ca. 0.5 mL acetic acid over ca. 10 min. The reaction was treated with tetrahydrofuran (20 mL), and additional portions of formalin (0.5 mL) and sodium cyanoborohydride (0.2 g) and stirred for 30 min. The reaction was concentrated to remove most of the organics (but not to dryness), partitioned between a minimum of dichloromethane/saturated sodium bicarbonate, and poured into a separatory funnel. The mixture was diluted with diethyl ether and the layers separated. The organics were washed with brine, dried over magnesium sulfate, and concentrated. The resulting residue was dissolved in ethanol (125 mL) and heated at reflux for 30 h. The reaction was concentrated to give viscous foam. The crude product was pumped on high vaccuum overnight. The resulting solid was dissolved in methanol and loaded onto a phenomenex strata strong cation exchange cartridge (giga tube, 20 g/60 mL). The tube was flushed with several volumes of methanol which were discarded. The product was eluted with 2 M ammonia in methanol to give the crude product (3.5 g). The material was dissolved in 15 mL of isopropanol at 60° C. and water added until the mixture went cloudy (only about 9 mL water). The mixture was seeded with a crystal of product. At first the material appeared to oil out, but it was stirred vigorously for a couple of minutes which gave a white precipitate. An additional 6 mL of water was added. The mixture was incubated at 50° C. for 2 h (occasionally stirring to agitate the bed of product). The material was warmed to 60° C., incubated at that temperature for 15 min, and then re-cooled to 50° C. and incubated at that temperature 2 h longer. The suspension was allowed to gradually warm to room temperature in the water bath and was filtered. The resulting precipitate was rinsed with cold 1:1 isopropanol/water and air dried to give crystalline freebase (2.45 g, 64%). $^1$H-NMR (CDCl$_3$, 500 MHz) δ 9.50 (bs, 1H), 7.51 (d, J=1.8 Hz, 1H), 7.26 (dd, J=8.8, 5.2 Hz, 2H), 7.07 (dd, J=8.8, 8.6 Hz, 2H), 7.02 (d, J=1.8 Hz, 1H), 4.50 (q, J=6.6 Hz, 1H), 3.43 (d, J=8.7 Hz, 1H), 3.29 (d, J=8.7 Hz, 1H), 2.59 (m, 1H), 2.53 (m, 1H), 2.29 (m, 1H), 2.21 (s, 3H), 2.20 (m, 1H), 2.12 (m, 1H), 2.09 (m, 1H), 1.99 (m, 1H), 1.90 (m, 1H), 1.41 (d, J=6.6 Hz, 3H); $^{13}$C NMR (126 MHz, CDCl$_3$) δ ppm 161.5 (d, J=247 Hz), 139.1, 137.0, 134.3, 128.6 (d, J=7.8 Hz), 128.3, 126.9, 125.2, 122.1, 117.7, 115.6 (d, J=21 Hz), 78.9, 78.1, 51.8, 51.7, 46.2, 40.3, 32.9, 32.6, 22.1. Mass spec.: 436.1 (MH)+. A portion of the material was converted to the hydrochloride salt by suspending the product (1.2 g, 2.75 mmol) in ethanol (10 mL), cooling to 0° C., and treatment with ethanolic hydrochloric acid (1.25M, 2.2 mL). The mixture was concentrated to give (R)-3,5-dichloro-7-(1-((4-(4-fluorophenyl)-1-methylpiperidin-4-yl)methoxy)ethyl)-1H-indazole hydrochloride (1.30 g, 100%). $^1$H-NMR (CD$_3$OD, 500 MHz) δ 7.46 (m, 1H), 7.40 (dd, J=9.2, 5.2 Hz, 1.5H), 7.31 (dd, J=8.9, 5.2 Hz, 0.5H), 7.08 (dd, J=8.9, 8.5 Hz, 1.5H), 6.98 (m, 1.2 H), 6.93 (d, J=1.5 Hz, 0.3H), 4.68 (q, J=6.4 Hz, 0.3H), 4.63 (q, J=6.7 Hz, 0.7H), 3.82 (d, J=9.8 Hz, 0.2H), 3.59 (q, J=7.0 Hz, 0.3H), 3.37-3.52 (m, 3H), 3.36 (d, J=9.2 Hz, 1H), 3.21 (d, J=9.2 Hz, 1H), 2.90 (s, 0.7H), 2.80 (m, 1.7H), 2.73 (s, 2.2H), 2.61 (m, 1.8H), 2.41 (m, 0.2H), 1.95-2.25 (m, 2H), 1.43 (m, 3H), 1.15 (m, 1.6H); $^{13}$C NMR (126 MHz, CD$_3$OD) δ ppm 162.3 (d, J=246 Hz), 162.0 (d, J=245 Hz), 141.1, 137.6, 135.5, 133.5, 129.4 (d, J=8.6 Hz), 129.14, 129.05, 127.8 (d, J=7.7 Hz), 12.72, 125.3, 125.1, 121.7, 117.24, 117.20, 115.8 (d, J=21 Hz), 115.0 (d, J=21 Hz), 79.0, 75.99, 75.85, 72.7, 65.9, 57.4, 51.5, 51.4, 50.84, 50.76, 42.8, 42.2, 40.5, 38.1, 30.1, 29.9, 29.5, 29.1, 21.20, 21.16, 17.4, 14.5.

EXAMPLE 101

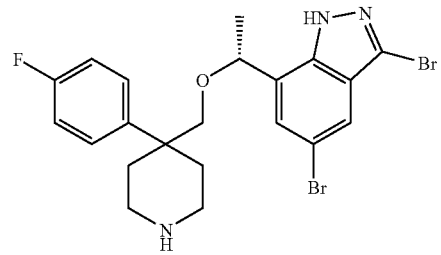

(R)-3,5-Dibromo-7-(1-((4-(4-fluorophenyl)piperidin-4-yl)methoxy)ethyl)-1H-indazole. (R)-tert-Butyl 4-((1-(3,5-dibromo-1H-indazol-7-yl)ethoxy)methyl)-4-(4-fluorophenyl)piperidine-1-carboxylate (99 mg, 0.16 mmol) was dissolved in trifluoroacetic acid (20% in dichloromethane, 6 mL) and stirred for 30 min. The reaction was concentrated and the resulting residue loaded onto a strong cation exchange cartridge in methanol. The cartridge was washed with several volumes of methanol which were discarded. The product was eluted with 2M ammonia in methanol and concentrated to give 82 mg (94%) as a foam solid. $^1$H-NMR (CDCl$_3$, 500 MHz) δ 7.62 (d, J=1.5 Hz, 1H), 7.25 (dd, J=9.5, 5.8 Hz, 2H), 7.12 (d, J=1.5 Hz, 1H), 7.03 (dd, J=8.6, 8.6 Hz, 2H), 4.46 (q, J=6.7 Hz, 1H), 3.44 (s, 2H), 3.36 (d, J=8.9 Hz, 1H), 3.24 (d, J=9.2 Hz, 1H), 2.87 (m, 2H), 2.68 (m, 2H), 2.14 (m, 1H), 2.03 (m, 1H), 1.84 (m, 2H), 1.41 (d, J=6.4 Hz, 3H); $^{13}$C NMR (126 MHz, CDCl$_3$) δ ppm 161.5 (d, J=246 Hz), 139.3, 137.3, 128.7, 128.61, 128.57, 127.7, 125.3, 121.7, 121.6, 115.6, 115.5, 114.3, 79.0, 77.8, 50.5, 42.5, 42.4, 41.4, 33.7, 33.4, 22.1.

EXAMPLE 102

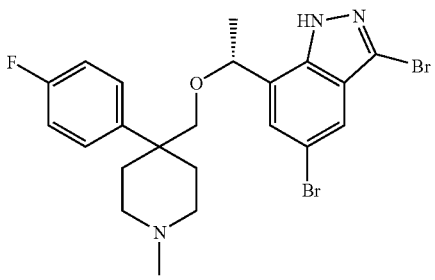

(R)-3,5-Dibromo-7-(1-((4-(4-fluorophenyl)-1-methylpiperidin-4-yl)methoxy)ethyl)-1H-indazole. (R)-3,5-Dibromo-7-(1-((4-(4-fluorophenyl)piperidin-4-yl)methoxy)ethyl)-1H-indazole (77 mg, 0.15 mmol) was dissolved in acetonitrile (1 mL) and treated with formalin (50 µL) and sodium cyanoborohydride (9.5 mg, 0.15 mmol) and one drop of acetic acid. The reaction was stirred at room temperature for 1 h. The reaction was poured into water and extracted with diethyl ether. The aqueous was made basic by addition of 4 M sodium hydroxide and extracted with diethyl ether. The ethereal was combined, washed with brine, dried over magnesium sulfate, and concentrated. The resulting residue was dissolved in 20% trifluoroacetic acid in dichloromethane and stirred at room temperature for 5 min. The solution was concentrated, loaded onto a strong cation exchange cartridge in methanol, and the cartridge washed with several volumes of methanol which were discarded. The product was eluted with 2M ammonia in methanol and concentrated to give 41 mg (52%). $^1$H-NMR (CDCl$_3$, 500 MHz) δ 10.09 (bs, 1H), 7.62 (d, J=1.5 Hz, 1H), 7.24 (dd, J=8.9 Hz, 5.2, 2H), 7.13 (d, J=1.5 Hz, 1H), 7.05 (dd, J=8.9, 8.5 Hz, 2H), 4.49 (q, J=6.7 Hz, 1H), 3.39 (d, J=8.9 Hz, 1H), 3.25 (d, J=8.9 Hz, 1H), 2.59 (m, 2H), 1.85-2.30 (m, 9H), 1.40 (d, J=6.7 Hz, 3H); $^{13}$C NMR (126 MHz, CDCl$_3$) δ ppm 161.6 (d, J=246 Hz), 137.2, 128.7, 128.63, 128.57, 127.68, 125.3, 121.7, 121.6, 115.7, 115.5, 114.3, 78.9, 77.9, 51.9, 51.7, 46.1, 40.3, 32.6, 32.3, 22.1.

EXAMPLE 103

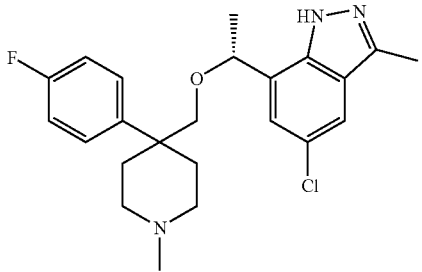

(R)-5-Chloro-7-(1-((4-(4-fluorophenyl)-1-methylpiperidin-4-yl)methoxy)ethyl)-3-methyl-1H-indazole. Prepared according to the procedure used to prepare (R)-3,5-dibromo-7-(1-((4-(4-fluorophenyl)-1-methylpiperidin-4-yl)methoxy) ethyl)-1H-indazole using (R)-5-chloro-7-(1-((4-(4-fluorophenyl)piperidin-4-yl)methoxy)ethyl)-3-methyl-1H-indazole as starting material. $^1$H-NMR (CDCl$_3$, 500 MHz) δ 9.82 (bs, 1H), 7.46 (d, J=1.5 Hz, 1H), 7.23 (dd, J=8.9, 5.5 Hz, 2H), 7.00 (dd, J=8.9, 8.5 Hz, 2H), 6.92 (d, J=1.8 Hz, 1H), 4.43 (q, J=6.4 Hz, 1H), 3.33 (d, J=8.9, 8.5 Hz, 2H), 6.92 (d, J=1.8 Hz, 1H), 4.43 (q, J=6.4 Hz, 1H), 3.33 (d, J=8.9 Hz, 1H), 3.24 (d, J=9.2 Hz, 1H), 2.40-2.65 (m, 5H), 1.85-2.30 (m, 9H), 1.38 (d, J=6.4 Hz, 3H); $^{13}$C NMR (126 MHz, CDCl$_3$) δ ppm 161.5 (d, J=246 Hz), 142.3, 136.7, 128.7 (d, J=7.7 Hz), 127.6, 125.3, 124.4, 124.0, 118.5, 115.3 (d, J=21 Hz), 78.7 (br), 78.1, 51.9, 51.8, 46.2, 40.4, 32.6, 32.4, 22.0, 11.9.

EXAMPLE 104

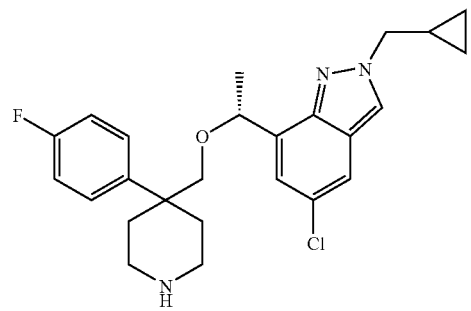

(R)-5-chloro-2-(cyclopropylmethyl)-7-((1-(4-fluorophenyl)piperidin-4-yl)methoxy)ethyl)-2H-indazole. $^1$H-NMR (CDCl$_3$, 300 MHz) δ 7.91 (s, 1H), 7.43 (m, 1H), 7.31-7.27 (m, 2H), 7.01-6.95 (m, 2H), 6.78 (m, 1H), 4.88 (q, J=6.2 Hz, 1H), 4.20 (d, J=7.32 Hz, 2H), 3.34 (m, 2H), 2.75-2.62 (m, 2H), 2.88-2.8 (m, 2H), 2.17-1.85 (m, 4H), 1.40 (d, J=6.6 Hz, 3H), 1.40-1.30 (m, 1H), 0.7-0.6 (m, 2H), 0.44-0.35 (m, 2H); $^{13}$C-NMR (CDCl$_3$, MHz) δ 161.1 (d, J=244.3 Hz), 145.0, 140.1, 135.2, 128.8, 128.6, 127.4, 122.3, 121.9, 121.4, 117.1, 114.9, 114.6, 73.7, 58.2, 42.6, 41.3, 33.6, 33.3, 22.7, 11.1, 4.1. LC/MS (HPLC method 3): $t_R$=2.93 min, 442.26(MH)$^+$.

EXAMPLE 105

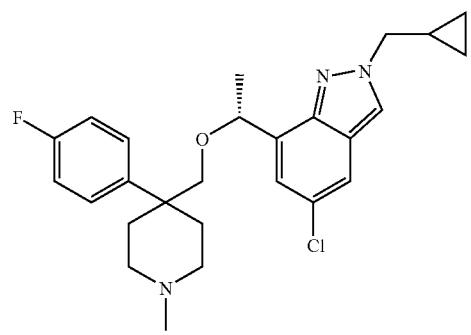

(R)-5-chloro-2-(cyclopropylmethyl)-7-(1-((4-(4-fluorophenyl)-1methylpiperidin-4-yl)methoxy)ethyl)-2H-indazole. $^1$H-NMR (CDCl$_3$, 500 MHz) δ 7.95 (s, 1H), 7.45 (m, 1H), 7.33-7.30 (m, 2H), 7.04-7.01 (m, 1H), 6.74 (s, 1H), 4.90 (q, J=6.4 Hz, 1H), 4.23 (d, J=Hz, 2H), 3.38 (m, 2H), 2.80-2.60 (m, 2H), 2.28 (s, 3H), 2.40-2.08 (m, 6H), 1.42 (d, J=6.4 Hz, 3H), 1.40-1.30 (m, 1H), 0.71-0.67 (m, 2H), 0.44-0.41 (m, 2H); ¹³C-NMR (CDCl₃, 126 MHz) δ 161.4 (d, J=244.7 Hz), 145.3, 135.2, 128.90, 128.84, 122.5, 122.1, 121.5, 118.0, 117.3, 115.2, 115.0, 74.0, 58.4, 53.3, 51.9, 51.8, 45.8, 40.3, 32.3, 31.9, 22.8, 11.3, 4.3. LC/MS (HPLC method 3): t$_R$=2.92 min, 456.29(MH)⁺.

J=245.7 Hz), 146.4, 135.4, 129.1, 128.9, 128.8, 123.9, 123.1, 122.9, 117.5, 115.5, 115.3, 113.3, 74.0, 53.5, 51.3, 51.2, 44.9, 41.1, 40.2, 31.3, 30.9, 22.8, 22.5. LC/MS (HPLC method 3): t$_R$=2.49 min, 441.3(MH)⁺.

EXAMPLE 106

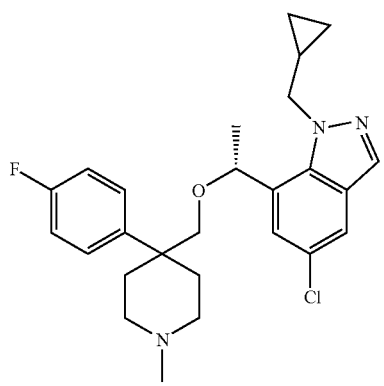

(R)-5-chloro-1-(cyclopropylmethyl)-7-(1-((4-(4-fluorophenyl)-1methylpiperidin-4-yl)methoxy)ethyl)-1H-indazole. ¹H-NMR (CDCl₃, 500 MHz) δ 7.87 (s, 1H), 7.51 (d, J=1.83 Hz, 1H), 7.27-7.23 (m, 2H), 7.07-7.03 (m, 2H), 6.82 (m, 1H), 4.90 (q, J=6.4 Hz, 1H), 4.32-4.28 (m, 1H), 4.10-4.16 (m, 1H), 3.35 (d, J=3.3 Hz, 1H), 3.24 (d, J=3.3 Hz, 1H), 2.95 (m, 2H), 2.45-2.35 (m, 3H), 2.39 (s, 3H), 2.24-2.14 (m, 3H), 1.42 (d, J=6.4 Hz, 3H), 1.09-1.06 (m, 1H), 0.57-0.46 (m, 2H), 0.36-0.31 (m, 2H); ¹³C-NMR (CDCl₃, 126 MHz) δ 159.7 (d, J=245.7 Hz), 135.7, 133.0, 128.8, 128.7, 127.8, 126.6, 126.3, 124.2, 119.3, 115.7, 115.6, 55.6, 51.3, 51.1, 44.7, 40.1, 31.1, 30.9, 23.4, 22.8, 22.6, 14.2, 12.2, 3.9, 3.7. Mass spec.: (MH)⁺. LC/MS (HPLC method 3): t$_R$=2.90 min, 456.3(MH)⁺.

EXAMPLE 107

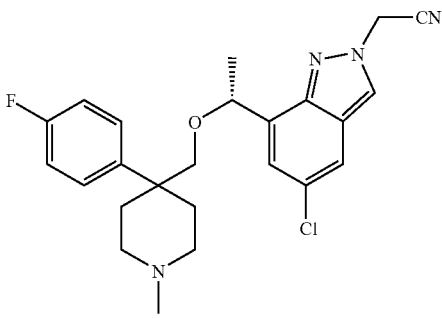

(R)-2-(5-chloro-7-(1-((4-(4-fluorophenyl)-1-methylpiperidine-4-yl)methoxy)ethyl)-2H-indazole-2-yl)acetonitrile. ¹H-NMR (CDCl₃, 500 MHz) δ 8.01 (s, 1H), 7.47 (m, 1H), 7.31-7.26 (m, 2H), 7.07-7.03 (m, 2H), 6.73 (m, 1H), 5.34 (s, 2H), 4.81 (q, J=6.4 Hz, 1H), 4.38-3.33 (m, 2H), 2.95-2.58 (m, 2H), 2.50-2.30 (m, 3H), 2.37 (s, 3H), 2.25-2.10 (m, 3H), 1.41 (d, J=6.4 Hz, 3H); ¹³C-NMR (CDCl₃, 126 MHz) δ 151.54 (d,

EXAMPLE 108

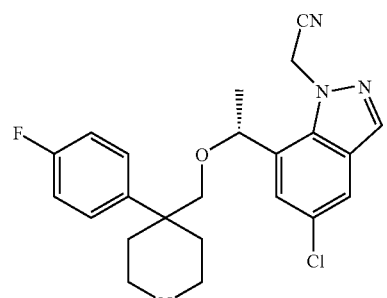

(R)-2-(5-chloro-7-(1-((4-(4-fluorophenyl)-1-methylpiperidine-4-yl)methoxy)ethyl)-1H-indazole-2-yl)acetonitrile. ¹H-NMR (CDCl₃, 500 MHz) δ 8.0 (s, 1H), 7.62 (d, J=2.0 Hz, 1H), 7.16-7.12 (m, 3H), 6.99-6.96 (m, 2H), 5.38 (d, J=17.7 Hz, 1H), 4.88 (d, J=18.0 Hz, 1H), 4.69 (q, J=6.7 Hz, 1H), 3.28 (dd, J=9.5 Hz, J=31.7 Hz, 2H), 2.75-2.60 (m, 2H), 2.30-2.17 (m, 3H), 2.27 (s, 3H), 2.15-1.95 (m, 3H), 1.58 (d, J=7.0 Hz, 3H); ¹³C-NMR (CDCl₃, 126 MHz) δ 161.5 (d, J=246.6 Hz), 136.2, 136.0, 128.8, 128.7, 127.7, 127.5, 127.1, 126.7, 120.6, 115.5, 115.4, 115.1, 53.5, 51.6, 51.5, 45.7, 40.1, 39.6, 32.3, 32.0, 21.7. LC/MS (HPLC method 3): t$_R$=2.53 min, 441.28 (MH)⁺.

EXAMPLE 109

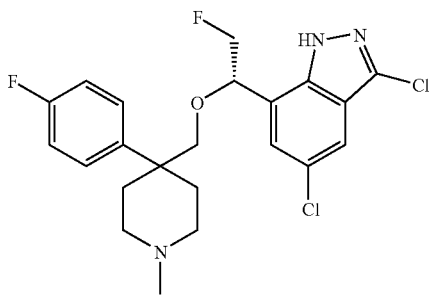

(S)-3,5-dichloro-7-(2-fluoro-1-((4-(4-fluorophenyl)-1-methylpiperidine-4-yl)methoxy)ethyl)-1H-indazole. ¹H-NMR (CDCl₃, 500 MHz) δ 7.57 (s, 1H), 7.27-7.25 (m, 2H), 7.08-7.03 (m, 3H), 4.60 (dt, J=5.2 Hz, J=18.3 Hz 1H), 4.53 (d, J=4.6 Hz, 1H), 4.43 (q, J=4.3 Hz, 1H), 3.51 (d, J=8.55 Hz, 1H), 3.38 (d, J=8.85 Hz, 1H), 2.72-2.58(m, 2H), 2.24 (s, 3H), 2.34-1.98 (m, 6H); ¹³C-NMR (CDCl₃, 126 MHz) δ 161.7 (d, J=246.6 Hz), 137.9, 134.2, 128.8, 128.7, 126.9, 126.7, 122.2, 122.0, 118.9, 115.8, 115.6, 85.6, 84.2, 80.8, 80.6, 51.7, 51.6, 46.0, 40.5, 32.3, 32.0. LC/MS (HPLC method 3): t_R=2.84 min, 454.0(MH)+.

EXAMPLE 110

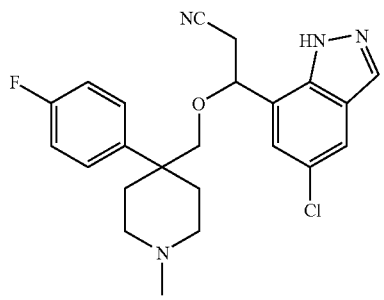

3-(5-chloro-1H-indazol-7-yl)-3-((4-(4-fluorophenyl)-1-methylpiperidine-4-yl)methoxy)propanenitrile. $^1$H-NMR (CDCl$_3$, 500 MHz) δ 7.93 (s, 1H), 7.65 (d, J=1.8 Hz, 1H), 7.30-7.27 (m, 2H), 7.10-7.07 (m, 2H), 7.03 (d, J=1.53 Hz, 1H), 4.69 (dd, J=4.88 Hz, J=8.24 Hz, 1H), 3.50 (d, J=8.55 Hz, 1H), 3.34 (d, J=8.85 Hz, 1H), 2.84-2.79 (m, 1H), 2.73-2.65 (m, 2H), 2.44-2.36 (m, 1H), 2.31-2.21 (m, 1H), 2.24 (s, 3H), 2.20-2.06 (m, 4H); $^{13}$C-NMR (CDCl$_3$, 126 MHz) δ 161.76 (d, J=246.6 Hz), 135.3, 134.2, 128.8, 128.8, 126.3, 125.2, 122.5, 120.7, 116.5, 115.9, 115.7, 51.7, 51.6, 46.0, 42.5, 40.5, 32.5, 32.1, 25.6. LC/MS (HPLC method 3): t_R=2.31 min, 427.2 (MH)+.

EXAMPLE 111

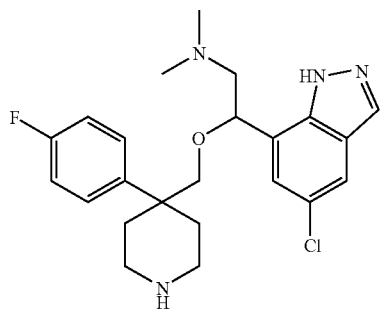

2-(5-chloro-1H-indazol-7-yl)-2-((4-(4-fluorophenyl)piperidine-4-yl)methoxy)-N,N-dimethylethanamine. $^1$H-NMR (CDCl$_3$, 500 MHz) δ 7.92 (s, 1H), ), 7.57 (d, J=1.83 Hz, 1H), 7.27-7.24 (m, 2H), 7.04-7.01 (m, 2H), 6.94 (d, J=1.22 Hz, 1H), 4.44 (t, J=5.19 Hz, 1H), 3.41 (d, J=8.85 Hz, 1H), 3.30 (d, J=8.85 Hz, 1H), 2.92-2.88 (m, 1H), 2.85-2.78 (m, 1H), 2.76-2.66 (m, 2H), 2.58 (d, J=5.19 Hz, 2H), 2.24 (s, 6H), 2.22-2.15 (m, 1H), 2.07-2.01 (m, 1H), 1.85-1.92 (m, 1H), 1.83-1.77 (m, 1H); $^{13}$C-NMR (CDCl$_3$, 126 MHz) δ 161.47 (d, J=246.68 Hz), 136.6, 133.8, 128.74, 128.68, 126.1, 125.7, 124.4, 119.1, 117.4, 115.4, 115.3, 80.4, 79.4, 72.5, 64.7, 50.7, 46.2, 42.1, 41.4, 33.8, 33.7. LC/MS (HPLC method 3): t_R=1.78 min, 431.2(MH)+.

EXAMPLE 112

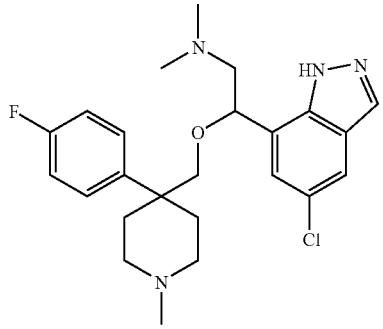

2-(5-chloro-1H-indazol-7-yl)-2-((4-(4-fluorophenyl)-1-methylpiperidine-4-yl)methoxy)-N,N-dimethylethanamine. $^1$H-NMR (CDCl$_3$, 500 MHz) δ 7.91 (s, 1H), ), 7.57 (d, J=1.83 Hz, 1H), 7.27-7.24 (m, 2H), 7.04-7.0 (m, 2H), 6.96 (d, J=1.83 Hz, 1H), 4.43 (t, J=5.19 Hz 1H), 3.43 (d, J=8.85 Hz, 1H), 3.30 (d, J=8.85 Hz, 1H), 2.59 (d, J=5.19 Hz, 2H), 2.60-2.53 (m, 1H), 2.52-2.44 (m, 1H), 2.26 (s, 6H), 2.20 (s, 1H), 2.16-2.06 (m, 2H), 2.05-1.98 (m, 1H), 1.94-1.88 (m, 1H); $^{13}$C-NMR (CDCl$_3$, 126 MHz) δ 161.5 (d, J=245.78 Hz), 136.6, 133.80, 128.79, 128.7, 126.1, 125.7, 124.5, 119.1, 117.4, 115.4, 115.2, 80.4, 72.5, 64.7, 51.9, 51.7, 46.3, 42.5, 40.3, 32.8, 32.6. LC/MS (HPLC method 3): t_R=1.74 min, 445.2(MH)+.

EXAMPLE 113

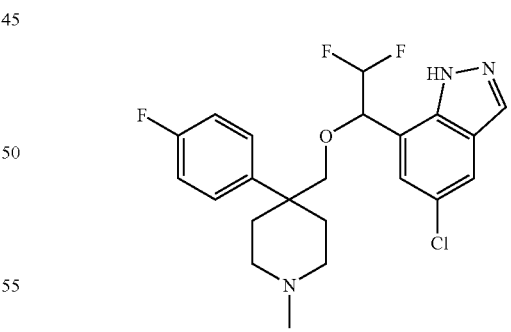

5-chloro-7(2,2-difluoro-1-((4-(4-fluorophenyl)-1-methylpiperidin-4-yl)methoxy)ethyl)-1H-indazole. $^1$H-NMR (CDCl$_3$, 500 MHz) δ 7.93 (s, 1H), 7.68 (d, J=1.83 Hz, 1H), 7.28-7.23 (m, 2H), 7.09-7.04 (m, 3H), 5.79 (dt, J=3.66 Hz, J=55.2 Hz, 1H), 4.46 (dt, J=3.66 Hz, J=11.6 Hz, 1H), 3.55 (d, J=8.85 Hz, 1H), 3.43 (d, J=9.16 Hz, 1H), 2.66-2.56 (m, 2H), 2.36-2.28 (m, 1H), 2.22 (s, 3H), 2.20-2.01 (m, 4H), 1.98-1.89 (m, 1H); $^{13}$C-NMR (CDCl$_3$, 126 MHz) δ 161.7 (d, J=246.6 Hz), 136.6, 133.8, 128.75, 128.69, 127.0, 126.0, 125.0, 120.9, 117.8, 115.8, 115.6, 115.5, 114.2, 81.5, 51.7, 51.6, 50.8, 46.0, 40.5, 32.4, 32.1. LC/MS (HPLC method 3): $t_R$=2.50 min, 438.2(MH)$^+$.

EXAMPLE 114

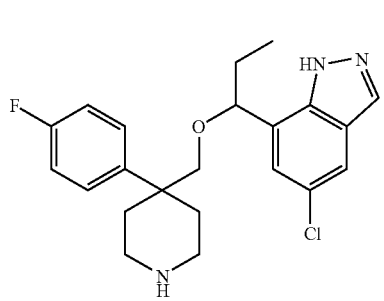

5-chloro-7-(1-((4-(4-fluorophenyl)piperidin-4-yl)methoxy)propyl)-1H-indazole. $^1$H-NMR (CDCl$_3$, 500 MHz) δ 7.89 (s, 1H), 7.57 (d, J=1.83 Hz, 1H), 7.27-7.23 (m, 2H), 7.07-7.03 (m, 2H), 6.97 (d, J=1.83 Hz, 1H), 4.21 (t, J=7.02 Hz, 1H), 3.36 (d, J=8.85 Hz, 1H), 3.24 (d, J=8.85 Hz, 1H), 2.93-3.0 (m, 1H), 2.92-2.86 (m, 1H), 2.81-2.74 (m, 1H), 2.74-2.67 (m, 1H), 2.28-2.20 (m, 1H), 2.10-2.01 (m, 1H), 2.01-1.93 (m, 1H), 1.89-1.79 (m, 2H), 1.69-1.61 (m, 1H), 0.83 (t, J=7.32 Hz, 3H); $^{13}$C-NMR (CDCl$_3$, 126 MHz) δ 163.55 (d, J=245.7 Hz), 135.9, 133.7, 128.7, 128.6, 126.5, 126.0, 124.8, 124.2, 115.6, 115.5, 84.1, 79.3, 50.8, 42.4, 42.3, 41.4, 33.4, 33.2, 29.5, 10.3. LC/MS (HPLC method 4): $t_R$=3.38 min, 402.1(MH)$^+$.

EXAMPLE 115

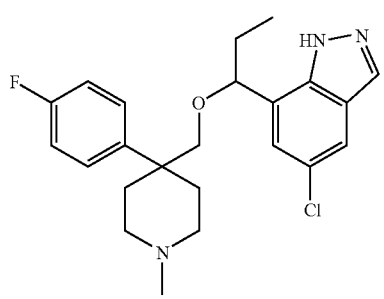

5-chloro-7-(1-((4-(4-fluorophenyl)-1-methylpiperidin-4-yl)methoxy)propyl)-1H-indazole. $^1$H-NMR (CDCl$_3$, 500 MHz) δ 7.88 (s, 1H), 7.56 (d, J=1.83 Hz, 1H), 7.27-7.23 (m, 2H), 7.08-7.03 (m, 2H), 6.96 (d, J=1.83 Hz, 1H), 4.22 (t, J=7.02 Hz, 1H), 3.35 (d, J=8.85 Hz, 1H), 3.24 (d, J=8.85 Hz, 1H), 2.68-2.50 (m, 2H), 2.23 (s, 3H), 2.36-2.12 (m, 3H), 2.12-2.02 (m, 2H), 2.0-1.90 (m, 1H), 0.83 (t, J=7.63 Hz, 3H); $^{13}$C-NMR (CDCl$_3$, 126 MHz) δ 161.6 (d, J=246.6 Hz), 135.9, 133.7, 128.73, 128.67, 126.5, 126.0, 124.8, 124.7, 119.0, 115.6, 115.4, 84.1, 75.0, 51.9, 51.7, 46.1, 40.5, 32.7, 32.4, 29.5, 10.3. LC/MS (HPLC method 1): $t_R$=3.19 min, 416.1 (MH)$^+$.

EXAMPLE 116

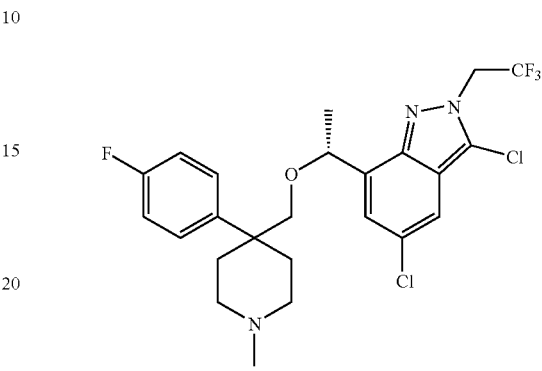

(R)-3,5-dichloro-7-(1-((4-(4-fluorophenyl-1-methyl)piperidine-4-yl)methoxy)ethyl)-2-(2,2,2-trifluoroethyl)-2H-indazole. $^1$H-NMR (CDCl$_3$, 500 MHz) δ 7.37 (d, J=1.83 Hz, 1H), 7.33-7.28 (m, 2H), 7.04-7.69 (m, 2H), 6.78 (m, 1H), 4.97 (q, J=7.93 Hz, 2H), 4.81 (q, J=6.41 Hz, 1H), 3.39-3.32 (m, 2H), 2.65-2.49 (m, 2H), 2.21 (s, 3H), 2.26-1.96 (m, 6H), 1.40 (d, J=6.41 Hz, 3H); $^{13}$C-NMR (CDCl$_3$, 126 MHz) δ 161.3 (d, J=244.7 Hz), 145.6, 136.2, 129.7, 128.98, 128.92, 124.6, 123.7, 121.4, 120.9, 119.6, 115.9, 115.1, 114.9, 73.4, 51.97, 51.91, 51.2, 50.9, 46.3, 40.4, 32.6, 32.2, 22.6. LC/MS (HPLC method 2): $t_R$=2.71 min, 518.4(MH)$^+$.

EXAMPLE 117

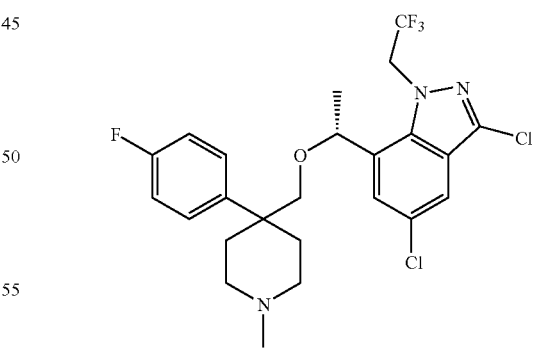

(R)-3,5-dichloro-7-(1-((4-(4-fluorophenyl-1-methyl)piperidine-4-yl)methoxy)ethyl)-2-(2,2,2-trifluoroethyl)-1H-indazole. $^1$H-NMR (CDCl$_3$, 500 MHz) δ 7.57 (d, J=1.83 Hz, 1H), 7.17-7.11 (m, 3H), 7.0-6.93 (m, 1H), 4.81-4.72 (m, 2H), 4.7-4.62 (m, 1H), 3.29 (d, J=8.85 Hz, 1H), 3.07 (d, J=9.16 Hz, 1H), 2.6-2.44 (m, 2H), 2.20 (s, 3H), 2.2-2.03 (m, 4H), 1.92-1.83 (m, 2H), 1.49 (d, J=6.71 Hz, 3H); $^{13}$C-NMR (CDCl$_3$, 126 MHz) δ 161.3 (d, J=246.7 Hz), 138.4, 135.6, 128.7, 127.9, 127.8, 127.4, 124.4, 124.3, 122.2, 119.0, 115.3, 115.1. LC/MS (HPLC method2): $t_R$=2.72 min, 518.4(MH)$^+$.

125.3, 122.0, 117.7, 79.1, 50.4, 42.6, 42.5, 41.7, 33.4, 33.3, 22.1. LC/MS (HPLC method 1): $t_R$=1.98 min, 403.8(MH)$^+$.

EXAMPLE 118

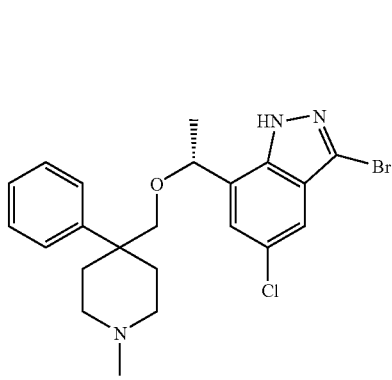

(R)-3-bromo-5-chloro-7-(1-((1-methyl-4-phenylpiperidin-4yl)methoxy)ethyl)-1H-indazole. $^1$H-NMR (CDCl$_3$, 500 MHz) δ 7.48 (d, J=1.83 Hz, 1H), 7.38-7.43 (m, 2H), 7.36-7.29 (m, 3H), 7.0 (d, J=1.83 Hz, 1H), 4.51 (q, J=6.41 Hz, 1H), 3.46 (d, J=10.1 Hz, 1H), 3.3 (d, J=8.85 Hz, 1H), 2.66-2.51 (m, 2H), 2.39-2.31 (m, 1H), 2.21 (s, 3H), 2.25-2.11 (m, 3H), 2.04-1.96 (m, 1H), 1.93-1.88 (m, 1H), 1.39 (d, J=6.71 Hz, 3H); $^{13}$C-NMR (CDCl$_3$, 126 MHz) δ 137.1, 134.1, 128.9, 128.6, 127.1, 126.95, 126.87, 125.2, 122.1, 117.6, 52.0, 51.9, 50.8, 46.3, 42.5, 40.7, 32.5, 22.9. LC/MS (HPLC method 1): $t_R$=1.99 min, 463.9(MH)$^+$.

EXAMPLE 119

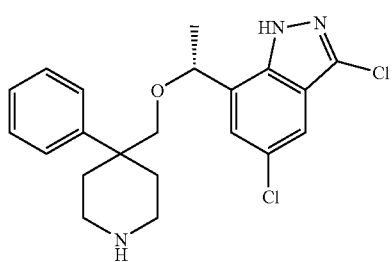

(R)-3,5-dichloro-7-(1-((4-phenylpiperidin-4yl)methoxy)ethyl)-1H-indazole. $^1$H-NMR (CDCl$_3$, 500 MHz) δ 7.48 (d, J=1.83 Hz, 1H), 7.40-7.35 (m, 2H), 7.32-7.28 (m, 3H), 7.0 (d, J=1.53 Hz, 1H), 4.47 (q, J=6.41 Hz, 1H), 3.42 (d, J=11.9 Hz, 1H), 3.29 (d, J=8.85 Hz, 1H), 2.95-2.82 (m, 2H), 2.78-2.65 (m, 2H), 2.27-2.19 (m, 1H), 2.13-2.05 (m, 1H), 1.93-1.77 (m, 2H), 1.39 (d, J=6.41 Hz, 3H); $^{13}$C-NMR (CDCl$_3$, 126 MHz) δ 143.5, 137.1, 133.9, 128.8, 128.6, 127.1, 126.9, 126.8,

EXAMPLE 120

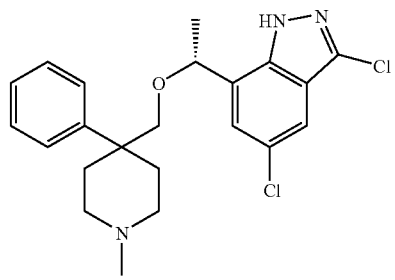

(R)-3,5-dichloro-7-(1-((1-methyl-4-phenylpiperidin-4yl)methoxy)ethyl)-1H-indazole. $^1$H-NMR (CDCl$_3$, 500 MHz) δ 7.43 (d, J=1.83 Hz, 1H), 7.42-7.37 (m, 2H), 7.36-7.29 (m, 3H), 7.0 (d, J=1.83 Hz, 1H), 4.50 (q, J=6.71 Hz, 1H), 3.45 (d, J=8.85 Hz, 1H), 3.29 (d, J=8.85 Hz, 1H), 2.65-2.52 (m, 2H), 2.38-2.31 (m, 1H), 2.25-2.11 (m, 3H), 2.2 (s, 1H), 1.38 (d, J=6.71 Hz, 3H); $^{13}$C-NMR (CDCl$_3$, 126 MHz) δ 136.9 128.8, 128.5, 127.1, 127.0, 126.9, 125.2, 124.6, 121.7, 118.3, 77.9, 52.0, 51.8, 50.7, 46.3, 40.7, 32.6, 32.4, 22.2. LC/MS (HPLC method 1): $t_R$=1.99 min, 417.95(MH)$^+$.

EXAMPLE 121

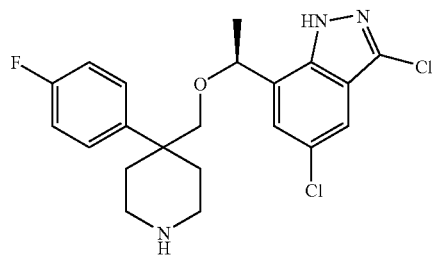

(S)-3,5-dichloro-7-(1-((4-(4-fluorophenyl)piperidin-4-yl)methoxy)ethyl)-1h-indazole. $^1$H-NMR (CDCl$_3$, 500 MHz) δ 7.49 (d, J=1.83 Hz, 1H), 7.25-7.22 (m, 2H), 7.05-7.01 (m, 2H), 6.99 (m, 1H), 4.46 (q, J=6.71 Hz, 1H), 3.35 (d, J=9.16 Hz, 1H), 3.24 (d, J=8.85 Hz, 1H), 2.91-2.81 (m, 2H), 2.74-2.62 (m, 2H), 2.14-2.11 (m, 1H), 2.06-2.01 (m, 1H), 1.92-1.80 (m, 2H), 1.40 (d, J=6.41 Hz, 3H); $^{13}$C-NMR (CDCl$_3$, 126 MHz) δ 161.5 (d, J=245.7 Hz), 139.2, 137.2, 134.1, 128.7, 128.6, 128.4, 126.9, 125.3, 122.0, 117.8, 115.6, 115.5, 79.0, 77.8, 50.4, 42.5, 41.4, 33.6, 33.3, 22.0. LC/MS (HPLC method 3): $t_R$=3.03 min, 422.1(MH)$^+$.

EXAMPLE 122

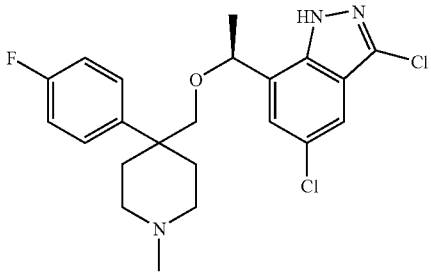

(S)-3,5-dichloro-7-(1-((4-(4-fluorophenyl)-1-methylpiperidin-4-yl)methoxy)ethyl)-1h-indazole. $^1$H-NMR (CDCl$_3$, 500 MHz) δ 7.49 (d, J=1.83 Hz, 1H), 7.27-7.22 (m, 2H), 7.07-7.02 (m, 2H), 7.0 (d, J=1.53 Hz, 1H), 4.49 (q, J=6.71 Hz, 1H), 3.40 (d, J=8.85 Hz, 1H), 3.26 (d, J=8.85 Hz, 1H), 2.61 (m, 2H), 2.29-2.05 (m, 4H), 2.19 (s, 3H), 2.02-1.97 (m, 1H), 1.94-1.88 (m, 1H), 1.39 (d, J=6.41 Hz, 3H); $^{13}$C-NMR (CDCl$_3$, 126 MHz) δ 161.6 (d, J=246.0 Hz), 137.1, 134.2, 128.74, 128.68, 128.4, 127.0, 125.3, 122.0, 117.7, 115.7, 115.5, 77.9, 53.5, 51.9, 51.7, 46.3, 40.3, 32.8, 32.5, 22.2. LC/MS (HPLC method 1): $t_R$=2.04 min, 435.9(MH)$^+$.

EXAMPLE 123

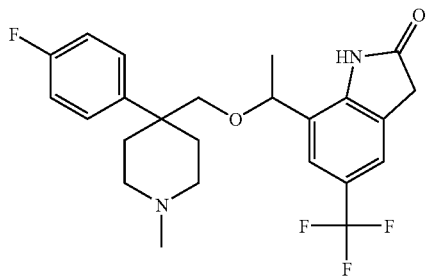

(±)-7-(1-((4-(4-fluorophenyl)-1-methylpiperidin-4-yl)methoxy)ethyl)-5-(trifluoromethyl)indolin-2-one. To a solution of 7-(1-((4-(4-fluorophenyl)piperidin-4-yl)methoxy)ethyl)-5-(trifluoromethyl)indolin-2-one (16 mg, 0.037 mmol) in dichloromethane (1.5 mL) was added formaldehyde (0.055 mL, 0.733 mmol) followed by sodium triacetoxyborohydride (9.32 mg, 0.044 mmol). The mixture was stirred at room temperature. After 1 hour, LC/MS showed complete conversion of starting material. The mixture was purified directly on SiO$_2$ eluting with 5% 2N NH$_3$ in methanol/dichloromethane. The product was obtained as a white foam (12.8 mg, 0.028 mmol, 77%). $^1$H-NMR (CDCl$_3$, 400 MHz) δ 7.56 (br.s., 1H), 7.31 (br.s., 1H), 7.21-7.28 (m, 3H), 7.11 (br.s. 1H), 7.03 (t, J=8.69 Hz, 2H), 4.28 (q, J=6.55 Hz, 1H), 3.41 (s, 2H), 3.30-3.37 (m, 1H), 3.22-3.29 (m, 1H), 2.48-2.65 (m, 2H), 2.19 (s, 3H), 2.06-2.29 (m, 2H), 1.84-2.01 (m, 2H), 1.28 (d, J=6.55 Hz, 3H); Mass spec. (M-H)$^-$: 449.6, (MH)$^+$: 451.3). This material was taken up in diethyl ether, cooled in an ice-water bath and 1.0 N HCl in diethyl ether was added (~100 μL). The solvent was removed to give the HCl salt as a yellow solid (14.5 mg, 0.030 mmol).

EXAMPLE 124

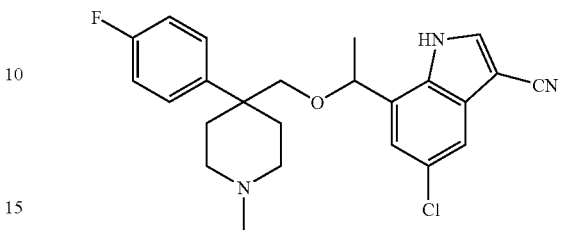

(±)-5-chloro-7-(1-((4-(4-fluorophenyl)-1-methylpiperidin-4-yl)methoxy)ethyl)-1H-indole-3-carbonitrile. (±)-tert-butyl 4-((1-(5-chloro-3-cyano-1H-indol-7-yl)ethoxy)methyl)-4-(4-fluorophenyl)piperidine-1-carboxylate (70 mg, 0.137 mmol) was stirred in TFA (2 mL, 26.0 mmol) at 0° C. for 20 minutes. The solvent was evaporated at a bath temperature of 23° C. The residue was taken up in Ethanol (5 mL), then triethylamine (1 mL), formaldehyde (0.102 mL, 1.367 mmol) and sodium triacetoxyborohydride (87 mg, 0.410 mmol) were added. The reaction was stirred 1 hour, then solvent was evaporated. The residue was taken up in aqueous sodium bicarbonate (10 mL) and extracted with ethyl acetate (4×10 mL). The organic phase was dried with MgSO$_4$ and evaporated. The residue was purified by chromatography on SiO$_2$ with 3%-5%% 2M ammonia in methanol/dichloromethane to give (±)-5-chloro-7-(1-((4-(4-fluorophenyl)-1-methylpiperidin-4-yl)methoxy)ethyl)-1H-indole-3-carbonitrile (55 mg, 0.129 mmol, 94% yield) as a clear oil. $^1$H-NMR (CDCl$_3$, 400 MHz) δ 8.27 (bs, 1H), 7.56 (d, J=1.8 Hz, 1H), 7.27 (m, 2H), 7.14 (d, J=2.8 Hz, 1H), 7.08 (t, J=8.5 Hz, 2H), 6.93 (d, J=1.8 Hz, 1H), 4.55 (q, J=6.5 Hz, 1H), 4.55 (m, 1H), 3.19 (d, J=8.6 Hz, 1H), 2.62 (m, 1H), 2.52 (m, 2H), 2.35 (m, 1H), 1.95-2.20 (m, 2H), 1.86 (m, 1H), 1.48 (m, 1H), 1.41 (d, J=6.5 Hz, 3H). LC/MS (HPLC method 4): $t_R$=2.84 min, 426.14(MH)+.

EXAMPLE 125

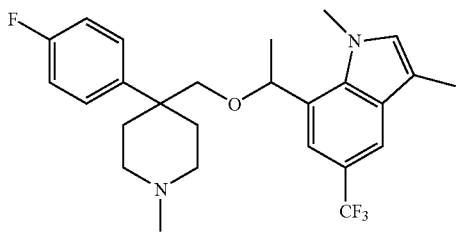

7-(1-((4-(4-fluorophenyl)-1-methylpiperidin-4-yl)methoxy)ethyl)-1,3-dimethyl-5-(trifluoromethyl)-1H-indole. Using the method for previous indole examples, 7-bromo-3-methyl-5-(trifluoromethyl)-1H-indole was converted into 7-(1-((4-(4-fluorophenyl)-1-methylpiperidin-4-yl)methoxy)ethyl)-1,3-dimethyl-5-(trifluoromethyl)-1H-indole. $^1$H-NMR (CDCl$_3$, 400 MHz) δ 7.67 (d, J=0.8 Hz, 1H), 7.20 (m, 2H), 7.13 (s, 1H), 6.98 (t, J=6.2 Hz, 1H), 3.85 (t, J=5.7 Hz, 1H), 3.73 (s, 3H), 3.34 (d, J=9.1 Hz, 1H), 3.16 (d, J=9.2 Hz, 1H), 2.87 (m, 2H), 2.41 (s, 3H), 2.29 (s, 3H), 2.10-2.70 (m, 5H), 1.81 (m, 1H), 1.44 (d, J=6.5 Hz, 3H). LC/MS (HPLC method 4): $t_R$=3.53 min, 463.34 (MH)+.

EXAMPLE 126

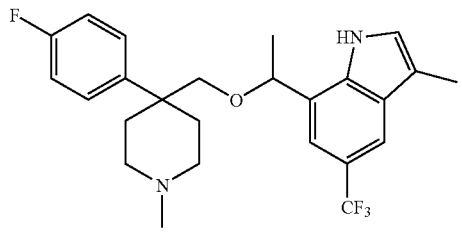

(±)-7-(1-((4-(4-fluorophenyl)-1-methylpiperidin-4-yl)methoxy)ethyl)-3-methyl-5-(trifluoromethyl)-1H-indole. Using the method for previous indole examples, 7-bromo-3-methyl-5-(trifluoromethyl)-1H-indole was converted into (±)-7-(1-((4-(4-fluorophenyl)-1-methylpiperidin-4-yl)methoxy)ethyl)-3-methyl-5-(trifluoromethyl)-1H-indole. $^1$H-NMR (CDCl$_3$, 400 MHz) δ 7.78 (bs, 1H), 7.68 (s, 1H), 7.23 (m, 2H), 7.07 (m, 3H), 6.58 (d, J=0.9 Hz, 1H), 4.56 (q, J=6.6 Hz, 1H), 3.38 (d, J=8.7 Hz, 1H), 3.18 (d, J=8.7 Hz, 1H), 2.67 (m, 1H), 2.55 (m, 1H), 2.26 (s, 3H), 2.23 (s, 3H), 2.00-2.50 (m, 5H), 1.90 (m, 1H), 1.42 (d, J=6.5 Hz, 3H). LC/MS (HPLC method 4): $t_R$=3.10 min, 449.59 (MH)+.

EXAMPLE 127

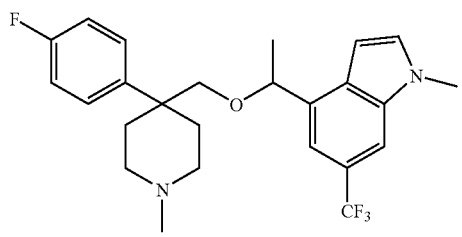

(±)-4-(1-((4-(4-fluorophenyl)-1-methylpiperidin-4-yl)methoxy)ethyl)-1-methyl-6-(trifluoromethyl)-1H-indole. Using the method for previous indole examples, 6-(trifluoromethyl)-1H-indole-4-carbaldehyde was converted into (±)-4-(1-((4-(4-fluorophenyl)-1-methylpiperidin-4-yl)methoxy)ethyl)-1-methyl-6-(trifluoromethyl)-1H-indole. $^1$H-NMR (CDCl$_3$, 400 MHz) δ 7.46 (s, 1H), 7.27 (m, 2H), 7.09 (d, J=3.2 Hz, 1H), 6.98 (m, 2H), 6.38 (d, J=2.6 Hz, 1H), 4.54 (q, J=6.5 Hz, 1H), 3.80 (s, 3H), 3.21 (m, 2H), 2.60 (m, 2H), 2.38 (s, 3H), 1.60-2.35 (m, 6H), 1.40 (d, J=6.9 Hz, 3H). LC/MS (HPLC method 4): $t_R$=3.31 min, 449.41 (MH)+.

EXAMPLE 128

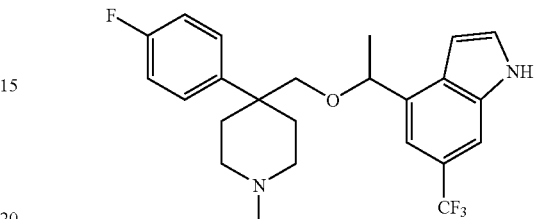

(±)-4-(1-((4-(4-fluorophenyl)-1-methylpiperidin-4-yl)methoxy)ethyl)-6-(trifluoromethyl)-1H-indole. Using the method for previous indole examples, 6-(trifluoromethyl)-1H-indole-4-carbaldehyde was converted into (±)-4-(1-((4-(4-fluorophenyl)-1-methylpiperidin-4-yl)methoxy)ethyl)-6-(trifluoromethyl)-1H-indole. $^1$H-NMR (CDCl$_3$, 400 MHz) δ 8.57 (bs, 1H), 7.54 (s, 1H), 7.26 (m, 2H), 7.06 (s, 1H), 6.98 (m, 2H), 6.46 (s, 1H), 4.54 (q, J=6.8 Hz, 1H), 3.21 (AB, Δv=21.5 Hz, J=9.2 Hz, 2H), 2.52 (m, 2H), 2.17 (s, 3H), 1.95-2.20 (m, 4H), 1.70 (m, 2H), 1.41 (d, J=6.4 Hz, 3H). LC/MS (HPLC method 4): $t_R$=2.67 min, 435.25 (MH)+.

EXAMPLE 129

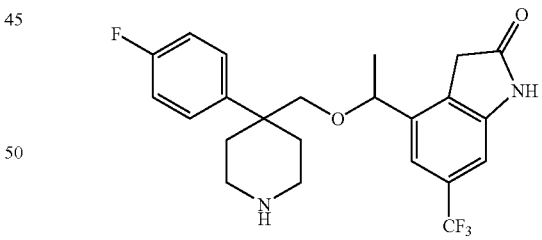

(±)-4-(1-((4-(4-fluorophenyl)piperidin-4-yl)methoxy)ethyl)-6-(trifluoromethyl)indolin-2-one, TFA. To a 7 mL vial was added tert-butyl 4-(4-fluorophenyl)-4-((1-(2-oxo-6-(trifluoromethyl)indolin-4-yl)ethoxy)methyl)piperidine-1-carboxylate (14 mg, 0.026 mmol) in MeOH (1 mL). The solution was stirred at rt and HCl gas was bubbled in for 10 seconds. The solution was stirred overnight at rt. The crude reaction mixture was purified on a reverse phase C18 column 5:95 Acetonitrile:water(TFA) to 95:5 Acetonitrile:water(TFA) affording 8 mg (56%) of the desired oxindole. $^1$H-NMR (CD$_3$OD, 400 MHz) δ ppm 7.38 (m, 2H), 7.08 (m, 2H), 6.98 (s, 1H), 6.97 (s, 1H), 4.38 (q, J=4 Hz, 1H), 3.43-3.13 (m, 6H), 3.98-2.84 (m, 2H), 2.53-2.35 (m, 2H), 2.18-2.04 (m, 2H), 1.32 (d, J=4 Hz, 3H). Mass spec.: 437.26 (MH)⁺.

EXAMPLES 130 AND 131

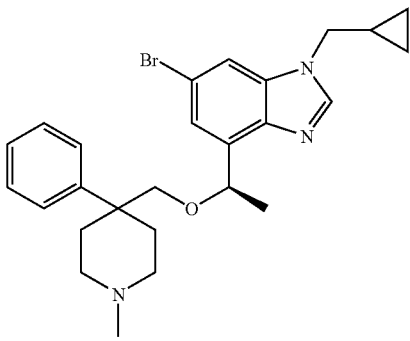

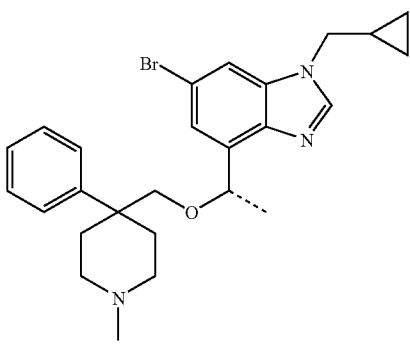

(R)-6-bromo-1-(cyclopropylmethyl)-4-(1-((1-methyl-4-phenylpiperidin-4-yl)methoxy)ethyl)-1H-benzo[d]imidazole and (S)-6-bromo-1-(cyclopropylmethyl)-4-(1-((1-methyl-4-phenylpiperidin-4-yl)methoxy)ethyl)-1H-benzo[d]imidazole. Racemic tert-butyl 4-((1-(6-bromo-1-((2-(trimethylsilyl)ethoxy)methyl)-1H-benzo[d]imidazol-4-yl)ethoxy)methyl)-4-phenylpiperidine-1-carboxylate (34 mg, 0.053 mmol) was dissolved in DMF (0.5 mL) and to this was added CsF (133 mg, 16.6 equiv). The mixture was heated at 80° C. for ~18 h. At the end DMF was evaporated in vacuo and the residue was subjected to extractive work up using EtOAc (30 mL), water (20 mL). Organic layer was dried (Na₂SO₄) and evaporated in vacuo. LC-MS analysis at this stage (HPLC method 19) indicated complete conversion to the required product [$t_R$=1.2 min, 514(MH)⁺]. The crude product was dissolved in DMF (0.5 mL) and stirred with Cs₂CO₃ (96 mg, 5.6 equiv) and cyclopropylmethylbromide (0.006 mL) for ~18 h. DMF was evaporated and the residue was subjected to extractive work up as mentioned before. LC-MS analysis (HPLC method 7) at this stage indicated complete conversion to the required alkylation product [$t_R$=3.2 min, 568(MH)⁺]. The crude alkylation product was purified by preparative HPLC (method 17). Fractions containing the required product were combined and evaporated in vacuo. The residue obtained was dissolved in HCOOH (0.3 mL,147 equiv) and formaldehyde (37%, 0.3 mL, 76 equiv) and heated at 70° C. for 18 h. At the end, after cooling to ambient temperature and diluting with MeOH to 2 mL the mixture was purified by preparative HPLC (method 18). Fractions containing the required product were evaporated in vacuo and the residue was subjected to chiral separation (SFC method 1). Fractions corresponding to peak #1 by SFC were pooled and evaporated in vacuo. The residue 5.3 mg (0.011 mmol) in MeOH (1 mL) was treated with 0.11 mL of 0.1 M succinic acid in water. Volatiles were evaporated to obtain (S)-6-bromo-1-(cyclopropylmethyl)-4-(1-((1-methyl-4-phenylpiperidin-4-yl)methoxy)ethyl)-1H-benzo[d]imidazole (IX) (6.7 mg, 0.9mol succinic acid/mol, assignment of absolute stereochemistry was tentative). 1H NMR (500 MHz, MeOD) δ ppm 8.23 (s, 1 H), 7.70 (d, J=1.8 Hz, 1 H), 7.38-7.45 (m, 4 H), 7.28-7.32 (m, 1 H), 5.05 (q, J=6.4 Hz, 1 H), 4.11 (d, J=7.0 Hz, 2 H), 2.77 (s, 1 H), 2.61 (s, 3 H), 2.53 (s, 3 H), 2.41-2.51 (m, 2 H), 2.24 (s, 1 H), 1.43 (d, J=6.4 Hz, 3 H), 1.35 (s, 1 H), 0.65-0.70 (m, 2 H), 0.44-0.49 (m, 2 H). 482(MH)⁺, [α]²⁰$_D$ (MeOH)=−54.8°. Fractions corresponding to peak #2 were processed in the same manner as above to obtain the opposite enantiomer, (R)-6-bromo-1-(cyclopropylmethyl)-4-(1-((1-methyl-4-phenylpiperidin-4-yl)methoxy)ethyl)-1H-benzo[d]imidazole as succinate salt (7 mg, 0.8 mol succinic acid/mol, assignment of absolute stereochemistry was tentative). Spectral characteristics were same as the other enantiomer. [α]²⁰$_D$ (MeOH)=+54.8°.

EXAMPLE 132

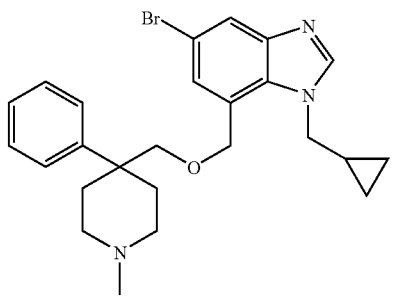

The free amine (18 mg, 0.036 mmol) was subjected to alkylation with cyclopropylmethyl bromide and the crude product was N-methylated using HCOOH and HCHO. The pure product (8 mg, 48% yield) had the following characteristics. 1H NMR (500 MHz, MeOD) δ ppm 8.22 (s, 1 H), 7.72 (d, J=1.8 Hz, 1 H), 7.42-7.45 (m, 2 H), 7.33-7.38 (m, J=7.8, 7.8 Hz, 2 H), 7.21-7.25 (m,2 H), 4.79 (s, 2 H), 4.11 (d, J=7.0 Hz, 2 H), 3.54-3.58 (m, 2 H), 2.24-2.32 (m, 4 H), 2.20-2.22 (m, 3 H), 2.07-2.14 (m, 2 H), 1.32-1.38 (m, 1H), 0.65-0.69 (m, J=8.0, 6.0, 4.6 Hz, 2 H), 0.45-0.48 (m, J=5.8, 4.7, 4.7 Hz, 2 H). 468 (MH)⁺.

EXAMPLES 133 AND 134

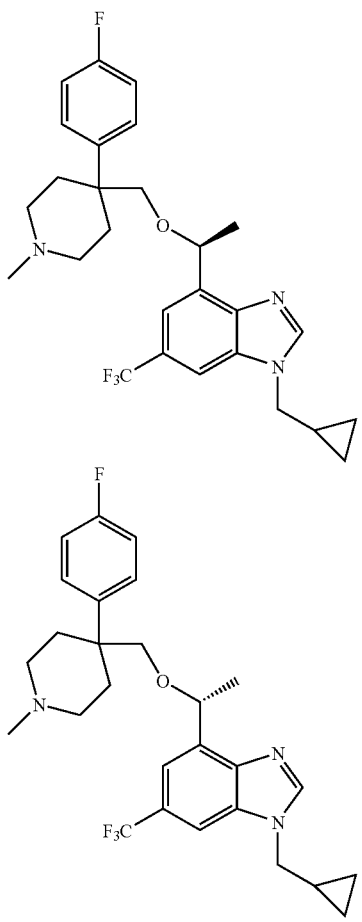

(S)-1-(Cyclopropylmethyl)-4-(1-((4-(4-fluorophenyl)-1-methylpiperidin-4-yl)methoxy)ethyl)-6-(trifluoromethyl)-1H-benzo[d]imidazole and (R)-1-(cyclopropylmethyl)-4-(1-((4-(4-fluorophenyl)-1-methylpiperidin-4-yl)methoxy)ethyl)-6-(trifluoromethyl)-1H-benzo[d]imidazole. tert-Butyl 4-((1-(1-(cyclopropylmethyl)-6-(trifluoromethyl)-1H-benzo[d]imidazol-4-yl)ethoxy)methyl)-4-(4-fluorophenyl)piperidine-1-carboxylate (174 mg, 0.302 mmol) was dissolved in HCOOH (4 ml) and HCHO (37 wt % solution in H$_2$O, 4 ml), the reaction mixture was heated at 75° C. for 3 days. At the end volatiles were removed in vacuo. To the residue was added 20 ml sat. NaHCO$_3$, the mixture was stirred for 30 min under ambient temperature. Then the mixture was extracted with ethyl acetate (90 mL). The organic layer was washed with sat. NaHCO$_3$ (20 mL), brine (20 mL), dried (Na$_2$SO$_4$) and concentrated. The residue was purified by preparative HPLC (HPLC method 16). The fractions with required product were collected and evaporated. The residue was lypholized to give 304 mg the product as racemate from which 203 mg was purified by SFC Chiral chromatography (SFC Method 2). Fractions corresponding to peak #1 by SFC were pooled and evaporated in vacuo. The residue 54 mg was treated with exactly equivalent amount of 0.1 M succinic acid in water. The succinate salt solution was lyophilized to obtain (−)-product (63 mg, assignment of absolute stereochemistry was tentative). $^1$H-NMR (500 MHz, CHLOROFORM-D) δ ppm 8.06 (s, 1 H), 7.55 (s, 1 H), 7.17-7.39 (m, 3 H), 6.87-7.07 (m, 2 H), 5.11 (q, J=6.4 Hz, 1 H), 4.02 (d, J=7.0 Hz, 2 H), 3.20-3.50 (m, 2 H), 2.40-2.69 (m, 2 H), 1.90-2.28 (m, 10 H), 1.44 (d, J=6.4 Hz, 3 H), 1.18-1.38 (m, 1 H), 0.62-0.82 (m, 2 H), 0.42 (q, J=5.2 Hz, 2 H); 490.34(MH)$^+$, [α]$^{20}_D$ (MeOH)= −36.4°. Fractions corresponding to peak #2 were processed in the same manner as above to obtain the opposite enantiomer as succinate salt (67 mg, assignment of absolute stereochemistry was tentative). Spectral characteristics same as the other enantiomer. [α]$^{20}_D$ (MeOH)=+35.5°.

EXAMPLES 135 AND 136

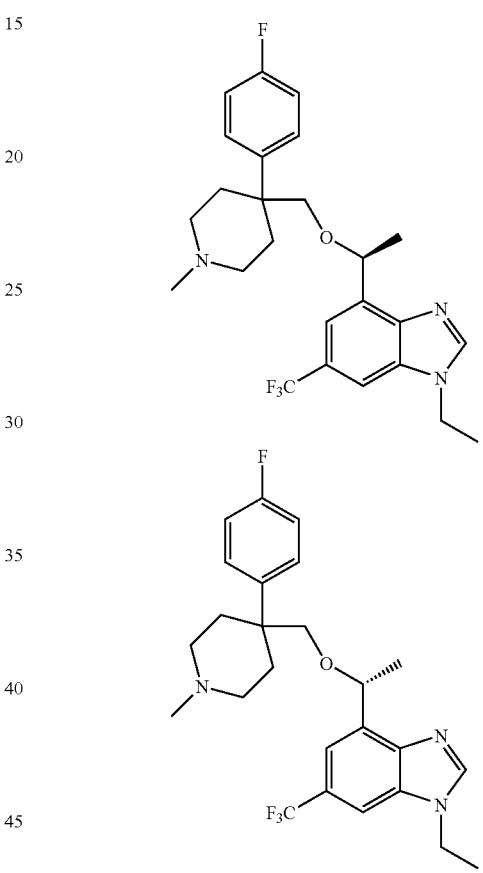

(S)-1-Ethyl-4-(1-((4-(4-fluorophenyl)-1-methylpiperidin-4-yl)methoxy)ethyl)-6-(trifluoromethyl)-1H-benzo[d]imidazole and (R)-1-ethyl-4-(1-((4-(4-fluorophenyl)-1-methylpiperidin-4-yl)methoxy)ethyl)-6-(trifluoromethyl)-1H-benzo[d]imidazole. Tert-Butyl 4-((1-(1-ethyl-6-(trifluoromethyl)-1H-benzo[d]imidazol-4-yl)ethoxy)methyl)-4-(4-fluorophenyl)piperidine-1-carboxylate (211 mg, 0.38 mmol) was dissolved in HCOOH (2 ml) and HCHO (37 wt % solution in H$_2$O, 1.5 ml) and the reaction mixture was heated at 75° C. for 3 days. The workup procedure, preparative HPLC purification are similar to those described above. The residue collected after HPLC purification was lyophilized to give 225 mg product as racemate, from which 211 mg was purified by SFC Chiral chromatography (SFC Method 3). Fractions corresponding to peak #1 by SFC were pooled and evaporated in vacuo. The residue was treated with exactly equivalent amount of 0.1 M succinic acid in water. The succinate salt solution was lyophilized to obtain (−)-product (72 mg, assignment of absolute stereochemistry was tentative). $^1$H-NMR (500 MHz, MeOD) δ ppm 8.38 (s, 1 H), 7.84 (s, 1 H), 7.37-7.49 (m, 2 H), 7.22 (s, 1 H), 7.02-7.15 (m, 2 H), 5.12 (q, J=6.2 Hz, 1 H), 4.40 (q, J=7.3 Hz, 2 H), 3.43-3.56 (m, J=8.5 Hz, 1 H), 3.17-3.30 (m, 2 H), 2.75-2.93 (m, 2 H), 2.67 (s, 3 H), 2.53 (s, 3 H), 2.36-2.52 (m, 2 H), 2.12-2.34 (m, 2 H), 1.53 (t, J=7.3 Hz, 3 H),1.46 (d, J=6.4 H, 3 H). 464.31(MH)$^+$, $[\alpha]^{20}{}_D$ (MeOH)=−40.7°. Fractions corresponding to peak #2 were processed in the same manner as above to obtain the opposite enantiomer as succinate salt (77 mg, assignment of absolute stereochemistry was tentative). Spectral characteristics were the same as the other enantiomer. $[\alpha]^{20}{}_D$ (MeOH)=+38.8°.

EXAMPLES 137 AND 138

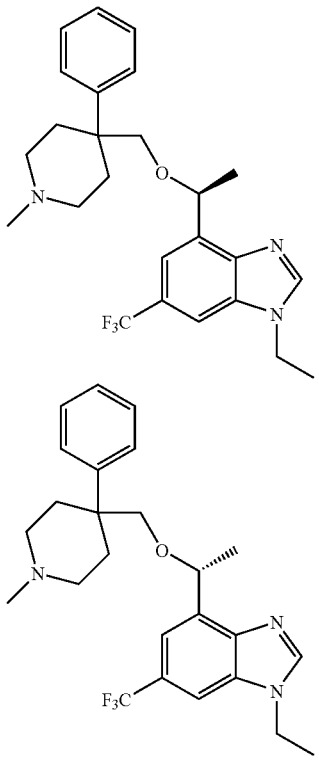

(S)-1-Ethyl-4-(1-((1-methyl-4-phenylpiperidin-4-yl)methoxy)ethyl)-6-(trifluoromethyl)-1H-benzo[d]imidazole and (R)-1-ethyl-4-(1-((1-methyl-4-phenylpiperidin-4-yl)methoxy)ethyl)-6-(trifluoromethyl)-1H-benzo[d]imidazole. Tert-Butyl 4-((1-(1-ethyl-6-(trifluoromethyl)-1H-benzo[d]imidazol-4-yl)ethoxy)methyl)-4-(4-fluorophenyl)piperidine-1-carboxylate (212 mg, 0.40 mmol) was dissolved in HCOOH (2 ml) and HCHO (37 wt % solution in H$_2$O, 1.5 ml) and the reaction mixture was heated at 75° C. for 3 days. The workup procedure, preparative HPLC purification are similar as described above. The residue collected after HPLC purification was lypholized to give 252 mg as racemate, from which 248 mg was purified by SFC Chiral chromatography (SFC Method 2 run time 18 min). Fractions corresponding to peak #1 by SFC were pooled and evaporated in vacuo. The residue was treated with exactly equivalent amount of 0.1 M succinic acid in water. The succinate salt solution was lyophilized to obtain (−)-product (79 mg, assignment of absolute stereochemistry was tentative). $^1$H-NMR (500 MHz, MeOD) δ ppm 8.38 (s, 1 H) 7.85 (s, 1 H) 7.23-7.47 (m, 6 H) 5.12 (q, J=6.4 Hz, 1 H) 4.40 (q, J=7.3 Hz, 2 H) 3.42-3.52 (m, 1 H) 3.16-3.30 (m, 2 H) 2.82 (m, 2 H) 2.62-2.69 (m, 3 H) 2.41-2.57 (m, 5 H) 2.16-2.35 (m, 2 H) 1.53 (t, J=7.3 Hz, 3 H) 1.46 (d, J=6.7 Hz, 3 H). 446.32(MH)$^+$, $[\alpha]^{20}{}_D$ (MeOH)=−39.2°. Fractions corresponding to peak #2 were processed in the same manner as above to obtain the opposite enantiomer as succinate salt (77 mg, assignment of absolute stereochemistry was tentative). Spectral characteristics same as the other enantiomer. $[\alpha]^{20}{}_D$ (MeOH)=+41.1°.

We claim:
1. A compound of Formula I

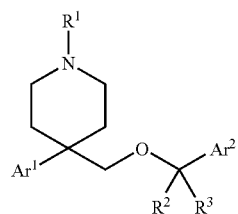

where:
R$^1$ is hydrogen or alkyl;
R$^2$ is hydrogen, alkyl, cyanoalkyl, haloalkyl, hydroxylalkyl, alkoxyalkyl, aminoalkyl, alkylaminoalkyl, dialkylaminoalkyl, cyano, carboxy, alkoxycarbonyl, aminocarbonyl, N-alkylaminocarbonyl, or N,N-dialkylaminocarbonyl;
R$^3$ is hydrogen or alkyl;
Ar$^1$ is phenyl or pyridinyl and is substituted with 0-3 substituents selected from the group consisting of halo, alkyl, haloalkyl, and cyano;
Ar$^2$ is indolyl, indazolyl, benzimidazolyl, or benzotriazolyl, and is substituted with 0-3 substituents selected from the group consisting of halo, alkyl, cycloalkyl, (cycloalkyl)alkyl, haloalkyl, cyanoalkyl, hydroxy, alkoxy, haloalkoxy, cyano, amino, alkylamino, dialkylamino, pyrrolidinyl, piperidinyl, piperazinyl, (alkyl)piperazinyl, morpholinyl, thiomorpholinyl, and Ar$^3$; and
Ar$^3$ is phenyl substituted with 0-3 substituents selected from the group consisting of halo, alkyl, haloalkyl, alkoxy, haloalkoxy, and cyano;
or a pharmaceutically acceptable salt thereof.

2. A compound of claim 1 where R$^2$ is hydrogen or alkyl and Ar$^2$ is indolyl, indazolyl, benzimidazolyl, or benzotriazolyl and Ar$^2$ is substituted with 0-3 substituents selected from the group consisting of halo, alkyl, cycloalkyl, (cycloalkyl)alkyl, haloalkyl, hydroxy, alkoxy, haloalkoxy, cyano, amino, alkylamino, dialkylamino, pyrrolidinyl, piperidinyl, piperazinyl, (alkyl)piperazinyl, morpholinyl, thiomorpholinyl, and Ar$^3$.

3. A compound of claim 1 where R$^1$ is hydrogen or methyl.

4. A compound of claim 1 where R$^2$ is hydrogen and R$^3$ is hydrogen.

5. A compound of claim 1 where R$^2$ is methyl and R$^3$ is hydrogen.

6. A compound of claim 1 where Ar$^1$ is phenyl or monohalophenyl.

7. A compound of claim 1 where Ar$^2$ is indazolyl and is substituted with 0-3 substituents selected from the group consisting of halo, alkyl, cycloalkyl, (cycloalkyl)alkyl, haloalkyl, cyanoalkyl, hydroxy, alkoxy, haloalkoxy, cyano, amino, alkylamino, dialkylamino, pyrrolidinyl, piperidinyl, piperazinyl, (alkyl)piperazinyl, morpholinyl, thiomorpholinyl, and Ar$^3$.

8. A compound of claim 1 selected from the group consisting of
- 7-Methyl-5-(((4-phenylpiperidin-4-yl)methoxy)methyl)-1H-indazole;
- 5-Bromo-7-(((4-phenylpiperidin-4-yl)methoxy)methyl)-1H-indazole;
- 4-(7-(((4-Phenylpiperidin-4-yl)methoxy)methyl)-1H-indazol-5-yl)benzonitrile;
- 4-(1-Methyl-7-(((4-phenylpiperidin-4-yl)methoxy)methyl)-1H-indazol-5-yl)benzonitrile;
- 4-(2-Methyl-7-(((4-phenylpiperidin-4-yl)methoxy)methyl)-2H-indazol-5-yl)benzonitrile;
- 5-Methyl-7-(((4-phenylpiperidin-4-yl)methoxy)methyl)-1H-indazole;
- 1,5-Dimethyl-7-(((4-phenylpiperidin-4-yl)methoxy)methyl)-1H-indazole;
- 2,5-Dimethyl-7-(((4-phenylpiperidin-4-yl)methoxy)methyl)-2H-indazole;
- 7-(((4-Phenylpiperidin-4-yl)methoxy)methyl)-5-(trifluoromethyl)-1H-indazole;
- 7-(((1-Methyl-4-phenylpiperidin-4-yl)methoxy)methyl)-5-(trifluoromethyl)-1H-indazole;
- 1-Methyl-7-(((4-phenylpiperidin-4-yl)methoxy)methyl)-5-(trifluoromethyl)-1H-indazole;
- 2-Methyl-7-(((4-phenylpiperidin-4-yl)methoxy)methyl)-5-(trifluoromethyl)-2H-indazole;
- 1-Methyl-7-(((1-methyl-4-phenylpiperidin-4-yl)methoxy)methyl)-5-(trifluoromethyl)-1H-indazole;
- 2-Methyl-7-(((1-methyl-4-phenylpiperidin-4-yl)methoxy)methyl)-5-(trifluoromethyl)-2H-indazole;
- 7-(((4-(4-Fluorophenyl)piperidin-4-yl)methoxy)methyl)-5-(trifuoromethyl)-1H-indazole;
- 7-(((4-(4-Fluorophenyl)-1-methylpiperidin-4-yl)methoxy)methyl)-5-(trifluoromethyl)-1H-indazole;
- 7-(((4-(4-Fluorophenyl)piperidin-4-yl)methoxy)methyl)-1-methyl-5-(trifluoromethyl)-1H-indazole;
- 7-(((4-(4-Fluorophenyl)piperidin-4-yl)methoxy)methyl)-2-methyl-5-(trifluoromethyl)-2H-indazole;
- 7-(((4-(4-Fluorophenyl)-1-methylpiperidin-4-yl)methoxy)methyl)-1-methyl-5-(trifluoromethyl)-1H-indazole;
- (±)-7-(1-((4-Phenylpiperidin-4-yl)methoxy)ethyl)-5-(trifluoromethyl)-1H-indazole;
- (±)-7-(1-((1-Methyl-4-phenylpiperidin-4-yl)methoxy)ethyl)-5-(trifluoromethyl)-1H-indazole;
- 7-(1-((4-(4-Fluorophenyl)piperidin-4-yl)methoxy)ethyl)-5-(trifuoromethyl)-1H-indazole;
- 7-(1-((4-(4-Fluorophenyl)-1-methylpiperidin-4-yl)methoxy)ethyl)-5-(trifluoromethyl)-1H-indazole;
- 7-(1-((4-(4-Fluorophenyl)piperidin-4-yl)methoxy)ethyl)-1-methyl-5-(trifluoromethyl)-1H-indazole;
- 7-(1-((4-(4-Fluorophenyl)-1-methylpiperidin-4-yl)methoxy)ethyl)-1-methyl-5-(trifluoromethyl)-1H-indazole;
- 7-(1-((4-(4-Fluorophenyl)-1-methylpiperidin-4-yl)methoxy)ethyl)-2-methyl-5-(trifluoromethyl)-2H-indazole;
- 7-(((4-Phenylpiperidin-4-yl)methoxy)methyl)-1H-indazole;
- 3-Cyclopropyl-7-(((4-phenylpiperidin-4-yl)methoxy)methyl)-5-(trifluoromethyl)-1H-indazole;
- 3-Bromo-7-(((4-phenylpiperidin-4-yl)methoxy)methyl)-5-(trifluoromethyl)-1H-indazole;
- 3-Methyl-7-(((4-phenylpiperidin-4-yl)methoxy)methyl)-5-(trifluoromethyl)-1H-indazole;
- (±)-5-Chloro-7-(1-((4-phenylpiperidin-4-yl)methoxy)ethyl)-1H-indazole;
- (±)-5-Chloro-7-(1-((1-methyl-4-phenylpiperidin-4-yl)methoxy)ethyl)-1H-indazole;
- (±)-5-Chloro-1-methyl-7-(1-((4-phenylpiperidin-4-yl)methoxy)ethyl)-1H-indazole;
- (±)-5-Chloro-2-methyl-7-(1-((4-phenylpiperidin-4-yl)methoxy)ethyl)-2H-indazole;
- (±)-3-Methyl-7-(1-((4-phenylpiperidin-4-yl)methoxy)ethyl)-5-(trifluoromethyl)-1H-indazole;
- (±)-3-Methyl-7-(1-((1-methyl-4-phenylpiperidin-4-yl)methoxy)ethyl)-5-(trifluoromethyl)-1H-indazole;
- 5-Cyclopropyl-7-(((4-phenylpiperidin-4-yl)methoxy)methyl)-1H-indazole;
- (±)-5-Bromo-7-(1-((4-(4-fluorophenyl)-1-methylpiperidin-4-yl)methoxy)ethyl)-1H-indazole;
- (±)-5-Cyclopropyl-7-(1-((4-(4-fluorophenyl)-1-methylpiperidin-4-yl)methoxy)ethyl)-1H-indazole;
- (±)-7-(1-((4-(4-Fluorophenyl)-1-methylpiperidin-4-yl)methoxy)ethyl)-1H-indazole-5-carbonitrile;
- (±)-7-(1-((4-(4-Fluorophenyl)-1-methylpiperidin-4-yl)methoxy)ethyl)-5-methyl-1H-indazole;
- (±)-4-7-(1-((4-(4-Fluorophenyl)-1-methylpiperidin-4-yl)methoxy)ethyl)-1H-indazole-5-yl)morpholino;
- 7-(1-((4-(4-Fluorophenyl)-1-methylpiperidin-4-yl)methoxy)ethyl)-N,N-dimethyl-1H-indazol-5-amine;
- (±)-7-(1-((4-(4-Fluorophenyl)-1-methylpiperidin-4-yl)methoxy)ethyl)-5-methoxy-1H-indazole;
- (±)-5-Fluoro-7-(1-((4-(4-fluorophenyl)-1-methylpiperidin-4-yl)methoxy)ethyl)-1H-indazole;
- 5-Cyclopropyl-7-(1-((4-(4-fluorophenyl)-1-methylpiperidin-4-yl)methoxy)ethyl)-1H-indazole;
- (±)-5-Chloro-7-(1-((4-(4-fluorophenyl)-1-methylpiperidin-4-yl)methoxy)ethyl)-3-methyl-1H-indazole;
- (±)-5-Chloro-3-cyclopropyl-7-(1-((4-(4-fluorophenyl)-1-methylpiperidin-4-yl)methoxy)ethyl)-1H-indazole;
- (±)-3-Bromo-5-chloro-7-(1-((4-(4-fluorophenyl)-1-methylpiperidin-4-yl)methoxy)ethyl)-1H-indazole;
- (±)-5-Chloro-2-cyclopropyl-7-(1-((4-(4-fluorophenyl)-1-methylpiperidin-4-yl)methoxy)ethyl)-2H-indazole;
- (±)-3,5-Dichloro-7-(1-((4-(4-fluorophenyl)-1-methylpiperidin-4-yl)methoxy)ethyl)-1H-indazole;
- (±)-1-(2,2-Difluoroethyl)-7-(1-((4-(4-fluorophenyl)-1-methylpiperidin-4-yl)methoxy)ethyl)-5-methyl-1H-indazole;
- (±)-2-(2,2-Difluoroethyl)-7-(1-((4-(4-fluorophenyl)-1-methylpiperidin-4-yl)methoxy)ethyl)-5-methyl-2H-indazole;
- (±)-1-(Cyclopropylmethyl)-7-(1-((4-(4-fluorophenyl)-1-methylpiperidin-4-yl)methoxy)ethyl)-5-methyl-1H-indazole;
- (±)-2-(Cyclopropylmethyl)-7-(1-((4-(4-fluorophenyl)-1-methylpiperidin-4-yl)methoxy)ethyl)-5-methyl-2H-indazole;
- (±)-1-Cyclopropyl-7-(1-((4-(4-fluorophenyl)-1-methylpiperidin-4-yl)methoxy)ethyl)-5-methyl-1H-indazole;
- 4-(1-Cyclopropyl-7-(((1-methyl-4-phenylpiperidin-4-yl)methoxy)methyl)-1H-indazol-5-yl)benzonitrile;
- 7-(((1-Methyl-4-phenylpiperidin-4-yl)methoxy)methyl)-5-(trifluoromethyl)-1H-indole;
- 1-Methyl-7-(((1-methyl-4-phenylpiperidin-4-yl)methoxy)methyl)-5-(trifluoromethyl)-1H-indole;
- 7-(((1-Methyl-4-(4-fluorophenyl)piperidin-4-yl)methoxy)methyl)-5-(trifluoromethyl)-1H-indole;
- 1-Methyl-7-(((1-methyl-4-(4-fluorophenyl)piperidin-4-yl)methoxy)methyl)-5-(trifluoromethyl)-1H-indole;
- (±)-7-(1-((1-Methyl-4-phenylpiperidin-4-yl)methoxy)ethyl)-5-(trifluoromethyl)-1H-indole;
- (±)-1-Methyl-7-(1-((1-methyl-4-phenylpiperidin-4-yl)methoxy)ethyl)-5-(trifluoromethyl)-1H-indole;

(±)-7-(1-((4-(4-Fluorophenyl)-1-methylpiperidin-4-yl)methoxy)ethyl)-5-(trifluoromethyl)-1H-indole;
(±)-7-(1-((4-(4-Fluorophenyl)-1-methylpiperidin-4-yl)methoxy)ethyl)-1-methyl-5-(trifluoromethyl)-1H-indole;
7-(1-((4-(4-Fluorophenyl)-1-methylpiperidin-4-yl)methoxy)ethyl)-1-methyl-5-(trifluoromethyl)-1H-indole;
4-(((1-Methyl-4-phenylpiperidin-4-yl)methoxy)methyl)-6-(trifluoromethyl)-1H-indole 2,2,2-trifluoroacetate;
1-Methyl-4-(((1-methyl-4-phenylpiperidin-4-yl)methoxy)methyl)-6-(trifluoromethyl)-1H-indole 2,2,2-trifluoroacetate;
7-(((4-(4-Fluorophenyl)-1-methylpiperidin-4-yl)methoxy)methyl)-1-methyl-5-(trifluoromethyl)-1H-benzo[d][1,2,3]triazole;
4-(((4-(4-Fluorophenyl)-1-methylpiperidin-4-yl)methoxy)methyl)-2-methyl-6-(trifluoromethyl)-2H-benzo[d][1,2,3]triazole;
4-(((4-(4-Fluorophenyl)-1-methylpiperidin-4-yl)methoxy)methyl)-1-methyl-6-(trifluoromethyl)-1H-benzo[d][1,2,3]triazole;
4-(1-(Cyclopropylmethyl)-2-(((1-methyl-4-phenylpiperidin-4-yl)methoxy)methyl)-1H-benzo[d]imidazol-5-yl)benzonitrile;
5-Bromo-1-(cyclopropylmethyl)-2-(((1-methyl-4-phenylpiperidin-4-yl)methoxy)methyl)-1H-benzo[d]imidazole;
6-Bromo-1-(cyclopropylmethyl)-2-(((1-methyl-4-phenylpiperidin-4-yl)methoxy)methyl)-1H-benzo[d]imidazole;
1-(Cyclopropylmethyl)-5-(2,4-dichlorophenyl)-2-(((1-methyl-4-phenylpiperidin-4-yl)methoxy)methyl)-1H-benzo[d]imidazole;
6-Cyclopropyl-1-(cyclopropylmethyl)-2-(((1-methyl-4-phenylpiperidin-4-yl)methoxy)methyl)-1H-benzo[d]imidazole;
1-(Cyclopropylmethyl)-2-(((1-methyl-4-phenylpiperidin-4-yl)methoxy)methyl)-5-(trifluoromethyl)-1H-benzo[d]imidazole;
1-(Cyclopropylmethyl)-2-(((1-methyl-4-phenylpiperidin-4-yl)methoxy)methyl)-6-(trifluoromethyl)-1H-benzo[d]imidazole; and
4-(((1-Methyl-4-phenylpiperidin-4-yl)methoxy)methyl)-6-(trifluoromethyl)-1H-benzo[d]imidazole;
or a pharmaceutically acceptable salt thereof.

9. A compound of claim 1 selected from the group consisting of

Methyl 2-(5-chloro-1H-indazol-7-yl)-2-((4-(4-fluorophenyl)-1-methylpiperidin-4-yl)methoxy)acetate trifluoroacetic acid salt;
2-(5-Chloro-1H-indazol-7-yl)-2-((4-(4-fluorophenyl)-1-methylpiperidin-4-yl)methoxy)acetic acid trifluoroacetic acid salt;
2-(5-Chloro-1H-indazol-7-yl)-2-((4-(4-fluorophenyl)-1-methylpiperidin-4-yl)methoxy)-N,N-dimethylacetamide trifluoroacetic acid salt;
2-(5-Chloro-1H-indazol-7-yl)-2-((4-(4-fluorophenyl)-1-methylpiperidin-4-yl)methoxy)ethanol trifluoroacetic acid salt;
5-Chloro-7-(1-((4-(4-fluorophenyl)-1-methylpiperidin-4-yl)methoxy)-2-methoxyethyl)-1H-indazole trifluoroacetic acid salt;
5-Chloro-7-(2-fluoro-1-((4-(4-fluorophenyl)-1-methylpiperidin-4-yl)methoxy)ethyl)-1H-indazole;
2-(5-Chloro-1H-indazol-7-yl)-2-((4-(4-fluorophenyl)-1-methylpiperidin-4-yl)methoxy)acetonitrile;
6-Chloro-4-(1-((4-(4-fluorophenyl)-1-methylpiperidin-4-yl)methoxy)ethyl)-1H-benzo[d]imidazol-2(3H)-one trifluoroacetic acid salt;
5-Chloro-7-(1-((4-(4-fluorophenyl)-1-methylpiperidin-4-yl)methoxy)ethyl)-1-methyl-1H-benzo[d]imidazol-2(3H)-one trifluoroacetic acid salt;
6-Chloro-4-(1-((4-(4-fluorophenyl)-1-methylpiperidin-4-yl)methoxy)ethyl)-1-methyl-1H-benzo[d]imidazol-2(3H)-one trifluoroacetic acid salt;
(R)-3,5-Dichloro-7-(1-((4-(4-fluorophenyl)piperidin-4-yl)methoxy)ethyl)-1H-indazole;
(R)-3,5-Dichloro-7-(1-((4-(4-fluorophenyl)-1-methylpiperidin-4-yl)methoxy)ethyl)-1H-indazole;
(R)-3,5-Dibromo-7-(1-((4-(4-fluorophenyl)piperidin-4-yl)methoxy)ethyl)-1H-indazole;
(R)-3,5-Dibromo-7-(1-((4-(4-fluorophenyl)-1-methylpiperidin-4-yl)methoxy)ethyl)-1H-indazole;
(R)-5-Chloro-7-(1-((4-(4-fluorophenyl)-1-methylpiperidin-4-yl)methoxy)ethyl)-3-methyl-1H-indazole;
(R)-5-chloro-2-(cyclopropylmethyl)-7-((1-(4-fluorophenyl)piperidin-4-yl)methoxy)ethyl)-2H-indazole;
(R)-5-chloro-2-(cyclopropylmethyl)-7-(1-((4-(4-fluorophenyl)-1methylpiperidin-4-yl)methoxy)ethyl)-2H-indazole;
(R)-5-chloro-1-(cyclopropylmethyl)-7-(1-((4-(4-fluorophenyl)-1methylpiperidin-4-yl)methoxy)ethyl)-1H-indazole;
(R)-2-(5-chloro-7-(1-((4-(4-fluorophenyl)-1-methylpiperidine-4-yl)methoxy)ethyl)-2H-indazole-2-yl)acetonitrile;
(R)-2-(5-chloro-7-(1-((4-(4-fluorophenyl)-1-methylpiperidine-4-yl)methoxy)ethyl)-1H-indazole-2-yl)acetonitrile;
(S)-3,5-dichloro-7-(2-fluoro-1-((4-(4-fluorophenyl)-1-methylpiperidine-4-yl)methoxy)ethyl)-1H-indazole;
3-(5-chloro-1H-indazol-7-yl)-3-((4-(4-fluorophenyl)-1-methylpiperidine-4-yl)methoxy)propanenitrile;
2-(5-chloro-1H-indazol-7-yl)-2-((4-(4-fluorophenyl)piperidine-4-yl)methoxy)-N,N-dimethylethanamine;
2-(5-chloro-1H-indazol-7-yl)-2-((4-(4-fluorophenyl)-1-methylpiperidine-4-yl)methoxy)-N,N-dimethylethanamine;
5-chloro-7(2,2-difluoro-1-((4-(4-fluorophenyl)-1-methylpiperidin-4-yl)methoxy)ethyl)-1H-indazole;
5-chloro-7-(1-((4-(4-fluorophenyl)piperidin-4-yl)methoxy)propyl)-1H-indazole;
5-chloro-7-(1-((4-(4-fluorophenyl)-1-methylpiperidin-4-yl)methoxy)propyl)-1H-indazole;
(R)-3,5-dichloro-7-(1-((4-(4-fluorophenyl-1-methyl)piperidine-4-yl)methoxy)ethyl)-2-(2,2,2-trifluoroethyl)-2H-indazole;
(R)-3,5-dichloro-7-(1-((4-(4-fluorophenyl-1-methyl)piperidine-4-yl)methoxy)ethyl)-2-(2,2,2-trifluoroethyl)-1H-indazole;
(R)-3-bromo-5-chloro-7-(1-((1-methyl-4-phenylpiperidin-4yl)methoxy)ethyl)-1H-indazole;
(R)-3,5-dichloro-7-(1-((4-phenylpiperidin-4yl)methoxy)ethyl)-1H-indazole;
(R)-3,5-dichloro-7-(1-((1-methyl-4-phenylpiperidin-4yl)methoxy)ethyl)-1H-indazole;
(S)-3,5-dichloro-7-(1-((4-(4-fluorophenyl)piperidin-4-yl)methoxy)ethyl)-1h-indazole;
(S)-3,5-dichloro-7-(1-((4-(4-fluorophenyl)-1-methylpiperidin-4-yl)methoxy)ethyl)-1h-indazole;
(±)-7-(1-((4-(4-fluorophenyl)-1-methylpiperidin-4-yl)methoxy)ethyl)-5-(trifluoromethyl)indolin-2-one;

(±)-5-chloro-7-(1-((4-(4-fluorophenyl)-1-methylpiperidin-4-yl)methoxy)ethyl)-1H-indole-3-carbonitrile;
7-(1-((4-(4-fluorophenyl)-1-methylpiperidin-4-yl)methoxy)ethyl)-1,3-dimethyl-5-(trifluoromethyl)-1H-indole;
(±)-7-(1-((4-(4-fluorophenyl)-1-methylpiperidin-4-yl)methoxy)ethyl)-3-methyl-5-(trifluoromethyl)-1H-indole;
(±)-4-(1-((4-(4-fluorophenyl)-1-methylpiperidin-4-yl)methoxy)ethyl)-1-methyl-6-(trifluoromethyl)-1H-indole;
(±)-4-(1-((4-(4-fluorophenyl)-1-methylpiperidin-4-yl)methoxy)ethyl)-6-(trifluoromethyl)-1H-indole;
(±)-4-(1-((4-(4-fluorophenyl)piperidin-4-yl)methoxy)ethyl)-6-(trifluoromethyl)indolin-2-one, TFA;
(R)-6-bromo-1-(cyclopropylmethyl)-4-(1-((1-methyl-4-phenylpiperidin-4-yl)methoxy)ethyl)-1H-benzo[d]imidazole;
(S)-6-bromo-1-(cyclopropylmethyl)-4-(1-((1-methyl-4-phenylpiperidin-4-yl)methoxy)ethyl)-1H-benzo[d]imidazole;
(S)-6-bromo-3-(cyclopropylmethyl)-4-(1-((4-phenylpiperidin-4-yl)methoxy)ethyl)-1H-benzo[d]imidazole;
(S)-1-(Cyclopropylmethyl)-4-(1-((4-(4-fluorophenyl)-1-methylpiperidin-4-yl)methoxy)ethyl)-6-(trifluoromethyl)-1H-benzo[d]imidazole;
(R)-1-(cyclopropylmethyl)-4-(1-((4-(4-fluorophenyl)-1-methylpiperidin-4-yl)methoxy)ethyl)-6-(trifluoromethyl)-1H-benzo[d]imidazole;
(S)-1-(Cyclopropylmethyl)-4-(1-((4-(4-fluorophenyl)-1-methylpiperidin-4-yl)methoxy)ethyl)-6-(trifluoromethyl)-1H-benzo[d]imidazole;
(R)-1-(cyclopropylmethyl)-4-(1-((4-(4-fluorophenyl)-1-methylpiperidin-4-yl)methoxy)ethyl)-6-(trifluoromethyl)-1H-benzo[d]imidazole;
(S)-1-Ethyl-4-(1-((1-methyl-4-phenylpiperidin-4-yl)methoxy)ethyl)-6-(trifluoromethyl)-1H-benzo[d]imidazole; and
(R)-1-ethyl-4-(1-((1-methyl-4-phenylpiperidin-4-yl)methoxy)ethyl)-6-(trifluoromethyl)-1H-benzo[d]imidazole;

or a pharmaceutically acceptable salt thereof.

10. The compound of claim 1 that is

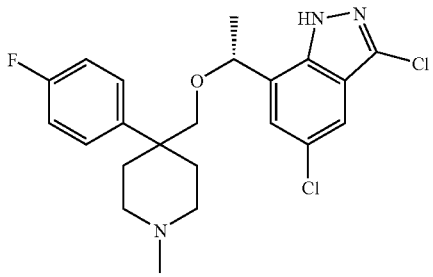

or a pharmaceutically acceptable salt thereof.

11. The compound of claim 10 where the salt is the hydrochloride.

12. A composition comprising a pharmaceutically acceptable amount of a compound of claim 1 and a pharmaceutically acceptable carrier.

13. The composition of claim 12 where the compound is

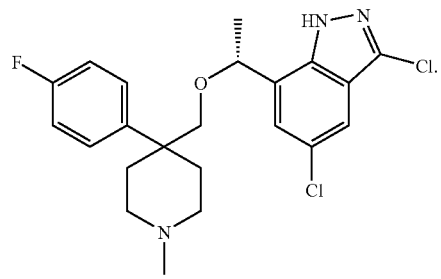

14. A method for treating a disorder associated with aberrant levels of tachykinins or serotonin comprising administering an effective amount of a compound of claim 1 to a patient afflicted with the disorder wherein the disorder is anxiety, depression, obsessive compulsive disorder, bulimia, panic disorder, post-traumatic stress disorder, alcohol dependence, or urinary incontinence.

15. The method of claim 14 where the disorder is anxiety.

16. The method of claim 14 where the disorder is depression, obsessive compulsive disorder, bulimia, panic disorder, post-traumatic stress disorder, alcohol dependence, or urinary incontinence.

17. The method of claim 14 where the compound is

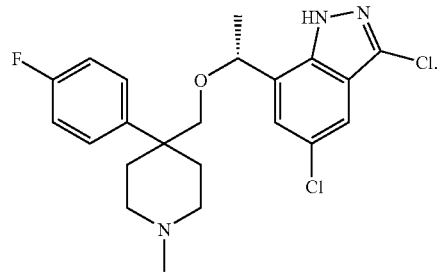

* * * * *

UNITED STATES PATENT AND TRADEMARK OFFICE
CERTIFICATE OF CORRECTION

PATENT NO.        : 8,026,257 B2                                     Page 1 of 1
APPLICATION NO.   : 12/165967
DATED             : September 27, 2011
INVENTOR(S)       : Andrew P. Degnan et al.

It is certified that error appears in the above-identified patent and that said Letters Patent is hereby corrected as shown below:

In the Claims:

Claim 8:

Column 320, line 20, change "(±)-4-7-" to -- (±)-4-(7- --.

Claim 9:

Column 322, line 21, change "-7-((1-(4-" to -- -7-(1-(4-(4- --.

Column 322, line 63, change "-1h-" to -- -1H- --.

Column 322, line 65, change "-1h-" to -- -1H- --.

Signed and Sealed this
Eleventh Day of September, 2012

David J. Kappos
*Director of the United States Patent and Trademark Office*